United States Patent
Tew et al.

(10) Patent No.: US 11,702,632 B2
(45) Date of Patent: Jul. 18, 2023

(54) EX VIVO METHOD OF GENERATING SUPER REGULATORY T CELLS FOR THE PREVENTION OF AUTOIMMUNE DISEASE

(71) Applicant: University of Massachusetts, Boston, MA (US)

(72) Inventors: Gregory N. Tew, South Deerfield, MA (US); Lisa M. Minter, Southampton, MA (US); Emrah Ilker Ozay, Amherst, MA (US)

(73) Assignee: University of Massachusetts, Boston, MA (US)

( * ) Notice: Subject to any disclaimer, the term of this patent is extended or adjusted under 35 U.S.C. 154(b) by 532 days.

(21) Appl. No.: 16/612,958

(22) PCT Filed: May 11, 2018

(86) PCT No.: PCT/US2018/032443
§ 371 (c)(1),
(2) Date: Nov. 12, 2019

(87) PCT Pub. No.: WO2018/209312
PCT Pub. Date: Nov. 15, 2018

(65) Prior Publication Data
US 2020/0163994 A1 May 28, 2020

Related U.S. Application Data

(60) Provisional application No. 62/505,698, filed on May 12, 2017.

(51) Int. Cl.
| | | |
|---|---|---|
| *C12N 5/00* | (2006.01) | |
| *C07K 16/40* | (2006.01) | |
| *C08G 61/12* | (2006.01) | |
| *C12N 5/0783* | (2010.01) | |
| *A61K 35/17* | (2015.01) | |
| *A61K 38/00* | (2006.01) | |
| *A61K 45/06* | (2006.01) | |
| *A61K 47/32* | (2006.01) | |
| *C07K 16/18* | (2006.01) | |
| *C12N 9/10* | (2006.01) | |
| *C12N 9/12* | (2006.01) | |

(52) U.S. Cl.
CPC ............ *C12N 5/0636* (2013.01); *C07K 16/40* (2013.01); *A61K 35/17* (2013.01); *A61K 38/00* (2013.01); *A61K 45/06* (2013.01); *A61K 47/32* (2013.01); *C07K 16/18* (2013.01); *C07K 2317/24* (2013.01); *C08G 61/12* (2013.01); *C08G 2261/3242* (2013.01); *C08G 2261/3342* (2013.01); *C12N 9/1007* (2013.01); *C12N 9/12* (2013.01); *C12Y 201/01077* (2013.01); *C12Y 207/11013* (2013.01)

(58) Field of Classification Search
CPC ........ C07K 16/40; A61K 35/17; C08G 61/12; C08G 2261/3242; C08G 2261/2261; C08G 2261/3342; C12N 5/0636
See application file for complete search history.

(56) References Cited

U.S. PATENT DOCUMENTS

| | | |
|---|---|---|
| 2015/0250862 A1 | 9/2015 | Cantor et al. |
| 2016/0324970 A1 | 11/2016 | Tew et al. |
| 2016/0354367 A1 | 12/2016 | Rao et al. |

FOREIGN PATENT DOCUMENTS

| | | |
|---|---|---|
| WO | WO-2011163637 A2 | 12/2011 |
| WO | WO-2016036976 A1 | 3/2016 |
| WO | WO-2018209312 A1 | 11/2018 |

OTHER PUBLICATIONS

Ozay et al (2016. Mol Ther. 24(12):2118-2130; published on-line Oct. 18, 2016).*
Wang et al, 2012. Frontiers in Immunology. 3: 1-8.*
Ozay et al, 2016. Mol Thera. 24(12): 2118-2130; published on-line Oct. 18, 2016.*
Benjamini et al, 1991. Immunology: A Short Course, 2nd edition, p. 40 only.*
Ferrara et al (2015. mAbs. 7(1): 32-41.*
Praveen et al (2009. Journal of Immunology. 182: 6022-6030).*
Ron et al (1999. Journal of Biological Chemistry. 274(38):27039-27046).*
Azadi et al (2006. Mol Cell Neurosci. 31: 756-773).*
Product Datasheet for "p-PKCθ (A-11): sc-271922", Santa Cruz Biotechnology, Inc; 1 page; no date indicated, no author indicated; downloaded from datasheets.scbt.com/sc-271922.pdf.*
Astarci et al (2012. FEBS Journal. 279: 2966-2986).*
"International Application Serial No. PCT/US2018/032443, International Search Report dated Aug. 21, 2018", 4 pgs.
"International Application Serial No. PCT/US2018/032443, Written Opinion dated Aug. 21, 2018", 6 pgs.
Lienkamp, K, et al., "Antimicrobial Polymers Prepared by ROMP with Unprecedented Selectivity: A Molecular Construction Kit Approach", Journal of the American Chemical Society vol. 130 Issue 30, (Jul. 30, 2008), 9836-9843.
"International Application Serial No. PCT/US2018/032443, International Preliminary Report on Patentability dated Nov. 21, 2019", 8 pgs.
Biterge, B., "Methylation of histone H4 at aspartate 24 by protein L-isoaspartate O-methyltransferase (PCMT1) links histone modifications with protein homeostasis", Sci Rep. Oct. 20, 2014;4:6674. doi: 10.1038 srep06674, (2014), 8 pgs.

(Continued)

*Primary Examiner* — Zachary C Howard
(74) *Attorney, Agent, or Firm* — Schwegman Lundberg & Woessner, P.A.

(57) ABSTRACT

The disclosure provides an ex vivo method to prepare regulatory T cells, a population of regulatory T cells with enhanced properties and methods of using the population or complexes useful to induce Tregs in a mammal. The ex vivo methods allows for the generation and expansion of super regulatory T cells for the prevention, inhibition or treatment of autoimmune disorders.

13 Claims, 172 Drawing Sheets
Specification includes a Sequence Listing.

(56) References Cited

OTHER PUBLICATIONS

Nagy, B Jr., "Impaired activation of platelets lacking protein kinase C-theta isoform", 113(11):2557-67. doi: 10.1182 blood-2008-07-169268., (Mar. 12, 2009), 11 pgs.

Perveen, K., "Validation of monoclonal antiPKC isozyme antibodies for fow cytometry analyses in human T cell subsets and expression in cord blood T cells", Sci Rep. Jun. 25, 2019;9(1):9263. doi: 10.1038 s41598-019-45507-2, (2019), 11 pgs.

Perveen, K., "Protein kinase Ctheta focusing at the cSMAC is a consequence rather than cause of TCR signaling and is dependent on the MEK ERK pathway", J Immunol. May 15, 2009;182(10):6022-30. doi: 10.4049 jimmunol.0800897, (2009), 2 pgs.

Ron, D., "Coordinated movement of RACK1 with activated betaIIPKC", J Biol Chem. Sep. 17, 1999;274(38):27039-46. doi: 10.1074 jbc. 274.38.27039, (1999), 1 pg.

Saito, H., "Chaperone protein L-isoaspartate (D-aspartyl) O-methyltransferase as a novel predictor of poor prognosis in lung adenocarcinoma", Hum Pathol Apr. 2016;50:1-10. doi: 10.1016j. humpath.2015.11.006. Epub Dec. 3, 2015., (2016), 2 pgs.

Seifollah, A., "Up-regulation and increased phosphorylation of protein kinase C (PKC) delta, mu and theta in the degenerating rd1 mouse retina", Mol Cell Neurosci. Apr. 2006;31(4):759-73. doi: 10.1016 j.mcn.2006.01.001. Epub Feb. 28, 2006, (2006), 2 pgs.

Wagner, A.M., "Post-translational protein modifications in type 1 diabetes: a role for the repair enzyme protein-L-isoaspartate (D-aspartate) O-methyltransferase?", Diabetologia. Mar. 2007;50(3):676-81. doi: 10.1007 s00125-006-0556-1. Epub Jan. 10, 2007, (2007), 2 pgs.

Zhao, H., "Construction of random tumor transcriptome expression library for creating and selecting novel tumor antigens", Tumour Biol. Sep. 2016;37(9):12877-12887. doi: 10.1007 s13277-016-5201-0. Epub Jul. 23, 2016, (2016), 1 pg.

"Phospho-PKC theta (Thr538) Recombinant Rabbit Monoclonal Antibody (F4H4L1)", invitrogen Catalog No. 700043, Thermofisher Scientific, 3 pgs., (Mar. 2009), 3 pgs.

"Phospho-PKC theta (Thr538) Polyclonal Antibody", Invitrogen Catalog No. PA5-97404, Thermofisher Scientific, 1 pg., (Mar. 2009), 1 pg.

"PRKCQ(Thr538) Polyclonal Antibody", Bioss Antibodies, bs-5585R, https: www.biossantibodies.com datasheets bs-5585R, (Mar. 2009), 2 pgs.

"Anti-Phospho-PKC theta (T538) PRKCQ Antibody", Boster Antibody, Catalog No. A01293T538-1, 2 pgs., (Mar. 2009), 2 pgs.

"Phospho-PKCO (Thr538) Antibody", Cell Signaling Technology, No. 9377, 3 pgs., https: www.cellsignal.comdatasheet.jsp?productId=9377andimages=1, (Mar. 2009), 3 pgs.

"Anti-PRKCQ PKC-Theta Antibody Rabbit anti-Human Polyclonal LSBio", Antibodies PRKCQ PKC-Theta LS Bio C117459., https: www.lsbio.com antibodies prkcq-antibody-pkc-theta-antibody-phospho-ser676-ihc-wb-western-Is-c117459 120592, (Accessed on Jan. 17, 2023), 2 pgs.

"Anti-PKC theta PRKCQ phospho T538 antibody ab63365 Abcam", Anti-PKC theta PRKCQ phospho T538 antibody Abcam 63365, https: www.abcam.com products primary-antibodies pkc-thetaprkcq-phospho-t538-antibody-ab63365.html, (Accessed on Jan. 17, 2023), 3 pgs.

"PKC theta Antibodies", Thermofisher Scientific primary antibodies, https: www.thermofisher.com antibody primary target pkc theta, (Accessed on Jan. 17, 2023), 5 pgs.

"Antibody A-11 SCBT Santa Cruz Biotechnology", p-PKC 0 Antibody (A-11) sc-271922, https: www.scbt.com p p-pkc-theta-antibody-a-11, (Accessed on Jan. 17, 2023), 3 pgs.

Nagy Jr., Bela, "Platelets and Thrombopoiesis, Impaired activation of platelets lacking protein kinase C-θ isoform", Blood. Mar. 12, 2009, 113(11) 2557-2567, https: www.ncbi.nlm.nih.gov pmc articles PMC2656276 ?report=printable, (Mar. 2009), 22 pgs.

\* cited by examiner

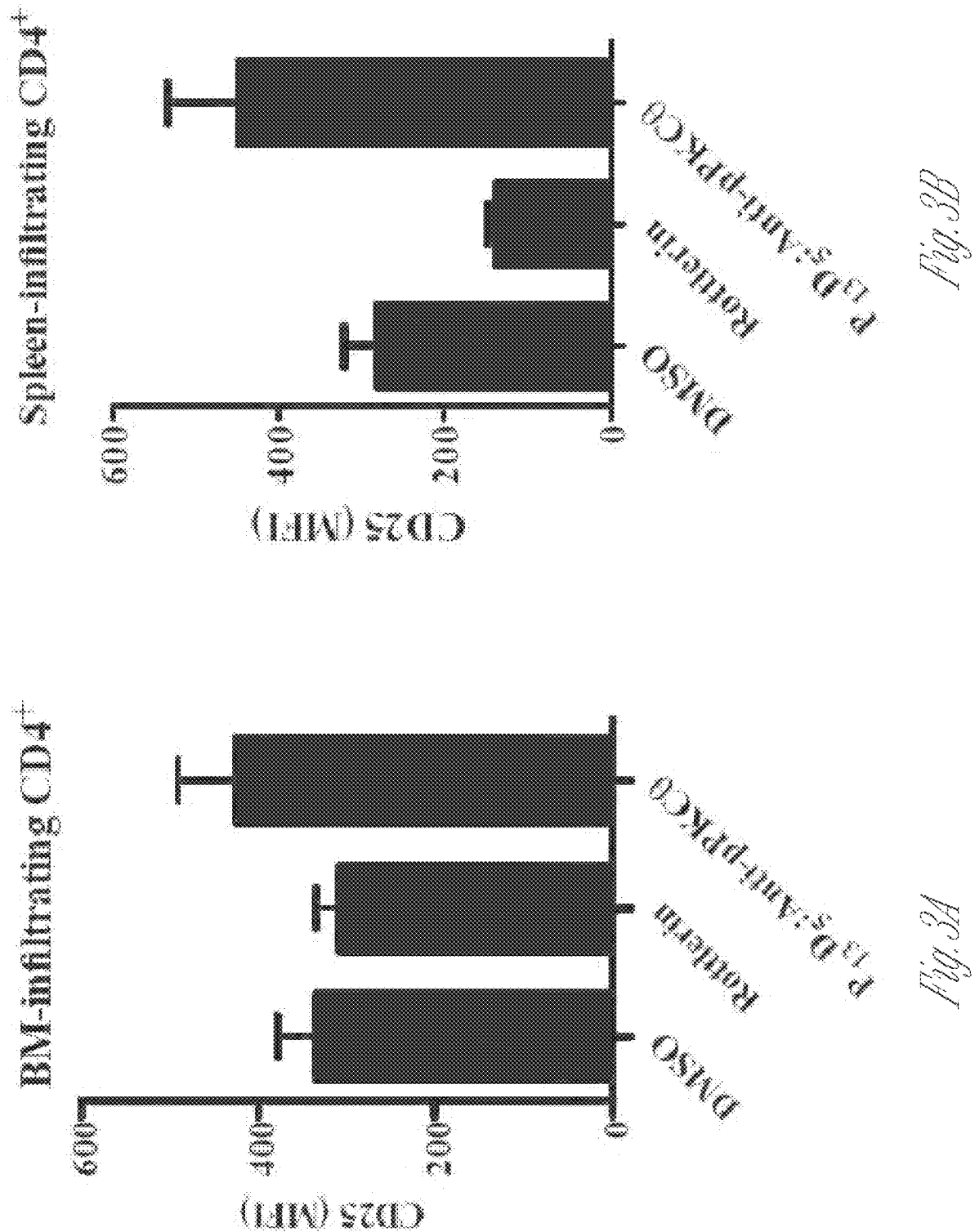

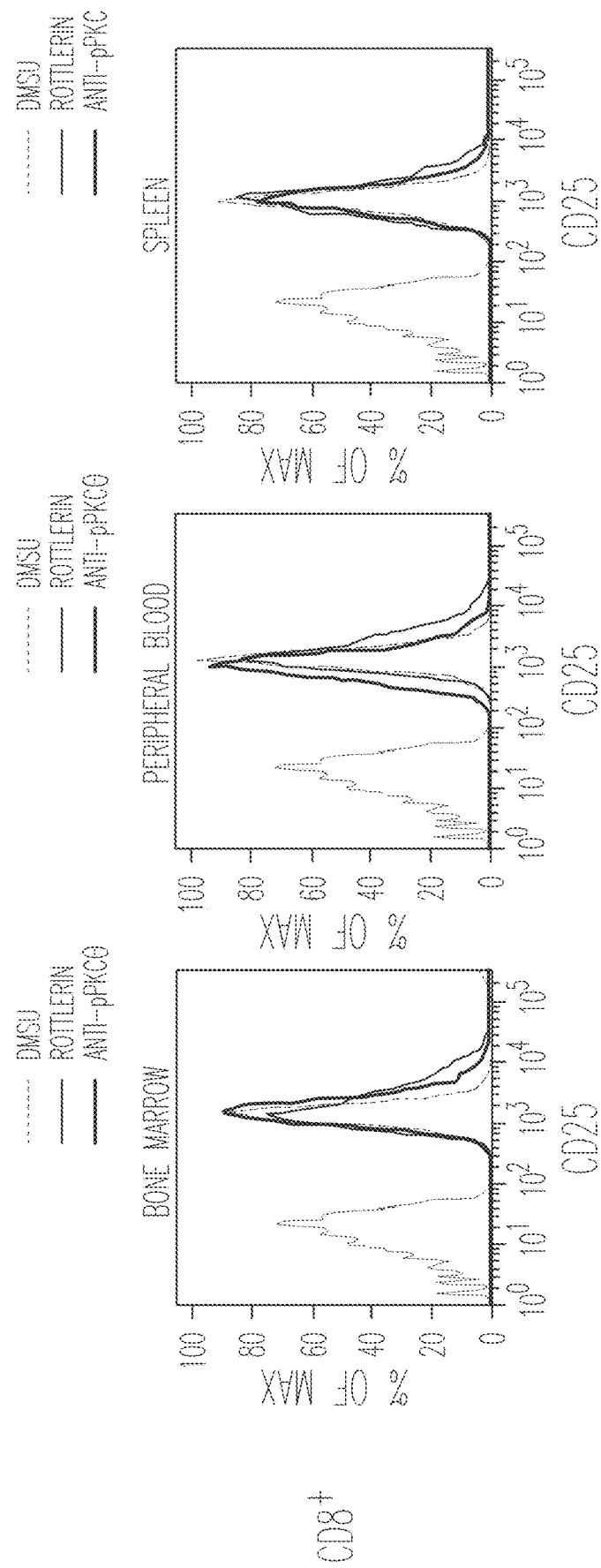

Fig. 5

ROTTLERIN

| CELL TYPE | PRKCQ | NOTCH1 | IL2 | CREL | MASTER TF | CYTOKINE |
|---|---|---|---|---|---|---|
| Th1 | UP | DOWN | - | - | DOWN | DOWN |
| Th2 | UP | UP | UP | - | - | - |
| Th17 | DOWN | - | DOWN | DOWN | DOWN | - |
| iTreg | DOWN | DOWN | - | - | - | - |

ANTI-pPKCθ

| CELL TYPE | PRKCQ | NOTCH1 | IL2 | CREL | MASTER TF | CYTOKINE |
|---|---|---|---|---|---|---|
| Th1 | - | DOWN | DOWN | - | DOWN | DOWN |
| Th2 | UP | UP | DOWN | - | - | UP |
| Th17 | DOWN | - | DOWN | DOWN | DOWN | DOWN |
| iTreg | UP | - | UP | UP | - | UP |

-: NO SIGNIFICANT CHANGE

SAMPLES
NON-iTreg DMSO
NON-iTreg ANTI-pPKCθ
iTreg DMSO
iTreg ROTTLERIN
iTreg ANTI-pPKCθ

GENES
CD45
CD47 (SHORT vs LONG FORM)
MALT1A

Anti-CD3+Anti-CD28 (n=1)

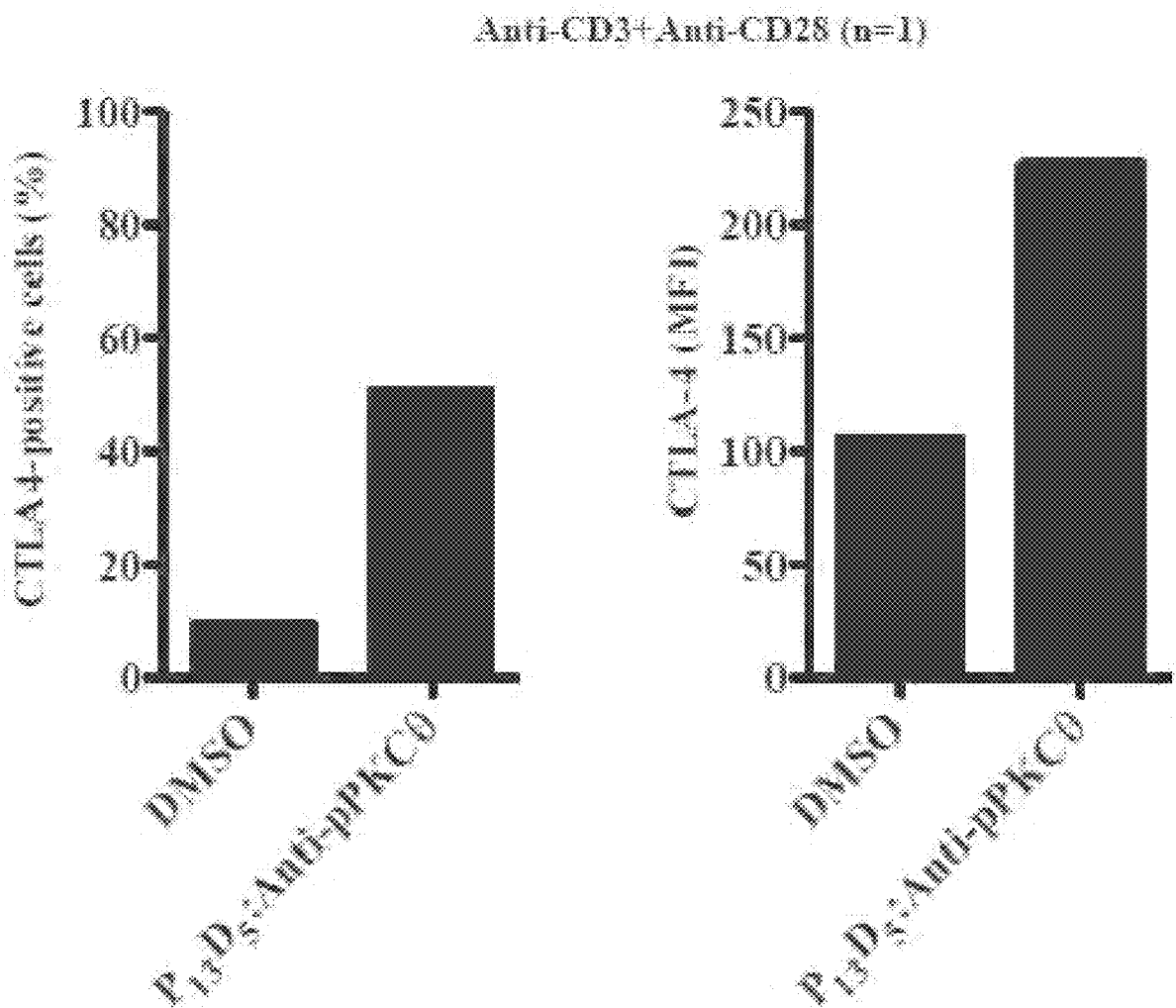
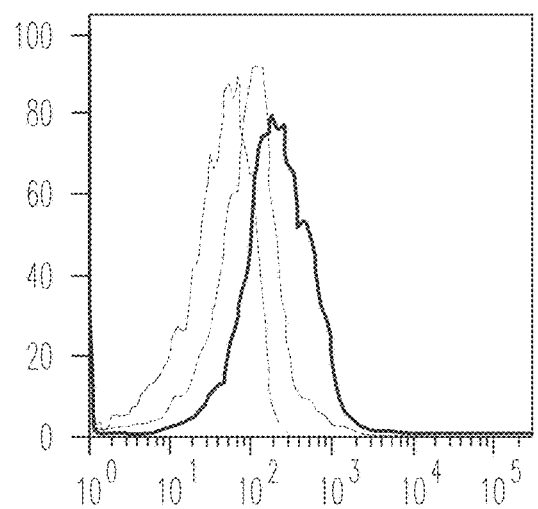
FIG. 11A  FIG. 11B
FIG. 11C

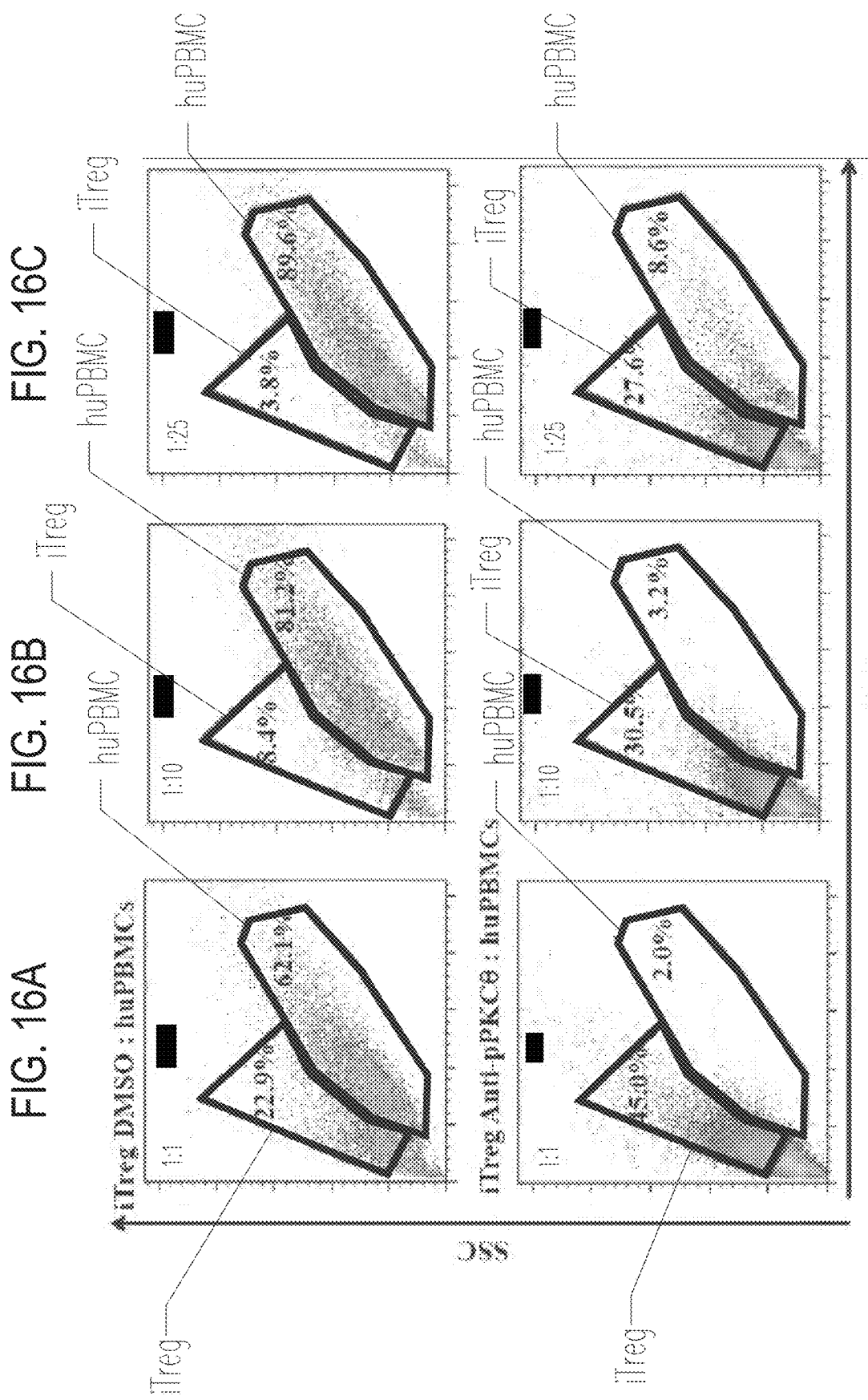

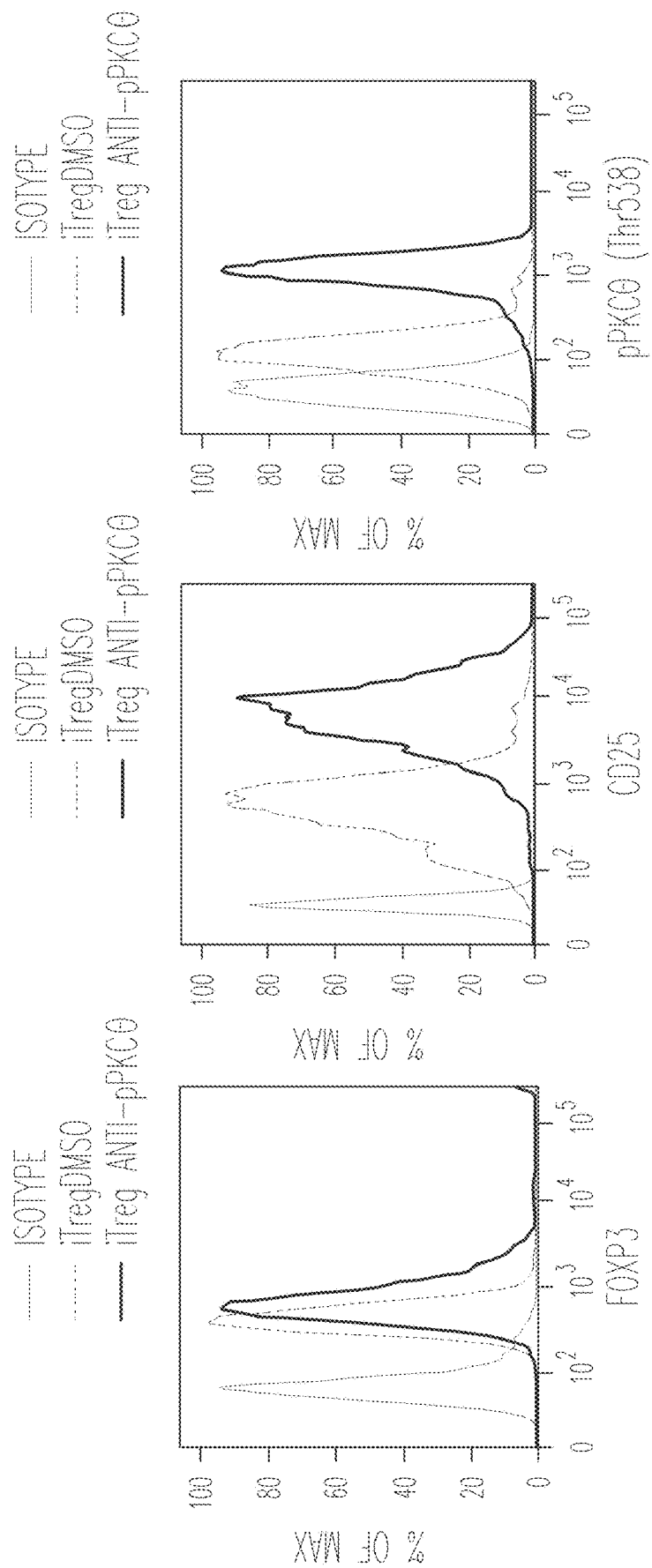

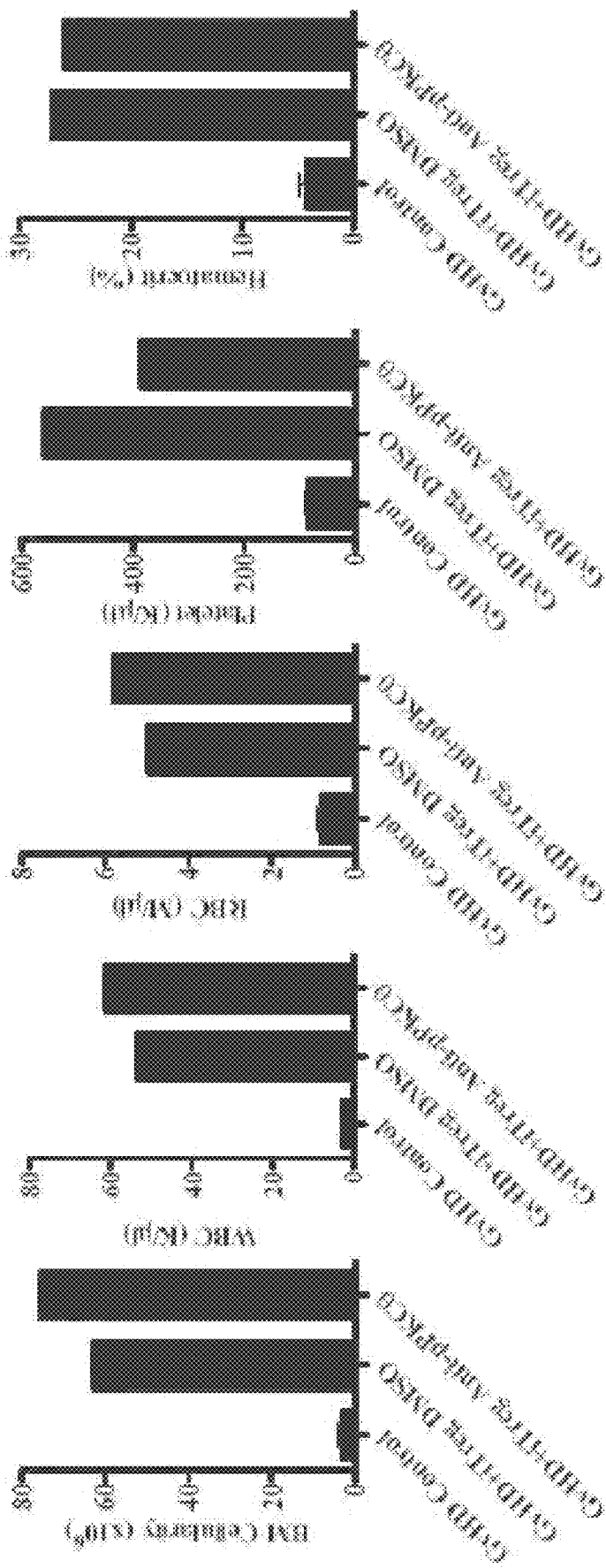

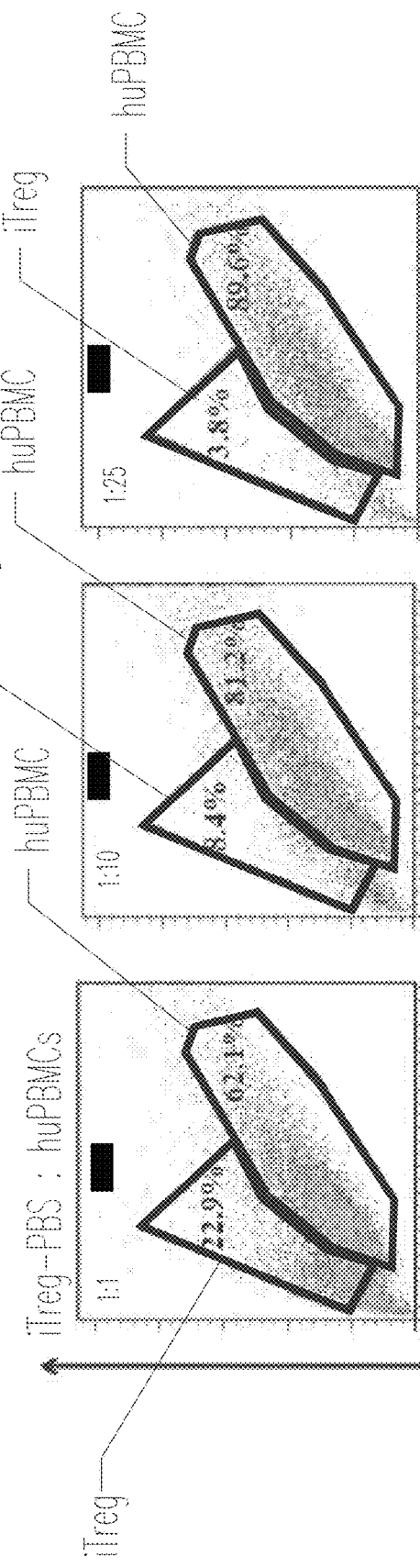
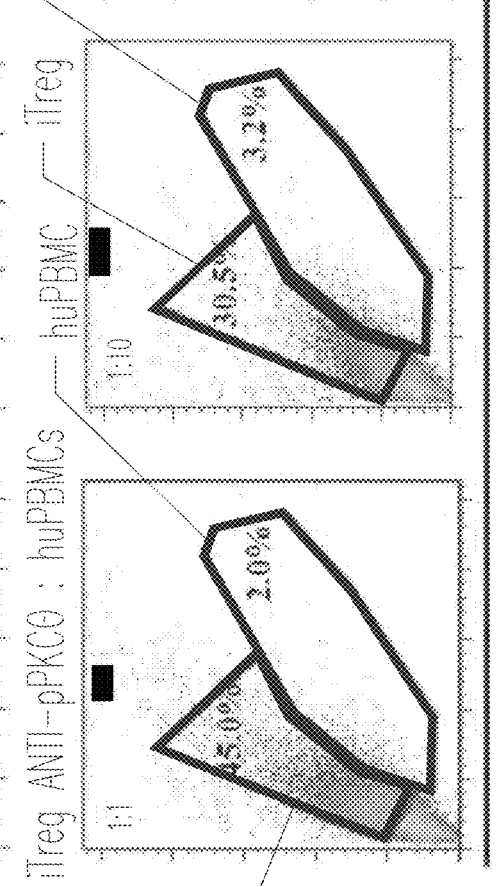
FIG. 30A  FIG. 30B  FIG. 30C
FIG. 30D  FIG. 30E  FIG. 30F

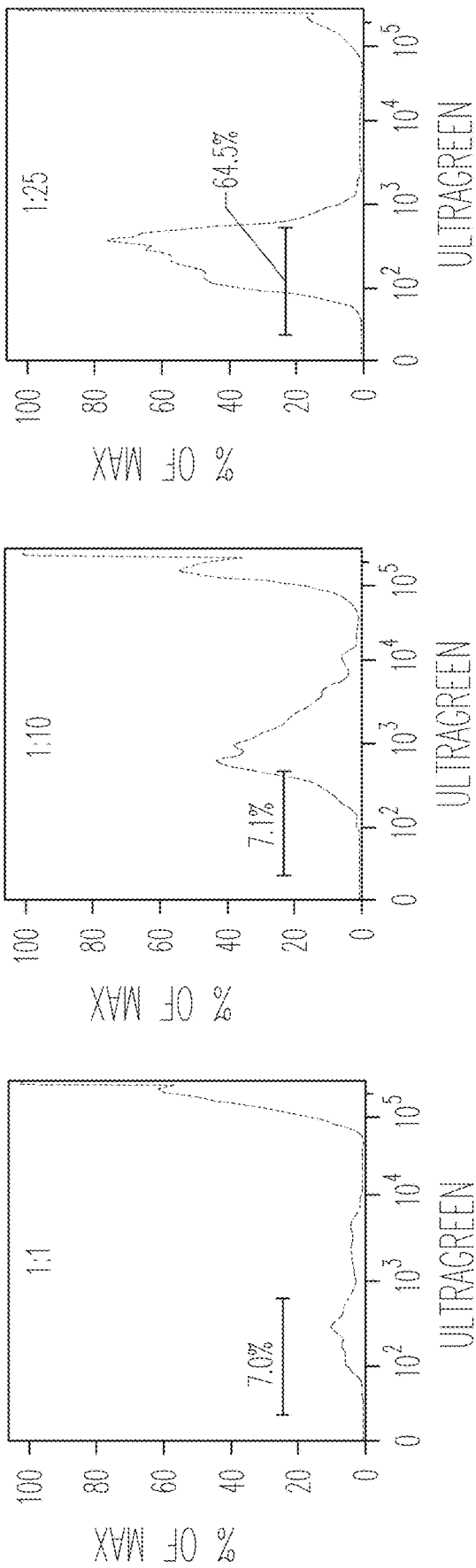

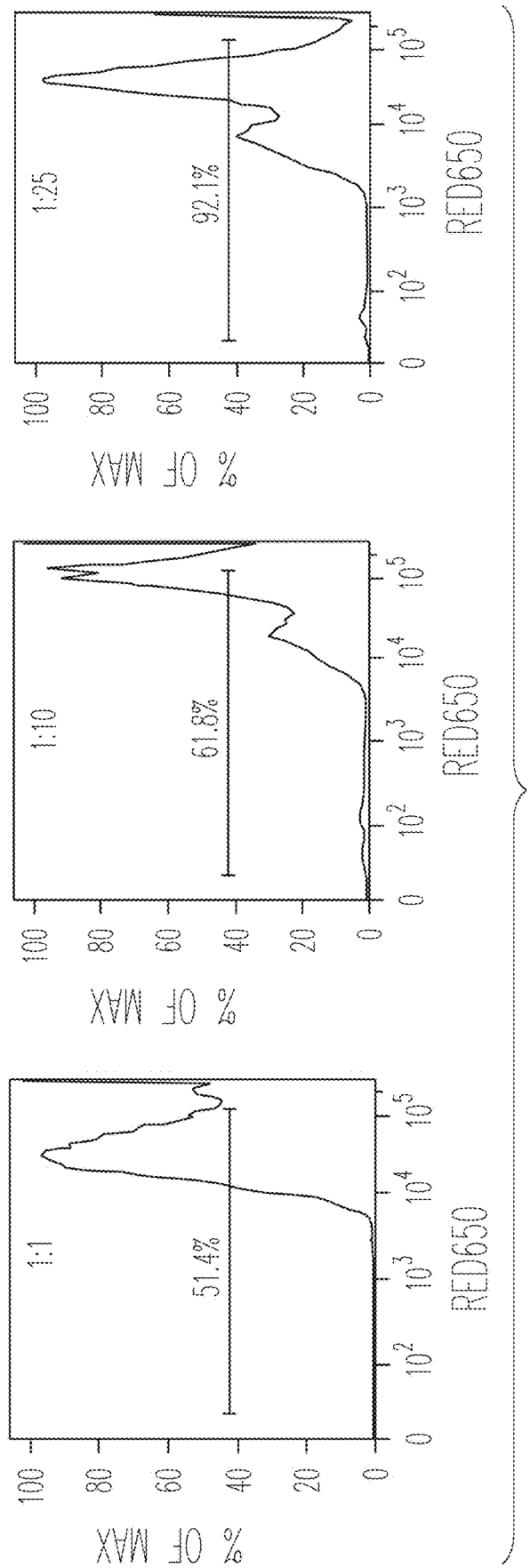

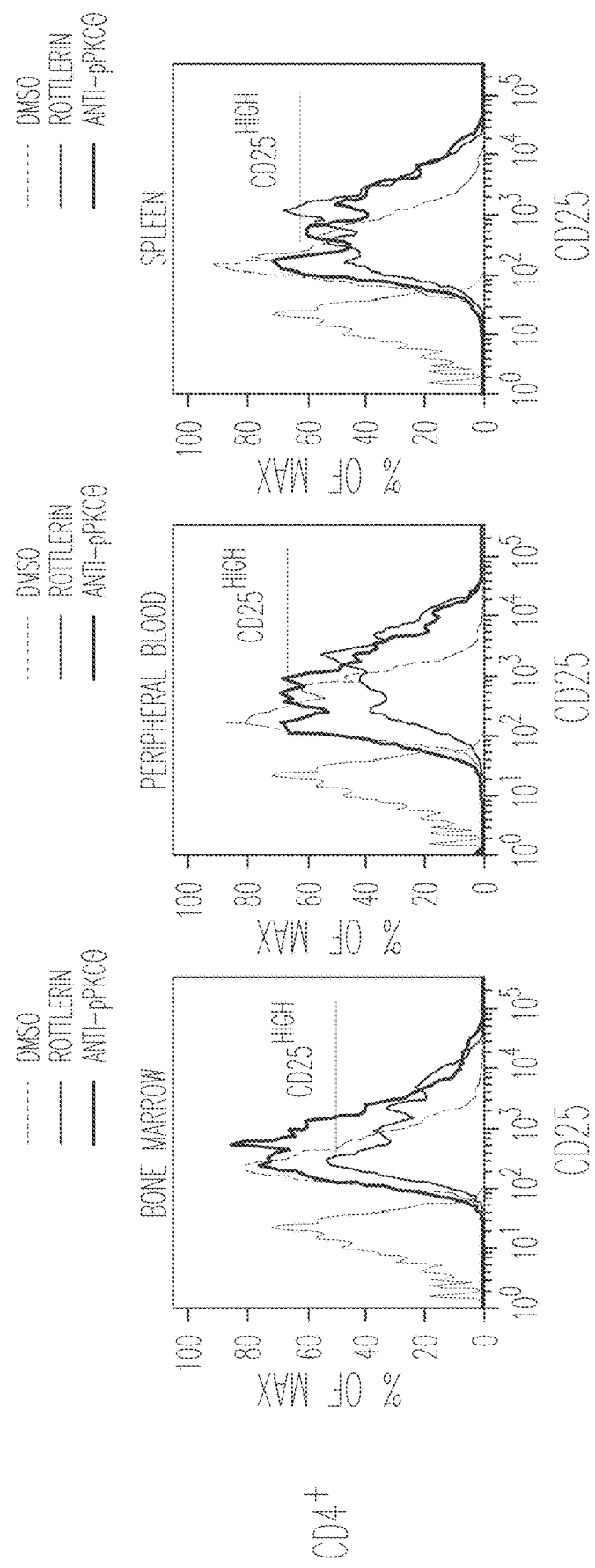

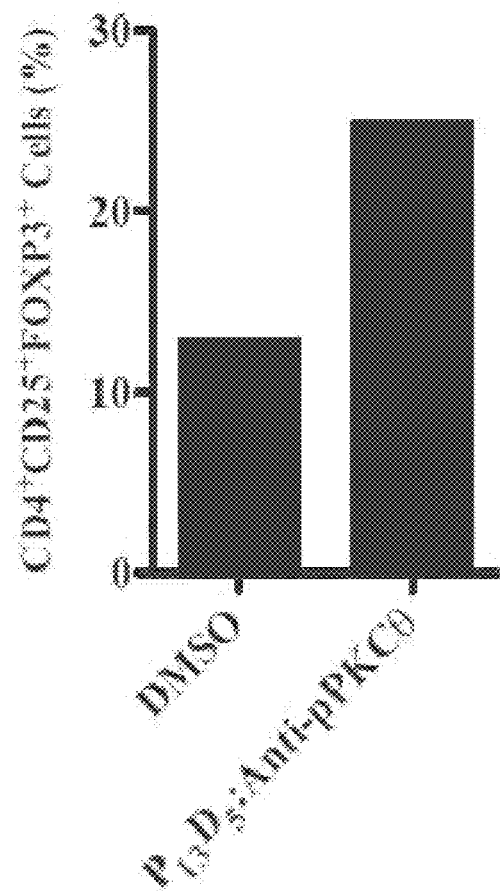
FIG. 40A
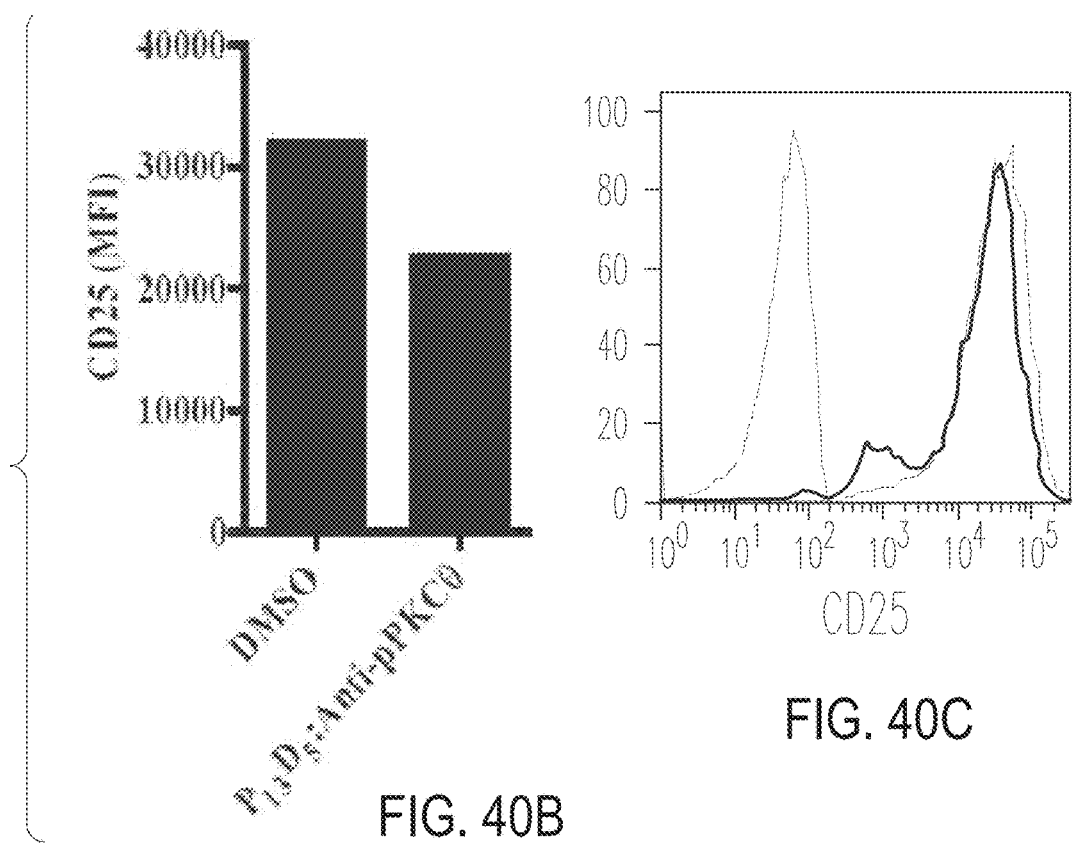
FIG. 40B
FIG. 40C

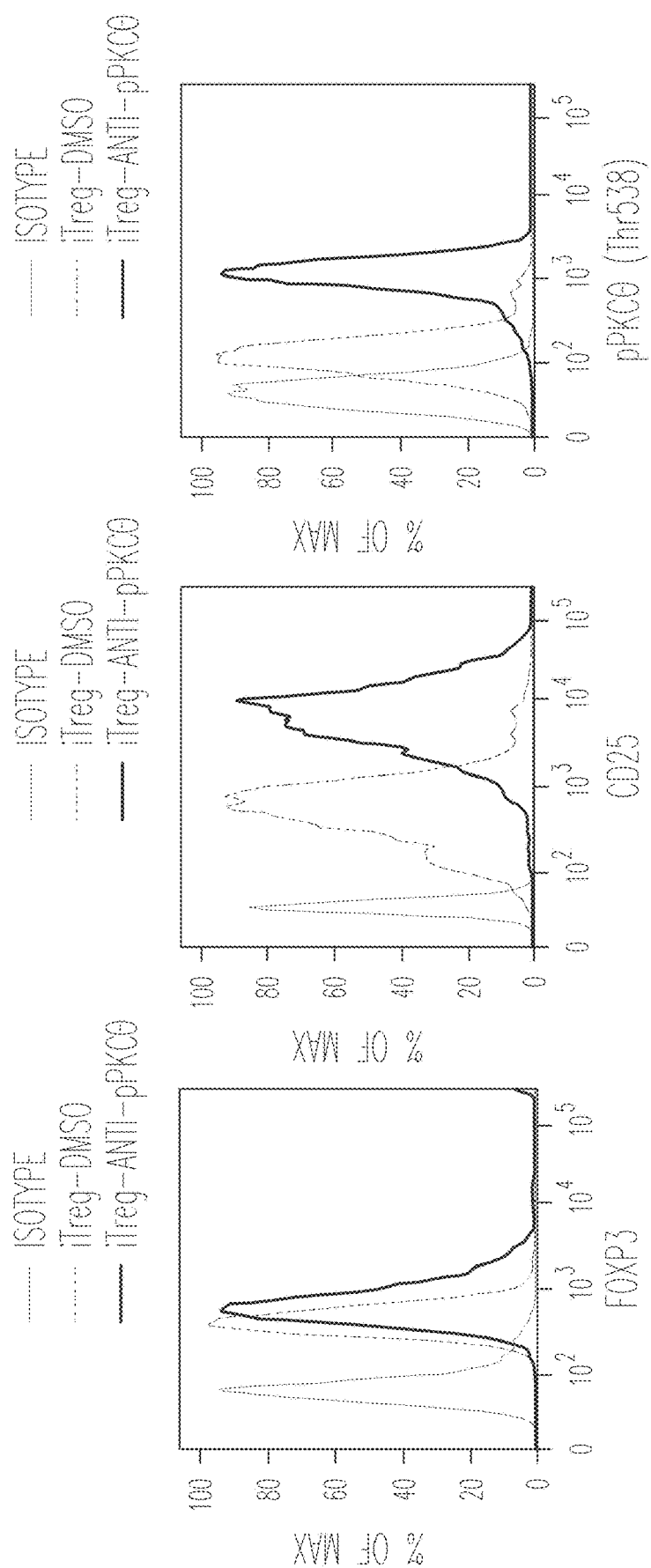

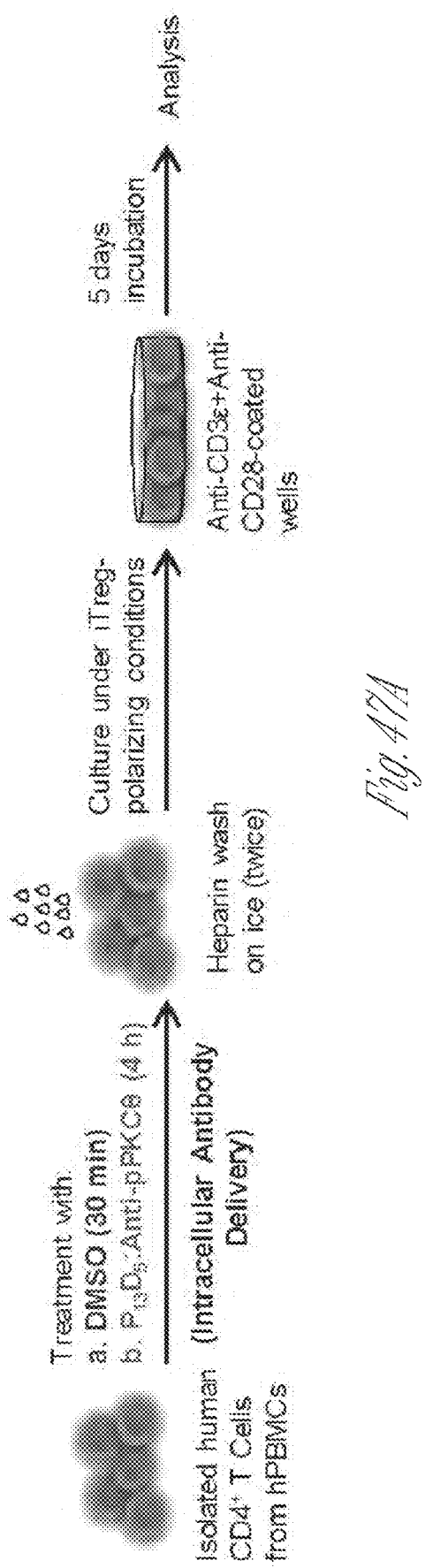
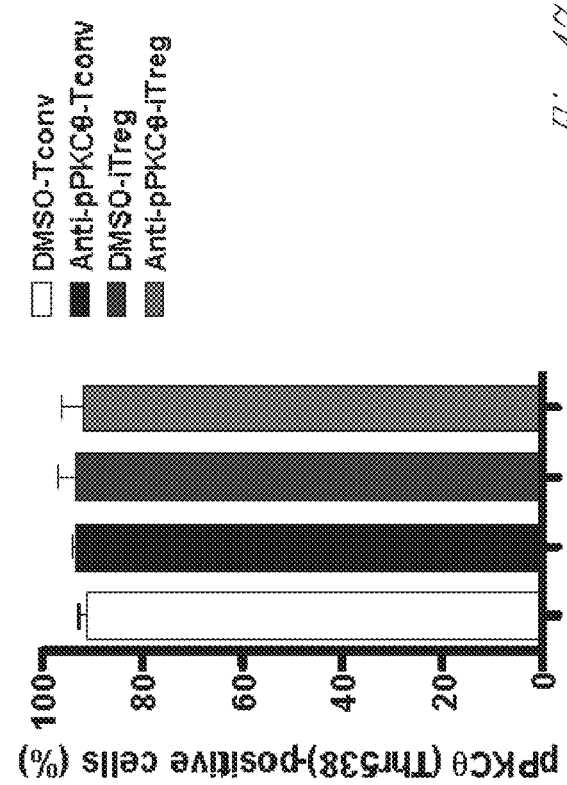
Fig. 47A
Fig. 47B

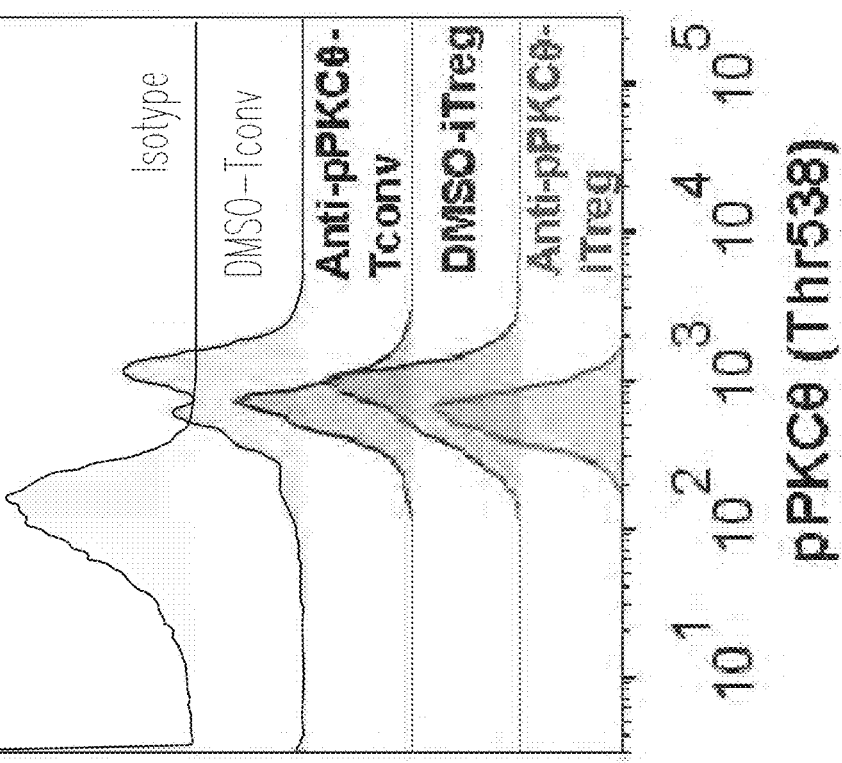
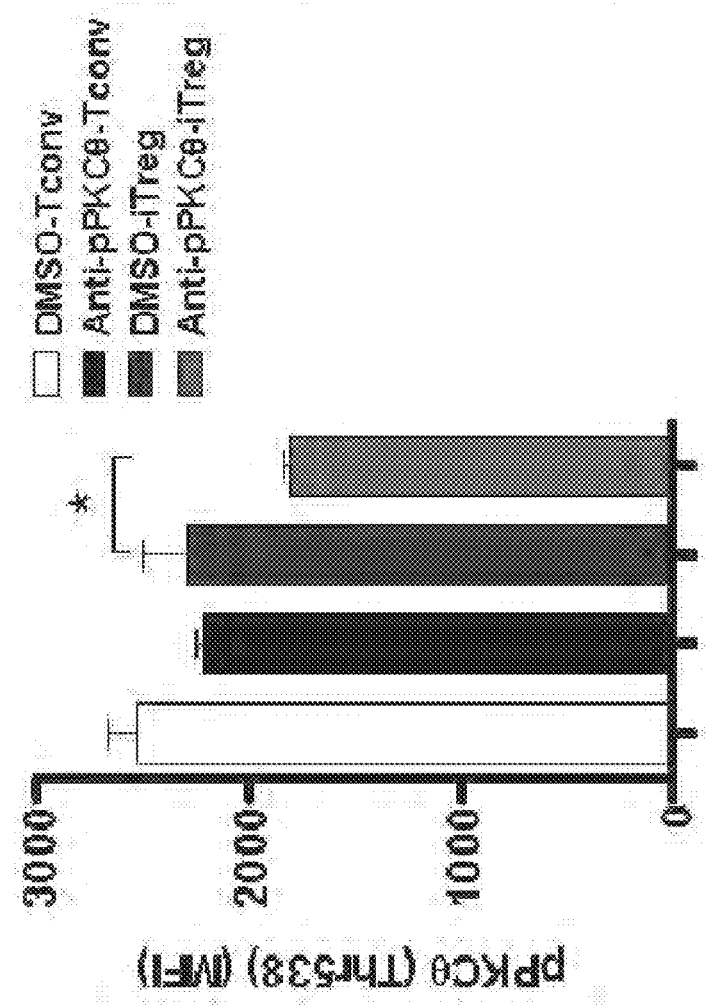
Fig. 47C

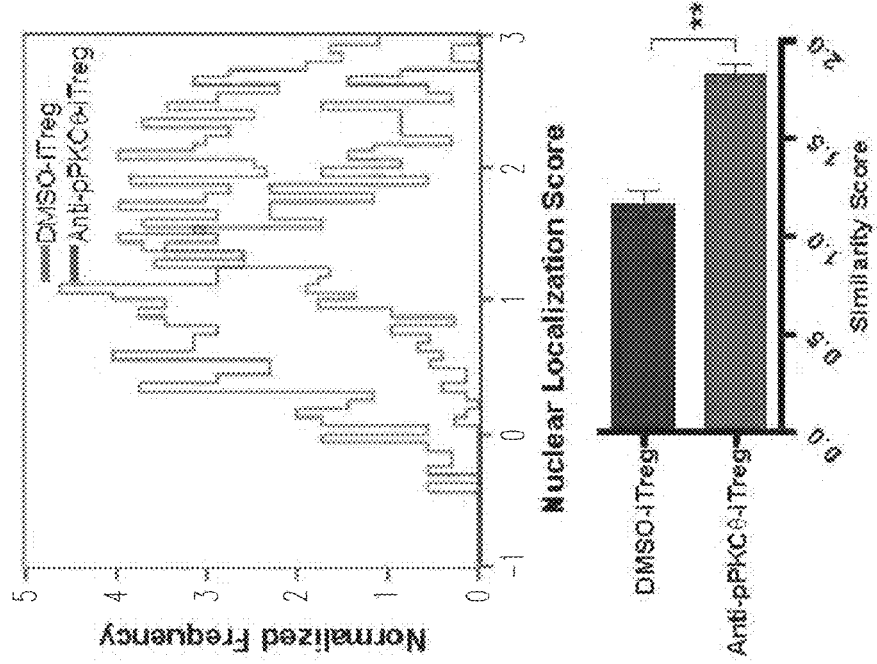
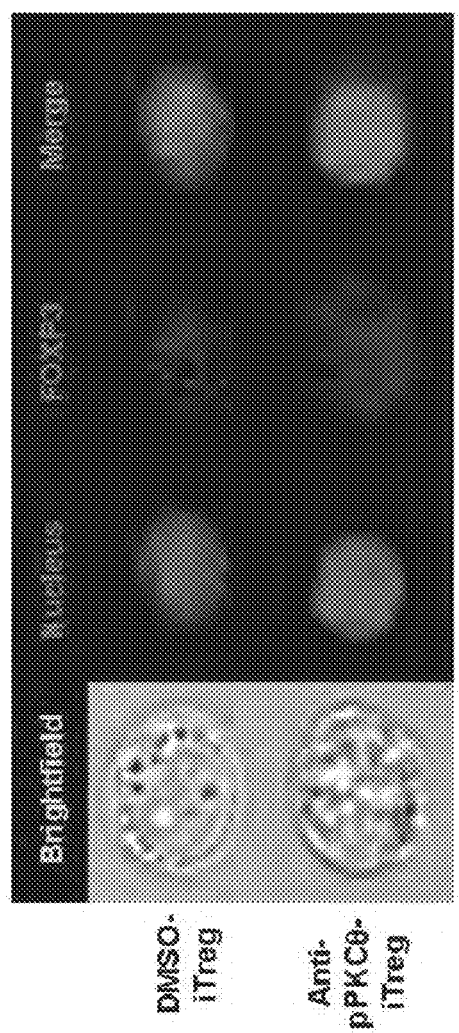
Fig. 49E

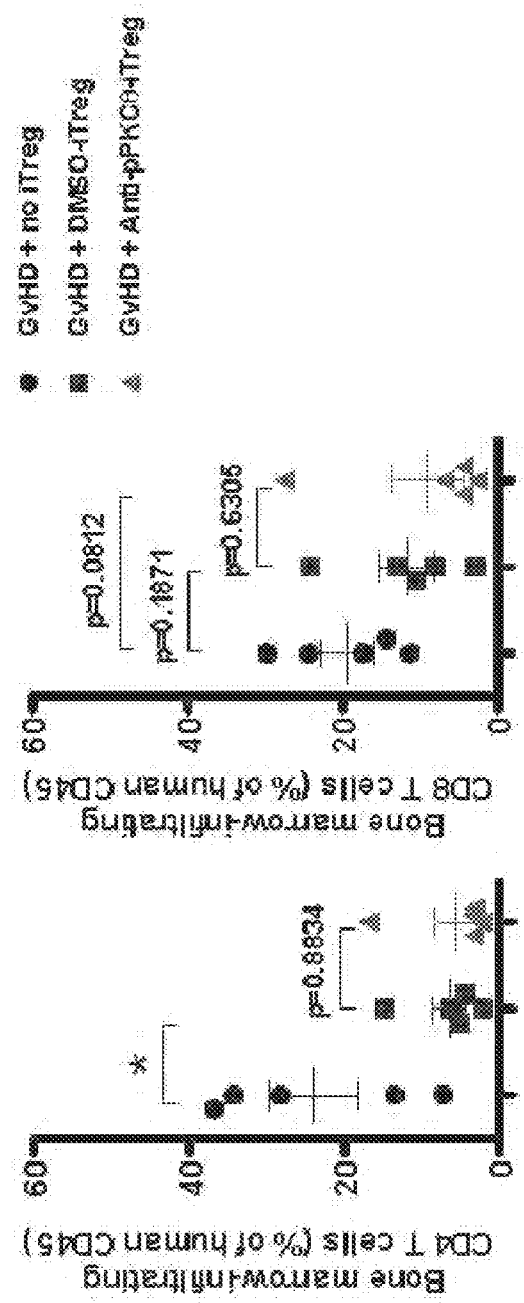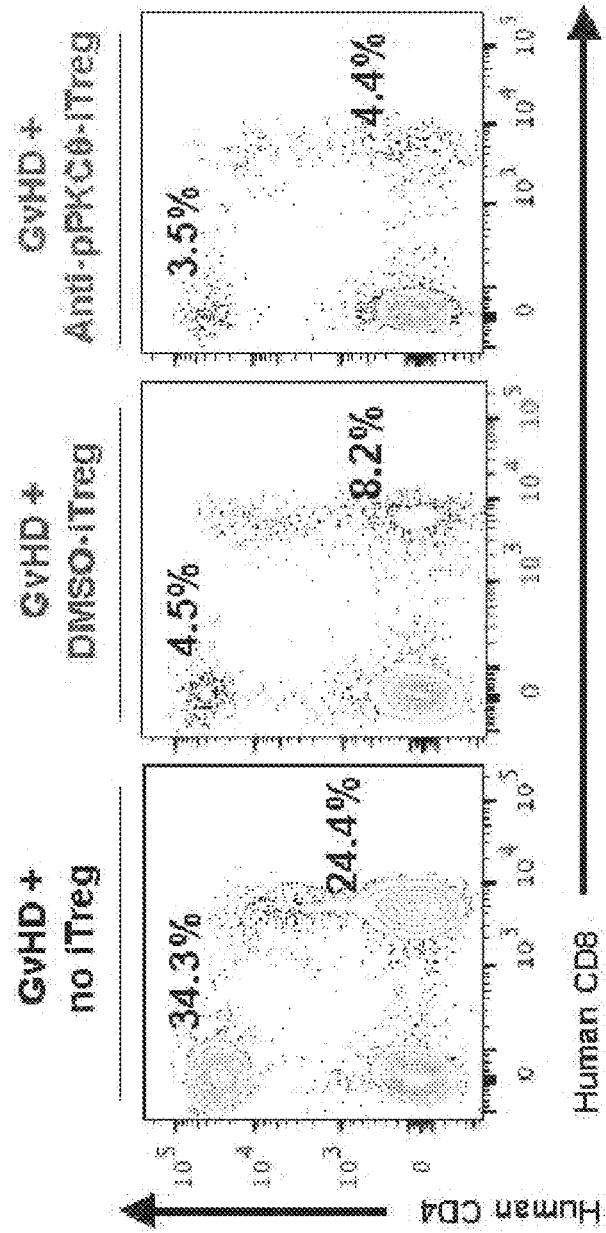
Fig. 50E

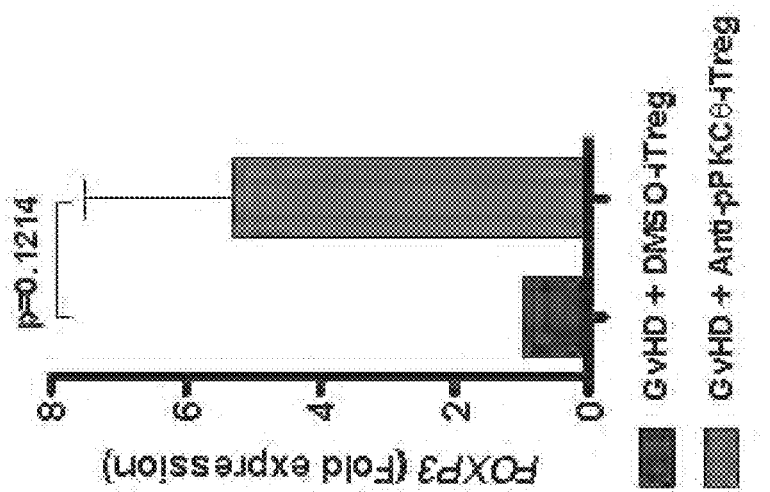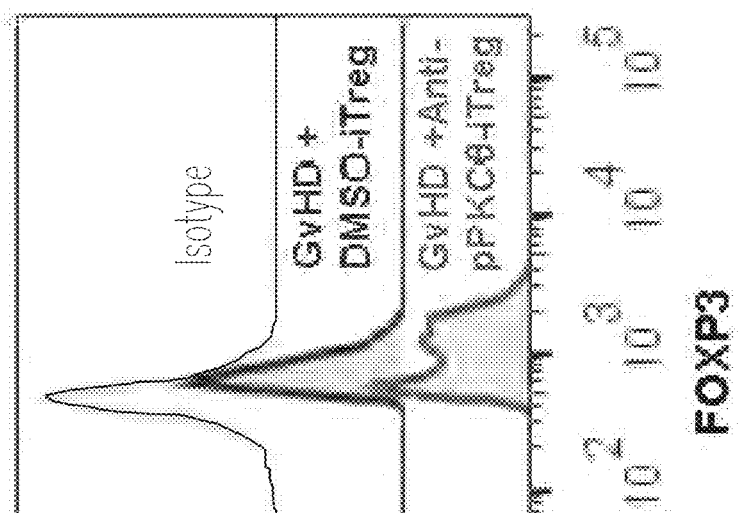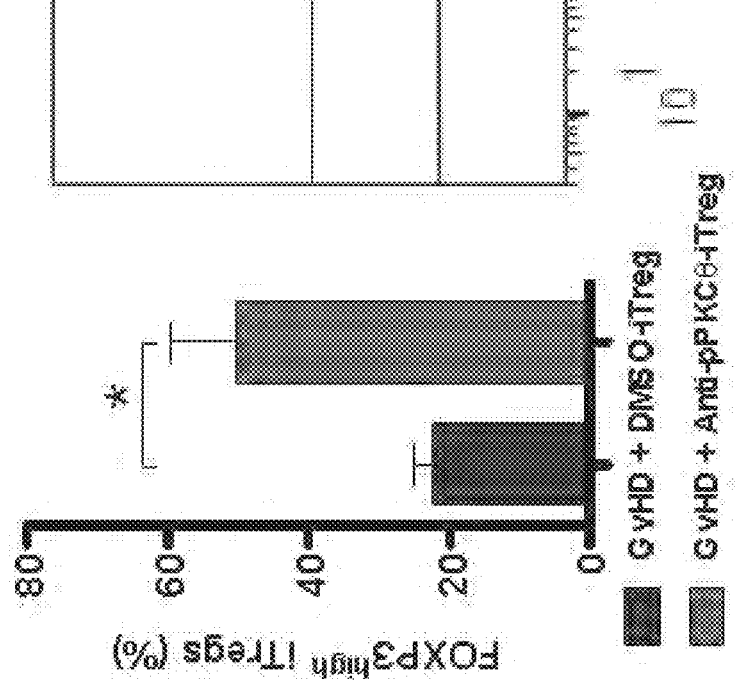
Fig. 51D

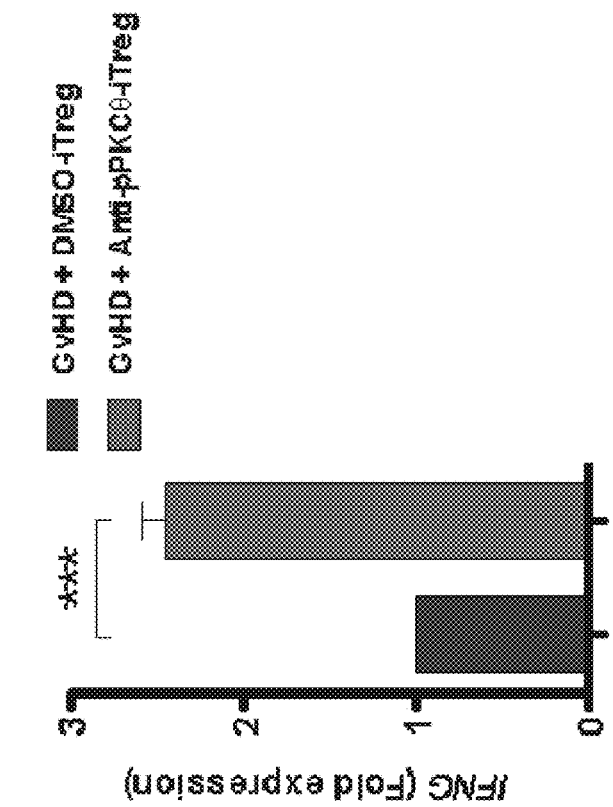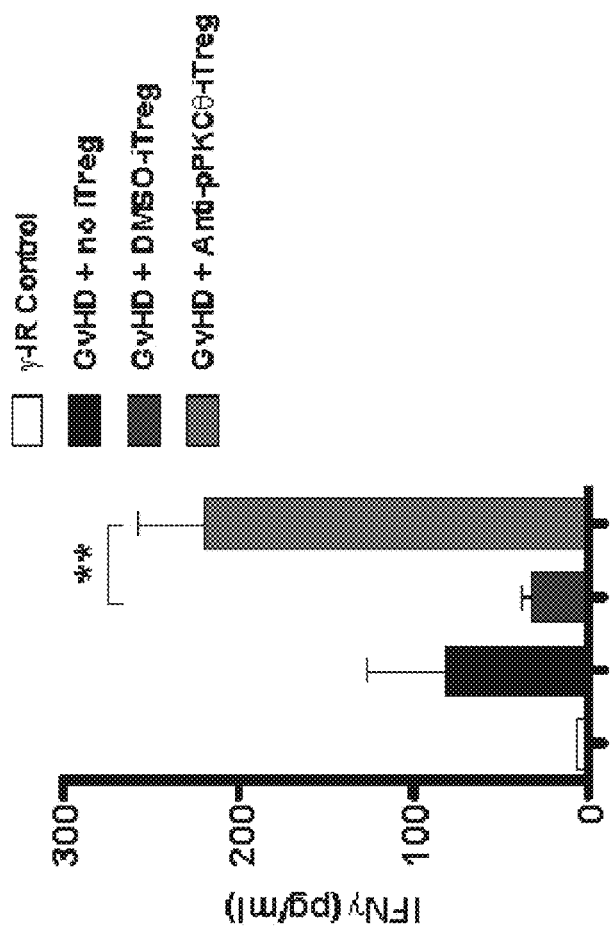
Fig. 51I

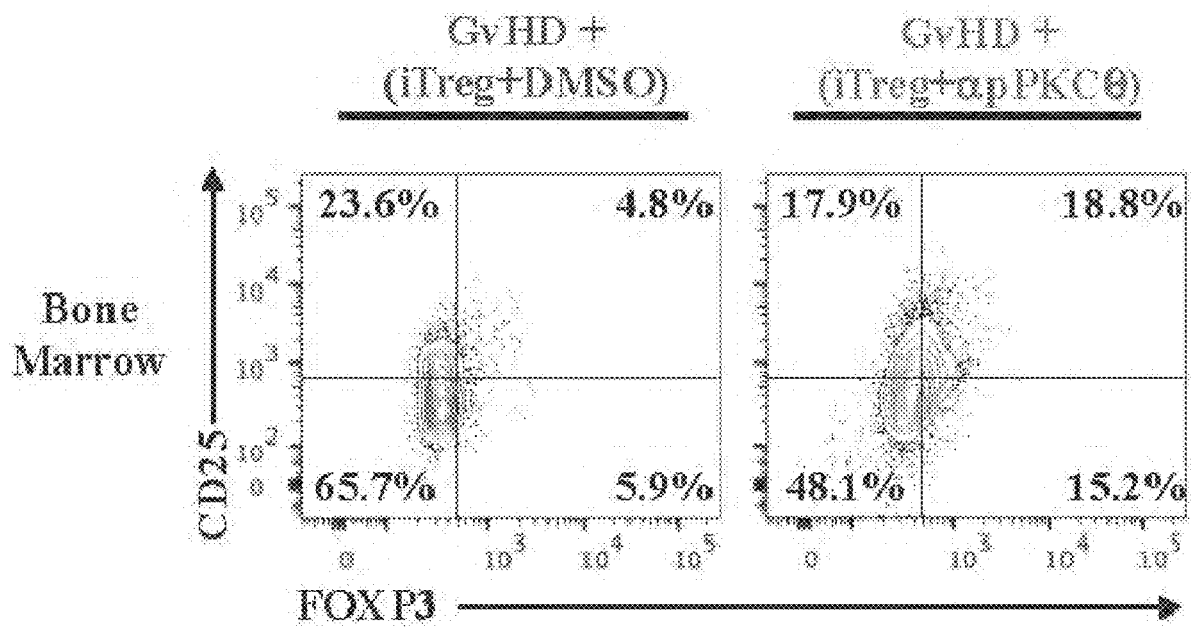
Fig. 52A
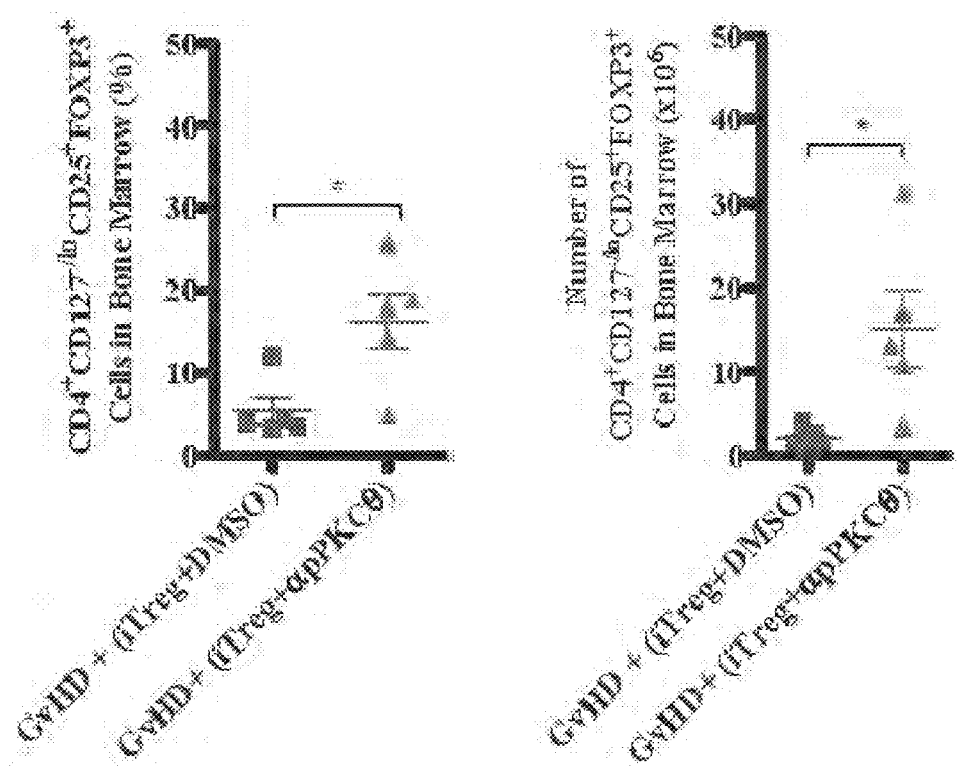
Fig. 52B
Fig. 52C

Bone Marrow
CD4⁺CD127⁻/ˡᵒCD25⁺FOXP3⁺ Cells
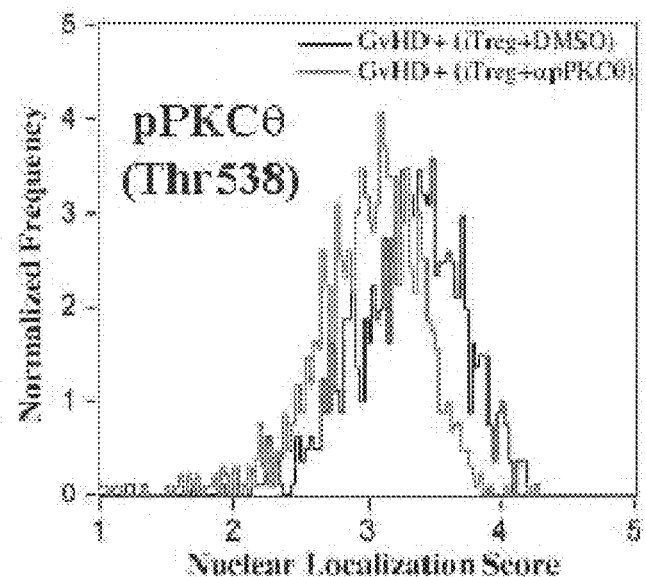
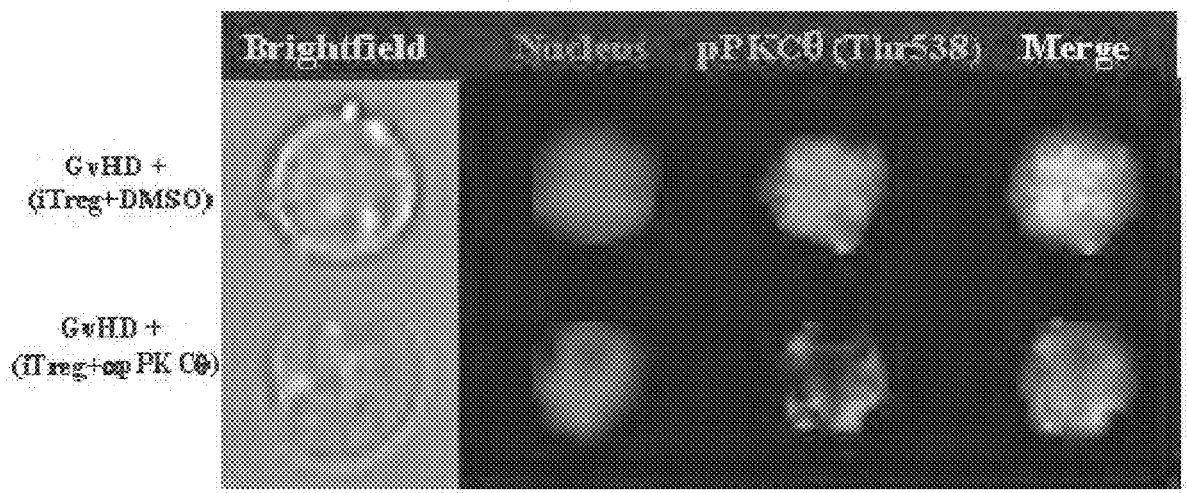
*Fig. 52F*

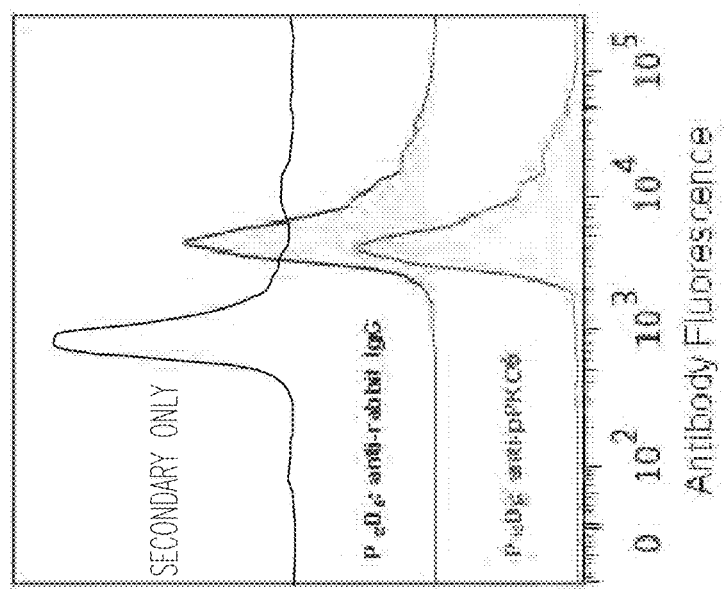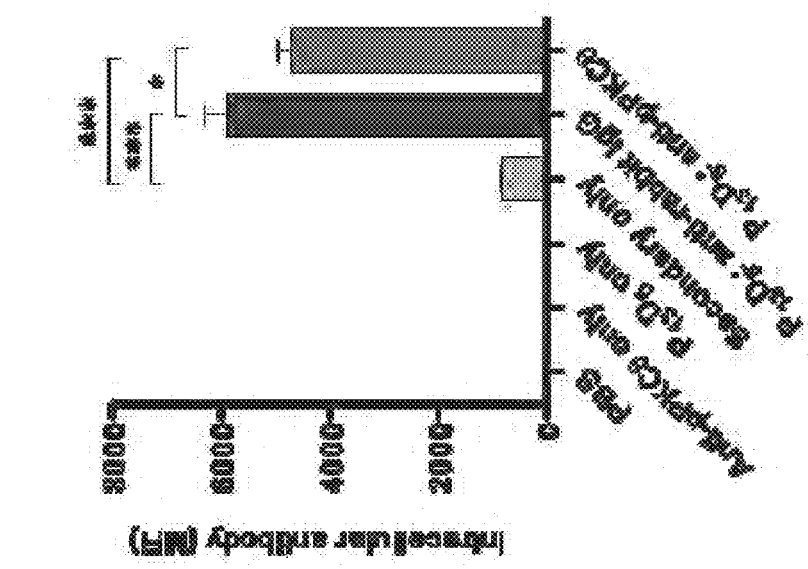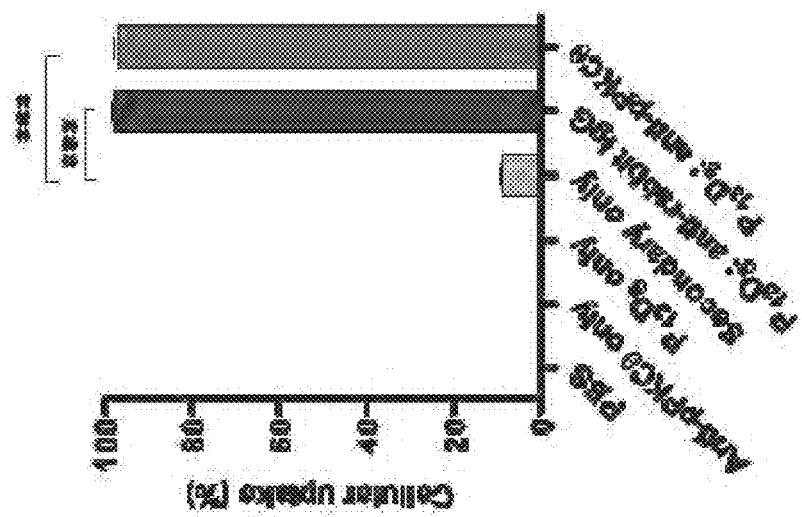
Fig. 53A

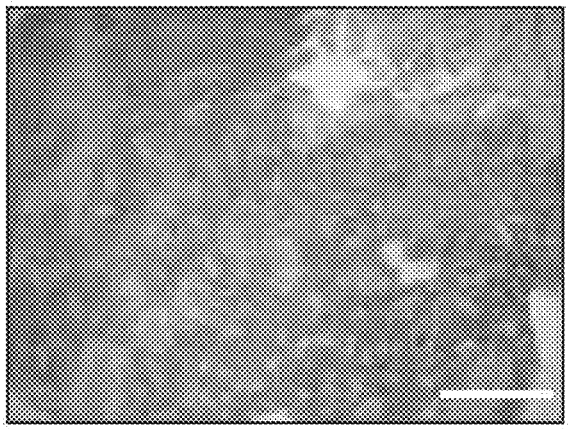 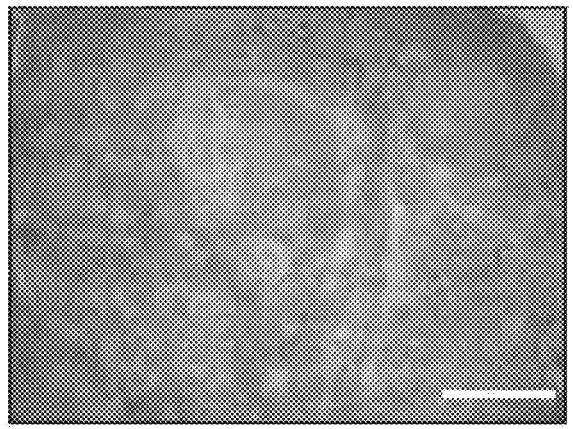 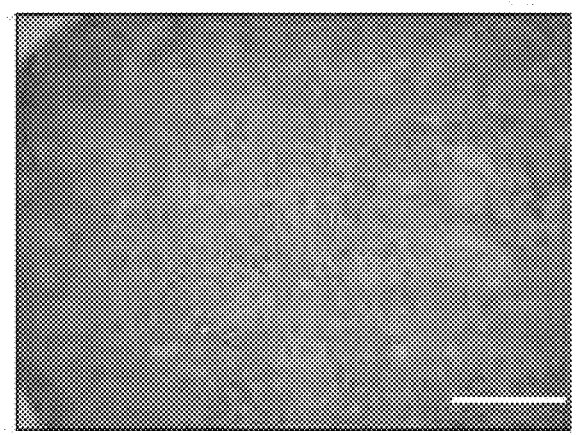
Fig. 54B

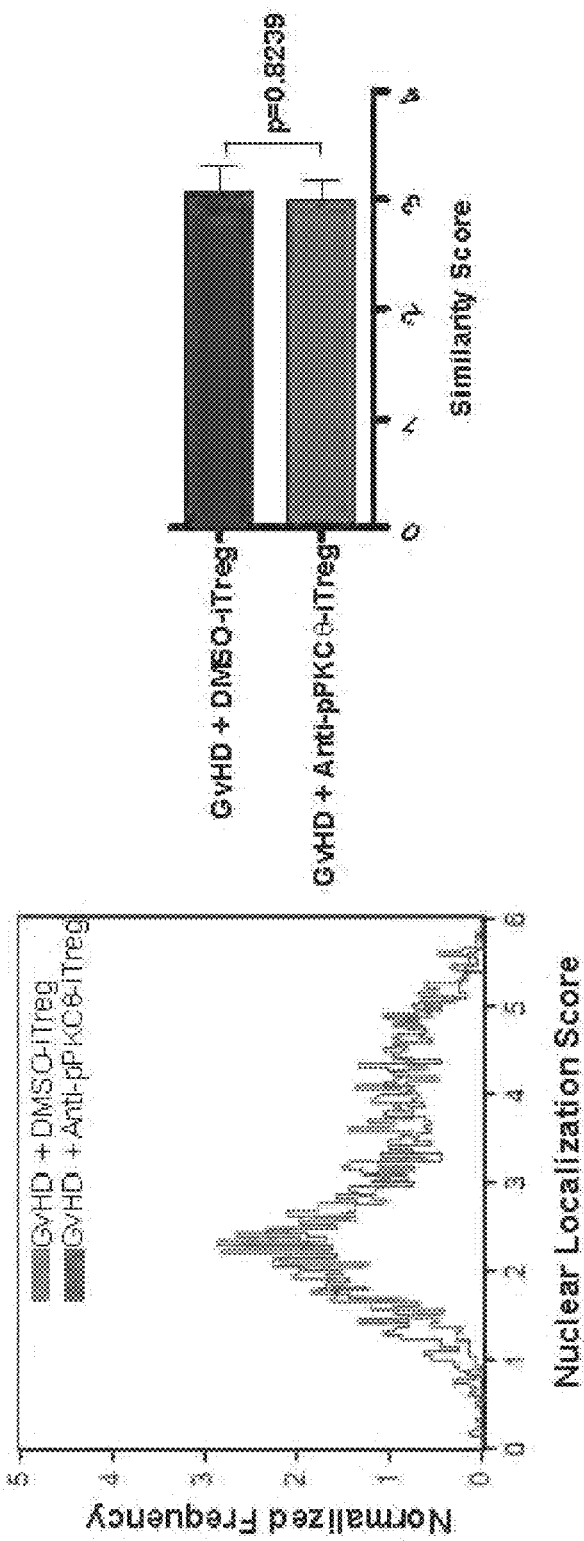
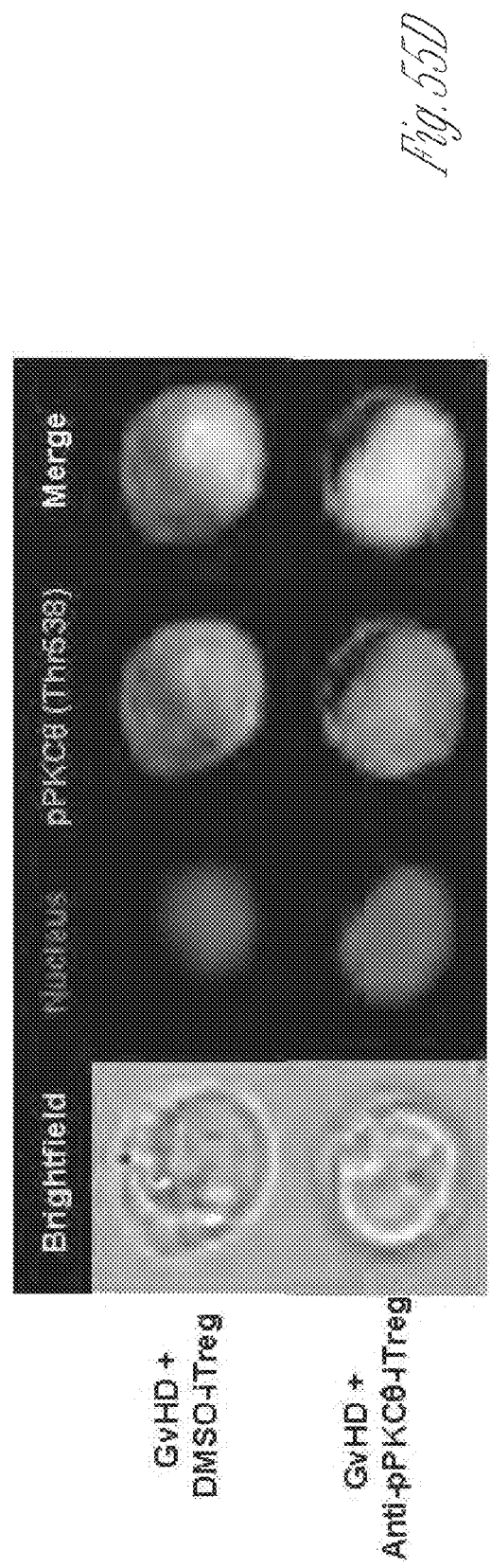
Fig. 55D

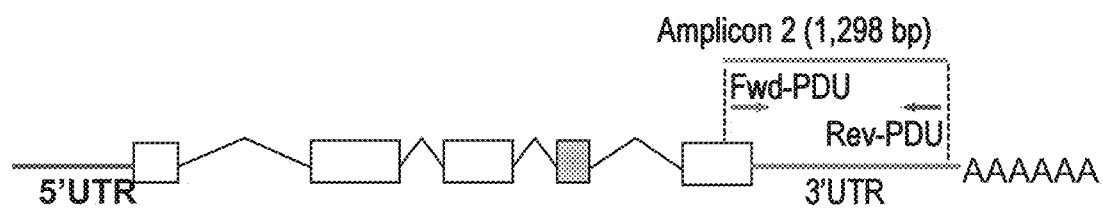
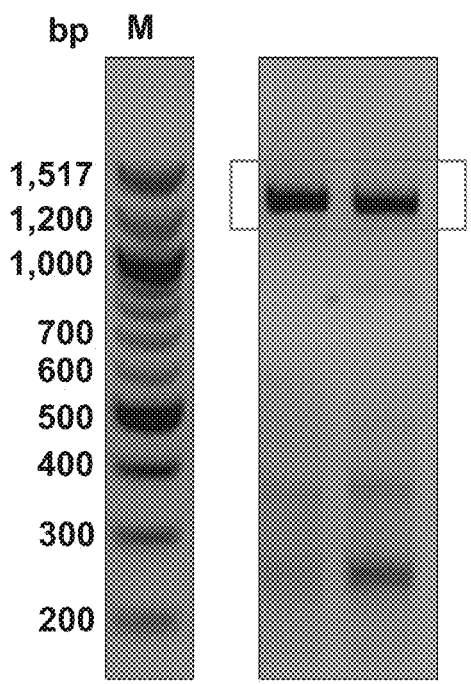
FIG. 57C

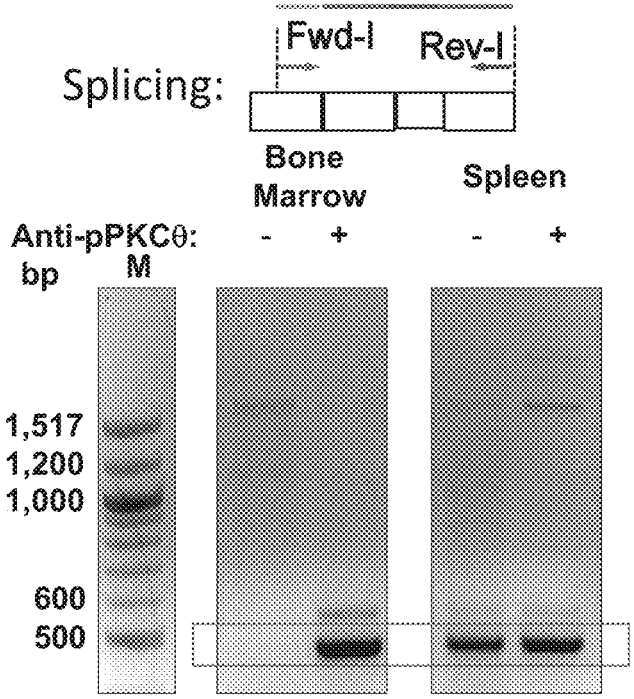
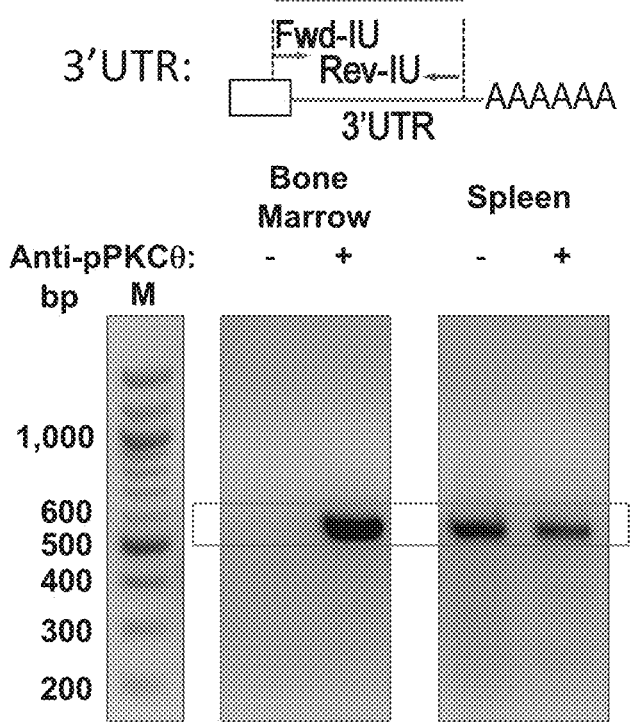
FIG. 58D

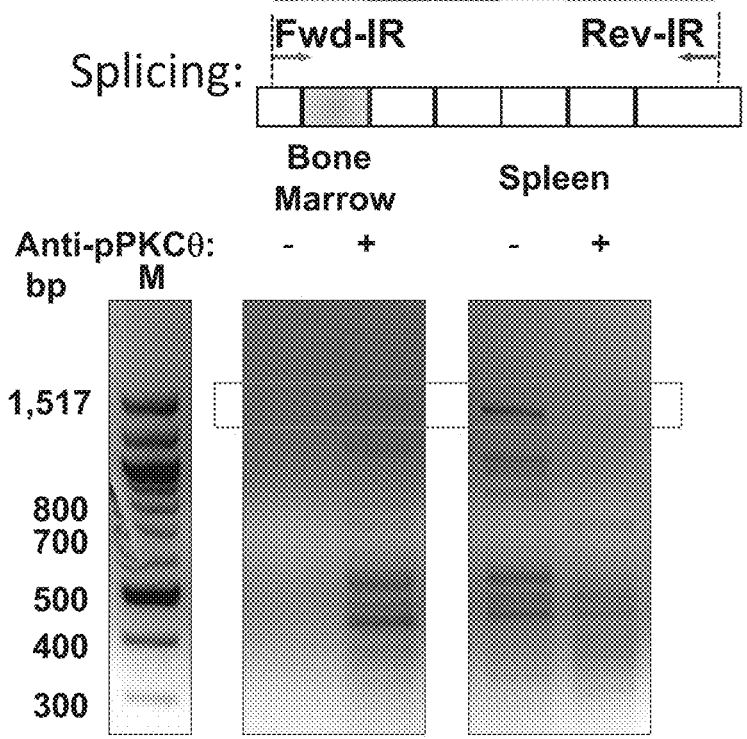
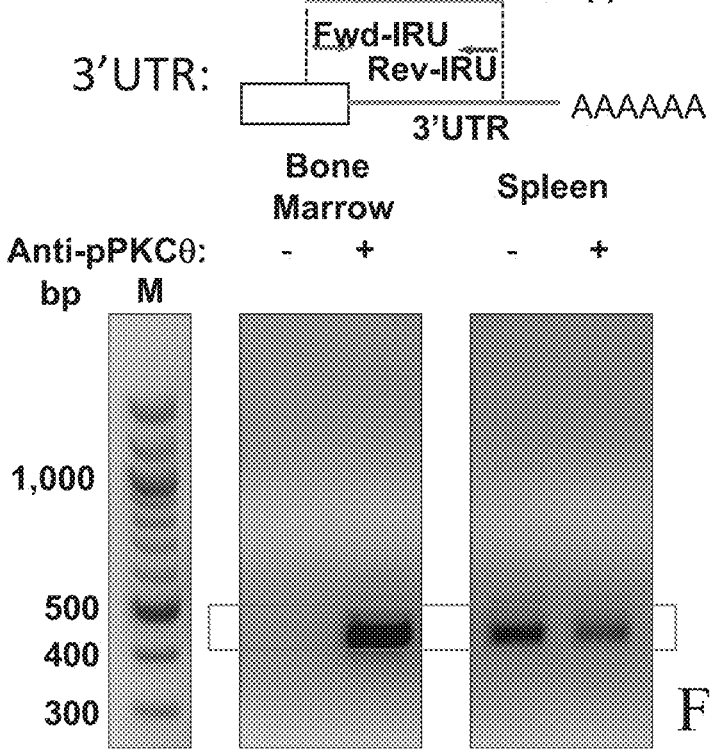
FIG. 58E

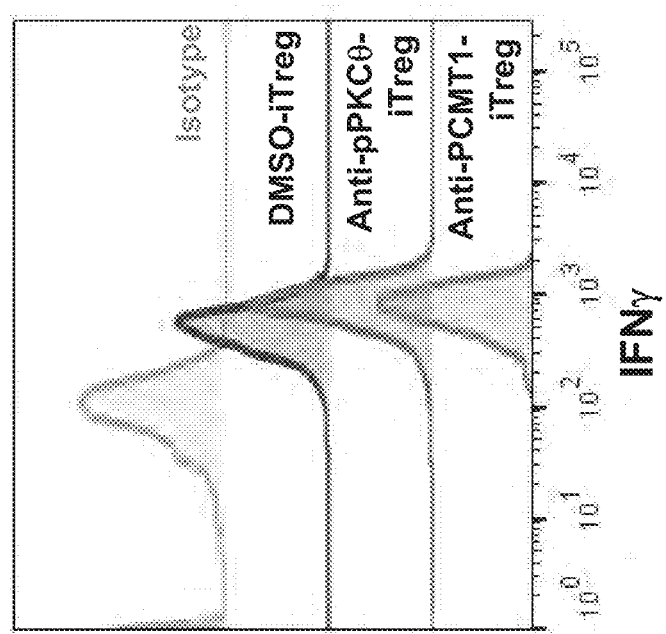
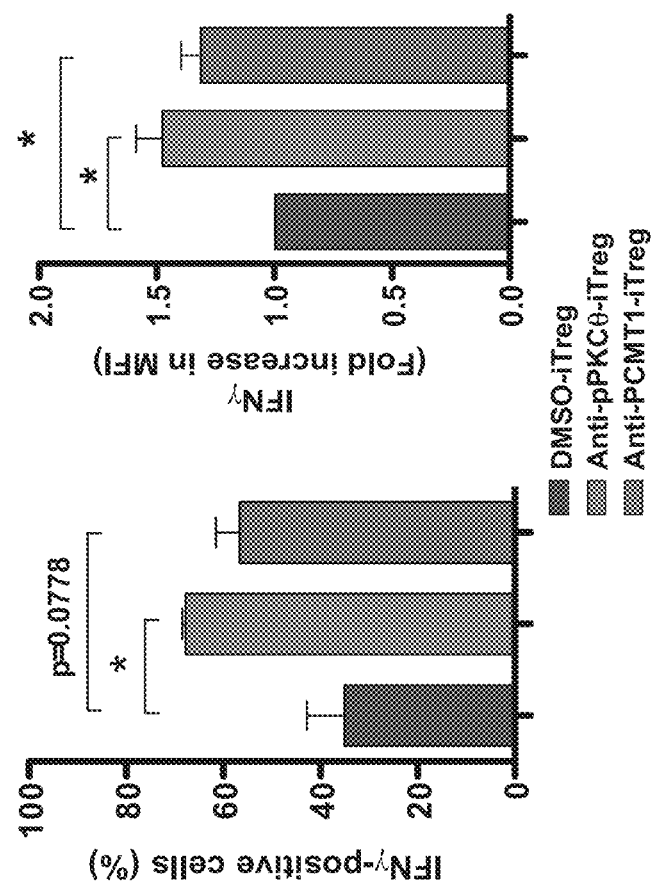
FIG. 60C

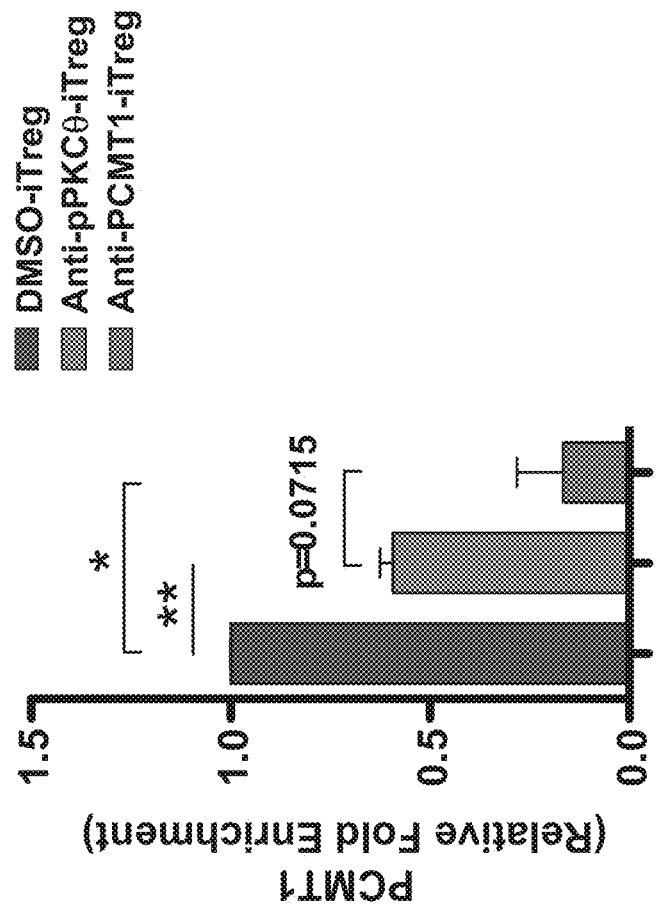
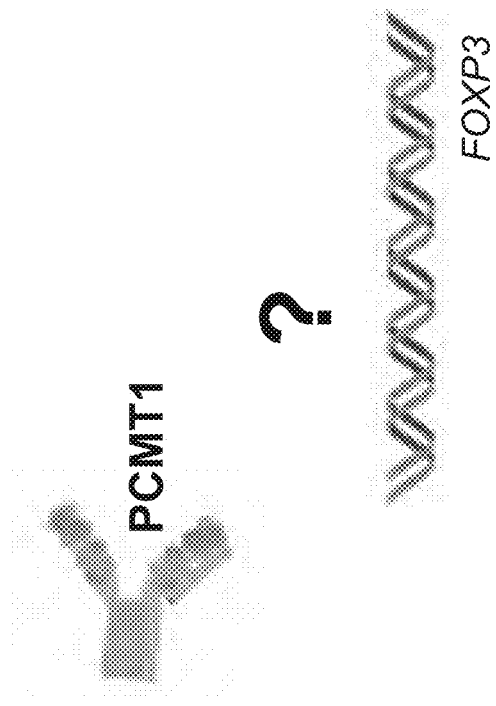
FIG. 61A

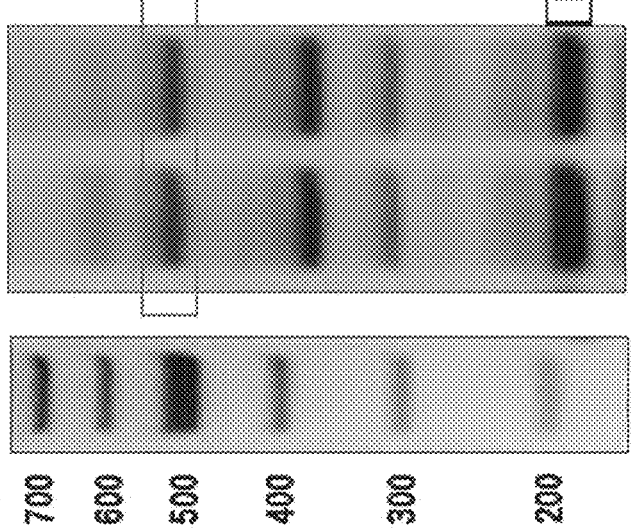
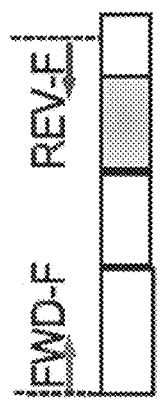
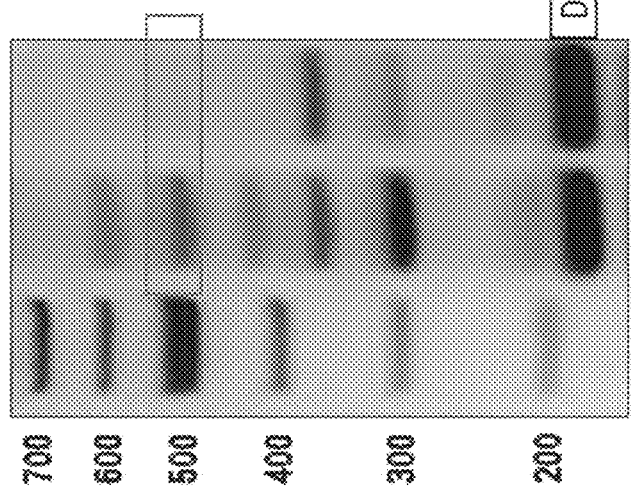
Fig. 62C

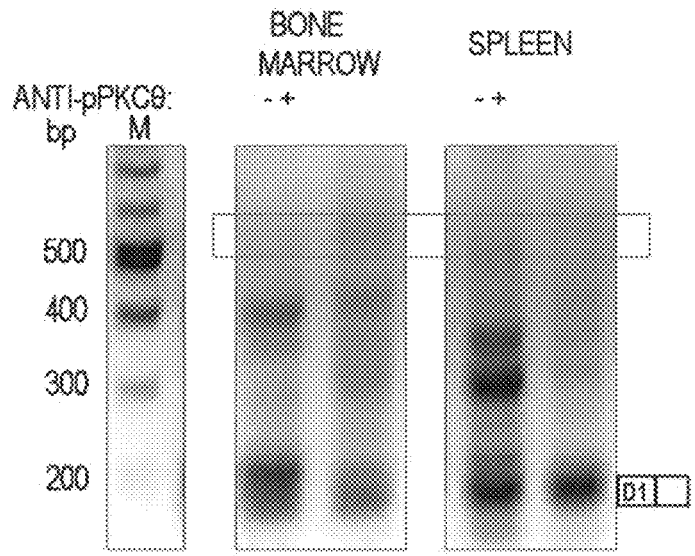
FIG. 63D
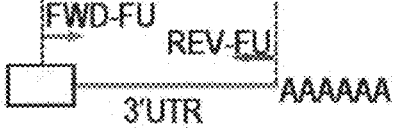
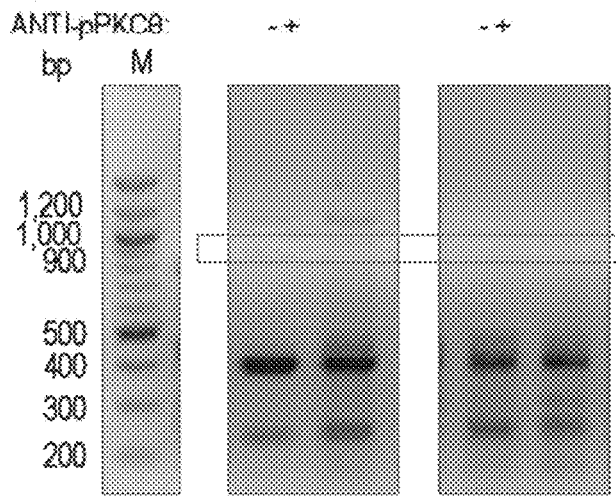
FIG. 63E

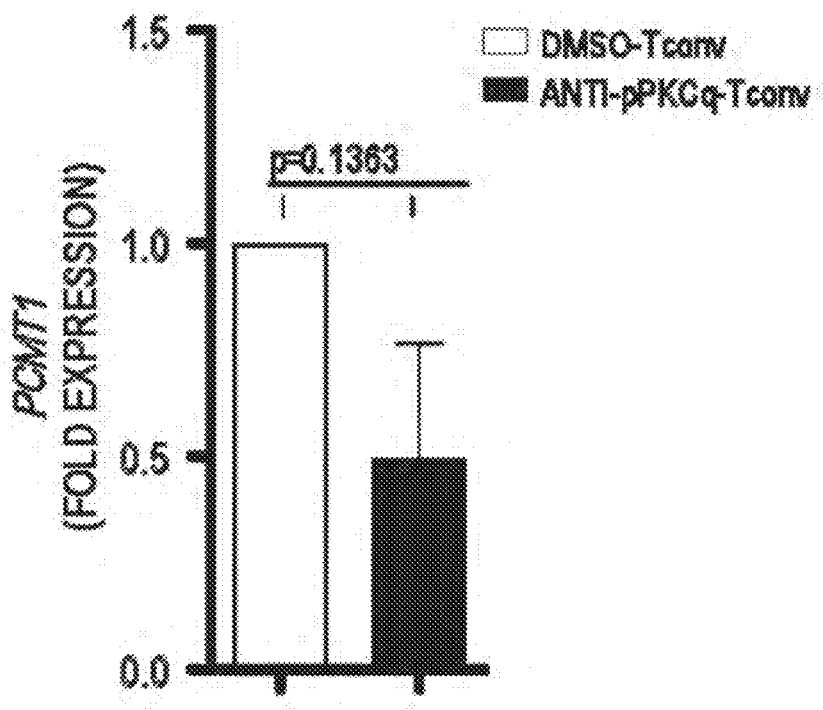
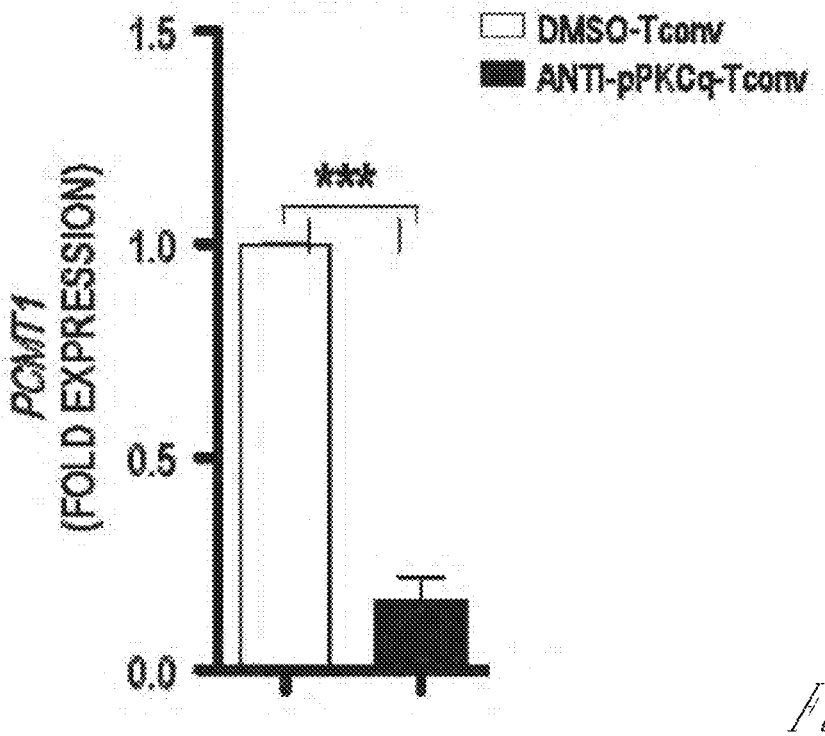
Fig. 64D

Fig. 65

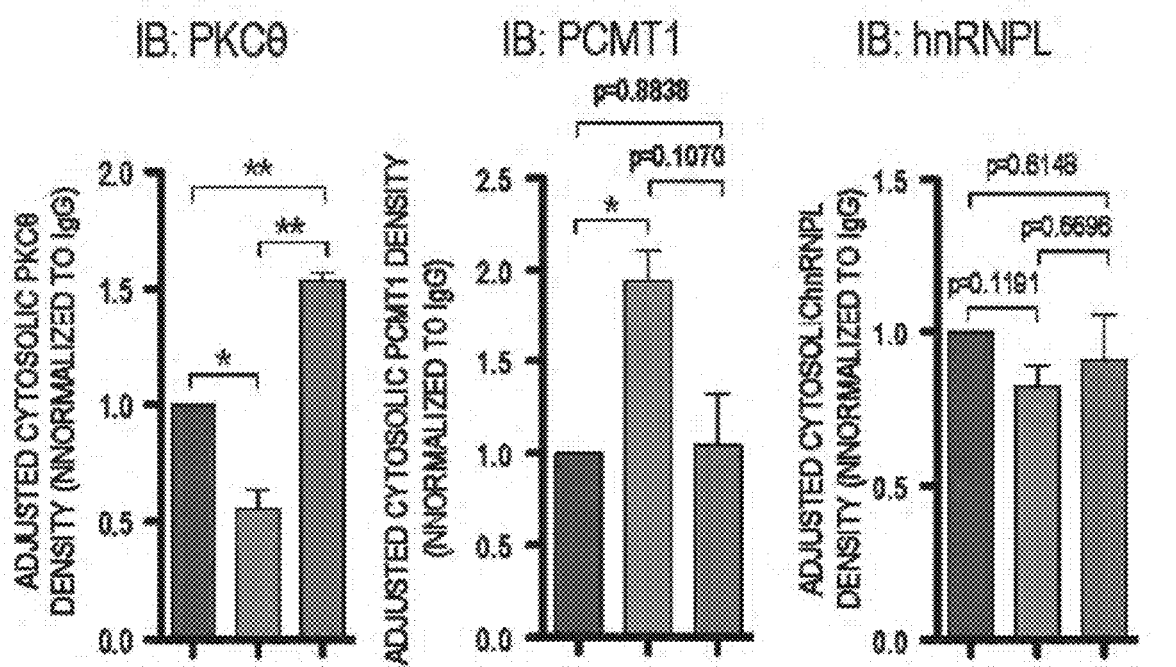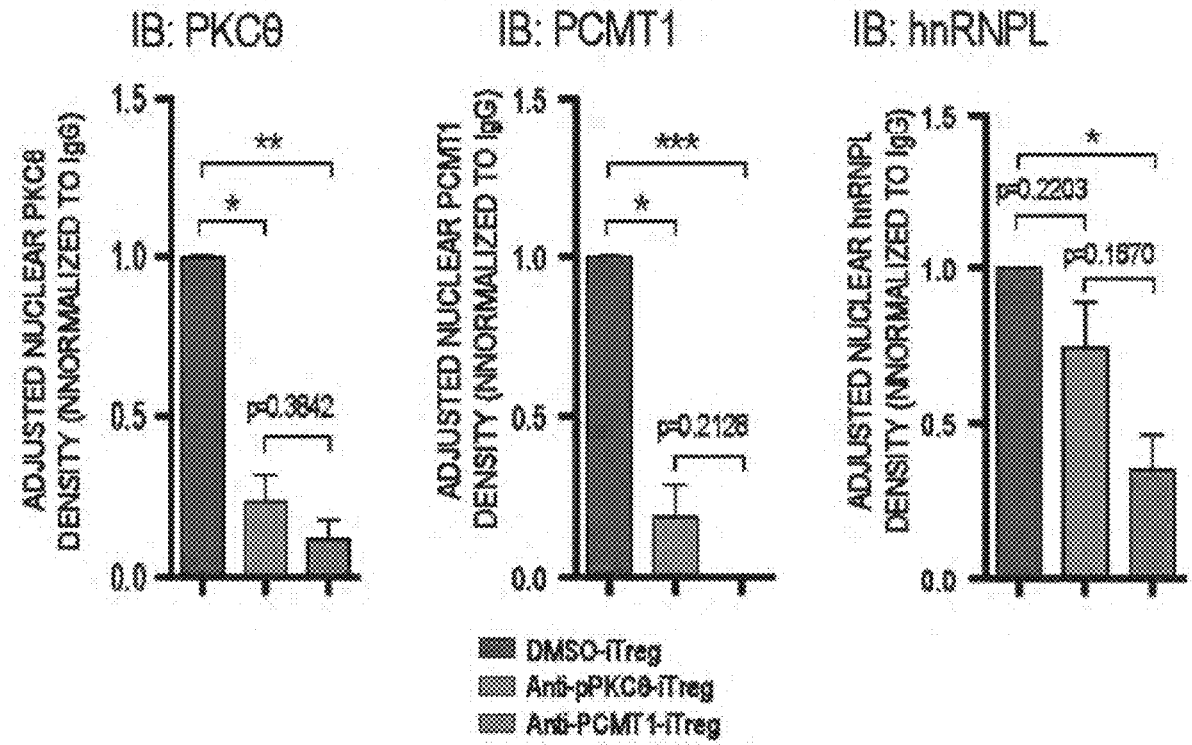
Fig. 66B

EX VIVO METHOD OF GENERATING SUPER REGULATORY T CELLS FOR THE PREVENTION OF AUTOIMMUNE DISEASE

CROSS-REFERENCE TO RELATED APPLICATIONS

This application is a U.S. National Stage Filing under 35 U.S.C. 371 from International Application No. PCT/US2018/032443 filed on May 11, 2018, which claims the benefit of the filing date of U.S. application Ser. No. 62/505,698, filed on May 12, 2017, the disclosures of which are incorporated by reference herein

BACKGROUND

Naïve CD4 T cells differentiate into different T helper subsets upon acquiring certain signals in peripheral tissues. Regulatory T cells are a subset of differentiated T helper cells that play a critical role in immunosuppression (Ohkura et al., 2013). The expression of CD25, FOXP3, CTLA-4, and phospho-STAT5 (pSTAT5) are associated with Treg function (Sakaguchi et al., 2010). Treg function is very critical for suppression of autoimmune responses and graft-versus-host disease (GvHD) in mice and humans. In autoimmunity, Tregs are negatively regulated by inflammatory cytokine milieu and their function is inhibited (Shevach, 2009). T cell receptor (TCR) signaling seems to inhibit Treg-mediated suppression. It was shown that a T cell-specific kinase, PKCθ, was sequestered in the cytosol away from the immunological synapse (IS) in Tregs, but not in effector T cells (Teff), implying that different localizations of PKCθ drives different functions (Zanin-Zhorov et al., 2010). Inhibition of PKCθ exerted differential effects on Tregs and Teffs (de Weerd et al., 2013). Furthermore, inhibition of PKCθ activity showed robust IS stabilization leading to enhanced Treg suppressive function (Zanin-Zhorov et al., 2010). However, Tregs from PKCθ-deficient mice were equally suppressive as Tregs from wild-type mice although Tregs from PKCθ-deficient mice were not as stable as wild-type Tregs suggesting that PKCθ maintains long-term function of Tregs (Gupta et al., 2008). These findings support the idea that inhibition of PKCθ in Tregs may be a substantial step towards Treg immunotherapy to treat autoimmunity and GvHD (Riley et al. 2009). Recent studies have demonstrated that PKCθ has a role in the nucleus and binds to chromatin as an integral component of transcription complexes (Sutcliffe et al., 2011). It was reported that NF-kB pathway is involved in PKCθ-mediated transcriptional regulation of several immune response genes (Sutcliffe et al., 2012).

SUMMARY

This disclosure utilizes Protein Transduction Domain Mimics (PTDMs) to carry across the cell membrane of purified, human CD4 T cells, a modulator of Protein kinase C-theta (PKCθ), e.g., of the phosphorylated species (Thr 538) of the T cell specific kinase PKCθ, (pPKCθ) to constrain the movement of pPKCθ within the T cell during a process of ex vivo regulatory T cell differentiation. In one embodiment the modulator is an antibody. As disclosed herein below, CD28 signal is important for iTreg differentiation. Specifically, it was found that on day 5, pPKCθ levels were reduced after anti-pPKCθ delivery. Upon delivery, pPKCθ was sequestered in cytosol, thus, it does not colocalize with Foxp3. Anti-pPKCθ delivery also prevented pPKCθ-NOTCH1 colocalization in the nucleus of iTregs. Further, anti-pPKCθ delivery enhanced expression of the co-inhibitory signal (CTLA-4) and of the transcriptional maintenance signal (pSTAT5). The suppressor cells remain at high frequency in co-culture up to 9 days. Stable iTregs showed high expression of CD25 and FOXP3. Anti-pPKCθ delivery may generate iTregs in vivo thereby resulting in GvHD suppression. CD47 marker is highly-expressed by iTregs and persisted upon anti-pPKCθ delivery.

In one embodiment, an ex vivo method to prepare regulatory T cells is provided. The method includes providing a composition comprising complexes comprising a polymer, e.g., one comprising a compound of formula (I), and a modulator of T cells that induces Tregs. In one embodiment, the modulator modulates PKCθ, e.g., the modulator may bind PKCθ or inhibit the function, stability, or cellular translocation of PKCθ. In one embodiment, the modulator is a modulator of protein L-isoaspartate methyltransferase. In one embodiment, the modulator modulates hnRNPL, AP1, hnRNPU, TRAF6, Notch1, Calmodulin, Notch2, Notch3, Carma1, Malt1, BCL10, NFkB subunits (p65, c-rel, p50, RelA, RelB), IKKalpha, IKKbeta,IKKgamma, LCK, Mst1, SIRT1, AMPK, LBK1, NFATcl, Calcineurin B, GLK, PLCgammal, mTORC2, SLP76, ZAP70, PDK1, PI-3K, DAG, or Itk. In one embodiment, the modulator comprises an antibody, e.g., a fragment thereof including single domain, scFv, Fv or Fab, or camelid antibodies. A population of mammalian cells comprising CD4 T cells is contacted with an amount of the composition and under conditions effective to induce an increased number of induced regulatory T cells (iTregs) relative to a corresponding population that is contacted with the polymer but not the modulator or contacted with the modulator but not the polymer, or not contacted with the composition. In one embodiment, the modulator comprises an antibody or a fragment thereof that binds PKCθ. In one embodiment, the antibody or the binding fragment thereof binds to pPKCθ, e.g., the phosphorylated form of PKCθ. In one embodiment, the antibody or the fragment comprises a humanized antibody. In one embodiment, the cells are human cells. In one embodiment, the population comprises peripheral blood mononuclear cells (PBMCs). In one embodiment, the population comprises CD4 T cells. In one embodiment, the cells are further contacted with anti-CD3 and anti-CD28 antibodies or fragments thereof. In one embodiment, the iTregs contacted with the composition have enhanced suppressor function relative to iTregs not contacted with the composition or contacted with the polymer but not the modulator or contacted with the modulator but not the polymer. In one embodiment, the iTregs contacted with the composition have increased amounts or concentrations of phospho-STAT5, and/or CTLA-4 relative to Tregs not contacted with the composition or contacted with the polymer but not the modulator or contacted with the modulator but not the polymer. In one embodiment, the iTregs contacted with the composition comprise cytosolic PKCθ. In one embodiment, the iTregs contacted with the composition have increased amounts or concentrations of CD25 and/or FOXP3 relative to iTregs not contacted with the composition or contacted with the polymer but not the modulator or contacted with the modulator but not the polymer. In one embodiment, the cells are not contacted with any one of TGF-β, IL2, trans-retinoic acid, a DNA methyltransferase inhibitor, a histone deacetyltrasnsferase inhibitor, butyrate, rapamycin, or any combination thereof.

Thus, culturing purified human CD4 T cells with PTDM-anti-pPKCθ under defined conditions induced these cells to adopt an induced regulatory T cell fate thus expanding the T cell population 10-fold and produces "super" regulatory T cells (PTDM-iTregs; anti-PKCθ-iTregs), endowed with significantly enhanced suppressor functions as measured both by in vitro and in vivo assays. In one embodiment, the enhanced (more potent) suppression is the result of inhibition of PKCθ function. Those super regulatory cells may be employed in therapies such as, but not limited to, a cell-based therapy used in the prevention of Graft-versus-Host Disease (GVHD), a major clinical barrier to the successful use of hematopoietic/bone marrow stem cell transplantation. In other applications, the PTDM-iTregs may be utilized as a cell-based therapy for autoimmune indications including, but not limited to, aplastic anemia, rheumatoid arthritis, Crohn's disease, type 1 diabetes, and/or multiple sclerosis.

Thus, the disclosure provides a method to increase graft survival in a mammal, to decrease the adverse constellation of clinical symptoms collectively known as GvHD that frequently accompany hematopoietic/bone marrow stem cell transplantation, or to decrease the immune-mediated pathogeneis and resultant symptoms of various autoimmune conditions, comprising: administering to a mammal in need thereof an effective amount of a composition comprising complexes of a polymer and a modulator of PKCθ. In one embodiment, the mammal is a human. In one embodiment the composition is administered before or after the graft is introduced to the mammal. In one embodiment, the composition is administered when the graft is introduced to the mammal. In one embodiment the PTDM-iTregs are derived from graft donor cells (allogeneic). In one embodiment the PTDM-iTregs are derived from patient cells (autologous).

In one embodiment the PTDM-iTregs are generated in vivo iTregs phenotypically express CD25, FOXP3, CTLA-4, and pSTAT5 and the transfer of blood cells enriched in iTregs likely prevents GvHD since it induces IL-10 and abrogates IFNγ secretion. Early iTreg administration in GvHD induction reduces disease symptoms and provides a survival benefit, and the therapy may include combinational therapy with CD4 and CD8 iTregs, e.g., to prevent or inhibit the disease, e.g., prevent rejection or inhibit symptoms of GvHD.

Thus, the disclosure provides a method to increase graft survival in a mammal, comprising: administering to a mammal in need thereof an effective amount of a composition comprising complexes of a polymer and a modulator of PKCtheta. Also provided a method to prevent, inhibit or treat an autoimmune disease in a mammal, comprising: administering to a mammal in need thereof an effective amount of a composition comprising complexes of a polymer and a modulator of PKCtheta In one embodiment, the mammal is a human. In one embodiment, the composition is administered before or after the graft is introduced to the mammal. In one embodiment, the composition is administered when the graft is introduced to the mammal. In one embodiment, the graft donor is the source of the CD4+ cells. In one embodiment, e.g., to prevent, inhibit or treat an autoimmune disease, the source of the CD4+ cells is the mammal to be treated. In one embodiment, the autoimmune disease includes but is not limited to Behget's disease, Celiac disease, chronic fatigue syndrome, Crohn's disease, diabetes mellitus type 1, endometriosis, fibromyaligia, Guillain-Barré syndrome, Graves' disease, gastritis, inflamatory bowel disease (IBD), Kawasaki's disease, lupus including systemic lupus, multiple sclerosis, Méniere's disease, myasthenia gravis, psoriasis, restless leg syndrome, rhematoid aethritis, scleroderma, thrombocytopenia, or ulcerative colitis.

iTregs phenotypically express CD25, Foxp3, CTLA-4, and pSTAT5 and the transfer of blood cells enriched in iTregs likely prevents GvHD since it induces IL-10 and abrogates IFNg secretion. Early iTreg administration in GvHD induction reduces disease symptoms and provides survival benefit, and the therapy may include combinational therapy with CD4 and CD8 iTregs, e.g., to prevent or inhibit the disease, e.g., prevent rejection or inhibit symptoms of GvHD.

BRIEF DESCRIPTION OF FIGURES

FIGS. 3A-B. Higher CD25 expression upon anti-pPKCθ Delivery in Bone Marrow Infiltrating CD4+ Cells (A) and Spleen Infiltrating CD4+ Cells (B).

FIGS. 4A-F. Higher CD25 expression upon anti-pPKCθ Delivery. CD4+ cells in bone marrow, peripheral blood and spleen (A-C) and CD8+ cells in bone marrow, peripheral blood and spleen (D-F).

FIG. 5. Samples and genes to be tested.

FIGS. 11A-C. Inhibitory co-receptor CTLA-4. A) Percent of CTLA-4 positive cells. B) MFI of CTLA-4. C) Histogram.

FIGS. 16A-F. Suppressors in DMSO- and anti-PKCtheta treated cells. A) iTreg:hPMBCs 1:1. B) iTreg:hPMBCs 1:10. C) iTreg:hPMBCs 1:25. D) iTreg anti-pPKCtheta:hPMBCs 1:1. E) iTreg anti-pPKCtheta:hPMBCs 1:10. F) iTreg anti-pPKCtheta:hPMBCs 1:25.

FIGS. 17A-F. Flow cytometry data for responders. A) iTreg:hPMBCs 1:1. B) iTreg:hPMBCs 1:10. C) iTreg:hPMBCs 1:25. D) iTreg anti-pPKCtheta:hPMBCs 1:1. E) iTreg anti-pPKCtheta:hPMBCs 1:10. F) iTreg anti-pPKCtheta:hPMBCs 1:25.

FIGS. 20A-C. Representative histograms. A) FOXP3. B) CD25. C) pPKCtheta.

FIGS. 22A-E. Day 17 analysis BM cellularity and blood counts. A) Bone marrow. B) White blood cells. C) Red blood cells. D) Platelet. E) Hematocrit.

FIGS. 30A-F. Flow cytometry data for treated and untreated iTregs. A) iTreg:huPMBCs 1:1. B) iTreg:huPMBCs 1:10. C) iTreg:huPMBCs 1:25. D) iTreg-antiPKCtheta:huPMBCs 1:1. E) iTreg-antiPKCtheta:huPMBCs 1:10. F) iTreg-antiPKCtheta:huPMBCs 1:25.

FIGS. 31A-F. Data for responders in treated and untreated iTregs. A) iTreg:huPMBCs 1:1. B) iTreg:huPMBCs 1:10. C) iTreg:huPMBCs 1:25. D) iTreg-antiPKCtheta:huPMBCs 1:1. E) iTreg-antiPKCtheta:huPMBCs 1:10. F) iTreg-antiPKCtheta:huPMBCs 1:25.

FIGS. 32A-F. Data for suppressors in treated and untreated iTregs. A) iTreg:huPMBCs 1:1. B) iTreg:huPMBCs 1:10. C) iTreg:huPMBCs 1:25. D) iTreg-antiPKCtheta:huPMBCs 1:1. E) iTreg-antiPKCtheta:huPMBCs 1:10. F) iTreg-antiPKCtheta:huPMBCs 1:25.

FIGS. 39A-C. PTDM-anti-phosphoPKCθ delivery into human PBMCs generates CD4 T cells with high CD25 expression. Human peripheral blood mononuclear cells (PBMCs) were treated, ex vivo, with 3 µM Rottlerin (PKCθ inhibitor) for 30 minutes at 37° C., with an equal volume of dimethyl sulfoxide (DMSO) as a vehicle control, or PTDM:anti-pPKCθ at a concentration of ratio of 1 µM:25 nM, for 4 hours at 37° C., prior to transferring into six-week-old female Nod-scidil2rgammac$^{null}$ (NSG) mice (Jackson Laboratory, Bar Harbor, Me.). Ten million untreated or treated PBMCs were injected through the tail vein of anesthetized NSG to induce disease in a pre-clinical, humanized model of GVHD. On day +17 after PBMC transfer, mice were humanely euthanized and bone marrow (A), peripheral blood (B), and spleens (C) were harvested. Human PBMCs were recovered, permeabilized with fix-perm buffer using the FoxP3 staining kit (BD Bioscience, San Diego, Calif.), following the manufacturer's directions, and stained with fluorescently-conjugated antibodies specific for human CD4 (BioLegend, San Diego, Calif.) and human CD25 (BioLegend, San Diego, Calif.). The median fluorescence intensity, a measure of protein expression on a per cell basis, was determined using flow cytometry. Data from stained samples were acquired using a BD Dual Fortessa LSR Flow Cytometer (Becton Dickinson). Histograms were generated using FlowJo Analysis Software (10.3, FlowJo, LLC, Ashland, Oreg.). Representative histograms of three independent experiments are shown (DMSO-treated control cells, red tracing; Rottlerin-treated cells, Blue tracing; PTDM:anti-pPKCθ-treated cells, Green tracing).

FIGS. 40A-E. PTDM-anti-phosphoPKCθ delivery into human CD4 T cells, generates 2.5-fold more CD4+CD25+Foxp3+ cells (A), compared to DMSO-treated cells, following in vitro iTreg differentiation. Human CD4 T cells were treated with DMSO or PTDM:anti-pPKCθ and resuspended in iTreg differentiation media for 5 days in the presence of anti-CD3 and anti-CD28 stimulation. At the end of 5 days, DMSO- and PTDM:anti-pPKCθ-generated iTregs were stained with PECy7-conjugated anti-CD25 (B-C) (BioLegend, San Diego, Calif.) and AF488-conjugated anti-Foxp3 (BioLegend, San Diego, Calif.) (D-E) and (a) percent of iTregs was quantified based on co-expression of CD25 and Foxp3 using flow cytometric analysis. Median fluorescent intensity of (b) CD25 and (c) Foxp3 expression in CD4+CD25+Foxp3+ T cells, and their respective representative histograms, are shown.

FIGS. 41A-L. Expression of functional markers for iTregs are altered in PTDM:anti-pPKCθ-generated iTregs. Human CD4 T cells were treated with DMSO or PTDM:anti-pPKCθ and resuspended in iTreg differentiation media for 5 days in the presence of anti-CD3 and anti-CD28 stimulation, as described. At the end of 5 days, DMSO- and PTDM:anti-pPKCθ-generated iTregs were stained with antibodies against phosphorylated PKCθ (T538; Cell Signaling Technology, Beverly, Mass.), phosphorylated STAT3 (Y705; ThermoFisher, Waltham, Mass.), phosphorylated STAT5 (Y694; ThermoFisher, Waltham, Mass.) and CTLA-4 (BioLegend, San Diego, Calif.). Percent positive cells and median fluorescence intensity, respectively, are shown for (A-C) pPKCθ (T538), (D-F) pSTAT3 (Y705), (G-I) pSTAT5 (Y694), and (J-L) CTLA-4 using flow cytometric approaches.

FIGS. 44A-F. Characterization of in vitro suppressive capabilities of PTDM:Anti-pPKCθ-generated iTregs. Human CD4 T cells were treated with DMSO, or PTDM:anti-pPKCθ and resuspended in iTreg differentiation media for 5 days in the presence of anti-CD3 and anti-CD28 stimulation, as described. At the end of 5 days a standard suppression assay was performed. Responder cells ($T_{res}$) were labeled with CytoTell™ UltraGreen dye (AAT Bioquest, Inc. Sunnyvale, Calif.) and stimulated with soluble anti-CD3 and anti-CD28, cross-linked on the cell surface using mouse IgG (R&D Systems, Minneapolis, Minn.). DMSO-generated- or PTDM:anti-pPKCθ-generated iTregs ($T_{sup}$) were added in to the responder cell culture at ratios of 1:1, 1:10, and 1:25 ($T_{sup}$: $T_{res}$), and cultured in standard cell culture medium for an additional 4 days at 37° C. DMSO- or PTDM:anti-pPKCθ-treated human CD4 T cells cultured for 5 days in the absence of iTreg differentiation media were used as controls. The percent suppression of (A) responder cells by iTregs generated under different conditions was determined using the following calculation (Percent of Suppression=(Percent of UltraGreen-positive cells on Day 0-Percent of UltraGreen-positive cells on Day 4) %. (B-C) Percentage of iTregs generated at the end of 5 days in culture was determined by staining cells with antibodies specific for CD25 and FOXP3. The co-expression of CD25 and FOXP3 on DMSO-generated and PTDM:anti-pPKCθ-generated iTregs was determined using flow cytometric approaches. Representative histograms showing the (D-F) median fluorescence intensity of CD25, FOXP3, and pPKCθ levels was measured in DMSO-generated and PTDM:anti-pPKCθ-generated iTregs at the end of the 4 day suppression assay.

FIGS. 49A-E. PTDM-iTres localize functional Treg markers to the nucleus while reducing nuclear pPKCθ.

Figure 1:
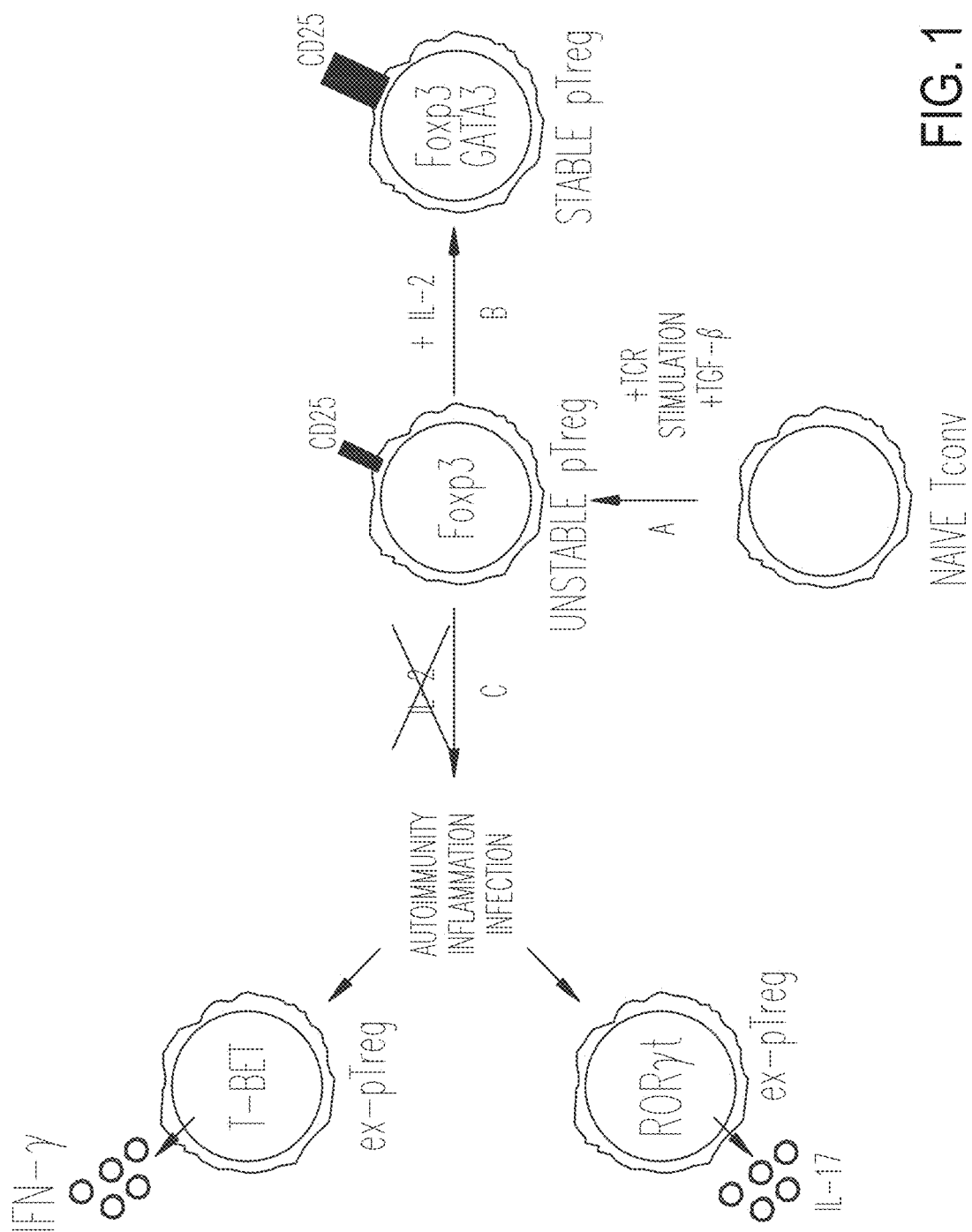
FIG. 1. IL-2 signal for Tregs contributes to stability of the cells.
Figure 2A:
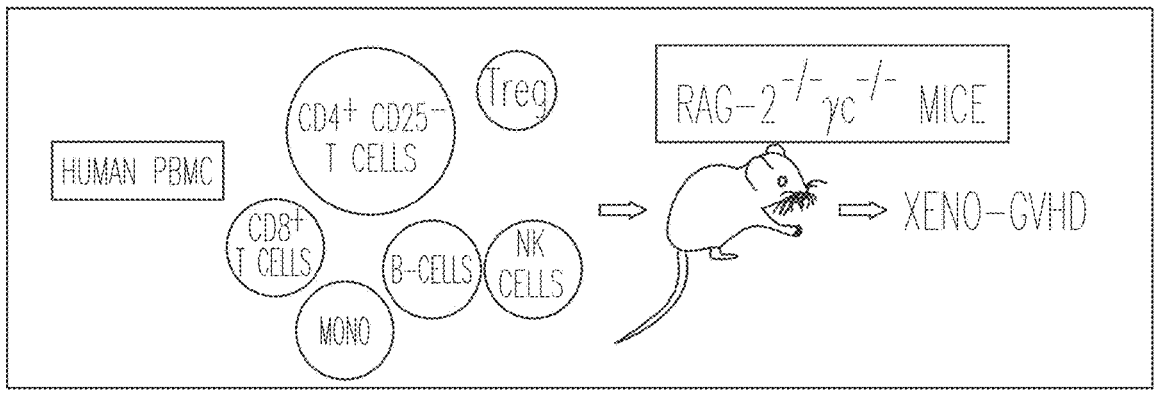
FIGS. 2A-C. Importance of Tregs in GvHD. A) Human PBMCs. B) After CD25+ depletion. C) Enriched in CD4+ CD25+ Treg.
Figure 2B:
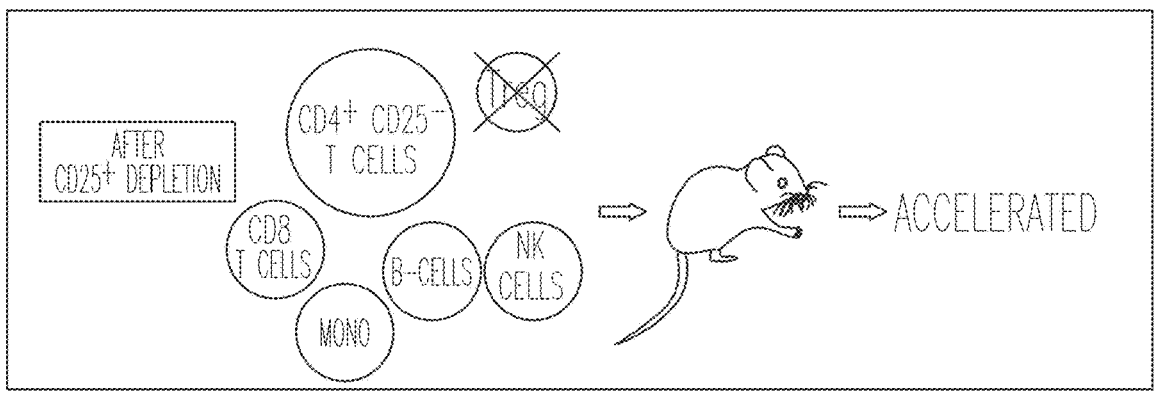
Figure 2C:
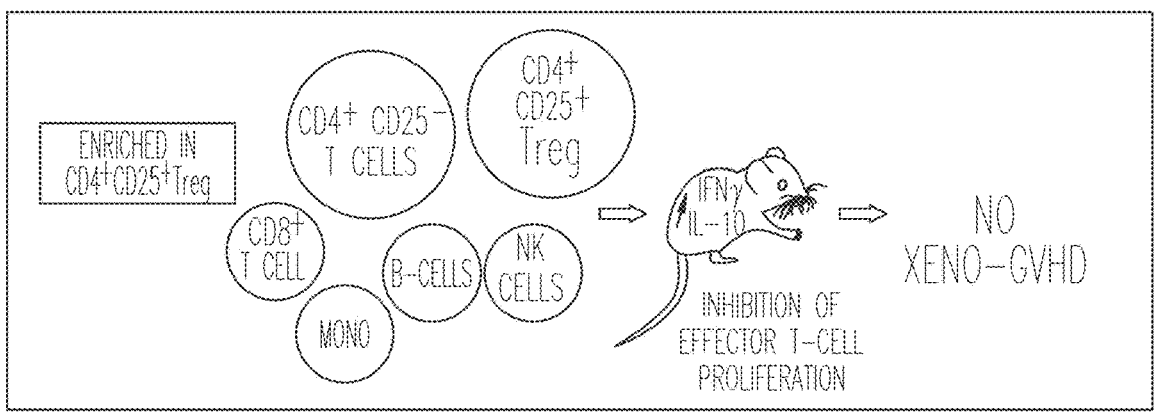
Figures 4A, 4B, 4C:
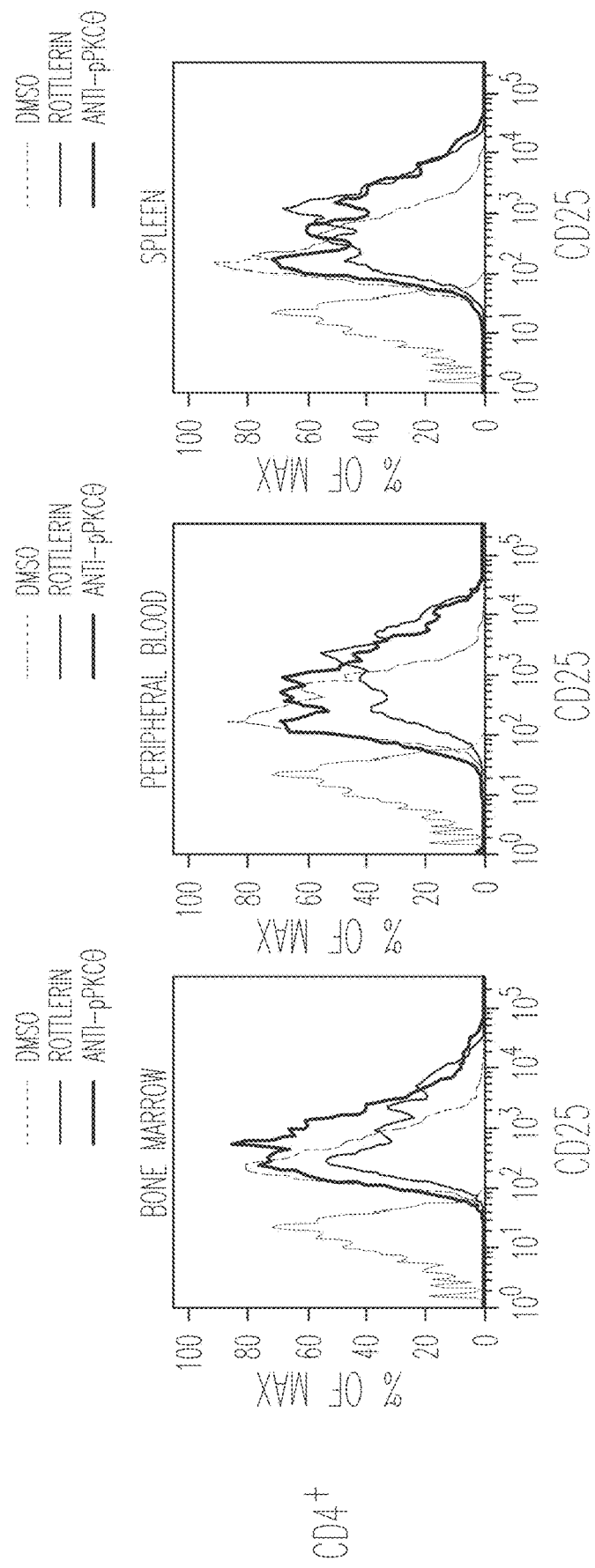

Nuclear localization data for FOXP3, pPKCθ (Thr538), pSTAT3 (Tyr705), and pSTAT5 (Tyr694) were assessed via AMNIS imaging flow cytometry and 1000 cells were counted to collect the data. (A) Nuclear localization score distribution of FOXP3-expressing cells (left panel), quantification of nuclear similarity scores for FOXP3 (middle panel), representative image showing nuclear FOXP3 in iTregs (right panel). (B) Nuclear localization score distribution of pPKCθ-expressing cells (left panel), quantification of nuclear similarity scores for pPKCθ (middle panel), representative image showing nuclear pPKCθ in iTregs (right panel). (C) Nuclear localization score distribution of pSTAT3-expressing cells (left panel), quantification of nuclear similarity scores for pSTAT3 (middle panel), representative image showing nuclear pSTAT3 in iTregs (right panel). (D) Nuclear localization score distribution of pSTAT5-expressing cells (left panel), quantification of nuclear similarity scores for pSTAT5 (middle panel), representative image showing nuclear pSTAT5 in iTregs (right panel). Data represent mean±SEM three independent experiments. Unpaired, two-tailed student t test was used for analysis; *p<0.05, **p<0.01.

FIGS. 50A-G. PTDM-iTregs behave as super-suppressive iTregs and express elevated levels of suppressive receptors, LAG-3 and PD-1, on their surface. (A) Experimental setup for in vitro suppression assay with UltraGreen-labeled responder cells and Red650-labeled suppressor cells mixed in three different ratios as shown. (B) Percent suppression efficiency of suppressor cells. (C) Flow cytometric analysis of iTregs on Day 4, in co-culture with responders. (D) Representative histogram, quantification of percent-positive, and MFI of surface LAG-3-expressing iTregs. (E) LAG3 mRNA transcript levels via qPCR. (F) Representative histogram, quantification of percent-positive, and MFI of surface PD-1-expressing iTregs. (G) PDCD1 mRNA transcript levels via qPCR. Data represent mean±SEM three independent experiments. Unpaired, two-tailed student t test was used for analysis; *p<0.05, p<0.01, *p<0.001.

FIGS. 51A-I. Adoptive transfer of super-suppressive PTDM-iTregs cells are highly efficacious in vivo in humanized GvHD model. (A) Schematic representation of adoptive transfer of in vitro differentiated iTregs into humanized GvHD model. (B) Bone marrow (BM) cellularity on day 17. (C) Blood counts of white blood cells (WBCs) and red blood cells (RBCs). (D) Percent of human CD45-positive cells in bone marrow, peripheral blood, and spleen on day 17. (E) Percent of human CD4 and CD8 T cells in bone marrow, peripheral blood, and spleen on day 17. (F) Histopathological analysis of spleen and sternum on day 17 following Hematoxylin & Eosin staining. (G) Clinical scores for GvHD. (H) Survival curve. (I) IFNγ concentration in the plasma. 5 mice were used per group. Data pooled from and represent mean±SEM of three independent experiments. Kaplan-Meier statistical analysis was performed for survival curve. Unpaired, two-tailed student t test was used for analysis; *p<0.05, p<0.01, *p<0.001.

FIGS. 52A-K. Super-suppressive PTDM-iTregs are long lasting in vivo and represent a unique population of FOXP3$^{hi}$PD-1$^{hi}$IFNγ$^{hi}$ iTregs. (A) Representative scatter plot for percent of CD4$^+$CD127$^{-/lo}$CD25$^+$FOXP3$^+$ iTregs in bone marrow on day 17. (B) Quantification of percent of CD4$^+$CD127$^{-/lo}$CD25$^+$FOXP3$^+$ iTregs in bone marrow on day 17. (C) Number of CD4$^+$CD127$^{-/lo}$CD25$^+$FOXP3$^+$ iTregs in bone marrow on day 17. (D) Representative histogram and MFI of FOXP3 expression in CD4$^+$CD127$^{-/lo}$CD25$^+$FOXP3$^+$ iTregs in bone marrow on day 17. (E) Representative histogram, percent positive, and MFI of pPKCθ expression in CD4$^+$CD127$^{-/lo}$CD25$^+$FOXP3$^+$ iTregs in bone marrow on day 17. (F) Representative histogram and representative image of nuclear pPKCθ-positive CD4$^+$CD127$^{-/lo}$CD25$^+$FOXP3$^+$ iTregs in bone marrow on day 17. (G) Representative histogram, percent positive, and MFI of PD-1 expression in CD4$^+$CD25$^+$FOXP3$^+$ iTregs in bone marrow on day 17. qPCR analysis of (H) FOXP3, (I) PDCD1, and (J) IFNG gene expression in CD4$^+$CD25$^-$CD127$^+$ (Naïve) and CD4$^+$CD25$^+$CD127$^-$ (iTreg) in bone marrow on day 17. (K) Representative histogram, percent positive, MFI of IFNγ expression, and IFNG mRNA transcript levels in Tconvs and iTregs in vitro. In vivo data pooled from 4 mice and represent mean±SEM of three independent experiments. In vitro IFNγ data represent mean±SEM of three independent experiments. Unpaired, two-tailed student t test was used for analysis; *p<0.05, p<0.01, *p<0.001.

Figure 53B:
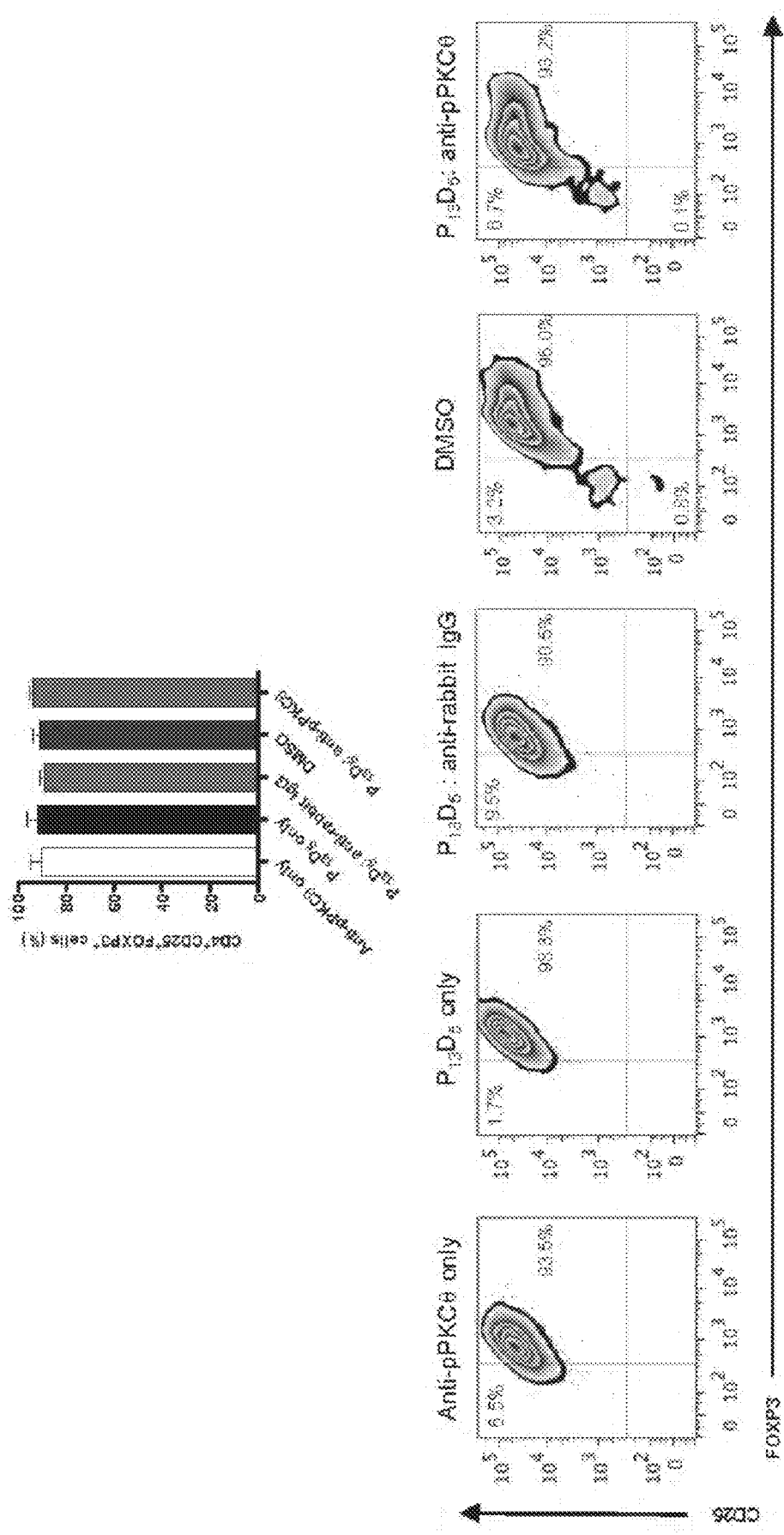

FIGS. 53A-B. Assessment of intracellular antibody delivery and determination of experimental controls. To verify that only antibody complexed to $P_{13}D_5$ synthetic peptides are delivered across the cell membrane, CD4 T cells were isolated and pre-treated for four hours with Phosphate Buffered Saline (PBS), anti-pPKCθ only, cell-penetrating $P_{13}D_5$ only, secondary antibody only, $P_{13}D_5$ complexed to anti-rabbit IgG, or $P_{13}D_5$ complexed to anti-pPKCθ, prior to in vitro differentiation into iTregs. At the end of the differentiation period, cells were permeabilized and stained with an anti-rabbit secondary antibody conjugated to Qdot 625. Flow cytometry was used to (A) determine percent of cells taking up $P_{13}D_5$-complexed antibody (left panel) and the extent to which $P_{13}D_5$-complexed antibody was delivered on a per cell basis (middle panel), as indicated by median fluorescent intensity of the bound Qdot-labeled secondary antibody. A representative histogram is shown in the far-right panel. In separate experiments, CD4 T cells were isolated and pre-treated for four hours with anti-pPKCθ only, cell-penetrating $P_{13}D_5$ only, $P_{13}D_5$complexed to anti-rabbit IgG, Dimethyl Sulfoxide (DMSO), or $P_{13}D_5$ complexed to anti-pPKCθ, prior to in vitro differentiation into iTregs. (B) The percent of iTreg cells successfully differentiated after the various pre-treatments was determined by flow cytometry following intracellular staining with anti-CD25 and anti-FOXP3. Representative histograms of CD25 and FOXP3 expression are shown in panels that correspond to the various pretreatment conditions. Only the DMSO-treated cells showed a similar expression pattern of CD25 and FOXP3, and, thus was used as the control for $P_{13}D_5$-anti-pPKCθ experiments throughout this study. Data represent mean±SEM three independent experiments. Unpaired, two-tailed students t test was used for analysis; *p<0.05, ***p<0.001.

Figure 54A:
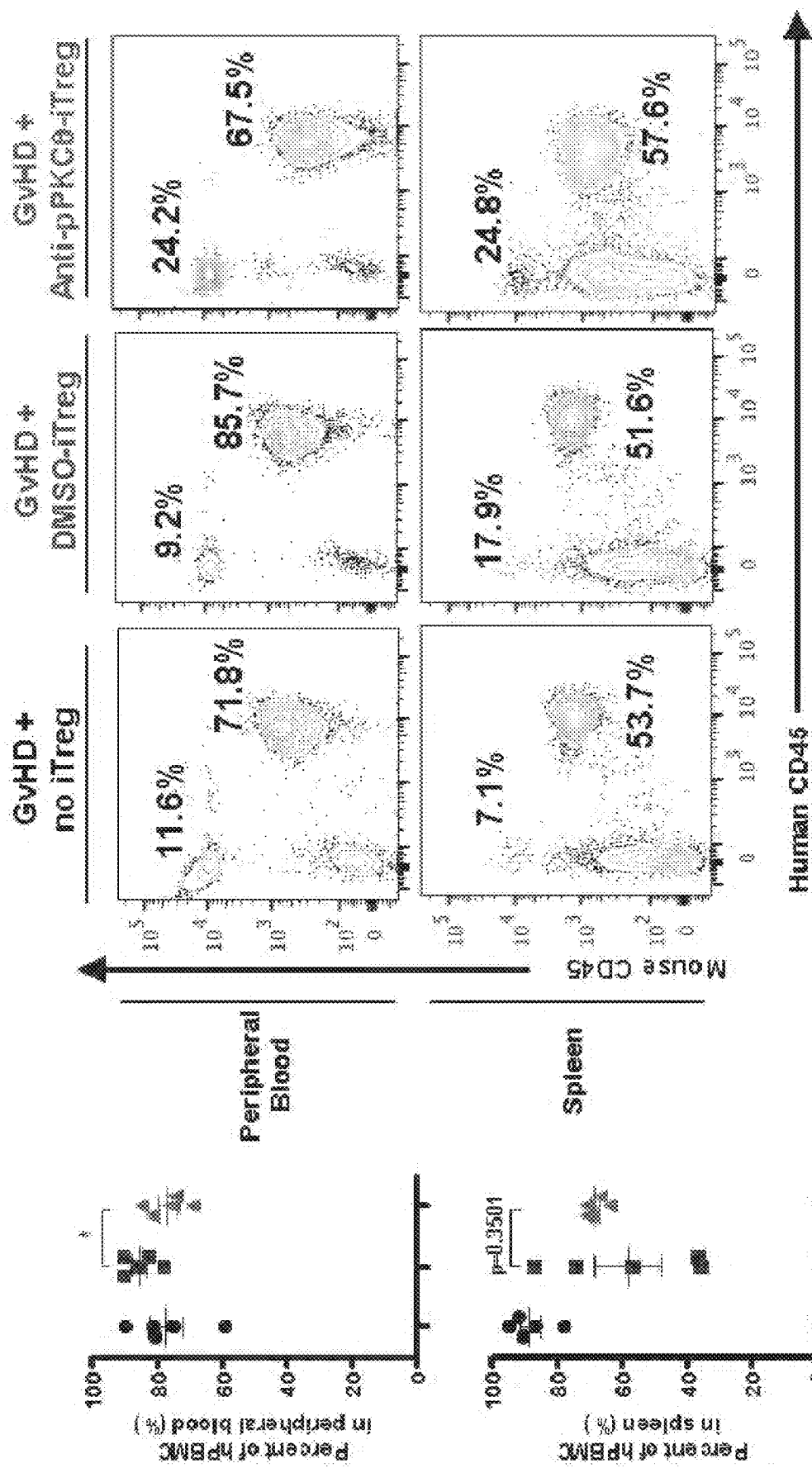
Figure 54C:
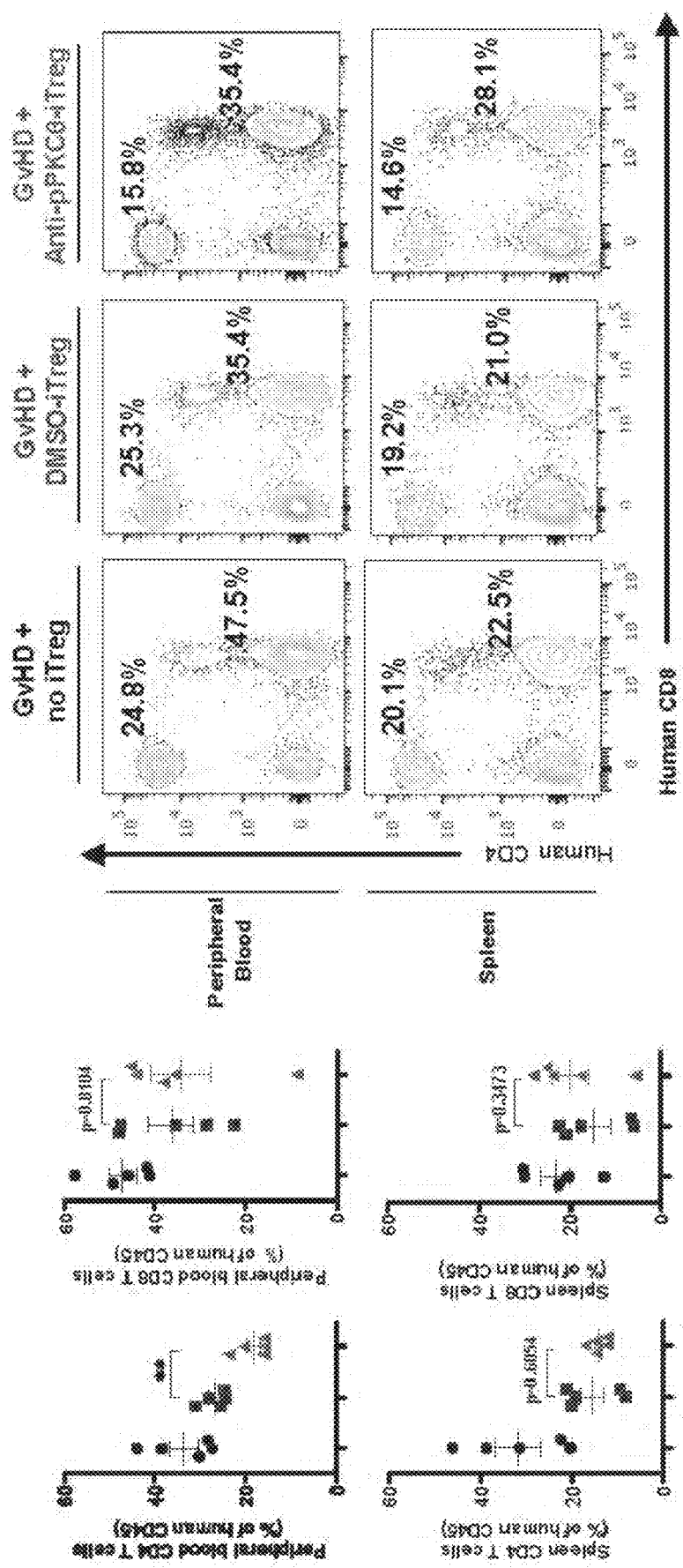

FIGS. 54A-C. Cellular distribution and bone-marrow protective effects of adoptively transferred iTreg in a humanized GvHD model on day 17. GvHD was induced in mice and cohorts were left untreated (GvHD+no iTregs) or treated with iTregs generated in the presence of DMSO (GvHD+DMSO iTregs) or after $P_{13}D$-anti-pPKC delivery (GvHD+anti-PKCθ-iTregs). (A) Aggregated data showing the percentages of hPBMCs in peripheral blood and spleen, together with representative flow cytometry dot plots. (B) Representative micrographs of spleens harvested 17 days after GvHD induction and stained with hematoxylin and eosin. (C) Aggregated data showing percentages of human CD4 and CD8 T cells recovered from peripheral blood and spleen, together with representative flow cytometry dot plots. 5 mice were used per group. Data pooled from and represent mean±SEM of three independent experiments. Unpaired, two-tailed student t test was used for analysis; *p<0.05, **p<0.01.

FIGS. 55A-E. Analysis of iTregs recovered from peripheral blood 17 days after GvHD induction in a humanized mouse model. GvHD was induced in mice and cohorts were treated with iTregs generated in the presence of DMSO (GvHD+DMSO iTregs) or after $P_{13}D_5$-anti-pPKCθ delivery (GvHD+anti-PKCθ-iTregs). (A) Aggregated data showing percent of CD4+CD25+FOXP3+ iTregs recovered from peripheral blood, together with representative dot plots showing CD25 and FOXP3 expression, in DMSO-iTregs and anti-pPKCθ-iTregs recovered from the peripheral blood of diseased mice 17 days after GvHD induction. (B) Aggregated data and representative histogram of $FOXP3^{high}$-iTregs in the peripheral blood of DMSO- or anti-pPKCθ-iTreg-treated mice 17 days after GvHD induction. (C) Aggregated data and representative histogram of $pPKCθ^{low}$-iTregs in the peripheral blood of DMSO- or anti-pPKCθ-iTreg-treated mice 17 days after GvHD induction. (D) Nuclear localization score histograms, aggregated data and representative images of nuclear pPKCθ-positive CD4+CD25+FOXP3+ iTregs in the peripheral blood of DMSO- or anti-pPKCθ-iTreg-treated mice 17 days after GvHD induction. (E) Aggregated data and representative histogram of $PD1^{high}$-iTregs in the peripheral blood of DMSO- or anti-pPKCθ-iTreg-treated mice 17 days after GvHD induction. 3-5 mice were used per group. Data pooled from and represent mean±SEM of three independent experiments. Unpaired, two-tailed student t test was used for analysis; *p<0.05.

FIGS. 56A-H. Analysis of iTregs recovered from spleens 17 days after GvHD induction in a humanized mouse model. GvHD was induced in mice and cohorts were treated with iTregs generated in the presence of DMSO (GvHD+DMSO iTregs) or after $P_{13}D_5$-anti-pPKCθ delivery (GvHD+anti-PKCθ-iTregs). (A) Aggregated data showing percent of CD4+CD25+FOXP3+ iTregs recovered from spleens, together with representative dot plots showing CD25 and FOXP3 expression in DMSO-iTregs and anti-pPKCθ-iTregs recovered from the spleens of diseased mice 17 days after GvHD induction. (B) Aggregated data and representative histogram of $FOXP3^{high}$-iTregs recovered from spleens of DMSO- or anti-pPKCθ-iTreg-treated mice 17 days after GvHD induction. (C) Aggregated data and representative histogram of $pPKCθ^{low}$-iTregs recovered from spleens of DMSO- or anti-pPKCθ-iTreg-treated mice 17 days after GvHD induction. (D) Nuclear localization score histograms, aggregated data and representative images of nuclear pPKCθ-positive CD4+CD25+FOXP3+ iTregs recovered from spleens of DMSO- or anti-pPKCθ-iTreg-treated mice 17 days after GvHD induction. (E) Aggregated data and representative histogram of $PD1^{high}$-iTregs recovered from spleens of DMSO- or anti-pPKCL□-iTreg-treated mice 17 days after GvHD induction. (F) FOXP3, (G) PDCD1, and (H) IFNG gene expression in CD4+CD25+(iTreg) cells recovered from the spleens of DMSO- or anti-pPKCθ-iTreg-treated mice 17 days after GvHD induction. 3-5 mice were used per group. Data pooled from and represent mean±SEM of three independent experiments. Unpaired, two-tailed student t test was used for analysis; *p<0.05, **p<0.01.

FIGS. 57A-F. Anti-pPKCθ delivery modulates splicing regulatory protein, p-SC35, and affects RNA processing in iTregs in gene-specific manner in vitro. (A) Cytoplasmic vs. nuclear distribution of p-SC35 in Anti-pPKCθ-iTregs was analyzed via western blot. Normalized densities for cytoplasmic p-SC35 were quantified according to tubulin. (B) Alternative splicing analysis of CD45 in iTregs via RT-PCR. Primers were designed to assess 3'UTR processing from the last exon to close to the end of 3'UTR and its cartoon representation for each gene was shown. (C) PDCD1, (D) FOXP3, (E) IFNG, and (F) IFNGR1 3'UTR lengths were analyzed via RT-PCR. Red frames indicate the expected am pl icon size for mature mRNA with its 3'UTR. Data represent mean±SEM of two or three independent experiments. Unpaired, two-tailed student's t test was used for analysis; ***p<0.001.

FIGS. 58A-E. RNA processing was altered in ex vivo-treated iTregs in tissue- and gene-specific manner in humanized mouse model of GvHD. hPBMCs were transferred on Day 0 together with Anti-pPKCθ- (or DMSO-) iTregs (3:1 ratio). On Day 17, tissues were harvested and iTregs were separated via magnetic beads against CD4+, CD25+, and CD127−. Total RNA was extracted from iTregs present in bone marrow and spleen on day 17. RT-PCR was performed to study alternative splicing and 3'UTR processing. (A) CD45 alternative splicing in bone marrow vs. spleen anti-pPKCθ-iTregs ex vivo. (B) PDCD1 variants and 3'UTR lengths were analyzed using specific primers in ex vivo treated iTregs homing to bone marrow or spleen. This analysis was also done for (C) FOXP3, (D) IFNG, and (E) IFNGR1. Red frames indicate the expected amplicon size and cartoon representation for expected amplicon size was shown for each gene. Data represent mean±SEM of three independent experiments from 5 mice per condition.

FIGS. 59A-F. PKCθ controls PCMT1 both post-transcriptionally and post-translationally in iTregs. (A) PCMT1 protein in cytoplasm and nucleus were detected via western blot and quantified based on loading control densities via ImageJ software. (B) Phosphorylation of nuclear PCMT1 was confirmed via lambda phosphatase treatment and together with a well known phosphorylated protein, STAT1, relevant to iTreg function. Total STAT1 and pSTAT1 (Y701) were quantified using ImageJ software. (C) PCMT1 gene expression was quantified via qPCR. (D) PCMT1 splicing and 3'UTR length were analyzed via RT-PCR in vitro. (E) PCMT1 gene expression was quantified via qPCR on Day 17 in bone marrow and spleen-infiltrating anti-pPKCθ-iTregs in humanized GvHD model. (F) In vivo analysis of PCMT1 splicing and 3'UTR length were performed via RT-PCR in humanized GvHD model. Red frames indicate the expected amplicon size. Data represent mean±SEM of two or three independent experiments. For in vivo experiment, 4 mice per group were used. Unpaired, two-tailed student's t test was used for analysis; p<0.01, and *p<0.001.

FIGS. 60A-G. Inhibiting PKCθ diminishes hnRNPL association with PCMT1 at both protein and RNA levels in iTregs. (A) Percentages of CD4+CD25+FQXP3+ T cells with their representative scatter plots upon cell-penetrating antipPKCθ or anti-PCMT1 treatment. (B) Percentage of FOXP3high iTregs and their FOXP3 median fluorescent intensities (MFI) along with their representative histograms. (C) Percentage of IFNγ-positive iTregs and fold increase in IFNγ MFI with their representative histograms. (D) Cytoplasmic vs. nuclear distribution of hnRNPL in Anti-pPKCθ-iTregs was analyzed via western blot. Normalized densities for cytoplasmic and nuclear hnRNPL were quantified according to tubulin and Histone H3, respectively. (E) Immunoprecipitation of cytosolic vs. nuclear hnRNPL with PKCθ and PCMT1 in iTregs. (F) Prediction of hnRNPL RNA binding motifs via Catalog of Inferred Sequence Binding Preferences of RNA Binding Proteins (CISBP-RNA) database in human. (G) Schematic of hnRNPL binding to PCMT1 3'UTR and hnRNPL association with cytosolic and nuclear PCMT1 mRNA. Red frames indicate the expected amplicon size. Data represent mean±SEM of two or three independent experiments. Unpaired, two-tailed student's t test was used for analysis; *p<0.05 and **p<0.01.

FIGS. 61A-D. PCMT1 can be a good target to increase stability of iTregs. (A) Chromatin immunoprecipitation of PCMT1 on FOXP3 gene in iTregs. (B) CpG islands and STAT5-binding sites on FOXP3 Treg-specific demethylated region (TSDR) in humans (SEQ ID NO: 60). (C) Bisulfite sequencing of ten different clones for FOXP3 TSDR CpG islands from each of the treatment. Percentages of demethylated CpGs #3, #4, #14, and #15 were quantified and shown as pie charts. (D) Nuclear localization of pSTAT5 (Tyr694) was shown via AMNIS ImageStream analysis. Representative cell frequency histograms showing nuclear pSTAT5-localizing cells along with representative images at 60× magnification. Quantification of nuclear pSTAT5 based on similarity score was also shown. Data represent mean±SEM two or three independent experiments. Unpaired, two-tailed t test was used for analysis; *p<0.05, p<0.01, *p<0.001.

FIGS. 62A-I. Effect of anti-pPKCθ delivery on alternative splicing in non-differentiated T cells (Tconvs) in vitro. (A) Alternative splicing analysis of CD45 in Tconvs via RT-PCR. Splicing analysis of (B) PDCD1, (C) FOXP3, (D) IFNG, and (E) JFNGR1 along with their schematic upon PKCθ inhibition in Tconvs. 3'UTR analysis of (F) PDCD1, (G) FOXP3, (H) JFNG, and (I) JFNGR1 3'UTR via RT-PCR in Tconvs. Red frames indicate the expected amplicon size. Data represent mean±SEM of two or three independent experiments.

FIGS. 63A-I. Effect of anti-pPKCθ delivery on RNA processing of na'ive T cells in vivo. hPBMCs were transferred on Day 0 together with anti-pPKCθ (or DMSO-) iTregs (3:1 ratio). On Day 17, tissues were harvested, and natve T cells were separated via magnetic beads against CD4+, CD25−, and CD127+. Total RNA was extracted from these natve T cells present in bone marrow and spleen on day 17. RT-PCR was performed to study alternative splicing and 3'UTR processing. (A) CD45 alternative splicing in bone marrow vs. spleen natve T cells. (B) PDCD1 variants and 3'UTR lengths were analyzed using specific primers in na'ive T cells homing to bone marrow or spleen. This analysis was also done for (C) FOXP3, (D) JFNG, and (E) IFNGR1. Red frames indicate the expected amplicon size. Data represent mean±SEM of two independent experiments from 5 mice per condition.

FIGS. 64A-E. PCMT1 splicing and 3'UTR analyses in Tconvs in vitro and in vivo. (A) PCMT1 protein in cytoplasm and nucleus was detected via western blot and quantified based on loading control densities via ImageJ software. (B) PCMT1 gene expression was quantified via qPCR in Tconvs. (C) PCMT1 splicing and 3'UTR length were analyzed in vitro. (D) PCMT1 gene expression was quantified via qPCR on Day 17 in bone marrow and spleen naïve T cells in iTreg-administered humanized GvHD model. (E) In vivo analysis of PCMT1 splicing and 3'UTR length were performed via RT-PCR in humanized GvHD model. Red frames indicate the expected amplicon size. Data represent mean±SEM of two or three independent experiments. For in vivo experiment, 4 mice per group were used. Unpaired, two-tailed student's t test was used for analysis; *p<0.05, p<0.01, and *p<0.001.

FIG. 65. hnRNPL binding sites on 3'UTR sequences of iTreg genes (SEQ ID Nos: 61-65). 3'UTR sequences (red sequences) were determined using Ensembl. These sequences were copied and run on RBPmap to define hnRNPL binding sites (bold in blue). Later, forward and reverse primers were designed to amplify these regions via RT-PCR (Primers were designed to bind black, bold sequences).

FIGS. 66A-G. Cytoplasmic vs. nuclear mRNA association with hnRNPL in anti-pPKCθ- or anti-PCMT1-iTregs. (A) Cytoplasmic vs. nuclear distribution of hnRNPL in Tconvs was analyzed via western blot. Normalized densities for cytoplasmic and nuclear hnRNPL were quantified according to tubulin and Histone H3, respectively. (B) Quantification of immunoprecipitated cytosolic and nuclear hnRNPL with PKCθ and PCMT1 in iTregs was performed via ImageJ software. (C) Schematic of RNA immunoprecipitation with hnRNPL. hnRNPL association with cytosolic and nuclear (D) PDCD1, (E) FOXP3, (F) IFNG, and (G) IFNGR1 mRNAs. Red frames indicate the expected amplicon size. Data represent mean±SEM of two independent experiments.

Figure 67A:
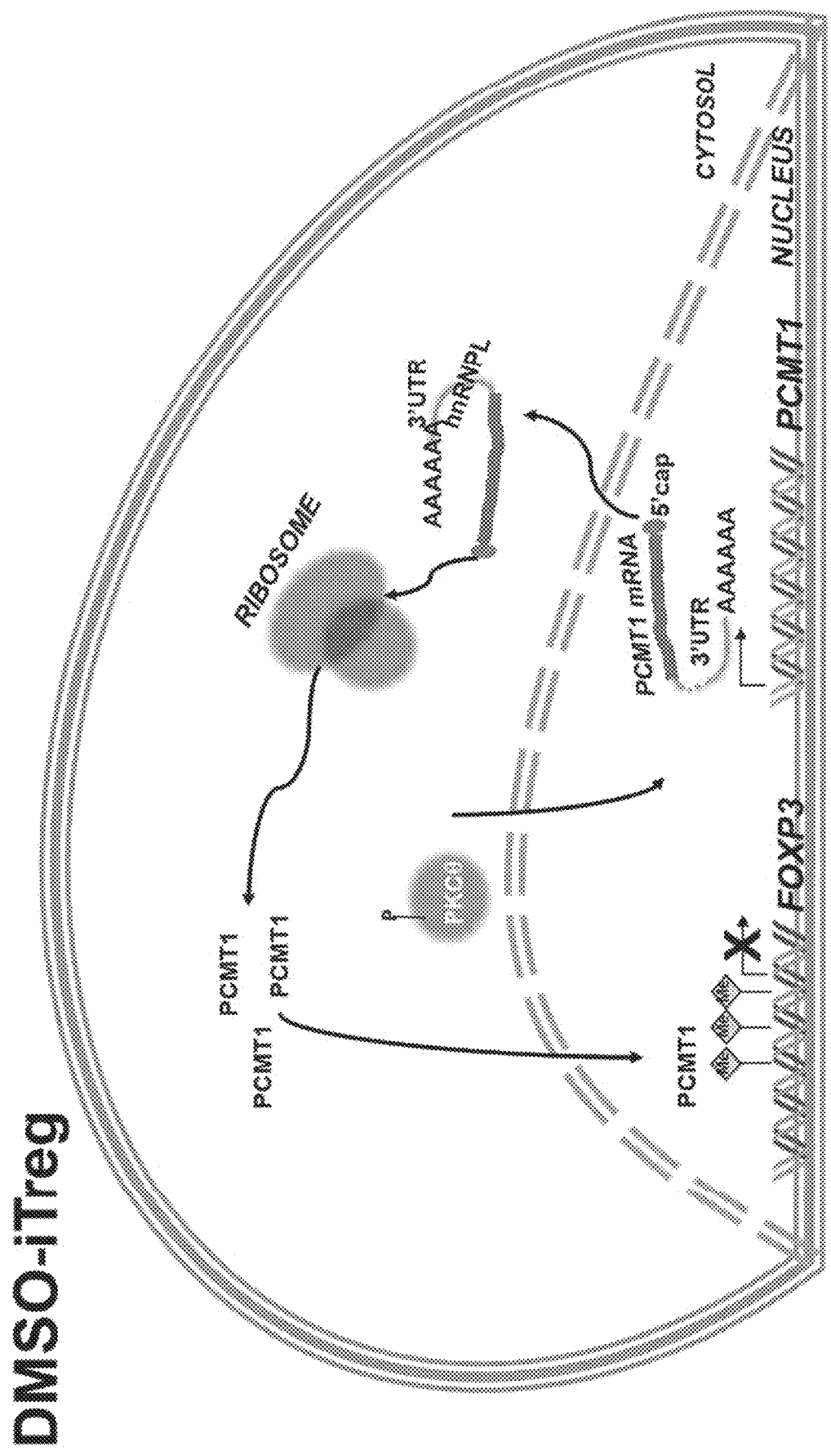
Figure 67B:
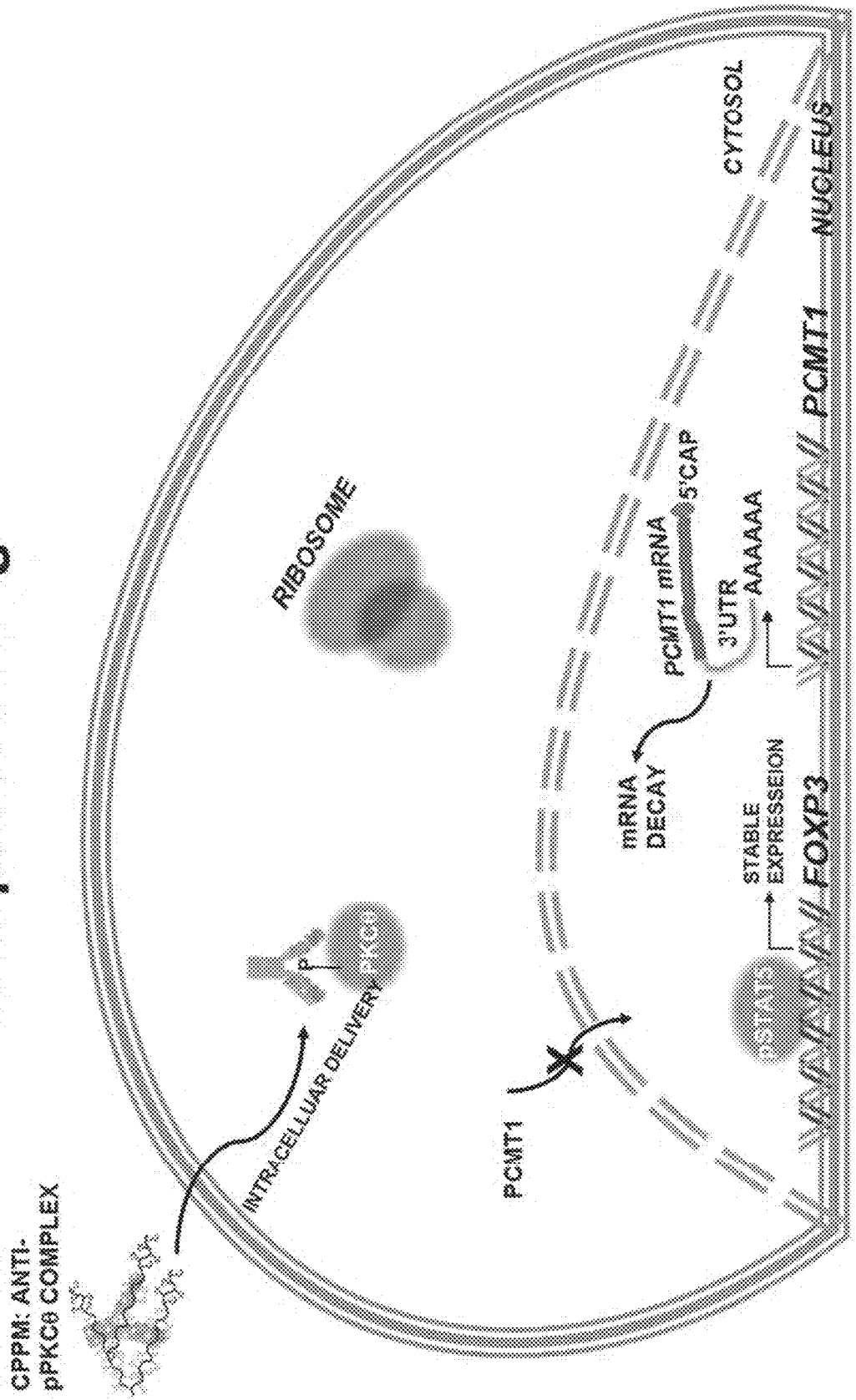

FIG. 67. Schematic of cells treated with DMSO-iTreg or anti-pPKCtheta-iTreg.

DETAILED DESCRIPTION

Protein kinase C enzymes comprise 3 subfamilies and 10 kinase isoforms that are structurally and functionally related. Different isoforms are activated either by proteolysis or translocation to the plasma membrane, where they associate with protein partners to mediate biological functions. Among the PKC enzymes, protein kinase C-theta (PKCθ) exhibits a selective pattern of tissue distribution with a predominant expression in T lymphocytes, platelets, and skeletal muscle. It translocates to the center of the immunological synapse (IS) in activated CD4 T cells following the integration of T cell receptor (TCR) and CD28 costimulatory signals. The full activation of PKCθ involves two steps: diacylglycerol (DAG) binding to its C1 domain and subsequent Threonine 538 (Thr538) phosphorylation within its activation loop. PKCθ regulates multiple transcription factors including NF-κB, AP-1, and NFAT which, individually and combined, initiate signals that are critical for T cell activation, proliferation, and differentiation. Recently, it has been suggested that PKCθ also translocates into the nucleus and associates with a chromatin-bound complex to regulate microRNA and T cell-specific gene expression programs. Immunological studies show that distinct PKC isoforms use unique mechanisms to regulate various distinct functions and, thus, are attractive therapeutic targets for modulating T cell-mediated adaptive immune responses.

Monoclonal antibodies have emerged as potential therapeutics for many diseases such as cancer, infection, and autoimmune disorders due to their unequalled target specificity. Furthermore, advancements in genetic engineering have paved the way for "humanizing" mouse monoclonal antibodies, creating versions for clinical use that are promising due to their greater safety and selectivity. However, targets of these antibody-based biologics are currently limited to cell surface or extracellular proteins because of their inability to pass through the cellular membrane.

Intracellular delivery of biologically active molecules remains a significant challenge. In some cases, these therapeutics can be taken up via receptor-mediated endocytosis. However, cellular entry via endocytic pathway poses its own hurdles, including escape from endosomes and avoiding lysosomal degradation. Therefore, how these macromolecules are designed and delivered are quite important. An approach to deliver such biologics involves using cell-penetrating peptides (CPPs), also known as protein transduction domains (PTDs), which are short sequences of peptides capable of translocating across the cell membrane. The first PTD identified was a short sequence of amino acids, consisting of the arginine-rich residues 48-60 of the HIV-1 TAT protein. Since the discovery of TAT, many cationic PTDs have been reported including R9, penetratin, VP22, transportan, pVEC, and Pep-1. Although all are able to translocate across cellular membranes, synthesizing these peptides is challenging due to their structural complexities and most requires covalent attachment to their cargoes for delivery. Recent studies demonstrate that incorporating key features of PTDs into simpler, tunable scaffolds improves uptake for a broad range of cell types. Mimics of PTDs within these scaffolds facilitate fine-tuning the chemical composition of delivery agents for application-specific needs. For instance, successful design of polymeric mimics of PTDs, also called protein transduction domain mimics (PTDMs), provides an easy, synthetic platform to deliver biological cargo such as siRNA and proteins with superior efficiency.

A PTDM capable of delivering an antibody that recognizes and modulates the activity of the intracellular protein, phosphorylated PKCθ (Thr538), via its delivery into hPBMCs, is described herein. Successful ex vivo transport of antibodies into human immune cells lays the foundation to further develop this platform as a potential clinical modality, especially regarding immunotherapy. In particular, as disclosed herein in Example 1, PKCθ actions can be specifically inhibited by anti-pPKCθ delivery via protein transduction domain mimics (PTDMs). Using PTDMs to transport an antibody specific for the phosphorylated Thr538 (T538) residue led to sequestration of PKCθ in the cytosol and diminished T cell activity. Moreover, this delivery strategy could be used to manipulate T cells ex vivo prior to their transfer into a humanized mouse model of GvHD. The ex vivo delivery of anti-pPKCθ into T cells prior to transfer attenuated disease severity and provided a significant survival benefit and in the GvHD model (Example 1)

CD4 T cells can be induced to adopt a regulatory T cell phenotype under prescribed culture conditions. Furthermore, inhibiting the function of the T cell-specific kinase, PKCθ, facilitates differentiation of CD4 T cells towards an induced regulatory T cell fate, iTregs are characterized by high CD25 and FOXP3 expression. Upon ex vivo delivery of PTDM:anti-pPKCθ into T cells, it was observed that there were $CD25^{high}$ populations in spleen, peripheral blood, and bone marrow in this GvHD model, suggesting a potential Treg population may have emerged. As described below, culturing CD4 T cells with PTDM-anti-pPKCθ prior to stimulation with anti-CD3 and anti-CD28, under prescribed culture conditions induces a regulatory T cell phenotype, and results in iTregs that are superior to those generated in the absence of PTDM-anti-pPKCθ delivery. In vitro and in vivo data support the enhanced suppressive capabilities of these ex vivo-generated iTregs. It may be that anti-PKCθ treatment modulates the activity of the splicosome, resulting in alternatively-spliced proteins that mediate stronger regulatory functions. These cells may be resistant to conversion to reactive T cells in the presence of proinflammatory cytokines and may retain their ability to kill residual tumor cells in a humanized Graft-versus-Leukemia model.

Exemplary Polymers for Use in the Compositions

In one aspect, the composition includes a compound having a structure corresponding to Formula (I):

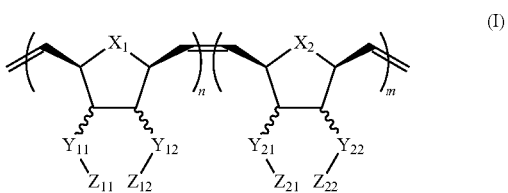

wherein
$X_1$, $X_2$ each is independently O, $CH_2$ or substituted $CH_2$;
$Y_{11}$, $Y_{12}$ each is independently a single bond or a linking group;
Z11, $Z_{12}$ each is independently hydrogen, or an $—N(R_z)_2$, alkyl, substituted alkyl, aryl, substituted aryl group, with the proviso that at least one of $Z_{11}$ and $Z_{12}$ comprises

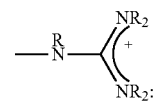

$N(R_z)_2$ or
$Y_{21}$, $Y_{22}$ each is independently a single bond or a linking group;
$Z_{21}$, Z22 each is independently hydrogen, an $—OR_z$, alkyl, substituted alkyl, aryl, substituted aryl group;
$R_z$ each is independently hydrogen, an alkyl, substituted alkyl, aryl, substituted aryl, poly(ethylene oxide) group;
R is hydrogen, a C1-C6 alkyl group or a poly(ethylene oxide) group; and
m, n each is independently an integer from about 2 to about 300.

In certain embodiments, m and n are independently integers from about 2 to about 50, for example from about to about 24, from about 6 to about 20, from about 8 to about 16 (e.g., 2, 3, 4, 5, 6, 7, 8, 9, 10, 11, 12, 13, 14, 15, 16, 17, 18, 19, 20, 21, 22, 23, 24). In certain embodiments, one or both m and n is 25 or greater, 30 or greater, 40 or greater.

In certain embodiments of the block co-polymer, each of $X_1$ and $X_2$ is O; each of Y11 and $Y_{12}$ is independently a linking group comprising a carbonyl group; each of Z11 and Z12 comprises

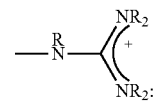

each of $Y_{21}$ and $Y_{22}$ is independently a linking group comprising a carbonyl group; each of $Z_{21}$, Z22 is $—OR_z$, wherein at least one $—OR$, comprises an aryl group; each R is hydrogen; and each of m and n is selected from an integer from about 2 to about 24.

In certain embodiments of the block co-polymer, each of $X_1$ and $X_2$ is O; each of Y11 and $Y_{12}$ is independently a linking group comprising a carbonyl group; each of Z11 and $Z_{12}$ comprises $N(R_z)_2$; each of $Y_{21}$ and $Y_{22}$ is independently a linking group comprising a carbonyl group; each of $Z_{21}$, $Z_{22}$ is $—OR_z$, wherein at least one $—OR$, comprises an aryl group; each R is hydrogen; and each of m and n is selected from an integer from about 2 to about 24.

In certain embodiments of the block co-polymer, each of $X_1$ and $X_2$ is $CH_2$; each of Y11 and $Y_{12}$ is independently a linking group comprising a carbonyl group; one of Z11 and $Z_{12}$ comprises

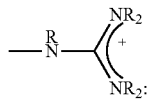

each of $Y_{21}$ and $Y_{22}$ is independently a linking group comprising a carbonyl group; each of $Z_{21}$, $Z_{22}$ is $—OR_z$, wherein at least one $—OR_z$ comprises an aryl group; each R is hydrogen; and each of m and n is selected from an integer from about 2 to about 24.

In certain embodiments of the block co-polymer, each of $X_1$ and $X_2$ is $CH_2$; each of Y11 and $Y_{12}$ is independently a linking group comprising a carbonyl group; one of $Z_{11}$ and $Z_{12}$ comprises $N(R_z)_2$; each of $Y_{21}$ and $Y_{22}$ is independently a linking group comprising a carbonyl group; each of $Z_{21}$, $Z_{22}$ is $—OR_z$, wherein at least one $—OR_z$ comprises an aryl group; each R is hydrogen; and each of m and n is selected from an integer from about 2 to about 24.

In certain embodiments of the block co-polymer, each of Y11, $Y_{12}$, $Y_{21}$ and $Y_{22}$ is independently a linking group comprising a carbonyl group and comprising a —O(CH2)q- or a —O(CH2)q-, wherein each q is independently an integer from about 1 to about 6 (e.g., 1, 2, 3, 4, 5, 6).

In certain embodiments, the block co-polymer is a component of a composition. The composition may further include a therapeutic agent having a biological effect under physiological conditions. The therapeutic agent may be a small molecule compound, a peptide, an antibody, a protein or a nucleic acid.

In certain embodiments, the block co-polymer is a component of a composition. The composition may further include a diagnostic agent capable of emitting a detectable signal. The diagnostic agent may include a fluorescent label, a radioactive label, or a quantum dot of label.

In another aspect, the composition includes a polymer having a structural unit of Formula (II):

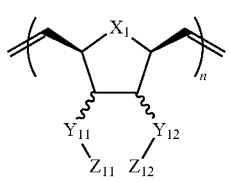

(II)

wherein
X1 is independently O, CH2 or substituted CH2;
$Y_{11}$, $Y_{12}$ each is independently a single bond or a linking group;
Z11, Z12 each is independently hydrogen, or an —N(R)2, alkyl, substituted alkyl, aryl, substituted aryl group, with the proviso that a least one of Z11 and Z12 comprises —

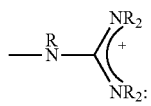

$N(R_z)_2$ or
$R_z$ each is independently hydrogen, an alkyl, substituted alkyl, aryl, substituted aryl, poly(ethylene oxide) group;
R is hydrogen, a C1-C6 alkyl group, or a poly(ethylene oxide); and
n is independently an integer from about 2 to about 300; and a therapeutic agent having a biological effect under physiological conditions.

In certain embodiments, n is an integer from about 2 to about 50, for example from about to about 24, from about 6 to about 20, from about 8 to about 16 (e.g., 2, 3, 4, 5, 6, 7, 8, 9, 10, 11, 12, 13, 14, 15, 16, 17, 18, 19, 20, 21, 22, 23, 24). In certain embodiments, one or both m and n is 25 or greater, 30 or greater, 40 or greater.

In some embodiments of the composition, the therapeutic agent comprises a small molecule compound. In some embodiments of the composition, the therapeutic agent comprises a peptide. In some embodiments of the composition, the therapeutic agent comprises an antibody. In some embodiments of the composition, the therapeutic agent comprises a protein. In some embodiments of the composition, the therapeutic agent comprises a nucleic acid.

In some embodiments of the composition, the polymer comprises a structural unit selected from:

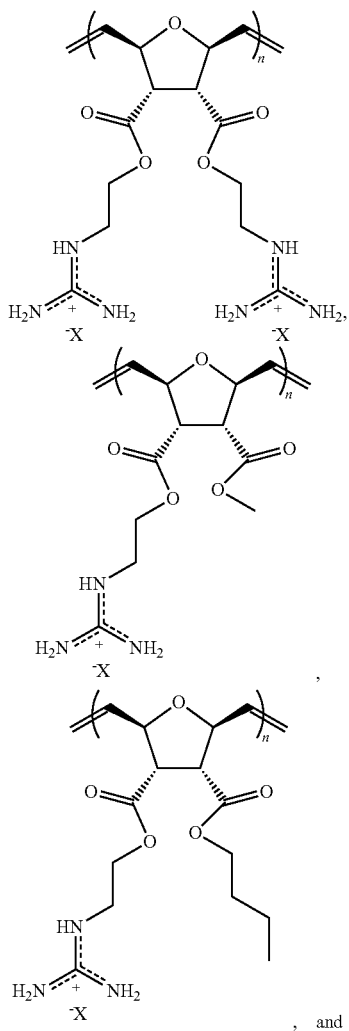

, and

-continued

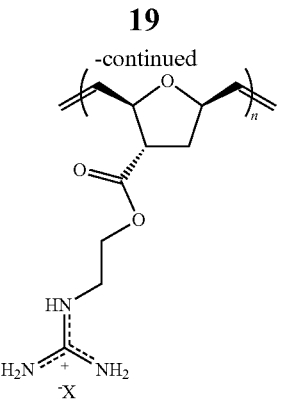

wherein each X is independently a counter anion.

In some embodiments of the composition, the polymer comprises a structural unit of the formula:

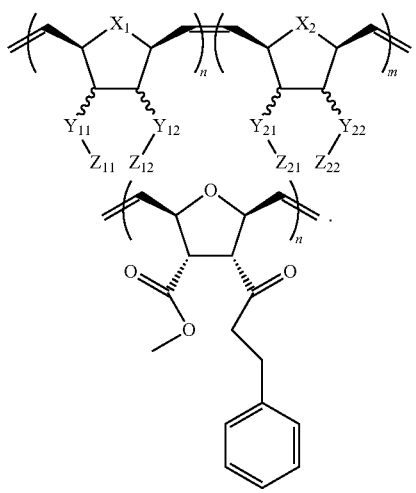
(I)

Each of Y11 and Y12 may be independently a linking group that includes a carbonyl group and —O(CH$_2$)$_q$—, wherein q is an integer from about 1 to about 6 (e.g., 1, 2, 3, 4, 5, 6).

In some embodiments, each of m and n is an integer from about 4 to about 16.

In another aspect, the composition includes a polymer having a monomer of Formula (II):

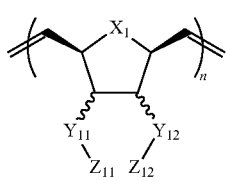
(II)

wherein
X$_1$ is independently O, CH$_2$ or substituted CH$_2$;
Y$_{11}$, Y$_{12}$ each is independently a single bond or a linking group;
Z11, Z12 each is independently hydrogen, an —N(R)2, alkyl, substituted alkyl, aryl, substituted aryl group, with the proviso that a least one of Z11 and Z12 comprises

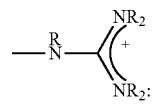

N(R$_z$)$_2$ or

R$_z$ each is independently hydrogen, an alkyl, substituted alkyl, aryl, substituted aryl, poly(ethylene oxide) group;

R is hydrogen, a C1-C6 alkyl group or a poly(ethylene oxide); and n is independently an integer from about 2 to about 300; and a diagnostic agent capable of emitting a detectable signal.

In some embodiments of the composition, the diagnostic agent includes a fluorescent label. In some embodiments of the composition, the diagnostic agent includes a radioactive label. In some embodiments of the composition, the diagnostic agent includes a quantum dot label.

In some embodiments, the composition includes the polymer comprising a structural unit selected from:

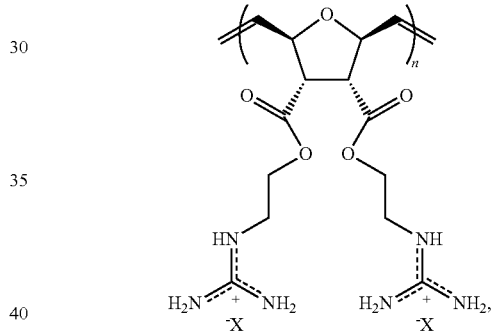

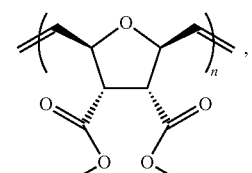

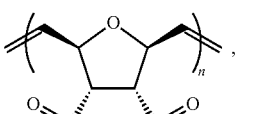
, and

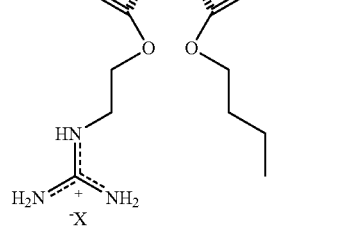

-continued

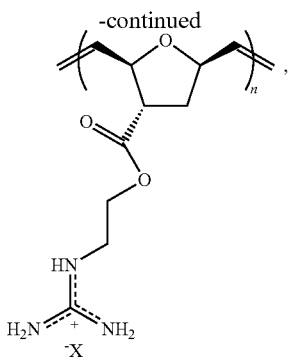

wherein each X is independently a counter anion.

Y11 and Y12 may be independently a linking group comprising a carbonyl group and comprising a —O(CH2)q- or a —O(CH2)q-, wherein q is an integer from about 1 to about 6. Each of m and n may be an integer from about 4 to about 16, for example.

The therapeutic or diagnostic agent may be covalently bonded to or non-covalently associated with the polymer of the invention.

In yet another aspect, the composition includes a block co-polymer having the Formula of (III):

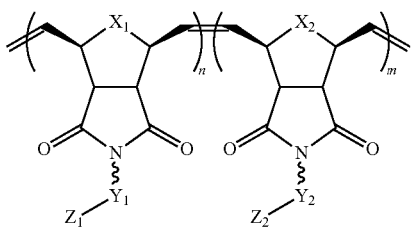

(III)

wherein
$X_1$, $X_2$ each is independently O, $CH_2$ or substituted $CH_2$;
$Y_1$ is a linking group;

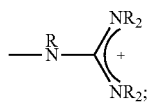

$Z_1$ comprises —N(R)2 or
$Y_2$ is a single bond or a linking group;
$Z_2$ is hydrogen, an alkyl or substituted alkyl group;
$R_z$ is hydrogen, an alkyl, substituted alkyl, aryl, substituted aryl group;
R is hydrogen, a C1-C12 alkyl group or a poly(ethylene oxide) group; and
m, n each is independently an integer from about 2 to about 300.

In certain embodiments, m and n are independently integers from about 2 to about 50, for example from about to about 24, from about 6 to about 20, from about 8 to about 16 (e.g., 2, 3, 4, 5, 6, 7, 8, 9, 10, 11, 12, 13, 14, 15, 16, 17, 18, 19, 20, 21, 22, 23, 24). In certain embodiments, one or both m and n is 25 or greater, 30 or greater, 40 or greater.

In some embodiments of the block co-polymer, each of X1 and X2 is O; $Y_1$ is a linking group comprising a carbonyl group; Y2 is a single bond; Z1 comprises

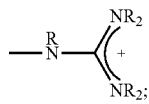

$Z_2$ is R; each R is hydrogen, an alkyl or substituted alkyl group; and each of m and n is selected from an integer from about 4 to about 24.

In some embodiments of the block co-polymer, each of X1 and X2 is O; Y1 is a linking group comprising a carbonyl group; Y2 is a single bond; Z1 comprises —N(R)2; Z2 is R; each R is hydrogen, an alkyl or substituted alkyl group; and each of m and n is selected from an integer from about 4 to about 24.

In some embodiments of the block co-polymer, each of X1 and X2 is O; each of Y1 and Y2 is a linking group comprising a carbonyl group; Z1 comprises

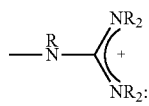

Z2 comprises —N(R)2; each R is hydrogen, an alkyl or substituted alkyl group; and each of m and n is selected from an integer from about 4 to about 24.

In certain embodiments, the block co-polymer has the formula of:

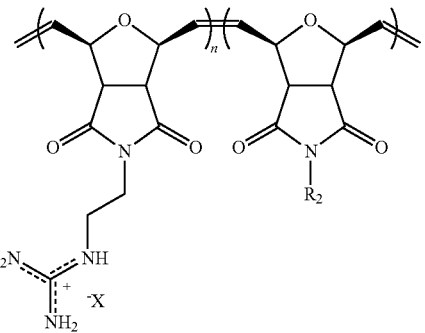

wherein R2 is a C1-C12 alkyl or substituted alkyl group, an aryl or substituted aryl group, or a poly(ethylene oxide) group; X is a counter anion.

In yet another aspect, the invention generally relates to a block copolymer that includes the structural unit of the formula:

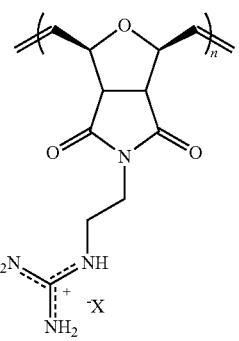

wherein X is a counter anion.

In certain embodiments, the block co-polymer may further include a structural unit of the formula:

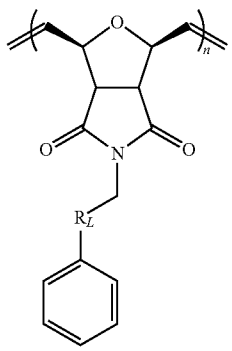

wherein RL is a —(CH2)q-, wherein q is an integer from about 1 to about 6 (e.g., 1, 2, 3, 4, 5, 6).

In certain embodiments, the block co-polymer may further include a structural unit of the formula:

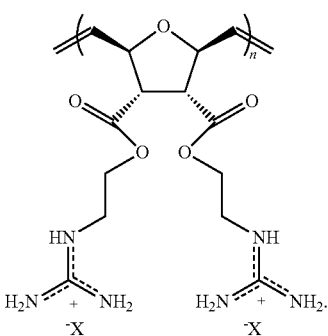

In yet another aspect, the composition includes a polymer having a structural unit of Formula (IV):

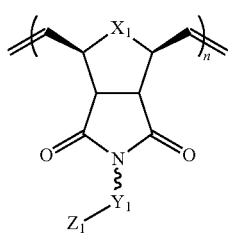
(IV)

wherein
$X_1$ is O, $CH_2$ or substituted $CH_2$;
$Y_1$ is a linking group;

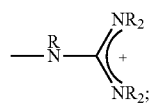

$Z_1$ is comprises —$N(R_z)_2$ or
$R_z$ is hydrogen, an alkyl, substituted alkyl, aryl, substituted aryl group;

R is hydrogen or a C1-C12 alkyl group or a poly(ethylene oxide) group; and
n is independently an integer from about 2 to about 300.
a diagnostic agent capable of emitting a detectable signal.

In some embodiments of the composition, the diagnostic agent includes a fluorescent label. In some embodiments of the composition, the diagnostic agent includes a radioactive label. In some embodiments of the composition, the diagnostic agent includes a quantum dot label.

In certain embodiments, the polymer comprises a structural unit of the formula:

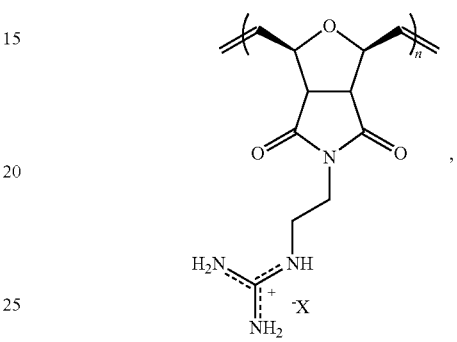

wherein X is a counter anion.

In one embodiment, the polymer comprises

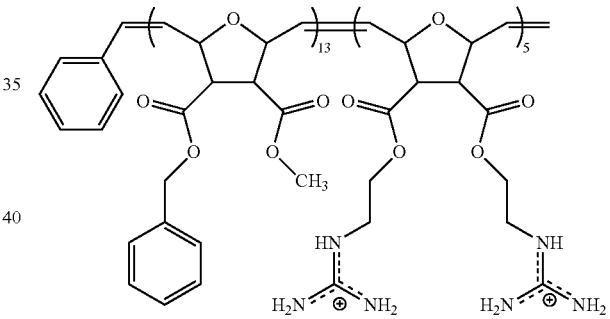

Antibodies

The term "antibody," as used herein, refers to a full-length immunoglobulin molecule or an immunologically-active fragment of an immunoglobulin molecule such as the Fab or F(ab')2 fragment generated by, for example, cleavage of the antibody with an enzyme such as pepsin or co-expression of an antibody light chain and an antibody heavy chain in, for example, a mammalian cell, or ScFv. The antibody can also be an IgG, IgD, IgA, IgE or IgM antibody. Full-length immunoglobulin "light chains" (about 25 kD or 214 amino acids) are encoded by a variable region gene at the amino-terminus (about 110 amino acids) and a kappa or lambda constant region gene at the carboxy-terminus. Full-length immunoglobulin "heavy chains" (about 50 kD or 446 amino acids), are similarly encoded by a variable region gene (about 116 amino acids) and one of the other aforementioned constant region genes, e.g., gamma (encoding about 330 amino acids). Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. In each pair of the tetramer, the light and heavy chain variable regions are together responsible for binding to an antigen, and the constant regions are responsible for the antibody effector functions. In addition to naturally occurring antibodies, immunoglobulins may exist in a variety of other forms including, for example, Fv, ScFv, Fab, and F(ab')$_2$, as well as bifunctional hybrid antibodies and in single chains. Thus, the term "antibody" includes antigen binding antibody fragments, as are known in the art, including Fab, Fab$_2$, single chain antibodies (scFv for example), chimeric antibodies, etc., either produced by the modification of whole antibodies or those synthesized de novo using recombinant DNA technologies.

Exemplary Embodiments

In one embodiment, an ex vivo method to prepare regulatory T cells is provided. The method includes providing a composition comprising complexes comprising a polymer comprising a compound of formula (I) and a modulator of PKCθ and/or a modulator of protein L-aspartate methyltransferase; and contacting a population of mammalian cells comprising T cells with an amount of the composition under conditions effective to induce an increased number of induced regulatory T cells (iTregs) relative to a corresponding population that is contacted with the polymer but not the imodulator or contacted with the modulator but not the polymer, or not contacted with the composition. In one embodiment, the modulator comprises an antibody or a fragment thereof that binds PKCθ or that binds protein L-aspartate methyltransferase. In one embodiment, the antibody or the binding fragment thereof binds to the phosphorylated form of PKCθ. In one embodiment, the antibody or the fragment comprises a humanized antibody. In one embodiment, the cells are human cells. In one embodiment, wherein the population comprises PBMCs. In one embodiment, the population comprises CD4 T cells. In one embodiment, the cells are further contacted with anti-CD3 and anti-CD28 or CD3- or CD28-binding fragments thereof. In one embodiment, the iTregs contacted with the composition have enhanced suppressor function relative to iTregs not contacted with the composition or contacted with the polymer but not the modulator or contacted with the modulator but not the polymer. In one embodiment, the iTregs contacted with the composition have increased amounts or concentrations of phospho-STAT5 and/or CTLA-4 relative to iTregs not contacted with the composition or contacted with the polymer but not the modulator or contacted with the modulator but not the polymer. In one embodiment, the iTregs contacted with the composition comprise cytosolic PKCθ. In one embodiment, the iTregs contacted with the composition have increased amounts or concentrations of CD25 or FOXP3 relative to iTregs not contacted with the composition or contacted with the polymer but not the modulator or contacted with the modulator but not the polymer. In one embodiment, the method includes isolating the iTregs contacted with the composition. A population of iTregs obtained by the method may have increased LAG3, PD-1, FOXP3, IFNγ, or any combination thereof, relative to cells contacted with the polymer but not the modulator, cells contacted with the modulator but not the polymer, or cells not contacted with the composition.

Also provided is a method to increase graft survival in a mammal. The method includes administering to a mammal prior to, during or after graft implant an effective amount of a composition of comprising the Tregs or a composition comprising complexes comprising a polymer comprising a compound of formula (I) and a modulator of PKCθ and/or a modulator of protein L-isoaspartate methyltransferase. In one embodiment, the mammal is a human. In one embodiment, the composition is administered before or after the graft is introduced to the mammal. In one embodiment, the composition is administered when the graft is introduced to the mammal. These super regulatory cells may be employed in therapies such as, but not limited to, a cell-based therapy used in the prevention of Graft-versus-Host Disease (GVHD), a major clinical barrier to the successful use of hematopoietic/bone marrow stem cell transplantation. In other applications, the PTDM-iTregs may be utilized as a cell-based therapy for autoimmune indications including, but not limited to, aplastic anemia, rheumatoid arthritis, Crohn's disease, type 1 diabetes, and/or multiple sclerosis. In one embodiment, the composition is parenterally administered. In one embodiment, the iTregs are derived from the graft donor (allogeneic). In one embodiment the iTregs are autologous.

Routes of Administration, Dosages and Dosage Forms

Administration of the composition in accordance with the present invention may be continuous or intermittent, depending, for example, upon the recipient's physiological condition, and other factors known to skilled practitioners. The administration of the composition may be essentially continuous over a preselected period of time or may be in a series of spaced doses. Both local administration, e.g., intracranial, intranasal or intrathecal, and systemic administration, e.g., using viruses that cross the blood-brain barrier, are contemplated.

One or more suitable unit dosage forms comprising the composition, which may optionally be formulated for sustained release, can be administered by a variety of routes including intracranial, intrathecal, or intransal, or other means to deliver to the CNS, or oral, or parenteral, including by rectal, buccal, vaginal and sublingual, transdermal, subcutaneous, intravenous, intramuscular, intraperitoneal, intrathoracic, or intrapulmonary routes. The formulations may, where appropriate, be conveniently presented in discrete unit dosage forms and may be prepared by any of the methods well known to pharmacy. Such methods may include the step of bringing into association the composition with liquid carriers, solid matrices, semi-solid carriers, finely divided solid carriers or combinations thereof, and then, if necessary, introducing or shaping the product into the desired delivery system.

The amount of composition administered to achieve a particular outcome will vary depending on various factors including, but not limited to, the genes and promoters chosen, the condition, patient specific parameters, e.g., height, weight and age, and whether prevention or treatment, is to be achieved.

Composition may conveniently be provided in the form of formulations suitable for administration, e.g., into the brain. A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences. By "pharmaceutically acceptable" it is meant a carrier, diluent, excipient, and/or salt that is compatible with the other ingredients of the formulation, and not deleterious to the recipient thereof.

Compositions may be formulated in solution at neutral pH, for example, about pH 6.5 to about pH 8.5, or from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, or from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is useful for buffers containing sodium ions. If desired, solutions of the above compositions can also be prepared to enhance shelf life and stability. Therapeutically useful compositions of the invention can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

The compositions can be provided in a dosage form containing an amount of the active agent in one or multiple doses.

Pharmaceutical formulations containing the composition can be prepared by procedures known in the art using well known and readily available ingredients. For example, the active agent can be formulated with common excipients, diluents, or carriers, and formed into tablets, capsules, suspensions, powders, and the like. The compositions can also be formulated as elixirs or solutions appropriate for parenteral administration, for instance, by intramuscular, subcutaneous or intravenous routes.

The pharmaceutical formulations can also take the form of an aqueous or anhydrous solution, e.g., a lyophilized formulation, or dispersion, or alternatively the form of an emulsion or suspension.

In one embodiment, the compositions may be formulated for administration, e.g., by injection, for example, bolus injection or continuous infusion via a catheter, and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

The formulations and compositions described herein may also contain other ingredients such as antimicrobial agents or preservatives.

The invention will be further described by the following non-limiting examples.

Example 1

Immature lymphocytes (CD25−Foxp3−pSTAT5−) after receiving TCR+CD28 signals, become immature iTreg precursors (CD25+Foxp3−pSTAT5−), which in turn when exposed to CD122, IL-2/IL-15 signals, become iTreg precursors (CD25+Foxp3−pSTAT5+) and then, in the presence of CD122, IL-2/IL-15 signals, become iTregs (CD25+ Foxp3+pSTAT5+). It was unknown, prior to testing, if naïve CD4 cells stimulated in the presence of $P_{13}D_5$:anti-PKCθ became Th1, Th2, Th17 or iTregs.

The protocol to be tested included purifying CD4 T cells, treating those cells with anti-PKCθ or rottlerin, washing the cells once with heparin and once with cold PBS, then resuspending the cells in iTreg differentiation media. The cells are counted and the density adjusted to $1\times10^6$ cells/mL. Those cells are then either plated onto anti-CD3 coated plates or incubated with anti-CD3 and anti-CD28, then incubated for 5 days, after which cells are analyzed.

Materials

Anti-human phospho PKCθ (Thr538, Monoclonal Rabbit IgG, Clone: F4H4L1) was purchased from Invitrogen (Carlsbad, Calif.). Human PBMCs were obtained from StemCell Technologies, Inc. (Vancouver, BC, Canada). Antibodies specific for human CD25, CD4, CD45, CD8, NOTCH1$^{1C}$, T-BET, IFNγ, and mouse CD45, and compatible with flow cytometry were purchased from eBioscience, Inc. (San Diego, Calif.). Flow cytometric data were acquired using an LSR II Flow Cytometer, LSRFortessa™ 5 laser (Becton Dickinson, Canaan, Conn.) and analyzed using DIVA 7.0 software (Becton Dickinson) or FlowJo (Treestar, Ashland, Oreg.).

Synthesis of MePh$_{13}$-b-dG$_5$ ($P_{13}D_5$)

We have recently described the synthesis of PTDMs. $P_{13}D_5$ was obtained by ring-opening metathesis polymerization (ROMP) using the Grubbs' third generation catalyst in dichloromethane. The final product was purified by dialysis against RO water and obtained by lyophilization.

Characterization of MePh$_{13}$-b-dG$_5$ ($P_{13}D_5$)

The molecular weight of $P_{13}D_5$ was assessed by gel permeation chromatography. After $P_{13}D_5$ was lyophilized, a sample was analyzed by GPC after calibration using a poly (methyl methacrylate; PMMA) standard. The molecular weight was determined and polydispersity index was calculated. To confirm the chemical composition, proton nuclear magnetic resonance spectroscopy ($^1$H-NMR) was performed. The sample was diluted in deuterated acetonitrile (CD$_3$CN).

Dynamic Light Scattering (DLS)

To characterize the complexation of PTDM and antibody, 1 μM of $P_{13}D_5$ and 25 nM of anti-pPKCθ were complexed in PBS (phosphate buffered saline, pH 7.2) at a specific ratio ($P_{13}D_5$:anti-pPKCθ:40:1). It was incubated for 30 min at room temperature (RT). Later, the complex was loaded into a spectrophotometric cuvette. The size of the complex was measured with a Malvern Zetasizer Nano ZSP instrument (Malvern Instruments, Ltd.)

Native Polyacrylamide Gel Electrophoresis and Silver Staining 4-20% Mini-PROTEAN TGX Precast protein gels were used to run $P_{13}D_5$:anti-pPKCθ complex along with $P_{13}D_5$ only and Anti-pPKCθ only. Each was loaded as 250 μl into individual gels with 7 cm well size and run for 35 min at 200 V in 1× Running buffer (25 mM Tris, 192 mM Glycine, pH 7.2) without the addition of sodium dodecyl sulfate (SDS) for native conditions. The electrodes were swapped since the charge of the complex is positive. Later, the gels were stained with 0.1% silver nitrate and 0.08% formalin (37%). They were imaged using a Syngene G-box gel documentation system (Syngene, A Division of Synoptics, Ltd.)

$P_{13}D_5$:anti-pPKCθ Complex Delivery into Human Peripheral Mononuclear Blood Cells (hPBMCs)

1 μM of $P_{13}D_5$ and 25 nM of anti-pPKCθ were complexed in PBS (phosphate buffered saline, pH 7.2) at a specific ratio ($P_{13}D_5$:anti-pPKCθ:40:1) and AbDeliverIN™:Anti-pPKCθ was complexed in PBS at the ratio recommended by the manufacturer's protocol. The complexes were incubated for 30 min at RT. hPBMCs were treated with the complexes for 4 hours at 37° C. Cells were then harvested and washed with PBS. Later, cells were thoroughly washed twice with 20 U/mL Heparin in PBS for 5 minutes on ice to remove surface-bound complexes outside cellular membrane. Pellets were resuspended in fresh RPMI complete media (10% fetal bovine serum, 100 U/mL penicillin-streptomycin, 1 mM sodium pyruvate, 2 mM L-Glutamine) seeded into 5 pg/mL anti-CD3ε-plus 2.5 pg/mL anti-CD28-coated tissue culture wells and stimulated for 24 hours at 37° C. After stimulation, cells were harvested and washed with PBS. They were fixed and permeabilized (Foxp3 staining kit, eBioscience, according to manufacturer's recommendation) for 30 min at 4° C., then stained with Alexa Fluor488-labeled anti-rabbit IgG (Cell Signaling Technology, Inc.) for 30 min at 4° C. Labeled cells were washed and analyzed by flow cytometry to measure delivery efficiency.

Cellular Viability Assay hPBMCs were stained with 7-Aminoactinomycin D (7-AAD, eBioscience) for 15 min at RT, then pelleted by centrifugation for 5 min. Cells were resuspended in 0.2% BSA in PBS and analyzed by flow cytometry.

Flow Cytometric Analyses of Marker Expression hPBMCs were treated with DMSO or 3 μM Rottlerin for 30 min or with $P_{13}D_5$:anti-pPKCθ for 4 hours at 37° C. Following treatment, cells were washed with PBS and resuspended in fresh RPMI complete media. Later, $P_{13}D_5$:anti-pPKCθ-treated cells were thoroughly washed twice with 20 U/mL Heparin in PBS for 5 minutes on ice to remove non-internalized complexes. Cells were stimulated by seeding into anti-CD3ε-plus anti-CD28-coated wells and incubated at 37° C. Some cells were stimulated for 24 hours prior to treatment. At 24, 48, and 72 hours after treatment, cells were harvested and washed with PBS. Then, hPBMCs were stained with antibodies specific for surface (CD25, CD69) or intracellular (NOTCH1$^{IC}$, T-BET) proteins and analyzed by flow cytometry.

Cell Proliferation Assay hPBMCs were treated with DMSO or 3 μM Rottlerin for 30 min or with $P_{13}D_5$:anti-pPKCθ for 4 hours at 37° C. Following treatment, cells were washed with PBS and resuspended in fresh RPMI complete media. Later, $P_{13}D_5$:anti-pPKCθ-treated cells were thoroughly washed twice with 20 U/mL Heparin in PBS for 5 minutes on ice. After washing with Heparin, cells were resuspended in prewarmed PBS+0.1% BSA and cells were labeled with carboxyfluorescein succinimidyl ester (CFSE) dye using the Cell Trace™ CFSE Cell Proliferation Kit (Thermo Scientific, Inc.) following the manufacturer's protocol. Cells were stimulated by seeding into anti-CD3ε-plus anti-CD28-coated wells and incubated at 37° C. for 7 days. Cell proliferation was measured daily by flow cytometric analysis.

Enzyme Linked Immunosorbent Assay (ELISA) for Cytokine Determination hPBMC culture supernatants were collected at designated timepoints and analyzed for cytokine secretion. 96-well Maxisorp plates were coated overnight at 4° C. with the appropriate capture antibody (anti-human IFNγ or anti-human IL-2; BD Biosciences, San Diego, Calif.). Non-specific protein binding was prevented by blocking wells with 10% FBS in PBS for 3 hours at RT. Culture supernatants and standards were diluted appropriately and added to wells. The plate was incubated overnight at 4° C., with continuous rocking. Biotinylated detection antibodies were added to wells followed by TMB substrate reagents (BD Biosciences) at a 1:1 ratio. Color development was monitored and the reaction was terminated by the addition of stop solution (2 N $H_2SO_4$). Absorbance was read at 450 nm using a microplate reader.

Cytokine concentrations were determined relative to the standard curves generated.

Nuclear vs. Cytosolic Protein Extraction $3 \times 10^6$ cells/mL hPBMCs were used for each sample. Cells were harvested 24 hours after anti-CD3ε plus anti-CD28 stimulation. Nuclear and cytosolic protein extracts were generated using NE-PER™ Nuclear and Cytoplasmic Extraction Reagents (Thermo Scientific, Inc., Agawam, Mass.). Protein concentration was determined by BCA Assay and 40 pg (cytoplasmic extract) or 50 pg (nuclear extract) of protein was separated by 8% SDS-PAGE. Total PKCθ was detected using rabbit polyclonal anti-PKCθ (C-18) (Santa Cruz Biotechnology, Inc., Dallas, Tex.).

Immunoblotting $2 \times 10^6$ cells/mL hPBMCs were used for each sample. Cells were harvested 24 hours after anti-CD3ε plus anti-CD28 stimulation, pelleted, and resuspended in RIPA lysis buffer containing protease and phosphatase inhibitors (25 mM Tris-HCl pH 7.6, 150 mM NaCl, 1% NP-40, 1% sodium deoxycholate, 0.1% SDS, Halt™ Protease and Phosphatase Inhibitor Cocktail). The suspension was centrifuged for 10 min at 4° C. The supernatants were collected as protein lysates, BCA assay was performed to determine protein concentration, and 30 pg of protein was loaded for immunoblotting. CARMA1 Ser652 phosphorylation was detected with anti-phospho-CARD11 (Ser652; Cell Signaling Technology, Inc., Danvers, Mass.). PKCθ Ser676 phosphorylation was detected with anti-phospho-PRKCQ (Ser676; LifeSpan Biosciences, Inc., Burlington, N.C.), and intracellular NOTCH1 levels were detected with anti-cleaved NOTCH1 (Va11744; Cell Signaling Technology, Inc.).

In Vitro Human Th1 Cell Differentiation Assay hPBMCs were sorted for CD4 T cells using FACSAria II flow sorter. Then, the cells were treated with DMSO or 3 μM Rottlerin for 30 min or with $P_{13}D_5$:anti-pPKCθ for 4 hours at 37° C. Following treatment, cells were washed once with PBS and twice with 20 U/mL Heparin in PBS for 5 minutes on ice. For Th1 differentiation, they were resuspended in human Th1 differentiation media (provided in CellXVivo™ human Th1 cell differentiation kit, R&D systems). The cells were plated on human anti-CD3-coated wells. Th1-polarized cells were incubated for 5 days. After 5 days of incubation for Th1 cells, the cells were washed with RPMI complete media and restimulated for 1 hour in the media with 50 ng/mL PMA and 1 μg/ml Ionomycin. Following the restimulation, they were incubated with Monensin for 3 hours before cytokine analysis via flow cytometry.

Ex Vivo Delivery of $P_{13}D_5$:Anti-pPKCθ Complex into hPBMCs Subsequently Transferred into NSG Mice Animal protocols were approved by the Institutional Animal Care and use Committee of the University of Massachusetts Amherst. NOD.Cg-Prkdc$^{scid}$ $^{II}$2rg$^{tm1Wjl}$/SzJ (NSG) mice were purchased from the Jackson Laboratory (Bar Harbor, Me.). Mice were conditioned with 2 Gy of total body irradiation using a $^{137}$Cs source then rested for 4-6 hours. hPBMCs were treated with DMSO or 3 μM Rottlerin for 30 min or with $P_{13}D_5$:anti-pPKCθ for 4 hours at 37° C.

10×10$^6$ treated hPBMCs in 150 μl of PBS were injected into mice via the tail vein. Body weight and disease symptoms were observed daily. Bone marrow, spleen, and peripheral blood were collected on day 17 to assess percent engraftment of hPBMCs (% positive human CD45/(% positive human CD45 cells +% positive mouse CD45 cells)) and infiltration of human CD4 and CD8$^+$ T cells. Also, the human CD4$^+$ and CD8$^+$ T cells were analyzed for CD25, pPKCθ (Thr538), NOTCH1$^{IC}$, and T-BET expression.

Assessment of GvHD

Some mice were assigned to survival studies to assess whether treating hPBMCs, ex vivo, with $P_{13}D_5$:anti-pPKCθ had a durable effect on the function of the transferred hPBMCs, in vivo. The severity of GvHD was assessed using a standardized scoring system, and which included five different criteria (weight loss, posture, activity, fur texture, and skin integrity). Mice were evaluated on daily basis and graded from 0 (the least severe) to 2 (the most severe) for each criterion. Clinical score was generated by adding grades for five criteria. When a clinical score of "8" was reached, mice were removed from the study and humanely euthanized. The day of removal from the study was recorded as the day of lethal GvHD induction.

Cytometric Bead Array

IL-2 and IFNγ cytokine levels in plasma collected from NSG mice were determined by using human IFNγ and IL-2 Flex Sets (BD Biosciences). Data were acquired using a Fortessa 5 Laser Flow Cytometer (BD Biosciences) and analyzed using FCAP array software (Soft Flow Inc.).

Results and Discussion

PTDM Design and Characterization

For this study, we utilized a single PTDM, MePh$_{13}$-b-dG$_5$ ($P_{13}D_5$), which has 13 repeats of a hydrophobic moiety and 5 repeats of a guanidinium monomer on a polyoxanorbornene di-ester polymer scaffold. The choice of $P_{13}D_5$ was based on our previous work that showed that increasing the number of phenyl groups increased the protein delivery efficiency.

$P_{13}D_5$ was synthesized using ROMP, allowing for controlled, facile synthesis of the block copolymer. The polymer structure was characterized by $^1$H-NMR and its molecular weight was determined by gel permeation chromatography. Later, $P_{13}D_5$ was complexed with anti-pPKCθ and the complex formation was shown both by dynamic light scattering and native gel electrophoresis. The size and polydispersity index (PDI) of $P_{13}D_5$:anti-pPKCθ complex was measured via dynamic light scattering. The high PDI for $P_{13}D_5$ only and Anti-pPKCθ only samples showed that there was an aggregation when present alone in solution. The low PDI and narrow size distribution (narrow peak around 1 μm size) for the $P_{13}D_5$-anti-pPKCθ mixture indicated that two components formed complexes. We confirmed the complex formation using native gel electrophoresis. The $P_{13}D_5$:anti-pPKCθ complex could be visualized on the native gel with an apparent molecular weight between 1,000-1,200 kDa. Anti-pPKCθ only could be detected as free antibody, migrating at approximately 150 kDa, and as aggregates with two different sizes of ~480 kDa and ~1,200 kDa. These results confirmed that no free antibody could be detected following complexing with $P_{13}D_5$ at the ratios used in this study.

Anti-pPKCθ (Thr538) Delivery into hPBMCs

The antibody that we complexed to $P_{13}D_5$ specifically recognizes human phosphorylated PKCθ (Thr538). We incubated the $P_{13}D_5$:anti-pPKCθ complex with hPBMCs then assessed the uptake efficiency and cellular toxicity. For comparison, we also tested anti-pPKCθ uptake with a commercially available antibody delivery reagent, AbDeliverIN™. To determine the amount of antibody delivered intracellularly, we subsequently permeabilized the hPBMCs then stained them with a fluorescently-labeled secondary antibody.

Using flow cytometric analysis, we detected robust fluorescence intensity in cells incubated with $P_{13}D_5$:anti-pPKCθ complexes and stained with the fluorescent secondary antibody. Approximately 60% of hPBMCs stained positively for Anti-pPKCθ with an average MFI of 4000 a.u., indicating highly-efficient Anti-pPKCθ delivery. This is in stark contrast to hPBMCs that were incubated with $P_{13}D_5$ alone, anti-pPKCθ alone, or AbDeliverIN™:Anti-pPKCθ complexes, prior to staining with fluorescent secondary antibody. Moreover, when we measured the amount of antibody present in the cells over time, we observed that Anti-pPKCθ could be detected for up to 72 hours. Cell viability for $P_{13}D_5$:anti-pPKCθ-treated PBMCs remained above 80%, suggesting the complex had minimal toxicity.

$P_{13}D_5$:Anti-pPKCθ Delivery into 'Unstimulated' hPBMCs Greatly Reduces their Activation Potential.

To determine whether intracellular anti-pPKCθ delivery neutralizes the actions of pPKCθ, we further analyzed cell proliferation, protein expression levels of signature T cell activation and differentiation molecules via flow cytometry, with and without $P_{13}D_5$:anti-pPKCθ treatment. We delivered $P_{13}D_5$:anti-pPKCθ to hPBMCs 4 hours before the cells were stimulated with plate-bound anti-CD3ε plus anti-CD28. Pre-treating hPBMCs prior to stimulation did not affect cell viability or cellular proliferation but resulted in a significant impact on biological function. Specifically, expression of the high-affinity IL-2 receptor, CD25, the earliest inducible cell surface glycoprotein, CD69, the intracellular, signaling-competent form of the NOTCH1 transmembrane receptor, NOTCH1$^{IC}$, and the Th1 transcriptional regulator, T-BET were all significantly reduced compared to levels in DMSO-treated cells. Rottlerin treatment was included as positive control since it is known to prevent Thr538 phosphorylation of PKCθ[9]. Pretreating hPBMCs with $P_{13}D_5$:anti-pPKCθ resulted in similar low levels of expression of all the assayed proteins, as did treatment with rottlerin.

Furthermore, expression of CD25, NOTCH1$^{IC}$, and T-BET all remained significantly lower in $P_{13}D_5$:anti-pPKCθ-treated cells, compared to DMSO controls, even at 72 hours after treatment. Compared with DMSO controls, CD69 levels were downregulated in $P_{13}D_5$:anti-pPKCθ-treated cells 24 hours after treatment and were not upregulated for 72 hours. To assess the functional impact on PKCθ activity of delivered $P_{13}D_5$:anti-pPKCθ, we also analyzed expression of two important pro-inflammatory cytokines produced by activated T cells, IFNγ and IL-2, using standard ELISA techniques. We observed that IFNγ and IL-2, both, were significantly lower after $P_{13}D_5$:anti-pPKCθ treatment during the 24 to 72 hour cell culture period, showing reduced levels that were comparable to those of rottlerin-treated cells. In addition, we asked whether $P_{13}D_5$:anti-pPKCθ treatment was reversible. To test this, we incubated hPBMCs with $P_{13}D_5$:anti-pPKCθ for 7 days and measured IFNγ and IL-2 levels via cytometric bead array analyses. We observed that IFNγ levels were similar by Day 5 after treatment whereas IL-2 levels were similar by Day 6 after treatment suggesting the early inhibitory effects of Anti-pPKCθ treatment were reversible within 5-6 days of treatment. Taken together, these results indicated that $P_{13}D_5$:anti-pPKCθ treatment of T cells prior to delivery of T cell receptor and costimulatory signals greatly reduced their activation potential.

$P_{13}D_5$:Anti-pPKCθ Delivery into 'Activated' hPBMCs Diminishes Expression of Downstream Activation Markers.

In humans, PKCθ in activated T cells contributes to the pathology of various aberrant immune conditions[30] and elevated levels of phosphorylated PKCθ (Thr538) have been observed both in activated CD4 and CD8 T cells. Therefore, we asked what effect delivering $P_{13}D_5$:anti-pPKCθ has on cells which have already been activated and show increased levels of phosphorylated PKCθ (Thr538). When hPBMCs were stimulated for 24 hours with anti-CD3ε plus anti-CD28, then incubated with $P_{13}D_5$:anti-pPKCθ, levels of CD25, NOTCH1$^{IC}$, and T-BET were significantly lower following an additional 24 hours of culture (48 hours from time of stimulation), compared to DMSO-treated cells. Interestingly, $P_{13}D_5$:anti-pPKCθ-treated cells did not upregulate these markers, even up to 72 hours after treatment (96 hours after stimulation). This was not due to toxicity of the treatment since cellular viability in $P_{13}D_5$:anti-pPKCθ-treated cells remained similar to DMSO-treated cells. Additionally, CD69 levels were not upregulated in $P_{13}D_5$:anti-pPKCθ-treated cells for 72 hours. Finally, stimulated cells treated with $P_{13}D_5$:anti-pPKCθ produced significantly lower amounts of IFNγ and IL-2 compared to DMSO-treated controls and, again, at levels comparable to those of rottlerin-treated sample.

We also asked whether anti-pPKCθ or $P_{13}D_5$, individually, exerted any biological effect on T cells. hPBMCs were treated either with anti-pPKCθ alone or with $P_{13}D_5$ alone, and levels of NOTCH1$^{IC}$ and T-BET were measured after 24 hours of stimulation. When compared to DMSO-treated cells, we found there were no significant differences in NOTCH1$^c$ or T-BET levels in anti-pPKCθ-only-treated or in $P_{13}D_5$-only-treated cells after 24 hours. These observations suggest complex formation between antibody and $P_{13}D_5$ is necessary for intracellular anti-pPKCθ delivery and modulation of PKCθ function.

$P_{13}D_5$:Anti-pPKCθ Delivery Alters the Activity and Localization of PKCθ in hPBMCs.

The PKCθ signaling pathway coordinates important signaling events to direct Th1 cell functions. Following its phosphorylation on Thr538, PKCθ is autophosphorylated at serine residues to become fully activated. pPKCθ will phosphorylate an intracellular scaffold protein, CARMA1, to facilitate formation of the macromolecular signaling aggregate known as the CARMA1/BCL10/MALT1 (CBM) complex. Assembly of the CBM components precedes, and is thought to be necessary for, liberation of NF-κB transcriptional regulators from their cytosolic inhibitory complexes. Moreover, it has been reported that pPKCθ is also able to translocate into the nucleus where it can associate with a chromatin-bound complex to regulate IL2 gene expression. Having demonstrated that $P_{13}D_5$:anti-pPKCθ delivery modulated biological functions, we asked whether this might be due to its interfering with specific downstream actions of PKCθ.

To address this question, we evaluated PKCθ autophosphorylation at Ser676 residue, CARMA1 phosphorylation, NOTCH1$^{IC}$ levels, as well as nuclear localization of PKCθ. Compared to control-treated cells, hPBMCs treated with $P_{13}D_5$:anti-pPKCθ showed reduced Ser676 autophosphorylation and decreased levels of CARMA1 phosphorylation. In addition, the level of cleaved NOTCH1$^{IC}$ was diminished following anti-pPKCθ delivery. Moreover, when we assessed the accumulation of total PKCθ in the nucleus, we noted that $P_{13}D_5$:anti-pPKCθ-treated cells exhibited less total PKCθ in the nucleus than did DMSO-treated cells. However, there was no change in cytosolic levels of total PKCθ. Thus, not only does $P_{13}D_5$:anti-pPKCθ delivery into hPBMCs reduce the activation potential of unstimulated cells for up to 72 hours after treatment, it also reduces the ability of stimulated cells to sustain increased expression of various markers of activation. Our mechanistic studies suggest this may result from the combination of reduced CARMA1 phosphorylation and impaired nuclear translocation of PKCθ in $P_{13}D_5$:anti-pPKCθ-treated cells.

Ex Vivo Delivery of $P_{13}D_5$:Anti-pPKCθ into hPBMCs Provides a Survival Benefit in a Lymphocyte Transfer, Humanized Mouse Model of Graft-Versus-Host Disease (GvHD).

Our in vitro experiments demonstrated that $P_{13}D_5$:anti-pPKCθ delivered into hPBMCs effectively reduced the functional activity of PKCθ up to 72 hours in culture. However, it was unclear how durable the effects of our ex vivo treatment would be if these treated cells were used in proof-of-principle, lymphocyte transfer experiments in a "humanized" model of GvHD, induced when hPBMCs are transferred into the NOD-scid-Il2γ$^{null}$ (NSG) strain of mice. In this graft (hPBMCs)-versus-host (NSG mouse) model, transferred lymphocytes acutely target the bone marrow of recipient mice resulting in lethal immune-mediated bone marrow failure within approximately 20 days. Th1 cells play an important role in the progression of GvHD. Moreover, PKCθ and NOTCH1 signaling are required for alloreactivity and GvHD induction. To evaluate the long-term effects of $P_{13}D_5$:anti-pPKCθ treatment on cells, we induced GvHD in three cohorts of mice. In one cohort, we induced GvHD by transferring DMSO-treated hPBMCs; in a second cohort we induced GvHD with $P_{13}D_5$:anti-pPKCθ-treated hPBMCs; in the third cohort we induced GvHD using hPBMCs pre-treated with rottlerin. We harvested mice on day 17 after GvHD induction to determine how well the transferred cells engrafted and expanded in target tissues such as the spleen and bone marrow, as well as in peripheral blood. Mice that received $P_{13}D_5$:anti-pPKCθ-treated cells showed a similar degree of hPBMC expansion as DMSO-treated control cells, indicating $P_{13}D_5$:anti-pPKCθ treatment did not affect cellular viability in vivo, following cell transfer. Additionally, we determined that infiltration of human CD and CD8 T cells into the target tissues were also similar in mice receiving DMSO-treated or $P_{13}D_5$:anti-pPKCθ-treated hPBMCs. To determine whether the effects of Anti-pPKCθ treatment were consistent with in vitro results, we measured levels of pPKCθ, T-BET, NOTCH1$^{IC}$, and CD25 in CD4$^+$ T cells infiltrating the bone marrow, in $P_{13}D_5$:anti-pPKCθ-treated hPBMCs, although the differences were not significant compared to DMSO or to rottlerin-treated hPBMCs. Furthermore, we did not see any upregulation in CD25 or NOTCH1$^{Ic}$ levels, as measured by flow cytometry. We also measured IL-2 and IFNγ levels in the plasma of mice from all three cohorts. Although IL-2 levels were similar in all animals evaluated. IFNγ levels were significantly lower in mice receiving $P_{13}D_5$:anti-pPKCθ-treated PBMCs, compared to mice receiving DMSO-treated control cells. We next asked whether delivering $P_{13}D_5$:anti-pPKCθ to hPBMCs prior to transferring them into recipient mice would affect GvHD severity and survival. Remarkably, GvHD clinical scores were significantly reduced and Kaplan-Maier analysis revealed a significant survival benefit when $P_{13}D_5$:anti-pPKCθ was delivered to hPBMCs prior to transfer, compared to mice that received DMSO-treated cells.

Two of three mice that received hPBMCs pre-treated with rottlerin did not show overt signs of disease. However, no human cells were detected in the peripheral blood of these mice, when they were removed from the study on day +70

(data not shown), suggesting GvHD was not induced in those mice since rottlerin treatment also had cytotoxic effects on hPBMCs. These observations are consistent with other data from our lab supporting the notion that PKCθ plays a critical role in T cell activation, proliferation, and survival. Collectively, our data demonstrate that we can modulate PKCθ activity in hPBMCs, ex vivo, using anti-pPKCθ delivery by $P_{13}D_5$. Furthermore, our in vivo proof-of-principle experiments suggest the effects of $P_{13}D_5$:anti-pPKCθ delivery are durable and may constitute the basis of a therapeutic strategy that targets the actions of intracellular proteins to alter disease progression.

Example 2

In order to investigate whether PTDM:anti-pPKCθ delivery affects Treg differentiation, we modified an existing in vitro differentiation assay used to generate induced Tregs (iTreg). Human CD4 T cells were isolated from total PBMCs and treated either with DMSO, as a control, or with PTDM:anti-pPKCθ. Later, the cells were resuspended in iTreg differentiation media. The cells were cultured for 5 days in anti-CD3+anti-CD28-coated tissue culture wells. The percentage of iTregs generated using PTDM:anti-pPKCθ treatment was approximately 2.5 fold higher, compared to compared to DMSO-treated cells. When we measured the expression of iTreg-specific phenotypic markers in those CD4+CD25+Foxp3+ T cells, we observed slightly decreased expression of CD25 and Foxp3 on PTDM:anti-pPKCθ treated cells, compared to DMSO-treated controls (FIG. 39).

Figure 40D:
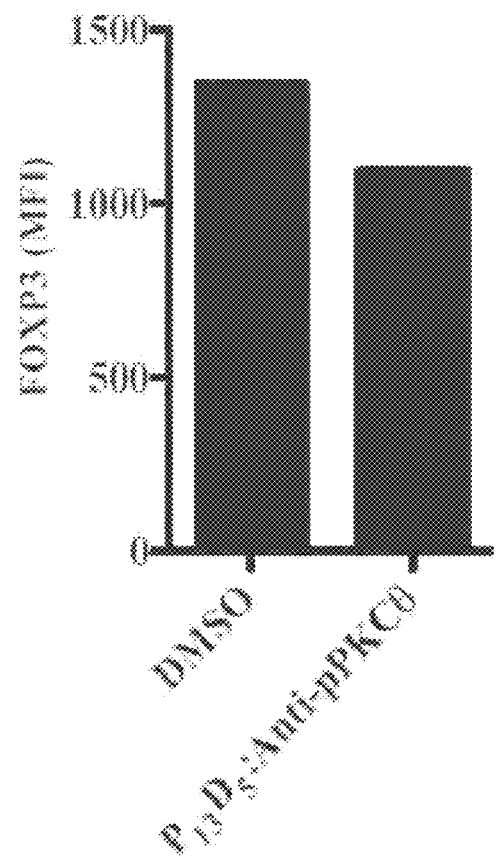
Figure 40E:
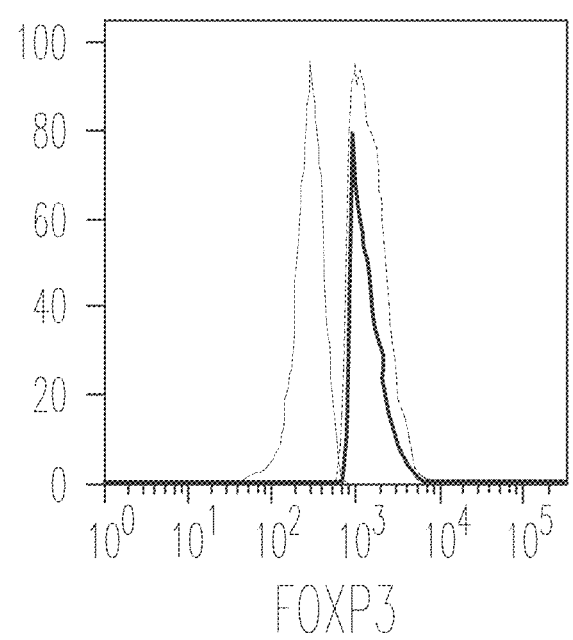
Figure 41A:
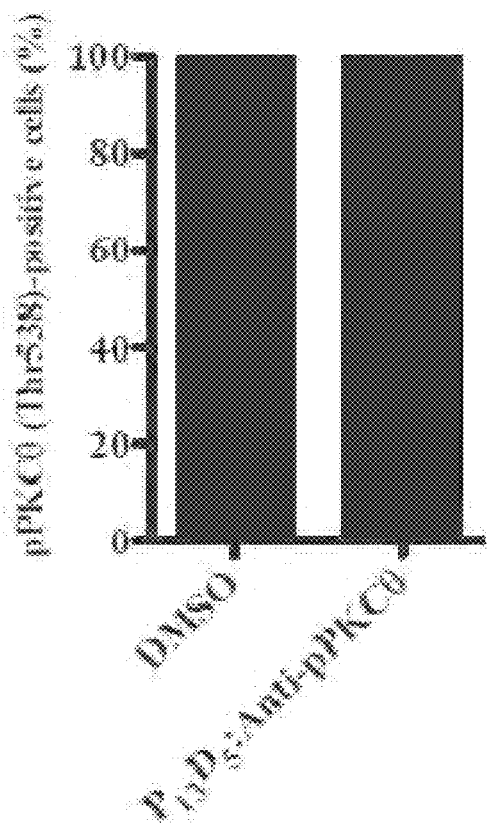
Figure 41B:
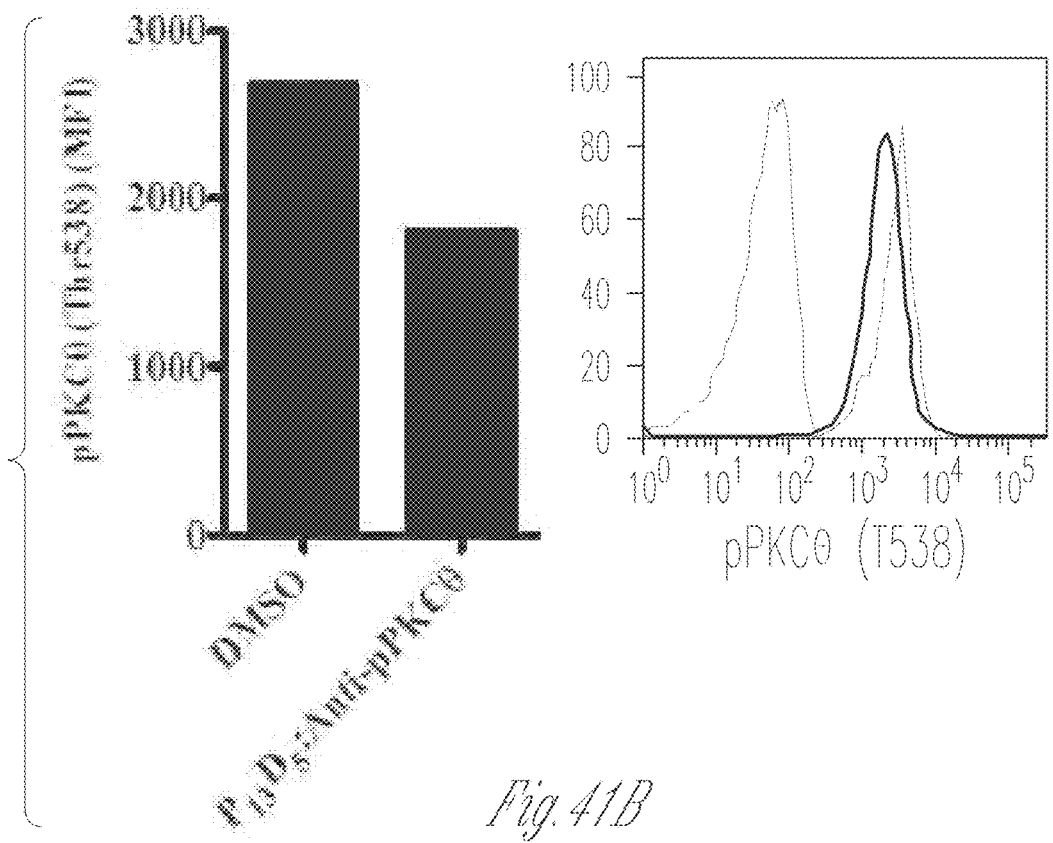
Figure 41C:
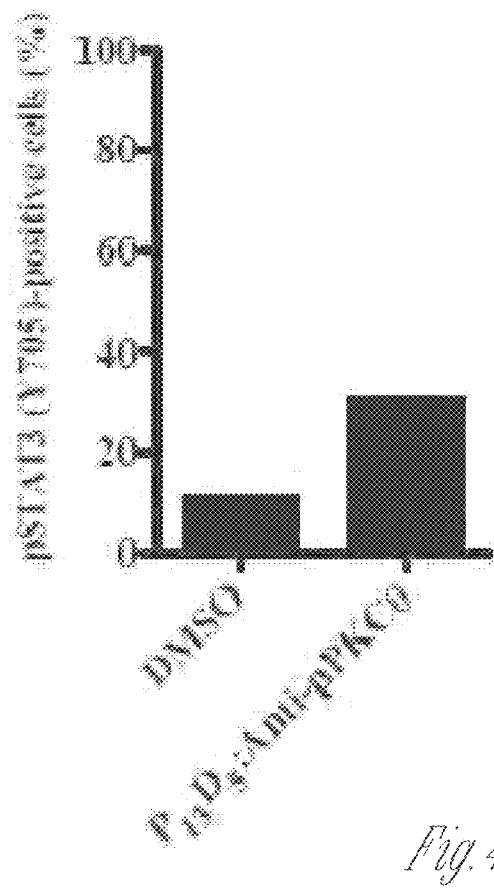
Figure 41D:
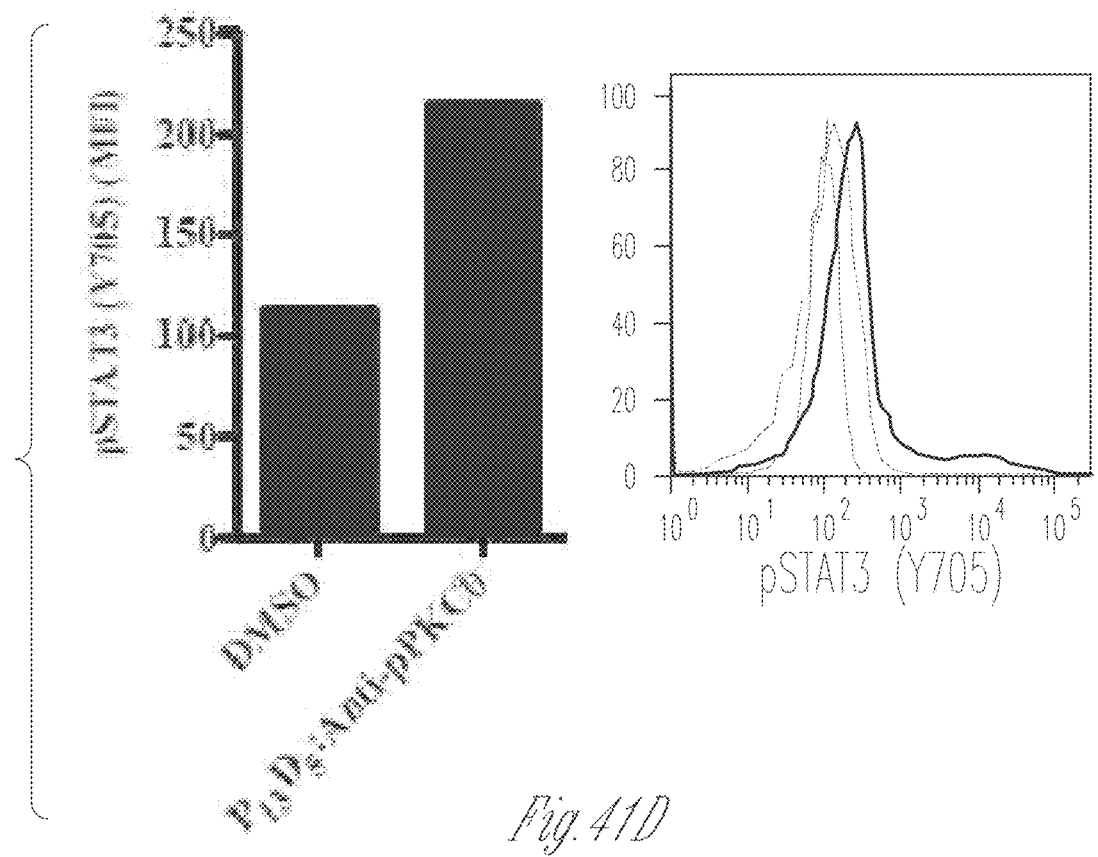
Figure 41E:
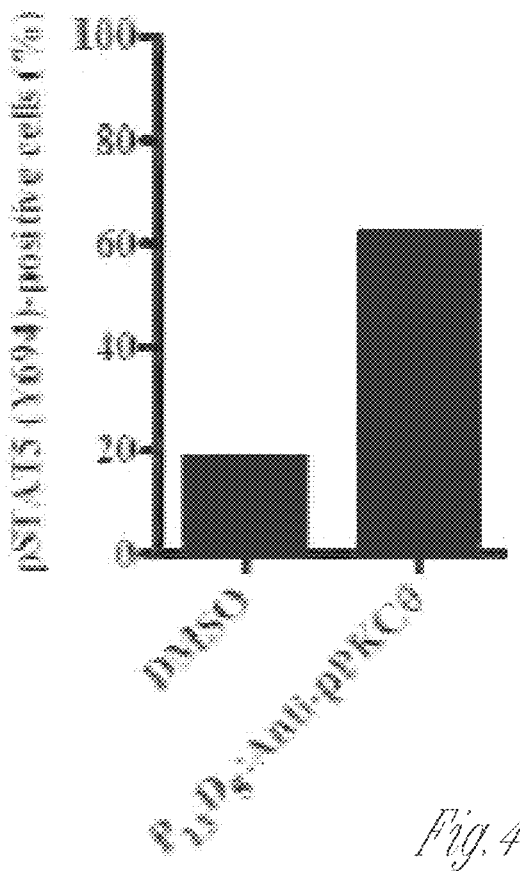
Figure 41F:
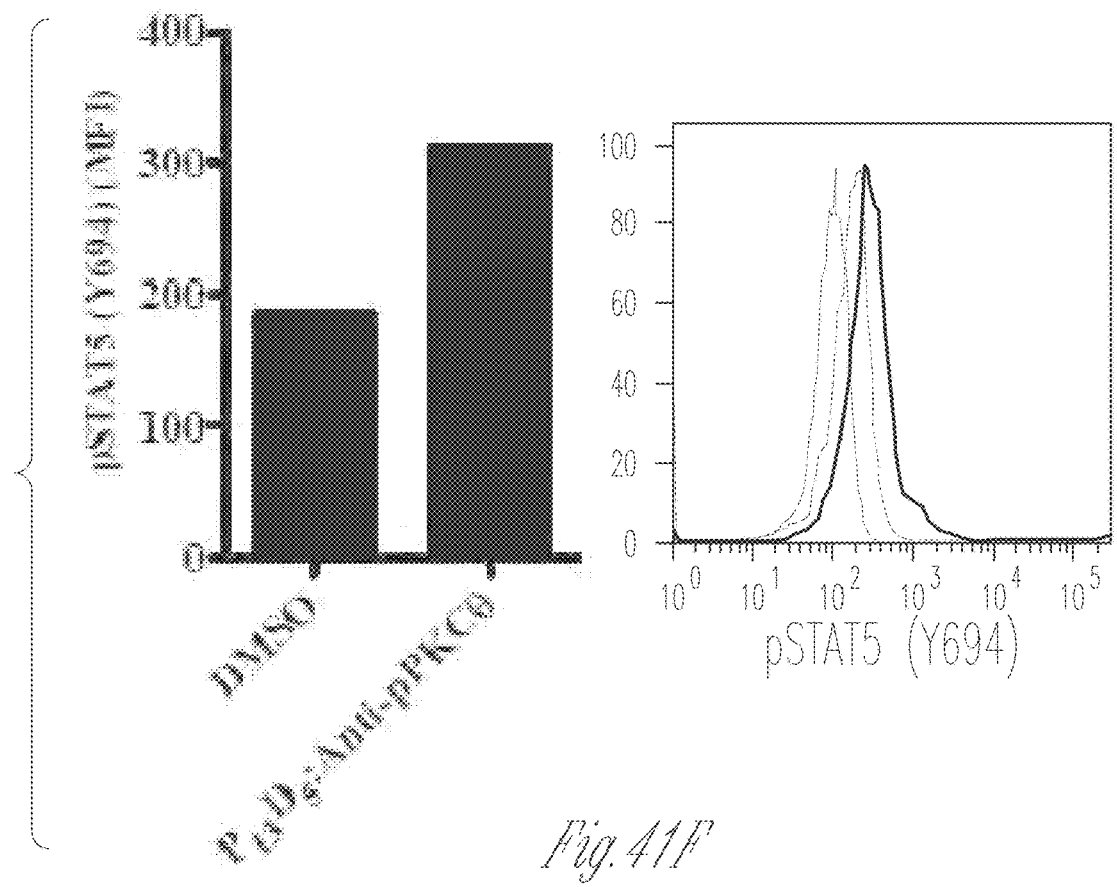
Figure 41G:
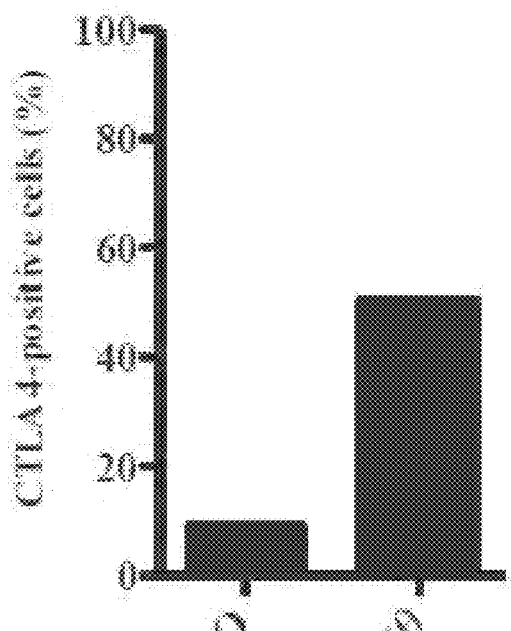
Figure 41H:
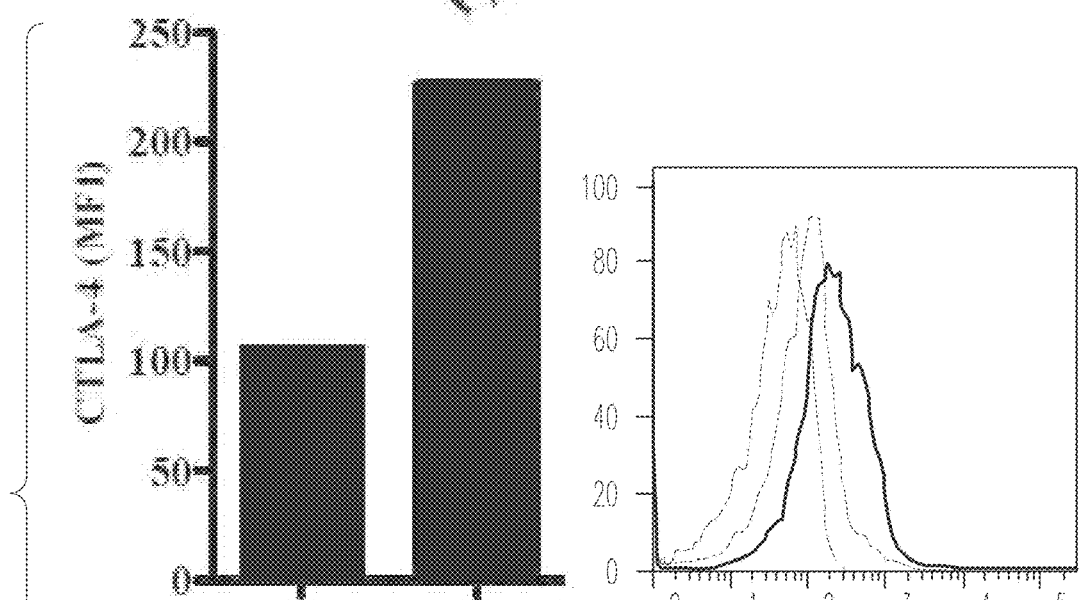
Figure 42C:
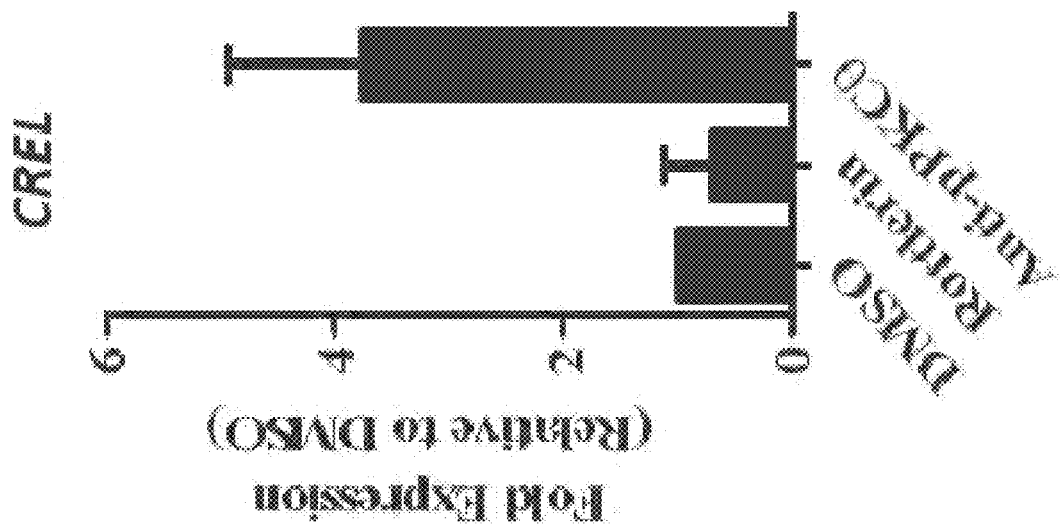
FIGS. 42A-E. Gene expression changes in PTDM:anti-pPKCθ-generated iTregs. Human CD4 T cells were treated with DMSO, Rottlerin, or PTDM:anti-pPKCθ and resuspended in iTreg differentiation media for 5 days in the presence of anti-CD3 and anti-CD28 stimulation, as described. At the end of 5 days, total RNA was isolated from DMSO- or PTDM:anti-pPKCθ-generated iTregs, using the (CellXVivo Human Treg Cell Differentiation Kit, R&D Systems, Minneapolis, Minn.) following the manufacturer's directions. RNA was converted to cDNA by incubating samples with M-MLV Reverse transcriptase enzyme (Promega, Madison, Wis.) and amplifying using oligoDTs and tandard PCR methods. Gene amplification was accomplished utilizing quantitative real-time PCR, using specific forward and reverse primers designed to amplify IL10 (A), FOXP3 (B), CREL (C), PRKCQ (D), and IL2 (E). Expression of these genes in DMSO-treated iTregs was set to "1.0". Fold differences in gene expression were calculated are shown relative to DMSO-treated iTreg control cells.
Figure 42B:
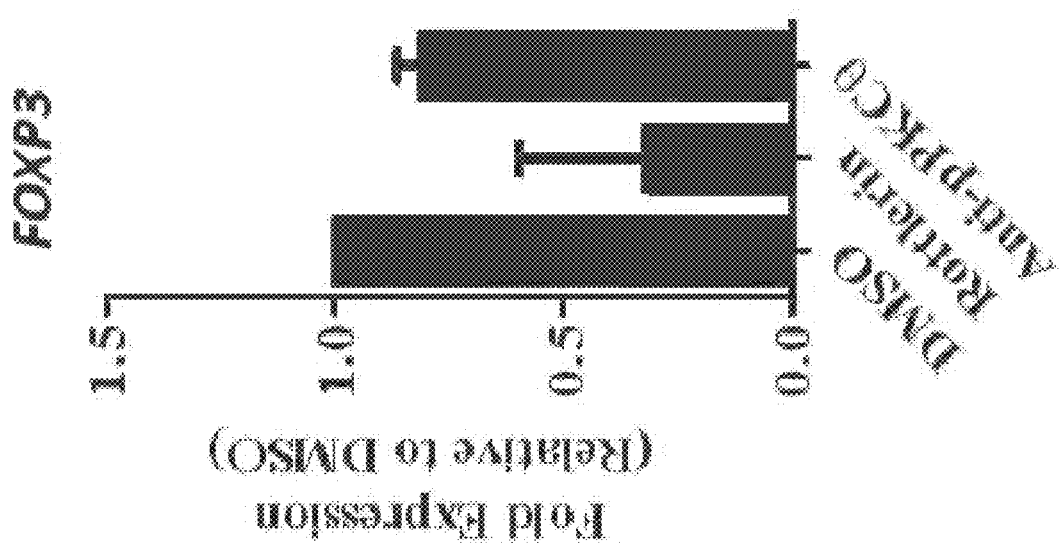
Figure 42A:
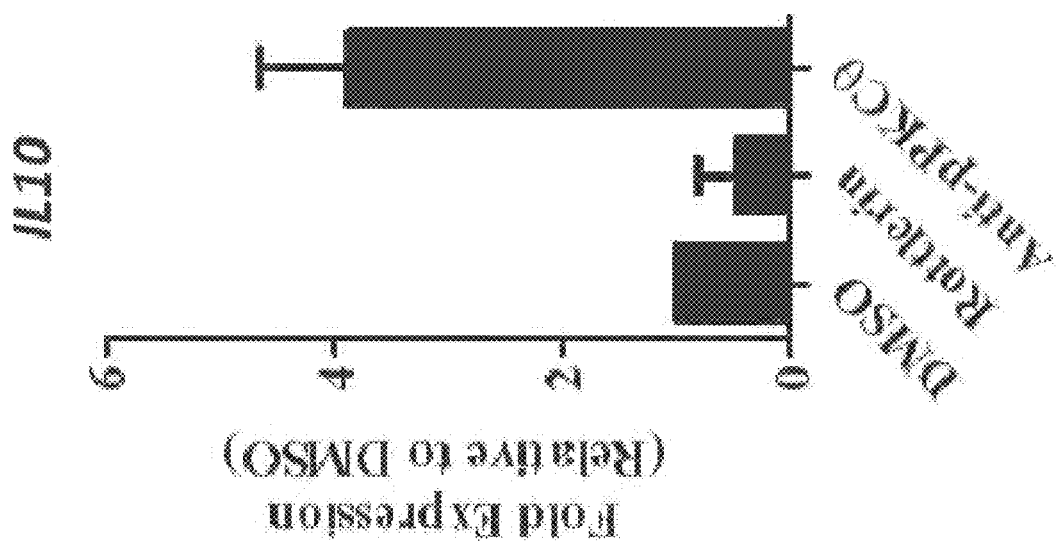
Figures 42D, 42E:
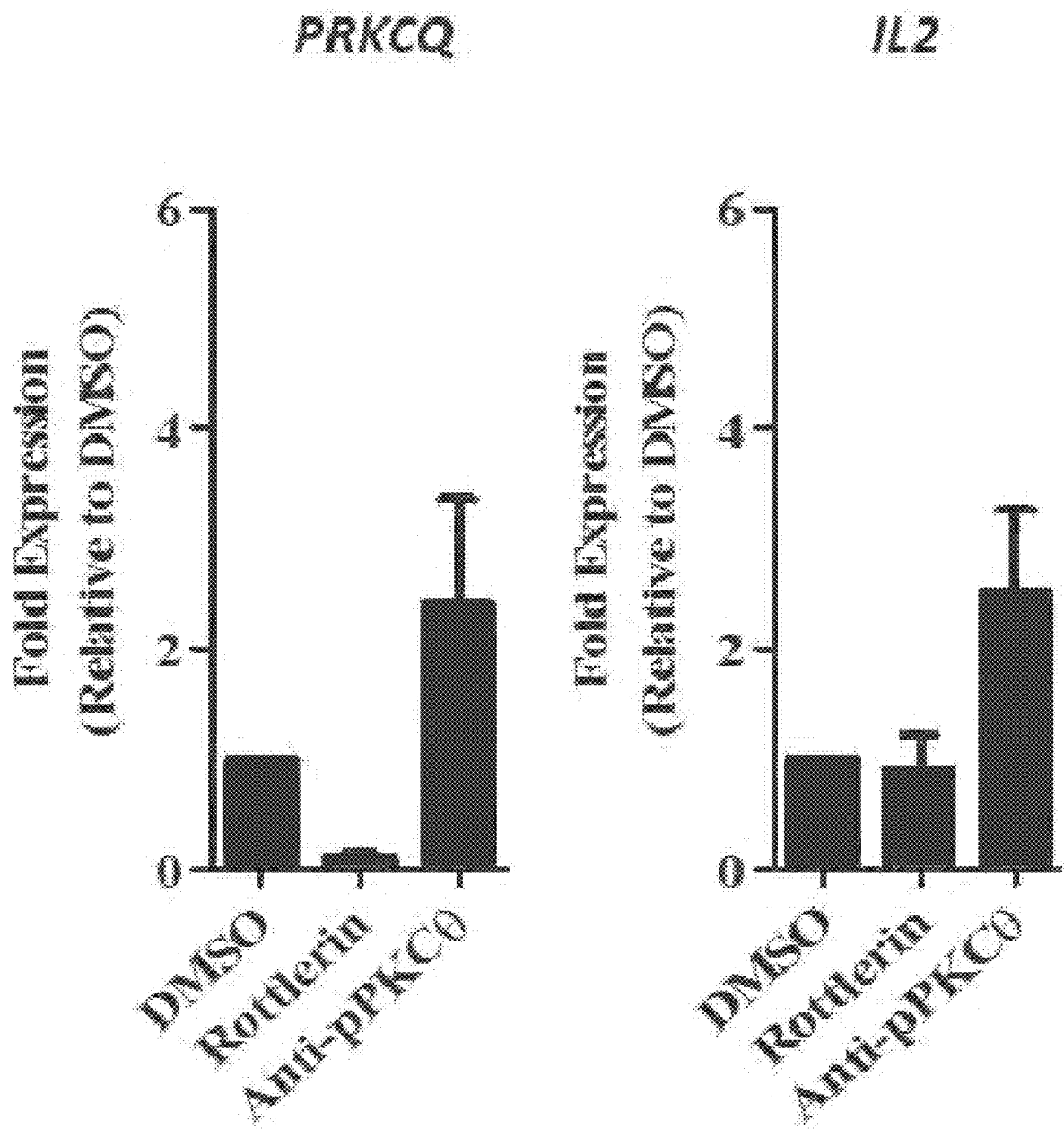

Next, we investigated whether functional markers for iTregs were altered following PTDM:anti-pPKCθ delivery. We determined the expression of phospho-PKCθ (T538), phospho-STAT3 (Y705), phospho-STAT5 (Y694), and CTLA-4, using flow cytometric approaches. We observed phosphorylation of PKCθ at T538 was reduced in PTDM:anti-pPKCθ-treated cells, suggesting an enhanced iTreg function. Moreover, when we analyzed PTDM:anti-pPKCθ-treated samples we noted increased percentages of cells staining positive for phospho-STAT5, and CTLA-4, as well as increased levels of each of these proteins, expressed on a per cell basis, compared to DMSO-treated cells. This supports the notion of that PTDM:anti-pPKCθ-treatment enhances iTreg differentiation in these cells (FIG. 40).

We further characterized the expression of several genes known to be important for iTreg-function. Using quantitative real-time polymerase chain reaction, we evaluated the expression of IL10, FOXP3, CREL, PRKCQ, and IL2. Our results showed that PTDM:anti-pPKCθ-delivery could alter the gene expression profiles of iTregs. For instance, IL10, CREL, and IL2 all were upregulated in PTDM:anti-pPKCθ-treated iTregs, compared to iTregs differentiated in the presence of DMSO (FIG. 42).

Figure 43:
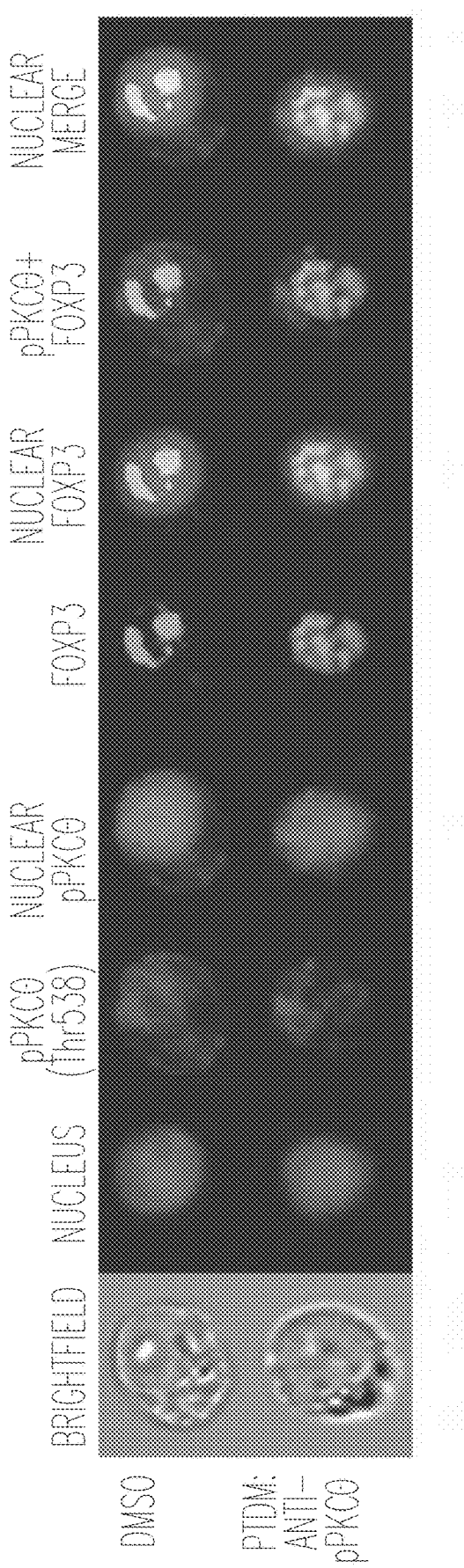
FIG. 43. Cellular localization of pPKCθ is altered in PTDM:anti-pPKCθ-generated iTregs. Human CD4 T cells were treated with DMSO, or PTDM:anti-pPKC☐ and resuspended in iTreg differentiation media for 5 days in the presence of anti-CD3 and anti-CD28 stimulation, as described. At the end of 5 days, the cells were stained with antibodies specific for unconjugated pPKCθ coupled with Qdot625-conjugated secondary antibody (ThermoFisher, Waltham, Mass.), AF488-conjugated FOXP3 (BioLegend, San Diego, Mass.), and DRAQ5 (ThermoFisher, Waltham, Mass.), which will stain nuclear material. Samples were acquired using an AMNIS ImageStream® X Imaging Flow Cytometer (EMD Millipore, Billerica, Mass.), and images were taken under the 60× magnification. Nuclear localization of pPKCθ or FOXP3 were determined using IDEAS Software (6.3, EMD Millipore) after applying the algorithm for nuclear masking. Nuclear co-localization pPKCθ and FOXP3 were similarly determined by applying the co-localization wizard following nuclear masking. Shown is a roster of representative cell images of DMSO-generated or PTDM:anti-pPKCθ-generated iTregs displayed under the following instrument conditions: "Brightfield" conditions (no fluorescence detected), nuclear stained material, phosphoPKCθ, a merged image indicating nuclear-resident phosphoPKCθ, FOXP3, a merged image indicating nuclear-resident FOXP3, a merged image representing co-localization of phosphoPKCθ and FOXP3, and a merged image indicating co-localized phospho-PKCθ and FOXP3 residing in the nucleus.

We have shown that PKCθ is sequestered in the cytosol after PTDM:anti-pPKCθ-delivery and that led to an altered ratio of cytosolic vs. nuclear PKCθ (Example 1). Therefore, we investigated whether PTDM:anti-pPKCθ-delivery also changes the localization of pPKCθ in iTregs after 5 days of in vitro differentiation. We utilized imaging flow cytometry to determine the nuclear localization of pPKCθ with or without PTDM:anti-pPKCθ-delivery. We observed that in PTDM:anti-pPKCθ-treated iTregs, most of the pPKCθ was found in the cytosol, whereas in DMSO-treated control cells, pPKCθ was found primarily in the nucleus 5 days after culture in iTreg differentiation media (FIG. 43). Moreover, we observed that pPKCθ colocalized in the nucleus with FOXP3 in DMSO-treated control iTregs, but this colocalization was lost in iTregs generated following PTDM:anti-pPKCθ delivery.

Figure 6B:
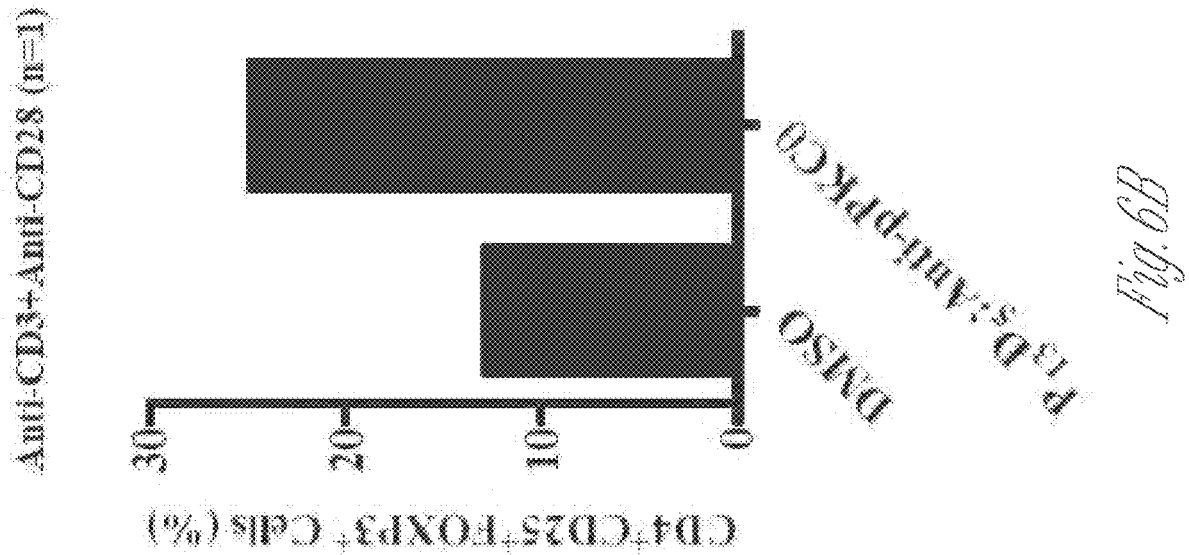
FIGS. 6A-B. Percent of differentiated iTregs. A) CD3+ cells. B) CD3+CD28+ cells.
Figure 6A:
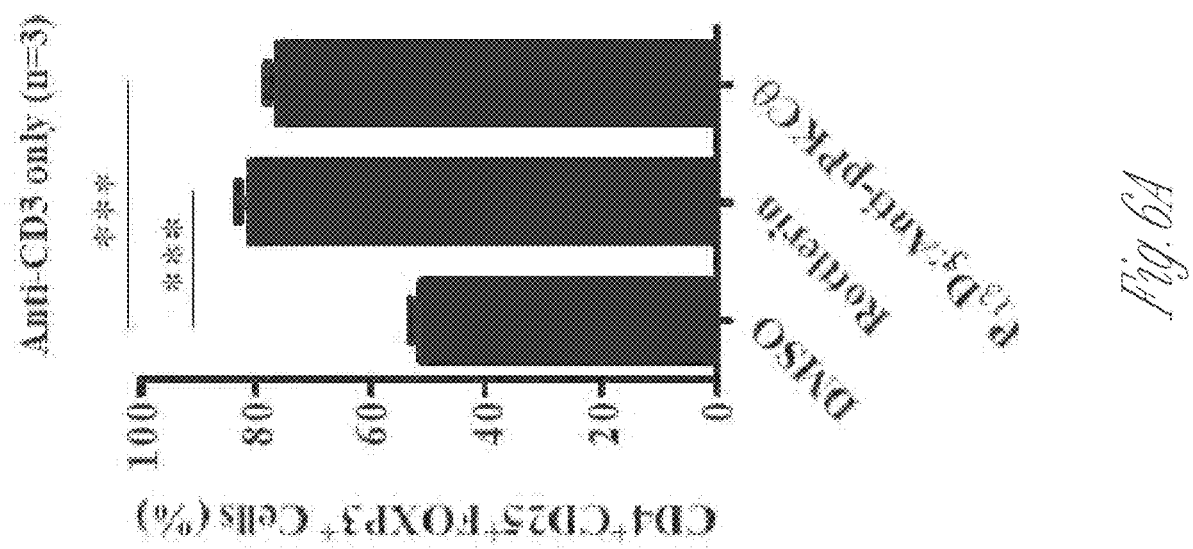
Figures 7A, 7B:
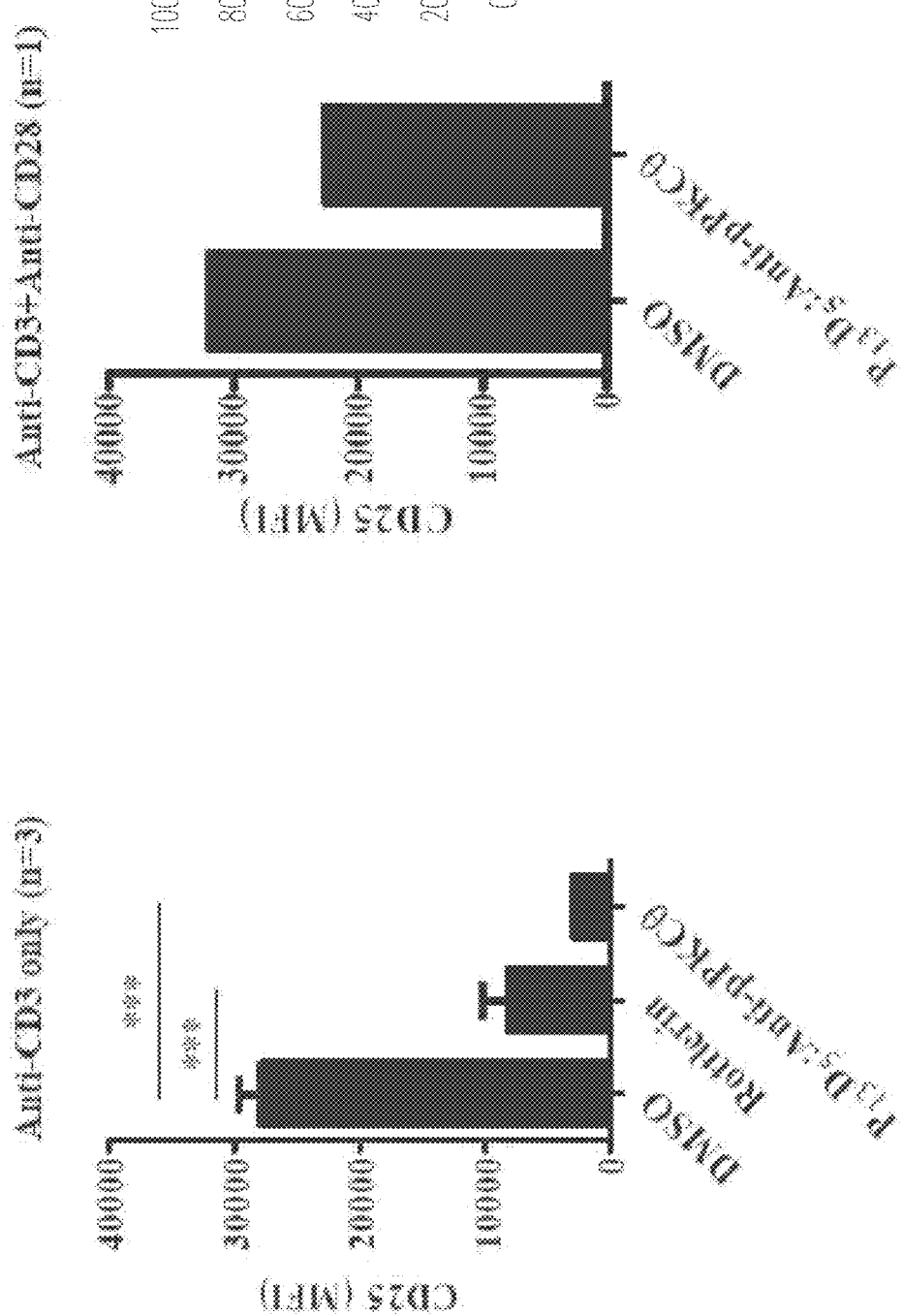
FIGS. 7A-B. CD25 levels in iTreg population. A) CD3+ cells. B) CD3+CD28+ cells.
Figures 8A, 8B:
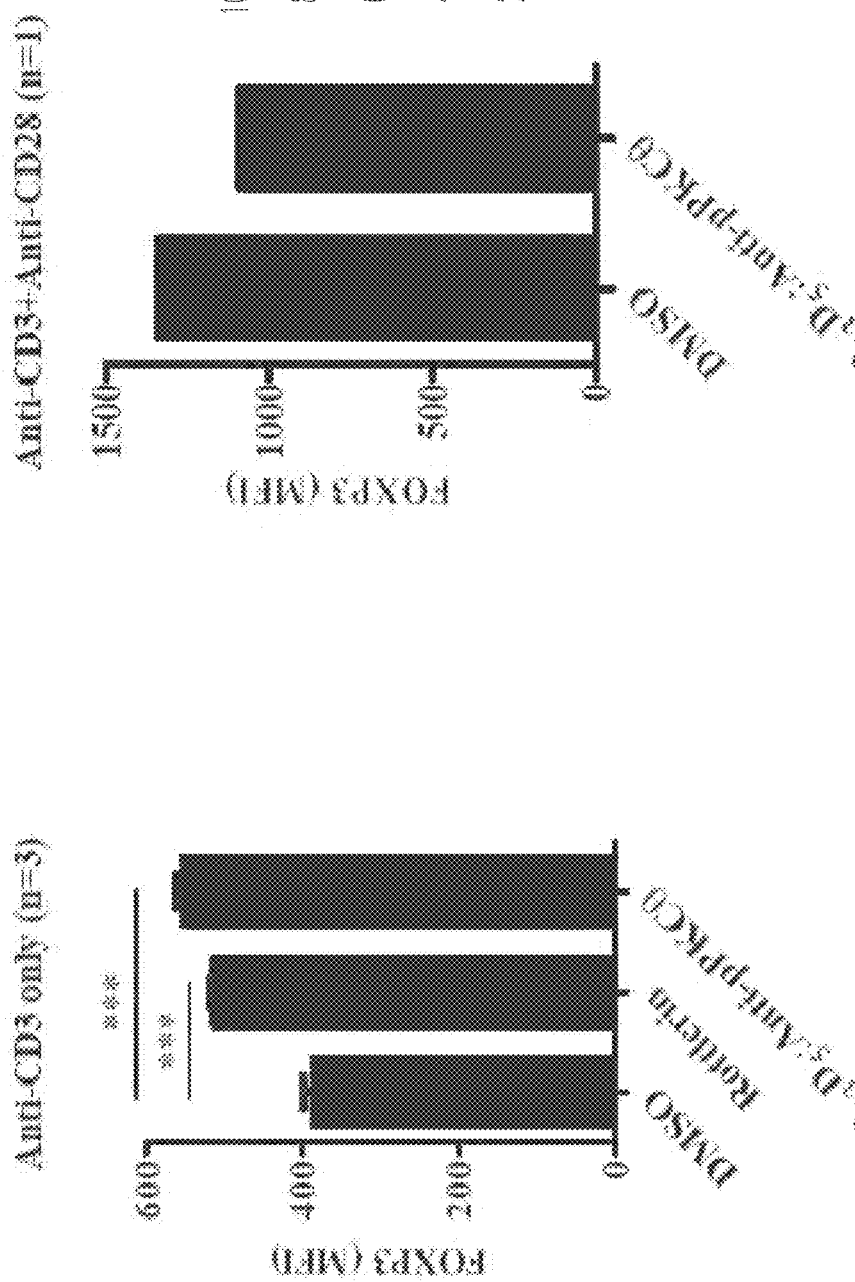
FIGS. 8A-B. Foxp3 levels in iTreg population. A) CD3+ cells. B) CD3+CD28+ cells.
Figure 9A:
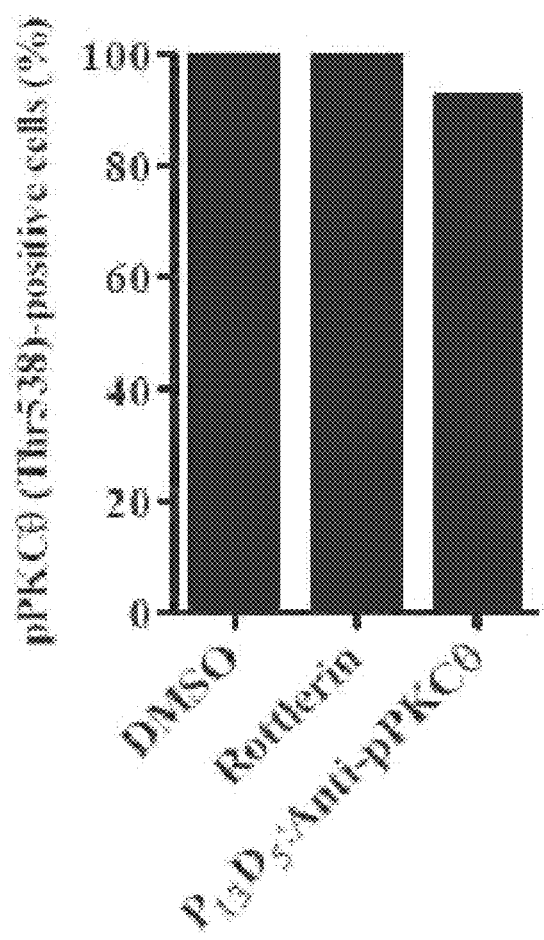
FIGS. 9A-E. pPKCθ levels in iTreg population. A-B) CD3+ cells. C-E) CD3+CD28+ cells.
Figure 9B:
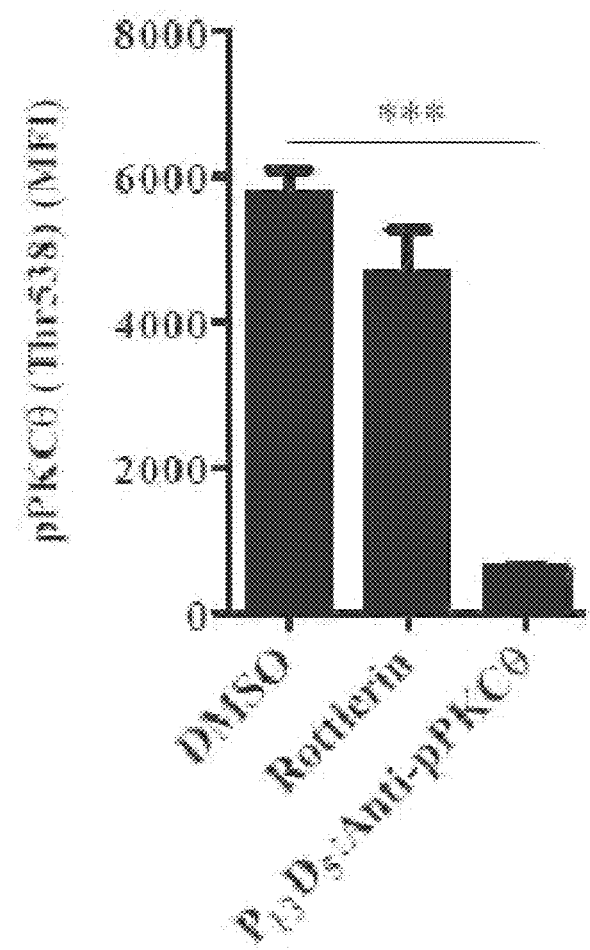
Figures 9C, 9D:
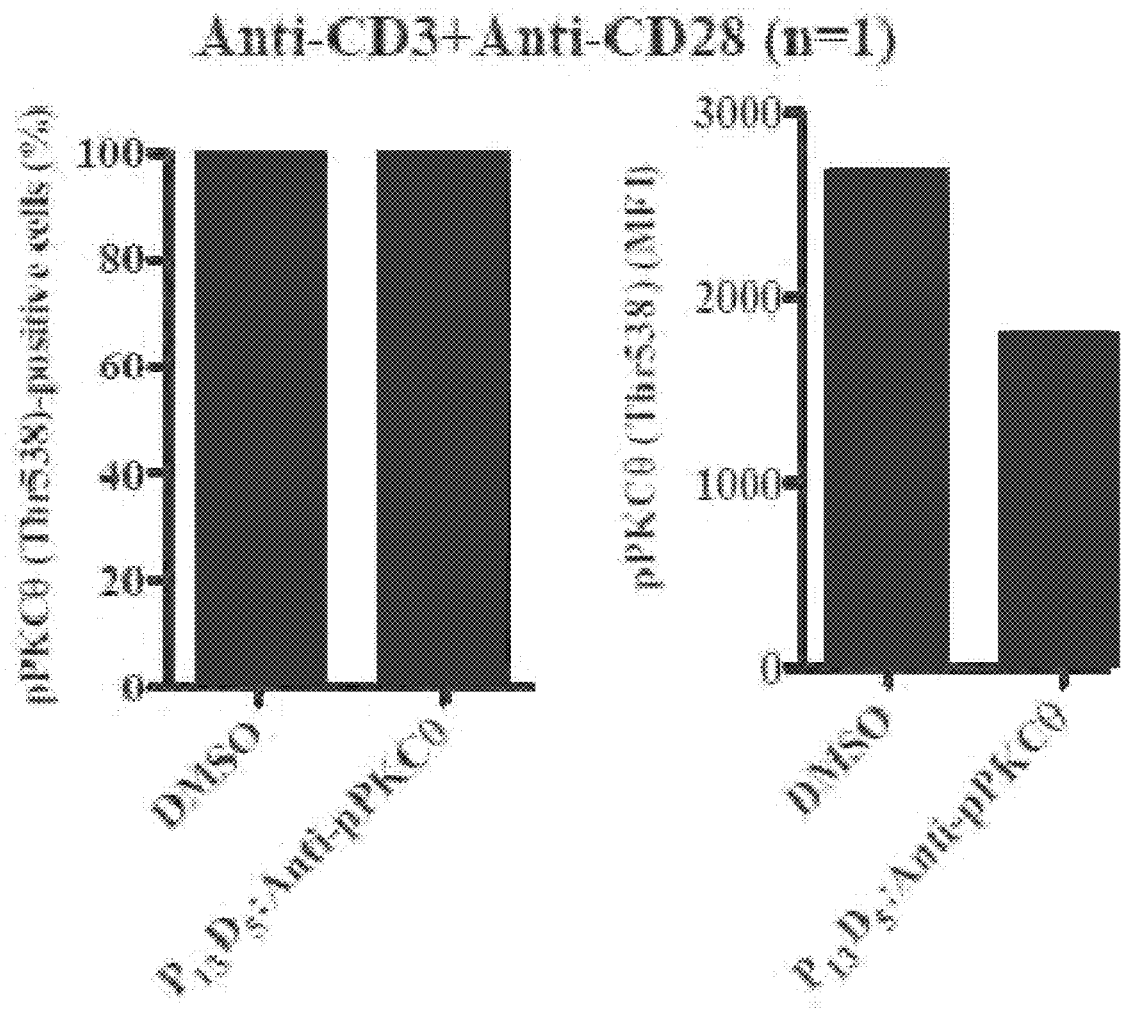
Figure 9E:
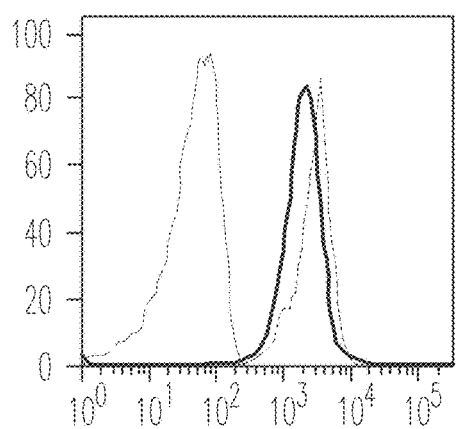
Figure 10A:
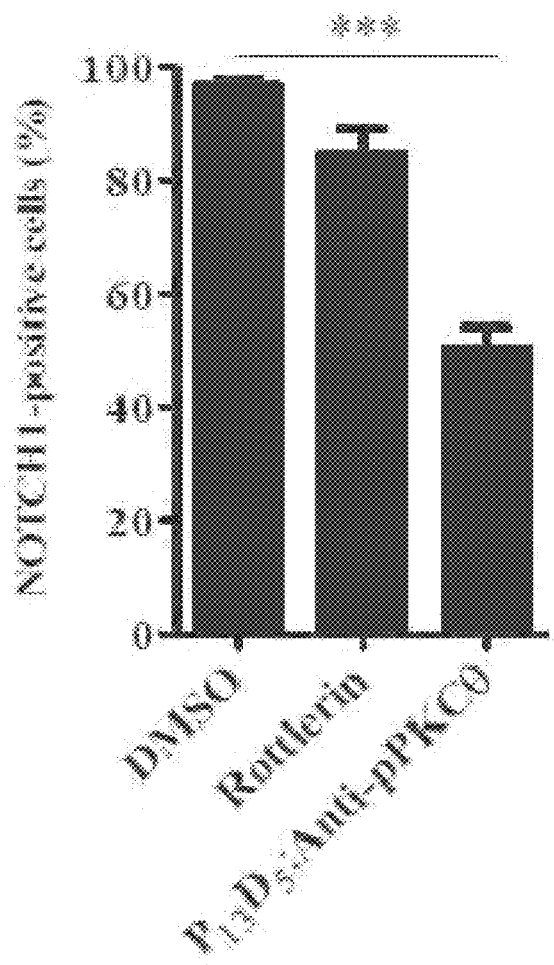
FIGS. 10A-E. NOTCH1 levels in iTreg population. A-B) CD3+ cells. C-E) CD3+CD28+ cells.
Figure 10B:
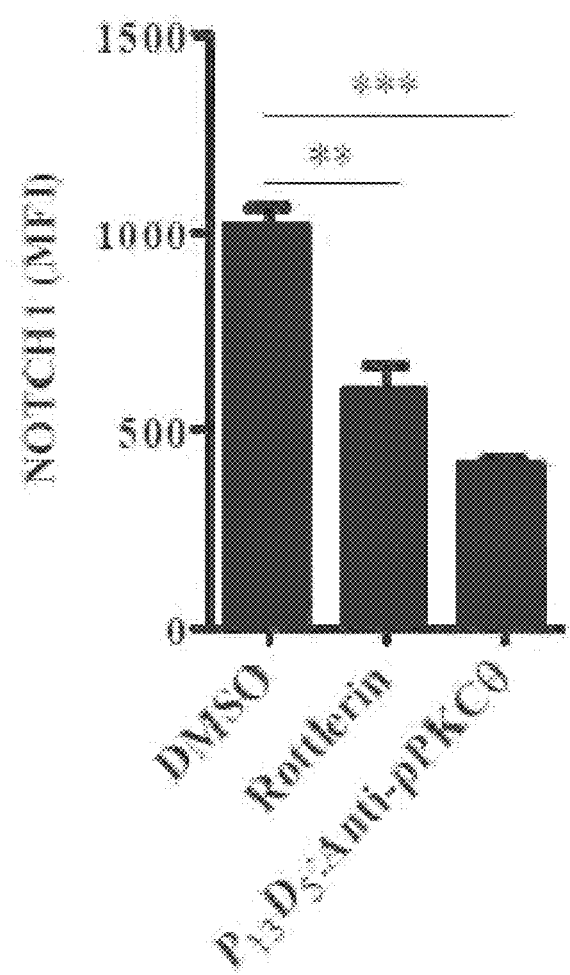
Figure 10C:
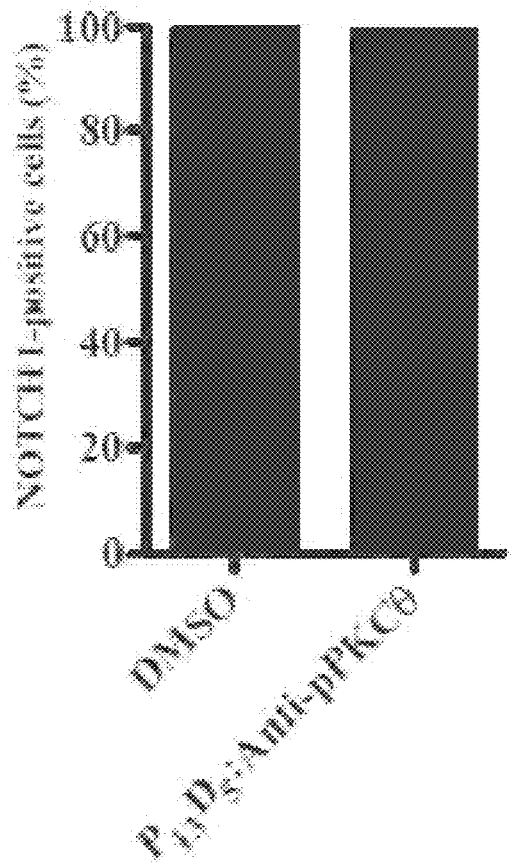
Figure 10D:
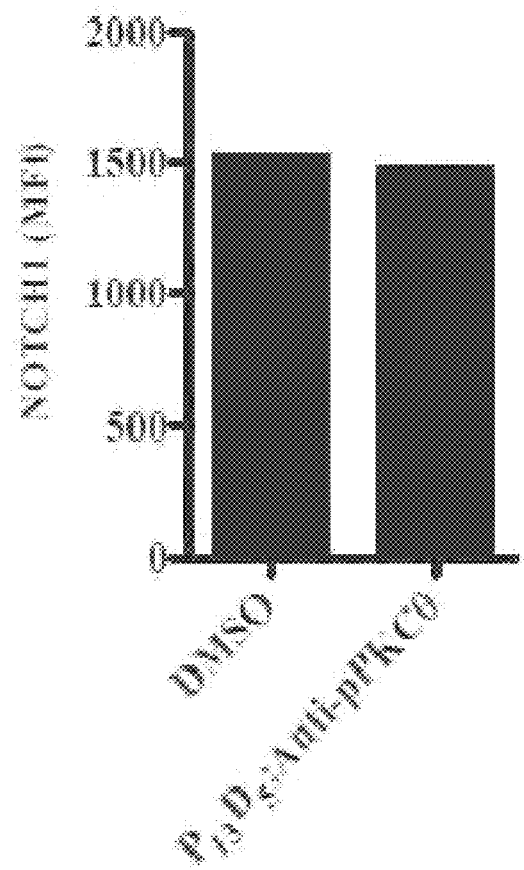
Figure 10E:
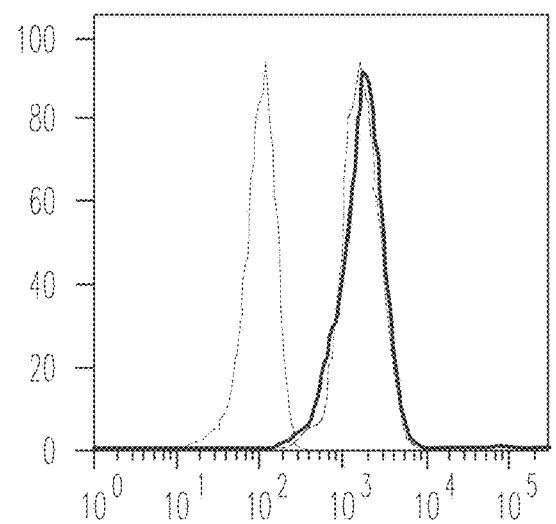
Figure 12A:
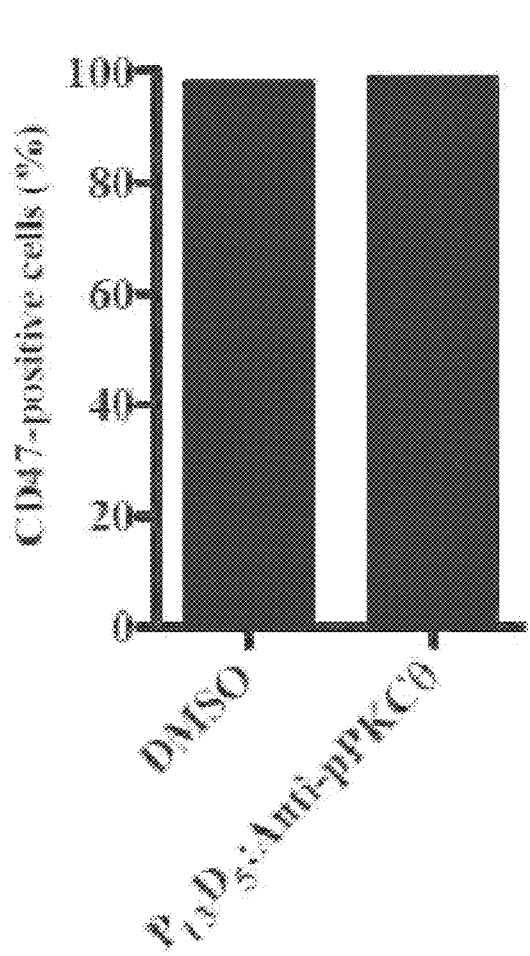
FIGS. 12A-C. CD47 expression (day 5). A) Percent of CD47 positive cells. B) MFI of CD47 cells. C) Histogram.
Figure 12B:
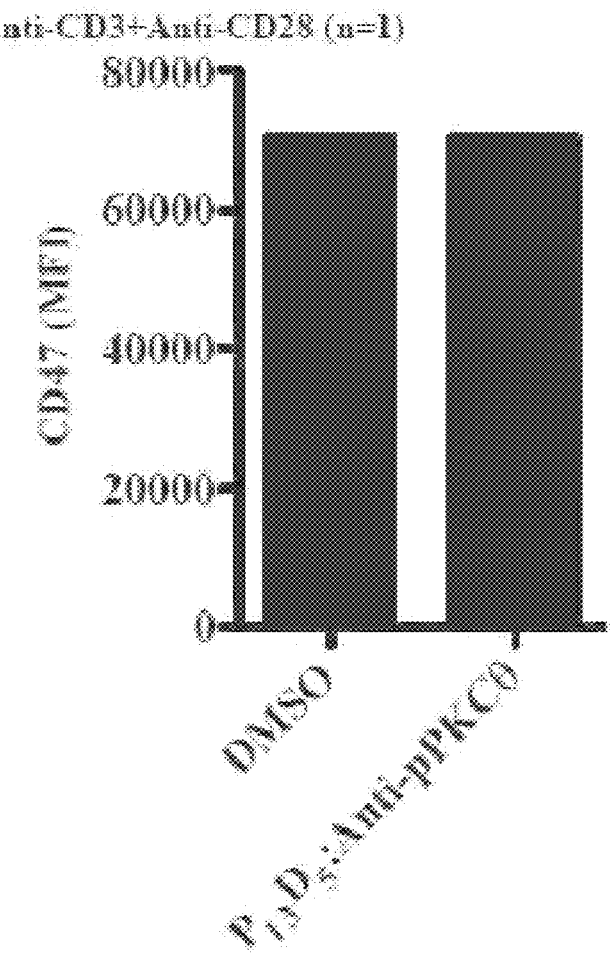
Figure 12C:
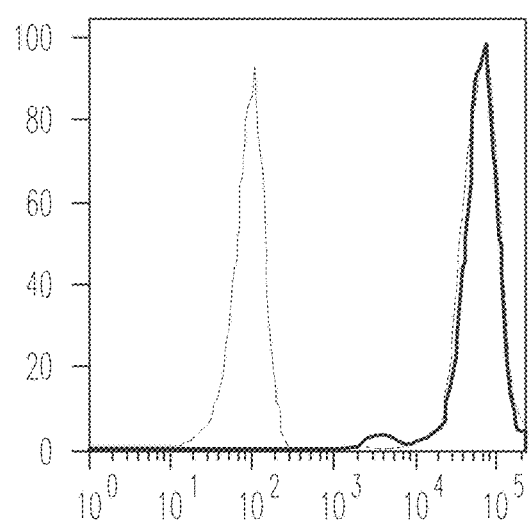
Figure 13A:
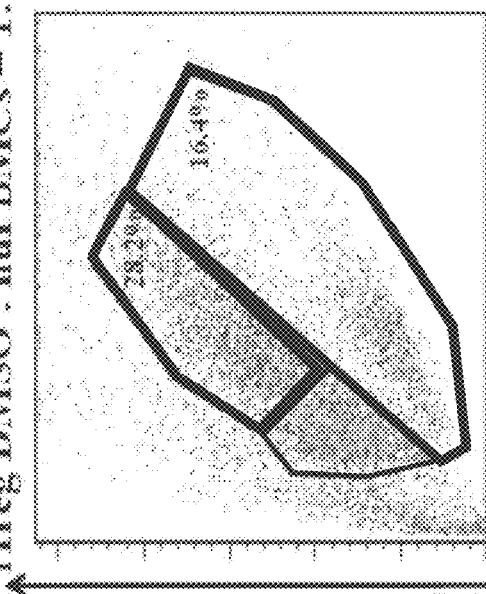
FIGS. 13A-D. CD28 signal in DMSO- and anti-PKCtheta treated cells. A) iTreg:hPMBCs 1:1. B) iTreg:hPMBCs 1:10. C) iTreg anti-pPKCtheta:hPMBCs 1:1. B) iTreg anti-PKCtheta:hPMBCs 1:10.
Figure 13B:
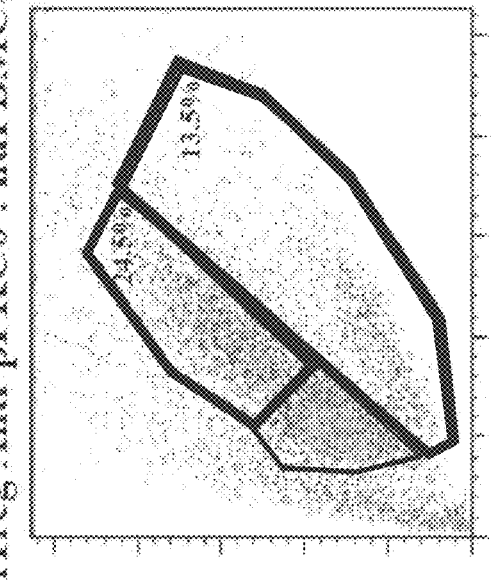
Figure 13C:
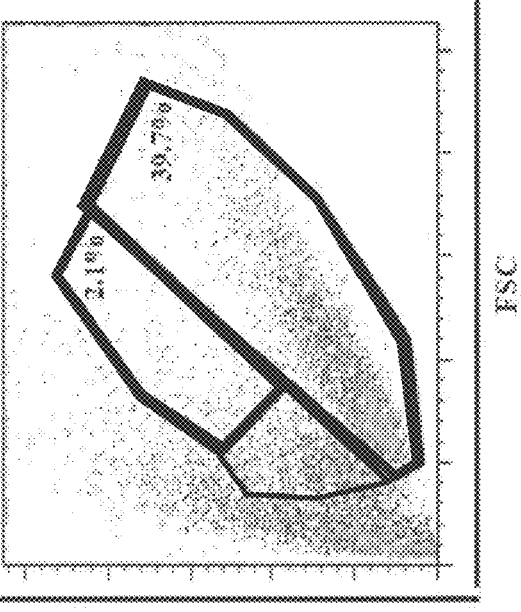
Figure 13D:
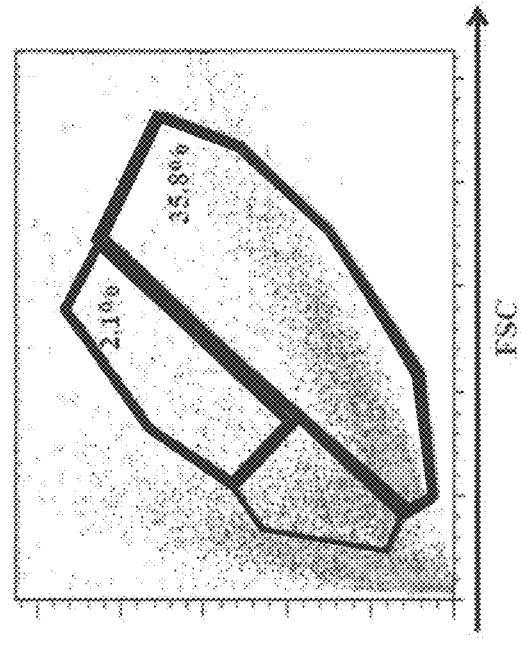
Figure 14A:
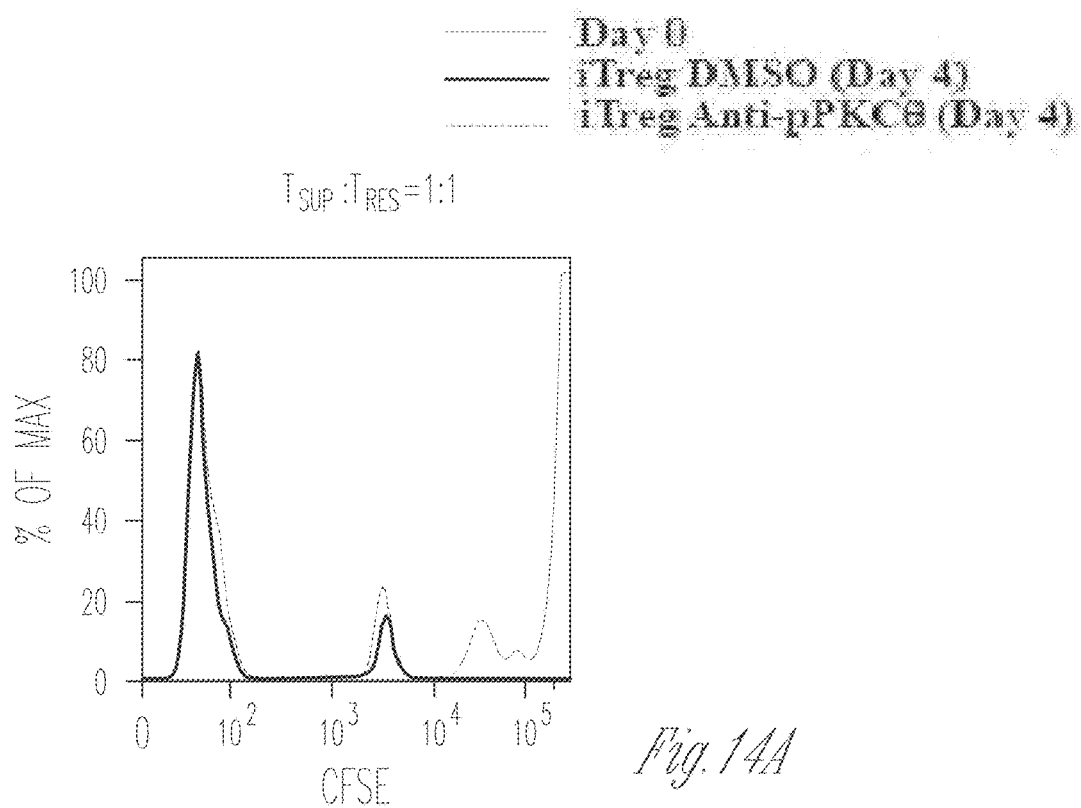
FIGS. 14A-B. CD28 signal in a proliferation assay in DMSO- and anti-PKCtheta treated cells. A) iTreg:hPMBCs 1:1. B) iTreg:hPMBCs 1:10.
Figure 14B:
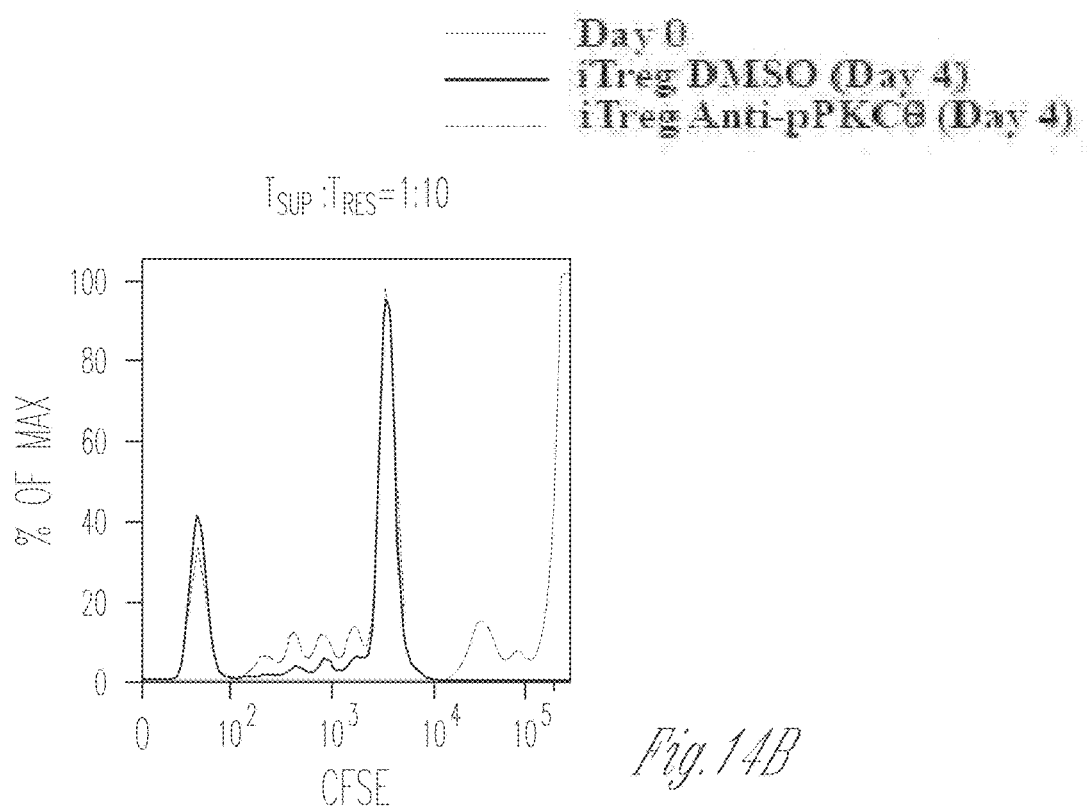
Figure 15C:
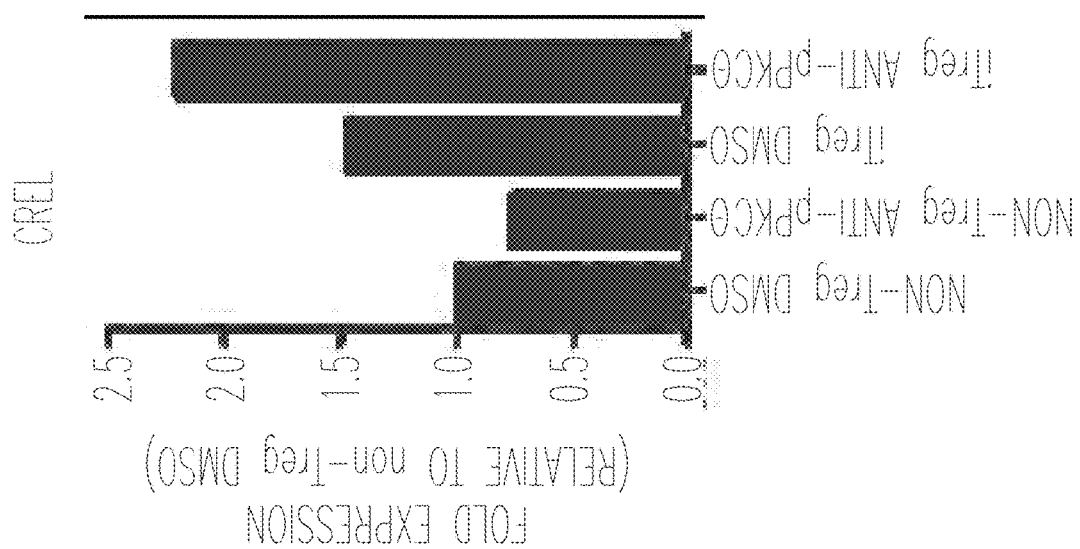
FIGS. 15A-F. Gene expression changes (day 5-anti-CD3 only). A) IL10. B) FOXP3. C) CREL. D) NOTCH1. E) PRKCQ. F) IL2.
Figure 15B:
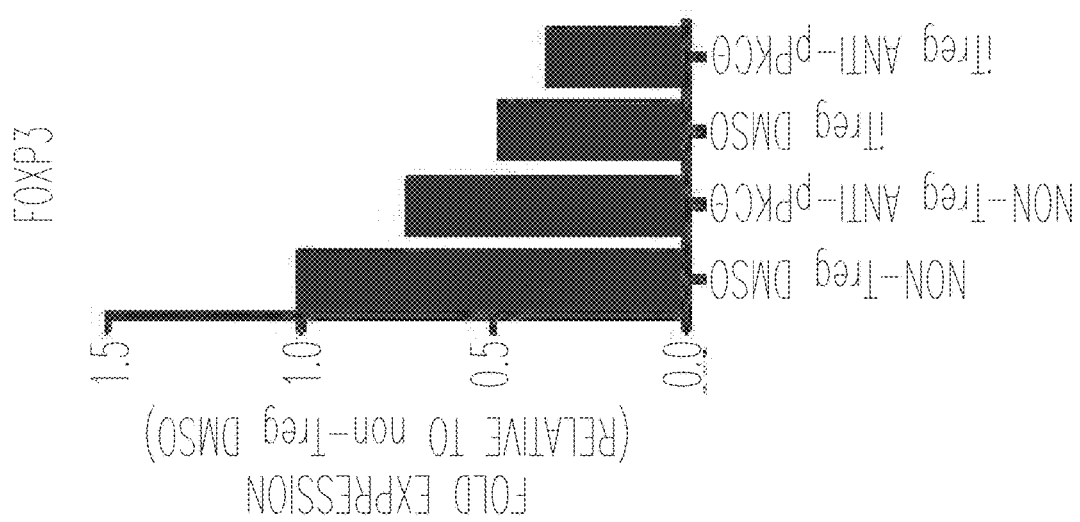
Figure 15A:
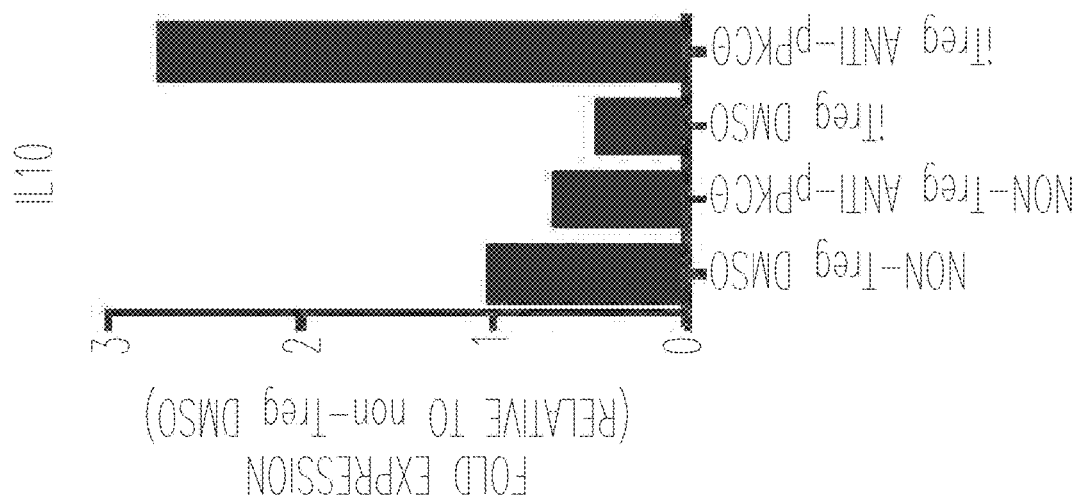
Figures 15D, 15E, 15F:
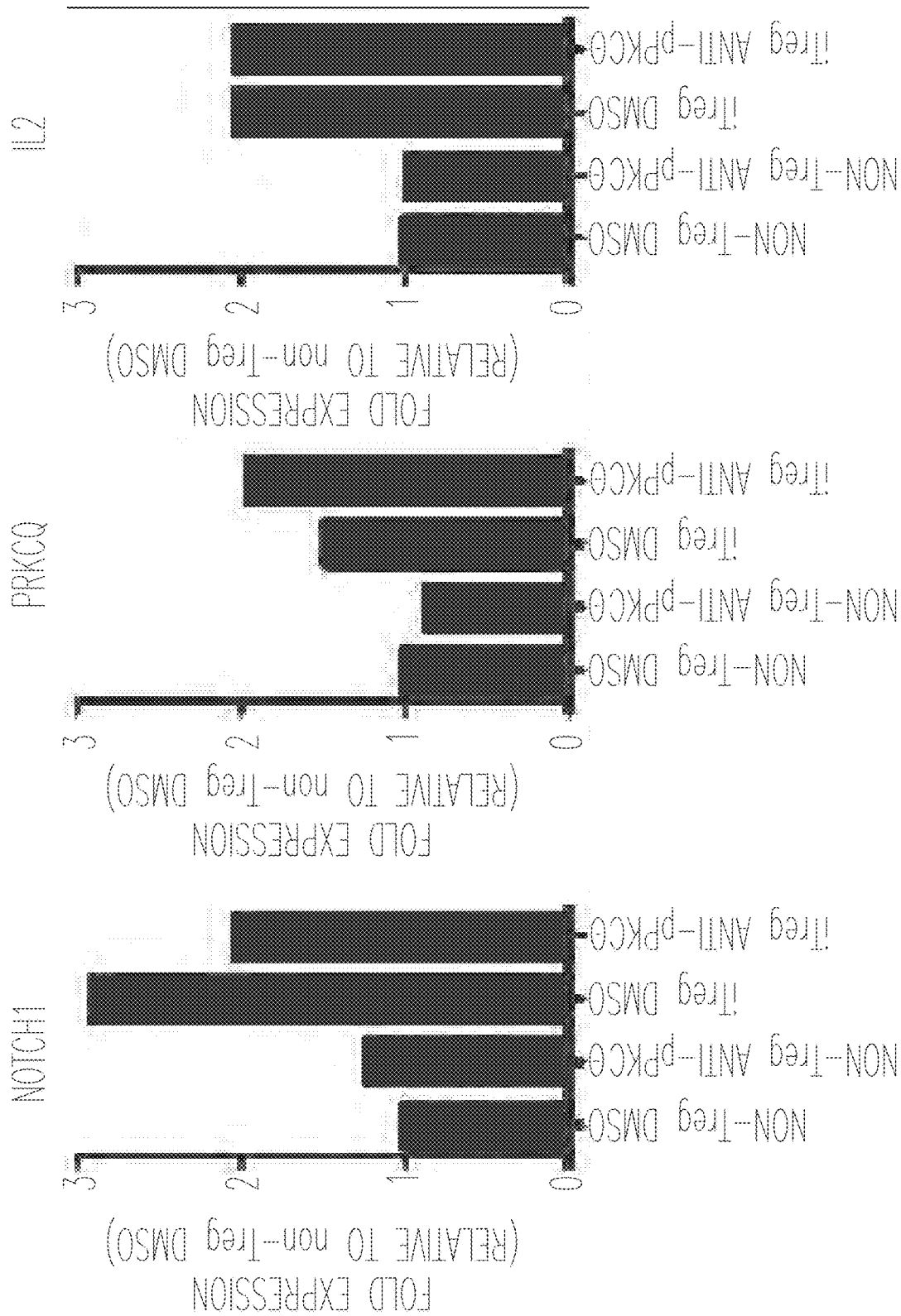
Figure 17C:
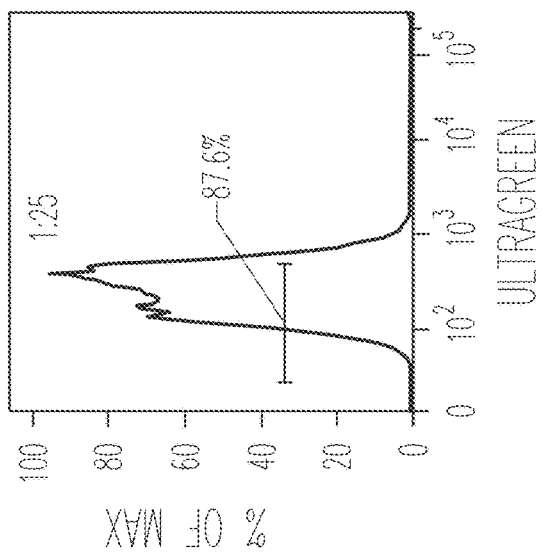
Figure 17B:
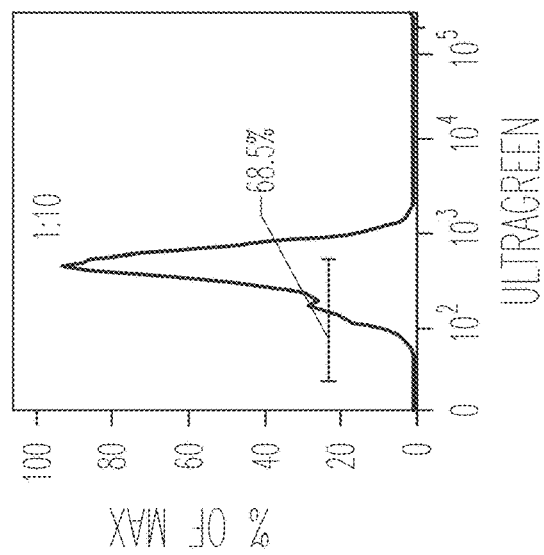
Figure 17A:
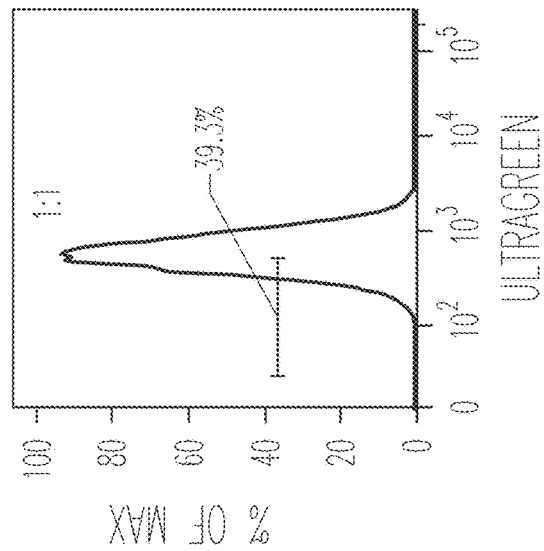
Figures 17E, 17F, 17G:
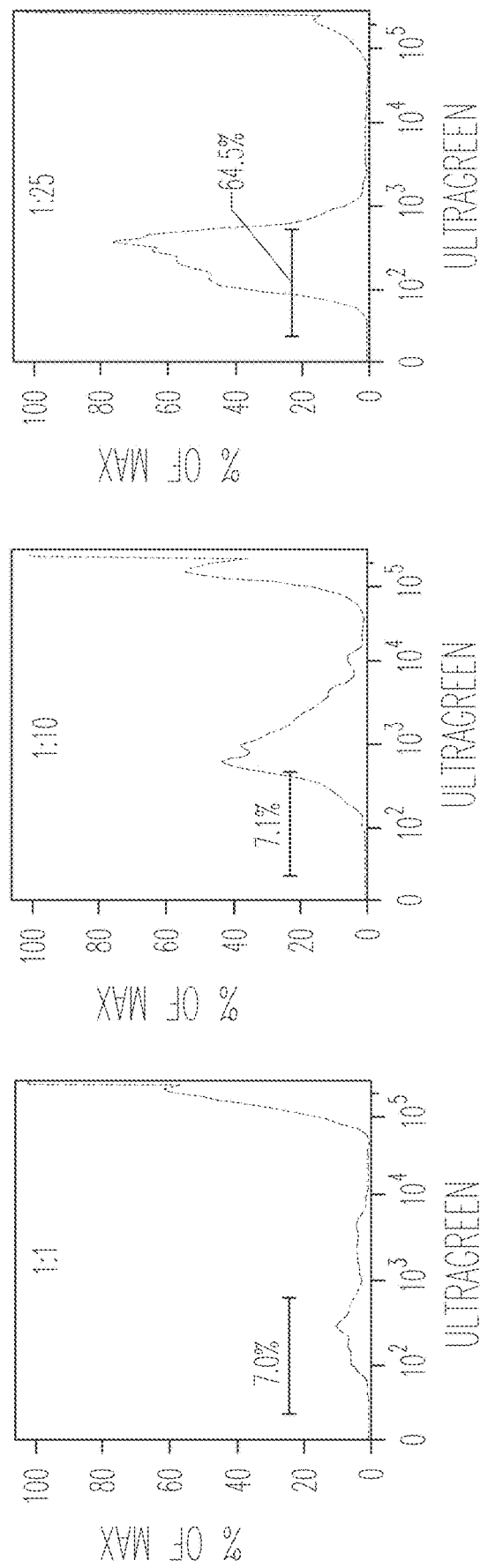
Figure 18C:
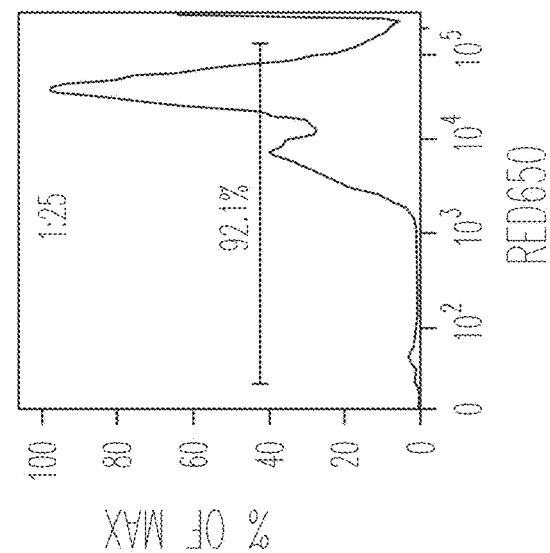
FIGS. 18A-F. Flow cytometry data for suppressors A) iTreg:hPMBCs 1:1. B) iTreg:hPMBCs 1:10. C) iTreg: hPMBCs 1:25. D) iTreg anti-pPKCtheta:hPMBCs 1:1. E) iTreg anti-pPKCtheta:hPMBCs 1:10. F) iTreg anti-pPKCtheta:hPMBCs 1:25.
Figure 18B:
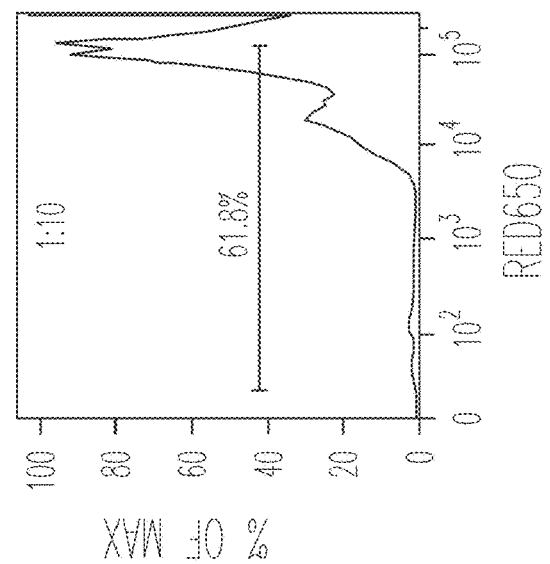
Figure 18A:
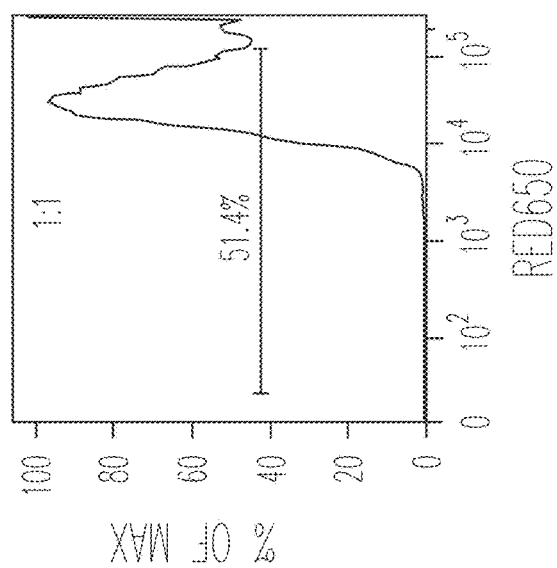
Figures 18D, 18E, 18F:
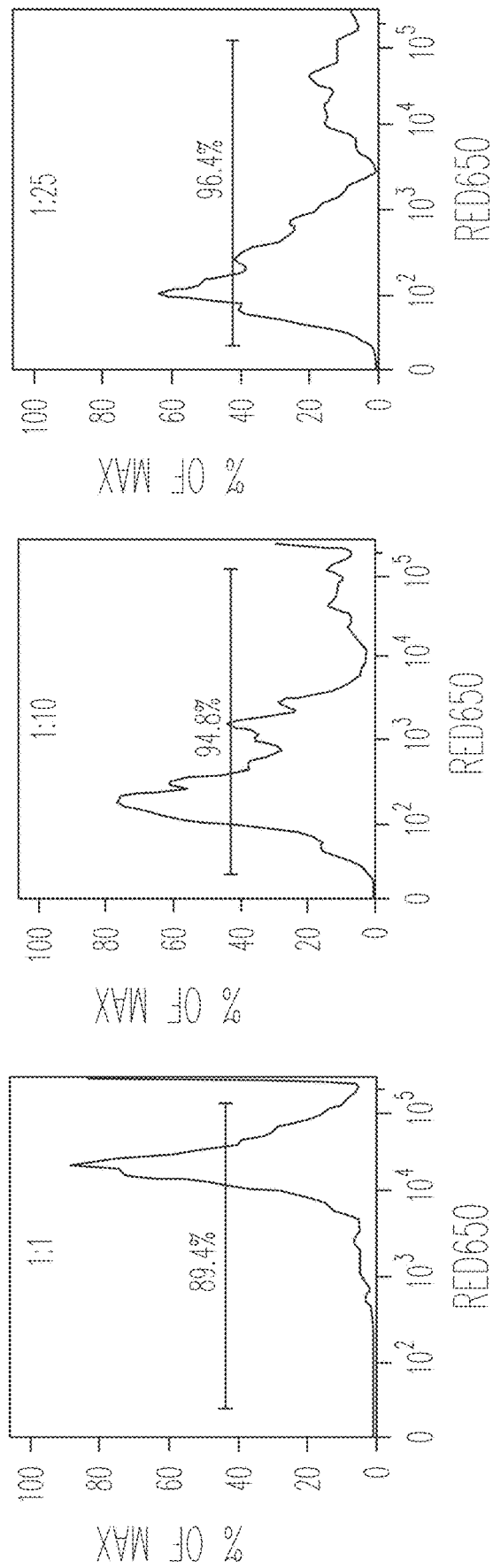
Figure 19A:
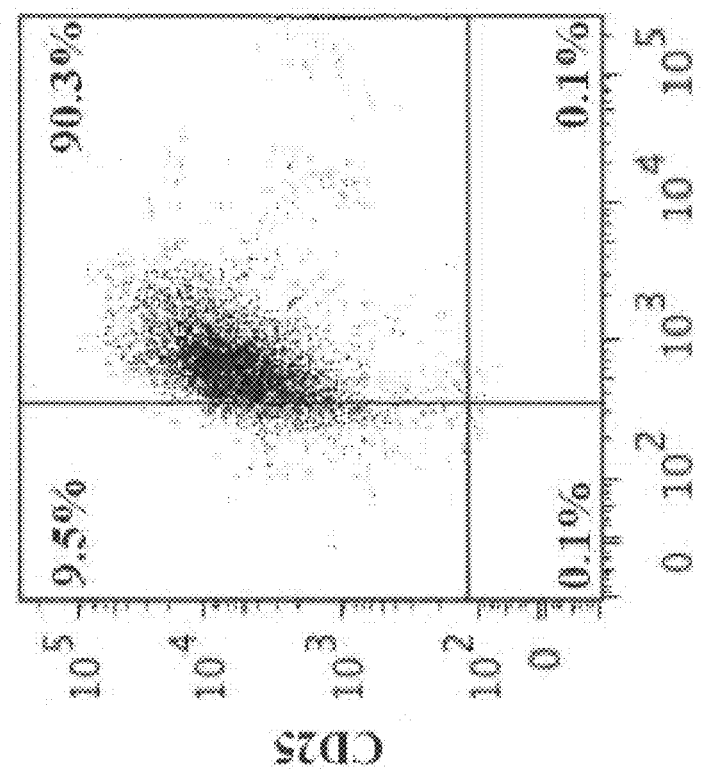
FIGS. 19A-B. Stable iTregs in co-culture. A) iTreg: hPMBCs 1:1. B) iTreg anti-pPKCtheta:hPMBCs 1:1.
Figure 19B:
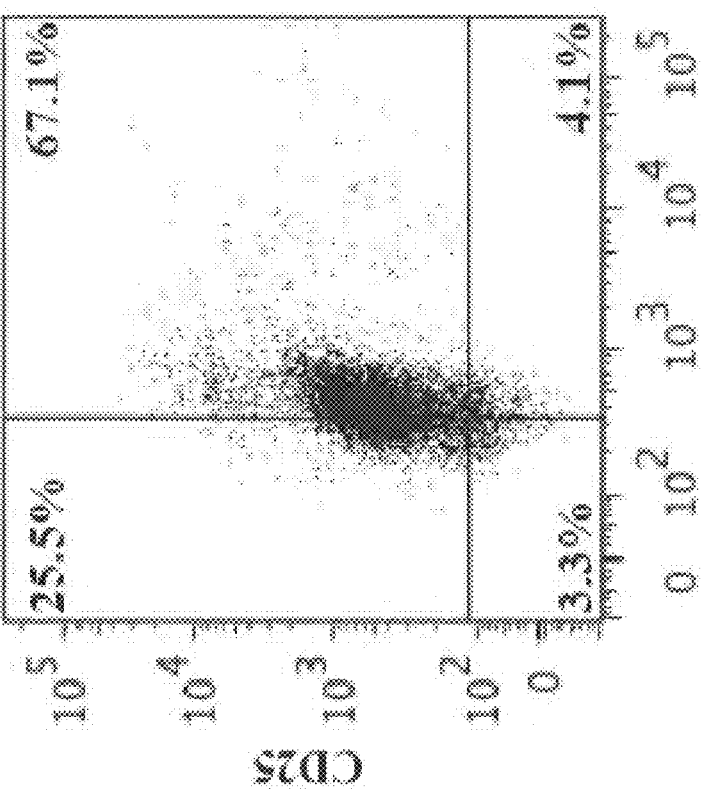
Figure 21:
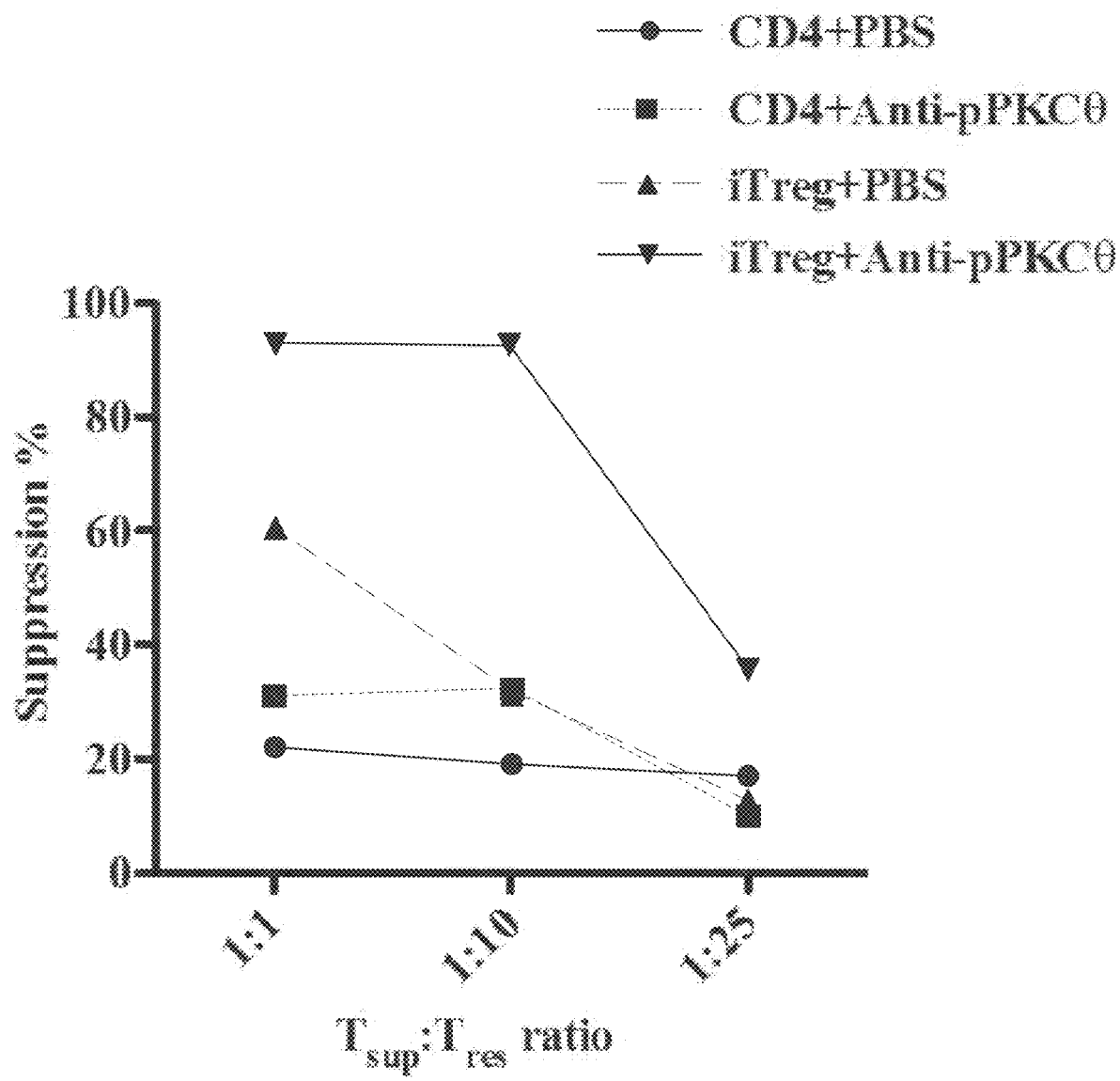
FIG. 21. Suppression % for various treatments and controls
Figure 24:
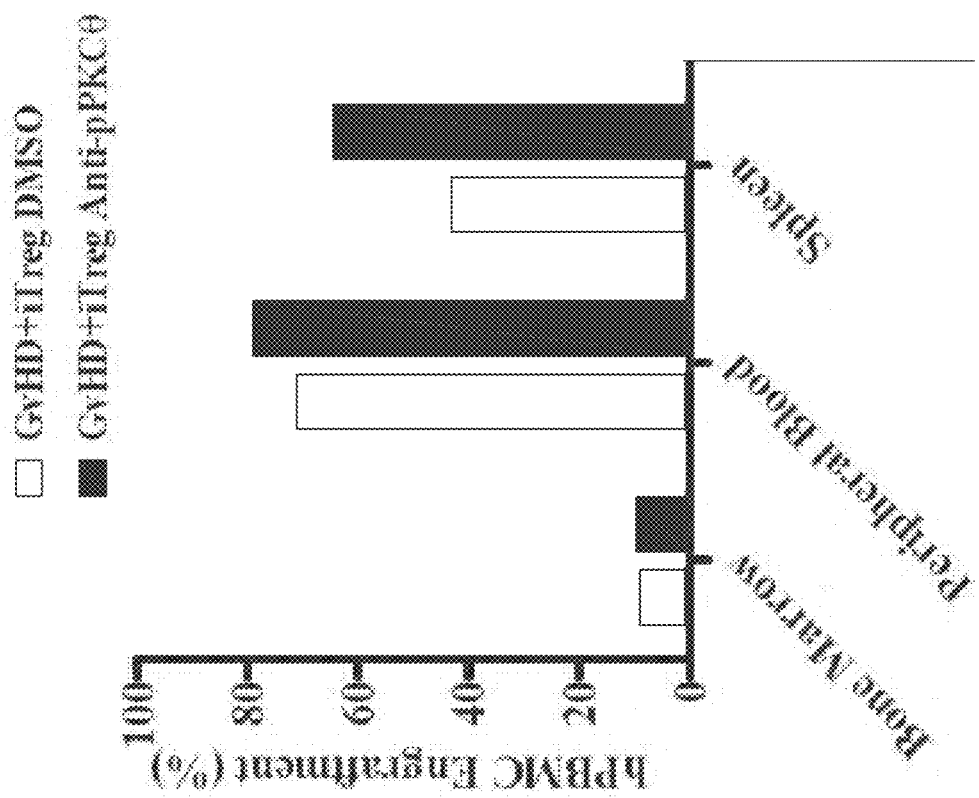
FIG. 24. Day 17 hPBMC engraftment.
Figure 23:
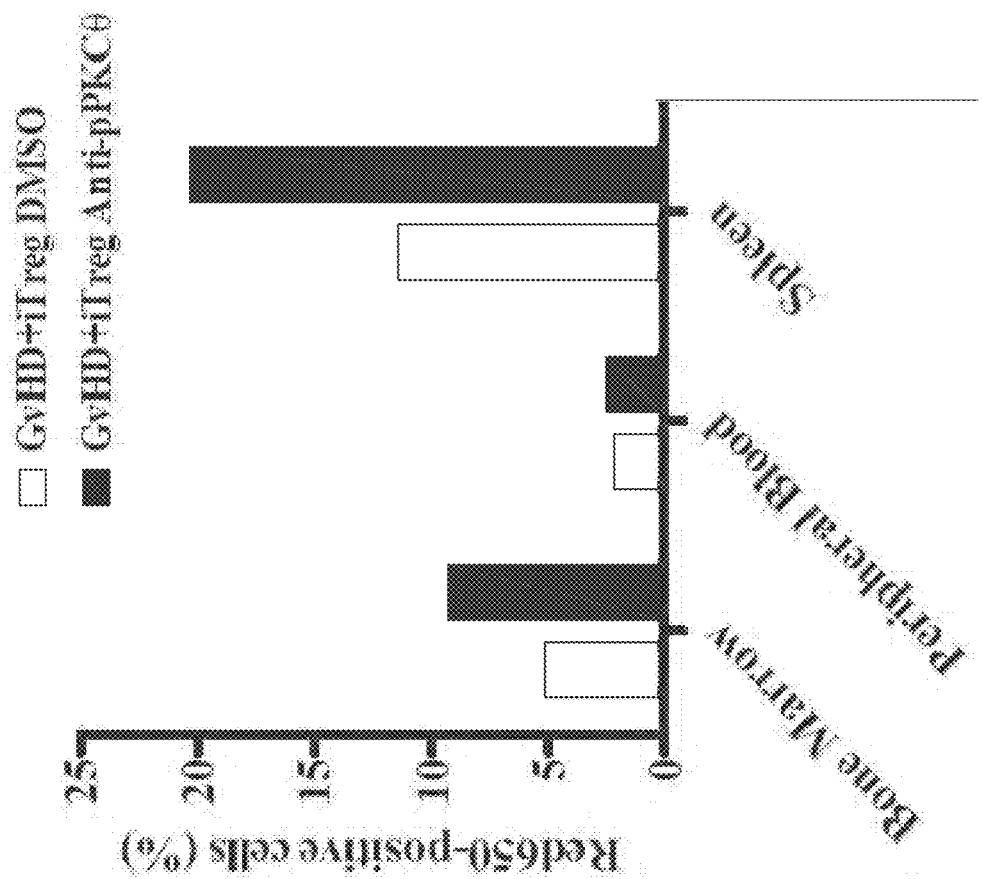
FIG. 23. Day 17 Red650 positive cells.
Figure 25:
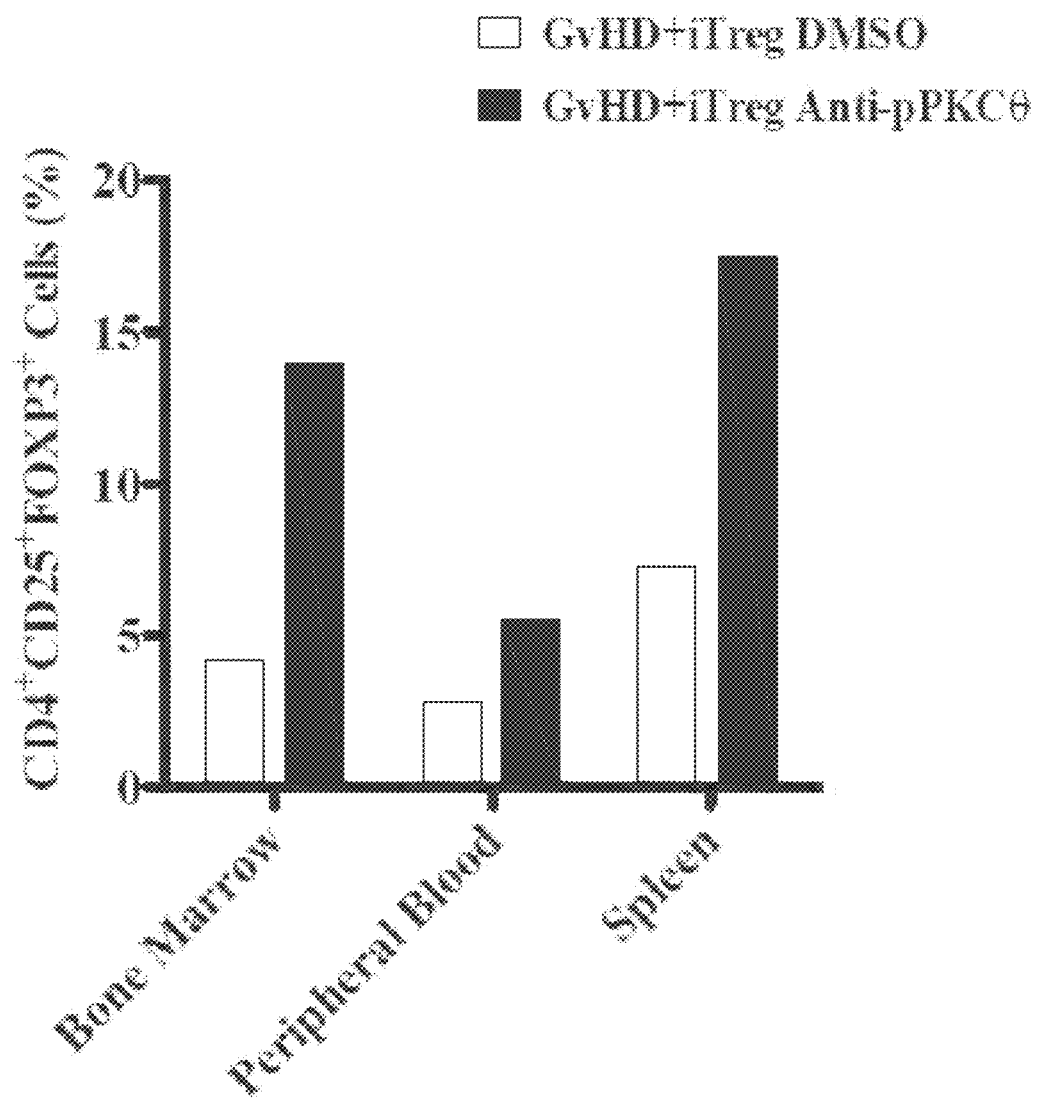
FIG. 25. Day 17 regulatory T cells.
Figure 26B:
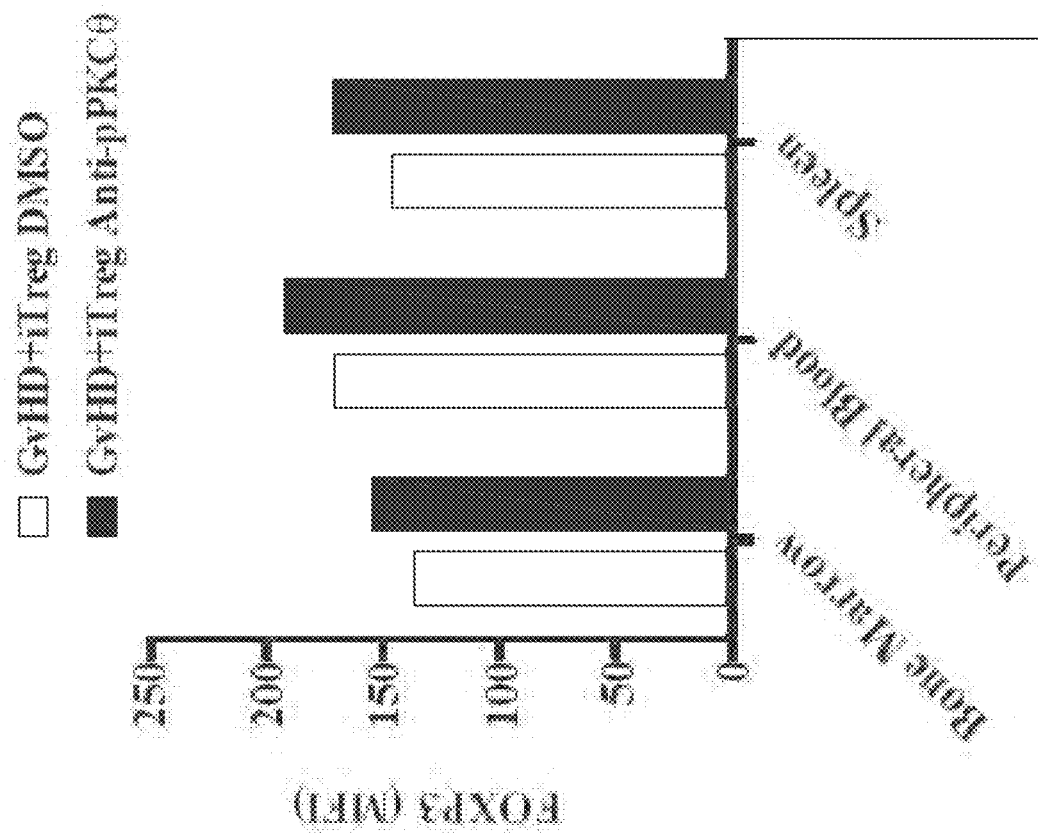
FIGS. 26A-B. Day 17 Protein levels only in iTregs. A) CD25. B) FOXP3.
Figure 26A:
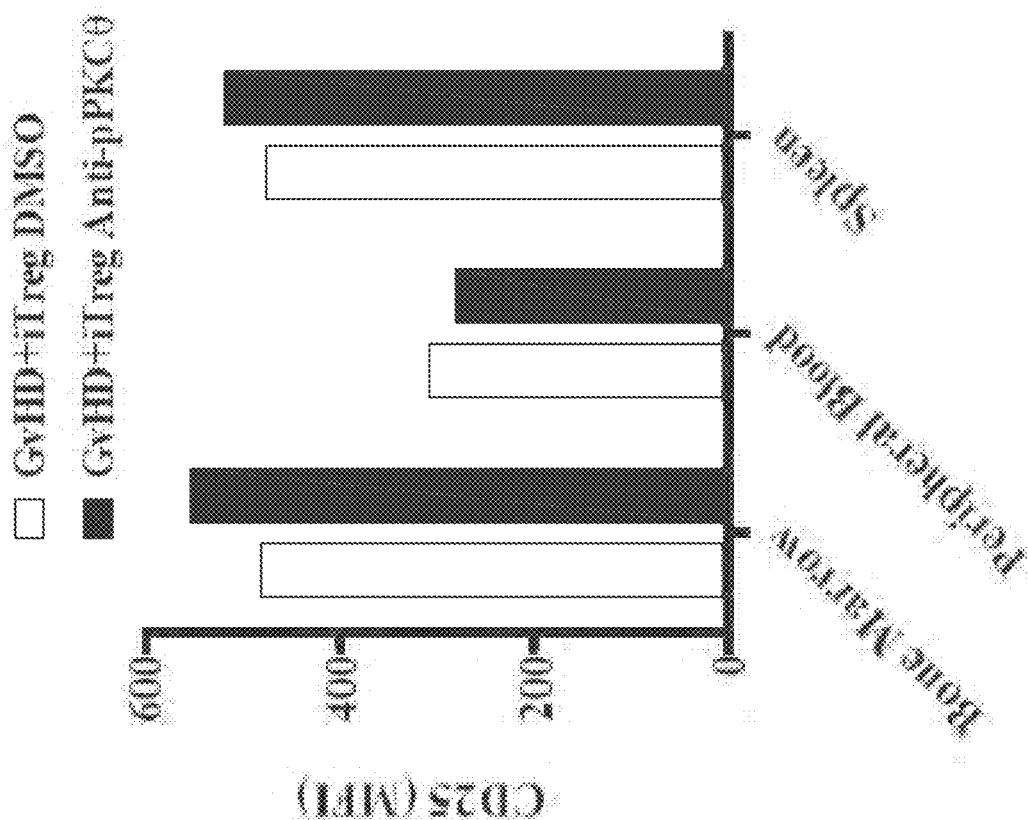
Figure 27B:
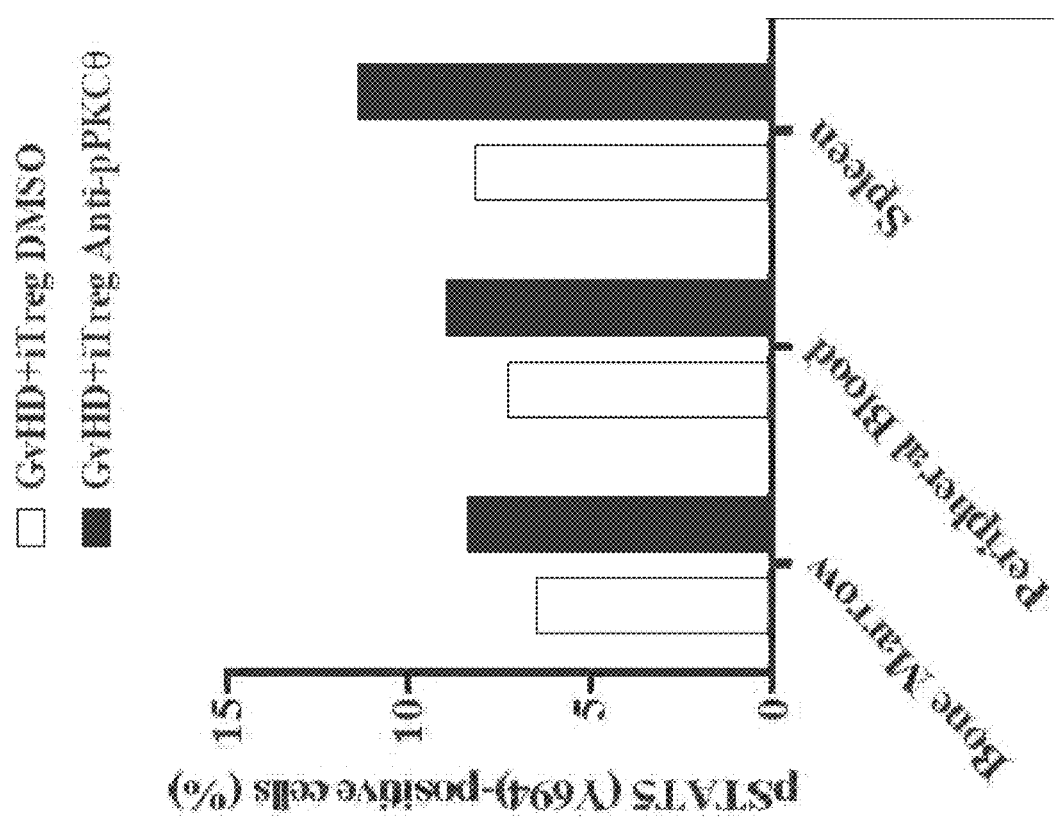
FIGS. 27A-E. Day 17 Protein levels only in iTregs. A) pPKCθ positive cells. B) pSTAT5 positive cells. C) MFI for CD47 cells. D) MFI for pPKCθ cells. E) MFI for pSTAT5 cells.
Figure 27A:
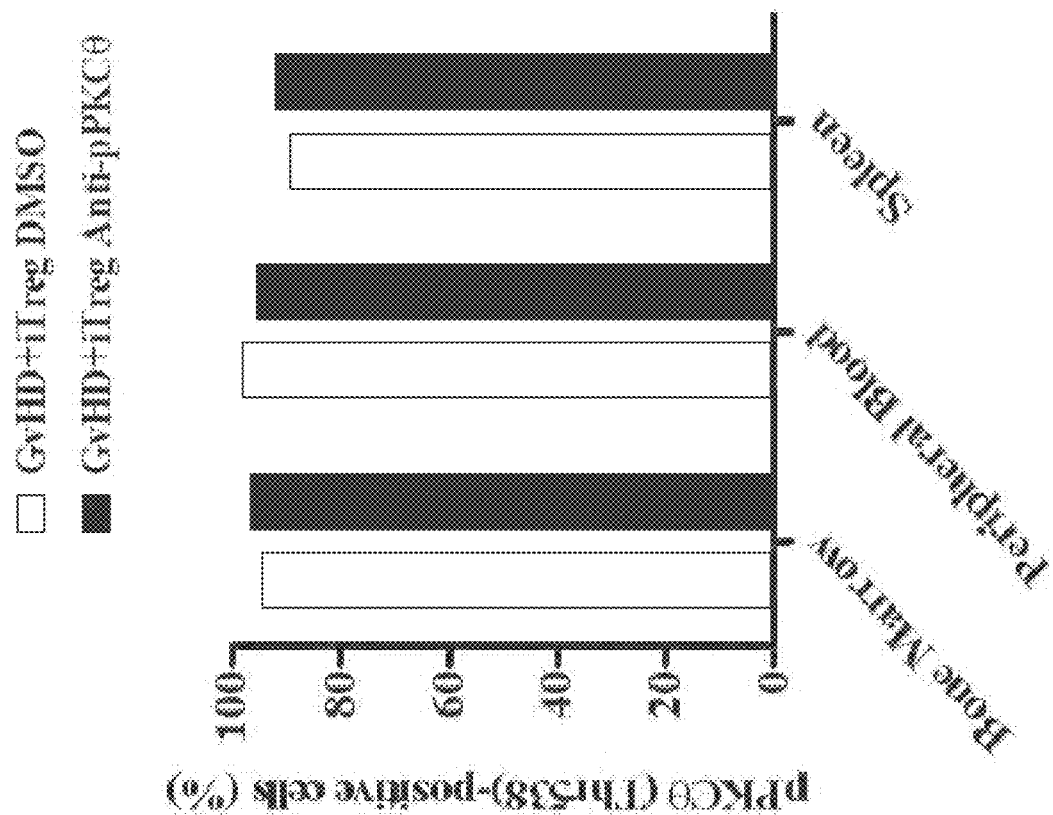
Figure 27D:
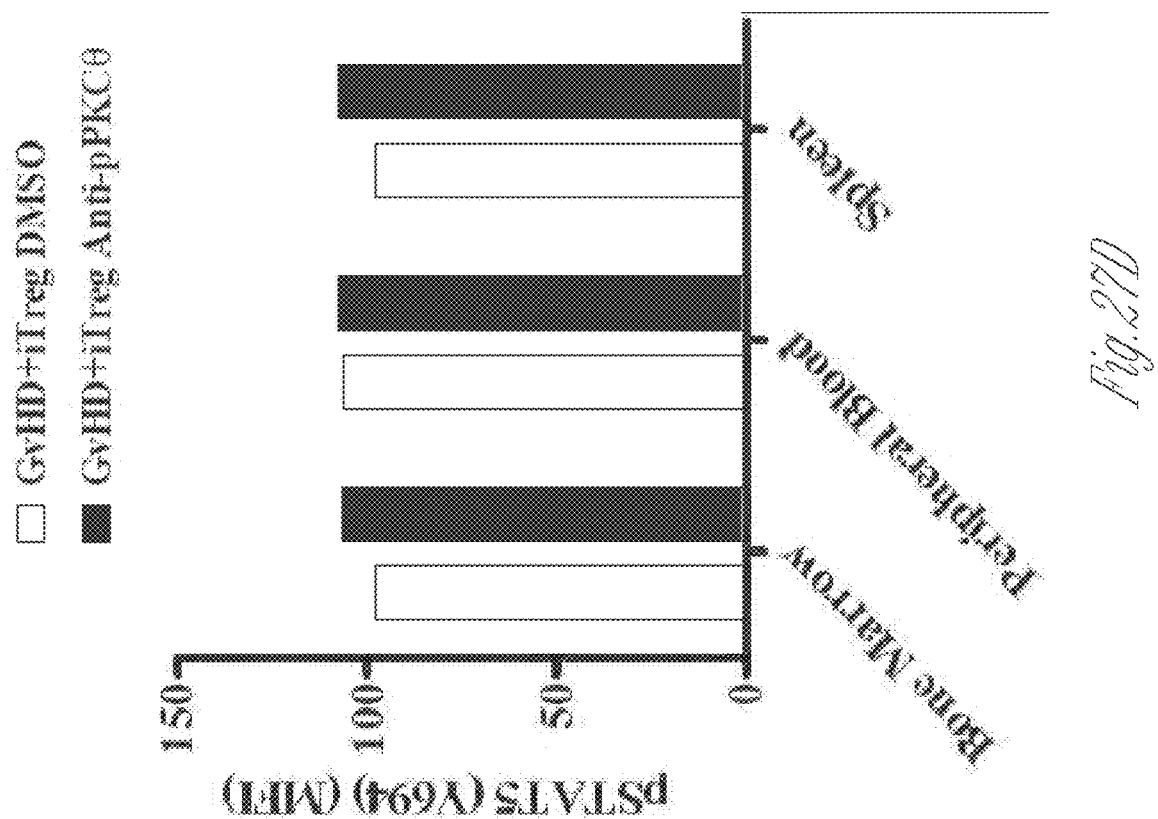
Figure 27C:
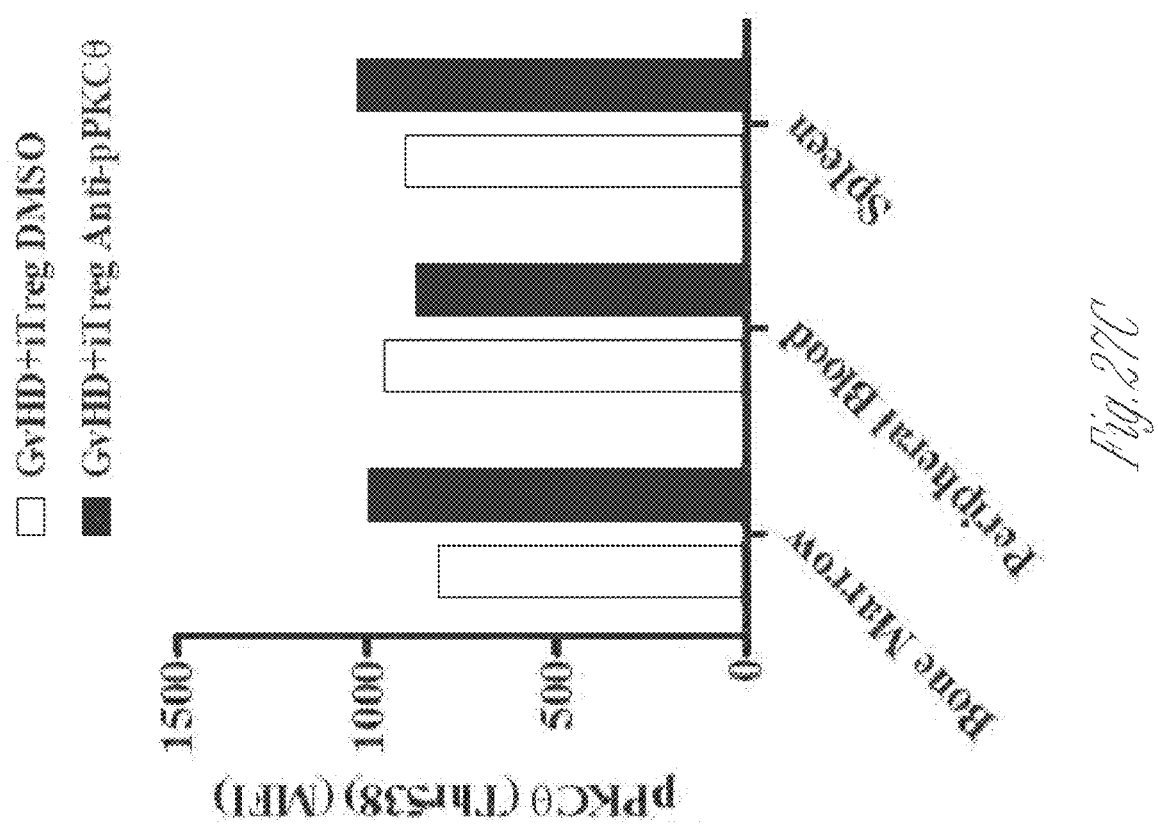
Figure 27E:
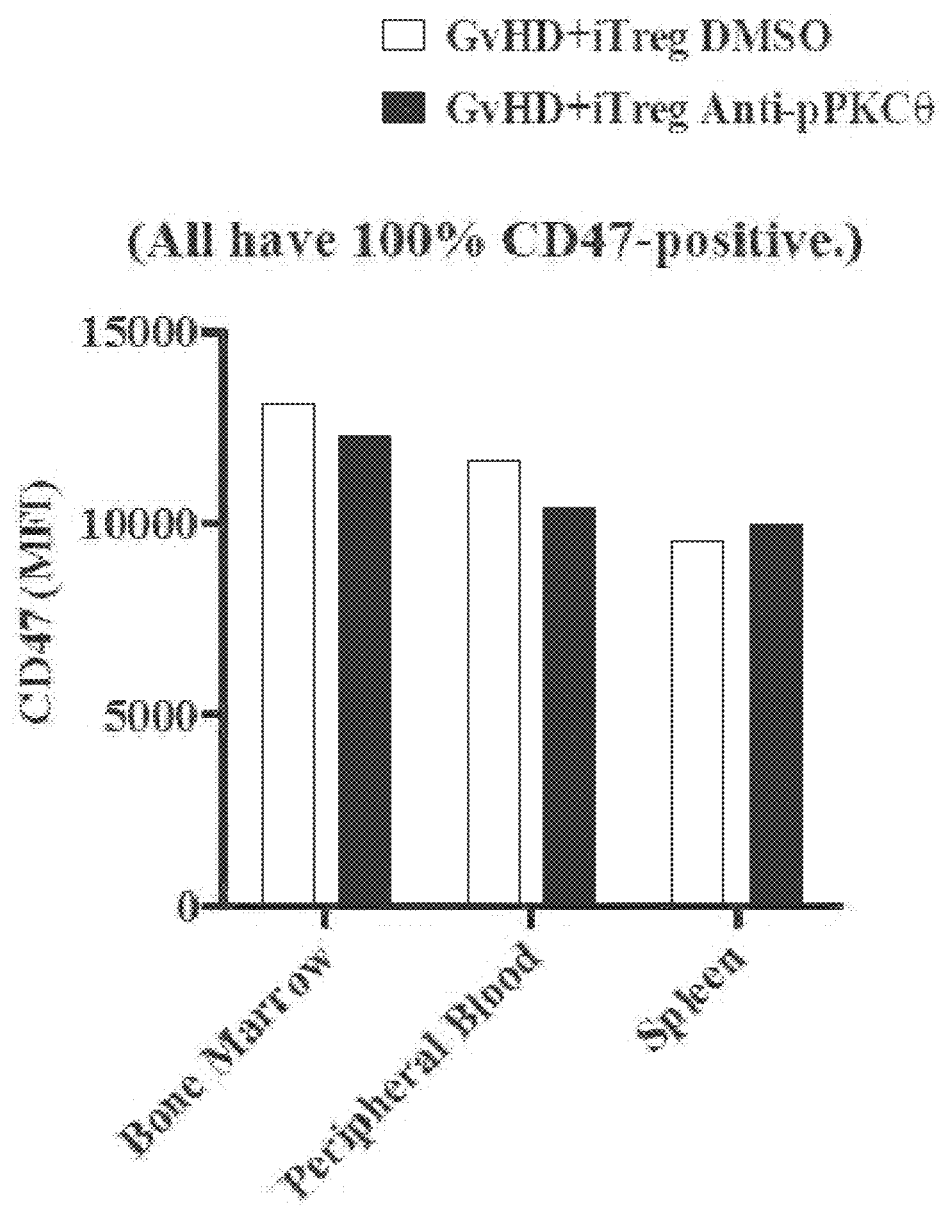
Figure 28:
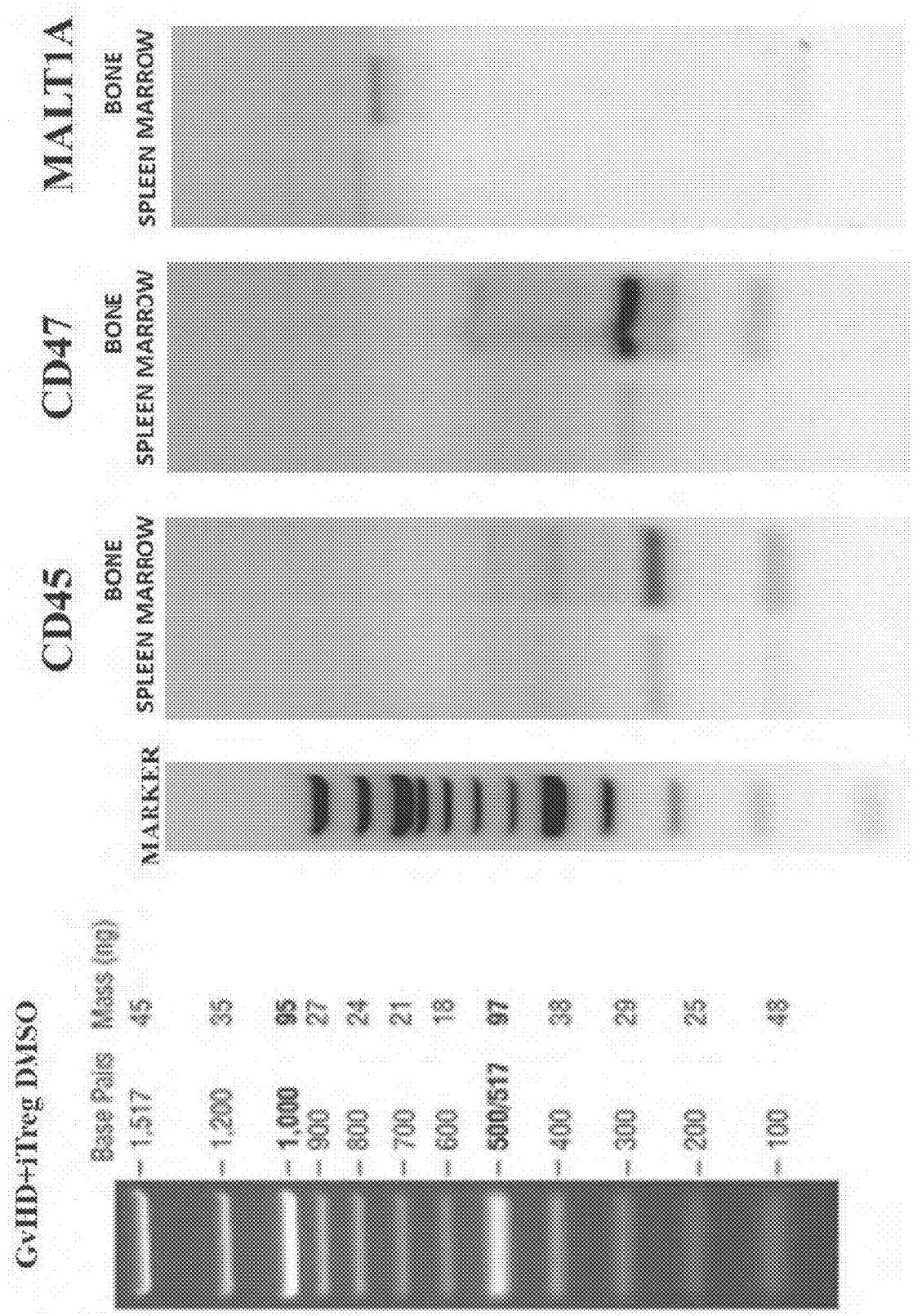
FIG. 28. Day 17 alternative splicing (CD4+CD25+ T cells).
Figure 29A:
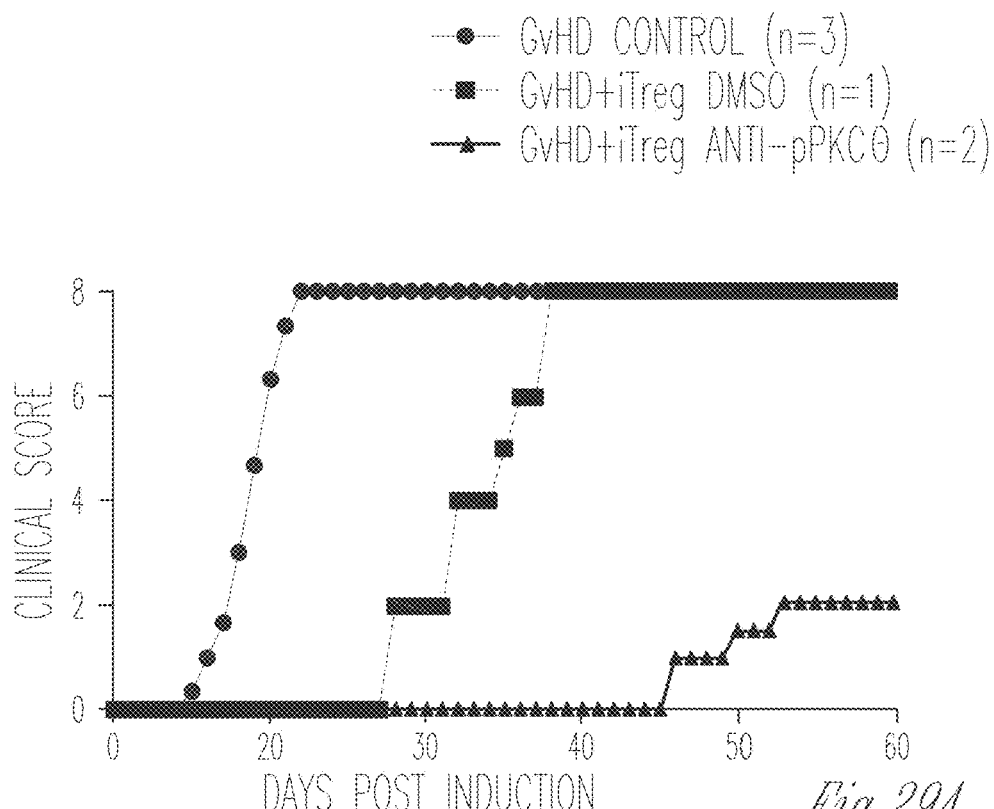
FIGS. 29A-B. Clinical score (A) and percent survivial (B).
Figure 29B:
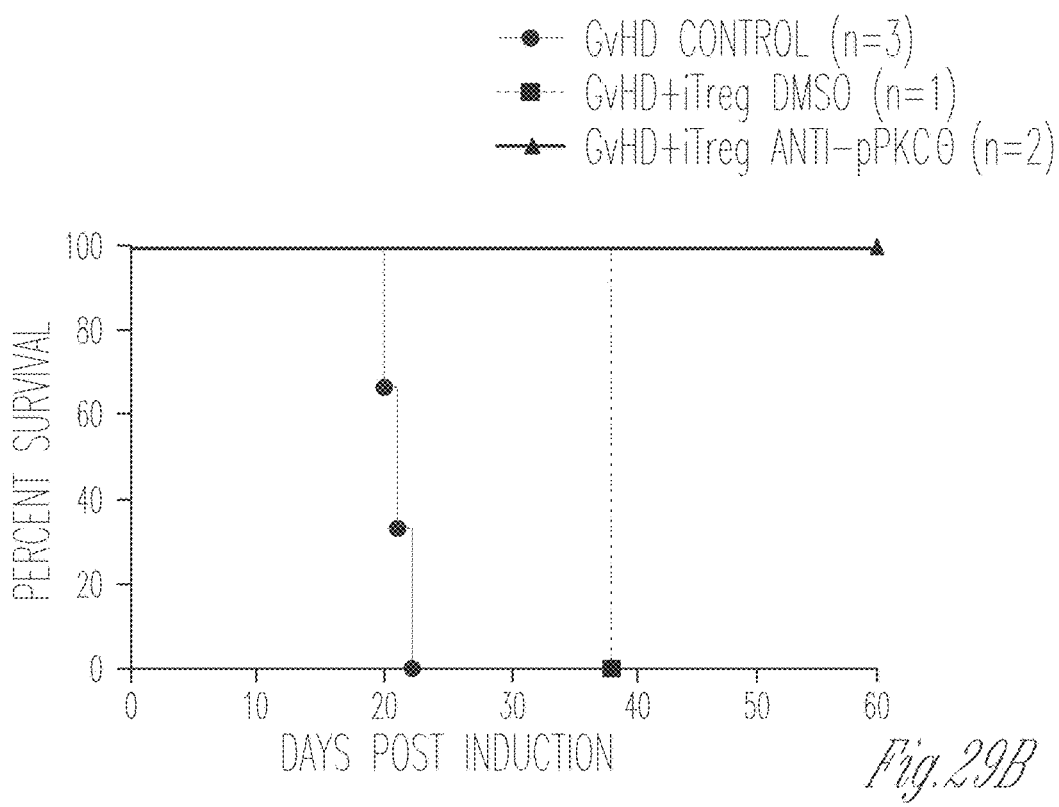
Figure 31C:
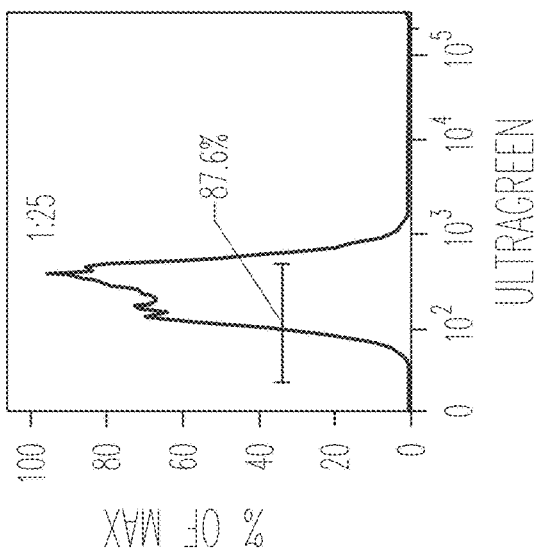
Figure 31B:
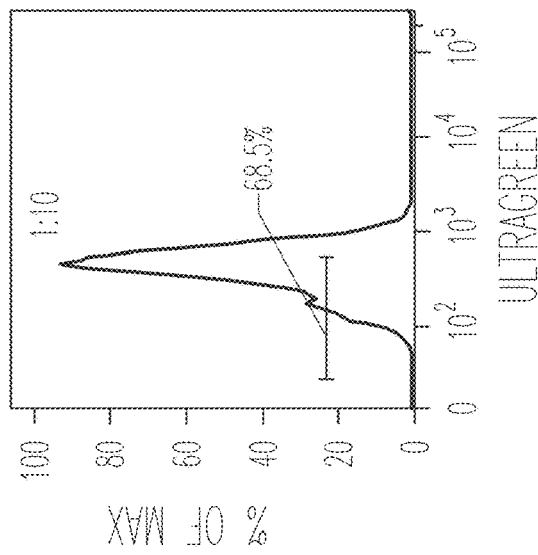
Figure 31A:
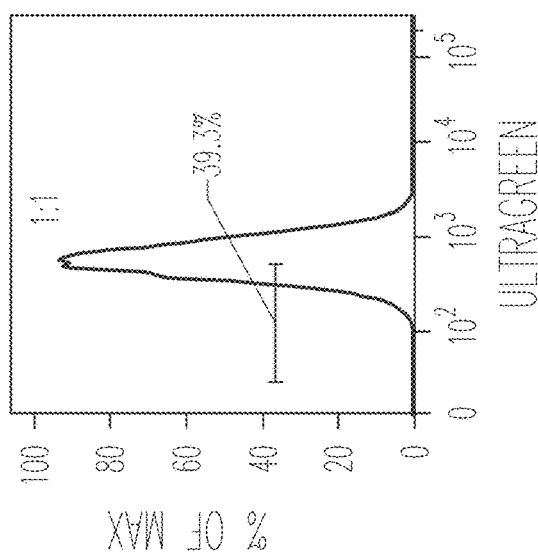
Figure 32B:
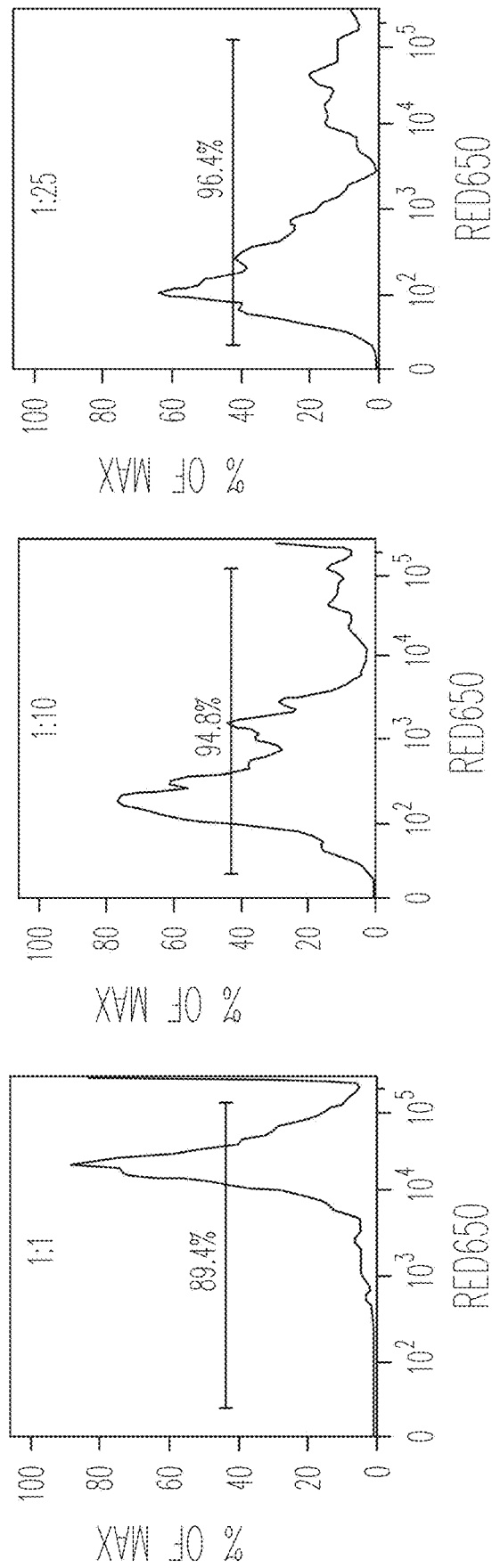
Figure 33B:
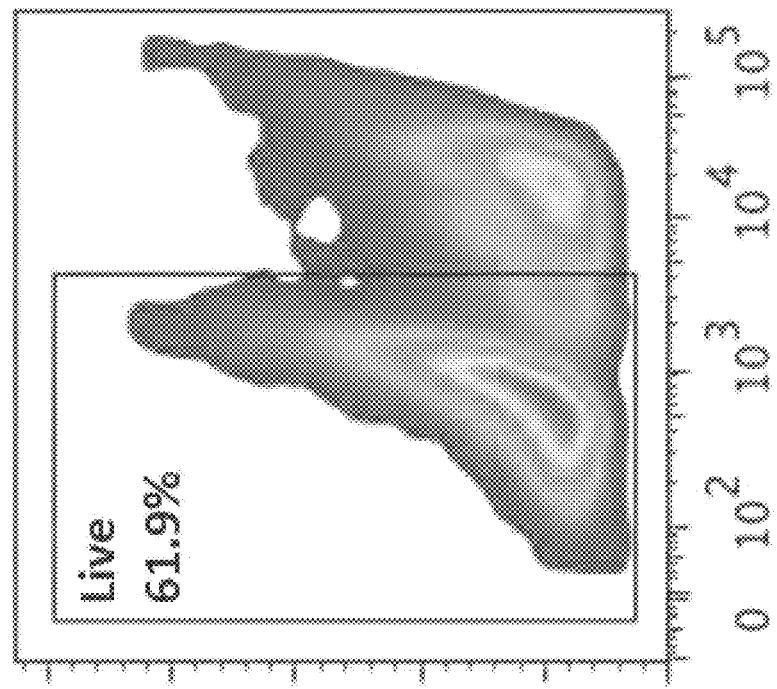
FIGS. 33A-B. Cellular viability. A) iTreg:huPMBCs 1:1. B) iTreg-antiPKCtheta:huPMBCs 1:1.
Figure 33A:
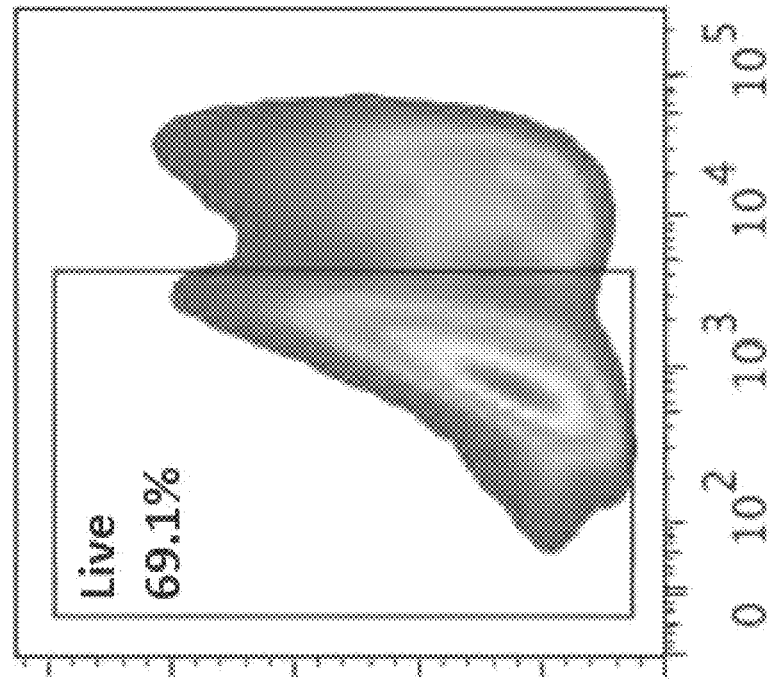
Figure 34B:
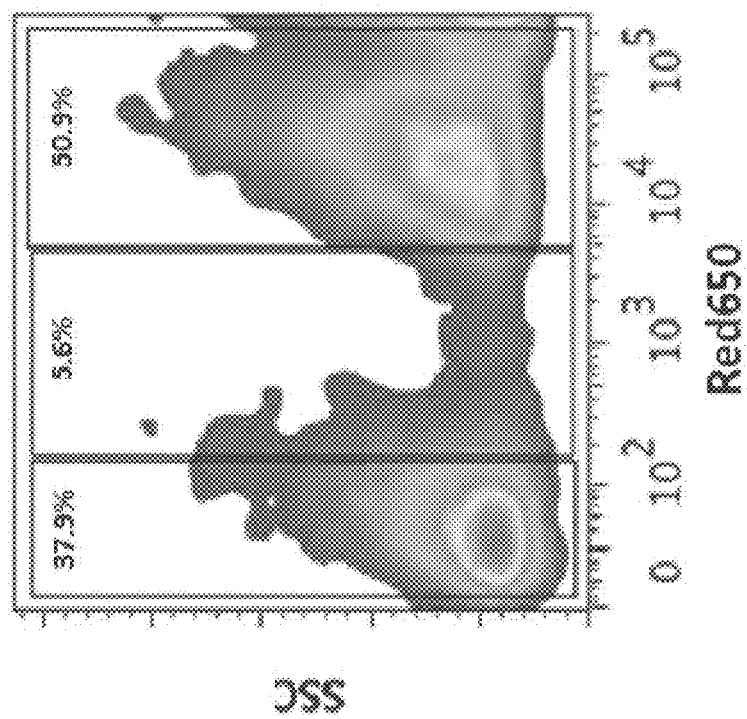
FIGS. 34A-B. Red650 populations. A) iTreg:huPMBCs 1:1. B) iTreg-antiPKCtheta:huPMBCs 1:1.
Figure 34A:
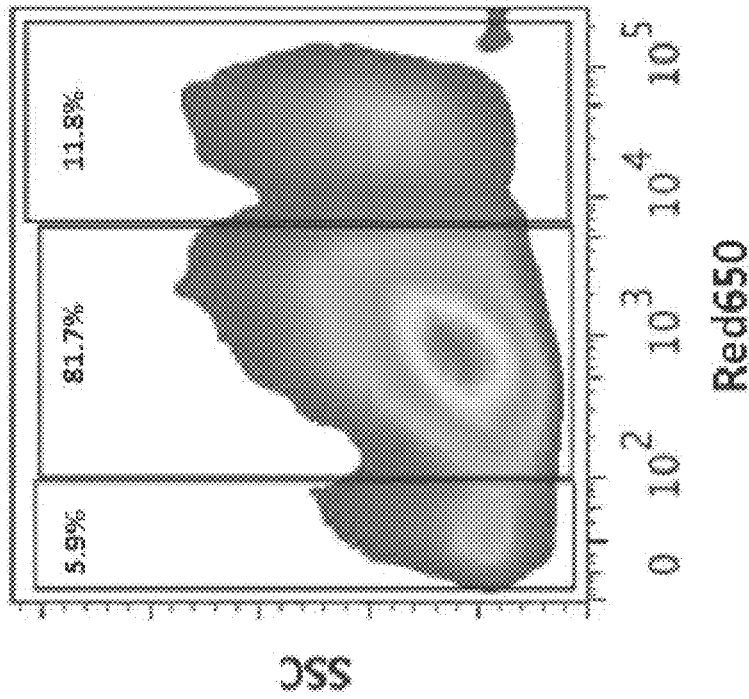
Figure 35B:
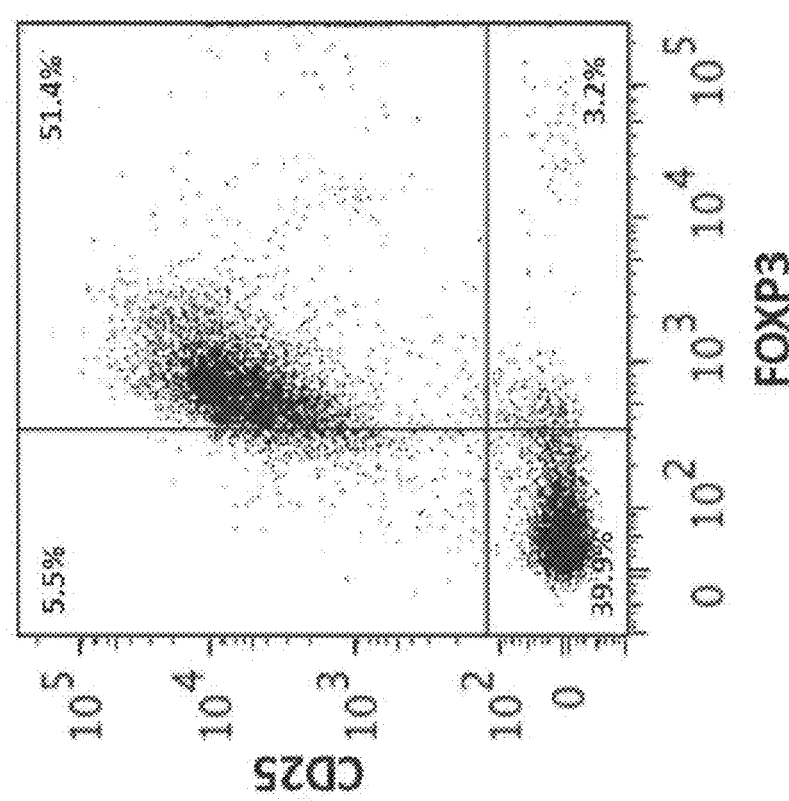
FIGS. 35A-B. Red650 high+med+low total in CD4+CD25+Foxp3+ T cells. A) iTreg:huPMBCs 1:1. B) iTreg-antiPKCtheta:huPMBCs 1:1.
Figure 35A:
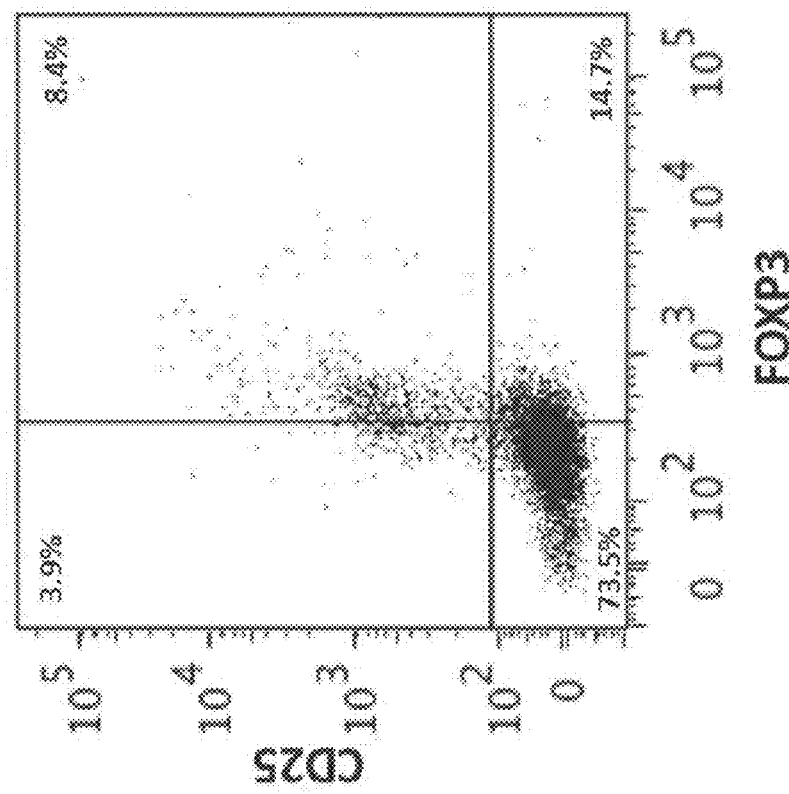
Figure 36B:

FIGS. 36A-B. Red650 high only population in CD4+CD25+Foxp3+ T cells. A) iTreg:huPMBCs 1:1. B) iTreg-antiPKCtheta:huPMBCs 1:1.
Figure 36A:
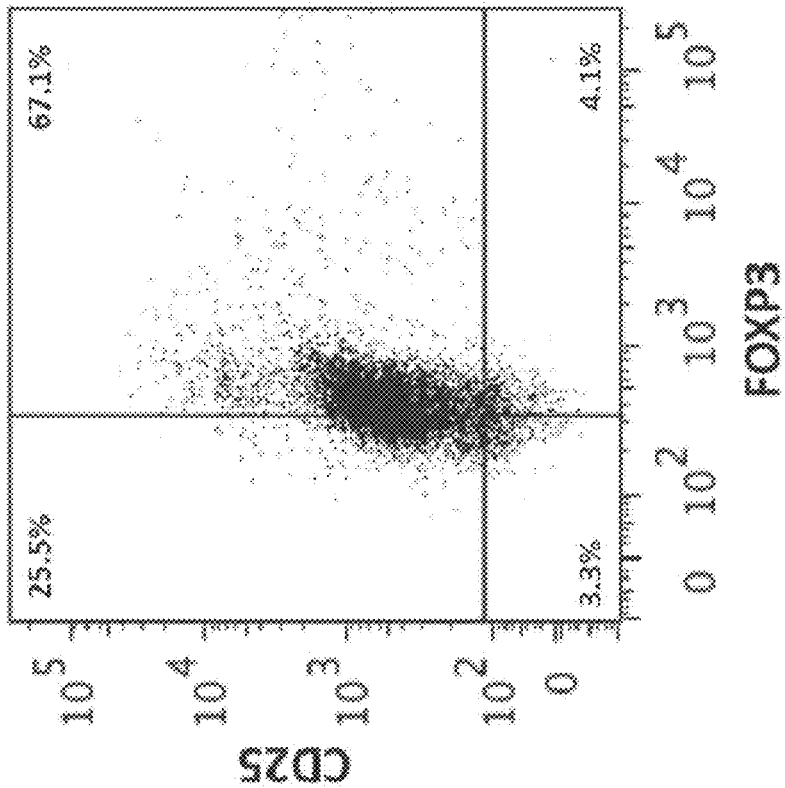
Figures 37A, 37B, 37C:
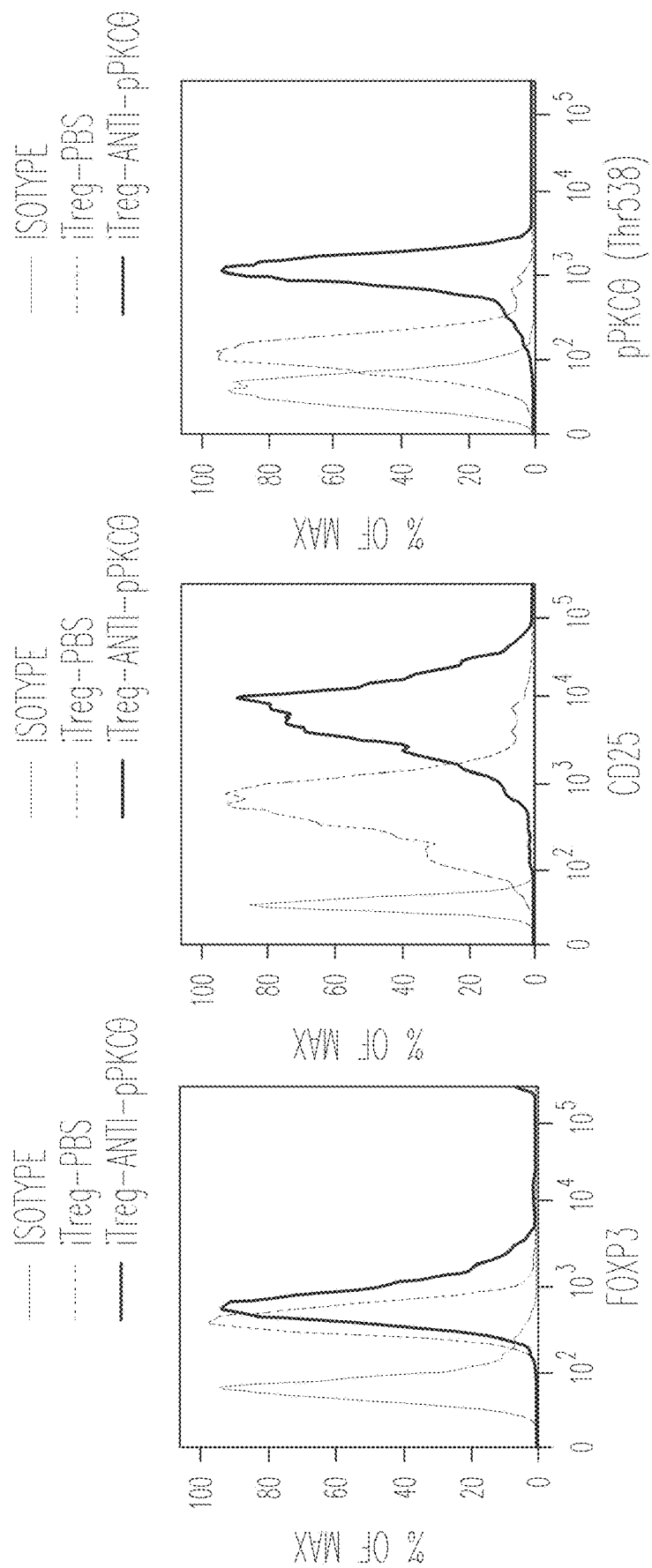
FIGS. 37A-C. Expression levels in treated and control cells. A) FOXP3. B) CD25. C) pPKCtheta.
Figure 38:
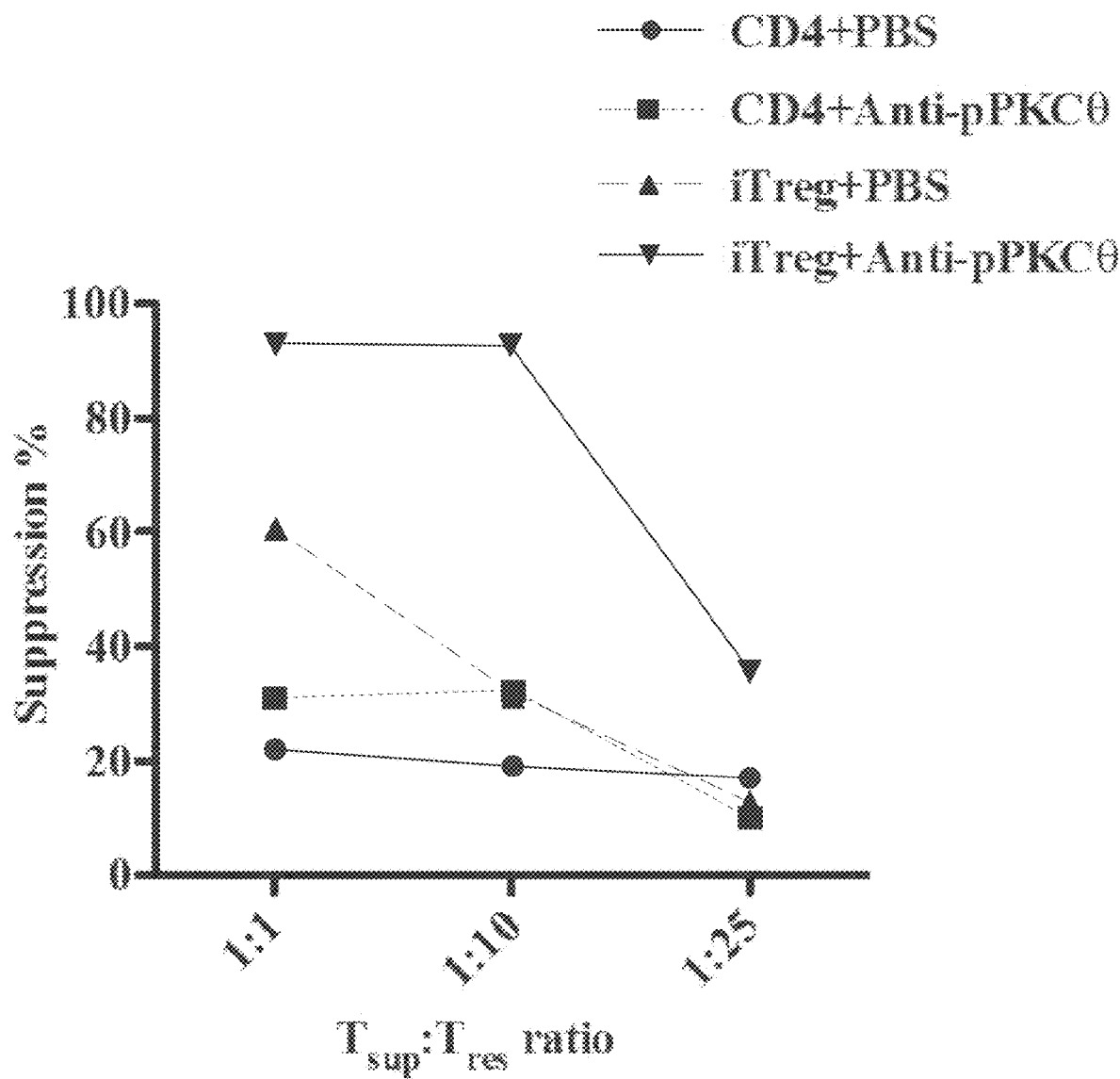
FIG. 38. Suppression % in treated and conrtol cells.
Figure 44A:
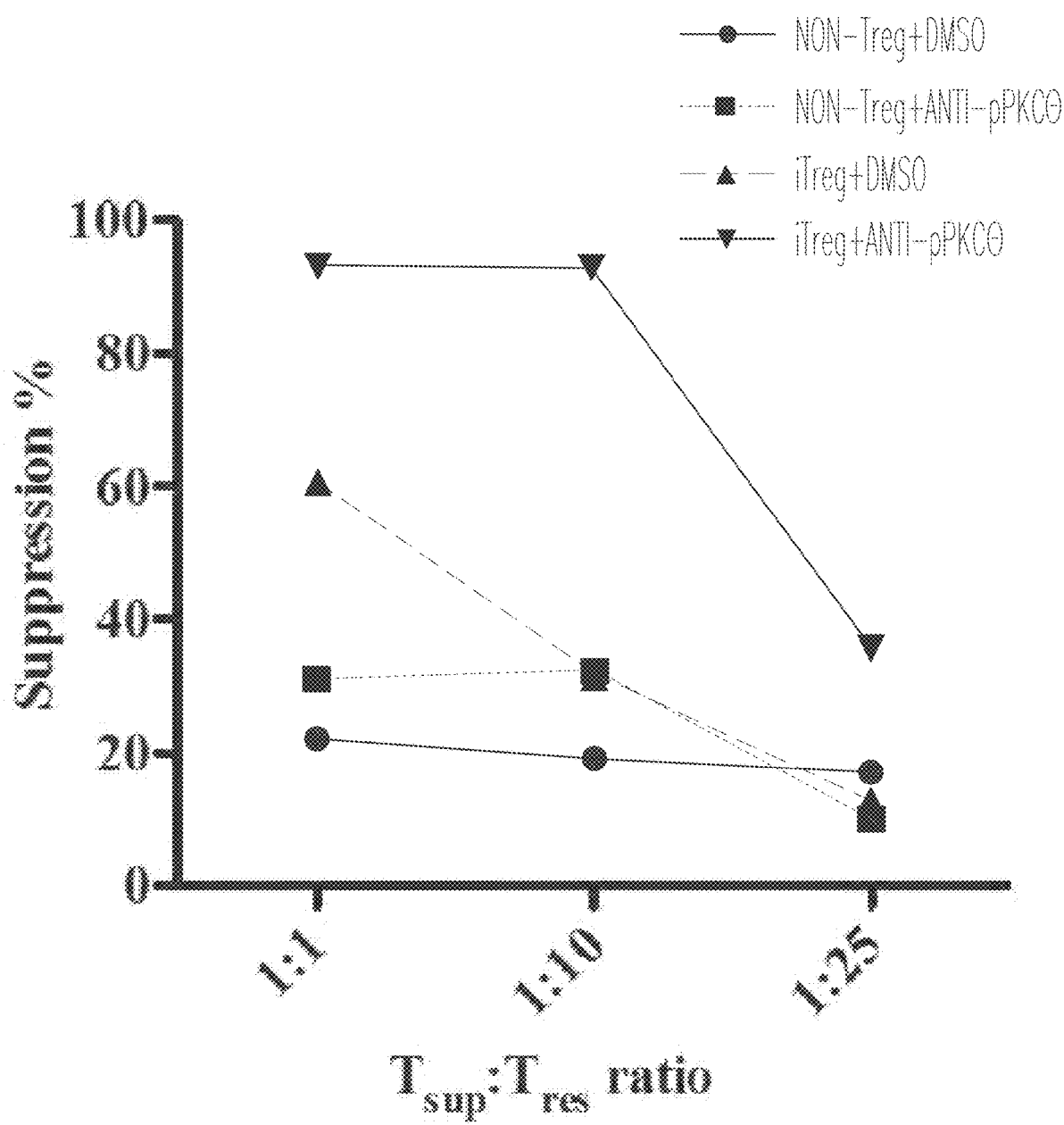
Figure 44C:
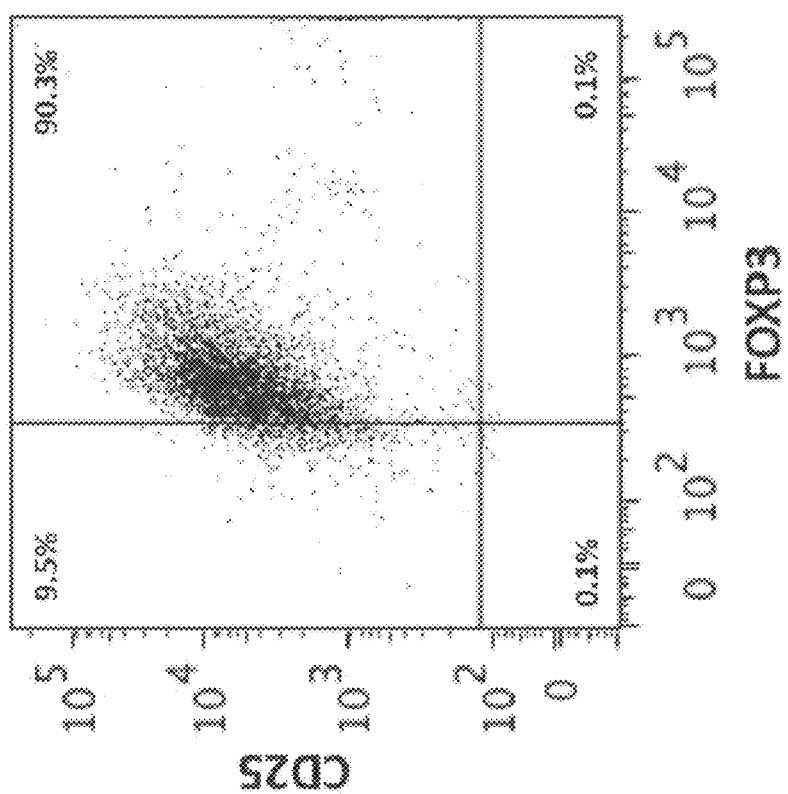
Figure 44B:
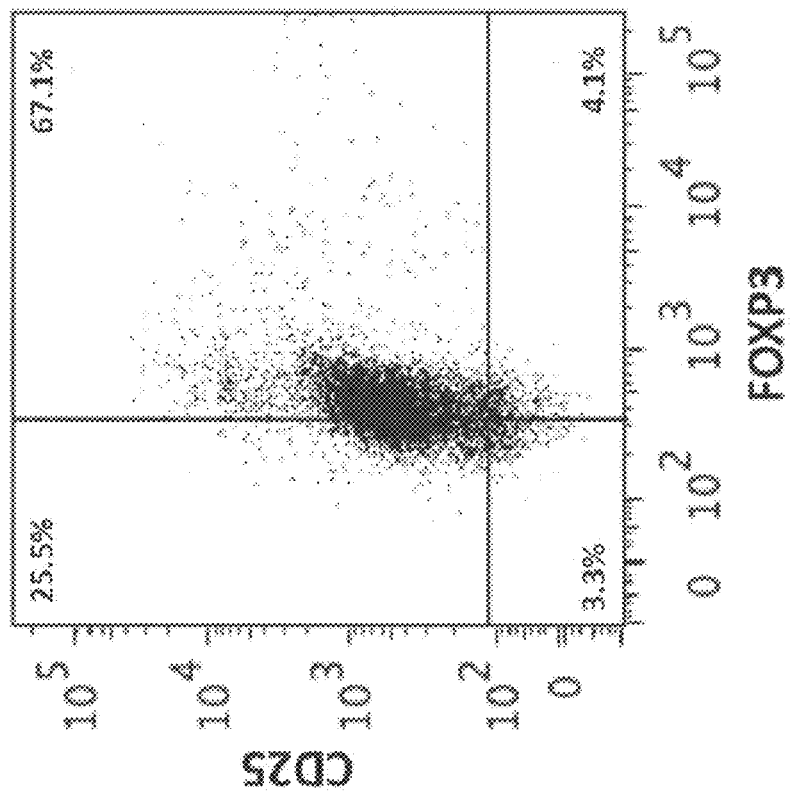

PTDM:anti-pPKCθ delivery increased functional markers of iTregs differentiated ex vivo, so we next evaluated the suppressive capabilities of these cells. We performed suppression assays whereby we labeled human PBMCs (responders, $T_{res}$) and added iTregs ($T_{sup}$) into the culture at different ratios. We measured cell proliferation of $T_{res}$ following 4 days of co-culture with iTregs generated either in the presence of DMSO or PTDM:anti-pPKCθ. After 4 days, we calculated the percent of proliferated $T_{res}$ and non-proliferated $T_{res}$. This allowed us to measure the suppression efficiency of Tregs. As shown in FIG. 6a, iTregs generated in the presence of PTDM:anti-pPKCθ suppressed the proliferation of responders with 96% efficiency (1:1, $T_{sup}$:$T_{res}$) and this efficiency persisted even at a ratio of 1:10, $T_{sup}$:$T_{res}$. We, therefore, called these cells 'super-suppressor' iTregs. Next, we determined the percent of CD4+CD25+Foxp3+ T cells present on day 4 after co-culture with $T_{res}$. We found there to be approximately 23% more PTDM:anti-pPKCθ-generated iTregs in co-culture on day +4, compared to their DMSO-treated iTreg counterparts, suggesting that PTDM:anti-pPKCθ delivery may stabilize iTreg phenotype by inducing CD25 and FOXP3 expression (FIG. 44). Additionally, these cells exhibited higher pPKCθ levels, suggesting that active PKCθ may be important for stable iTreg function (FIG. 44).

Figure 45A:
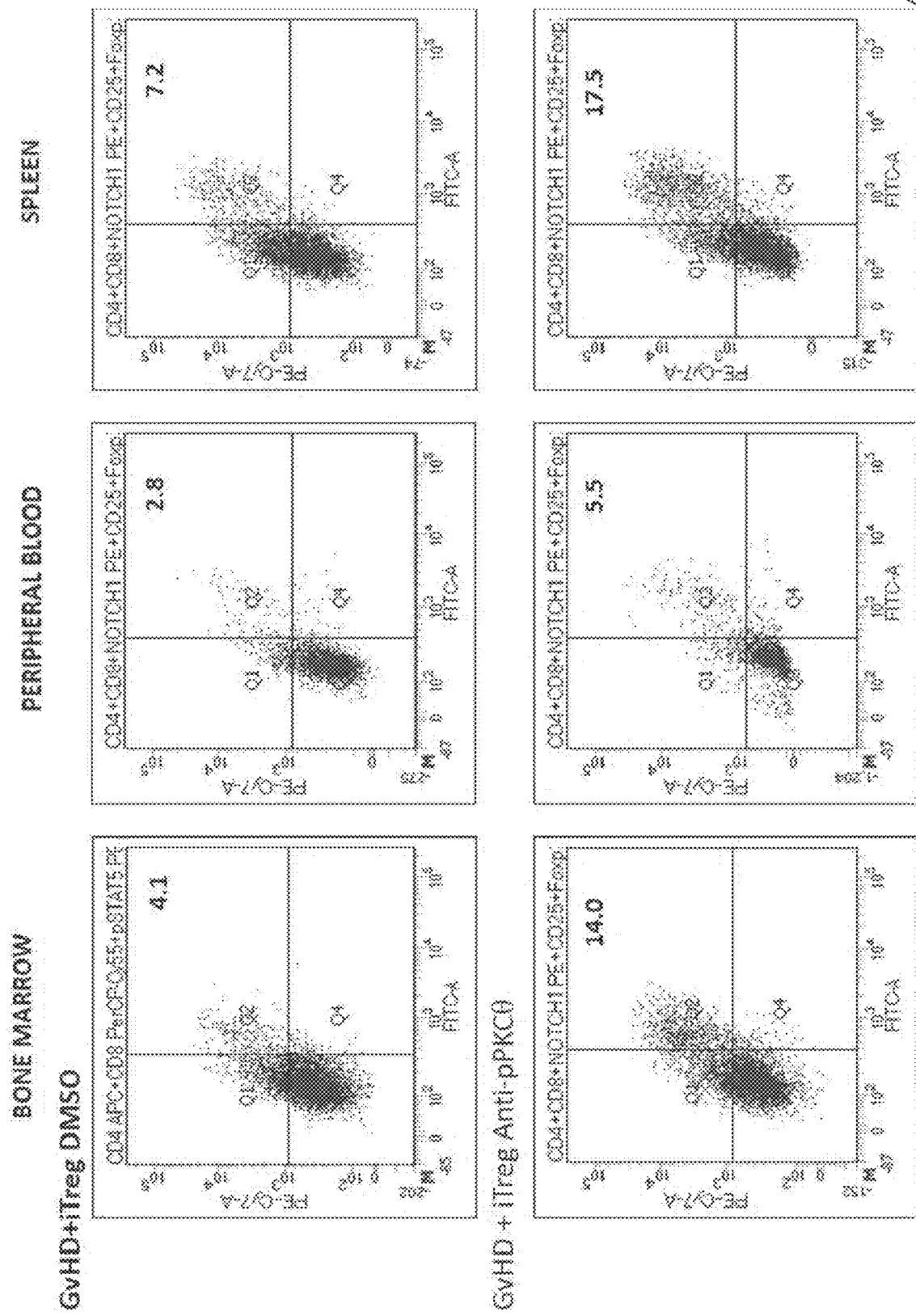
FIGS. 45A-D. PTDM:anti-pPKCθ-generated iTreg persist in vivo and provide a significant survival benefit in a humanized model of GvHD. GvHD was induced in NSG mice by transferring $10 \times 10^6$ hPBMC on Day 0. Mice also received, no iTregs, DMSO-generated iTregs or PTDM:anti-pPKCθ-generated iTregs, transferred at simultaneously at a ratio of 1:3 (iTreg:hPBMC). iTregs were labeled with the intravital dye CytoTell™ Red650 (AAT Bioquest, Inc., Sunnyvale, Calif.) to aid in recovering and analyzing iTreg. Animals were humanely sacrificed 17 days after disease induction and tissues were harvested to assess the GvHD progression and presence of Tregs. Additionally, some animals were placed on a survival study to assess clinical outcome and survival benefit of administering DMSO-generated- or PTDM:anti-pPKCθ-generated iTregs. On day 17 after disease induction (a) percent of Tregs present in bone marrow, peripheral blood, and spleen of mice that received DMSO-generated- or PTDM:anti-pPKCθ-generated iTregs was determined by co-expression of CD25 and FOXP3. Disease severity was determined by (b) assessing bone marrow cellularity on day 17. For survival studies, disease progression was determined using a set of defined criteria, and GvHD clinical score assessed daily beginning 10 days after disease induction. The (c) clinical scores and (d) survival of mice that received no iTregs (n=1), or DMSO-generated- (n=1) or PTDM:anti-pPKCθ-generated iTregs (n=2) is shown.
Figure 45B:
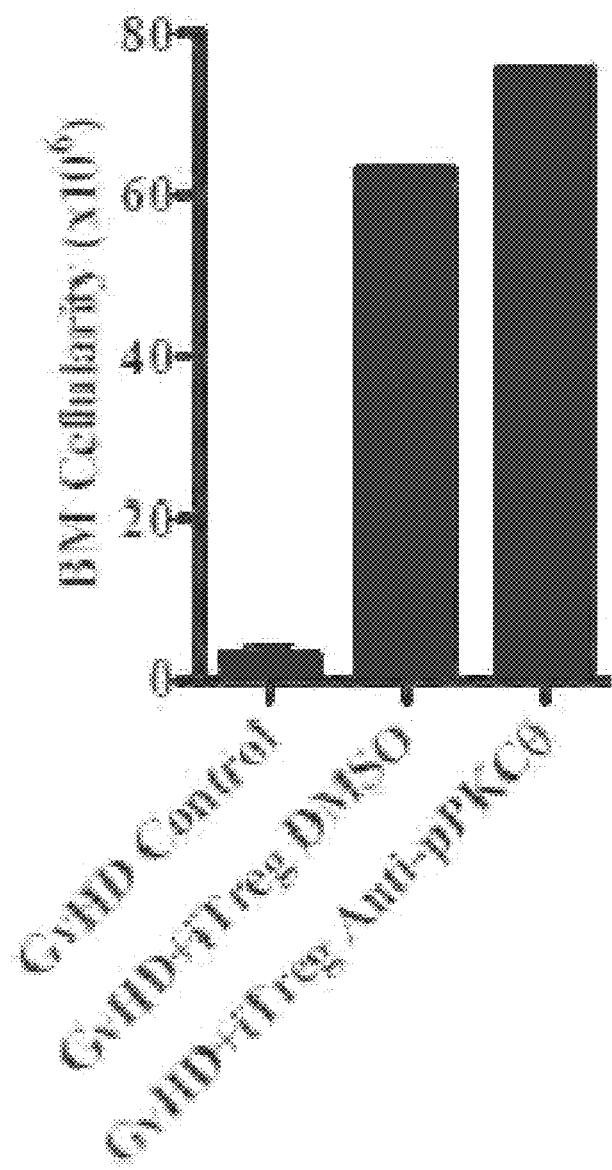
Figure 45C:
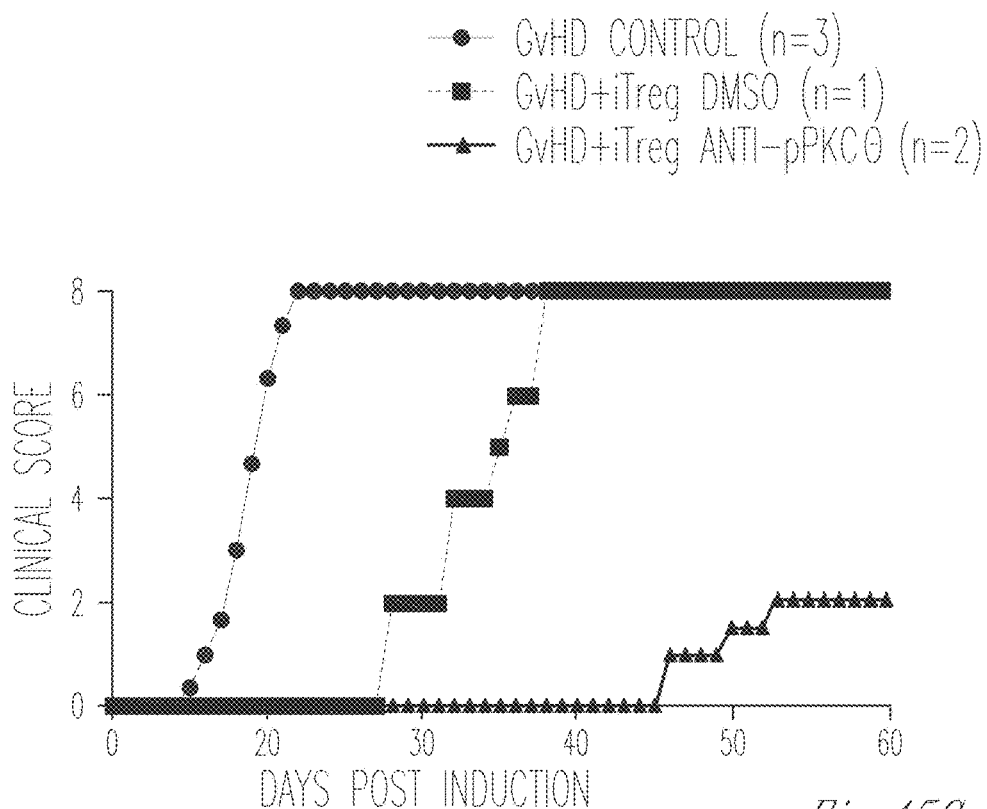
Figure 45D:
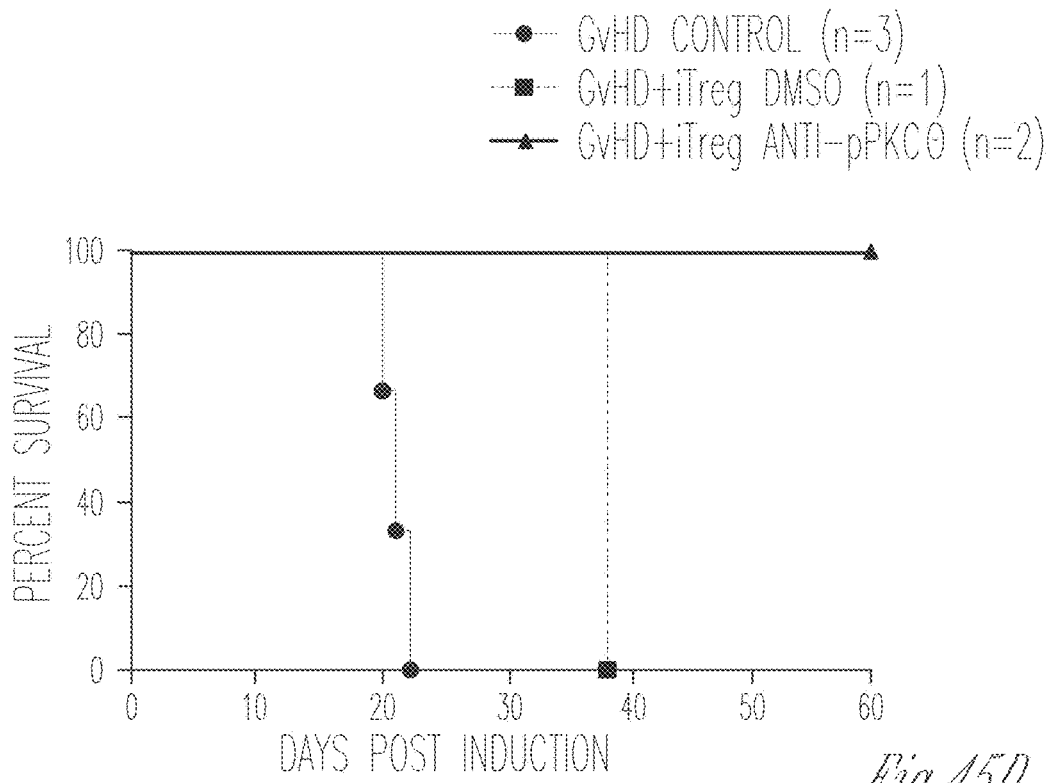
Figure 46A:
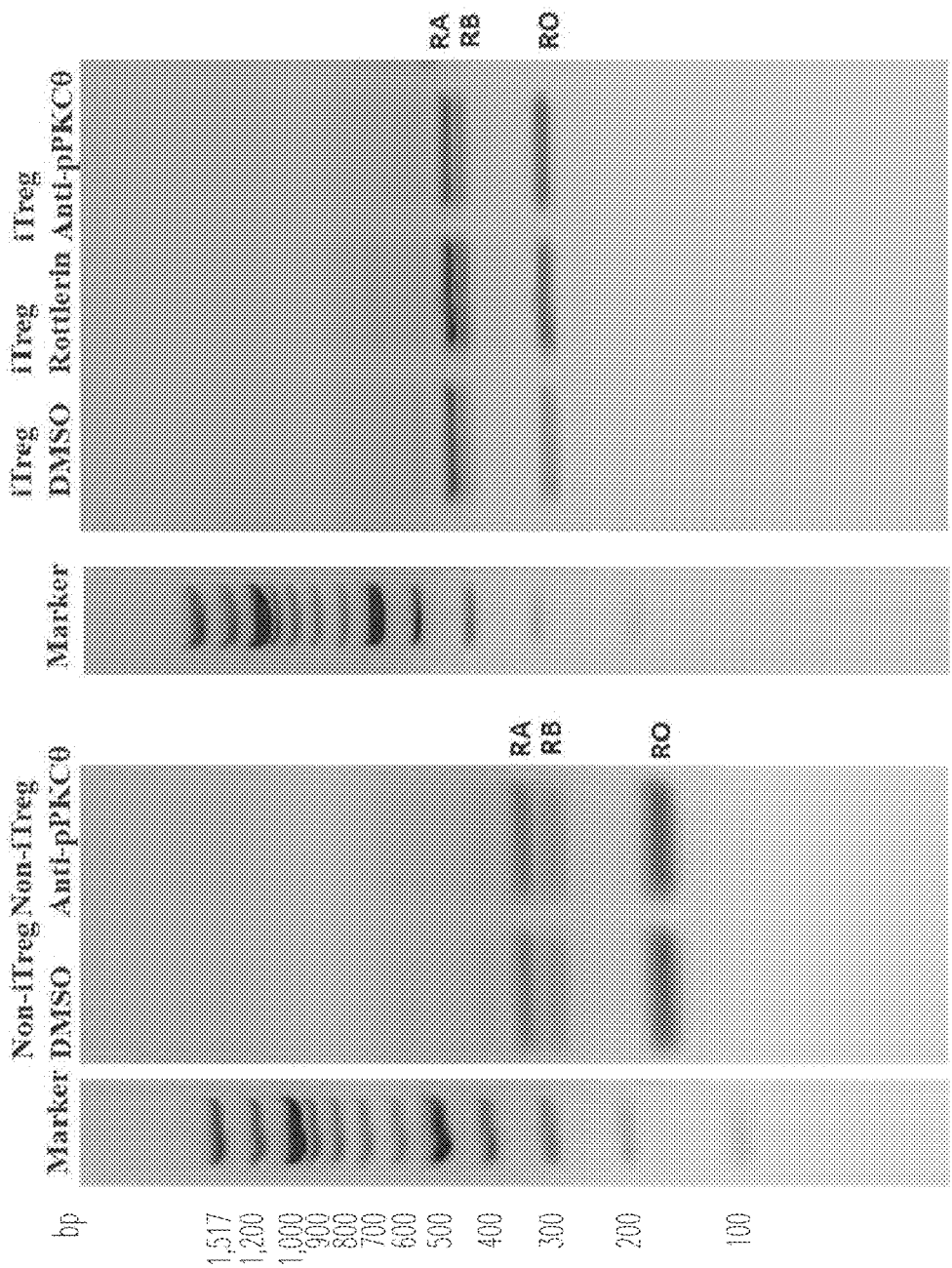
FIGS. 46A-D. PTDM-iTregs show unique splicing of genes important in iTreg function. Human CD4 T cells were treated with DMSO, or PTDM:anti-pPKCθ and resuspended in iTreg differentiation media for 5 days in the presence of anti-CD3 and anti-CD28 stimulation, as described. At the end of 5 days, total RNA was isolated from DMSO- or PTDM:anti-pPKCθ-generated iTregs, using CellXVivo Human Treg Cell Differentiation Kit (R&D Systems, Minneapolis, Minn.) following the manufacturer's directions. RNA was converted to cDNA by incubating samples with M-MLV Reverse Transcriptase enzyme (Promega, Madison, Wis.) and amplifying using oligoDTs and standard PCR methods. Gene amplification was accomplished utilizing quantitative real-time PCR, using specific forward and reverse primers designed to amplify CD45 (A), CD47 (B), MALT1A (C), and MALT1B (D) genes. Following amplification, 1 ig of each PCR product was separated on a 2% agarose gel and imaged using the Syngene G-Box gel documentation system (Syngene Ltd., Cambridge, UK) to evaluate transcript lengths and generation of alternatively spliced isoforms.
Figure 46B:
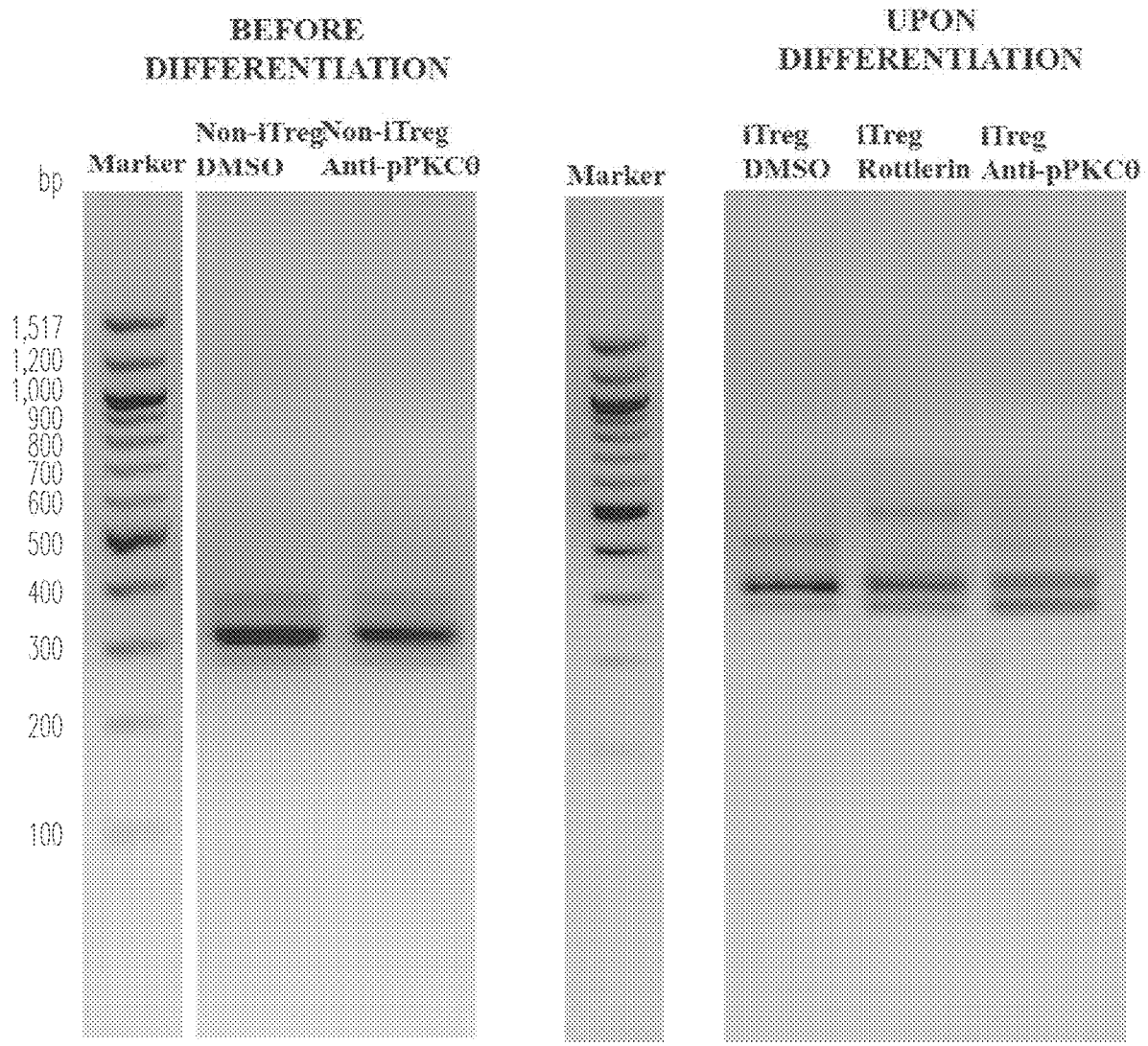
Figure 46C:
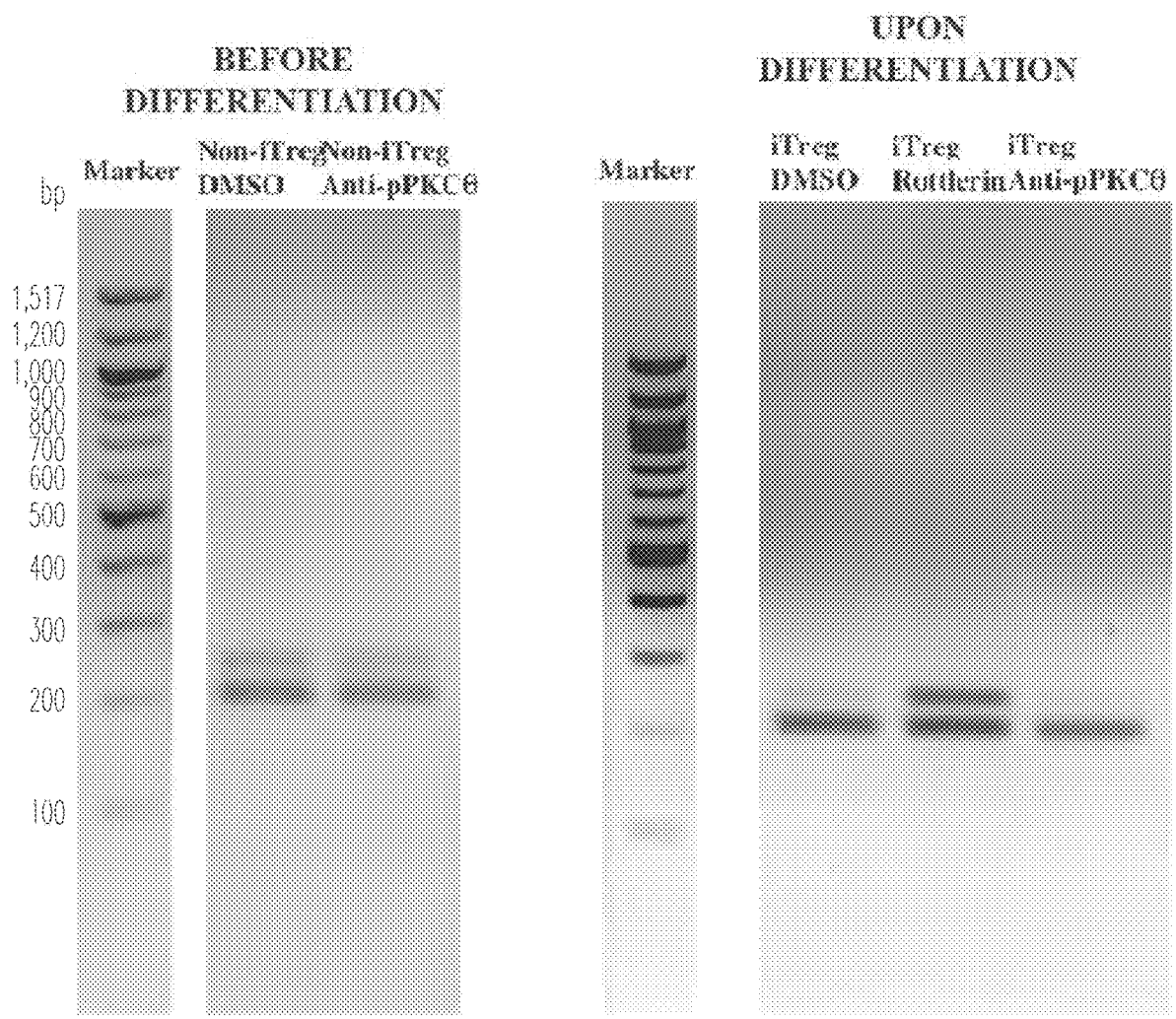
Figure 46D:
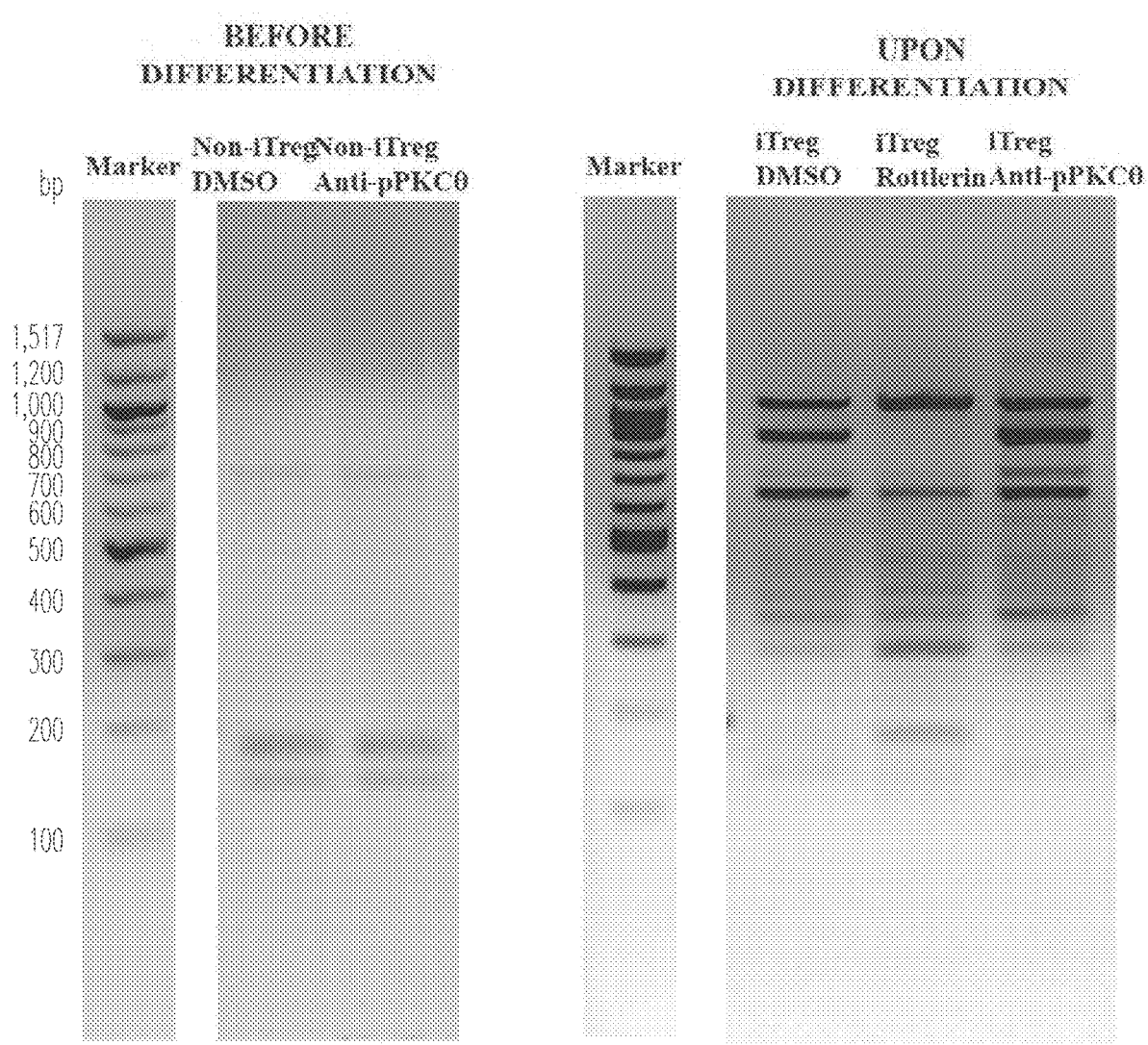

Ex vivo differentiation of iTregs following PTDM:anti-pPKCθ delivery generated 'super-suppressor' iTregs that were exceptionally efficient at suppressing proliferation when co-cultured with $T_{res}$. Given these results, we sought to determine whether these iTregs were also potent suppressors in vivo, utilizing a model of humanized GvHD. We transferred untreated CD4 T cells, DMSO-generated iTregs, or PTDM:anti-pPKCθ-generated iTregs, each labeled with a fluorescent intracellular dye to track the cells in vivo, together with unlabeled human PBMCs at a ratio of 1:3 (iTreg:hPBMC), into NSG mice on day 0 of GvHD induction. We harvested animals by humane euthanasia on day +17, then analyzed whether these fluorescently-labeled cells still persisted in target organs. We collected bone marrow, peripheral blood, and spleen and found that there were approximately 3-fold more PTDM:anti-pPKCθ-generated iTregs present in bone marrow and spleen in the animals receiving these cells, compared to animals that received DMSO-generated iTregs at the same 1:3 (iTreg:hPBMC), ratio (FIG. 45). We assessed bone marrow cellularity as a read out of attenuated GvHD, and found slightly greater bone marrow cellularity in animals that received PTDM:anti-pPKCθ-generated iTregs, compared to those that received DMSO-generated iTregs (FIG. 45). However, compared to the animal that received DMSO-generated iTregs, mice that received PTDM:anti-pPKCθ-generated iTregs on the day of GvHD induction survived more than twice as long, and exhibited a clinical score of "0" when the animal that received DMSO-generated iTregs was removed from the study, showing a clinical score of "8" (FIGS. 45C & D; respectively).

Both in vitro and in vivo data show promising results about generating supersuppressor iTregs after PTDM:anti-pPKCθ delivery. These iTregs exert higher production of certain functional proteins such as pSTAT5, and CTLA-4 providing an enhanced Treg function. We also show that PKCθ is sequestered in the cytosol and may influence all the downstream pathways that are associated to Treg stability. It seems that nuclear role of PKCθ at this point may be important to control Treg stability since we see diminished levels of nuclear PKCθ in 'supersuppressor' iTregs. The role of nuclear PKCθ still remains elusive and recently, it was reported that PKCtheta directly phosphorylates an important splicing factor, SC35, at both RS and RRM domains. RS domain mediates subcellular localization, nuclear export and functions as a splicing activator. RRM domain recognizes and binds to RNA and mediates subcellular localization and alternative splicing specificity of RNA (McCuaig et al., 2015). It is known that certain genes such as CD45 are alternatively spliced differently in effector, memory, and regulatory T cells. RO form of CD45 in Tregs is mainly associated with effector and memory features, whereas, RA form is associated with naïve and resting features (Booth et al., 2010). In order to investigate if, mechanistically, PKCθ sequestration changes the dynamics of alternative splicing in Tregs, we delivered PTDM:anti-pPKCθ to human CD4 T cells and differentiated the cells into iTregs for 5 days. On day 5, we harvested cells, collected RNA and evaluated expression of alternative splice variants using quantitative real time PCR. We found that PTDM:anti-pPKCθ delivery significantly changes the pattern of alternative splicing for several genes that are important for Treg stability and function, including CD45, CD47, MALT1A, and MALT1B (FIG. 46). This indicates that nuclear PKCθ in Tregs regulates alternative splicing to generate different isoforms. The data suggest that PTDM:anti-pPKCθ delivery, through its increased retention of pPKCθ in the cytosol, modulates alternative splicing to generate more stable transcripts of several different genes, and ultimately enhancing iTreg function.

Example 3

Regulatory T cells (Tregs) help maintain immunological tolerance and dampen inflammatory responses. Administering patient-derived Tregs can prevent immune-mediated tissue destruction of graft-vs-host disease (GvHD), which often accompanies hematopoietic stem cell transfer. Isolating, expanding, and maintaining the long-term in vivo suppressive capacity of Tregs constitute important barriers to their greater use in the clinic. Neutralizing the activity of the T cell-specific kinase, Protein Kinase C theta (PKCθ), which promotes T cell effector functions and represses Treg differentiation, may augment Treg immunosuppression and stability. Here, we used a synthetic, cell-penetrating peptide mimic to deliver, intracellularly, antibodies recognizing phosphorylated PKCθ (anti-pPKCθ into primary human CD4 T cells, then induced their ex vivo differentiation into regulatory T cells (anti-pPKCθ-iTregs). Anti-pPKCθ-iTregs displayed increased abundance of the Treg transcriptional regulator, Forkhead box P3 (FOXP3), the surface-bound immune checkpoint receptor, Programmed Death receptor-1 (PD-1), and pro-inflammatory interferon gamma (which has previously been ascribed to a specific population of stable, suppressive human iTregs. The capacity of anti-pPKCθ-iTregs to suppress, in vitro, was 10-fold greater than that of iTregs differentiated without anti-pPKCθ. When administered at the time of disease induction in a humanized model of GvHD, anti-pPKCθ-iTregs were superior to iTregs in attenuating lethal outcomes. Thus, constraining pPKCθ function during ex vivo differentiation, using a highly-specific, cell-penetrating antibody-delivery technique, produces a high number of FOXP3$^{high}$PD-1$^{high}$IFNgamma$^{high}$ iTregs that are long-lasting and highly efficacious in preventing GvHD in a preclinical model. This antibody-delivery approach may overcome critical obstacles currently encountered in the generation of patient-derived iTregs as a cell-based therapy for immune modulation.

Introduction

Naïve CD4 T cells differentiate into unique T helper subsets in response to specific signals generated in peripheral tissues. Regulatory T cells (Tregs) are a subset of differentiated T helper cells that function to mitigate immune responses and maintain immunological tolerance (Ohkura et al., 2013). In humans, Tregs are characterized in vivo as CD4$^+$CD25$^+$CD127$^-$FOXP3$^+$ cell, and can consistently confer suppressive properties across species and in multiple disease models (Hori et al., 2003; Khattri et al., 2003; Sakaguchi et al., 2010; Brunkow et al., 2001; Fontneot et al. 2005; Liu et al., 2006; Simonetta et al., 2010). Treg function is critical for attenuating autoimmune responses, mediating allotransplant tolerance, controlling tumor and microbial immunity, and preventing graft rejection in mice and humans, as well as suppressing the immune-mediated tissue destruction of graft-versus-host disease (GvHD), which frequently accompanies hematopoietic stem cell transplantation (Ohkura et al., 2013; Fontenot et al., 2005; Gangyly et al., 2014; Lee et al., 2015; Komanduri et al., 2011; Lu et al., 2012; Pankratz et al., 2014). In autoimmune conditions, Treg function can be negatively regulated by the inflammatory cytokine milieu (Shevach, 2009). Appropriate localization to secondary lymphoid organs and subsequent expansion are necessary for Treg suppressive function in vivo (Nguyen et al., 2007).

One means by which Tregs suppress alloresponsive T cells is through multiple co-inhibitory receptors, via cell-cell contact. Increased surface concentration of neuropilin-1 (NRP1), Program Death receptor-1 (PD-1), Lymphocyte Activation Gene-3 (LAG-3), and Cytotoxic T Lymphocyte-Associated protein-4 (CTLA-4), on Tregs can competitively block contact between antigen presenting cells (APC) with naïve T cells (Raimondi et al., 2006; Delgoffe et al., 2013; Do et al., 2016; Matheu et al., 2015). The immunological synapse (IS), the supramolecular signaling complex that coalesces in an ordered fashion at the contact point between naïve T cells and antigen-loaded dendritic cells (DC), is also organized differently in Tregs. Following stimulation through the T cell receptor (TCR), the T cell-specific kinase, Protein Kinase C theta (PKCθ is phosphorylated at threonine 538, and translocates to the center-most region of the IS. Here, it links activation signals from the TCR with costimulatory signals provided by CD28, culminating in transcription of immune-responsive genes (Isakove et al, 2002; Gupta et al., 2008; Sun et al., 20001 Sumoza-Toledo et al. 2006; Sedwick et al., 2004; Barouch-Betov et al., 2005; Manicassamy et al., 2006; Manicassamy et al., 2007). Interestingly, PKC is the only PKC isoform recruited to the center of the IS. However, unlike in effector T cells, in Tregs PKCθ is sequestered away from the central domain of the IS (Boschelli et al., 2009; Roybal et al., 2010). Through this differential positioning in the IS, PKCθ promotes activation of effector T cell functions at the expense of regulatory T cell programs (Sun et al., 2000; Ryobal et al., 2010; Gruber et al., 2009). Inhibiting the actions of PKCθ with small molecule inhibitors or using siRNA approaches enhances the suppressive capacity of Treg cells, restores impaired function of Tregs from rheumatoid arthritis patients, and blocks the autoimmune response in a mouse model of colitis (Zhang et al., 2013; Zanin-Zhoriv et al., 2010). Therefore, attenuating PKCθ activity in Tregs may be a valuable component in Treg adoptive immunotherapy when used to treat autoimmune conditions or GvHD (Zanon-Zhorov et al., 2010)

Initial evidence showed PKCθ is required for fully-functional mature, but not immature, T cell responses, by bridging stimuli received through the TCR to downstream signals generated by nuclear factor-kappa B (NF-κB) transcriptional regulators (Sun et al., 2000). More recent work demonstrated that immune cells from PKCθ-deficient mice, transplanted together with T cell-depleted bone marrow (BM) stem cells from wild-type mice, did not induce GvHD in recipients. This is in contrast to the majority of recipient mice that died from GvHD when wild-type immune cells were transferred together with BM stem cells (Sun, 2012). PKCθ-deficient immune cells did not confer GvHD; however, they retained their ability to protect recipient mice from bacterial and viral infections, as well as to afford immune depletion of residual leukemia cells. These and follow-up studies reinforce the notion that inhibiting PKCθ activity during BM transplantation may constitute a beneficial approach to limiting the severity of GvHD, while maintaining important anti-tumor surveillance.

Effectively and specifically blocking PKCθ function is challenging, due to the high structural homology it shares with eight other, more broadly-expressed family members. As a result, many existing small molecule PKCθ inhibitors have toxic or off-target effects and show sub-optimal penetration into T cells (Isakov, 2012; Mochly-Rosen et al., 2012). In contrast, using antibodies to modulate cell surface receptor function, either positively or negatively, is now a widely-accepted immunotherapeutic approach. However, because of its intracellular residence PKCθ is not a suitable candidate for antibody-targeting strategies. Recently we developed and reported on a highly-specific, successful strategy for routine and effective intracellular antibody delivery using cell-penetrating peptide mimics and demonstrated its powerful application by targeting a phosphorylated threonine residue (Thr 538) of activated (p)PKCθ in the context of T cell immunomodulation. Manipulating primary T cells ex vivo, via intracellular anti-pPKCθ delivery, constrained pPKCθ in the cytosol and reduced the capacity of these cells to adopt a pro-inflammatory T helper type 1 cell fate. The ex vivo anti-pPKCθ treatment produced a durable, non-cytotoxic effect on transferred cells, persisting for several weeks. This was demonstrated by substantially reduced disease severity and significantly extended survival when these cells were used to induce GvHD in a humanized mouse model, compared to mice that received non-manipulated T cells (Ozay et al., 2016).

Naïve CD4 T cells can be induced to differentiate in vitro into regulatory T cells (iTregs). In an allogenic mouse model of BM transplantation, adoptively transferring iTregs provided beneficial relief from disease by suppressing immune-mediated, acute GvHD (Nyugen et al., 2007). This approach has now entered the clinic where cellular immunotherapy by adoptive transfer of iTregs is now recognized as a realistic and efficacious option to treat immune-mediated conditions (Ganguly et al., 2009). The first in-human trial of adoptive iTreg therapy delivered encouraging outcomes for preventing GvHD associate with allogeneic stem cell transplantation and offer great promise for treating autoimmune diseases and allograft rejection.

Here, we report that ex vivo delivery of an antibody specific for phosphorylated PKCθ using cell-penetrating peptide mimics, enhances the differentiation and expansion of iTregs in culture. Moreover, anti-pPKCθ-treated iTregs exhibited increased suppressive properties, in vitro, as characterized by increased concentration of surface of the co-inhibitory receptor, PD-1. Anti-pPKCθ iTregs could be detected, in vivo, up to 17 days after their administration into recipient mice and, compared to non-treated iTregs, were highly efficacious in preventing GvHD in a humanized model. Therefore, intracellular delivery of anti-pPKCθ into human CD4 T cells may represent an approach that overcomes obstacles associated with in vitro expansion and sustained in vivo stability, and provide a powerful, reproducible, and effective means of generating iTregs for therapeutic application.

Materials and Methods

Animals

All animal studies were approved by, and conducted under the oversight of, the Institutional Animal Care and Use Committee of the University of Massachusetts, Amherst. Seven-week old female NOD.Cg-Prkdc$^{scid}$ $^{II}$2rg$^{tm1 WjI}$/SzJ (NSG) mice, were purchased from the Jackson Laboratories (Bar Harbor, Me.). Upon arrival, these mice were rested for one week prior to use. Mice were housed under pathogen-free conditions in micro-isolator cages and received acidified water (pH 3.0) supplemented with two types of antibiotics (trimethoprim+sulfamethoxazole) throughout the duration of the experimental procedures.

Antibodies and Reagents

Antibodies used in this study were acquired from: (1) BioLegend: CD3epsilon (Purified, Clone: UCHT1), CD28 (Purified, Clone: CD28.2), CD4 (BV711, Clone: RPA-T4), CD8 (APC/Cy7, Clone: RPA-T8), CD25 (Biotin, Clone: BC96) CD25 (AF700, Clone: BC96), CD25 (PE/Cy7, Clone: BC96), CD45RA (BV510, Clone: HI100), CD45RO (PE, Clone: UCHL1), CD127 (Biotin, Clone: A019D$_5$), CD127 (AF700, Clone: A019D$_5$), CTLA-4 (APC, Clone: BNI3), FOXP3 (AF488, Clone: 150D), LAG-3 (BV421, Clone: 11C3C65), NRP1 (PerCP/Cy5.5, Clone: 12C2), PD-1 (APC/Fire750, Clone: EH12.2H7), (2) eBioscience: CD4/CD8 cocktail (FITC/PE, Clones: RPA-T4, RPA-T8), human CD45 (PE, Clone: 2D$_1$), NOTCH1 (PE, Clone: mN1A), pSTAT3 Tyr705 (PE, Clone: LUVNKLA), pSTAT5 Tyr694 (PE, Clone: SRBCZX), (3) BD Biosciences: mouse CD45 (FITC, Clone: 30-F11), IFNgamma(APC, Clone: B27), (4) GeneTex: NOTCH1 (FITC, Clone: mN1A), (5) Cell Signaling Technology: Histone H3 (Unconjugated, anti-mouse, Clone:96C10), pPKCθ (Unconjugated, anti-rabbit, Thr538), Total PKCθ (Unconjugated, Clone: E117Y), (6) Sigma: alpha-Tubulin (Unconjugated, anti-mouse, Clone: B-5-1-2), (7) Life Technologies: Phospho-PKC theta (Thr538) (Unconjugated, Clone: F4H4L1), F(ab')2-Goat anti-rabbit IgG (H+L) secondary antibody (Qdot625, polyclonal). For nuclear staining, DRAQ5™ was obtained from Thermo Scientific. Live/dead staining was performed utilizing either Zombie aqua or Zombie violet fixable viability kit purchased from BioLegend. For in vitro suppression assay, cells were tracked via labeling with CytoTell™ Ultra-Green or CytoTell™ Red650 purchased from AAT Bioquest, Inc.

Human iTreg Differentiation Coupled with Intracellular P$_{13}$D$_5$:Anti-pPKCθ Delivery 1 µM of P$_{13}$D$_5$ and 25 nM of anti-pPKCθ (Thr538, Clone: F4H4L1) were complexed in PBS (phosphate buffered saline, pH 7.2) at a specific ratio (P$_{13}$D$_5$:anti-pPKCθ=40:1). The PTDM: antibody complex was incubated for 30 min at RT. Meanwhile, CD4$^+$ T cells were isolated from human PBMCs (purchased from StemCell Technologies, Inc.) using the MojoSort™ Human T Cell Isolation Kit (BioLegend). Isolated human CD4 T cells were treated with the PTDM: antibody complex for 4 hours at 37° C. (some cells were treated with DMSO, as vehicle control). Cells were harvested and washed with PBS. Later, cells were thoroughly washed twice with 20 U/mL heparin in PBS for 5 minutes on ice to remove surface-bound complexes outside cellular membrane. For iTreg differentiation, CellXVivo™ Human Treg Differentiation Kit (R&D Systems) was used and iTreg Differentiation Media was prepared using X-VIVO™ 15 Chemically Defined, Serum-free Hematopoietic Cell Medium according to manufacturer's instructions. Treated cell pellets were then resuspended in iTreg differentiation media and seeded onto 5 μg/mL of anti-CD3ε-plus 2.5 μg/mL of anti-CD28-coated tissue culture wells and stimulated for 5 days at 37° C.

Immunoblotting iTreg cells were harvested on day 5 of differentiation. Nuclear and cytosolic extracts were prepared by using NE-PER™ M Nuclear and Cytosolic Extraction Kit (Thermo Scientific). 1×SDS Laemmli Buffer was added into the samples for running on 8% SDS-PAGE for western blot. The blots were probed with anti-pPKCθ (Thr538) and anti-total PKCθ for further analysis. Anti-α-Tubulin was probed for cytosolic loading control and anti-histone H3 was probed for nuclear loading control.

Protein Subcellular Localization Via AMNIS Imaging Flow Cytometry

For in vitro analysis, iTreg cells were harvested on day 5 of differentiation. For in vivo analysis, bone marrow, spleen, and peripheral blood were collected on day +17 and single cell suspensions were prepared from each organ. Cells were surface-stained for CD4 BV711 and CD25 PECy7. Each sample was then fixed and permeabilized according to the manufacturer's directions using the Foxp3 Staining Buffer Kit (BD Biosciences, Billerica, Mass.) and stained for FOXP3 AF488, pPKCθ (Thr538) followed by Qdot625-labeled secondary antibody, pSTAT3 (Tyr705) PE, or pSTAT5 (Tyr694) PE. Nuclei were stained using the cell-permeable DRAQ5™ Fluorescent Probe (ThermoFisher Scientific, Waltham, Mass.). The cells were visualized and quantified using an ImageStream® x Mark II Imaging Flow Cytometer (EMD Millipore, Billerica, Mass.). Subcellular localizations and nuclear similarity scores of FOXP3, pPKCθ (Thr538), pSTAT3, and pSTAT5 proteins were determined using the Nuclear Localization Wizard and the IDEAS® Software following masking of nuclear and non-nuclear regions, to quantify proteins localized in and out of the nucleus.

In Vitro Suppression Assay

On day 0, human CD4 T cells were plated on anti-CD3+ anti-CD28-coated wells and differentiated for 5 days in iTreg differentiation media. On day 5, iTreg cells (suppressors) were loaded with a cell tracker dye, Red650 (APC fluorescence). Total hPBMCs (responders) were thawed and stimulated in suspension with anti-CD3+anti-CD28, followed by crosslinking with mouseanti-IgG. After soluble stimulation, the cells were loaded with another cell tracker dye, UltraGreen (FITC fluorescence). Following loading, responders were seeded on tissue culture plate and suppressors were added onto the responders at various ratio. Cells were co-cultured for 4 days to assess proliferation of responders. On day 9, percent of in vitro suppression efficiency of the suppressors was calculated as Suppression (%)=100%−FITC-negative cells (%).

Surface Vs. Intracellular Expression of Co-Inhibitory Receptors iTreg cells were harvested on day 5 of differentiation. Cells were stained with Zombie Aqua viability dye. For surface only expression (Staining 1), cells were directly stained for LAG-3 BV421, PD-1 APC/Fire750, CTLA-4 APC or NRP1 PerCP/Cy5.5. For surface+intracellular expression (Staining 2), cells were fixed and permeabilized according to the manufacturer's directions using the Foxp3 Staining Buffer Kit followed by staining with those fluorescently-conjugated co-inhibitory receptor antibodies. Samples were run on BD LSRFortessa™ Flow Cytometer (Becton Dickinson) and median fluorescent intensities (MFI) for each protein was calculated. For intracellular only expression, MFI of Staining 1 was subtracted from MFI of Staining 2.

Quantitative Real Time PCR (Q-PCR)

Total RNA was isolated from samples via Quick-RNA Isolation Kit (Zymo Research) according to the manufacturer's protocol. 1 pg of total RNA was reverse transcribed to cDNA using dNTPs (New England Biolabs, Inc.), M-MuLV reverse transcription buffer (New England Biolabs), oligo-DT (Promega), RNase inhibitor (Promega), and M-MuLV reverse transcription (New England Biolabs, Inc.) on a Mastercycler gradient Thermal Cycler (Eppendorf). The qPCR primers used in this study were listed in Table 1. Q-PCR was performed in duplicate with 2×SYBR Green qPCR Master Mix (BioTool) using the RealPlex$^2$ system (Eppendorf). Q-PCR conditions were as follows: 95° C. for 1 min, 95° C. for 25 s, 62° C. for 25 s (40 cycles), 95° C. for 1 min, 62° C. for 1 min, and 95° C. for 30 s. Relative gene expression was determined using the ΔΔCt method. The results are presented as the fold expression in gene expression normalized to the housekeeping gene β-actin for cells and relative to Tconv+DMSO sample for in vitro experiments and Naïve+DMSO for in vivo experiments.

TABLE 1

List of qPCR primers used in this study

| Gene | Forward Primer (5'-3') | Reverse Primer (5'-3') |
| --- | --- | --- |
| ACTB (House-keeping) | GTTGTCGACGACGAGCG (SEQ ID NO: 1) | GCACAGAGCCTCGCCTT (SEQ ID NO: 2) |
| CTLA4 | CTACCTGGGCATAGGCAA CG (SEQ ID NO: 3) | GCTTTTCACATTCTGGCT (SEQ ID NO: 4) |
| FOXP3 | TGACCAAGGCTTCATCTG TG (SEQ ID NO: 5) | GAGGAACTCTGGGAATGTGC (SEQ ID NO: 6) |
| IFNG | CTCTTGGCTGTTACTGCC AGG (SEQ ID NO: 7) | CTCCACACTCTTTTGGATGC T (SEQ ID NO: 8) |
| IL10 | GGTTGCCAAGCCTTGTCT GA (SEQ ID NO: 9) | AGGGAGTTCACATGCGCCT (SEQ ID NO: 10) |
| LAG3 | TCACTGTTCTGGGTCTGG AG (SEQ ID NO: 11) | CACTTGGCAGTGAGGAAAGA (SEQ ID NO: 12) |
| NRP1 | AAGGTTTCTCAGCAAACT ACAGTG (SEQ ID NO: 13) | GGGAAGAAGCTGTGATCTGG TC (SEQ ID NO: 14) |
| PDCD1 | CCCTGGTGGTTGGTGTCG T (SEQ ID NO: 15) | GCCTGGCTCCTATTGTCCCT C (SEQ ID NO: 16) |
| PRKCQ | CTATCAATAGCCGAGAAA CCATG (SEQ ID NO: 17) | CTCATCCAACGGAGACTCCC (SEQ ID NO: 18) |
| STAT5A | ACATTTGAGGAGCTGCGA CT (SEQ ID NO: 19) | CCTCCAGAGACACCTGCTTC (SEQ ID NO: 20) |

In Vivo Suppression Analysis Via Adoptive Transfer of iTregs in Humanized GvHD Model hPBMCs from a healthy donor were used to isolate total CD4 T cells and subsequently treated with $P_{13}D_5$:antipPKCθ complex. They were differentiated for 5 days into iTregs as previously described.

On day 4, total hPBMCs from the same donor were thawed and rested overnight in fresh RPMI complete media (10% fetal bovine serum, 100 U/mL penicillin-streptomycin, 1 mM sodium pyruvate, 2 mM L-Glutamine) at 37° C. in 5% $CO_2$ incubator. On day 5, NOD.Cg-Prkdc$^{scid}$ Il2rg$^{tm1Wjl}$/SzJ (NSG) mice were conditioned with 2 Gy of total body irradiation using a $^{137}$Cs source then rested for 4-6 hours. $10\times10^6$ of total hPBMCs was mixed with $3.3\times10^6$ of iTreg cells and adoptively transferred into irradiated NSG mice via the tail vein. Body weight and disease symptoms were observed daily. On day 17, some animals were humanely sacrificed for tissue analysis. After $CO_2$ asphyxiation, peripheral blood was obtained via cardiac puncture. Sterna and spleens were collected for histology. Bone marrow (BM) cells were recovered from the tibias and femurs of both legs by flushing the bones with complete RPMI media. Splenocytes were isolated by manipulation through a 40 μm filter. Red blood cells were lysed in ACK lysis buffer, and the remaining white blood cells were enumerated using Trypan Blue exclusion. White and red cell counts were performed using scil Vet ABC™ Hematology Analyzer (scil Animal Care Company GmbH). Bone marrow, spleen, and peripheral blood were assessed for percent engraftment of hPBMCs (% positive human CD45/(% positive human CD45 cells +% positive mouse CD45 cells)) and infiltration of human CD4$^+$ and CD8$^+$ T cells. Also, the human CD4$^+$ T cells were analyzed for CD25, CD127, FOXP3, CTLA-4, LAG-3, NRP1, PD-1, pPKCθ (Thr538), and pSTAT5 (Tyr694) expression.

GvHD Clinical Scoring

GvHD severity was assessed using a standardized scoring system, as previously described (Ozay et al., 2016), and which included five different criteria (weight loss, posture, activity, fur texture, and skin integrity). Mice were weighed, evaluated daily, and graded from 0 (the least severe) to 2 (the most severe) for each criterion, beginning on day +12 after disease induction. Daily clinical scores were generated by adding greded scores for the five criteria. When a total clinical score of "8" was reached, mice were removed from the study and humanely euthanized. The day of removal from the study was recorded as the day of lethal GvHD induction.

Magnetic Sorting of Ex Vivo iTregs for mRNA Analysis

Spleen and bone marrow were collected from NSG mice on day +17 post-GvHD induction. BM cells were recovered from the tibias and femurs. Splenocytes were isolated by manipulation through a 40 μm filter. Red blood cells were lysed in ACK lysis buffer, and the remaining white blood cells were enumerated using Trypan Blue exclusion. Afterwards, cells were incubated with human CD4 T lymphocyte enrichment cocktail (BD Biosciences) followed by an incubation with BD IMag™ Streptavidin Particles Plus (BD Biosciences) to deplete non-CD4 T cell fraction. Biotinylated anti-CD127 antibody and biotinylated anti-CD25 antibody followed by an incubation with BD IMag™ Streptavidin Particles Plus were sequentially used to obtain iTreg cell fraction (negative fraction from anti-CD127 incubation and positive fraction from anti-CD25 fraction) and naïve T cell fraction (positive fraction from anti-CD127 incubation and negative fraction from anti-CD25 incubation). After cells were isolated, total RNA isolation procedure was followed.

Histology

Sterna and spleens harvested on day +17 were fixed overnight in 10% NBF (VWR), sterna were decalcified 48 h (Cal-Rite; Richard Allen Scientific), preserved in 70% ethanol at 4° C. until processed, paraffin-embedded, sectioned, and stained with hematoxylin and eosin.

LEGENDPlex™ Bead-Based Immunoassay

Peripheral blood for cytokine analysis was obtained in heparin-coated syringes on day +17 from animals via cardiac puncture, immediately following humane euthanasia. The LEGENDPlex™ Human Th1/Th2 panel (8-plex; BioLegend) was used to determine the levels of IL-2, IL-4, IL-5, IL-6, IL-10, IL-13, IFNγ and TNFα. Data were acquired on BD LSRFortessa™ Flow Cytometer and analyzed using LEGENDPlex™ Software, Version 7.0 (BioLegend).

Statistical Analysis

The results are shown are the mean±SEM; all in vitro experimental replicates were repeated at least three times. All in vivo experimental replicates were repeated in three separate experiments. Unpaired, two-tailed student t test using (Prism5; GraphPad Software, San Diego, Calif.) was used for statistical comparison of two groups, with Welch's correction applied when variances were significantly different. Survival benefit was determined using Kaplan-Meier analysis with an applied log-rank test. P values of <0.05 were considered significantly different.

Results

Intracellular Delivery of Anti-pPKCθ Prevents Nuclear Accumulation of pPKCθ in iTregs In fully-activated CD4 T cells, PKCθ is phosphorylated on Thr538 by germinal center kinase-like kinase (GLK) downstream of co-stimulatory signals provided by CD28 engagement on the cell surface. This activated form of PKCθ is important for inhibiting Treg function, and may mediate these effects through an AKT/Foxo1/3 pathway (Ma et al.). Additionally, PKCs in iTregs is sequestered away from the IS, suggesting Thr538 phosphorylation and recruitment to the IS, both, may be important for PKCθ to exerts its inhibitory actions on iTreg formation. We previously demonstrated we could utilize a synthetic, cell-penetrating peptide mimic ($P_{13}D_5$) to achieve highly-efficient intracellular antibody delivery into human primary T cells, ex vivo (Ozay et al., 2016). Non-covalently complexing $P_{13}D_5$ with an antibody that specifically recognizes PKCθ when it is phosphorylated at residue threonine 538 (anti-pPKCθ), reduced nuclear translocation of pPKCθ, attenuated downstream signaling, and compromised Th1 differentiation (Taylor et al., 2004). Here, we predicted that delivering anti-pPKCθ into iTregs would similarly alter pPKC+ translocation to the nucleus. We isolated CD4 T cells from human peripheral blood mononuclear cells (PBMC) and incubated them either with $P_{13}D_5$: anti-pPKCθ complex (anti-pPKCθ-iTregs), or with DMSO as a vehicle control (DMSO-iTregs), because $P_{13}D_5$ is suspended in DMSO prior to complexing. In addition, we treated cells with either anti-pPKCθ only, $P_{13}D_5$ only, or $P_{13}D_5$: anti-rabbit IgG prior to differentiation. We found the delivery efficiency of anti-pPKCθ or anti-rabbit IgG as a non-specific control) into CD4 T cells was around 90% as shown in FIG. 53A. We subsequently differentiated CD4 T cells into iTregs over the 5 days' culture using polarizing reagents from a commercially available kit (FIG. 47A). We deviated from the manufacturer's directions, which suggested stimulating cells only with anti-CD3, by also cross-linking the CD28 receptor. Signaling through CD28 provides co-stimulatory signals necessary to induce PKCθ phosphorylation on Thr 538 and, thus, generate the target epitope recognized by anti-pPKCθ. We saw a similar polarization pattern to DMSO-treated condition (control for iTreg polarization) only when $P_{13}D_5$: anti-pPKCθ was delivered prior to the polarization suggesting that $P_{13}D_5$: anti-pPKCθ complexes delivered into CD4 T cells did not alter the observed in vitro polarization of iTregs as other controls did (FIG. 53B).

Figure 47D:
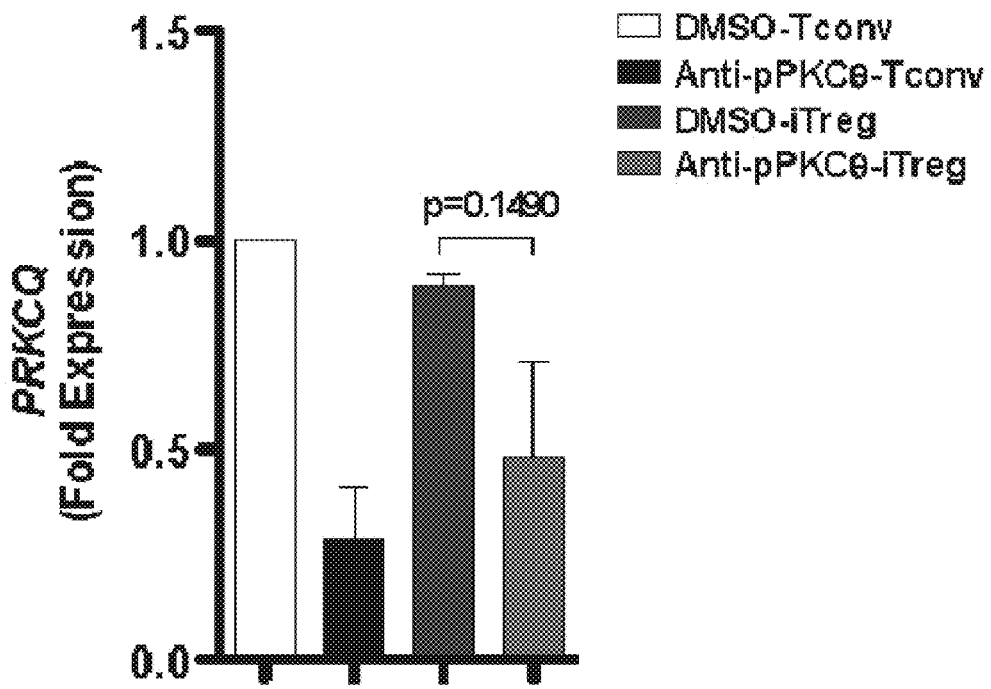
FIGS. 47A-G. Anti-pPKCθ delivery generates $CD4^+$ $CD25^+$ $FOXP3^{hi}$ iTregs in vitro. (A) Schematic of in vitro iTreg differentiation protocol in the presence of cell-penetrating PTDM-anti-pPKCθ. (B) Representative scatter plot of iTregs based on their CD25 and FOXP3 expression. (C) Quantification of the percentage of total $CD4^+$ $CD25^+$ T cells. (D) Percent of FOXP3-negative cells within $CD4^+$ $CD25^+$ T cell gate. (E) Percent of FOXP3-positive cells within $CD4^+CD25^+$ T cell gate. (F) Representative histograms and median fluorescent intensity (MFI) of CD25 expression within $CD4+CD25+FOXP^3$ T cell gate. (G) Representative histograms and median fluorescent intensity (MFI) of FOXP3 expression within $CD4^+CD25^+FOXP3^+$ T cell gate. Data represent mean±SEM of three independent experiments. Unpaired, two-tailed student t test was used for analysis; *p<0.05, p<0.01, *p<0.001.
Figure 47E:
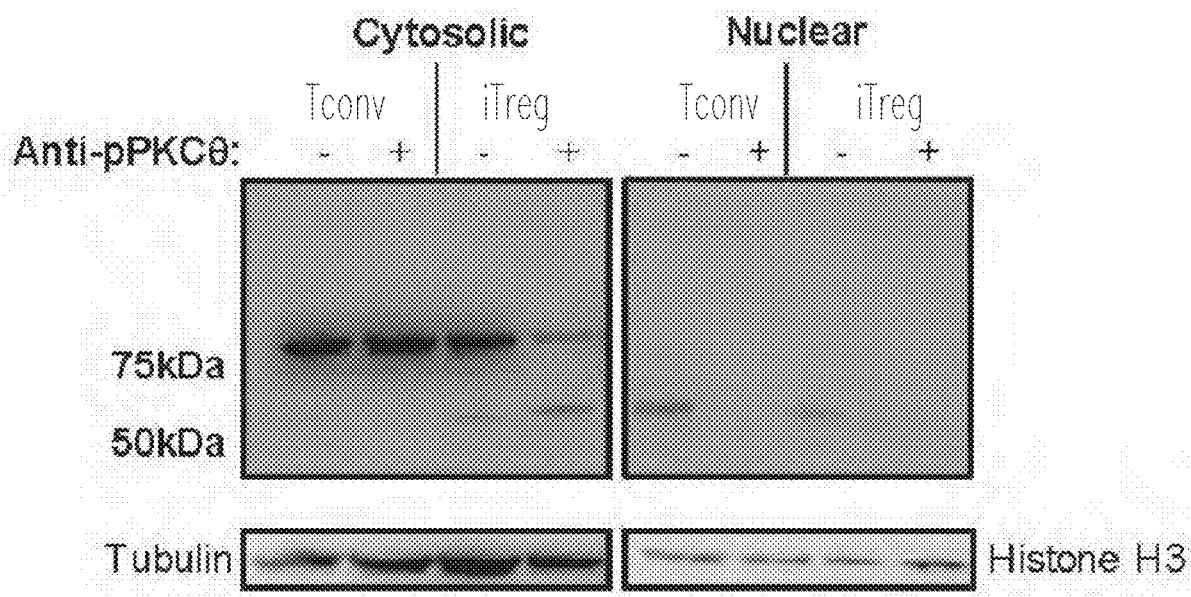
Figure 47H:
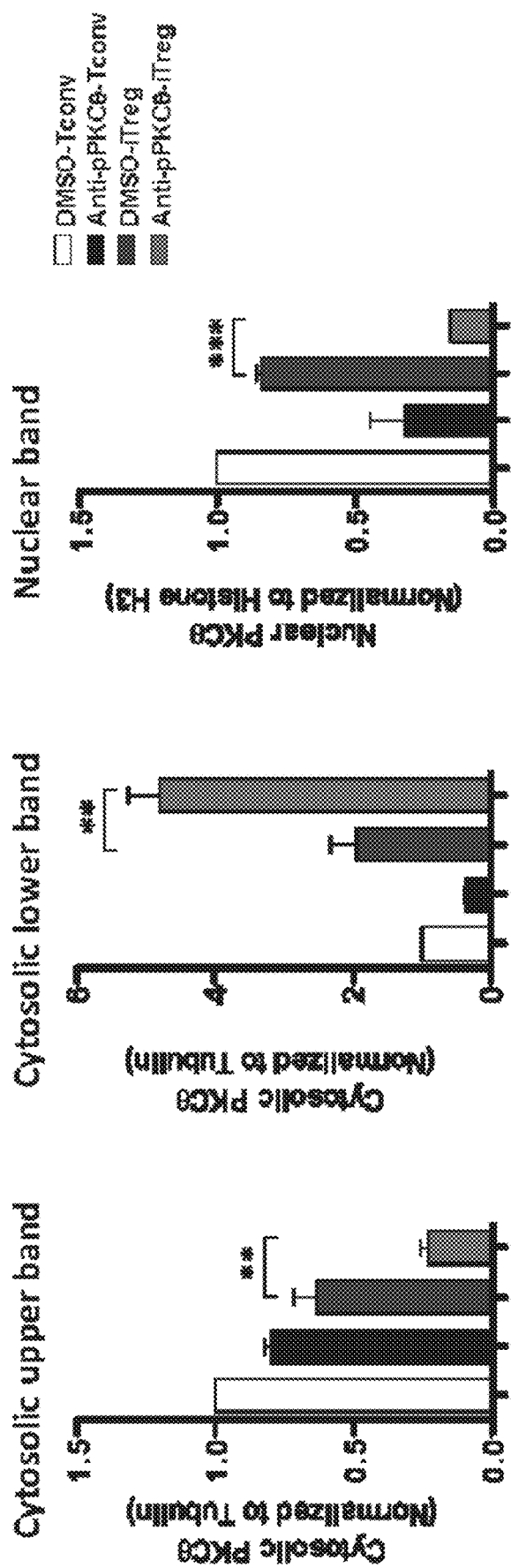
Figure 47G:
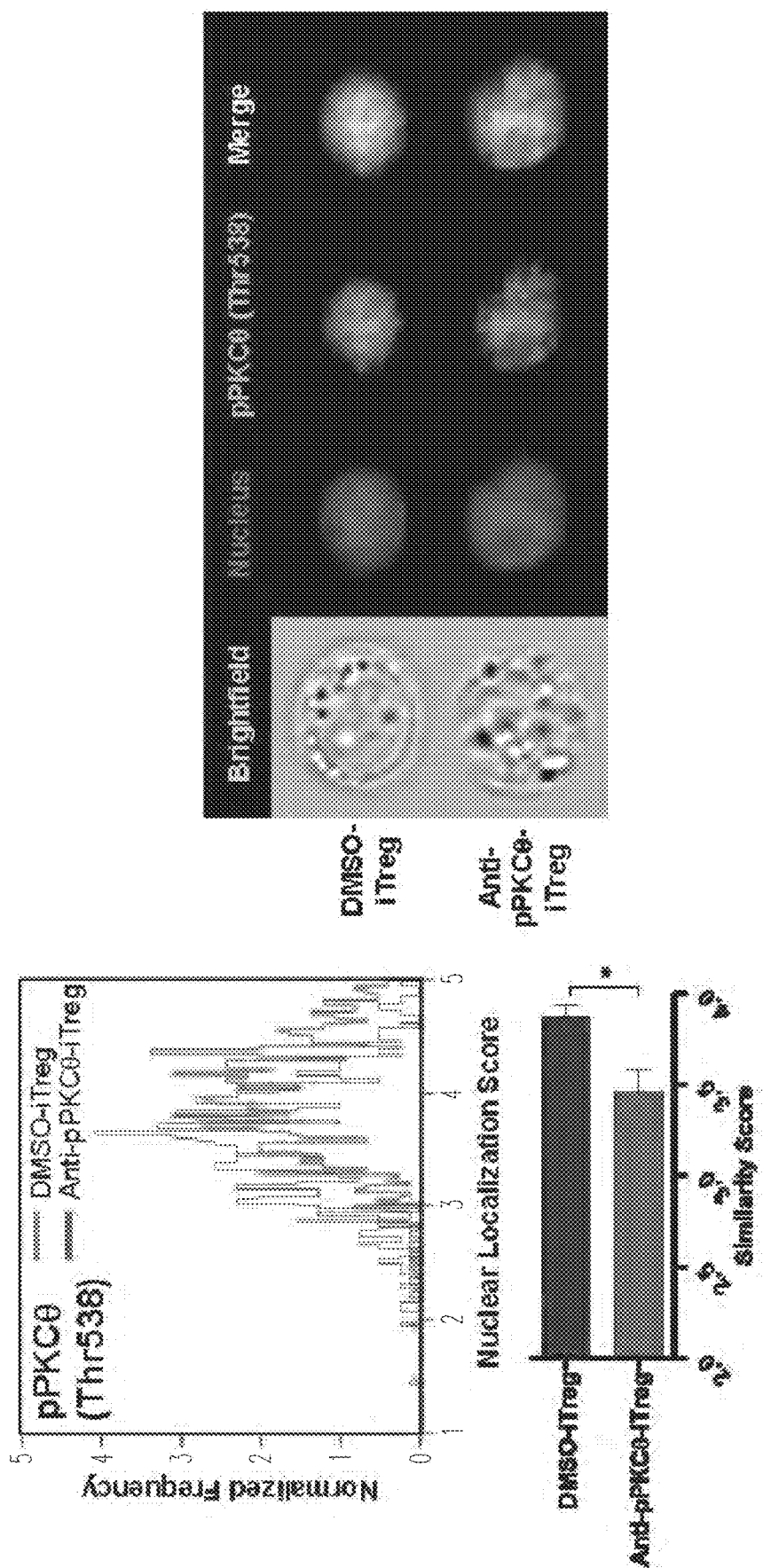

We first used flow cytometry to quantify total pPKCθ in DMSO- and anti-pPKCθ-treated conventional (Tconv), stimulated T cells and in iTregs, without distinguishing its intracellular compartmentalization. We observed similar percentages of pPKCθ-positive cells in Tconv and iTreg populations (FIG. 47B). However, pPKCθ was less abundant in anti-pPKCθ-iTregs, on a per cell basis, as indicated by Median Fluorescence Intensity (MFI), than in DMSO-iTregs (FIG. 47C), in the absence of significant differences in PRKCQ gene expression (FIG. 47D). PKCθ can function both in the nucleus and the cytosol. Therefore, we further quantified PKCθ cytoplasmic and nuclear distribution in Tconvs and iTregs. There was strong cytosolic expression of the 82 kDa protein, as expected, in Tconvs and in DMSO-iTregs. Consistent with the flow cytometric assessment of pPKCθ, there was much less of this isoform in the cytosol of anti-PKCθ-iTregs (FIG. 47E). Of note, we detected a smaller, about 55 kDa PKCθ isoform in the cytosol of iTregs that was enhanced by anti-pPKCθ delivery. This lower molecular weight band was also detected in the nuclear lysates from DMSO-treated Tconvs and iTregs (FIG. 47E, F). Interestingly, nuclear expression of the smaller isoform was not evident in anti-pPKCθ-treated Tconvs or -iTregs, suggesting that it is preferentially constrained in the cytosol when anti-pPKCθ is delivered intracellularly. We next used imaging flow cytometry to quantify the abundance of pPKCθ in the nucleus of Tconv and iTregs. Nuclear pPKC protein was significantly reduced in anti-pPKCθ-iTregs, but not in DMSO-iTregs or in Tconv (FIG. 47G). Altogether, these data demonstrate that $P_{13}D_5$-mediated delivery of anti-pPKCθ into CD4 T cells alters the cellular distribution of pPKCθ within in vitro differentiated iTregs.

Generating CD4$^+$CD25$^{high}$FOXP3$^{high}$ iTregs In Vitro Using Cell-Penetrating Anti-pPKCθ

Figure 48A:
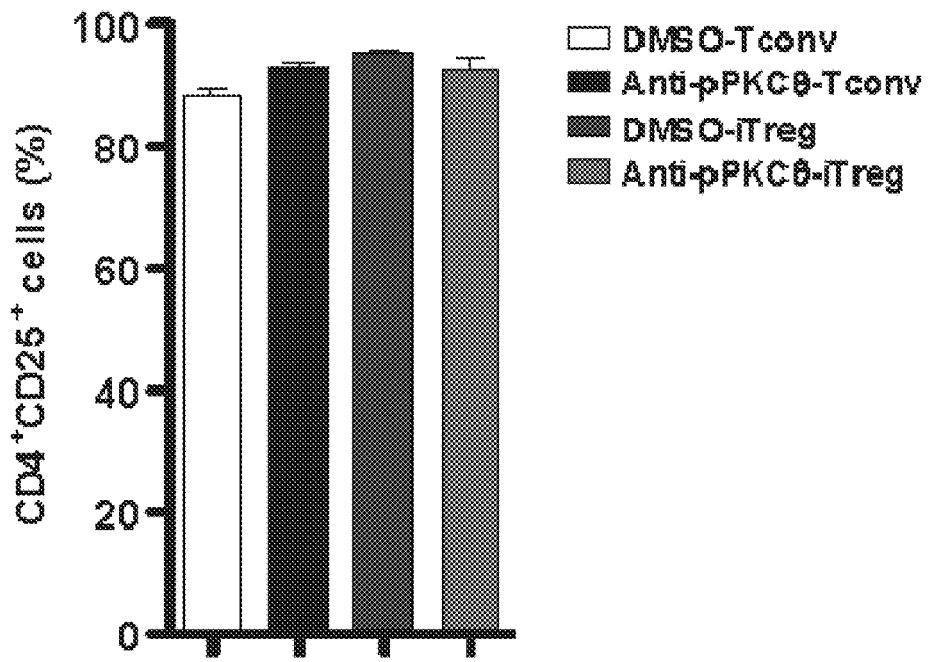
FIGS. 48A-F. pPKCθ is diminished in both cytosol and nucleus in PTDM-iTregs. (A) Representative histogram of pPKCθ-positive cells upon anti-pPKCθ delivery during iTreg differentiation (and non-differentiating conditions). (B) Percent pPKCθ-positive cells and MFI of pPKCθ expression. (C) Representative blots for nuclear vs. cytosolic distribution of total PKCθ in conventional T cells (Tconvs) and iTregs upon anti-pPKCθ delivery assessed by western blot. (D) Quantification of relative density of cytosolic PKCθ for both lower and upper band seen in (C). (E) Quantification of relative density of nuclear PKCθ. Data represent mean±SEM three independent experiments. Unpaired, two-tailed student t test was used for analysis; *p<0.05, p<0.01, *p<0.001.
Figure 48B:
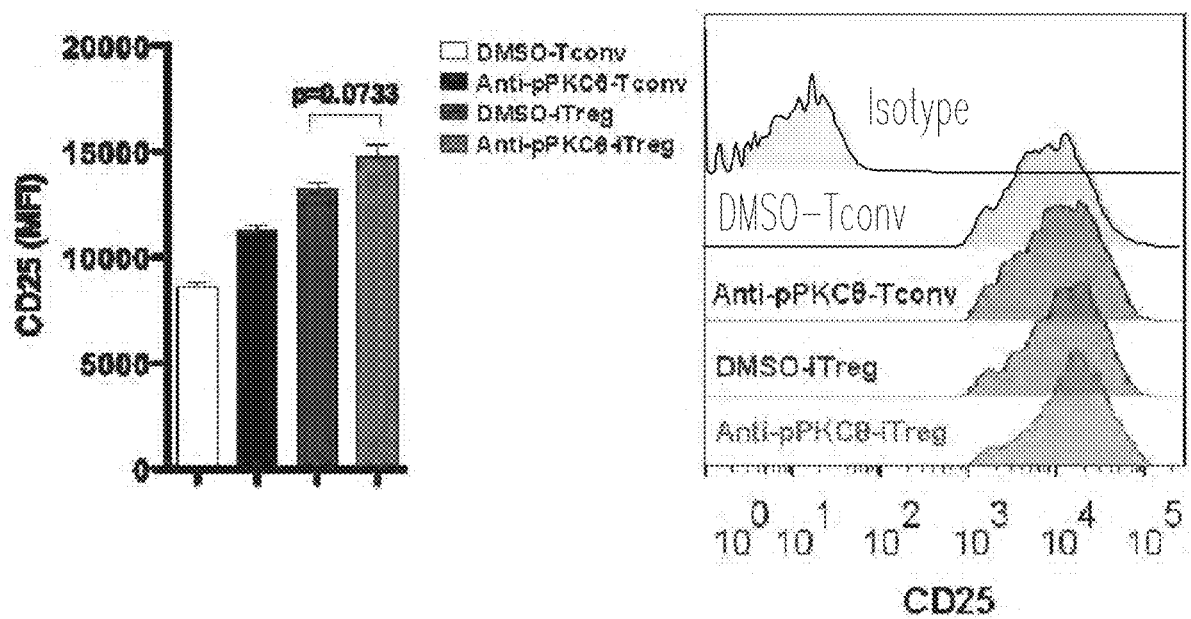
Figure 48C:
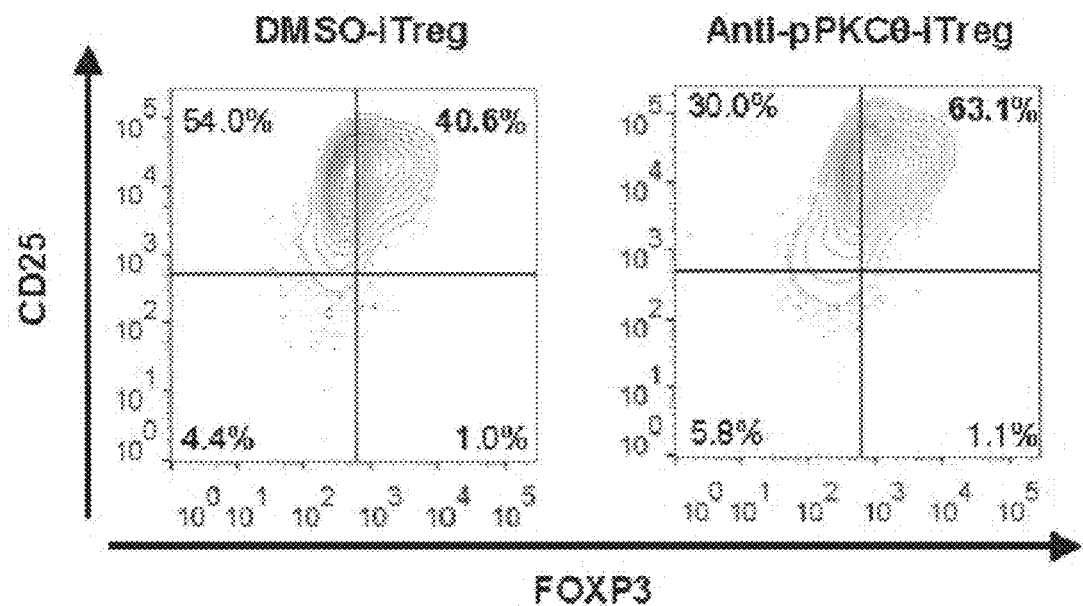
Figure 48D:
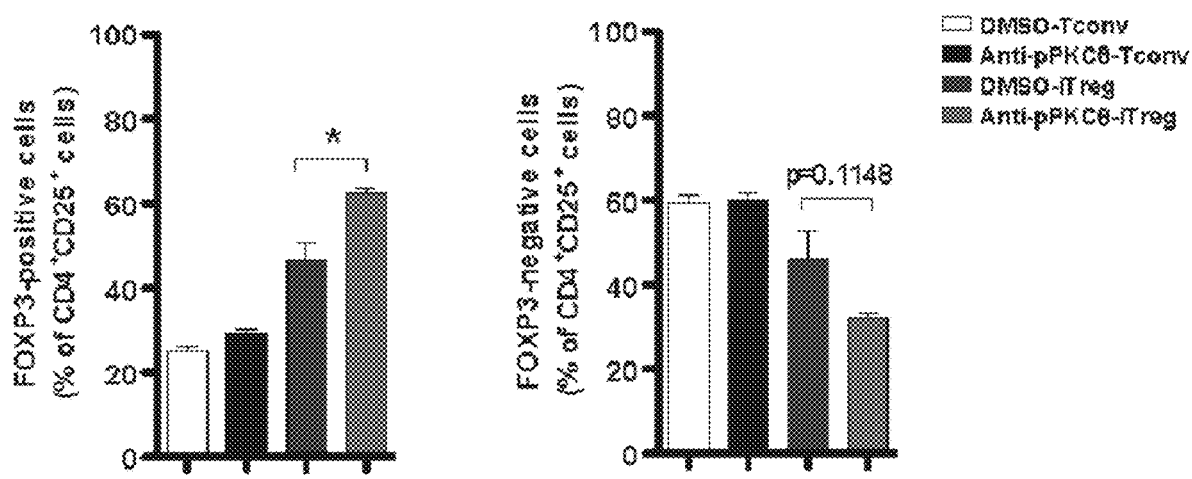
Figure 48E:
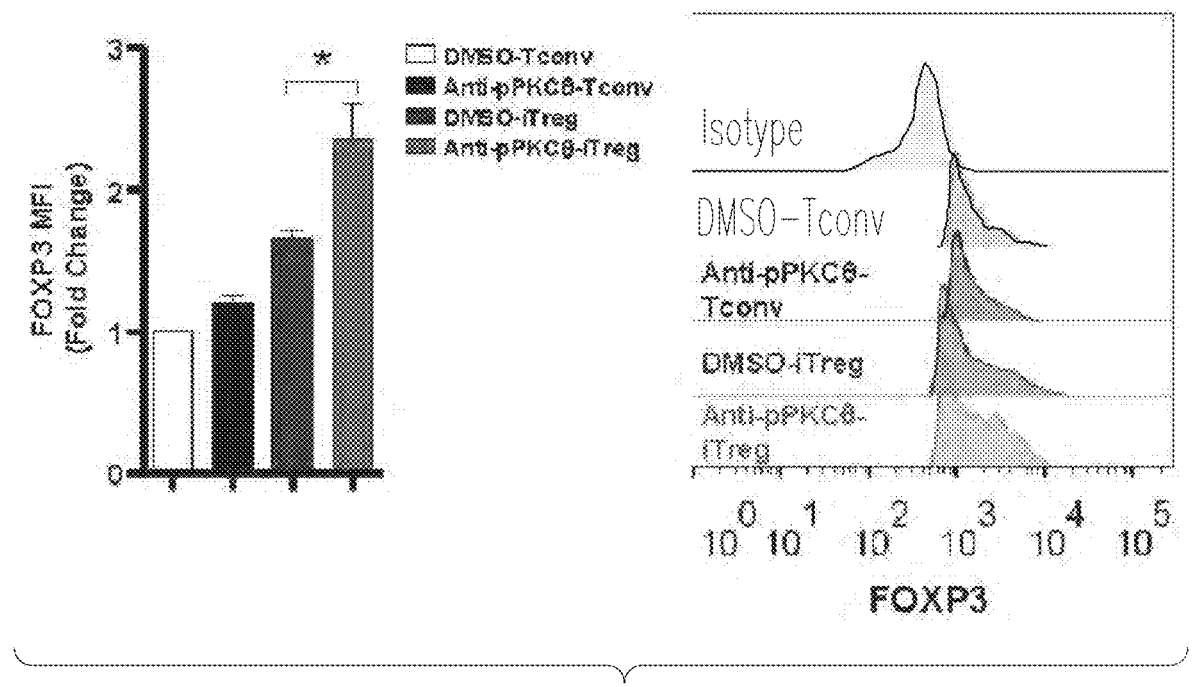
Figure 48F:
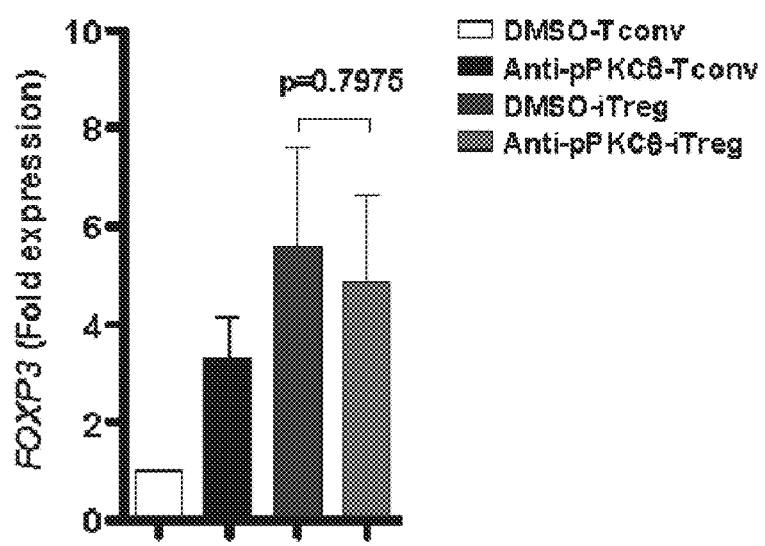

Reduced nuclear accumulation of PKC in anti-pPKC-iTregs is consistent with a reported nuclear role for PKCθ in pro-inflammatory gene regulation in human CD4 T cells (Sutcliffe et al.). In complementary studies, Zanin-Zhorov provided compelling evidence that using a small molecule inhibitor to block PKCθ activity in CD4 T cells enhanced their regulatory phenotype. However, cell toxicity and off-target effects constitute two major obstacles to using small molecule inhibitors to intervene in signaling pathways. We predicted that inhibiting the actions of PKC using the exquisitely-specific binding of anti-pPKCθ, delivered ex vivo into the cytosol of human CD4 T cells, would enhance the in vitro differentiation of functional, stable iTregs. CD25 is the high-affinity subunit of the IL2 receptor, and high surface expression is a hallmark of regulatory T cells. Greater than 90% of differentiated iTregs exhibited high surface CD25, regardless of whether they were treated with anti-pPKCθ (FIG. 48A). On a per cell basis, the concentration of surface CD25 on anti-pPKC-iTregs was increased over than that expressed on DMSO-iTregs or on Tconv cells (FIG. 48B). We further stratified iTregs, phenotypically, using flow cytometry to quantify the percent of CD4$^+$CD25$^{high}$ cells that also expressed the signature iTreg master transcriptional regulator, FOXP3. When we applied this gating strategy, we found anti-pPKCθ delivery enhanced the percentage of FOXP3-expressing CD4$^+$CD25$^{high}$ cells following iTreg polarization (FIG. 48C, D). By comparison, nearly 50% of CD4$^+$CD25$^{high}$ DMSO-iTregs remained FOXP3-negative (FIG. 48D). We also assessed whether FOXP3 abundance varied between treatments. In parallel to increased CD25 expression on anti-pPKCθ-iTregs, we observed significantly more FOXP3 protein in anti-pPKC-iTregs, compared to DMSO-iTregs (FIG. 48E). This was notable, because FOXP3 gene expression in iTregs did not differ between the treatments (FIG. 48F) and suggests that anti-pPKC treatment may act to increase the stability of FOXP3. These results demonstrate that, when peripheral CD4 T cells are activated in vitro, using methods that mimic physiological activation and co-stimulatory signals, then cultured with a defined polarizing cocktail, CD4 T cells can be successfully differentiated into iTregs. However, delivering anti-pPKC across the cell membrane prior to differentiating CD4 T cells, generated a greater percentage of CD4$^+$CD25$^{high}$FOXP3$^{high}$ iTregs in vitro, and increased the concentration of FOXP3 expressed by these iTregs, as well.

Anti-pPKCθ-iTreg Cells Exhibit Superior Suppressive Capabilities In Vitro

Figure 49A:
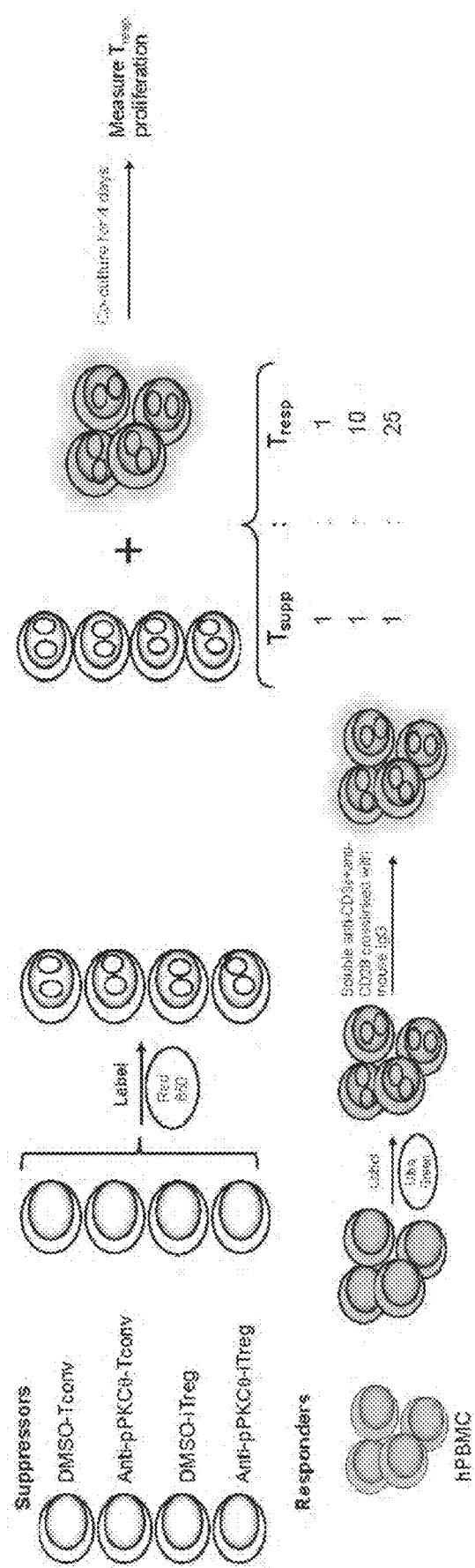
Figure 49B:
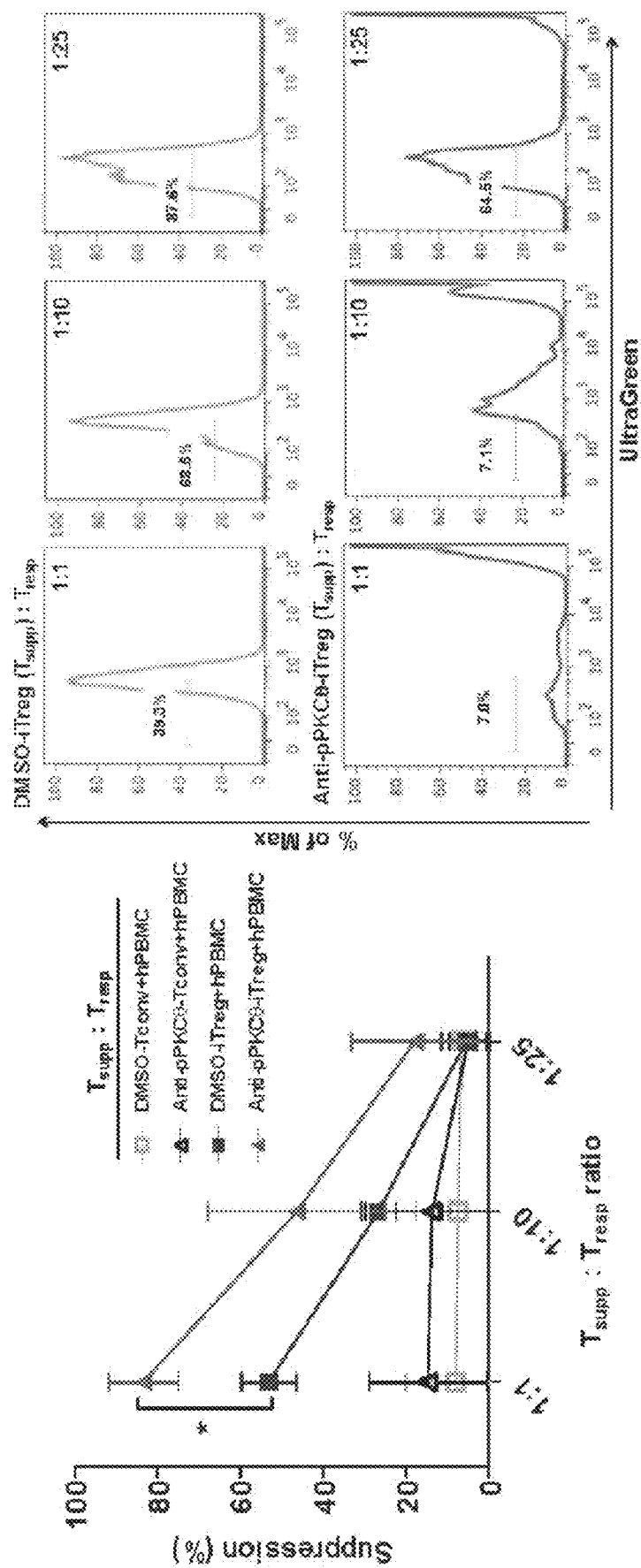

Tregs function to suppress the activity of nearby T cells, through mechanisms that are both direct (i.e. cell-cell contact) and indirect (i.e. release of anti-inflammatory cytokines). Regulatory T cells that are defined by the CD4$^+$CD25$^{high}$FOXP3$^{high}$ phenotype, and which were increased in the iTreg population following anti-pPKCθ delivery, are presumed to possess potent suppressive capabilities. However, an iTreg phenotype, alone, does not convey functional suppression. Therefore, we utilized a standard, in vitro suppression assay to ask whether anti-pPKC delivery generated iTregs with superior suppressive activity, compared to their DMSO-iTreg counterparts. We activated human peripheral blood mononuclear cells (hPBMCs), mimicking physiological conditions by stimulating them with soluble anti-CD3 and anti-CD28. We labeled these responder cells ($T_{resp}$) with the vital dye, UltraGreen, and mixed them in culture at three different ratios with ex vivo-differentiated suppressor iTregs ($T_{supp}$). We used a second vital dye, Red650, which emits fluorescence at a longer wave length, to label the $T_{supp}$ cells (FIG. 49A). When fluorescently labeled cells proliferate in culture, their fluorescence intensity diminishes by about half with each cell division. With this approach, we could use flow cytometry to track the proliferative responses of $T_{resp}$ and $T_{supp}$ at the end of the four-day co-culture. Strikingly, anti-pPKC-iTregs suppressed with nearly 10-fold greater potency than did DMSO-iTregs, when cultured together with stimulated PBMCs (Dty. 50B).

Figure 49C:
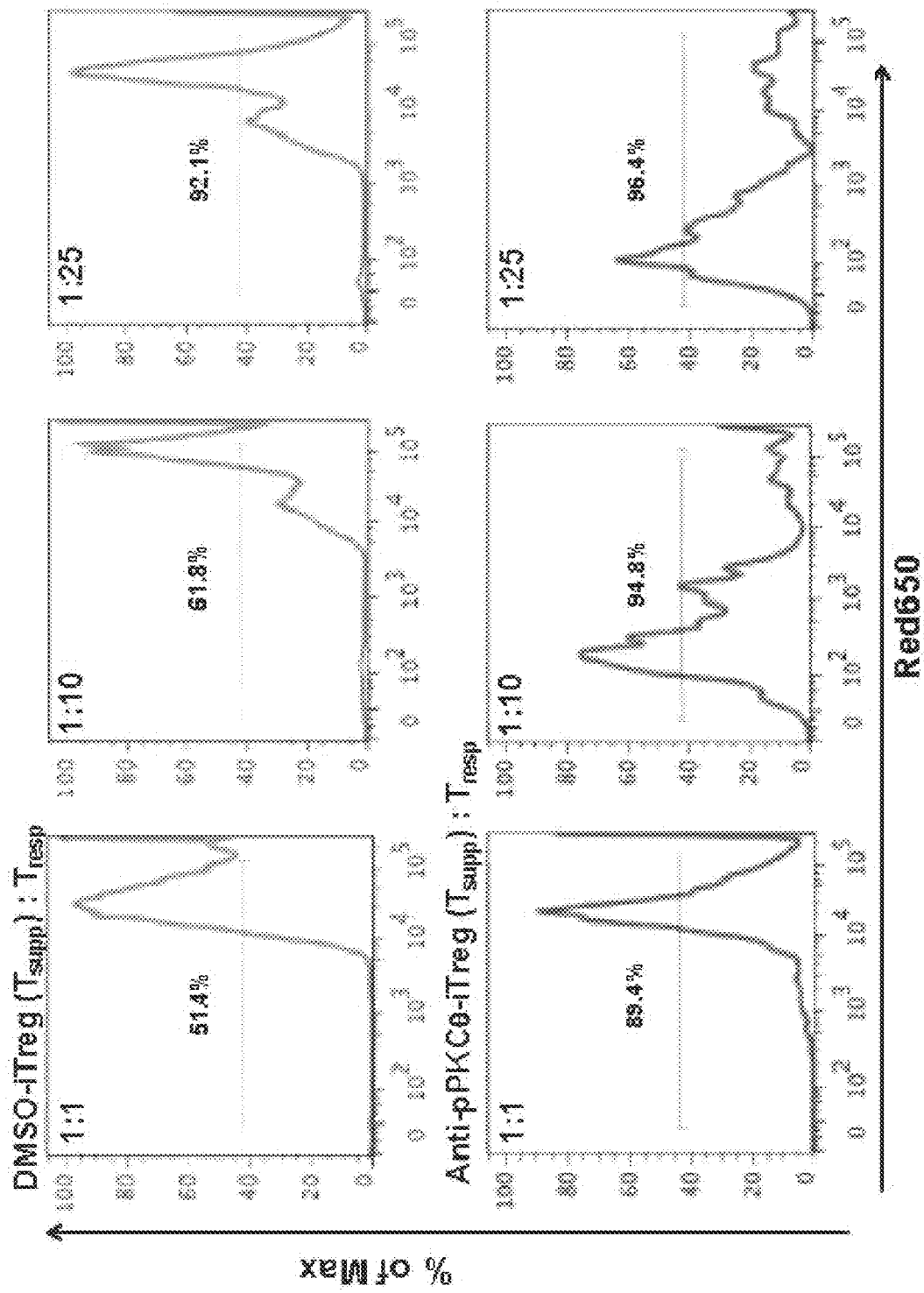
Figure 49D:
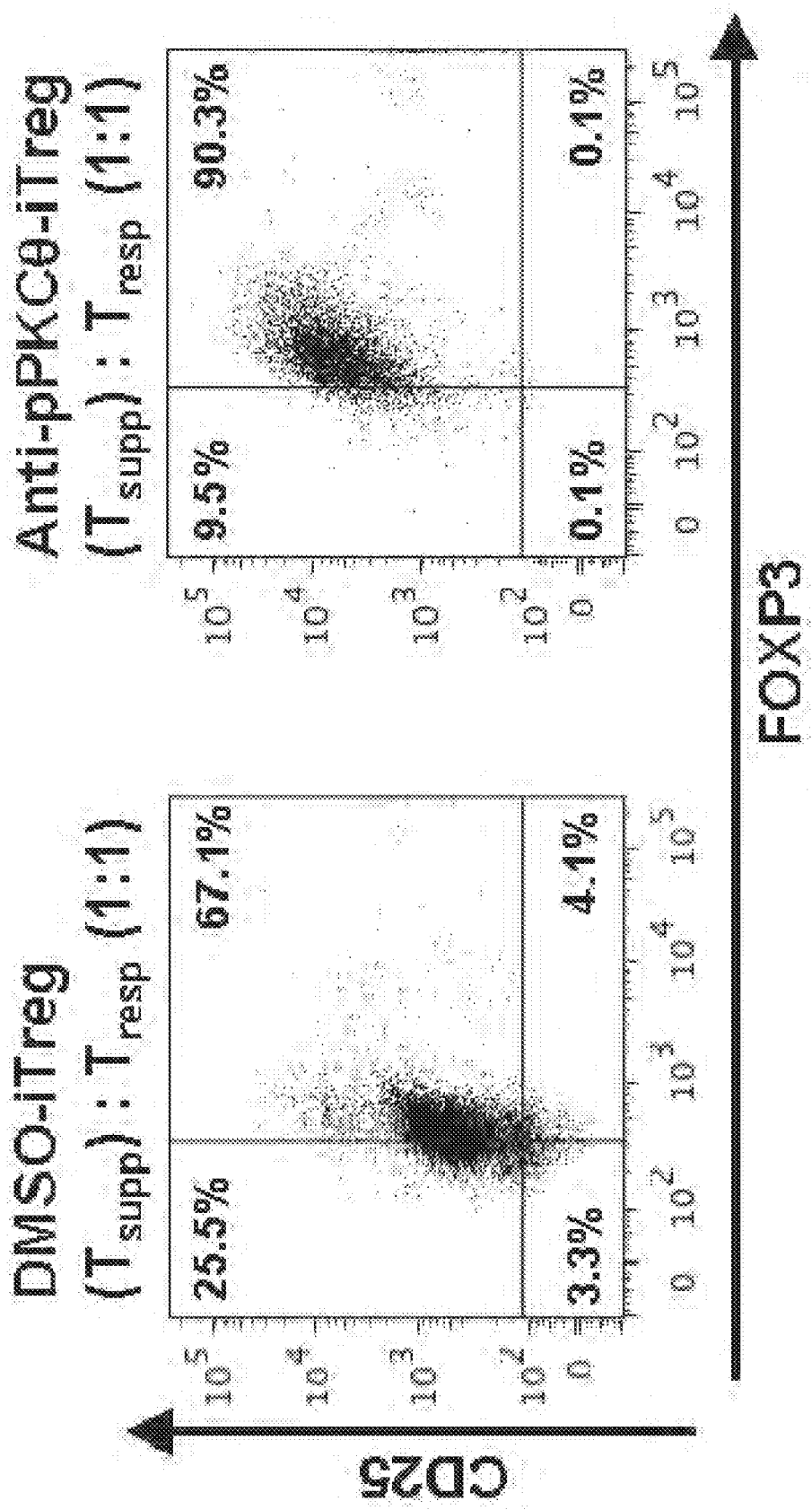

Furthermore, anti-pPKCθ-iTregs proliferated in culture more extensively than did DMSO-iTregs, as indicated by the much-reduced fluorescence intensity of Red650 (FIG. 49C). This was also reflected in the overall percentages of iTregs at the end of the co-culture period, when we detected significantly higher percentages of CD4$^+$CD25$^{high}$FOXP3$^{high}$ cells in co-cultures with anti-pPKCθ-iTregs compared to those with DMSO-iTregs (FIG. 49D). Following activation, CD4$^+$CD25$^-$Tconv and CD4$^+$CD25$^+$ iTregs, both, increase expression of FOXP3. However, FOXP3 in Tconv remains mostly in the cytosol, while in iTregs, FOXP3 is localized primarily to the nucleus. Furthermore, when a mutant form of FOXP3 was expressed in Jurkat T cells and was constrained to the nuclear compartment, it endowed these transfected cells with suppressive capabilities. To ask whether there were differences in the cellular distribution of FOXP3 in DMSO- and anti-pPKCθ-iTregs, we again used imaging flow cytometry to assess FOXP3 localization. As indicated by the increased positive nuclear similarity score, we detected significantly more nuclear FOXP3 in anti-pPKCθ-iTregs, than in DMSOiTregs, consistent with their enhanced suppressive capacity (FIG. 49E). These finding support the notion that the superior suppressive capabilities of anti-pPKCθ-iTregs is associated with the increased nuclear content of FOXP3.

Figure 50A:
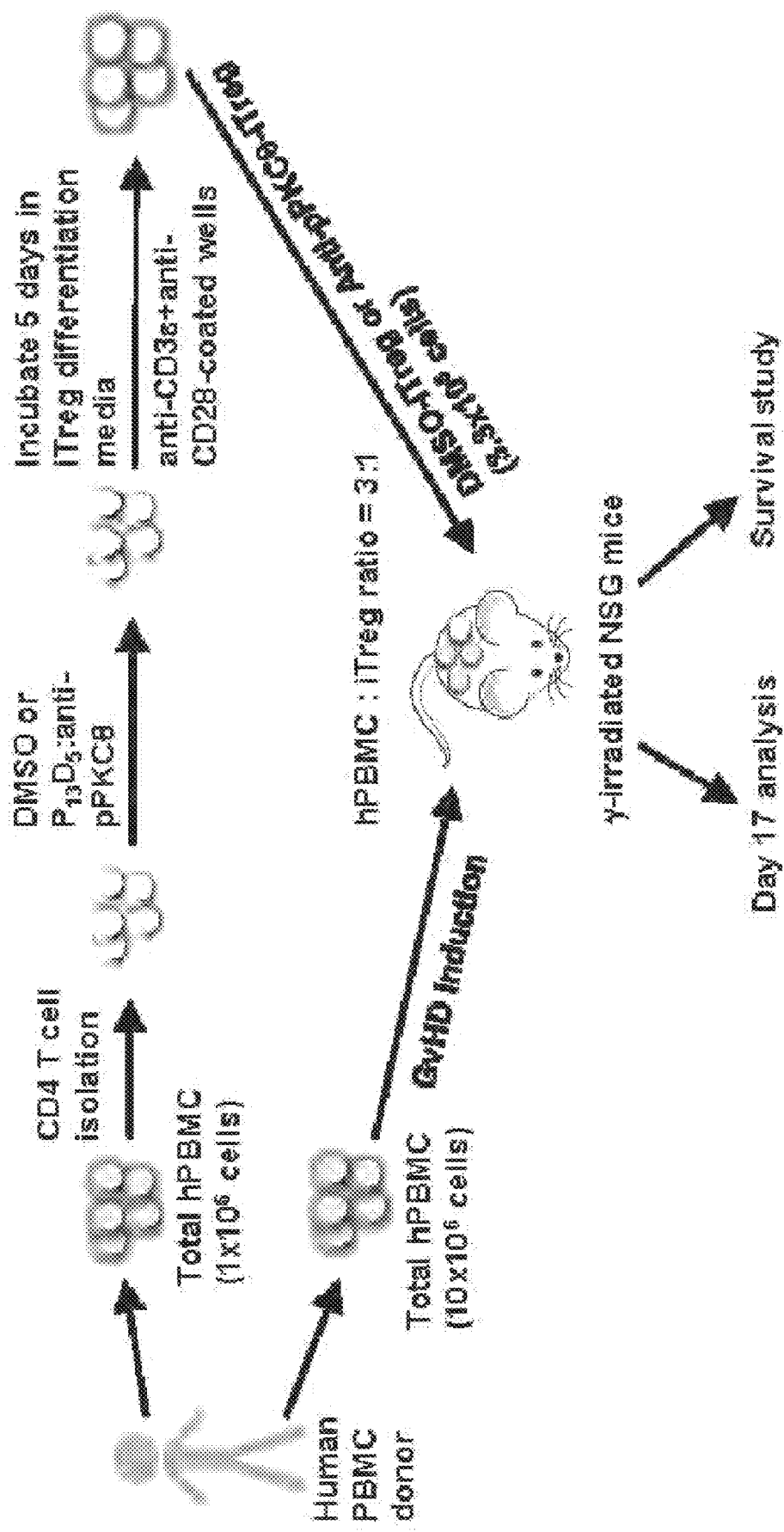

Administering Anti-pPKCθ-iTregs Attenuates Disease in a Humanized Mouse Model of GvHD Animal models, including humanized mouse models of GvHD, have contributed significantly to our understanding of healthy and defective human hematopoiesis, enabling the translation of promising therapeutics into clinical applications (Boieri et al., 2016; Theocharides et al., 2016). Specifically, adoptive immunotherapy using Tregs in GvHD models represents a viable strategy for understanding T cell biology, as well as Treg-mediated suppression, facilitating their advancement for clinical use (Trzonkowski et al., 2015; Hanhn et al., 2015). iTreg abundance correlated with attenuated GvHD severity and increased long-term graft tolerance, without the need for drug-induced immunosuppression (Rancarolo et al., 2007; Spence et al., 2015; Tang et al., 2013; Rosa Banchett et al., 1994). We explored the translational potential of anti-pPKCθ-iTregs, using a pre-clinical mouse model of acute GvHD (Ozay et al., 2016). In this mouse model PBMCs (graft) are transferred, via the tail vein, into recipient (host) NOD-scidIL2rgamma$^{null}$ (NSG) mice that have been lightly irradiated. The BM is the target of immune-mediated destruction, with symptoms peaking approximately 17 days after the PBMCs are transferred. This model is uniformly fatal, and mice succumb to lethal BM failure approximately three weeks after disease induction (Ozay et al., 2016). To test the translational potential for anti-pPKCθ-treated iTregs for use as a cell-based prophylaxis for GvHD, we differentiated iTregs from a single donor, ex vivo, without or with anti-pPKCθ delivery. We used PBMCs from the same donor to induce GvHD in host mice (FIG. 50A). Our rationale for this approach stems from the understanding that immune-competent T cells residing in the graft are activated and expand in the host as the result of conditioning regimens that produce a pro-inflammatory setting. We reasoned that, if peripheral blood CD4 T cells from the donor were differentiated into iTregs ex vivo before administering to the host at the time of BM transplantation, they would prevent expansion of alloreactive T cells in the host and attenuate acute GvHD. To test this hypothesis, we transferred ex vivo-differentiated iTregs, together with disease-inducing PBMCs, at a ratio of 1:3 into NSG mice. We chose this "responder: suppressor" ratio guided by our in vitro suppression results (FIG. 49). On day +17, we analyzed the peripheral blood, spleen, and BM of diseased animals to evaluate the efficacy of iTreg transfer.

To confirm equivalent disease induction across all the cohorts, we evaluated the extent to which the transferred PBMCs expanded in vivo. We collected samples from the peripheral blood and spleens of mice with GvHD that received no iTregs, that received DMSO-iTregs, or that received anti-pPKC-iTregs and evaluated the percentage of cells that expressed the human leukocyte antigen, CD45, as a measure of cellular expansion after transfer. The percentages of human CD45 positive cells detected in the peripheral blood and spleens of GvHD mice did not differ greatly, regardless of whether they also received iTregs, and the overall cellularity of the spleens also appeared similar when stained with hematoxylin and eosin (FIG. 54A, B). When we refined our analyses of cells by subsets, we noted fewer circulating CD4 T cells in mice treated with anti-pPKCθ-iTregs, but otherwise there were no significant differences in the percentages of human CD4 or CD8 T cells between treated or untreated animals (FIG. 54C).

Figure 50B:
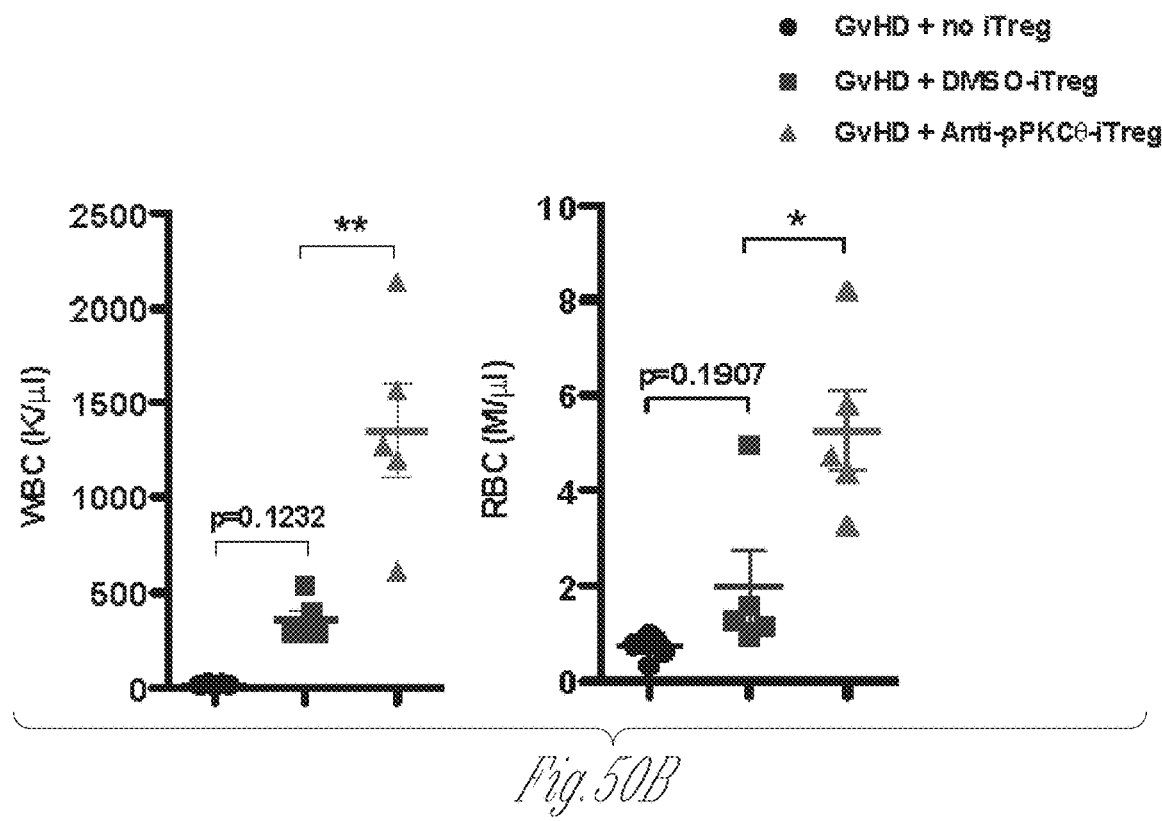
Figure 50C:
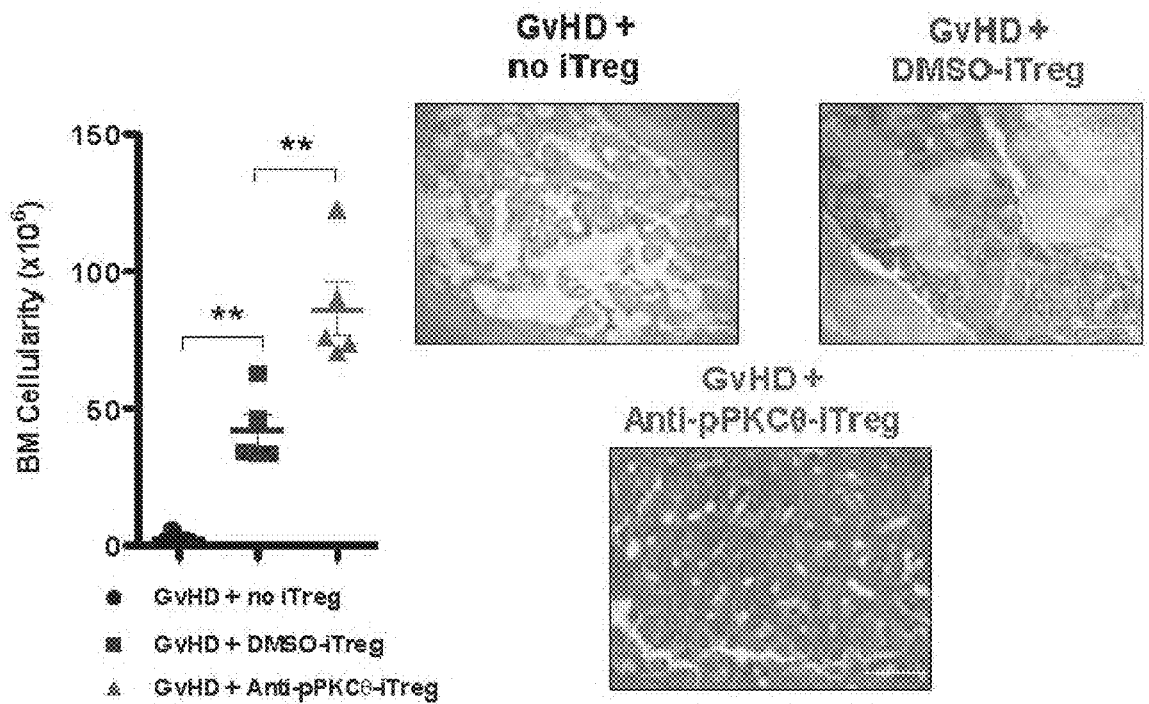
Figure 50D:
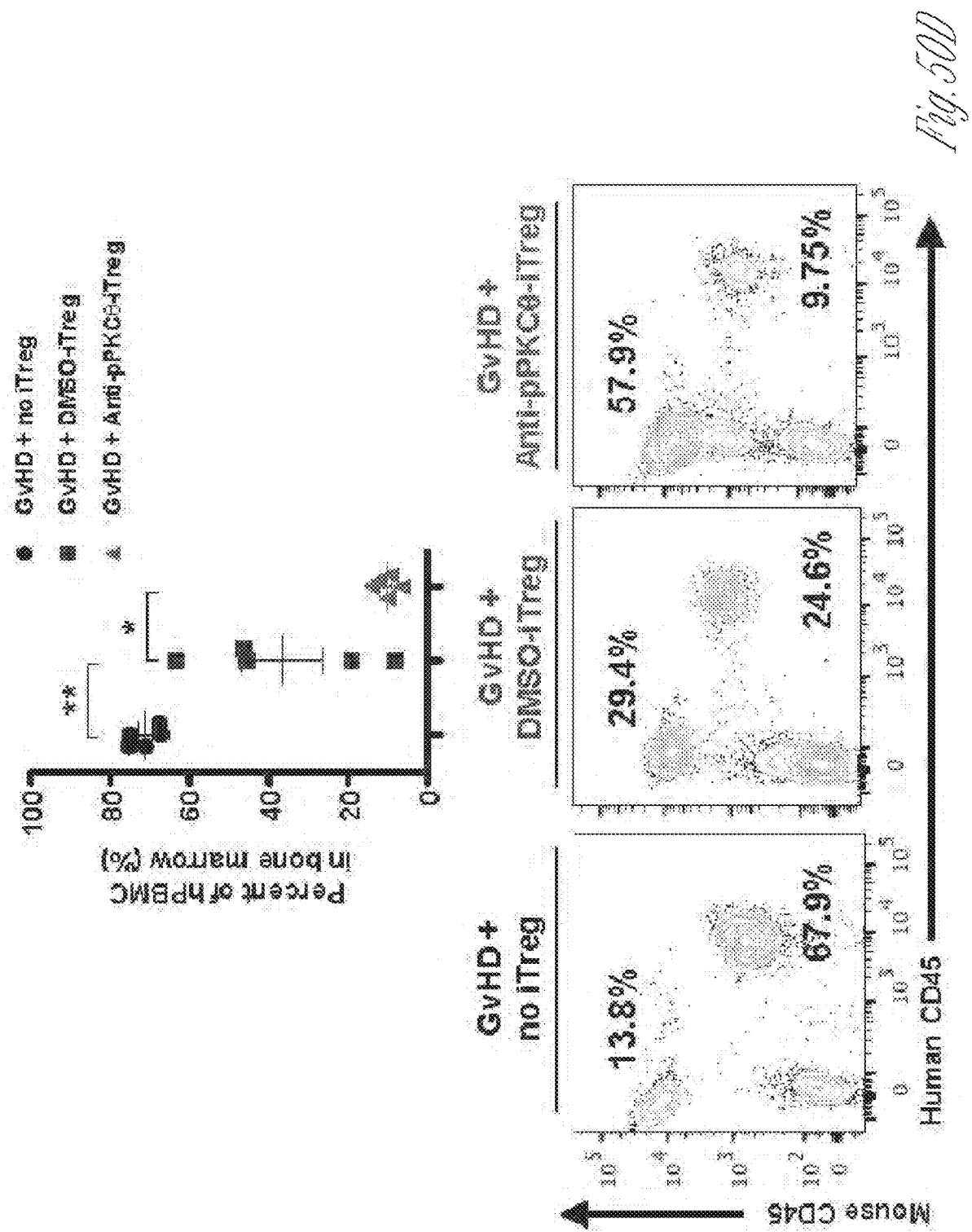

Hematopoiesis in the BM gives rise to circulating white and red blood cells. Pancytopenia is a hallmark of the GvH-mediated BM failure that accompanies this model. Transferring DMSO-iTregs when GvHD was induced afforded discernable protection to circulating white and red blood cells, and this protection was greatly enhanced in mice which received anti-pPKCθ-iTregs (FIG. 50B). Similarly, when we evaluated BM cellularity, either by counting nucleated cells in the BM or by histological assessment (FIG. 50C), it was evident that administering anti-pPKCθ-iTregs at the time of disease induction provided robust protection of the BM compartment. This was likely due to differences in the percentages of PBMCs that had infiltrated the BM by day +17 (FIG. 50D). However, the distribution of T cells recruited to the BM by this time was similar in mice that received iTregs, regardless of how these cells were differentiated prior to infusion (FIG. 50E). These results led us to conclude that treating mice with anti-pPKCθ-iTregs may alter the kinetics of T cell migration into the BM, rather than the percentages of BM-infiltrating CD4 and CD8 T cells.

Figure 50F:
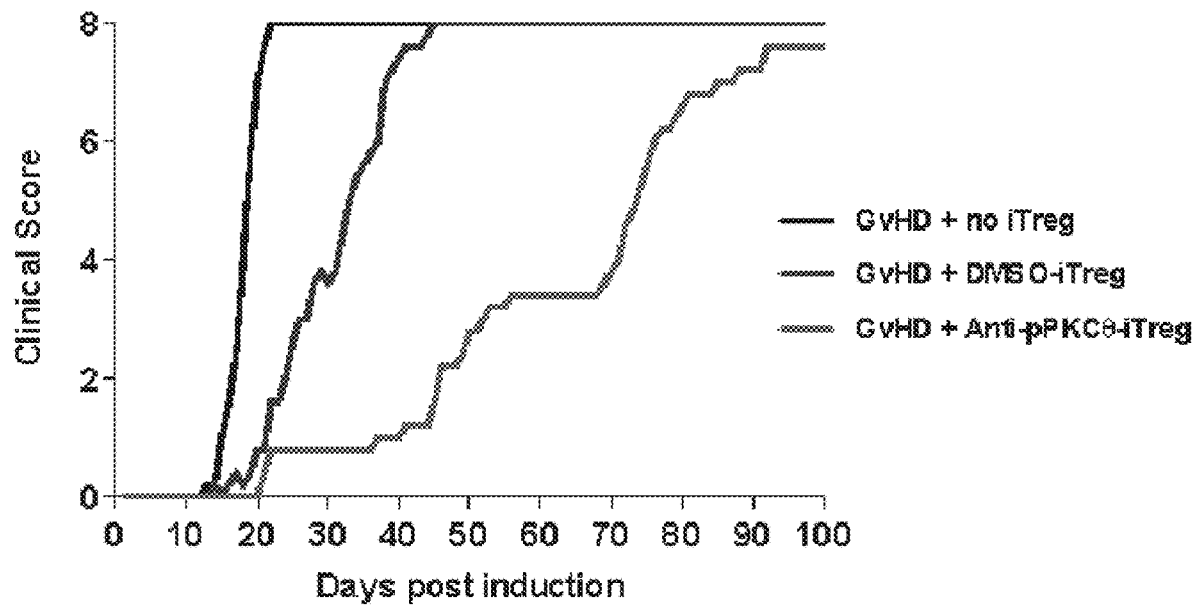
Figure 50G:
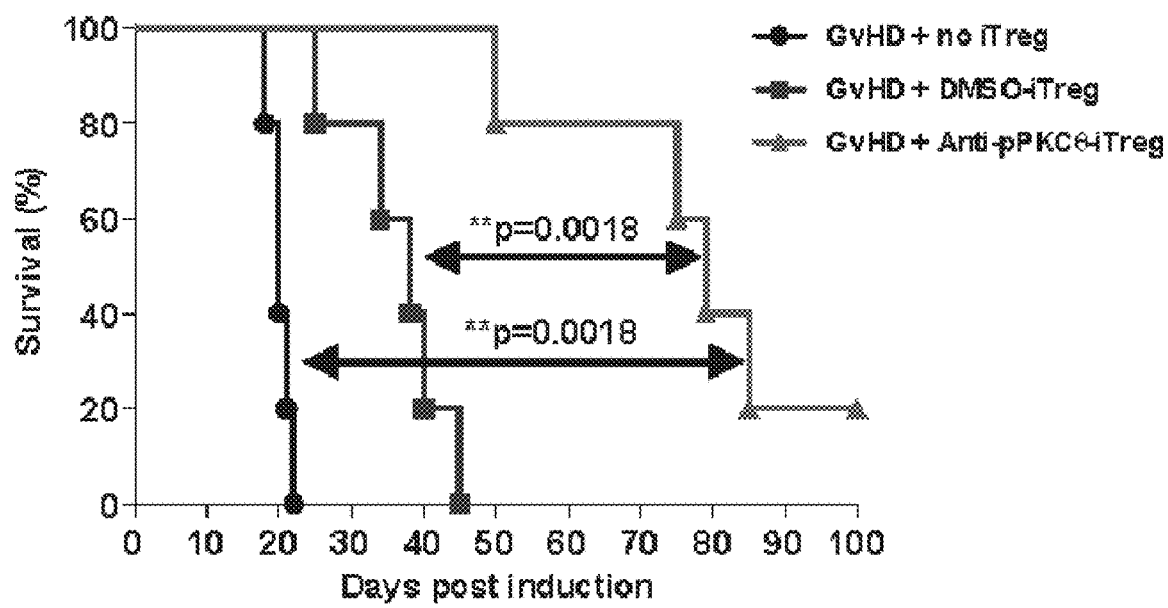
Figure 51A:
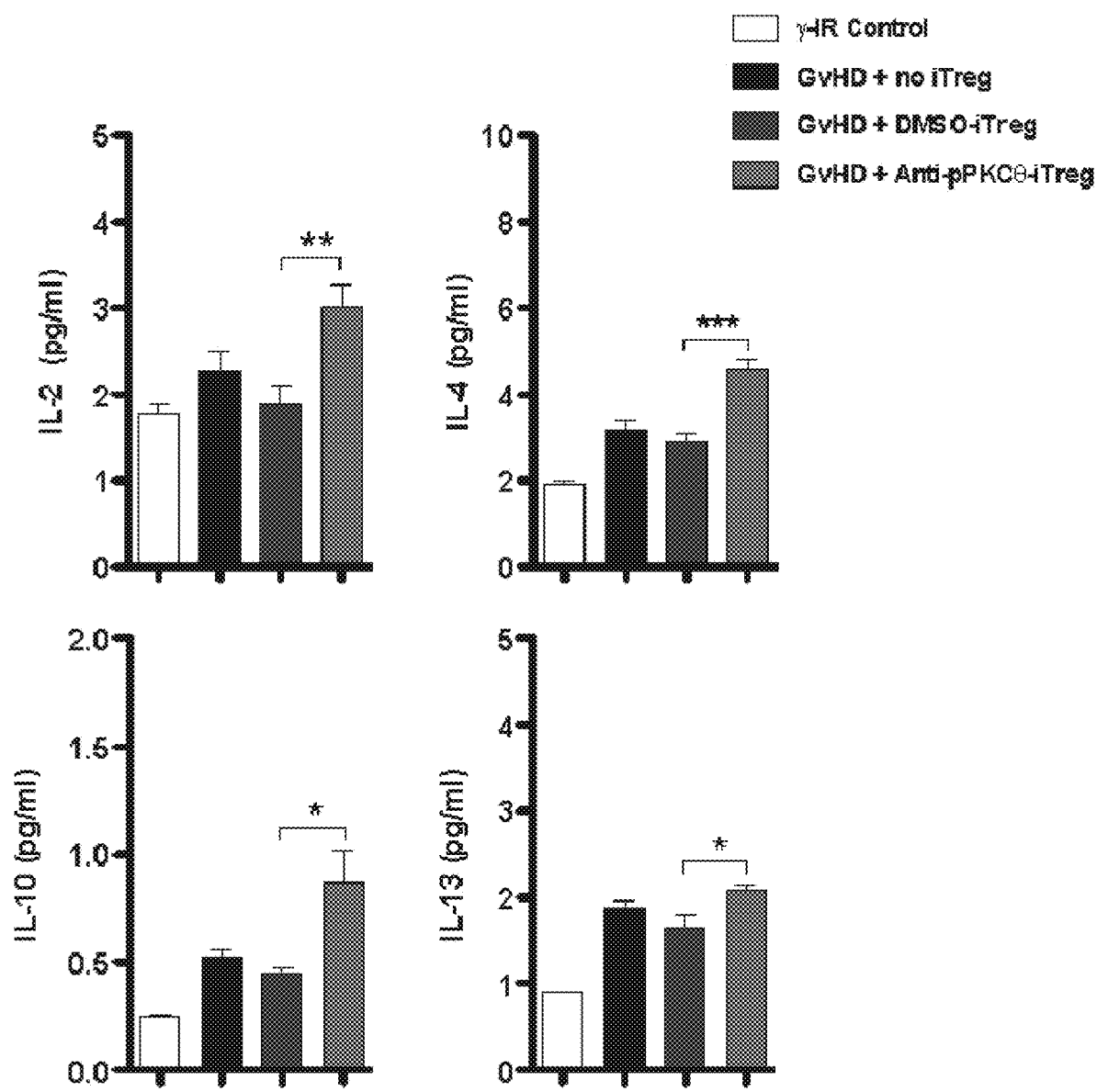
Figure 51B:
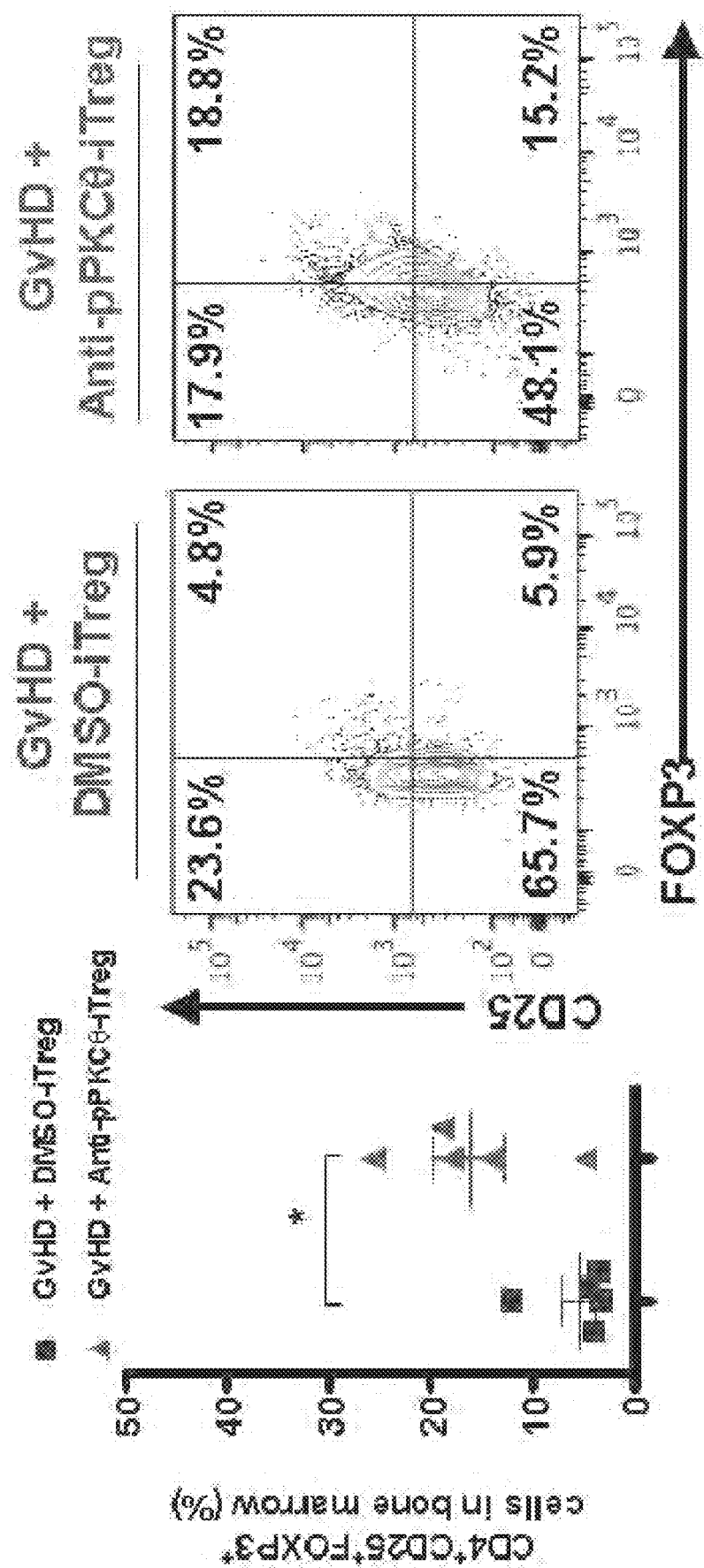
Figure 51C:
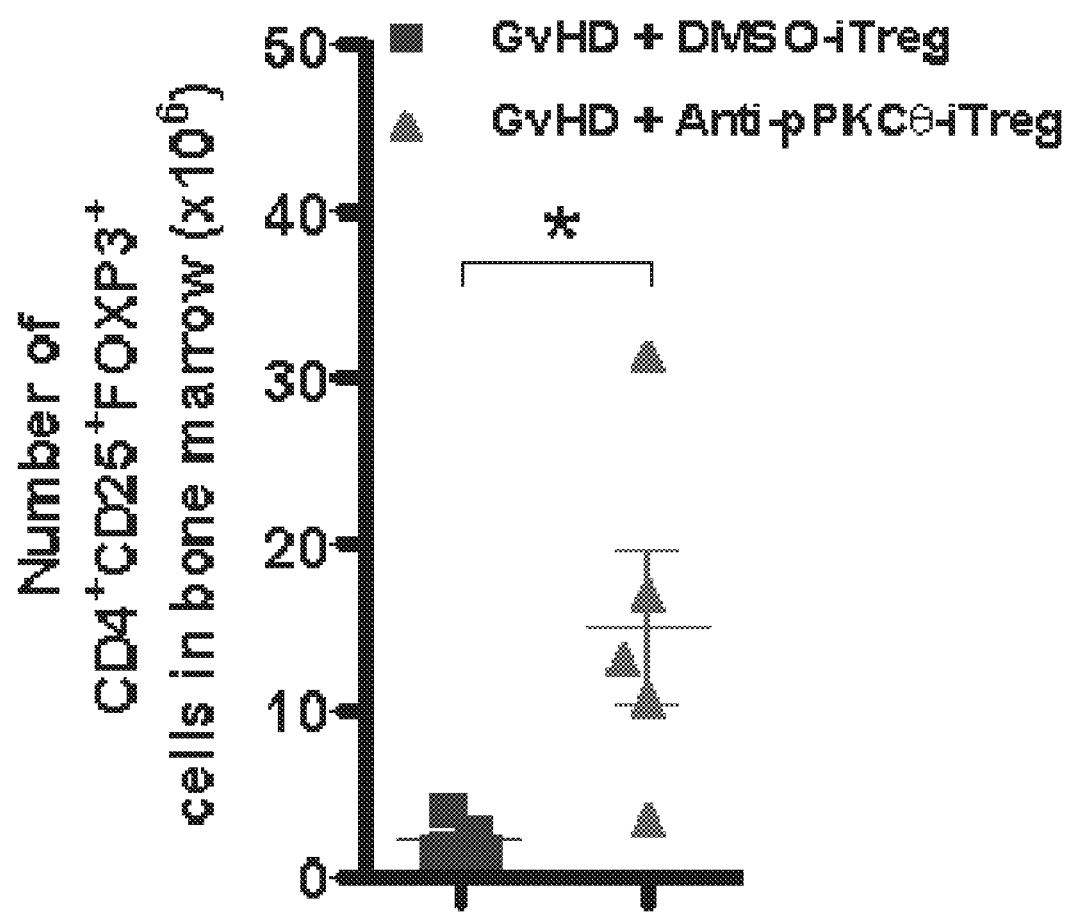
Figure 51H:
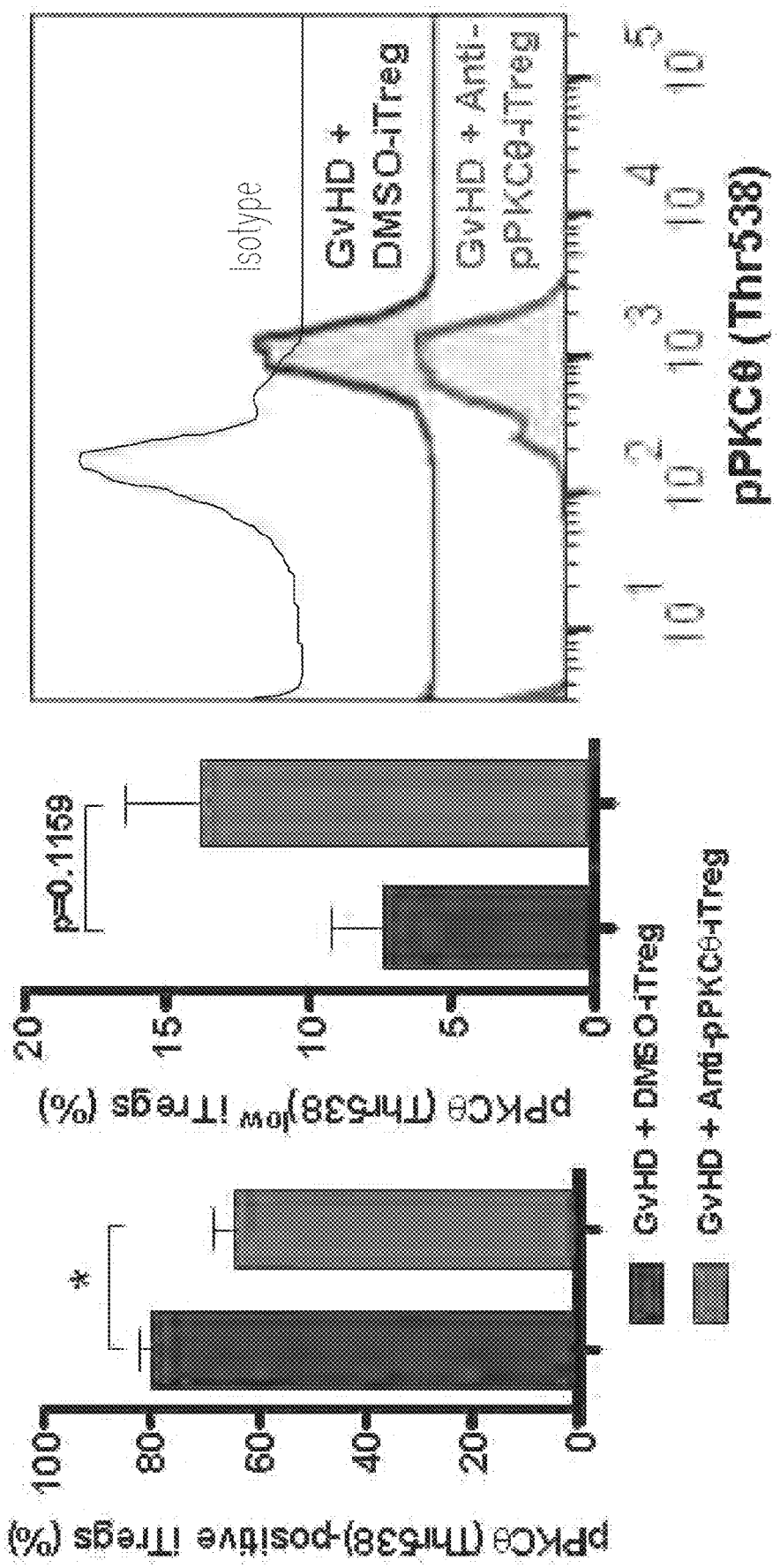
Figure 51F:
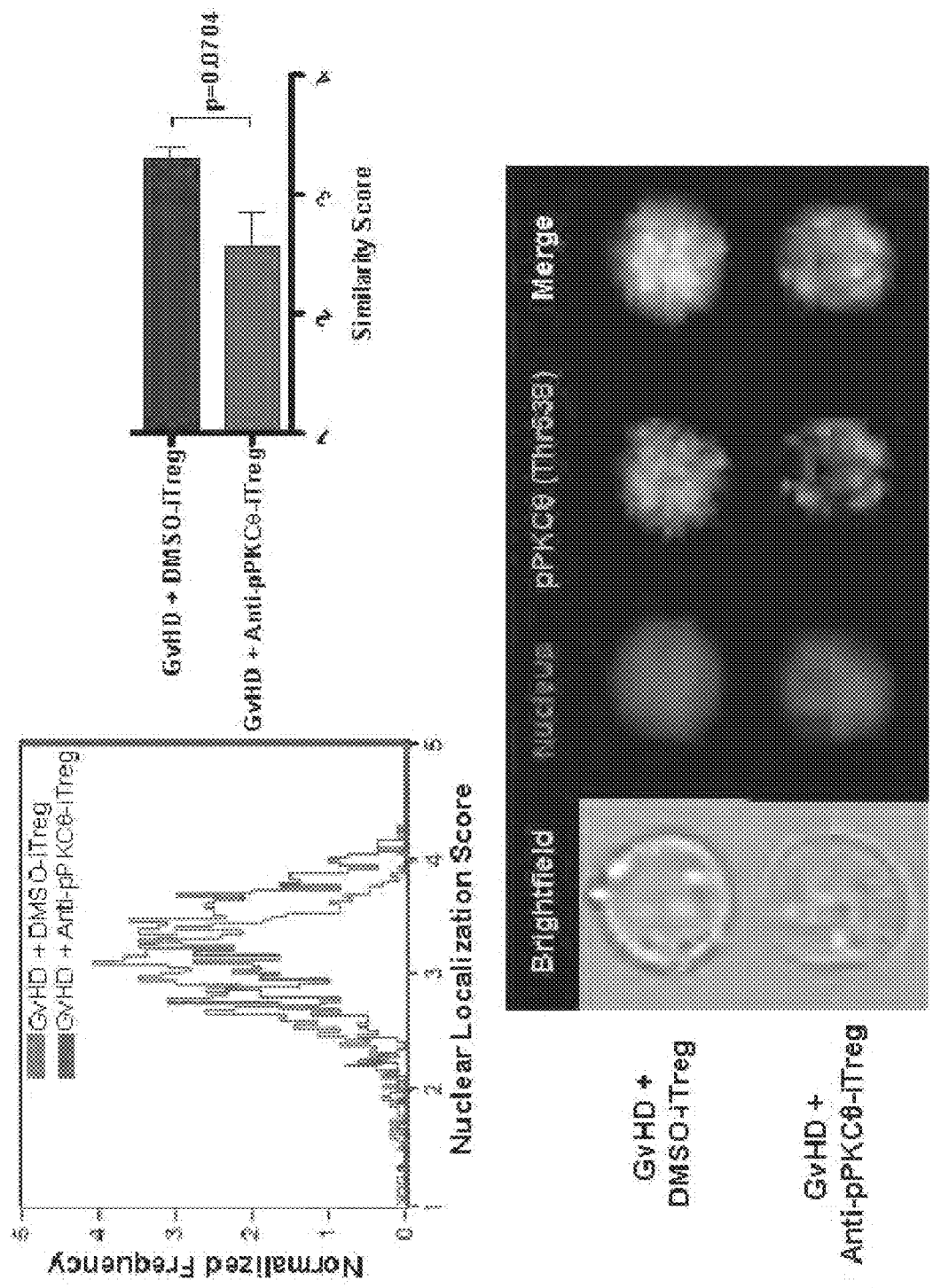
Figure 51G:
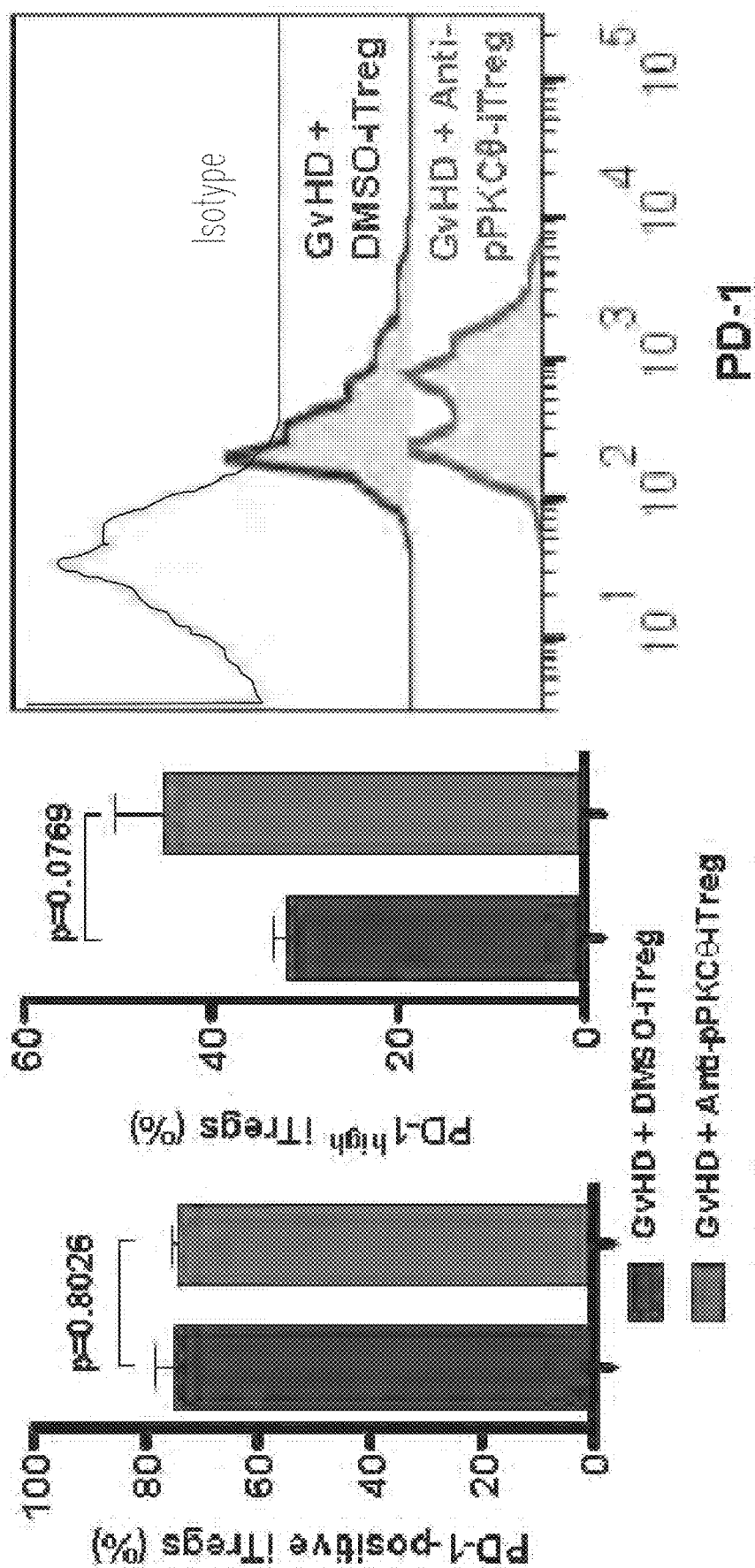
Figure 51H:
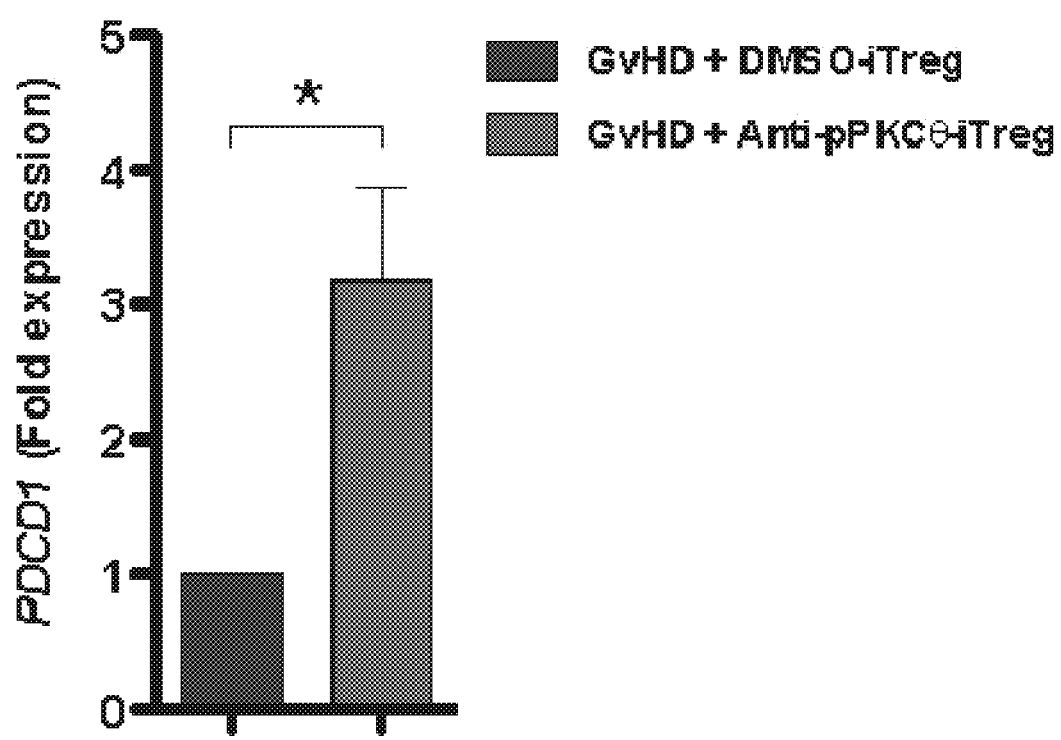
Figure 52D:
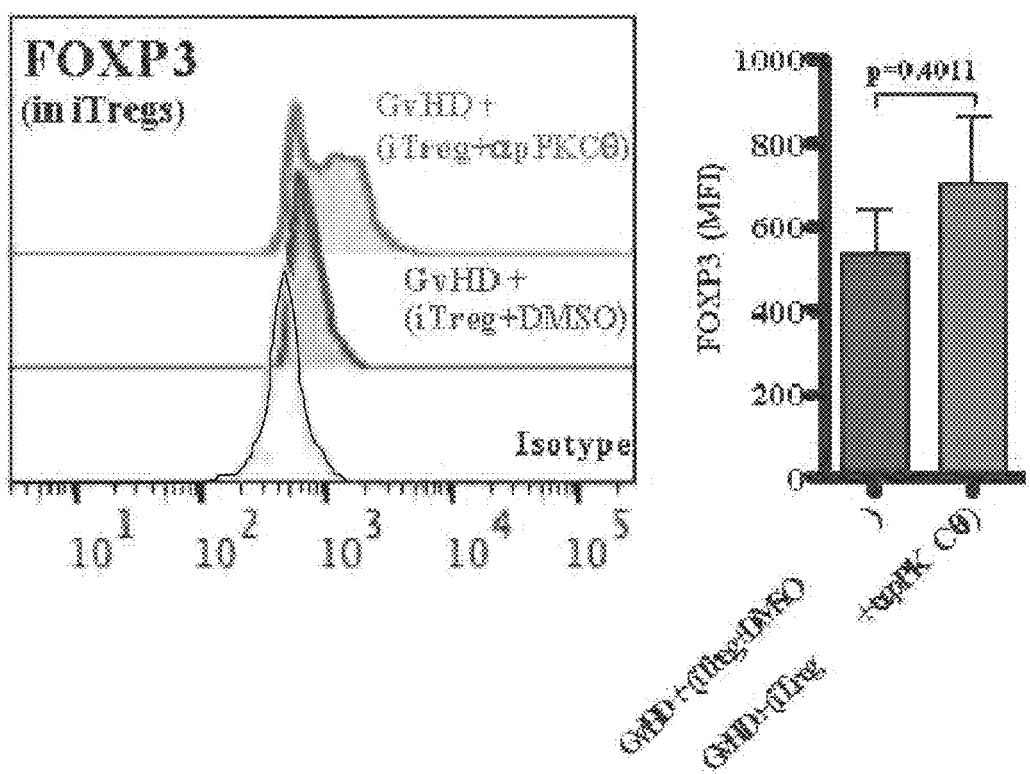
Figure 52E:
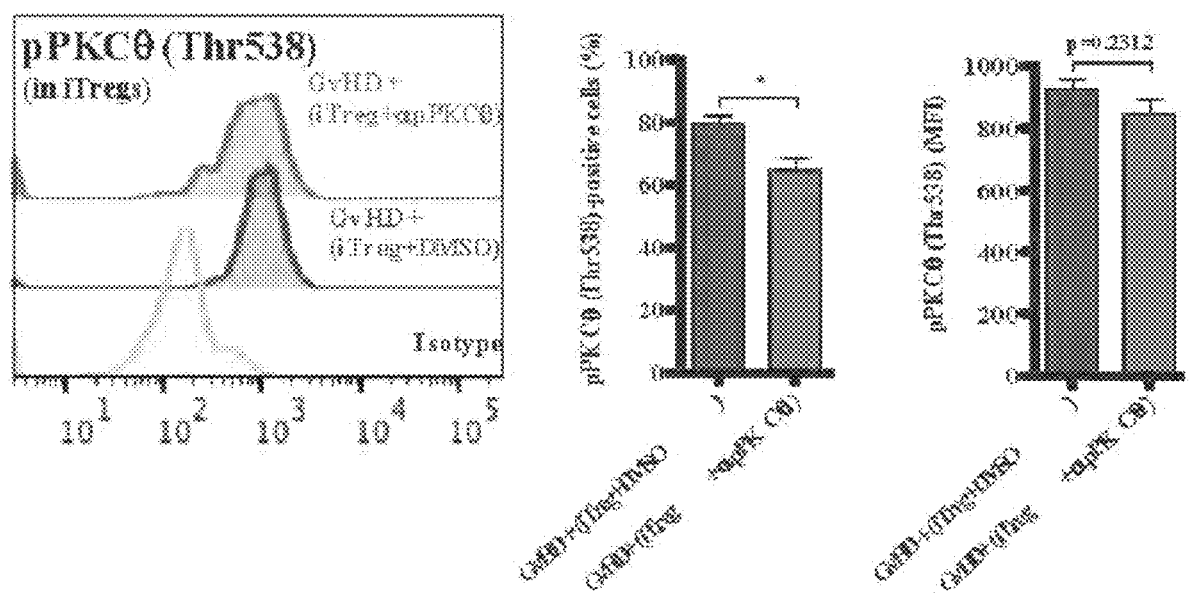
Figure 52C:
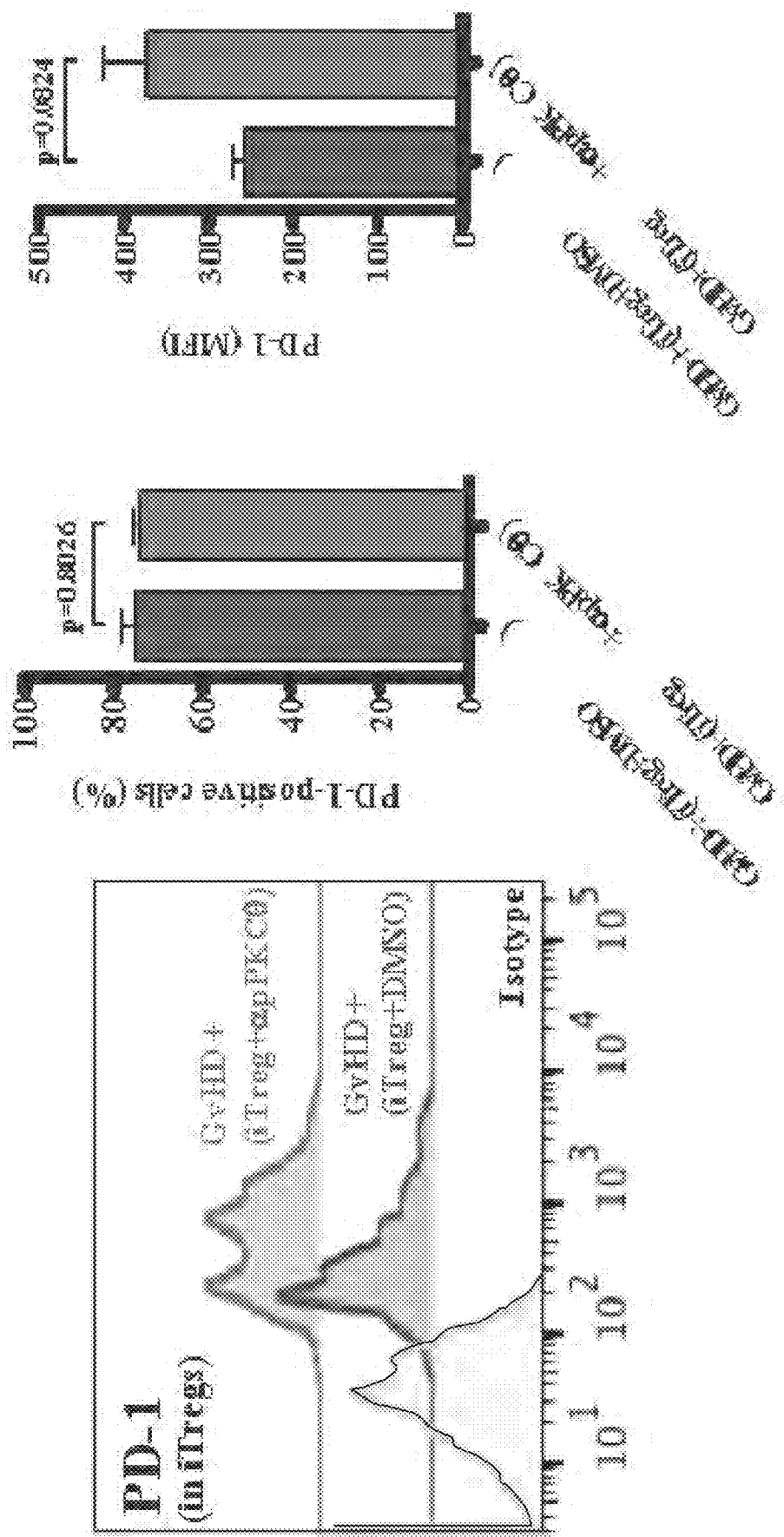
Figure 52J:
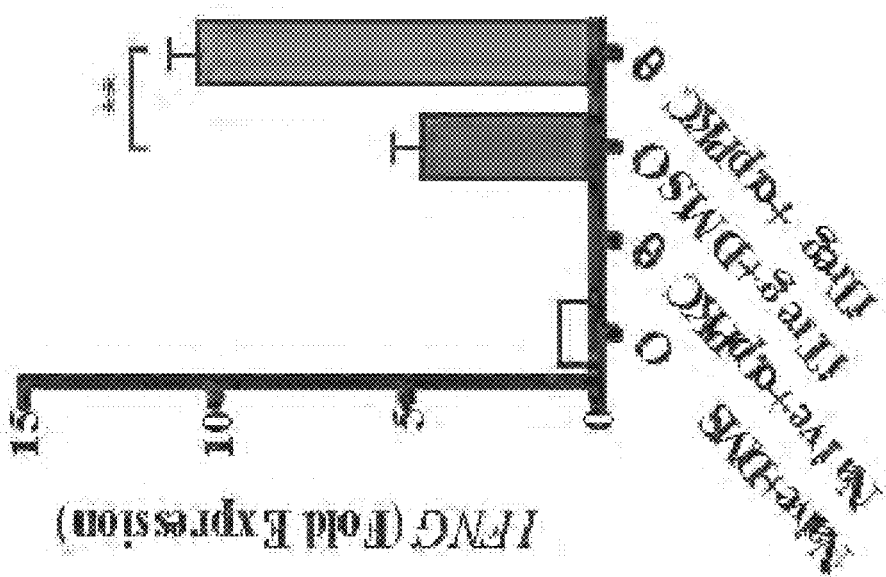
Figure 52I:
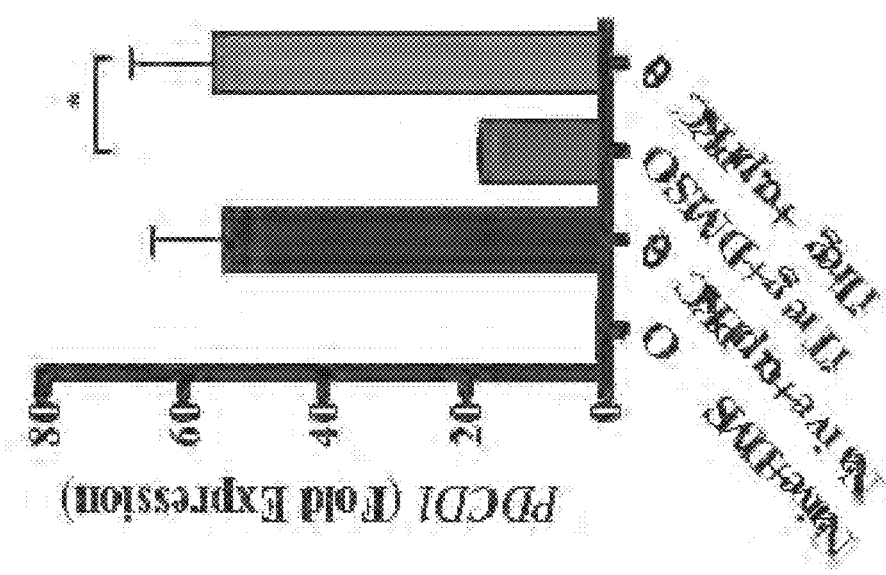
Figure 52H:
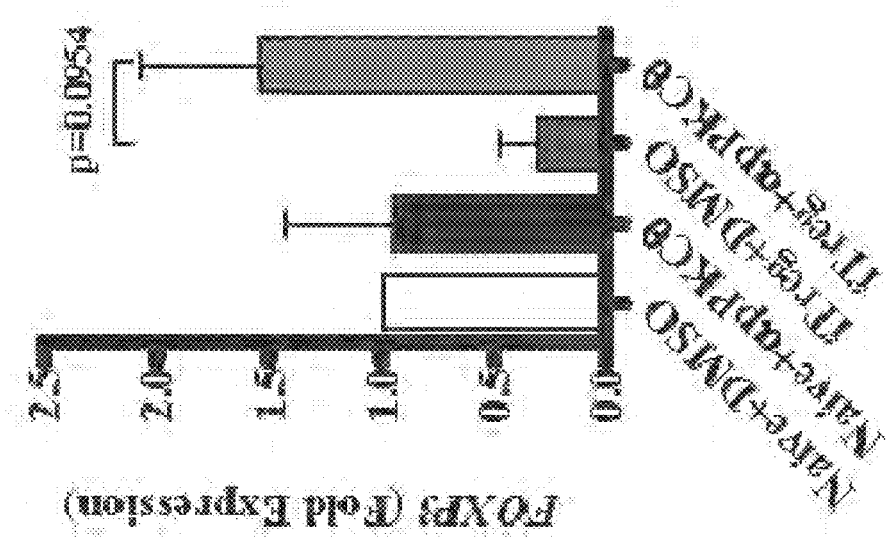
Figure 52K:
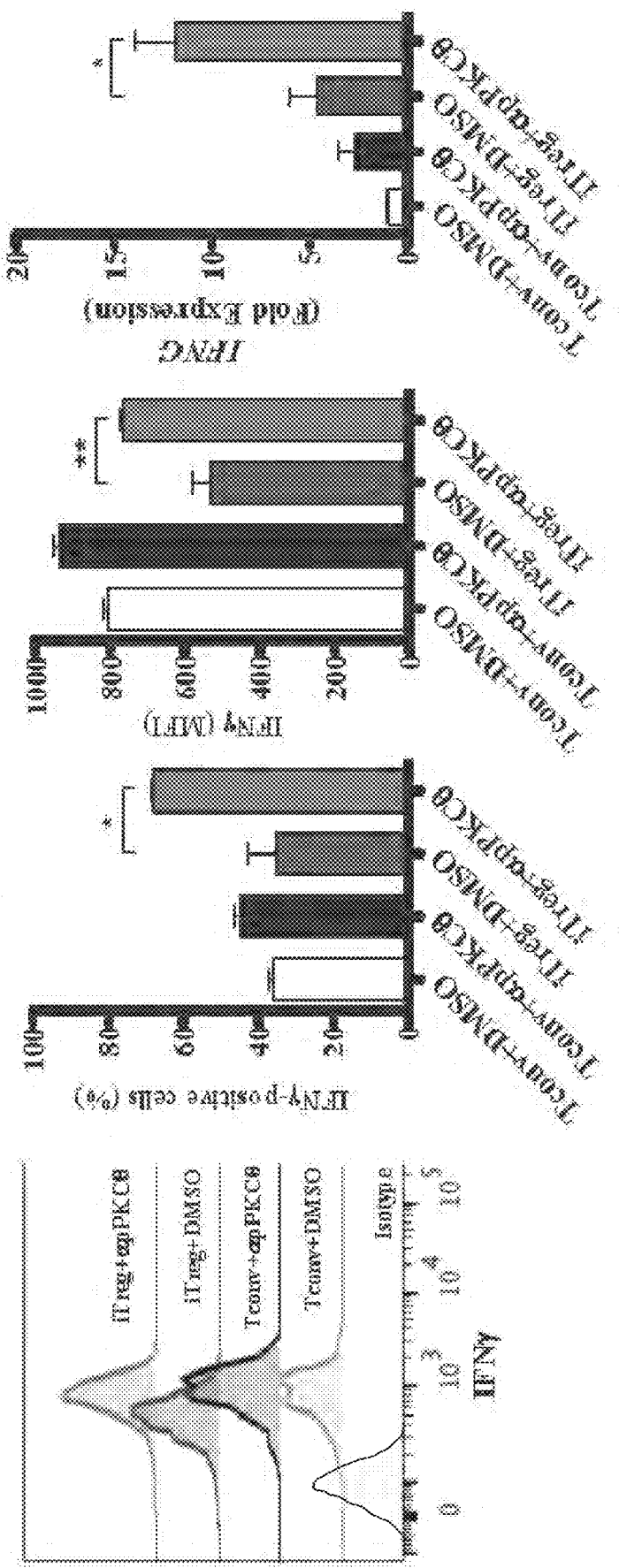

We next evaluated whether administering iTregs attenuated disease severity in a humanized mouse model of GvHD. Treating diseased mice with DMSO-iTregs reduced their cumulative GvHD clinical score, and nearly doubled their median survival time, compared to untreated mice with GvHD (38 days vs. 21 days, respectively; FIG. 50F, G). More remarkable was the rescue from GvHD that co-administering anti-pPKCθ-iTregs had in this model. As a cohort, mice that received anti-pPKCθ-iTregs had less severe symptoms of disease, as compared to mice that received DMSO-iTregs, or no treatment, respectively (FIG. 50F). As we expected, mice that exhibited less severe symptoms also lived longer. The median length of survival for mice treated with anti-pPKCθ-iTregs was twice that of DMSO-iTreg-treated mice, and nearly four times that of untreated mice (78 days vs. 38 days vs. 21 days; FIG. 51G). Quite unexpectedly, one of the five mice treated with anti-pPKCθ-iTregs exhibited full rescue from lethal GvHD, surviving a full 100 days after disease induction. Overall, these in vivo results demonstrated that anti-pPKCθ-treated iTregs were highly efficacious as a cell-based therapy when infused at the time of disease induction, in a humanized mouse GvHD model.

Intracellular Anti-pPKCθ Delivery Generates a Unique Population of FOXP3$^{high}$PD-1$^{high}$IFNγ$^{high}$ iTregs In this pre-clinical model of GvHD, BM destruction is mediated by T helper (Th) type 1 responses resulting from an imbalances Th1/Th2 response. When we measured circulating cytokines in mice treated with anti-pPKC-iTregs, we detected significantly increased Interleukin (IL)-2, and IL-10, both of which enhance the immunosuppressive functions of Tregs, in vivo. Signature Th2 cytokines, IL-4 and IL-13, which can counteract Th1 responses, were also increased in the circulating plasma of anti-pPKCθ-iTreg-treated mice (FIG. 51A), suggesting anti-pPKC-iTregs affect Th cell responses in vivo.

Figure 55A:
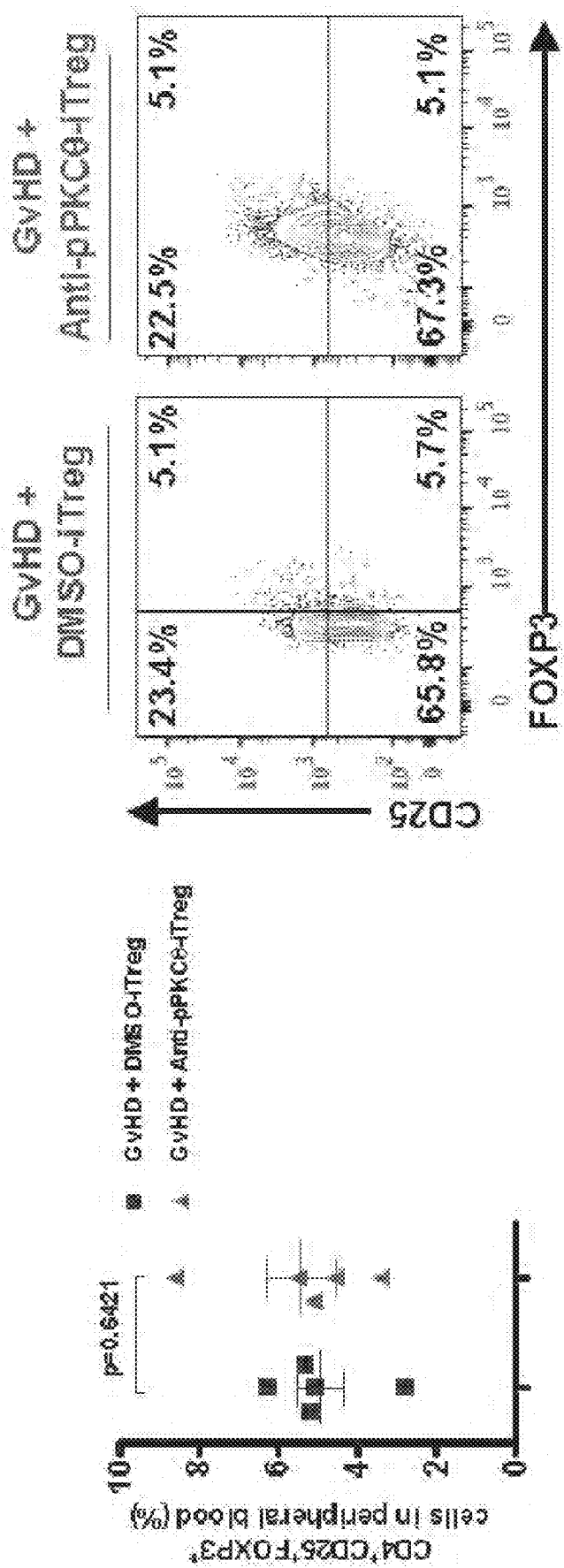
Figure 55B:
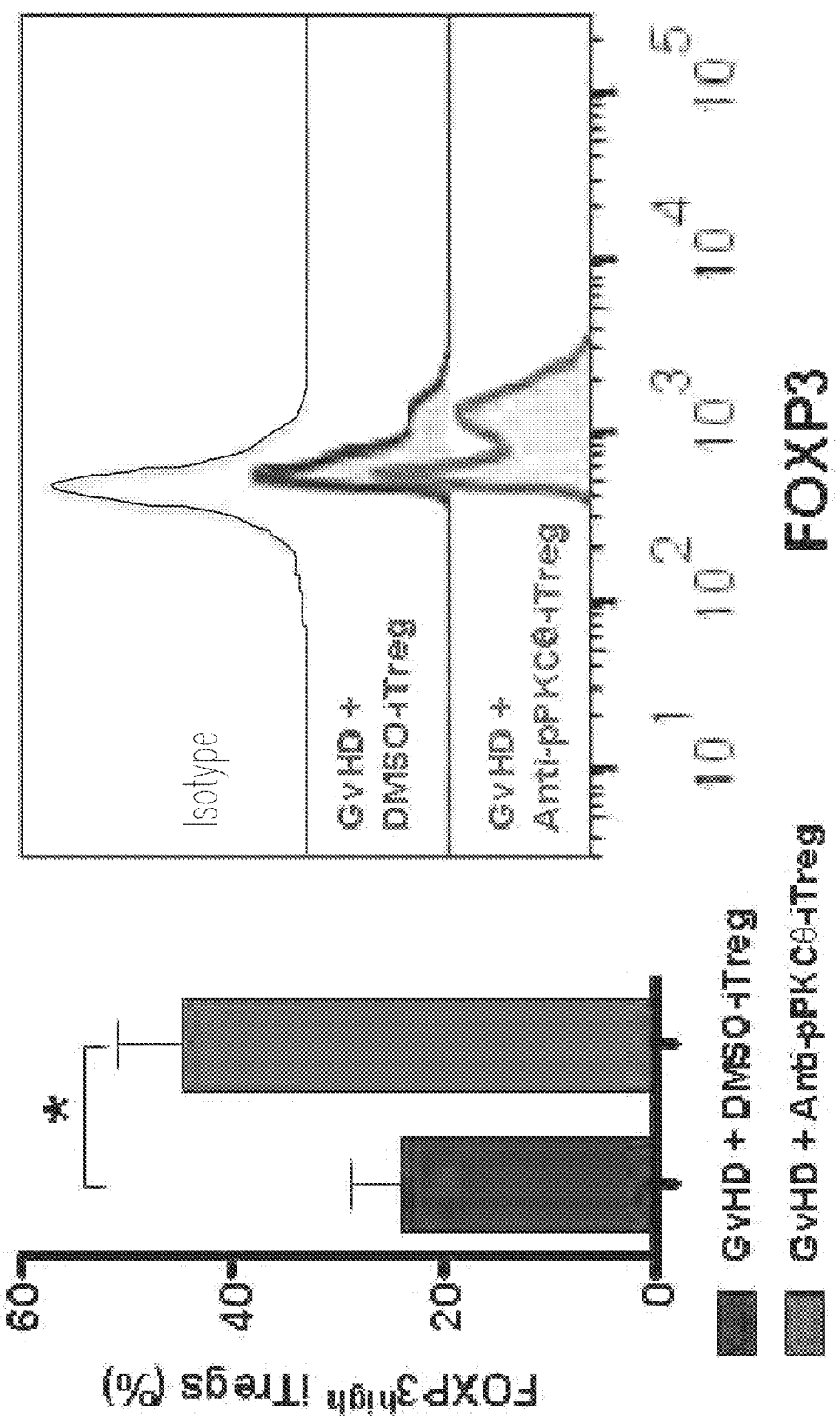
Figure 55C:
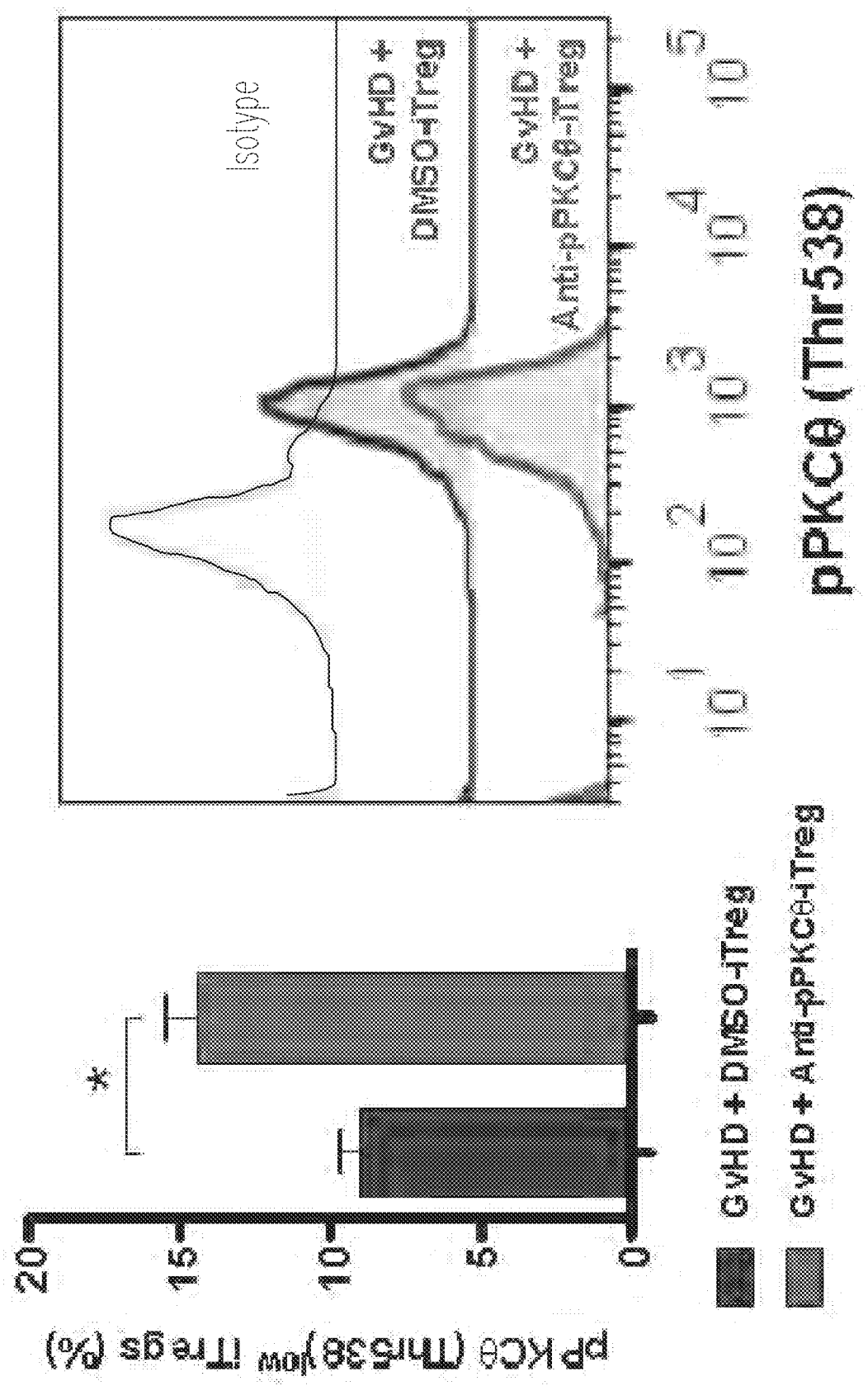
Figure 56A:
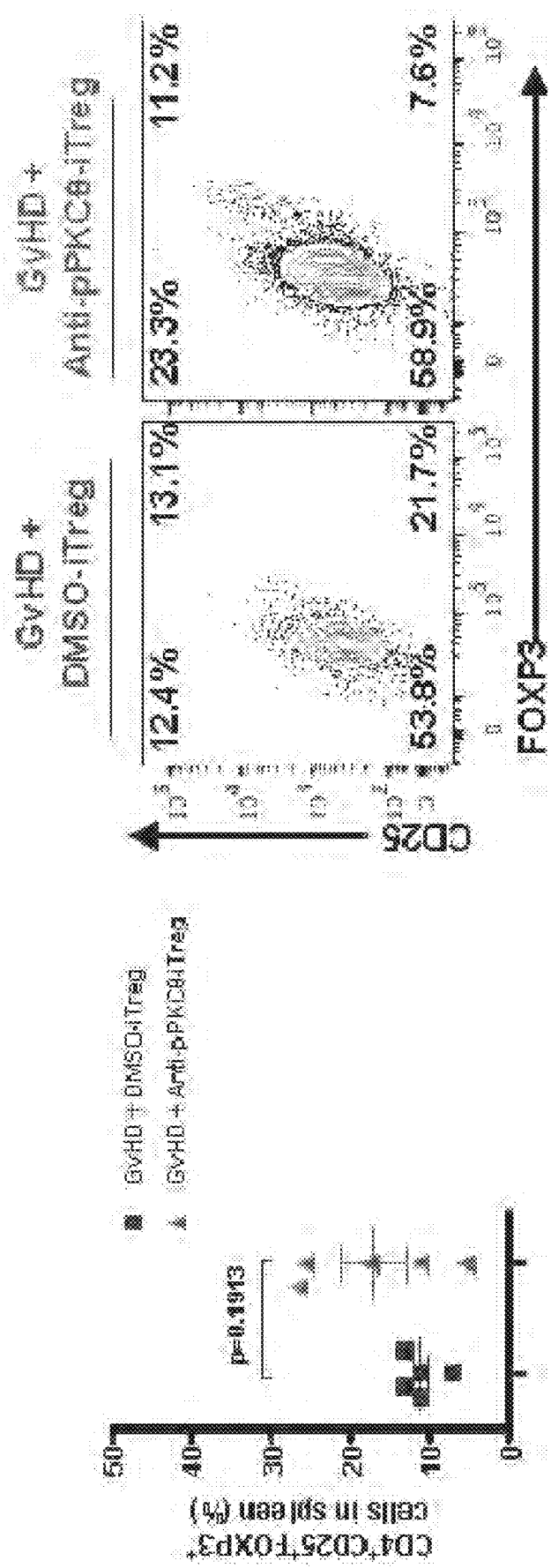
Figure 56B:
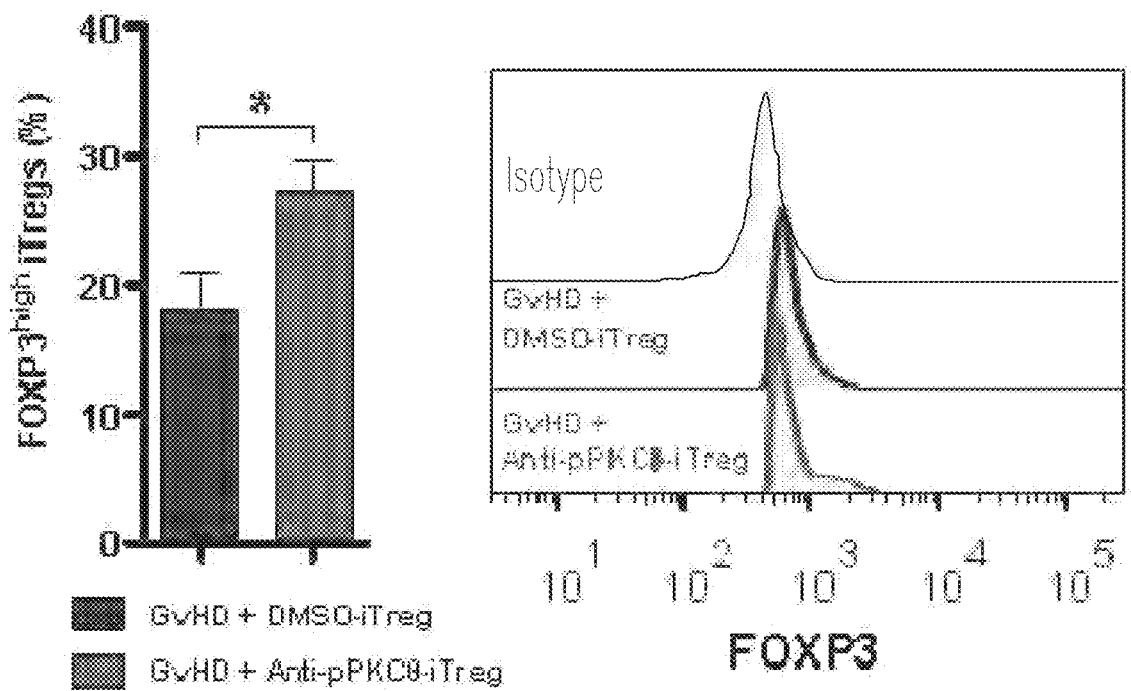
Figure 56C:
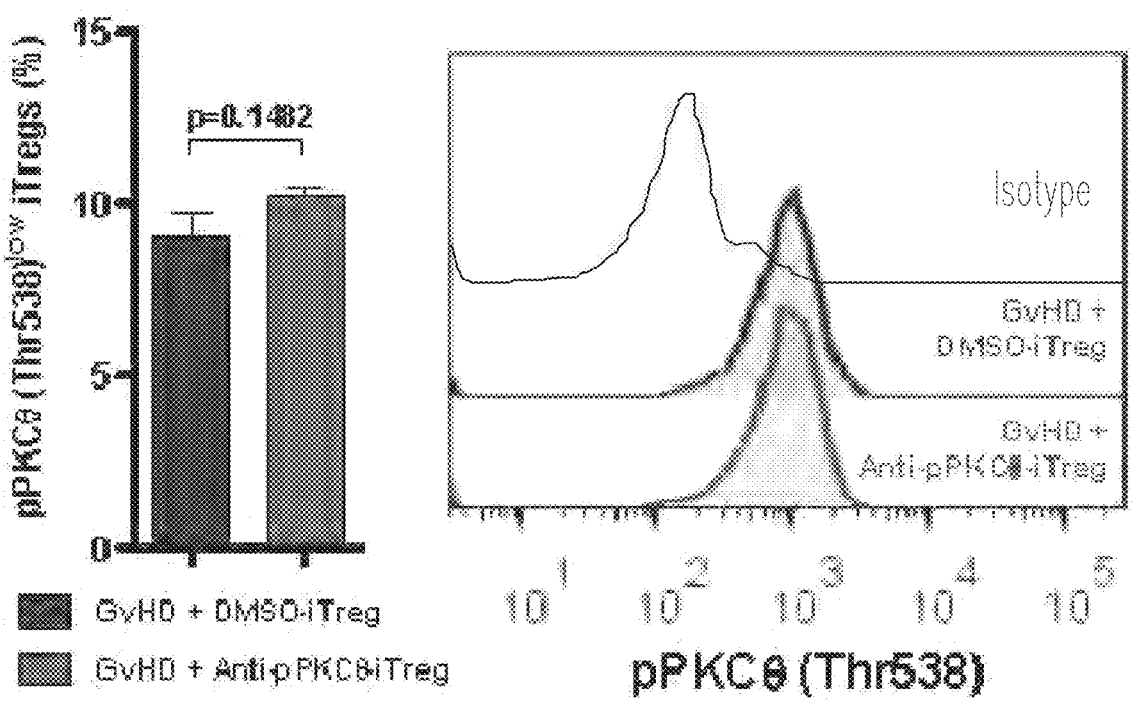
Figure 56D:
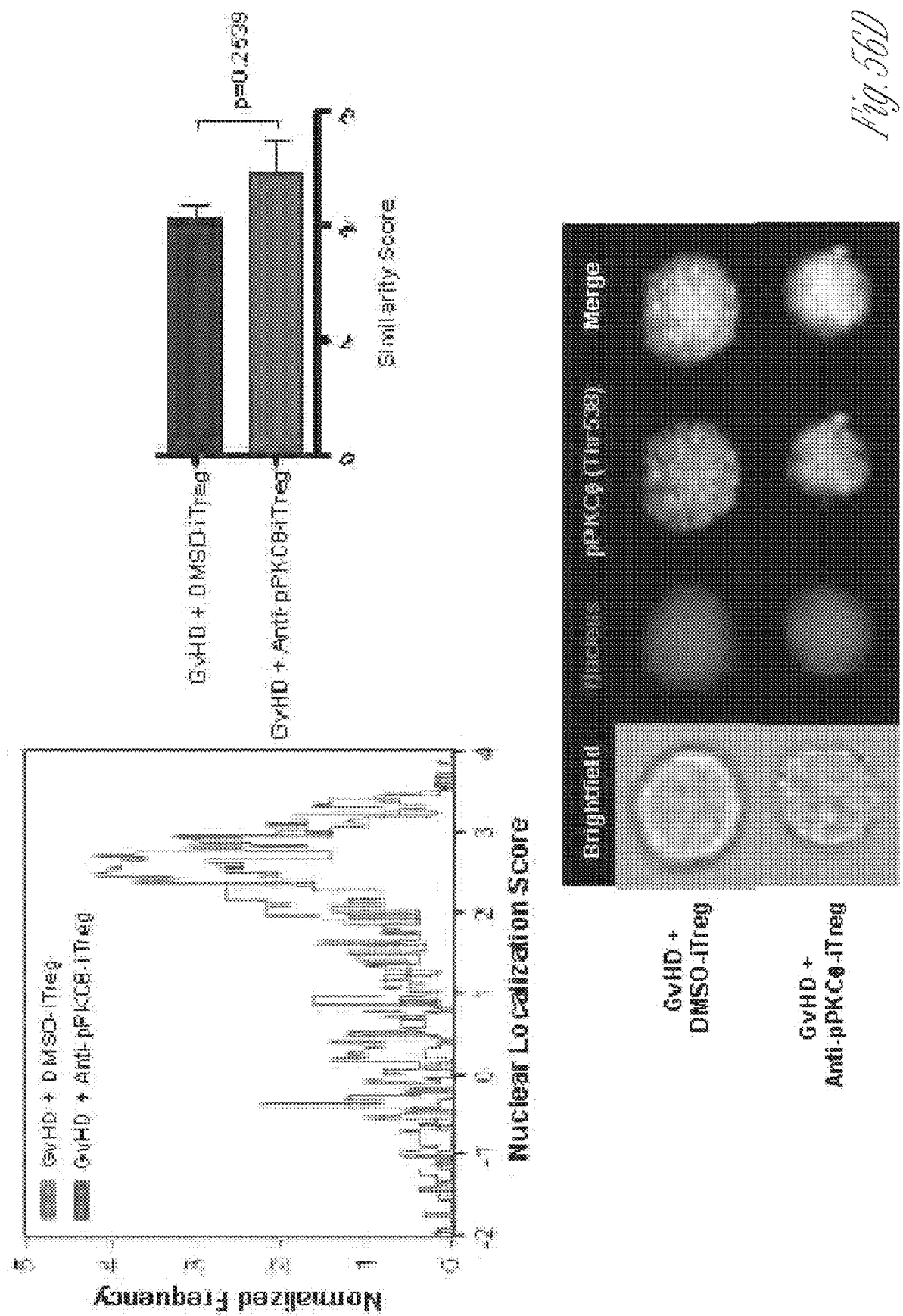

Administering anti-pPKCθ-iTregs proved superior in reducing the severity of GvHD and extending survival in the humanized mouse model. Accumulating evidence suggests that in vitro-expanded Tregs have unstable FOXP3 expression and may lose their suppressive properties when encountering proinflammatory conditions, such as those that characterize the GvHD milieu, in vivo (Beres et al., 2013) Therefore, we sought to better evaluate the in vivo stability of anti-pPKCθ-iTregs, compared to iTregs generated without anti-pPKCθ delivery. We identified iTregs based on CD4, CD25, and FOXP3 expression, as was shown in previous reports (Fang et al., 2013; Bremm et al., 2011; Tronkowski et al., 2009). We first gated on CD4+ T cells within the live cell population. We then quantified the CD25+FOXP3+ population within this gate. Intriguingly, we saw significantly higher percentages, as well as total numbers, of CD4+CD25+FOXP3+ iTregs in the BM of mice that received anti-pPKCθ-iTregs, compared to animals that received DMSO-iTregs (FIG. 51B, C). The percentage of FOXP3$^{high}$ cells among BM-infiltrating iTregs was also significantly greater in mice that received anti-pPKCθ-iTregs (FIG. 51D). Furthermore, FOXP3 expression in anti-pPKCθ-iTregs isolated from the BM was greater than its expression in DMSO-iTregs although it did not reach the significance (FIG. 51D). The percentages of iTregs in peripheral blood and spleen did not differ greatly between treatments (FIG. 55A, 56A). However, there was consistently higher FOXP3$^{high}$ iTreg population in peripheral blood and spleen (FIG. 55B, 56B). Interestingly, when we further analyzed the CD4+CD25+FOXP3+ iTreg population recovered from the BM of mice treated with anti-pPKCθ-iTregs, we found a significantly lower percentage of cells that stained positively for pPKCθ, and an increased percentage that was pPKCθ$^{low}$, compared to mice treated with DMSO-iTregs (FIG. 51E). In addition, pPKCθ$^{low}$ iTregs were significantly higher in peripheral blood, but not in spleen, of anti-pPKCθ-iTreg-treated mice (FIG. 55C, 56C). Consistent with our in vitro data, BM-infiltrating anti-pPKCθ-iTregs accumulated less (although not significant) nuclear pPKCθ than was measured in DMSO-iTregs (FIG. 5F), but we did not observe differences in pPKCθ nuclear localization among iTregs that were circulating in the peripheral blood or that had trafficked to the spleen (FIG. 55D, 56D).

Figure 55E:
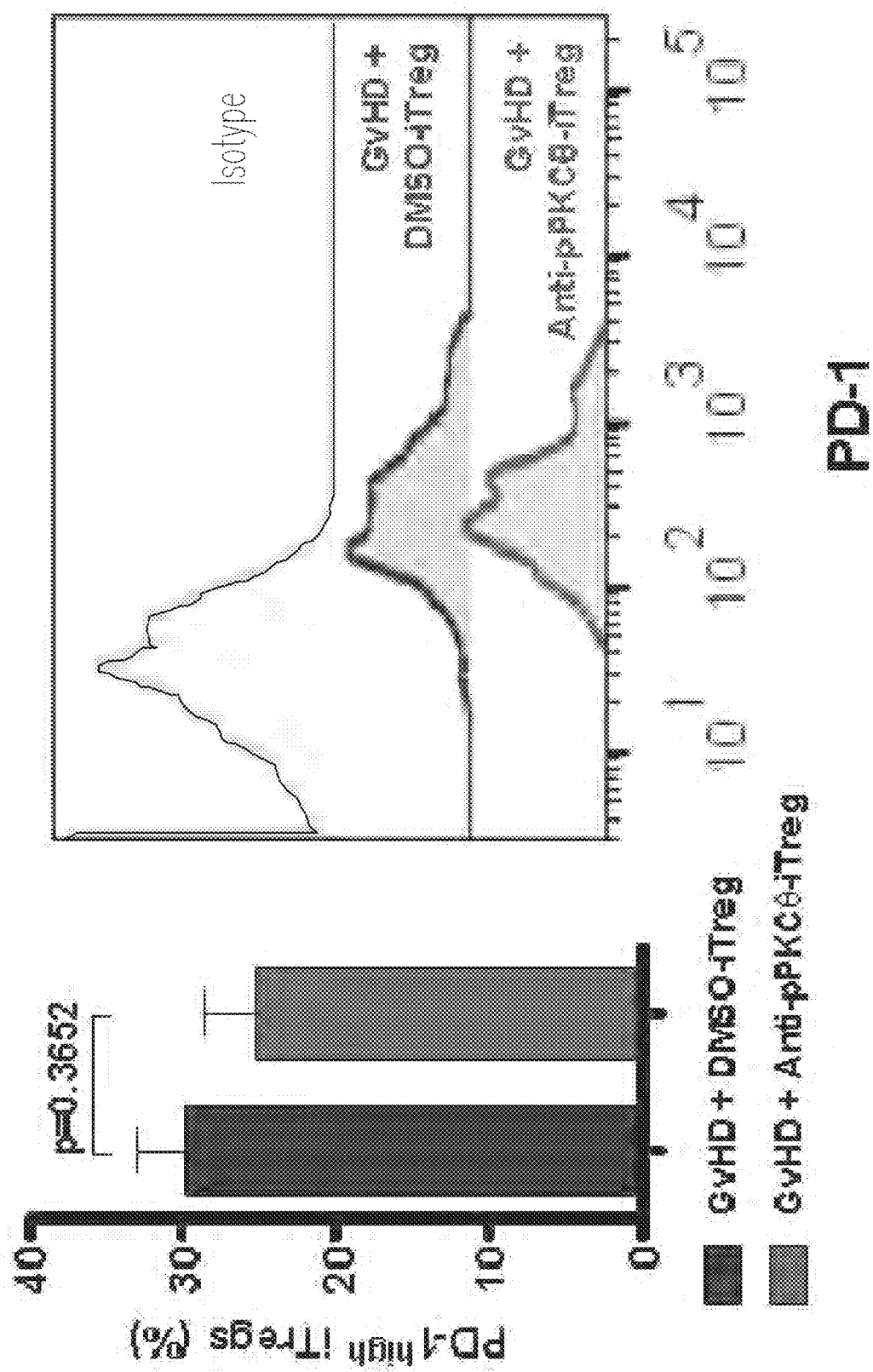
Figure 56E:
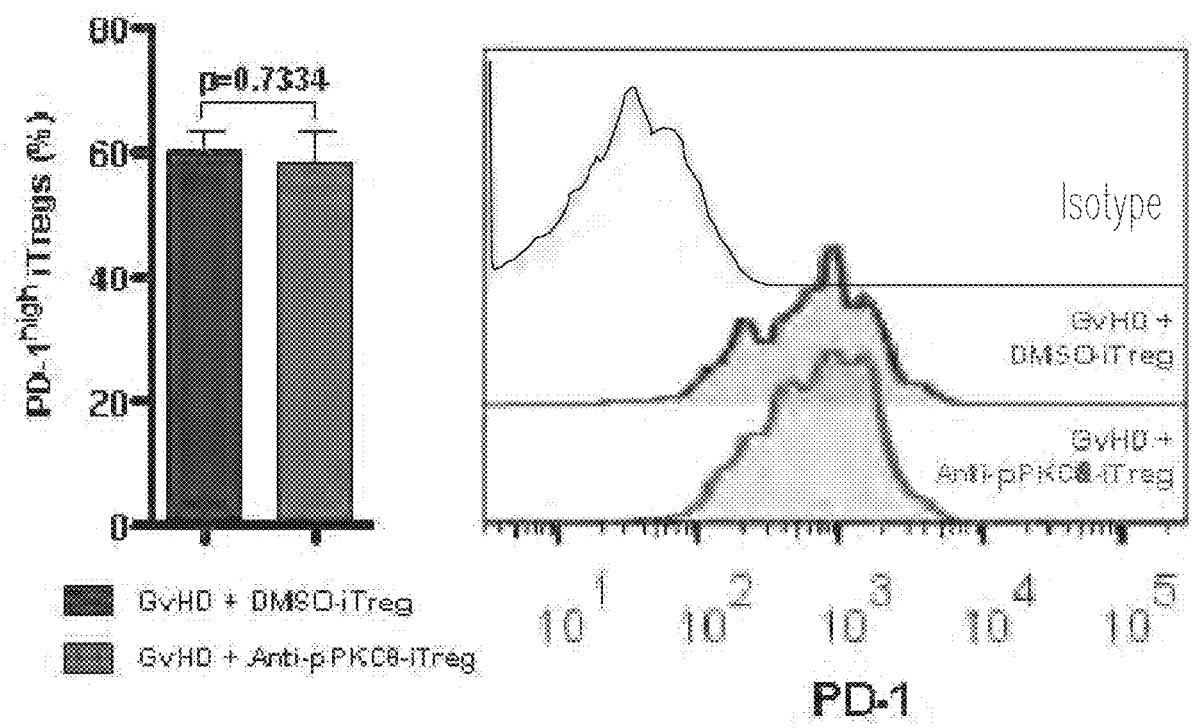
Figure 56H:
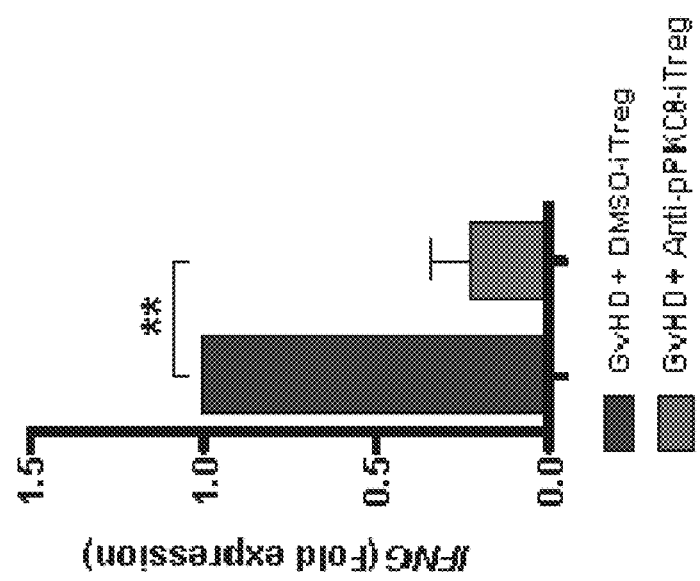
Figure 56G:
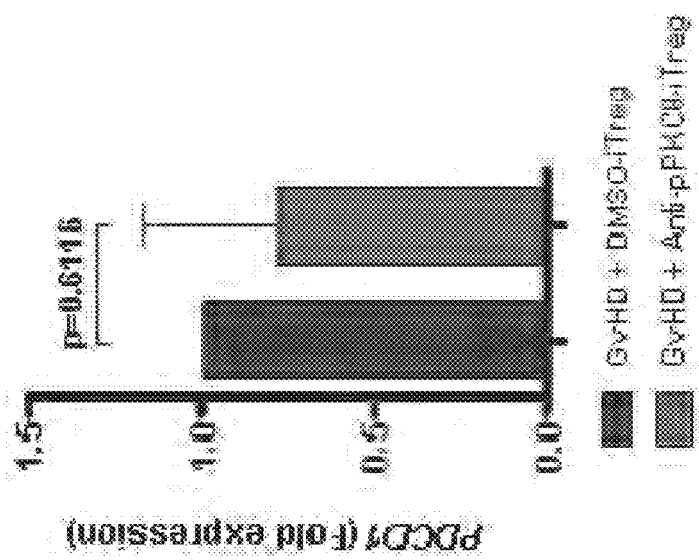
Figure 56F:
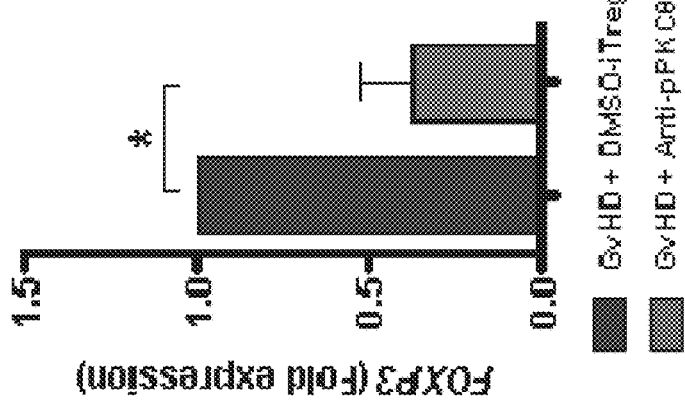

One means by which iTregs can suppress activated T cells is through cell contact-dependent mechanisms, specifically by upregulating the immune-inhibitory receptor, PD-1, which will engage its cognate ligands, PD-L1/PD-L2 on activated T cells. We noted a significantly greater percentage of PD-1$^{high}$-expressing BM iTregs in mice that received anti-pPKCθ-iTregs than in the mice transferred with DMSO-iTregs, although total percentage of PD-1-positive iTregs seemed comparable between the cohorts (FIG. 51G). On the other hand, we did not observe any difference in PD-1$^{high}$ iTregs isolated from peripheral blood or spleen of mice from either cohort. (FIG. 55E, 56E). Altogether, these results indicate that, compared to transferring DMSO-iTregs, infusing anti-pPKCθ-iTregs at the time of GvHD induction results in significantly more iTregs in the BM of diseased mice. Furthermore, treating mice with these anti-pPKCθ-iTregs results in higher percentages of pPKCθ$^{low}$ and PD-1$^{high}$ populations in the BM, suggesting they play a contributing role to reducing disease severity.

In addition to evaluating protein expression, we also investigated transcriptional changes by measuring gene expression in iTregs. We used magnetic beads to sort iTreg (CD4+CD127−CD25+) populations found within the BM, peripheral blood, and spleen, on day +17 post-GvHD induction. Of interest, we observed significantly higher levels of PDCD1 transcripts in iTregs isolated from the BM of the mice treated with anti-pPKCθ-iTregs relative to those of mice receiving DMSO-iTregs (FIG. 51H). Splenic iTregs did not show any difference in FOXP3 or PDCD1 mRNA levels (FIG. 55F, G). Quite unexpectedly, we found that mice treated with anti-pPKCθ-iTregs had expressed elevated IFNG mRNA in the iTregs isolated from BM, compared to those from DMSO-iTreg-treated mice (FIG. 51I). These findings led us to evaluate plasma levels of IFNγ in iTreg-treated mice. In contrast to DMSO-iTreg-treated mice, we measured significantly greater levels of circulating IFNγ in mice that received anti-pPKCθ-iTregs (FIG. 51I). However, IFNG mRNA expression in splenic iTregs of anti-pPKCθ-iTreg-treated mice was significantly lower than the ones in DMSO-iTreg-treated mice, suggesting that the trafficking of IFNγ-producing iTregs is altered in different treatments (FIG. 55H).

Tregs mediate direct inhibition through co-inhibitory receptors expressed on their cell surface, binding to co-inhibitory ligands that are upregulated on effector T cells. NRP1, PD-1, LAG-3, and CTLA-4 are the major co-inhibitory receptors expressed on Tregs. Co-inhibitory receptor-ligand engagement increases contact time with and leads to decreased cytokine production by effector T cells. However, these receptors are effective in cell-to-cell suppression only when they are expressed on cell surface ((Raimoni et al., 2006; Wang et al., 2001; Woo et al., 2010). For instance, freshly isolated, naturally occurring Tregs retain PD-1 in intracellular compartments and upon TCR signaling will translocate PD-1 to the cell surface and, subsequently, become more suppressive. Therefore, we measured both intracellular and surface expression of co-inhibitory receptors following iTreg differentiation. Anti-pPKCθ-treated iTregs had significantly more surface LAG-3, compared to DMSO-treated iTregs, despite the similarity in LAG3 gene expression (FIG. 49E, F, 56C). However, the most striking difference we observed was the increased concentration of surface PD-1 on anti-pPKCθ-treated iTregs. Both the surface protein and the gene expression of PD-1 were significantly more abundant compared to DMSO-iTregs (FIG. 51G, H, 53A). Conversely, we measured significantly less intracellular PD-1 in anti-pPKCθ-iTregs (FIG. 56D). Collectively, these data indicate that anti-pPKCθ delivery into CD4 T cells generate iTregs that acquire higher surface expression of co-inhibitory LAG-3 and PD-1 and are nearly 10-fold more potent than iTregs differentiated without anti-pPKCθ treatment.

To assess the effects of anti-PKCθ delivery on IFNγ expression in iTregs, we set up an in vitro differentiation experiment and measured both the protein and gene expression levels of IFNγ in the differentiated iTregs. Remarkably, there were significantly higher percentage of IFNγ-expressing iTregs with enhanced IFNγ production both at the protein and gene level upon intracellular pPKCθ delivery (FIG. 51I, 52B). These results demonstrated that anti-pPKCθ delivery in iTregs reprogrammed their differentiation in vitro and resulted in a unique iTreg population co-expressing higher FOXP3, PD-1, and IFNγ with superior suppression ability. More importantly, these in vitro generated anti-pPKCθ-treated iTregs preserved their phenotype and function in vivo reinforcing the idea of their promising clinical efficacy as cell-based therapy.

Discussion

In our previous study we demonstrated, for the first time, that PKCθ actions could be specifically inhibited in human CD4 T cells by using cell-penetrating peptide mimics to deliver anti-PKCθ. Targeting the phosphorylated Thr538 residue of PKCθ using this approached to sequestration of PKCθ in the cytosol and diminished T cell activity. In this report, we demonstrate that targeting phosphorylated PKCθ using cell-penetrating anti-pPKCθ delivery favored iTreg differentiation and expansion in vitro. Anti-pPKCθ-treated iTregs exhibited significantly enhanced suppressive capacity in vitro, as characterized by overexpression of co-inhibitory receptors, PD-1 and LAG-3. In addition, these super-suppressive iTregs showed enhanced in vivo stability, as they could still be detected 17 days after administration into mice, in a humanized model of GvHD, and appeared to be highly efficacious in preventing GvHD. Overall, inhibiting PKCθ using a cell-penetrating antibody modulated iTreg differentiation resulting in a unique population that co-expresses higher FOXP3, PD-1, and IFNγ.

The use of therapeutic antibodies to target aberrant signaling pathways has demonstrated efficacy as a biotherapy in the clinic, since antibodies are very specific and are generally well-tolerated by patients. However, clinical applications are currently limited to cell surface or extracellular targets due to limitations in tissue penetration (Beck et al., 2010; Chan et al., 2010; Brekke et al., 2003; Torhilin et al., 2009). Current FDA-approved immunosuppressive antibodies have the disadvantage of targeting common pathways such as calcium signaling (anti-integrin $\alpha_{IIb}\beta_3$: Abciximab, anti-CD20: Rituximab), T cell stimulation (anti-CD3: OKT3-muromonab), T cell costimulation (anti-PD-1: Nivolumab, Pembrolizumab, anti-CTLA-4: Ipilimumab), IL-2 signaling (anti-CD25: Basiliximab, Daclizumab) or global T cell deletion (anti-thymocyte globulin: ATG, anti-CD52: Alemtuzumab; Tang et al., 2013; Nurden et al, 2004; Stroopinsky et al., 2012; Benekli et al., 2006; Barbee et al., 2015; Bowyer et al., 2016; Hsieh et al., 2017; Chae et al., 2017; Wartewig et al., 2017; Brennan et al., 2006; Kandus et al., 2010; Ontaneda et al., 2013). Thus, there is an unmet need to target intracellular molecules with higher penetration, using therapeutic antibodies, soas to avoid off-target effects and provide greater patient safety (Beck et al., 2010; Chan et al., 2010; Brekke et al., 2003; Daugherty et al., 2006). Our strategy shows the strength of using cell-penetrating peptide mimics to deliver therapeutic antibodies successfully into T cells. Cell-penetrating antibodies allow targeting of any intracellular molecule with high specificity and safety, thereby allowing the identification of novel targets and manipulation of specific molecular pathways within the treated cells.

Beyond the use of therapeutic antibodies, cell-based therapies have entered the clinic and hold the promise of developing personalized medicine to minimize adverse side effects and provide long-term treatment for immunological and other diseases (Tang et al., 2013; Fishbach et al., 2013). Especially, T cell therapy has shown remarkable efficacy in treating recurrent cancers, GvHD, and type I diabetes. The prospect of administering Tregs for the treatment of T cell-mediated diseases is gaining momentum. In early studies, Treg-based immunotherapy was used to treat GvHD in a mouse model of bone marrow transplantation (BMT; Komanduri et al., 2011; Wood et al., 2003; Hahn et al., 2015; Sela et al., 2011; Heinrichs et al., 2010). Administering freshly isolated Tregs, together with a BM allograft, has been shown to ameliorate GvHD and assist in successful engraftment (Ganguly et al., 2014; Trzonkowski et al., 2015; Pilat et al., 2010; Parmar et al., 2016). Of note, treating GvHD in the context of BMT was selected as the first indication for in-human clinical trials to test the feasibility and safety of administering Tregs as a cell-based therapy (Roncarolo et al, 2007; Tang et al., 2013; Rosa Bacchetta et al., 1994; Blazar et al., 2012). Following their infusion, Tregs can exert their suppressive function by inhibiting effector T cell activation, cytokine production, and migration, in vivo.They can downregulate dendritic cell maturation in a cell contact-dependent manner, inhibit monocyte and macrophage survival through Fas-FasL signaling, and restrain neutrophil activity by promoting apoptosis in these cells (Misra et al., 2004; Venet et al., 2006; Taams et al., 2005; Lewkowicz et al., 2006). Thus, Treg therapy conveys multiple benefits including antigen-specific immunosuppression, long-lasting immune regulation, and, being a customized cell product designed for each patient, shows very low side effects (Roncarolo et al., 2007; Abou-El-Enein et al., 2017). However, there are several obstacles that limit Treg-based immunotherapy. Tregs must be collected from a patient's peripheral blood and must be expanded in vitro. The number of circulating Tregs in humans is estimated at $0.25 \times 10^9$. In mice, $30 \times 10^6$ of Tregs provided long-term graft survival when combined with the deletion of donor-reactive T cells from the hosts, suggesting approximately $30 \times 10^9$ of Tregs would be needed for human GvHD therapy (Tang et al., 2013). Therefore, ex vivo expansion is clearly required to produce the number of Tregs needed for a cell-based therapy. Expanded iTregs need to be characterized, phenotypically, as immunosuppressive. Recent studies showed that, instead of isolating and expanding natural Tregs from patients, ex vivo, converting CD4+CD25− T cells into iTregs by culturing them with several biologics (such as TGFβ, IL-2, all-trans retinoic acid, DNA methyltransferase (DNMT) inhibitors, histone deacetylase (HDAC) inhibitors butyrate, rapamycin, etc.) generated induced regulatory T cells with enhanced immunosuppressive capacity, thus making iTregs more attractive for immunotherapy (Ohkura et al., 2013; Singer et al., 2014; Benson et al., 2007). In our study, we found that intracellular anti-pPKCθ delivery, significantly increased the suppressive capacity of iTregs, which also expanded efficiently in vitro. Anti-pPKCθ-treated iTregs expressed higher amounts of nuclear FOXP3, nuclear pSTAT5 (Tyr694), surface PD-1, and surface LAG-3 that contribute to their immunosuppressive function, compared to DMSO-treated iTregs. This strategy appears to be highly efficient for in vitro iTreg generation.

Other obstacles to successful Treg-based immunotherapy include Treg instability, plasticity, and trafficking, in vivo. It is a concern whether iTreg cells generated in vitro can sustain FOXP3 expression and suppressive function upon transfer (Ohkura et al., 2013; Singer et al., 2014; Li et al., 2014). Additionally, Tregs in order to effectively exert their immunosuppressive function, Tregs must reach the target organs (Booth et al., 2010; Shi et al., 2012). In our study, we utilized a humanized mouse model of GvHD, in which the BM is the organ targeted by immune destruction (Ozay et al., 2016). Following hPBMC transfer, activated donor T cells migrate to the BM and destroy hematopoietic stem cells. Our results demonstrate that mice receiving anti-pPKCθ-treated iTregs at the time of GvHD induction, showed a significantly greater percent of BM-infiltrating iTregs, together with sustained FOXP3 expression, thus providing a greater benefit for attenuating GvHD in the long-term. Furthermore, the phenotype of anti-pPKCθ-treated iTregs recovered from the BM of treated mice exhibited an immunophenotype very similar to those differentiated in vitro using anti-pPKCθ, suggesting these in vitro generated iTregs are exceptionally stable.

PKCθ is phosphorylated on residue Thr538 during its full activation and, later, it translocates to the nucleus and to the immunological synapse, and studies suggest inhibiting PKCθ may be a novel its opposing actions in effector T cells and Tregs. It was shown that inhibiting PKCθ function in Tregs enhanced their suppressive function both in vitro and in vivo (Zanin-Zhorov et al., 2010; Sun et al., 2012). However, these studies utilized small molecule inhibitors that lacked specificity in targeting PKCθ actions, as other PKC family members, such as PKCα and PKCδ, could be affected by those inhibitors. We harnessed the high degree of specificity intrinsic to antibodies to target PKCθ in iTregs using cell-penetrating peptides for intracellular delivery, that reduced PKCθ phosphorylation and enhanced suppressive function in iTregs. Just how inhibiting PKCθ instills transcriptional changes, as well as co-inhibitory receptor expression on the cell surface, remains to be fully elucidated. Several studies showed PKCθ localizes closely to PD-1 in the cytosol (Yokosuka et al., 2012; Sheppard et al., 2004). We noted a significant reduction in cytosolic PKCθ and higher surface PD-1 expression (Sutcliffe et al., 2011; Sutcliffe et al., 2012; Suttcliffe et al., 2011). Further studies will elucidate the potential connection between cytosolic PKCθ and PD-1 signaling as a means of enhanced iTreg suppressive function. Interestingly, we observed that nuclear PKCθ was completely sequestered in the cytosol following anti-pPKCθ delivery. Nuclear PKCθ has been shown to interact with RNA polymerase II, histone kinases, histone deacetylases, and chromatin modifiers to regulate gene expression. Therefore, further studies are required to illuminate the critical role of nuclear PKCθ in the context of transcriptional and post-transcriptional control of Treg differentiation program.

In this study, anti-pPKCθ-treated iTregs exhibited a unique phenotype, exhibiting elevated IFNγ expression both in vitro and in vivo. IFNγ acts as a paradoxical cytokine in immune responses and inflammatory processes. It can promote Th1 function and T cell migration to the site of inflammation and initiate proinflammatory signaling events. In contrast, IFNγ leads to activation of multiple cellular and molecular events leading to peripheral conversion of CD4$^+$CD25$^-$ T cells to CD4$^+$CD25$^+$ Tregs to regulate overt inflammation. IFNγ was demonstrated to enhance T cell migration into the central nervous system and promote Th1-driven experimental autoimmune encephalomyelitis (EAE) as well as experimental autoimmune uveitis (Wang et al., 2006; Horwitz et al., 1997; Olsson, 1995; Ferber et al., 1996; Willenborg et al., 1996; Krakowski et al., 1996; Caspi et al., 1994). Unexpectedly, blocking IFNγ did not prevent, but rather exacerbated, the severity of the disease. Unexpectedly, IFNγ promoted the conversion of CD4$^+$CD25$^-$ T cells into CD4$^+$CD25$^+$ Tregs, that ultimately suppressed the autoimmune response. Another study showed the conversion of CD4$^+$CD25$^-$ T cells into FOXP3-expressing Tregs by copolymer-I (COP-I) treatment. COP-I-mediated conversion was IFNγ-mediated as recombinant IFNγ treatment further enhanced the number of FOXP3-expressing iTregs and T cells of IFNγ-knockout mice treated by COP-I were failed to induce FOXP3 expression both in vitro and in vivo (Hong et al., 2005). Furthermore, STAT1, an important mediator in IFNγ signaling, was found to be critical in the induction of CD4$^+$CD25$^+$ Tregs (Nishibori et al., 2004). We observed higher levels of IFNγ in the plasma of the mice that received anti-pPKCθ-treated iTregs, as well as a greater percentage of CD4$^+$CD25$^+$FOXP3$^+$ iTregs in vivo. In vitro-differentiated anti-pPKCθ-treated iTregs also showed significantly higher IFNγ production, suggesting IFNγ may act both as an exogenous and endogenous factor to promote iTreg differentiation and enhance their function.

It has been argued that the source of IFNγ is critical to distinguishing pro- or anti-inflammatory responses in GvHD Wood et al., 2006). Considering Th1 cells as one mediator of GvHD progression due to their upregulated IFNγ expression, IFNγ has been implicated as a pathogenic cytokine promoting BM destruction in GvHD (Lin et al., 2014). However, the functional consequences of IFNγ production by Tregs in GvHD remain unexplored. Moreover, allogeneic donor FOXP3-expressing Tregs appeared to express IFNγ upon BMT and prevented the development of lethal GvHD (Taylor et al., 2002; Hoffmann et al., 2002). However, donor Tregs treated with neutralizing anti-IFNγ monoclonal antibody or Tregs cells from IFNγ-knockout donor mice failed to prevent lethal GvHD (Koenecke et al., 2012; Lu et al., 2009). In healthy individuals, IFNγ-producing iTregs comprises only 0.04% of all CD4 T cells in the peripheral blood and this population showed 5-fold increase of IFNG mRNA expression upon allo-antigenic stimulation after renal transplantation. These renal transplant recipients had lower numbers of activated B cells, CD4 and CD8 T cells, suggesting an immunoregulatory role for IFNγ-producing Tregs. Of note, IFNγ produced by Tregs functioned in an autocrine fashion, and these cells were still able to suppress IFNγ production by the responder cells in co-cultures (Daniel et al., 2014; Chowdary Venigalla et al., 2012). More interestingly, several studies showed that only in patients with good, long-term graft function were IFNγ-positive Tregs identified. This population of Tregs seemed to be more suppressive and stable than IFNγ-negative Tregs and showed higher FOXP3 expression which correlated with reduced methylation of the FOXP3 Treg-specific demethylated region (TSDR; Daniel et al., 2015; Trojan et al., 2017; Daniel et al., 2016). Consistent with these observations, our results support the notion that anti-pPKCθ-treated iTregs exhibit enhanced suppressive functions and provide long-term attenuation of GvHD, in part, due to their increased IFNγ expression. Further studies are required to investigate exactly how PKCθ modulates IFNγ expression in iTregs and whether IFNγ production by these iTregs upregulate PD-1 and other co-inhibitory receptor expression as well as regulating FOXP3 TSDR methylation, potentiating iTreg suppressive capacity and stability.

Our results, together with evidence from the literature, demonstrate that modulating PKCθ function in iTregs stabilizes their regulatory phenotype and enhances their immunosuppression capabilities both in vitro and in vivo. Intracellular anti-pPKCθ delivery, using cell-penetrating peptide mimics, is an innovative and promising strategy to fine-tune iTreg differentiation to generate and expand a unique suppressive population. Anti-pPKCθ-treated iTregs co-express higher FOXP3, PD-1, LAG-3, and IFNγ consistent with a highly suppressive iTreg phenotype. More importantly, adoptively transferring anti-pPKCθ-treated iTregs into mice, using a humanized mouse model of GvHD attenuates disease symptoms and provides a significant survival benefit.

Example 4

T cell receptor (TCR) signaling, together with cytokine-induced signals, can differentially regulate RNA processing to influence T helper versus regulatory T cell (Treg) cell fate. Protein kinase C (PKC) family members have been shown to function in alternative splicing and RNA processing in various cell types. T cell-specific PKCθ, a molecular regulator of TCR downstream signaling, was found to phosphorylate splicing factors and affect post-transcriptional control of T cell gene expression. Recently, we reported that delivering a cell-penetrating pPKCθ antibody into CD4 Tcells prior to in vitro iTreg differentiation, augments their suppressive activity and stability and reprograms their transcriptional signature. Here, we explored how intracellular anti-pPKCθ delivery fine-tunes iTreg differentiation though its differential effects on RNA processing. We identified PKCθ signaling as a critical modulator of two key RNA regulatory factors, hnRNPL and PCMT1, and loss of PKCθ function initiated a "switch" in iTreg post-transcriptional organization. More interestingly, we discovered that protein L-isoaspartyl methyltransferase (PCMT1) acts as an iTreg instability factor by methylating the FOXP3 promoter. Targeting PCMT1 using a cell-penetrating antibody revealed a way to modulate RNA processing to confer stable Treg function.

Immunological signals emanating at the T cell receptor (TCR) culminate in translation of mRNA in immune cells. Depending on the input, alterations in this process can be mediated by RNA binding protein (RBP) assemblies to coordinate downstream biological outcomes, such as T cell activation, tolerance, and plasticity. Modifications in RBP-mediated post-transcriptional regulation can influence cellular reactivity during inflammatory responses and autoimmunity (Kafasla et al., 2014). RBPs include two main classes of proteins: heterogeneous nuclear ribonucleoproteins (hnRNPs) that bind to splicing silencers and serine-arginine-rich (SR) proteins that bind to splicing enhancers (Black, 2003; Matlin et al., 2005; Hung et al., 2008; Kornblihtt et al., 2013; Cooper et al., 2009; Wang et al., 2013). Although these proteins were initially discovered as spliceosome components regulating alternative splicing, they are involved in numerous other cellular processes such as transcription, chromatin dynamics, mRNA stability, mRNA nuclear export, and translation (Melton et al., 2007; Ip et al., 2007; Lee et al., 2007; Shav-Tal et al., 2002). These multifunctional RBPs remain bound to mRNA, facilitating nucleation of other regulatory proteins that aid in mRNA export to the cytoplasm and subsequent translation (Kornblihtt et al., 2013; Keene, 2007; Han et al., 2010). By necessity, these proteins are tightly regulated, including by phosphorylation in response to cellular stimuli, which can alter their activity and subcellular localization (Allemand et al., 2005; Blaustein et al., 2005; Patel et al., 2001; Patel et al., 2005; Van Oordt et al., 2000).

TCR-mediated signaling pathways effect multiple changes in cell morphology and function through alternative splicing and orchestrating interaction of positively- and negatively-regulating RBPs with 3' untranslated regions (3'UTRs; Kafasla et al., 2014; Black, 2003; Matlin et al., 2005; Ip et al., 2007; Crabtree et al., 1994; Weiss et al., 1994). Many immunological effectors, including cytokines and chemokines, harbor 3'UTR regulatory elements which enable fine-tuning immunological response in response to cellular requirements (Ganguly et al., 2015; Meininger et al., 2016; Uehata et al., 2013). Alternative splicing and RNA processing can be regulated in tissue- and cell-specific fashion, downstream of specific environmental cues (Grabowski, 1998; Wang et al., 1997; Chalfant et al., 1998; Konig et al., 2012; Screaton et al., 1997; Smith et al., 1997; Wang et al., 1997; Xie et al., 1998). However, the molecular mechanisms that convey differences in post-transcriptional regulation remain an area of active investigation.

For example, alternative splicing of leukocyte surface protein, CD45, represents one well-characterized example of how external stimuli result in changes in expression of alternatively-spliced proteins (Trowbridge et al., 1991; Trobridge et al., 1994; Lynch et al., 2000; Heyd et al., 2010; Oberdoerffer et al., 2008) Protein kinase C (PKC) and Ras signaling induce exon skipping within the CD45 gene, generating alternate forms of CD45 that exhibit reduced phosphatase activity (Lynch et al., 2000; Hermiston et al., 2002; Lynch et al., 2004; Rothrock et al., 2003). Different CD45 isoforms are generated by multi-protein complexes of RBPs, including hnRNPL (Lemaire et al., 1999; Screaton et al., 1995; Fu, 1995; Manley et al., 1996; Preul3ner et al., 2012; House et al., 2006). Studies in the immune cells have focused on hnRNPL, a critical nuclear RBP with four RNA recognition motifs, and capable of mediating basal splicing, mRNA stability, and nuclear export (Hui et al., 2003a; Hui et al., 2003b; Overdoerffer et al., 2008; Rossbach et al., 2009; Gaudreau et al., 2016). hnRNPL binds to CA-repeat motifs and CA-rich elements, thereby repressing exon skipping (House et al., 2006; Waterston et al., 2002; Rothrock et al., 2005; Guang et al., 2005). T cell activation can induce post-translational modifications of hnRNPL to increase its silencing activity (Oberdoerffer et al., 2008; Gaudreau et al., 2012; Vu et al., 2013). Because hnRNPL activity is higher in resting cells, they these cells express primarily the longer CD45 isoforms, CD45RA and or CD45RB. In contrast, in activated and memory T cells, where hnRNPL activity is low, elevated levels of the shortest isoform, CD45RO, can be seen (Oberdoerffer et al., 2008). CD45 isoform expression in regulatory T cells (Tregs) has also been associated with FOXP3 stability and Treg suppressive capacity, as well as with Treg homing in vivo (Booth et al., 2010). Furthermore, differential splicing and mRNA processing regulated by TCR and hnRNPL are key drivers of T helper versus regulatory T cell fate choice. hnRNPL knock down suppressed Treg induction, suggesting that hnRNPL, as an mRNA regulatory protein, is critical to maintaining the integrity of Treg differentiation programs (Hawse et al., 2017).

Tregs function to control immune responses and maintain self-tolerance within the immune system (Pillai et al., 2007; Vignali et al., 2008; Rudensky, 2012; Gavin et al., 2006). Demethylation of the Treg-specific demethylated region (TSDR) located within the intronic sequence of the FOXP3 promoter, is a pre-requisite for stable FOXP3 expression and Treg suppressive function (Overacre et al., 2015; Schmidt et al., 2016; Polansky et al., 2008; Lal et al., 2009). Our previous studies demonstrated we could modulate T cell fate by delivering a cell-penetrating antibody directed against phosphorylated PKCθ (pPKCθ), and intracellular anti-pPKCθ delivery into human CD4 T cells prior to in vitro iTreg differentiation could generate highly stable induced Tregs (iTregs) with a unique phenotype (Ozay et al., 2016) and STM paper). Inhibiting PKCθ function and localization in iTregs resulted in superior suppressive capacity and correlated with unusual transcriptional changes, both in vitro and in vivo. This led us to investigate how these transcriptional changes were regulated by PKCθ during iTreg differentiation. An interesting, potential link between PKCθ and transcriptional diversity has been explored in T cells (McCuaig et al., 2015; Tabellini et al., 2003; Boronenkov et al., 1998). PKCθ directly phosphorylates the splicing factor, SC35, on its RNA recognition motif and serine-arginine-rich (SR) domain (McCuaig et al., 2015; Qian et al., 2011; Colwill et al., 1996; Prasad et al., 2003). PKCθ and SC35 colocalize with RNA polymerase II and active histone marks to enhance transcriptional elongation (McCuaig et al., 2015). Moreover, SC35 binds to exonic splicing enhancers and coordinates alternative splicing, RNA stability, mRNA export, and translation (Cazalla et al., 2002; Lin et al., 2008; Zhong et al., 2009; Kavanagh et al., 2005; Graveley et al., 1998; Chandler et al., 1997; Hammarskjold et al., 2017). Intriguingly, a FOXP3 stabilizing protein, TIP60, was shown to promote SC35 degradation via acetylation at lysine residue 52 in close proximity to the PKCθ phosphorylation sites, suggesting PKCθ may act to regulate splicing factors in the context of Treg suppressive function (Edmond et al., 2011; Bin Dhuban et al., 2017). Given that PKCθ phosphorylates SC35 and controls epigenetic and transcriptional regulation in T cells, we hypothesized that PKCθ may regulate alternative splicing and, further, RNA processing during iTreg differentiation.

In this report, we show that intracellular anti-pPKCθ delivery prior to iTreg differentiation effectively "switches" alternative splicing and RNA processing programs to favor stable over plastic iTreg phenotypes. PKCθ critically modulates two key RNA regulatory factors, hnRNPL and PCMT1, thereby reprogramming mRNA splicing, stability, nuclear export, and translational control. More interestingly, we demonstrated that PCMT1 acts as a Treg instability factor by methylating the FOXP3 promoter. Targeting PCMT1 using a cell-penetrating antibody revealed a novel, attractive way to modulate RNA processing to confer stable Treg function.

Materials and Methods

Animals

All animal studies were approved by, and conducted under the oversight of, the Institutional Animal Care and Use Committee of the University of Massachusetts, Amherst. Seven-week old female NOD.Cg-Prkdc$^{scid}$ Il2rg$^{tm1Wjl}$/SzJ (NSG) mice, were purchased from the Jackson Laboratories (Bar Harbor, Me.). Upon arrival, these mice were rested for one week prior to use. Mice were housed under pathogen-free conditions in micro-isolator cages and received acidified water (pH 3.0) supplemented with two types of antibiotics (trimethoprim+sulfamethoxazole) throughout the duration of the experimental procedures.

Antibodies and Reagents

Western blot antibodies used in this study were acquired from: (1) Santa Cruz Biotechnology: p-SC35 (anti-mouse, Clone: SC35), (2) Novus Biologicals: hnRNPL (anti-mouse, Clone: 4D$_{11}$), (3) LifeSpan Biosciences: PCMT1 (anti-rabbit, polyclonal), (4) Thermo Fisher: pSTAT1 (Y701) (anti-mouse, Clone: KIKS10803), (5) BioLegend: total STAT1 (anti-mouse, Clone: 10C4B40), (6) Cell Signaling Technology: pAKT (S473) (anti-rabbit, polyclonal), total AKT (anti-rabbit, polyclonal), HuR (anti-rabbit, Clone: D9W7E), hnRNPLL (anti-rabbit, polyclonal), Histone H3 (anti-mouse, Clone: 96C10). (7) Sigma: α-Tubulin (anti-mouse, Clone: B-5-1-2). (8) GeneTex: Regnase-1 (ZC3H12A) (anti-rabbit, polyclonal). (9) Proteintech Group: hnRNPU (anti-rabbit, polyclonal).

Flow cytometry antibodies used in this study are acquired from: (1) BioLegend: CD4 (BV711, Clone: RPA-T4), CD25 (PECy7, Clone: BC96), CD127 (AF700, Clone: A019D5), FOXP3 (AF488, Clone: 150D), (2) BD Bioscience: IFNγ (APC, Clone: B27), (3) LifeSpan Biosciences: PCMT1 (Unconjugated, anti-rabbit, polyclonal), (4) Life Technologies: F(ab')2-Goat anti-rabbit IgG (H+L) secondary antibody (Qdot625, polyclonal). Live/dead staining was performed utilizing either Zombie aqua fixable viability kit purchased from BioLegend.

Human iTreg Differentiation Upon Intracellular $P_{13}D_5$:αpPKCθ or $P_{13}D_5$:αPCMT1 Delivery 1 μM of $P_{13}D_5$ and 25 nM of apPKCθ (Thr538, Life Technologies, Clone: F4H4L1) or 1 μM of $P_{13}D_5$ and 25 nM of αPCMT1 (LifeSpan Biosciences, polyclonal) were complexed in PBS (phosphate buffered saline, pH 7.2) at a specific ratio (PTDM: Antibody=40:1). The PTDM: antibody complex was incubated for 30 min at RT. Meanwhile, CD4$^+$ T cells were isolated from human PBMCs (purchased from StemCell Technologies, Inc.) via MojoSort™ Human T Cell Isolation Kit (BioLegend). Isolated human CD4$^+$ T cells were then treated with the PTDM: antibody complex for 4 hours at 37° C. (some cells were treated with DMSO as vehicle control). Cells were harvested and washed with PBS. Later, cells were thoroughly washed twice with 20 U/mL heparin in PBS for 5 minutes on ice to remove surface-bound complexes outside cellular membrane. For iTreg differentiation, CellXVivo™ Human Treg Differentiation Kit (R&D Systems) was used and iTreg Differentiation Media was prepared using X-VIVO™ 15 Chemically Defined, Serum-free Hematopoietic Cell Medium according to manufacturer's instructions. Treated cell pellets were then resuspended in iTreg differentiation media and seeded onto 5 μg/mL of anti-CD3ε-plus 2.5 μg/mL of anti-CD28-coated tissue culture wells and stimulated for 5 days at 37° C.

Immunoblotting iTreg cells were harvested on day 5 of differentiation. Nuclear and cytosolic extracts were prepared by using NE-PER™ Nuclear and Cytosolic Extraction Kit (Thermo Scientific). 1×SDS Laemmli Buffer was added into the samples for running on 8% SDS-PAGE for western blot. The blots were probed for RNA-binding proteins for further analysis. Anti-α-Tubulin was probed for cytosolic loading control and anti-histone H3 was probed for nuclear loading control.

In Vivo RNA Analysis of iTregs in Humanized GvHD Model hPBMCs from a healthy donor were used to isolate total CD4$^+$ T cells and subsequently treated with $P_{13}D_5$: αpPKCθ complex. They were differentiated for 5 days into iTregs as previously described. On day 4, total hPBMCs from the same donor were thawed and rested overnight in fresh RPMI complete media (10% fetal bovine serum, 100 U/mL penicillin-streptomycin, 1 mM sodium pyruvate, 2 mM L-Glutamine) at 37° C. in 5% $CO_2$ incubator. On day 5, NOD.Cg-Prkdc$^{scid}$ Il2rg$^{tm1Wwjl}$/SzJ (NSG) mice were conditioned with 2 Gy of total body irradiation using a $^{137}$Cs source then rested for 4-6 hours. 10×10$^6$ of total hPBMCs was mixed with 3.3×10$^6$ of iTreg cells and adoptively transferred into irradiated NSG mice via the tail vein. Body weight and disease symptoms were observed daily. On day 17, some animals were sacrificed for tissue analysis. Bone marrow cells were recovered from the tibias and femurs and splenocytes were isolated by manipulation through a 40 μm filter. Red blood cells were lysed in ACK lysis buffer, and the remaining white blood cells were enumerated using Trypan Blue exclusion. Afterwards, cells were incubated with human CD4 T lymphocyte enrichment cocktail (BD Biosciences) followed by an incubation with BD IMag™ Streptavidin Particles Plus (BD Biosciences) to deplete non-CD4 T cell fraction. Biotinylated anti-CD127 antibody and biotinylated anti-CD25 antibody followed by an incubation with BD IMag™ Streptavidin Particles Plus were sequentially used to obtain iTreg cell fraction (negative fraction from anti-CD127 incubation and positive fraction from anti-CD25 fraction) and naïve T cell fraction (positive fraction from anti-CD127 incubation and negative fraction from anti-CD25 incubation). After cells were isolated, total RNA isolation procedure was followed.

Quantitative Real Time PCR (qPCR)

Total RNA was isolated Quick-RNA Isolation Kit (Zymo Research) according to the manufacturer's protocol. 1 μg of total RNA was reverse transcribed to cDNA using dNTPs (New England Biolabs, Inc.), M-MuLV reverse transcription buffer (New England Biolabs), oligo-DT (Promega), RNase inhibitor (Promega), and M-MuLV reverse transcription (New England Biolabs, Inc.) on a Mastercycler gradient Thermal Cycler (Eppendorf). Primers for PCMT1 were designed as: forward primer (5'-GCTGAAGAAGCCCCT-TATGA-3'; SEQ ID NO:21) and reverse primer (5'-TCTTCCTCCGGGCTTTAACT-3'SEQ ID NO:22). Q-PCR was performed in duplicate with 2×SYBR Green qPCR Master Mix (BioTool) using the Mx3000P system (Agilent Technologies). Q-PCR conditions were as follows: 95 C for 1 min, 95 C for 25 s, 62 C for 25 s (40 cycles), 95 C for 1 min, 62 C for 1 min, and 95 C for 30 s. Relative gene expression was determined using the ΔΔCt method. The results are presented as the fold expression in gene expression normalized to the housekeeping gene β-actin (ACTB) for cells and relative to Tconv+DMSO sample for in vitro experiments and Naïve+DMSO for in vivo experiments.

Reverse Transcriptase PCR (RT-PCR) for Splicing and 3'UTR Analyses

Total RNA was isolated Quick-RNA Isolation Kit (Zymo Research) according to the manufacturer's protocol. 0.5 µg of total RNA was reverse transcribed to cDNA using random hexamers (Integrated DNA Technologies) with M-MuLV reverse transcriptase (New England Biolabs, Inc.) on a Mastercycler gradient Thermal Cycler (Eppendorf). Splicing primers (Table 2) and 3'UTR primers (Table 3) were specifically designed for the genes analyzed in this study. PCRs (35 cycles) were performed using Phusion High-Fidelity DNA Polymerase (New England Biolabs, Inc.) followed by resolution on 2% agarose gel. PCR conditions were: initial denaturation at 98C (30 sec), annealing at 98C (5 sec), 52C (20 sec), 72C (1 min), final extension at 72C for 5 min. The amplicons were imaged via G:BOX gel documentation system (Syngene).

Lambda Phosphatase Treatment

Cells were lysed RIPA buffer (150 mM NaCl, 1% IgeCal-CA 360, 0.1% SDS, 50 mM Tris, pH-8.0, 0.5% Sodium deoxycholate). Lysates were treated with 100 units of lambda protein phosphatase (New England Biolabs, Inc.) in the presence of 1 mM $MnCl_2$ for 1 h at 30° C. 1×SDS Laemmli Buffer was added into the samples and they were boiled for 5 min at 95° C. The samples were run on 8% SDS-PAGE for western blot analysis.

hnRNPL Immunoprecipitation

Cells were harvested on day 5 of iTreg differentiation. They were lysed in immunoprecipitation lysis buffer (50 mM HEPES, pH 7.8, 250 mM NaCl, 1% NP-40, Protease+Phosphatase inhibitors). DynaBeads (Protein G) were coupled with 3 µg of anti-hnRNPL (4D11, Novus Biologicals) in the presence of 1% BSA in PBS and incubated for 2 hours at 4° C. with rotation. After the incubation, the antibody-coupled DynaBeads were washed six times with 1 mL of immunoprecipitation wash buffer (Tris-HCl, pH 8.0, 200 mM NaCl, 0.1% NP-40). Later, cell lysates were incubated with antibody-coupled DynaBeads for 1 hour at 4° C. using rotator. Subsequently, they were washed beads six times with 0.5 mL of immunoprecipitation wash buffer. 1×SDS Laemmli Buffer was added into the samples for running on 8% SDS-PAGE for western blot. The blots were probed with anti-hnRNPL, anti-PKCθ, and anti-PCMT1 for further analysis.

RNA Immunoprecipitation

After harvesting the cells on day 5 of differentiation, they were lysed in RNA immunoprecipitation lysis buffer (50 mM HEPES, pH 7.8, 250 mM NaCl, 1% NP-40, 1× Protease+Phosphatase inhibitors, 100 U/ml RNase inhibitor). DynaBeads (Protein G) were coupled with 3 µg of anti-hnRNPL ($4D_{11}$, Novus Biologicals) or anti-IgG (control antibody) in the presence of 1% BSA in PBS and incubated for 2 hours at 4° C. with rotation. After the incubation, the antibody-coupled DynaBeads were washed six times with 1 mL of immunoprecipitation wash buffer (Tris-HCl, pH 8.0, 200 mM NaCl, 0.1% NP-40). Cell lysates were incubated with antibody-coupled DynaBeads for 1 hour at 4° C. using rotator. Subsequently, they were washed beads six times with 0.5 mL of immunoprecipitation wash buffer+100 U/mL RNase inhibitor. RNA was purified via Quick-RNA Isolation Kit (Zymo Research) according to the manufacturer's protocol to further use on RT-PCR experiments.

ChIP-qPCR

Cells were crosslinked with 1% formaldehyde, lysed in sodium dodecyl sulfate (SDS) lysis buffer (1% SDS, 10 mM EDTA, and 50 mM Tris, pH 8.1), and sonicated with a Bioruptor Sonicator (Diagenode). Cell lysates were incubated with 2 mg anti-PCMT1 (LifeSpan Biosciences, polyclonal) or normal rabbit IgG (Santa Cruz Biotechnology, Inc.) coupled to DynaBeads at 4° C. for 2 hours. Protein-DNA complexes were recovered with Dynabeads, washed, eluted with elution buffer (1% SDS, 0.1 M $NaHCO_3$), and reverse crosslinked overnight at 65° C. DNA was purified by proteinase K digestion and extracted with Phenol-Chloroform extraction. Aqueous phase was transferred into a fresh tube and the DNA was precipitated with 3 M sodium acetate containing 2 ml glycogen and 4 volumes of ethanol by keeping overnight at −20° C. Genes were amplified using qPCR primers designed as follows: human FOXP3: forward (5'-TGACCAAGGCTTCATCTGTG-3'; SEQ ID NO:23), reverse (5'-GAGGAACTCTGGGAATGTGC-3'; SEQ ID NO:24), human IFNG: forward (5'-CTCTTGGCTGT-TACTGCCAGG-3'; SEQ ID NO:25) and reverse (5'-CTC-CACACTCTTTTGGATGCT-3'; SEQ ID NO:26). Q-PCR was performed in duplicate with 2×SYBR Green qPCR Master Mix (BioTool) using the Mx3000P system (Agilent Technologies). Q-PCR conditions were as follows: 95 C for 1 min, 95 C for 25 s, 62C for 25 s (40 cycles), 95 C for 1 min, 62C for 1 min, and 95 C for 30 s. Relative gene expression was determined using the ΔΔCt method. The results are presented as the fold expression in gene expression normalized to the housekeeping gene β-actin (ACTB) for cells and relative to Tconv+DMSO sample.

Bioinformatics for RNA-Binding Protein Motifs

Splice variants, intron-exon sequences, and 3'UTR sequences were analyzed and obtained from Ensembl. RNA-binding protein motifs for hnRNPL were analyzed via CISBP-RNA database (Ray et al., 2013). Later, 3'UTR sequences were analyzed for hnRNPL-binding sites via RBPmap (Paz et al., 2014).

Bisulfite Sequencing

Sodium bisulfite modification of genomic DNA was carried out using the EZ DNA Methylation Direct Kit (Zymo Research) according to the manufacturer's protocol. Bisulfite-treated DNA was PCR amplified using the following methylation-specific primers via ZymoTaq™ DNA polymerase (Zymo Research): forward primer: 5'-TGTTTGGGGGTAGAGGATTT-3' (SEQ ID NO:27) and reverse primer: 5'-TATCACCCCACCTAAACCAA-3'(SEQ ID NO:34). PCR conditions were followed as: initial denaturation at 950C for 10 min, 40 cycles of denaturation at 950C for 30 sec+annealing at 550C for 40 sec+extension at 720C for 1 min, and final extension at 720C for 7 min. Amplified DNA product was gel purified using GeneJET gel extraction kit (Thermo Scientific) and cloned into µMiniT™ 2.0 cloning vector using NEB PCR Cloning Kit (New England Biolabs, Inc.). Competent cells were transformed with the vector. 10 individual positive bacterial colonies were selected from which recombinant plasmid DNA was purified and sequenced with sanger sequencing (Genewiz).

Statistical Analysis

The results are shown are the mean±SEM; all in vitro experimental replicates were repeated at least three times. All in vivo experimental replicates were repeated in three separate experiments. Unpaired, two-tailed Student's t test using (Prism5; GraphPad Software, San Diego, Calif.) was used for statistical comparison of two groups, with Welch's correction applied when variances were significantly different. Survival benefit was determined using Kaplan-Meier analysis with an applied log-rank test. P values of ≤0.05 were considered significantly different.

Results

Figure 57A:
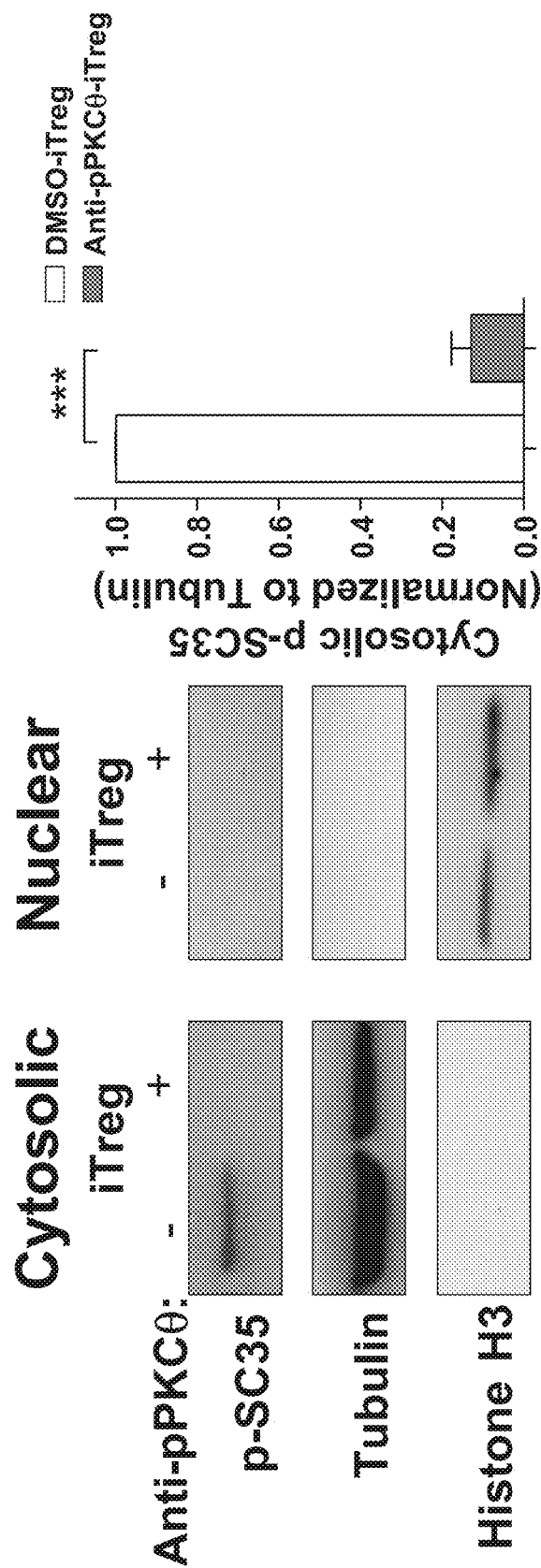
Figure 62A:
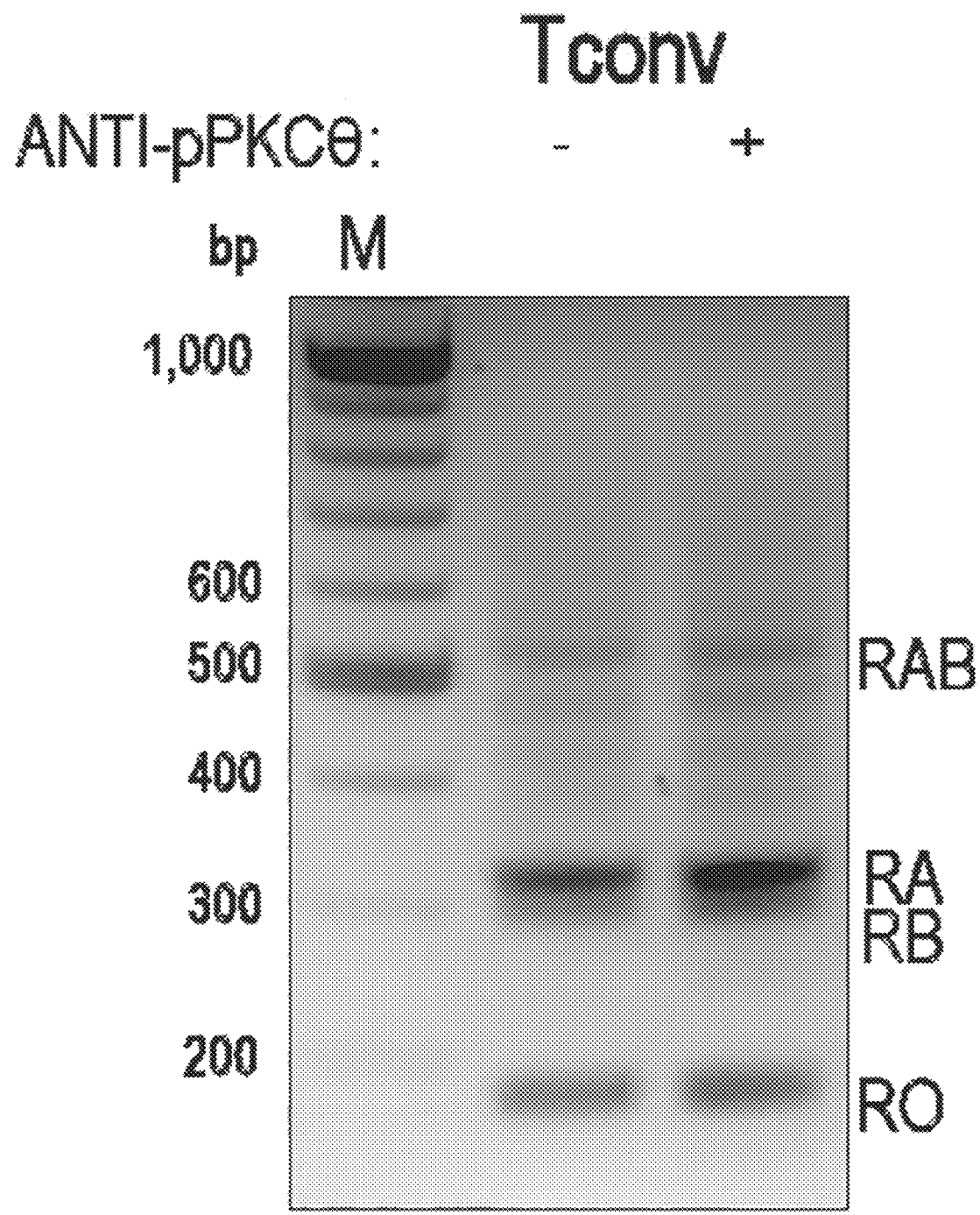

Modulation of Splicing Regulatory Proteins and RNA Processing Following Ex Vivo Anti-pPKCθ Delivery into iTregs PKCθ has been described as a negative regulator of Treg cell differentiation (ref). It has also been linked to the splicing machinery in CD4 T cells, through its demonstrated phosphorylation of the splicing regulator, SC35. Therefore, we sought to determine whether PKCθ may affect iTreg differentiation by modulating regulatory and splicing proteins. We previously showed we could modulate pPKCθ activity, ex vivo, using novel protein transduction domain mimics to efficiently carry a functional antibody across the membrane of human CD4 T cells (Ozay 2016). In this study, we utilized this same approach to probe the function of PKCθ during iTreg differentiation, ex vivo, by culturing human CD4 T cells with (iTreg+anti-pPKCθ) or without (iTreg+DMSO) anti-pPKCθ delivery, prior to polarization (FIG. 62A). As additional controls, we also cultured CD4 T cells (Tconv) with (Tconv+anti-pPKCθ) or without (Tconv+DMSO), anti-pPKCθ delivery for the same length of time, but in the absence of iTreg polarizing conditions. After five days of differentiation, we assessed the cytosolic and nuclear distribution of a panel of splicing and RNA binding proteins, shown to be important during iTreg differentiation, including p-SC35 (FIG. 57A). We observed that pSC35 expression was abrogated in iTregs differentiated with anti-pPKCθ. This was not entirely unexpected, as SC35 has been reported to be a substrate of PKCθ, and loss of pSC35 confirms that anti-pPKCθ delivery attenuates PKCθ activity.

Figure 57B:
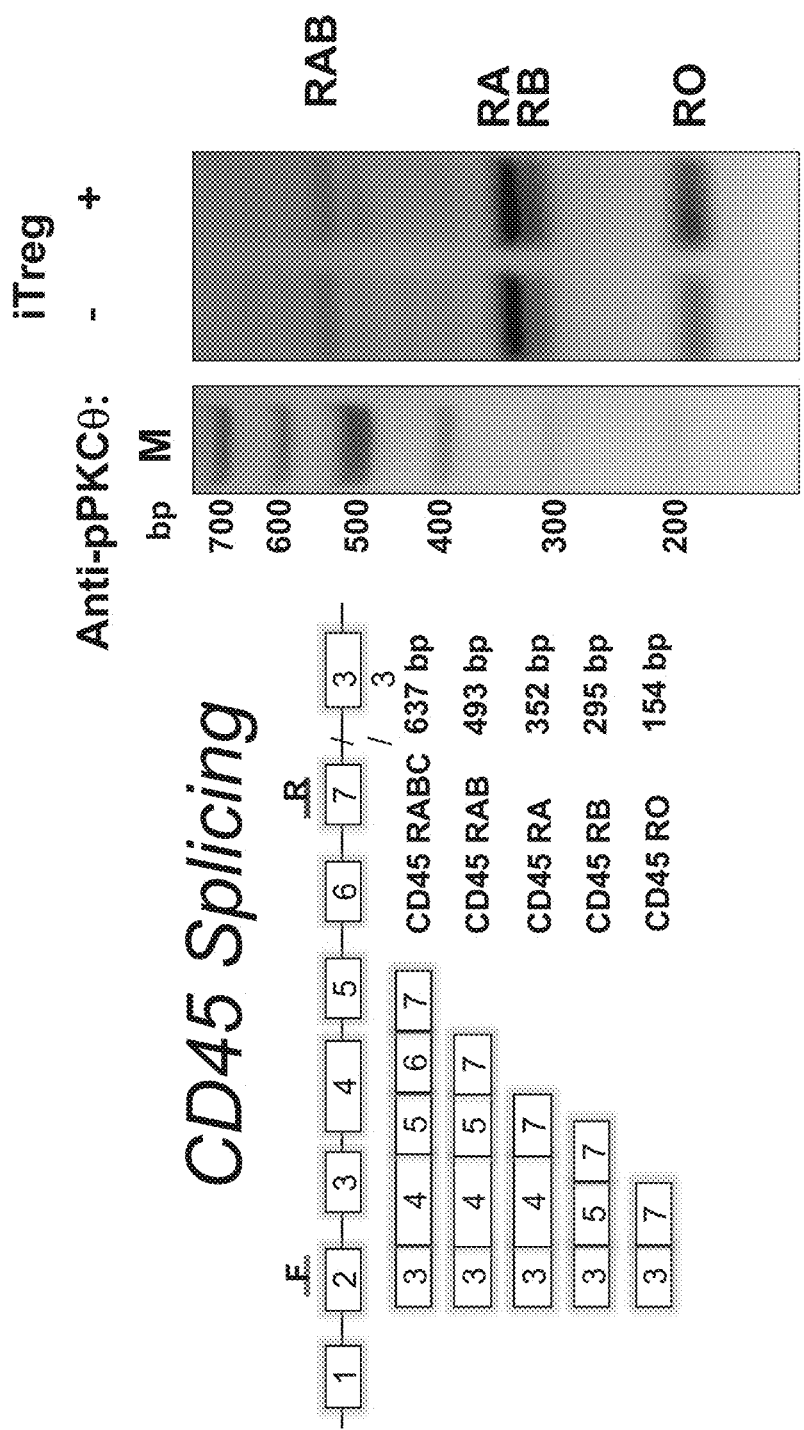
Figure 57D:
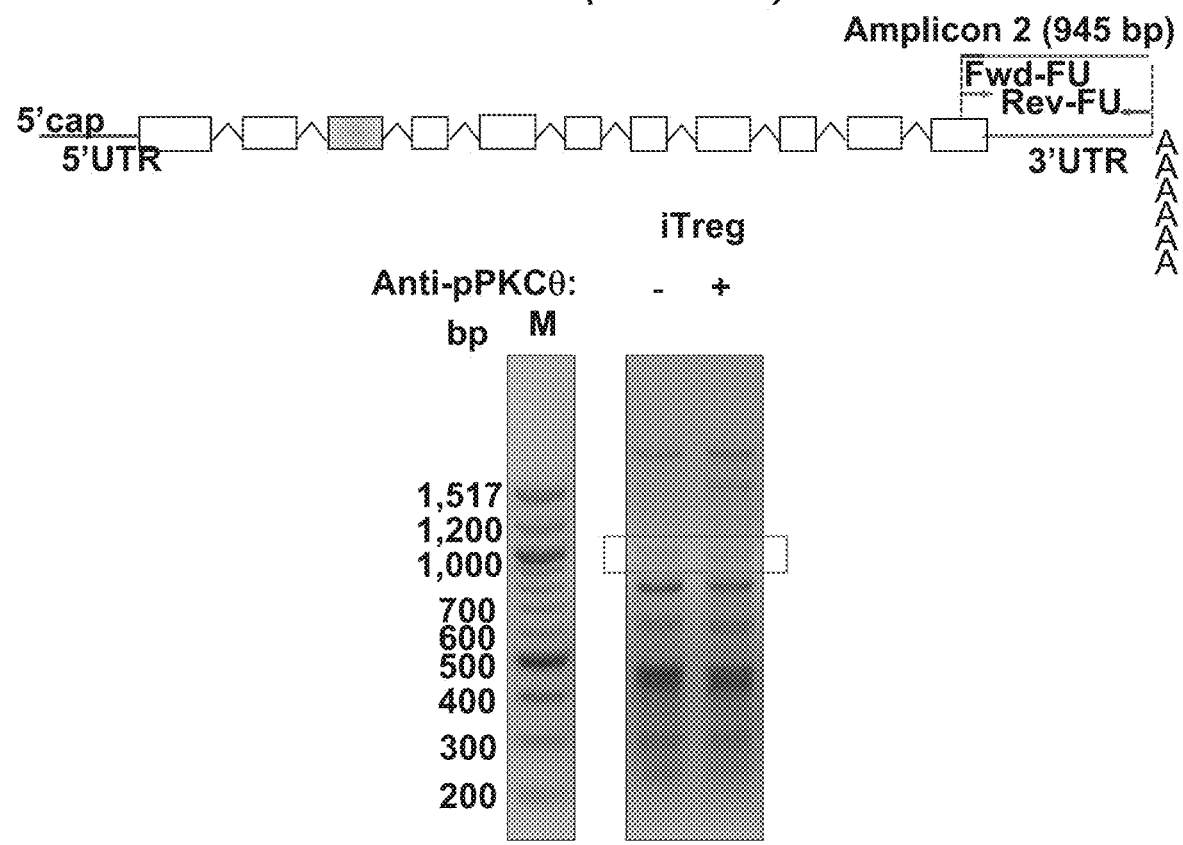
Figure 57E:
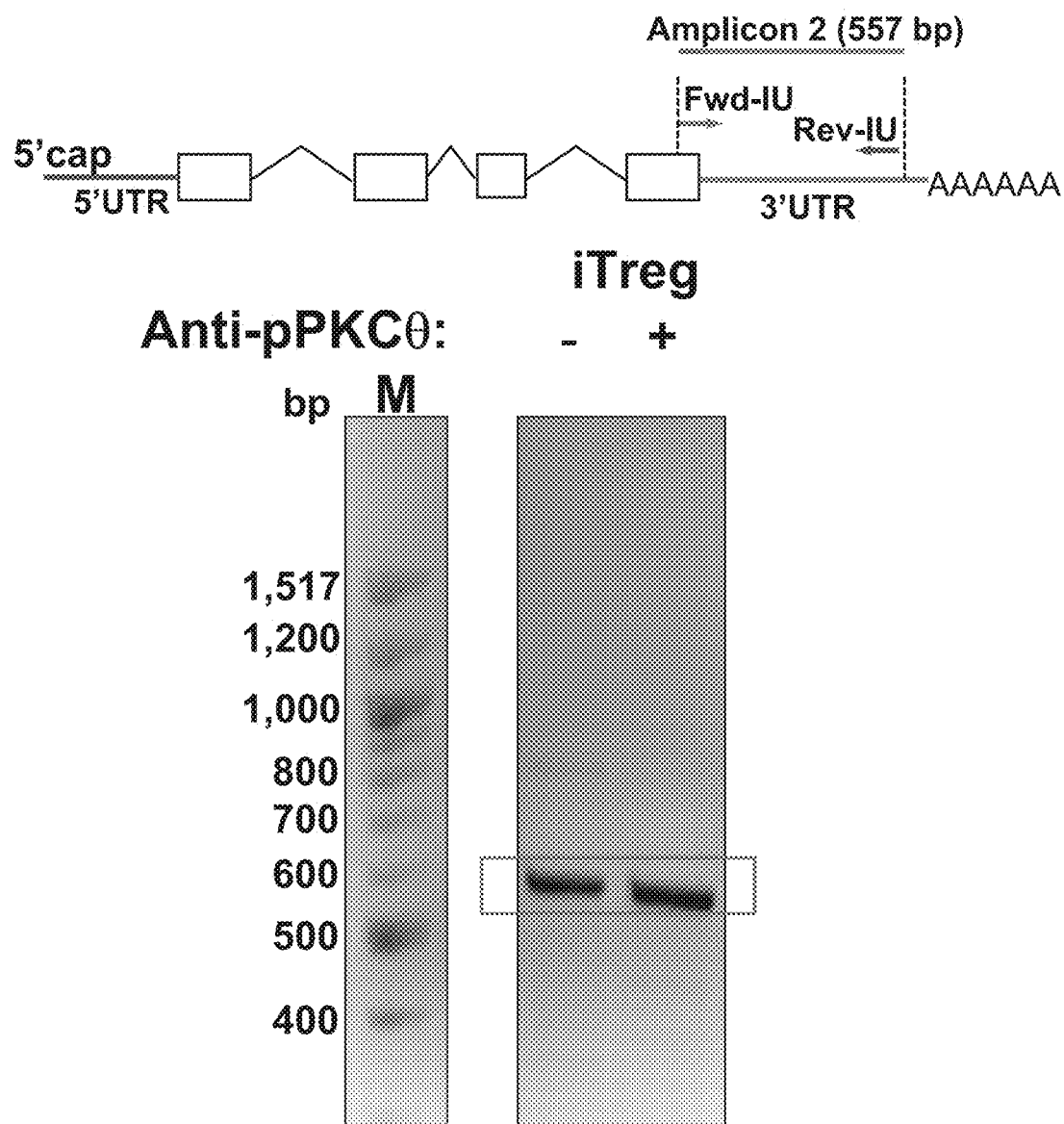
Figure 57F:
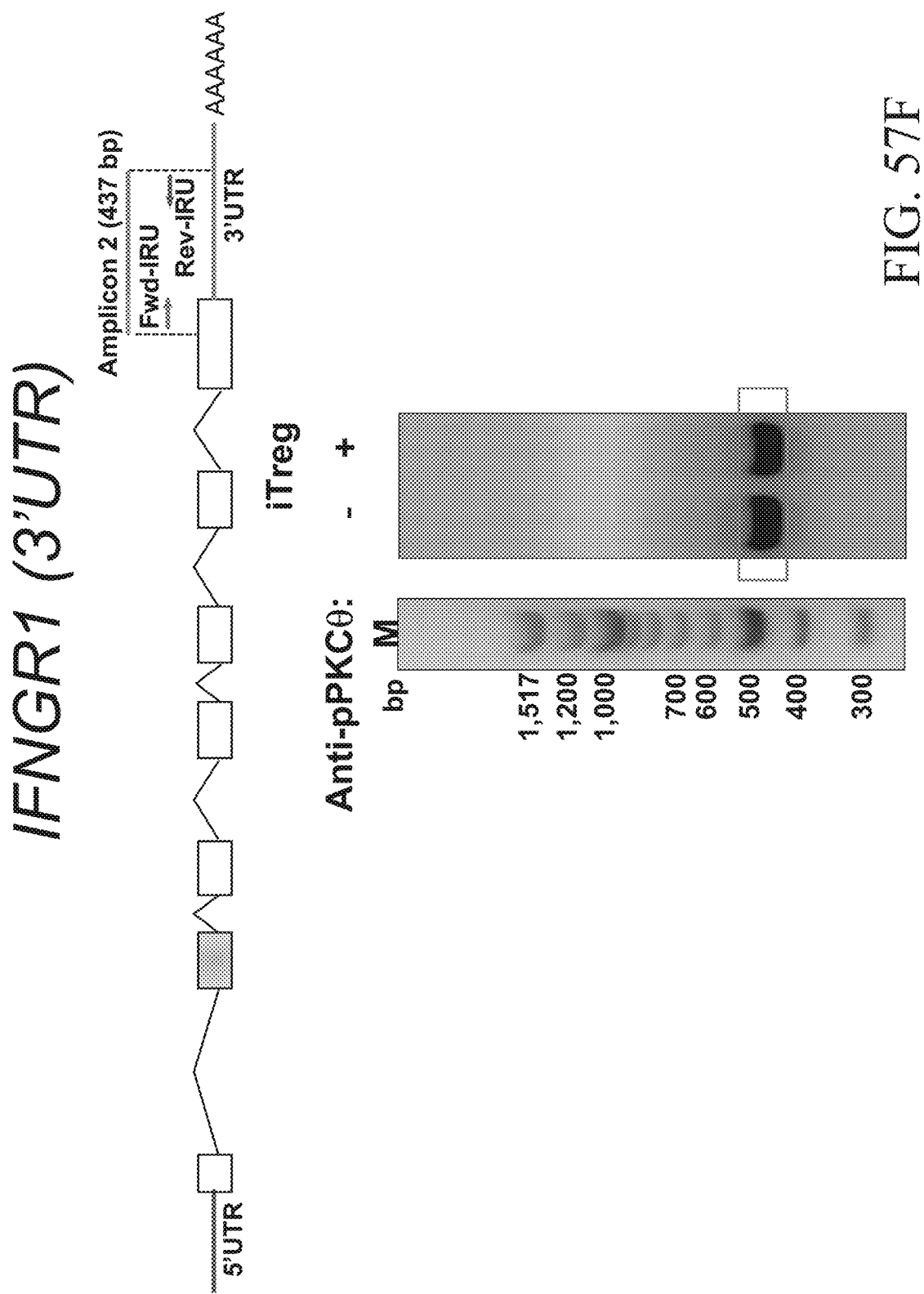
Figure 62B:
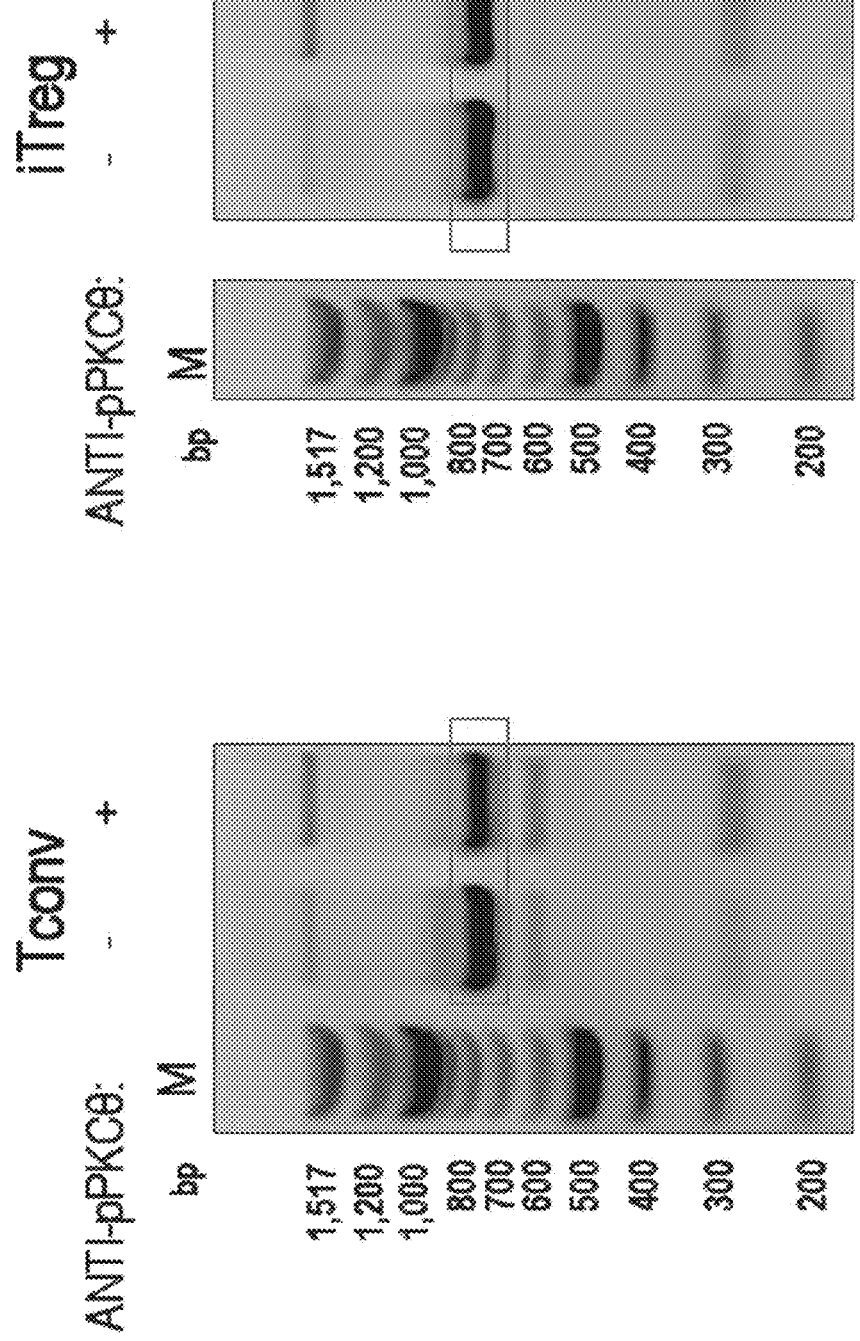
Figure 62D:
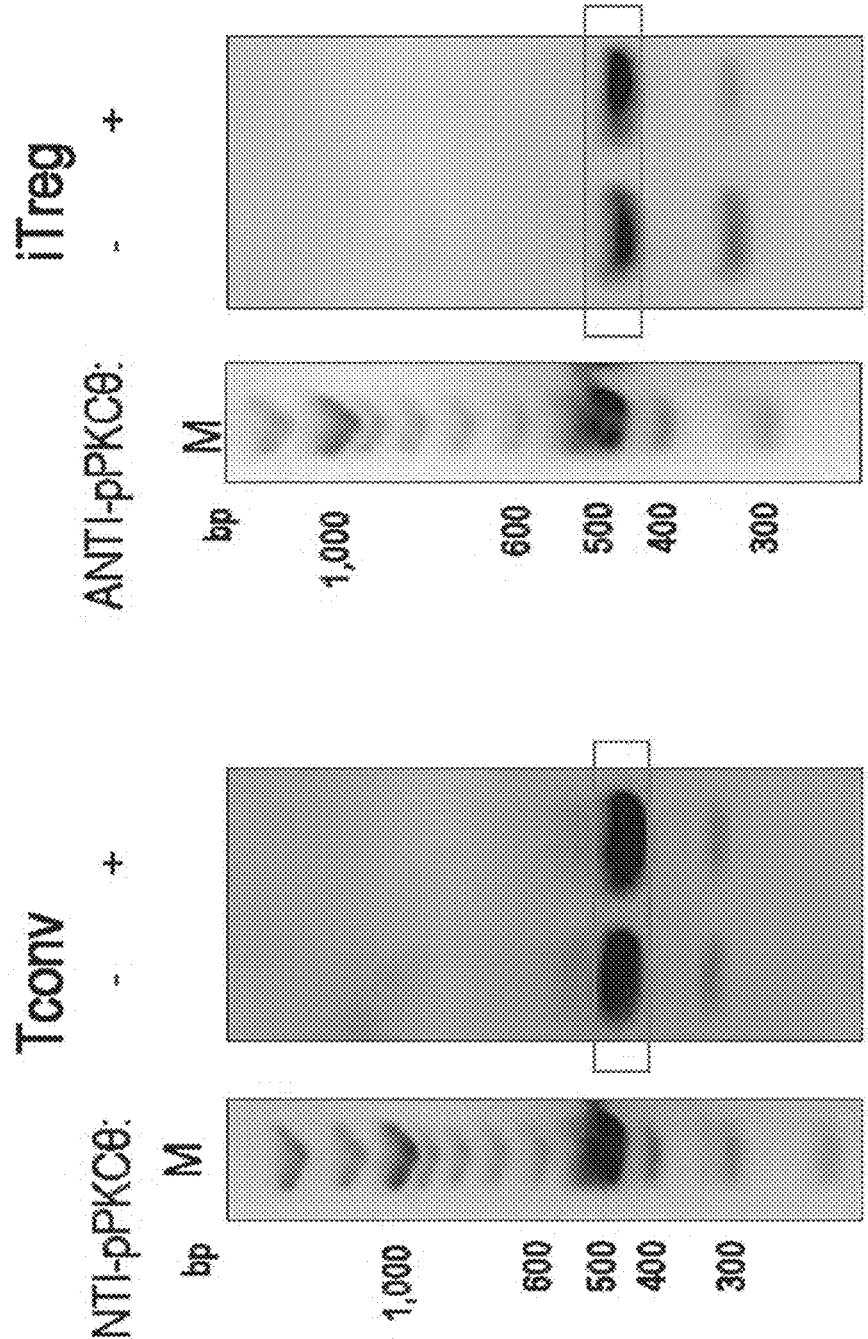
Figure 62H:
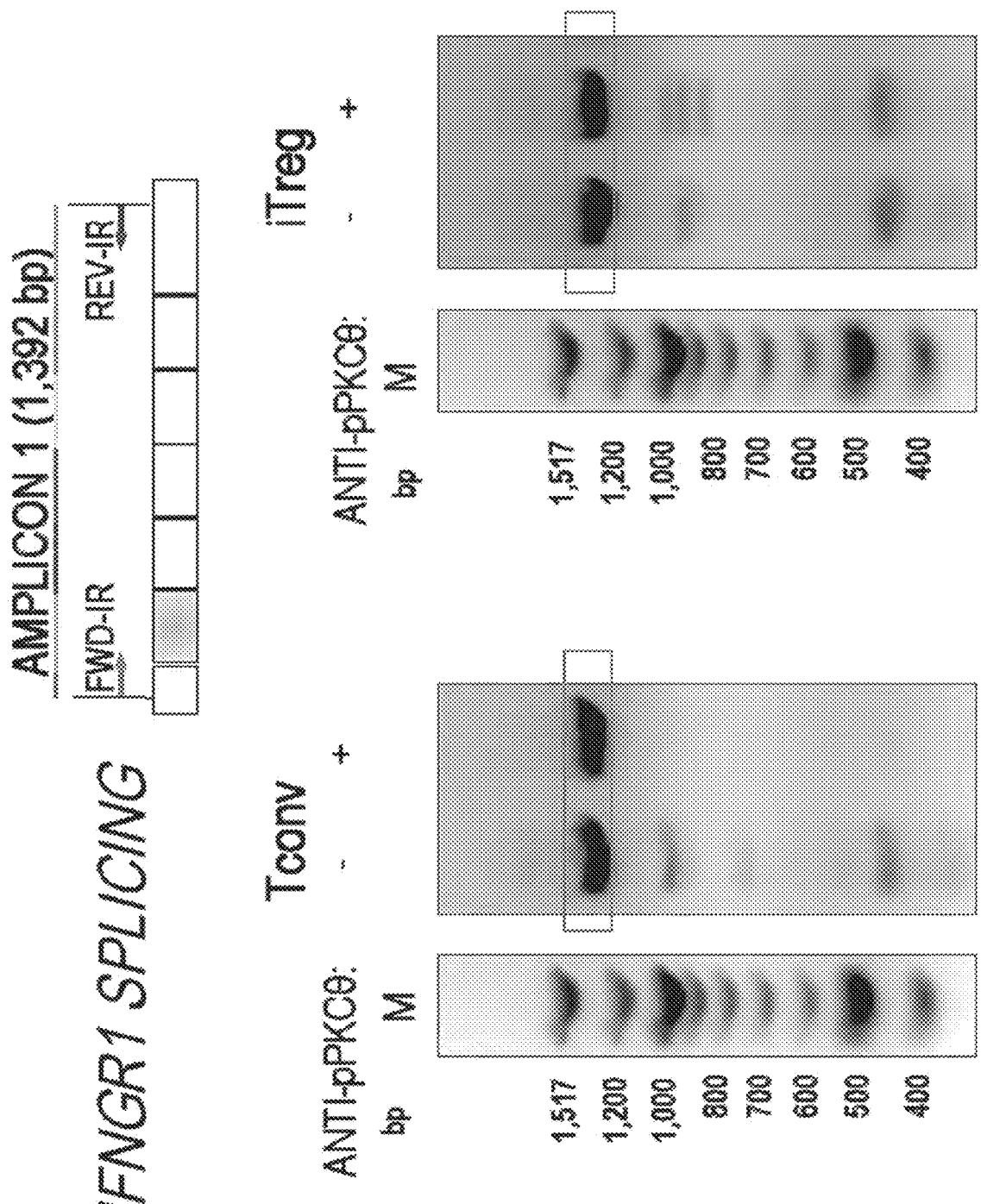
Figure 62F:
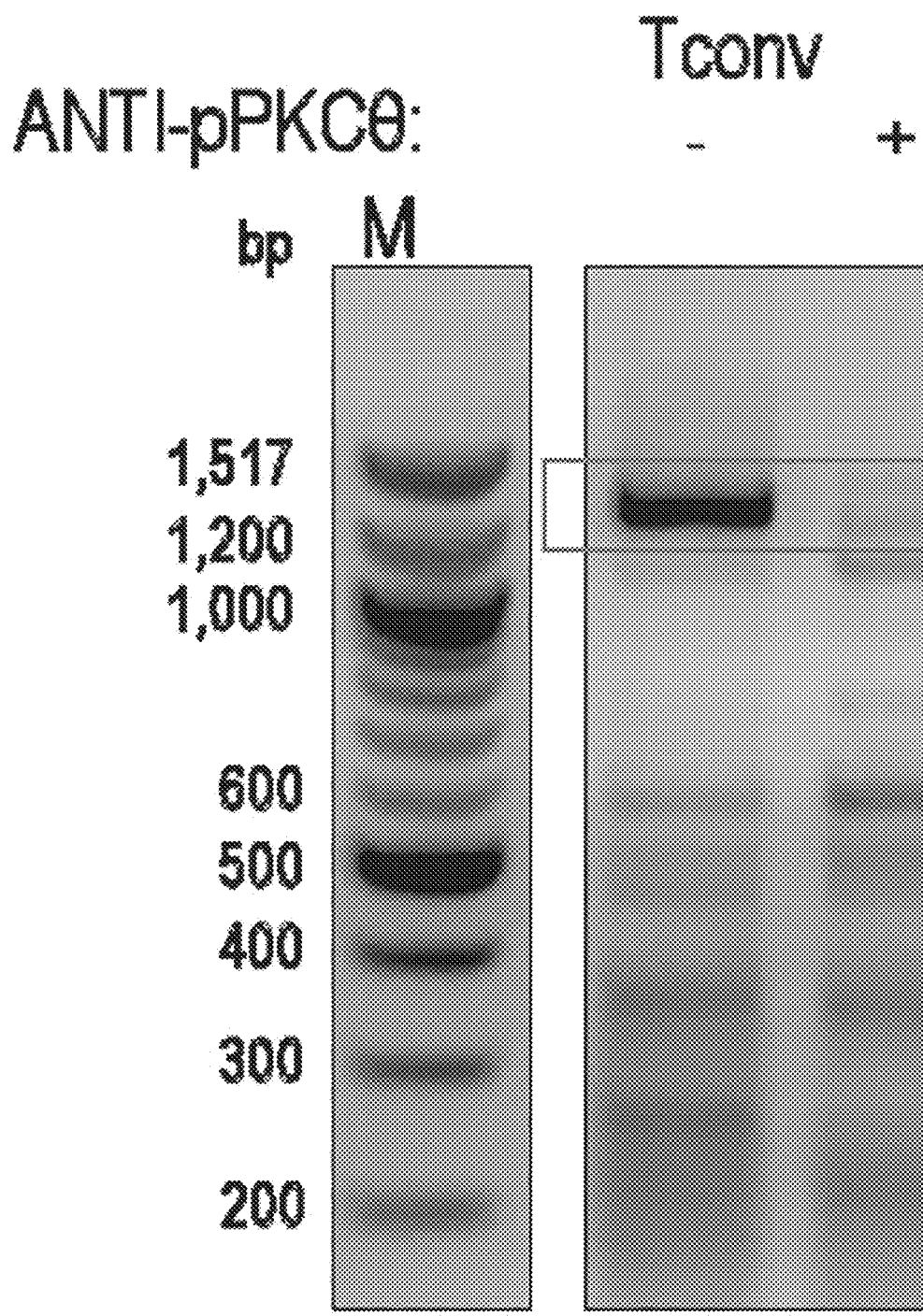
Figure 62G:
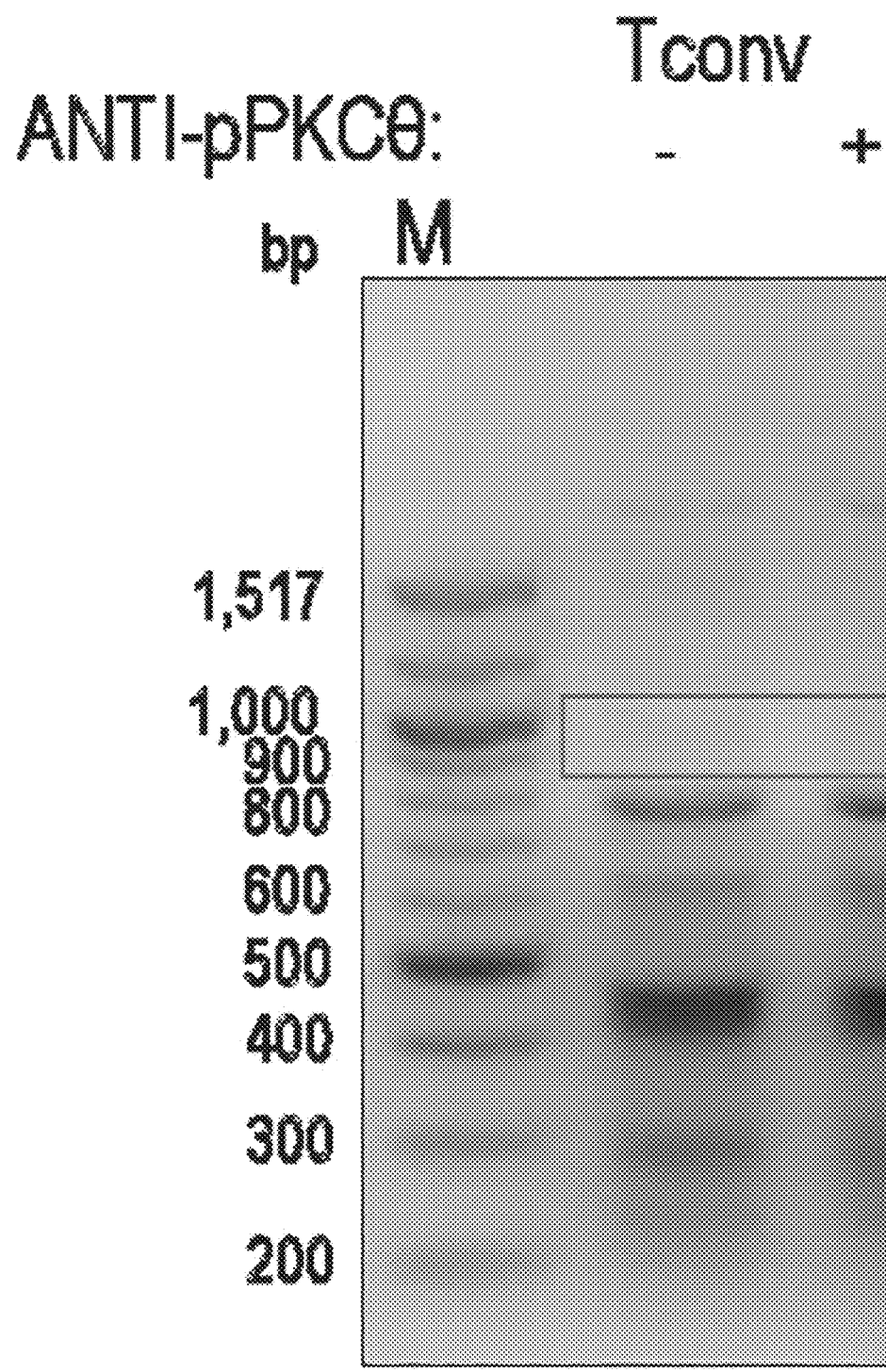
Figure 62H:
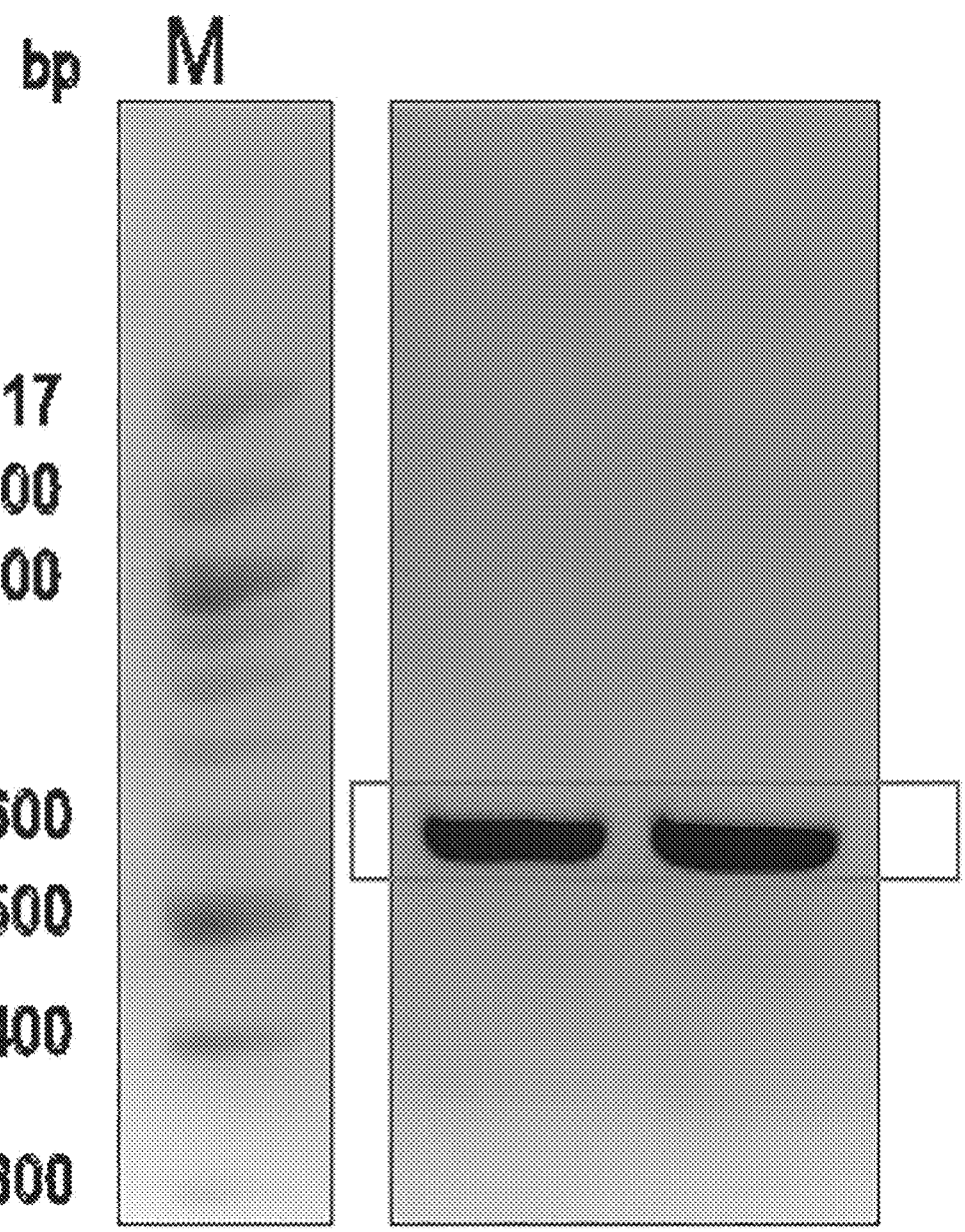
Figure 62I:
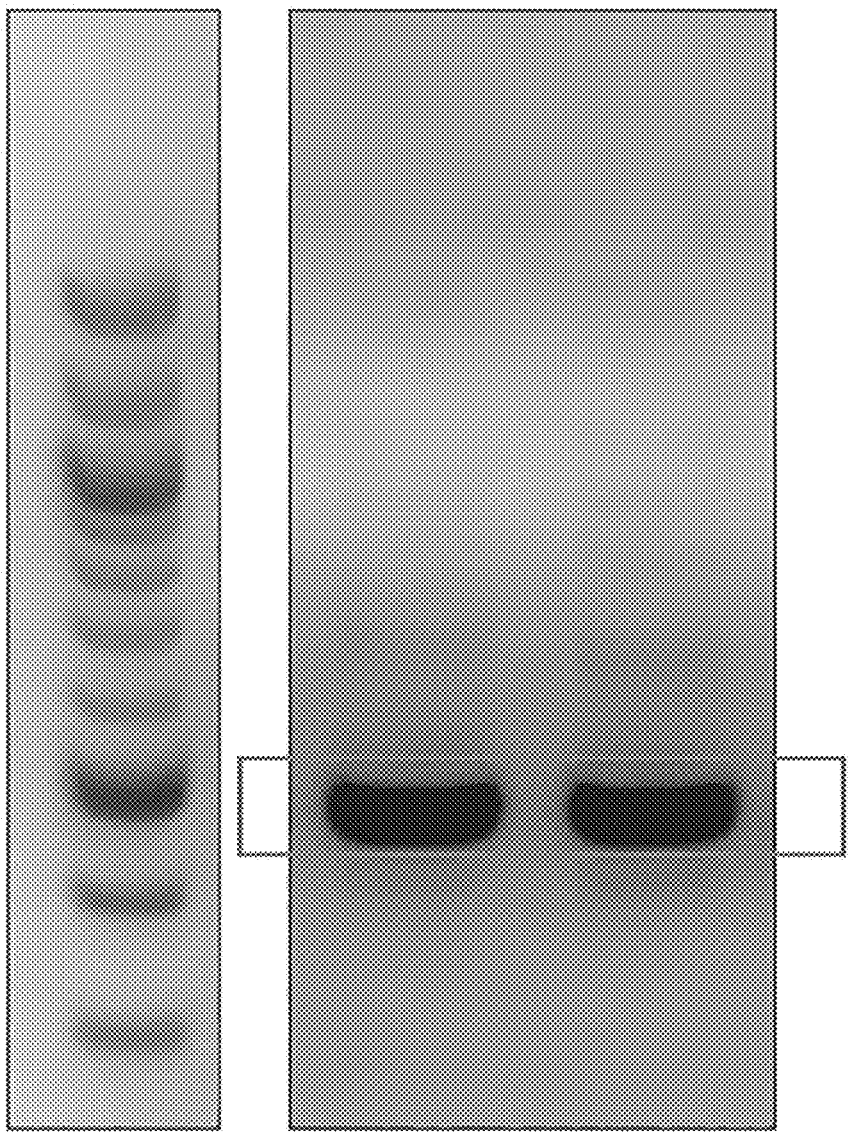

Since the SC35 splicing regulator was affected by anti-pPKCθ delivery to iTregs, we questioned whether there were differences in alternative splicing and 3'UTR processing in key iTreg molecules. The proper generation of 3'UTRs is critical for mRNA stability, since 3'UTRs include recognition motifs for RBPs that may stabilize or destabilize which mRNA through their influences on mRNA degradation and silencing. In addition, shorter 3'UTR lengths are associated with stable mRNA production and increased protein translation in a signal-dependent manner (Gruber et al., 2014). Immune cells recruit specific RBPs to the site of translation and form riboclusters. Arrangement of RBPs on the 3'UTR elements (AU-rich and CA-rich elements) in the riboclusters determine whether mRNA will be translated or directed to nonsense-mediated decay. CD45 splicing is heavily studied in T cells and is regulated by hnRNPL. Therefore, we examined CD45 splicing in iTregs, as a proof of concept. We noted anti-pPKCθ delivery increased RB and RO forms both in Tconvs and iTregs with respect to untreated cells (FIG. 57B, 62B). In a companion study, anti-pPKCθ-treated iTregs showed unique characteristics including higher FOXP3, PD1, and IFNγ expression. Given the fact that FOXP3 and PD1 have been reported to undergo alternative splicing (Nielsen et al., 2005; Ryder et al., 2010; Smith et al., 2006), we were interested in determining whether anti-pPKCθ delivery affected RNA processing of key iTreg genes. We analyzed splicing patterns and 3'UTR lengths of PDCD1, FOXP3, IFNG, and IFNGR1. Conventional mRNAs for those genes consist of: exon 1-2-3-4-5 (PDCD1), exon 2-3-4-5 (FOXP3), 4 exons (IFNG), and 7 exons (IFNGR1). We observed similar splicing patterns for all four genes in iTregs with or without anti-pPKCθ treatment (FIG. 62B-E). Anti-pPKCθ delivery into Tconvs resulted in similar spliced forms, except for FOXP3 mRNA, which showed a truncated sequence following anti-pPKCθ treatment (FIG. 62-1c). Interestingly, anti-pPKCθ delivery affected 3'UTR processing in a gene-specific manner. When we evaluated these four genes in iTregs, we noted PDCD1 mRNA variants with markedly shorter 3'UTR lengths following anti-pPKCθ treatment compared, to untreated cells (FIG. 57C), while FOXP3, IFNG, and IFNGR1 3'UTR lengths did not change after the treatment (FIG. 57D-F). Expression of a shorter 3'UTR sequence in PDCD1, is consistent with increased expression of surface PD-1 observed on iTregs differentiated following anti-pPKCθ delivery. Collectively, these results indicate that PKCθ modulates splicing regulators and RNA processing in a cell- and gene-specific context.

Figure 58A:
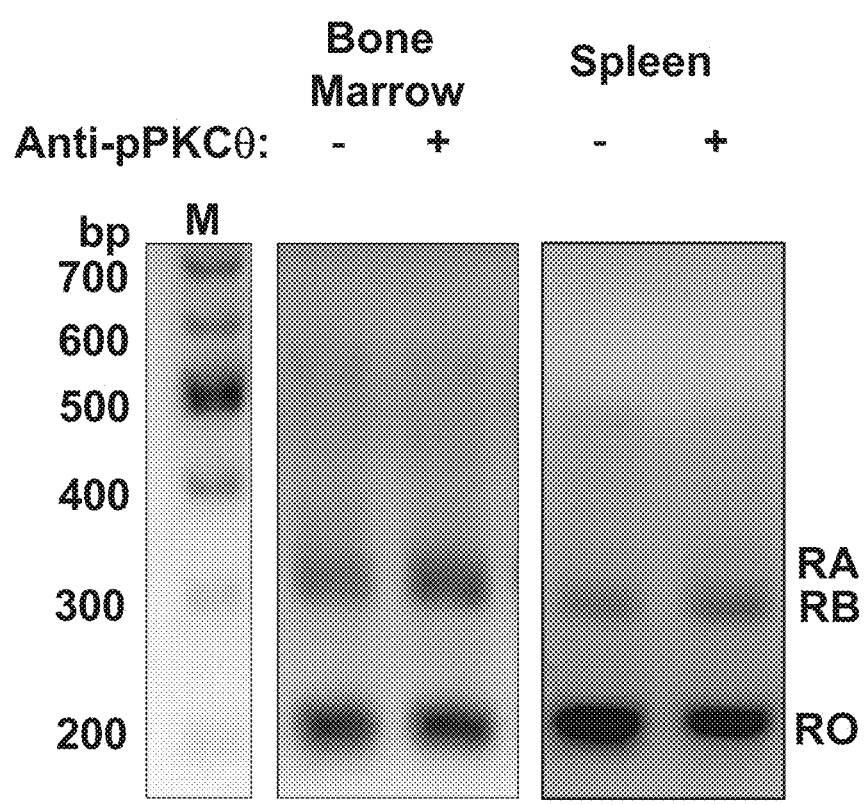
Figure 58B:
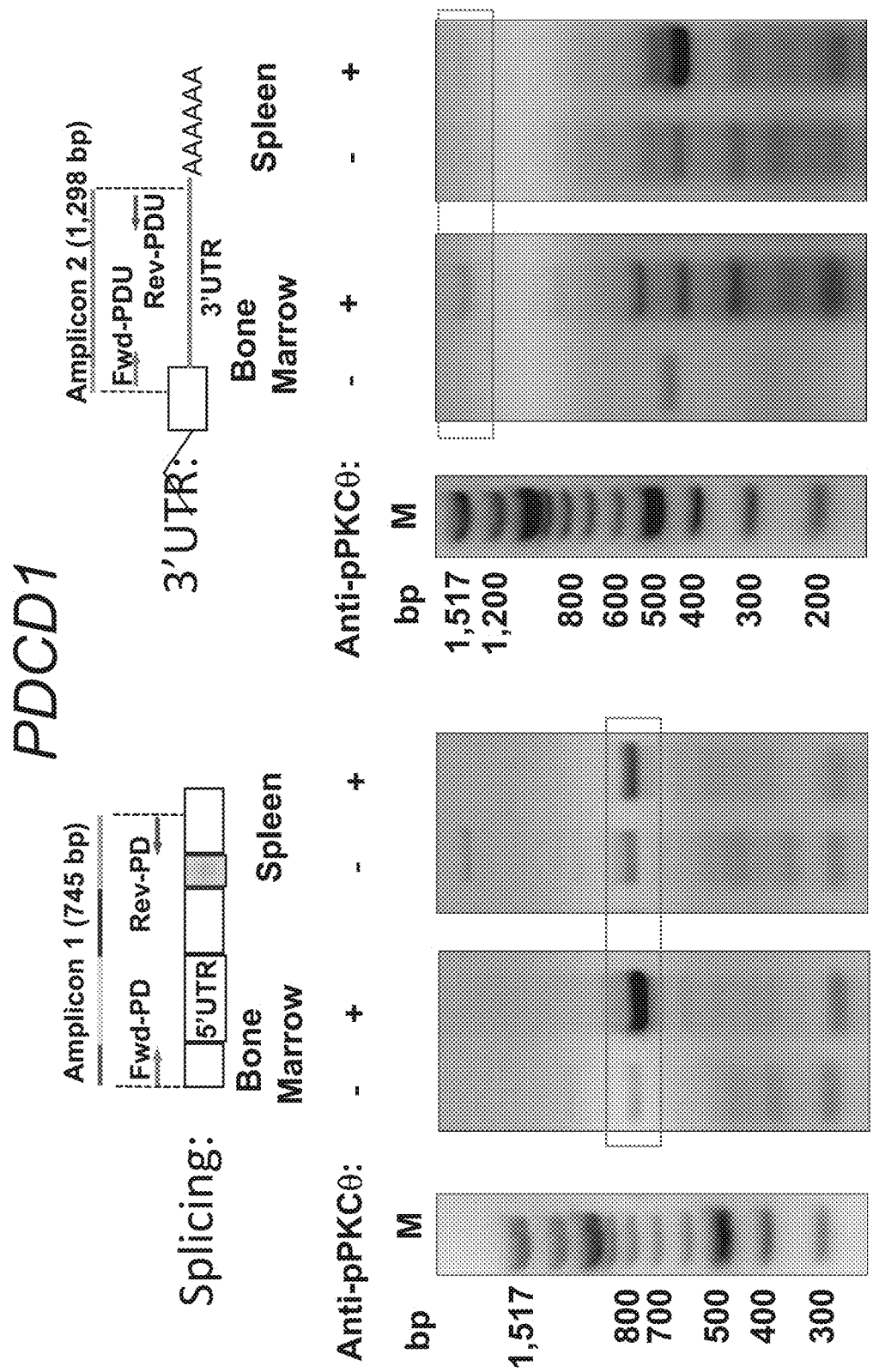
Figure 58C:
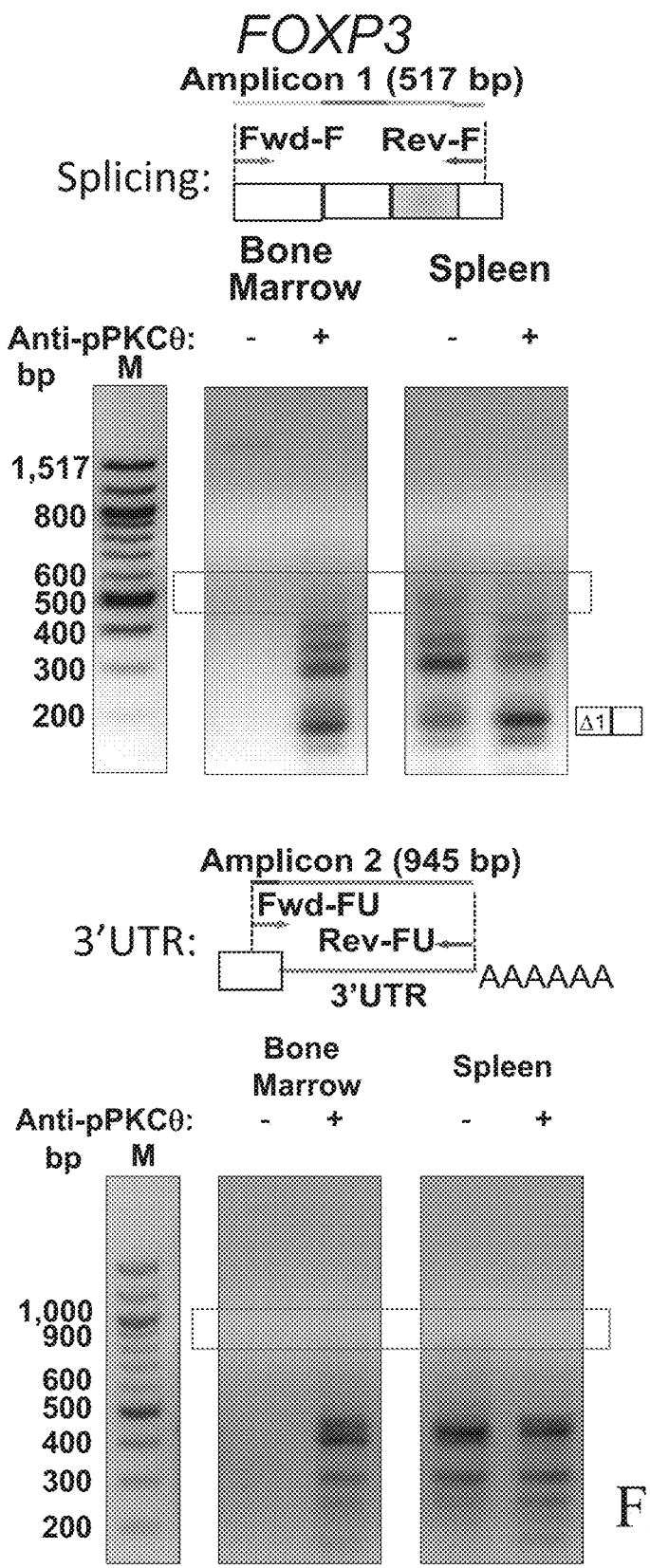
Figure 63A:
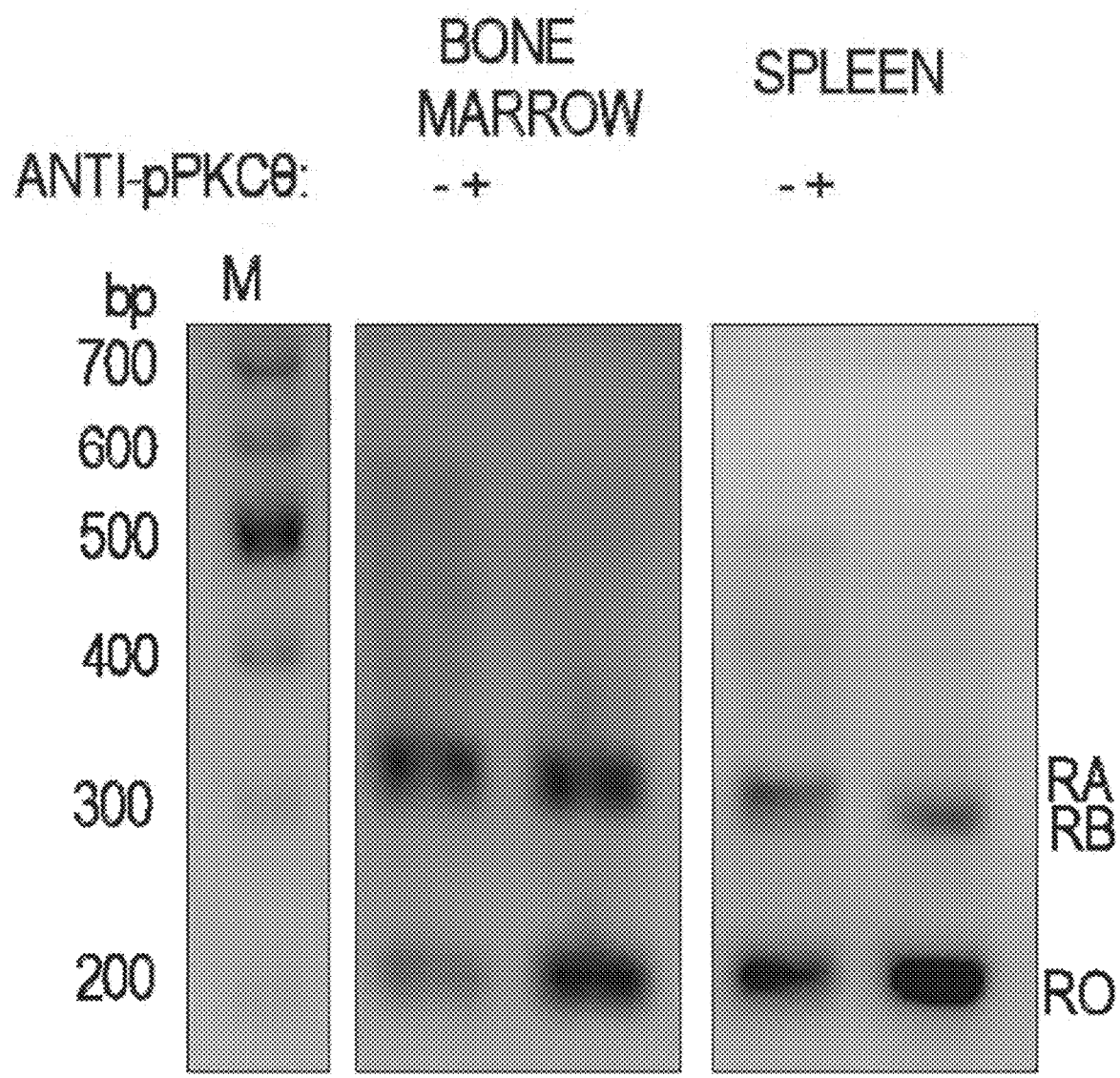
Figures 63B, 63C:
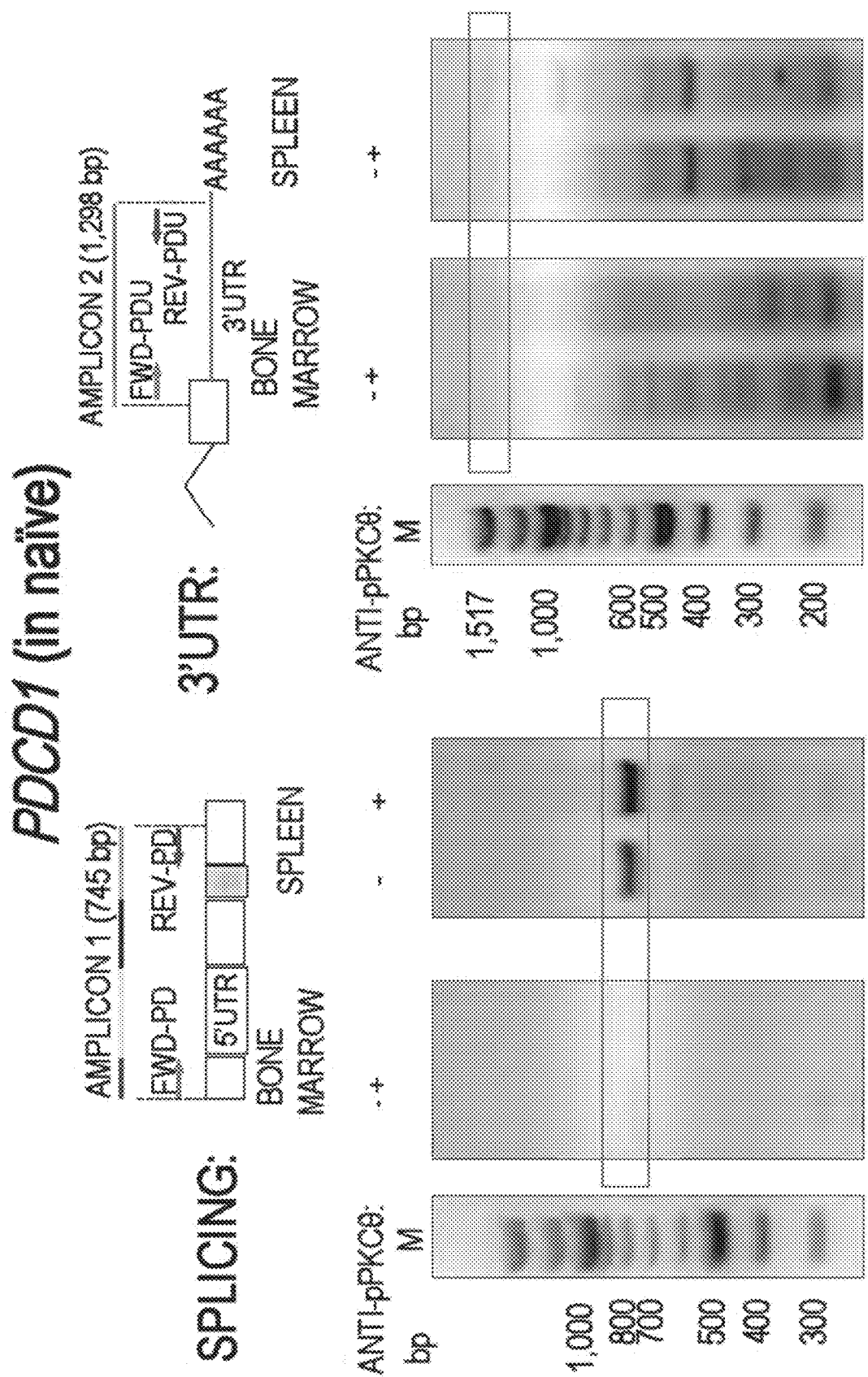
Figure 63F:
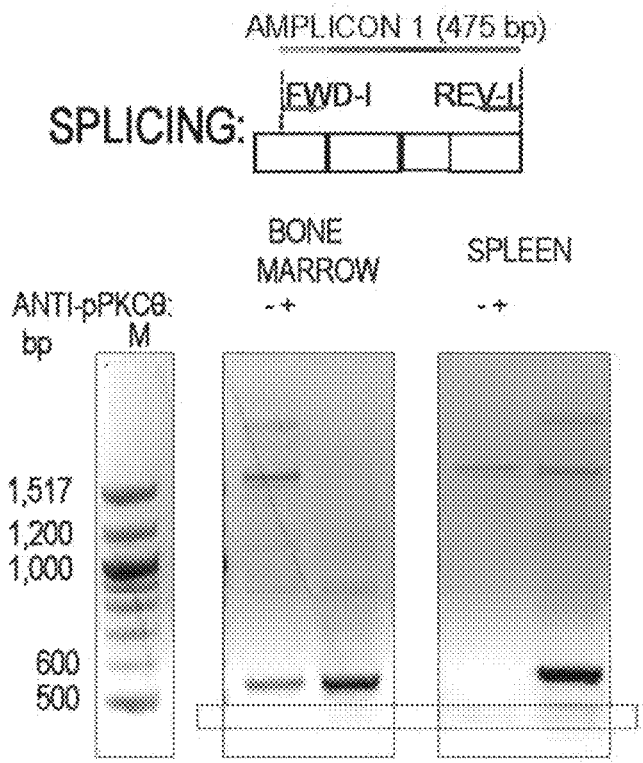
Figure 63G:
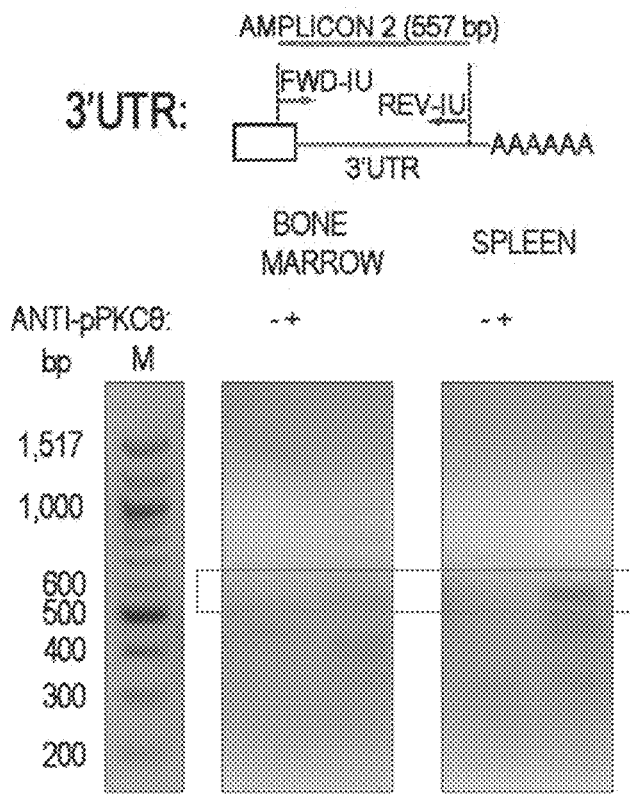
Figure 63H:
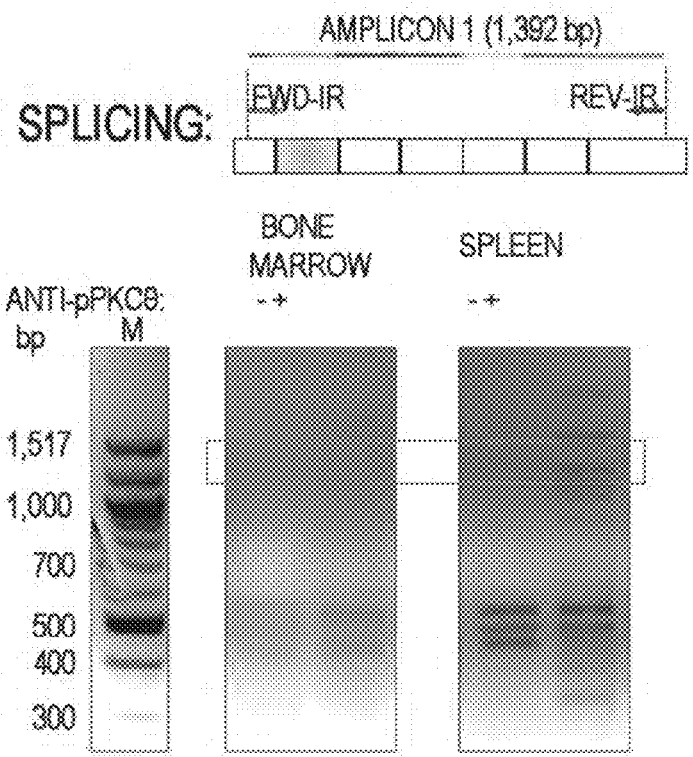
Figure 63I:
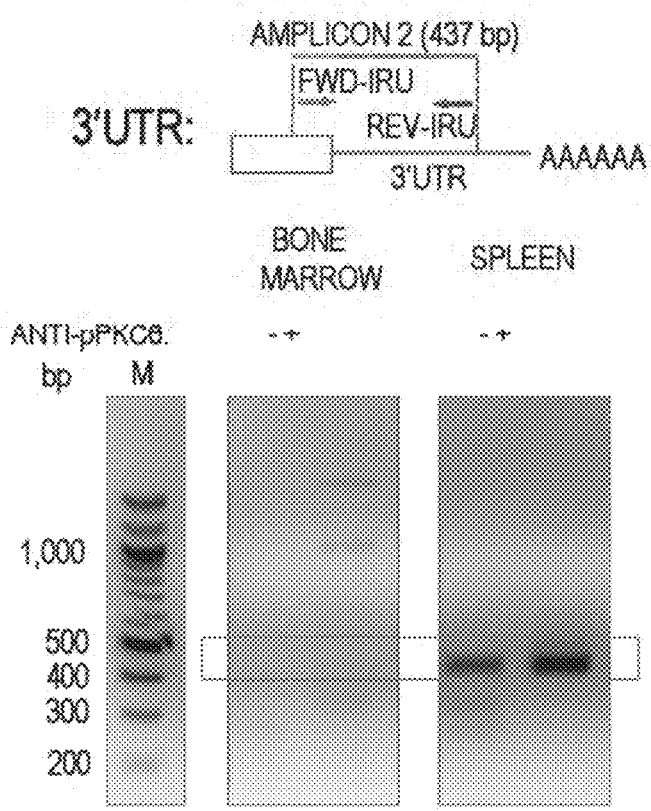

In Vivo Durability of Tissue-, Cell-, and Gene-Specific Modulation of RNA Processing in Ex Vivo-Treated iTregs While we noted increases in CD45RB and CD45RO expression in iTregs differentiated following ex vivo anti-pPKCθ delivery, we did not observe robust differences in alternative splicing of PDCD1, FOXP3, IFNG or IFNGR1. However, iTregs can behave differently in vivo due to their differential trafficking and exposure to cytokines. Furthermore, reports suggest these, and other, influences may prime Tregs to further impact alternative splicing in response to external signals. We sought to address this possibility by analyzing the expression of PDCD1, FOXP3, IFNG, and IFNGR1 in iTregs isolated from the bone marrow (BM) and spleen of mice, using a humanized model of graft-vs-host disease (GvHD). In this pre-clinical model, lethal GvHD results from acute BM-infiltration of destructive immune cells, approximately three weeks after human peripheral blood mononuclear cells are transferred into lightly irradiated NOD.Cg-Prkdc$^{scid}$ Il2rg$^{tm1Wjl}$/SzJ (NSG) mice. In our parallel study, we determined that administering anti-pPKCθ-treated iTregs, at the time of disease induction, were highly efficacious in preventing GvHD. We detected high numbers of anti-pPKCθ-treated iTregs in the BM at the peak day of the disease (day 17) and these exhibited a unique and stable gene expression pattern. To determine whether alternate RNA processing leads to formation of more stable mRNA variants in these iTregs, we adoptively transferred anti-pPKCθ-treated iTregs into humanized GvHD mice on the day of GvHD induction and analyzed RNA processing in iTregs on day +17. We used magnetic beads to sort cells from BM and spleen based on their CD4, CD25, and CD127 expression. Compared to untreated iTregs, we found that CD45 splicing was highly affected in CD4$^+$CD25$^{hi}$CD127$^-$ iTregs that migrated to the BM, but not those entering the spleen, following anti-pPKCθ treatment (FIG. 58A, FIG. 63B). When we analyzed naïve T cells, we found they expressed similar patterns of CD45 splice variants in both tissues, regardless of iTreg treatment (FIG. 63A). These data suggest that ex vivo anti-pPKCθ delivery into iTregs conveys durable alterations in CD45 splicing and are iTreg-specific. When we further assessed iTregs recovered from the BM and spleens of diseased mice, we found that in anti-pPKCθ treated iTregs, PDCD1 and FOXP3, both, displayed differences mRNA expression. PDCD1 transcript expression was increased both in BM- and spleen-infiltrating anti-pPKCθ treated iTregs, and showed extensive editing in 3'UTR length, suggesting that more stable transcripts are generated in these cells (FIG. 58B). Intriguingly, the expression pattern of FOXP3 splice variants in anti-pPKCθ-treated iTregs recovered from the BM was completely different from those of untreated iTregs (FIG. 58C). By comparison, we did not detect pronounced differences in splice variants expressed in untreated and anti-pPKCθ-treated iTregs, or isolated from spleens of diseased mice (FIG. 58B, C), or in naïve T cells isolated from either tissue (FIG. 63B-E). Furthermore, we were unable to amplify FOXP3 expression using primers spanning 3'UTR in untreated iTregs in the bone marrow, suggesting that FOXP3 mRNA is highly unstable in these iTregs (FIG. 58C).

Consistent with the alterations in PDCD1 and FOXP3 that we observed to be unique to BM-infiltrating anti-pPKCθ-treated iTregs, we also noted distinct and exclusive mRNA splicing and 3'UTR editing of IFNG and IFNGR1 in these cells as well (FIG. 58D, E). IFNG and IFNGR1 mRNA splice variants were amplified in all iTregs recovered from spleens (FIG. 58D, E). We discovered that the naïve T cells recovered from BM and spleens also showed some treatment-specific differences. Specifically, in naïve T cells, we could amplify stable FOXP3 mRNA variants isolated from BM and spleen (FIG. 63C), but we could only detect stable PDCD1 in naïve T cells from spleens (FIG. 63B). Additionally, although we detected IFNG mRNA splice variants in naïve T cells in BM (FIG. 63D), they were lacking IFNGR1 mRNA, due to differential 3'UTR editing (FIG. 63E). This raises the intriguing prospect that anti-pPKCθ-treated iTregs exert a cell-extrinsic effect on naïve T cells in the BM, that makes them refractory to the effects of IFNγ signaling, although further experimentation is needed to test this possibility. Altogether, these data suggest that alternative splicing and 3'UTR shortening, both, of key iTreg genes were selectively modulated in anti-pPKCθ iTregs, during in vivo immune responses, and this occurred in a tissue-, cell-, and gene-specific fashion.

Post-Translational and Post-Transcriptional Regulation of PCMT1 in iTregs

The protein repair enzyme, protein L-isoaspartate (D-aspartate) methyltransferase (PCMT1), repairs damaged proteins by methylating the carboxyl group of L-isoaspartate or D-aspartyl residues (Misra et al., 2002). Additionally, PCMT1 regulates critical cellular processes such as RNA maturation, stability, export, histone homeostasis, and post-translational control (Enunlu et al., 2003; Yang et al., 2013; Dufu et al., 2010; MacKay et al., 2012). PCMT1 also shares many similarities with two other methyltransferases shown to methylate proteins and RNA: S-adenosylmethionine-dependent protein arginine methyltransferase (PRMT) and PRIP-interacting protein with methyltransferase domain (PIMT), respectively.

Proteomic studies showed that the absence of PCMT1 diminishes the amount of two crucial RNA regulators, poly(rC)-binding protein 2 (PCBP2) involved in mRNA stability and DX39B involved in mRNA export to the cytoplasm, in the whole proteome (Yang et al., 2013). Moreover, PCMT1 is a part of the TREX mRNA export complex and interacts with several key RNA binding proteins such as hnRNPU, hnRNPD, hnRNPA2, and hnRNPM (Dufu et al., 2010). We hypothesized that PCMT1 regulates splicing regulatory proteins and, thus, affected alternative splicing, RNA maturation, stability, and export in iTregs. Therefore, we investigated PCMT1 regulation in the context of iTreg differentiation with and without anti-pPKCθ delivery.

Figure 59A:
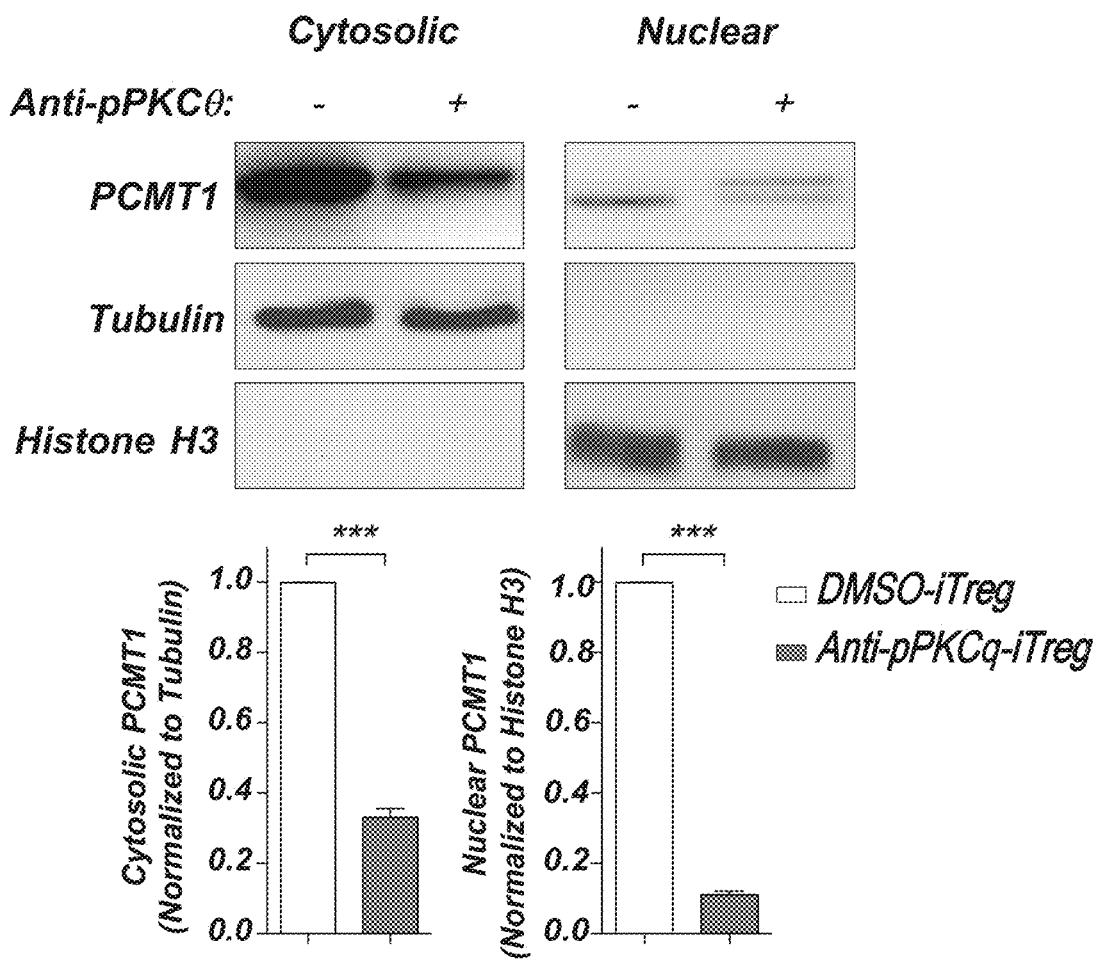
Figure 59B:
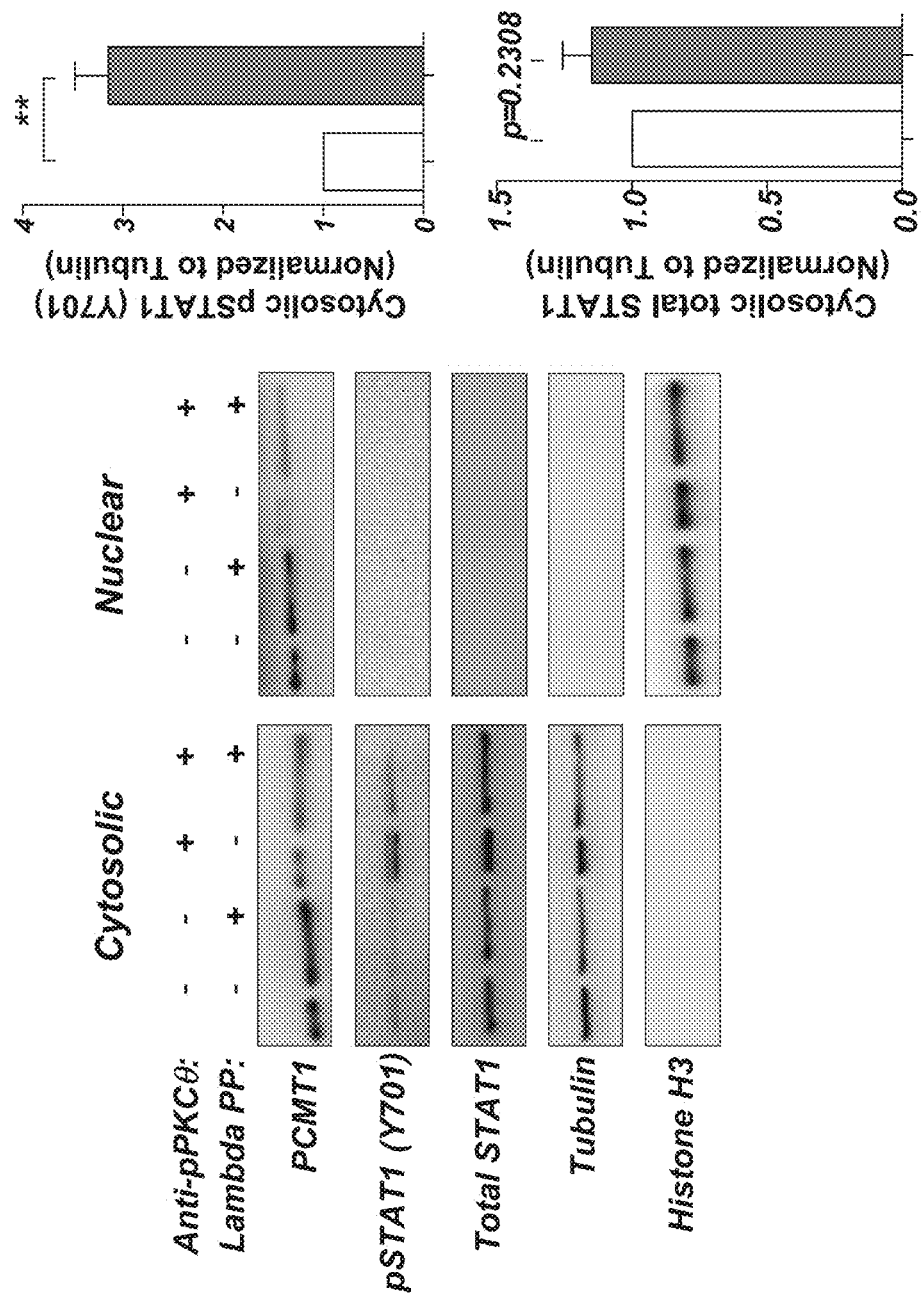
Figure 59C:
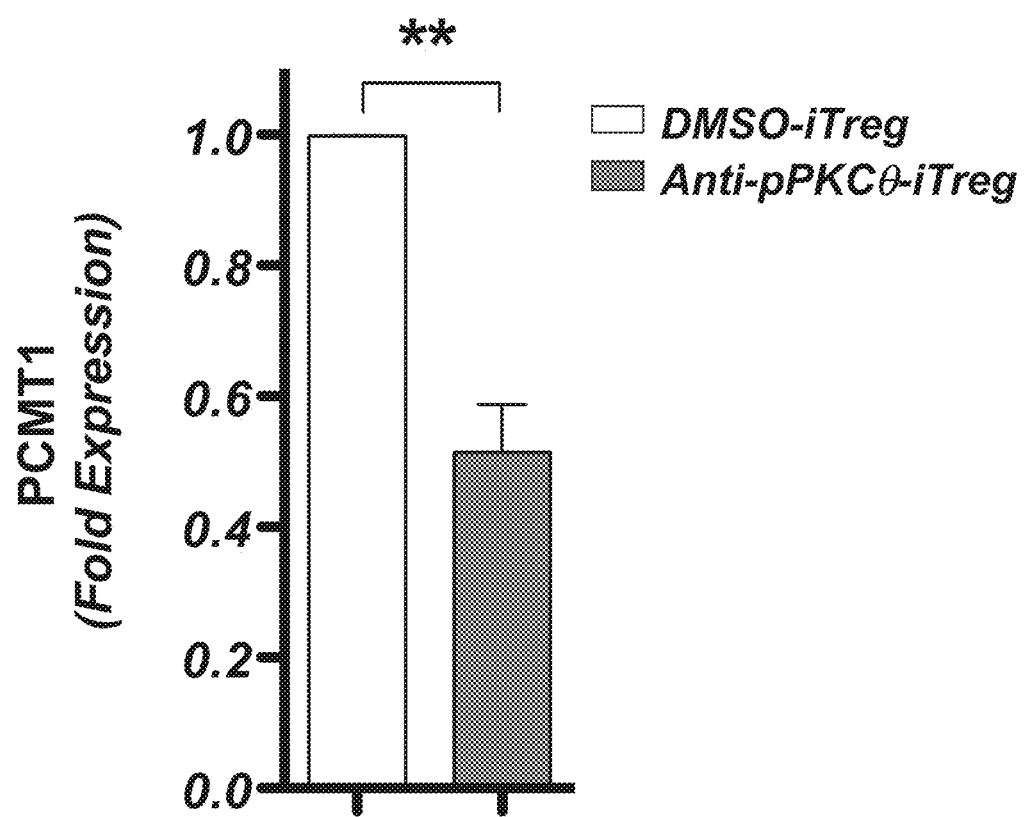
Figure 64A:
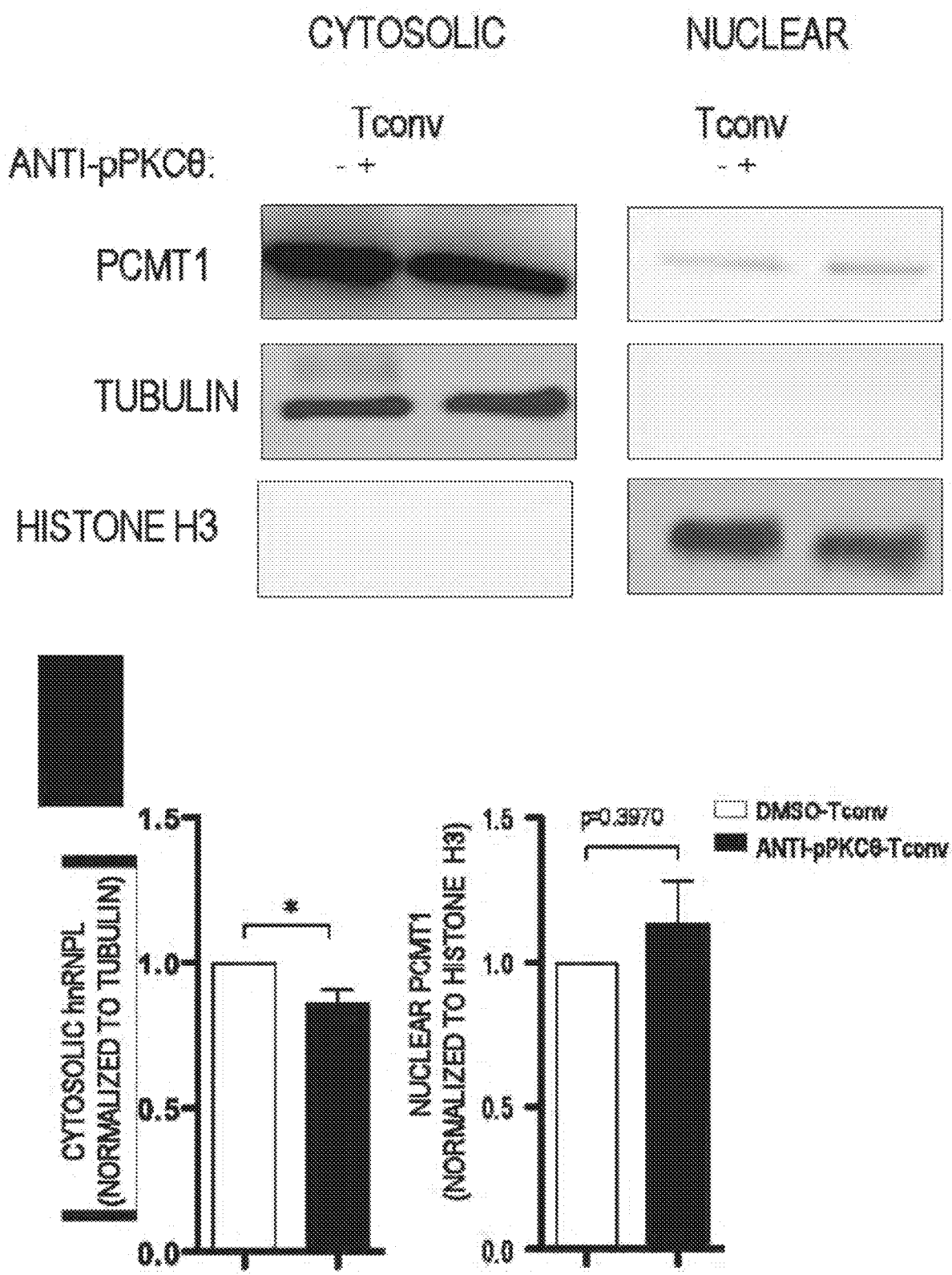
Figure 64B:
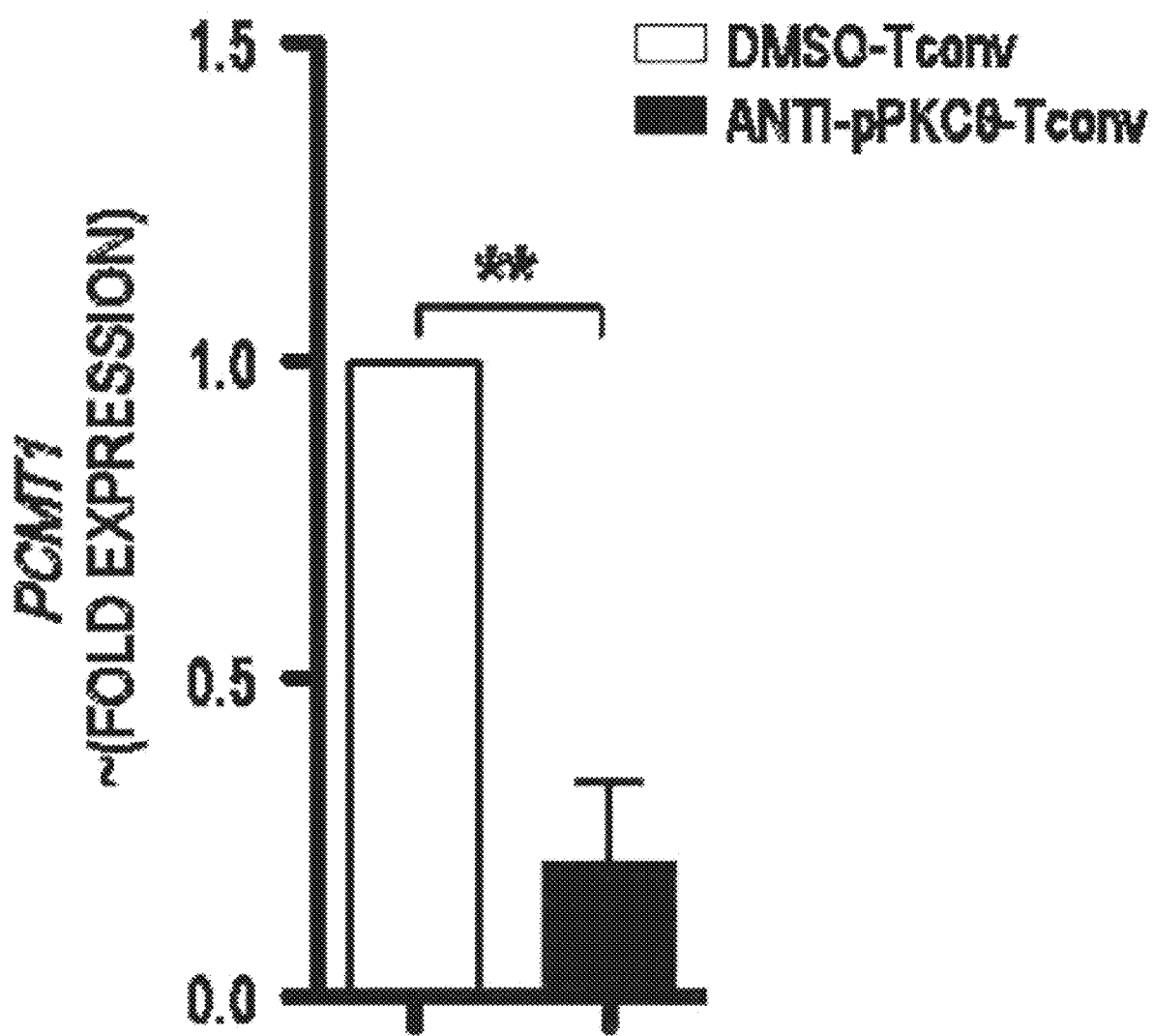

PCMT1 was expressed at high levels in the cytosol but we could also detect it in the nucleus of iTregs (FIG. 59A). Following anti-pPKC delivery, cytosolic and nuclear PCMT1 protein levels, both, were significantly diminished (FIG. 59A). This observation was accompanied by a downward trend in its gene expression (FIG. 59C), although this did not reach statistical significance. We also noted that PCMT1 downregulation, following anti-pPKCθ treatment, in Tconvs as supported by qPCR and immunoblotting results (FIG. 64A, B). Interestingly, we detected two separate PCMT1 bands in the nuclear lysates of iTregs treated with anti-pPKCθ, raising the possibility of nuclear PCMT1 phosphorylation (FIG. 59B). We generated additional cytosolic and nuclear samples, and treated half of each sample with lambda phosphatase, to determine the whether the upper band represented phosphorylated PCMT1. We also included pSTAT1 (Y701) as an internal control, as it is also associated with iTreg function. We observed that pSTAT1 signals were lost following phosphatase treatment. Of note, the upper band of nuclear PCMT1 was also diminished upon phosphatase treatment, suggesting that nuclear PCMT1 is phosphorylated in iTregs treated with anti-pPKCθ (FIG. 59C). Furthermore, anti-pPKCθ delivery into iTregs, significantly increased pSTAT1 (Y701) levels (FIG. 59), consistent with reports of high pSTAT1 expression highly-suppressive iTregs. This observation was accompanied by a downward trend in its gene expression (FIG. 59C), although this did not reach statistical significance.

Figure 59D:
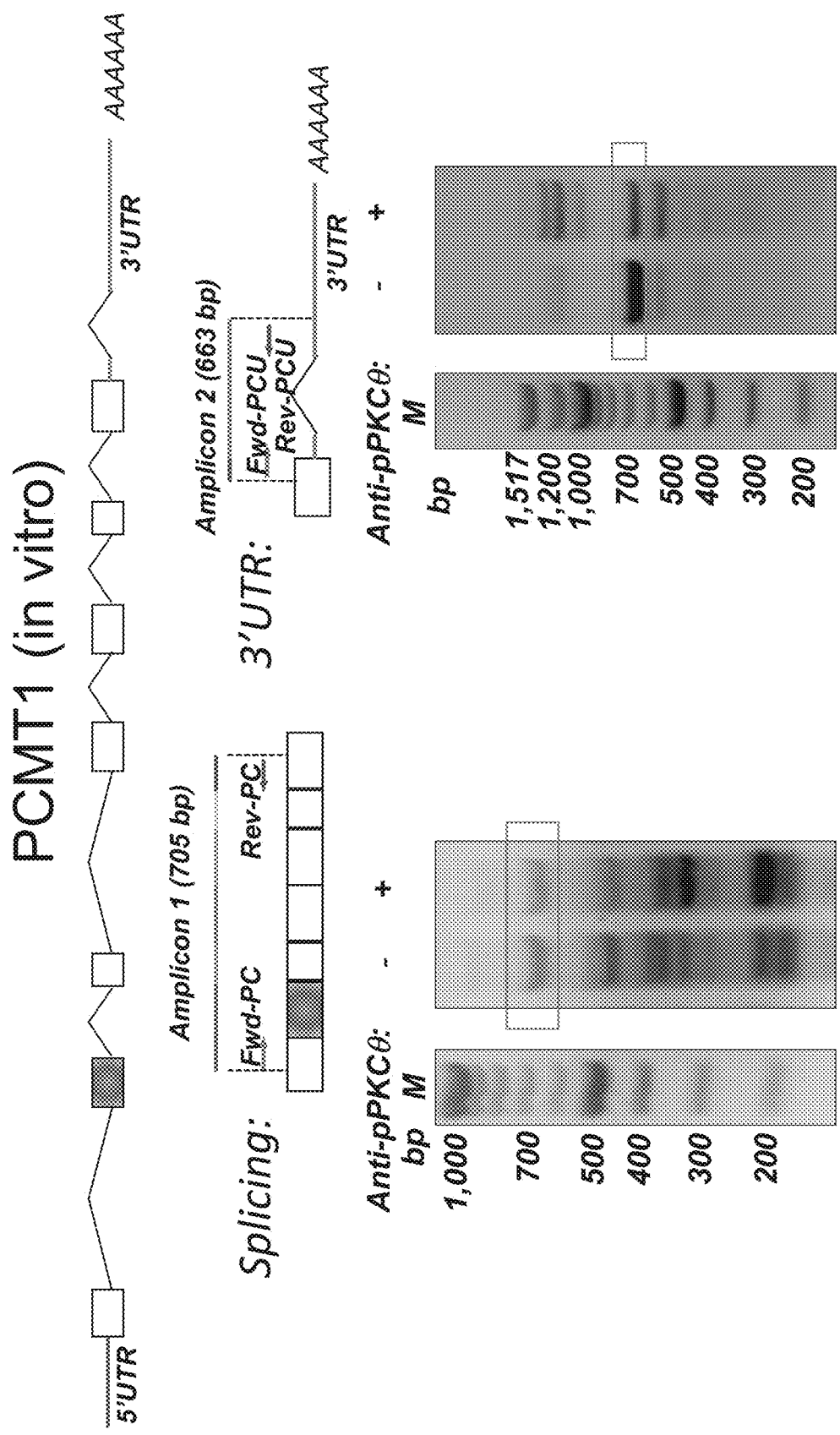
Figure 59E:
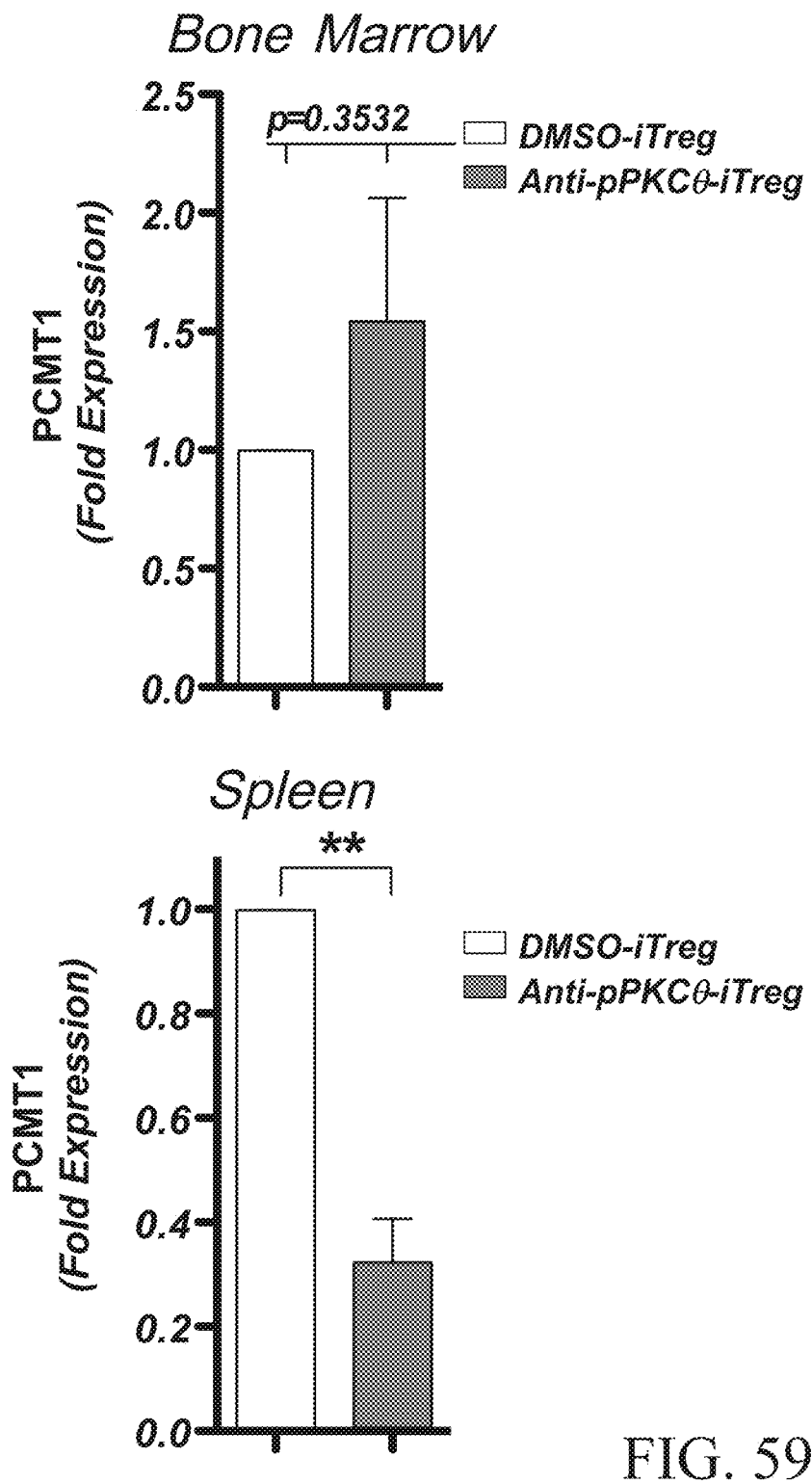
Figure 59F:
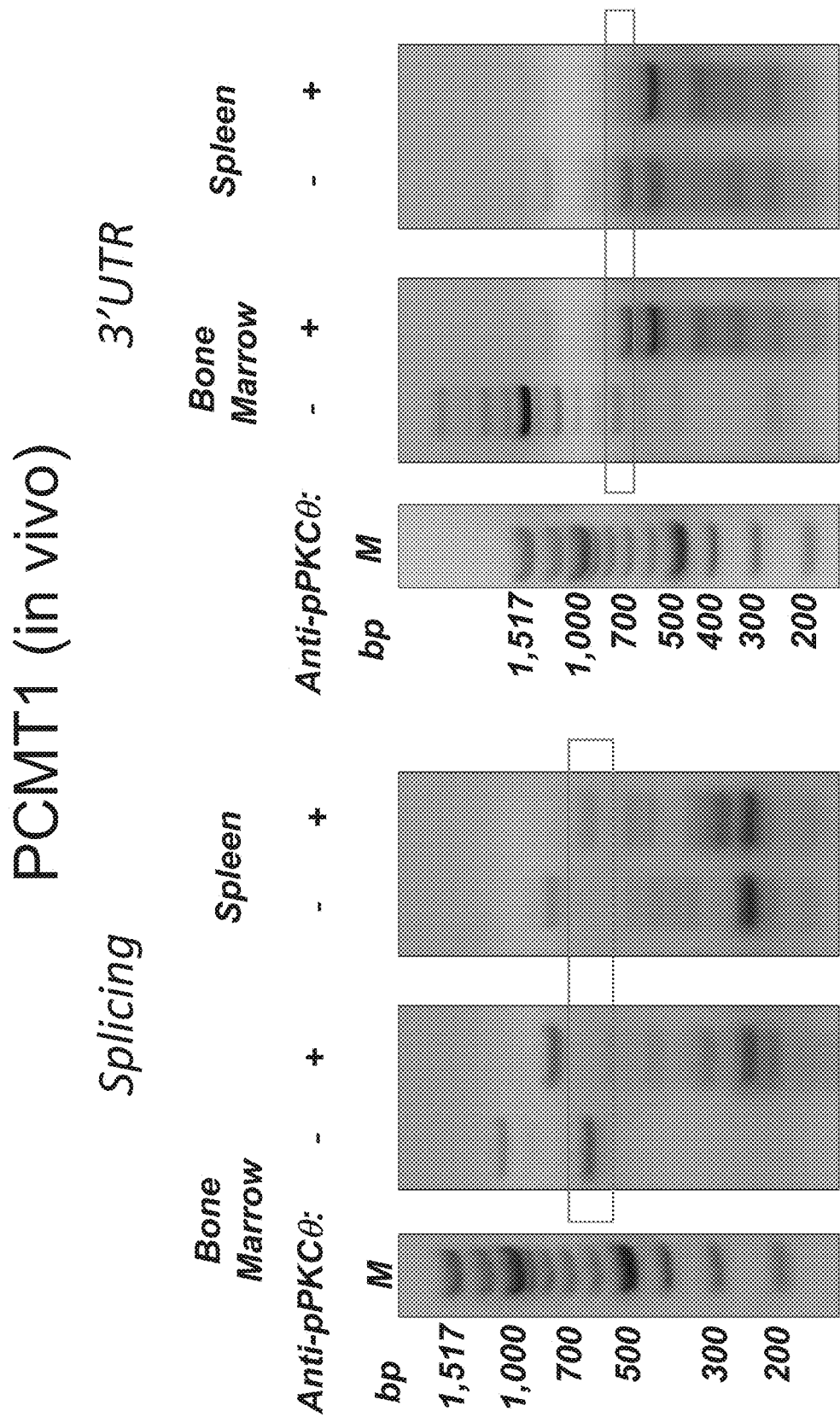
Figure 64C:
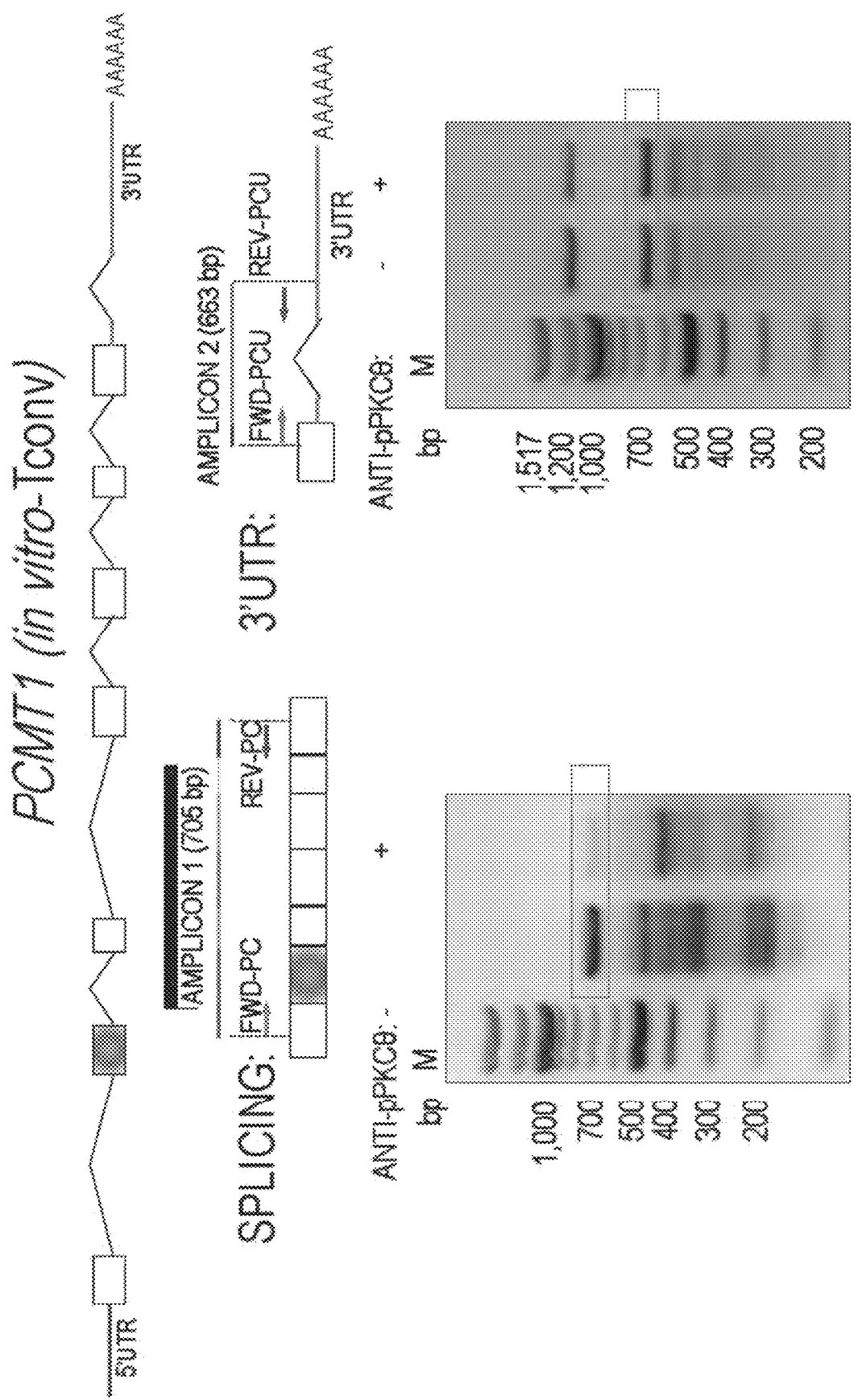
Figure 64E:
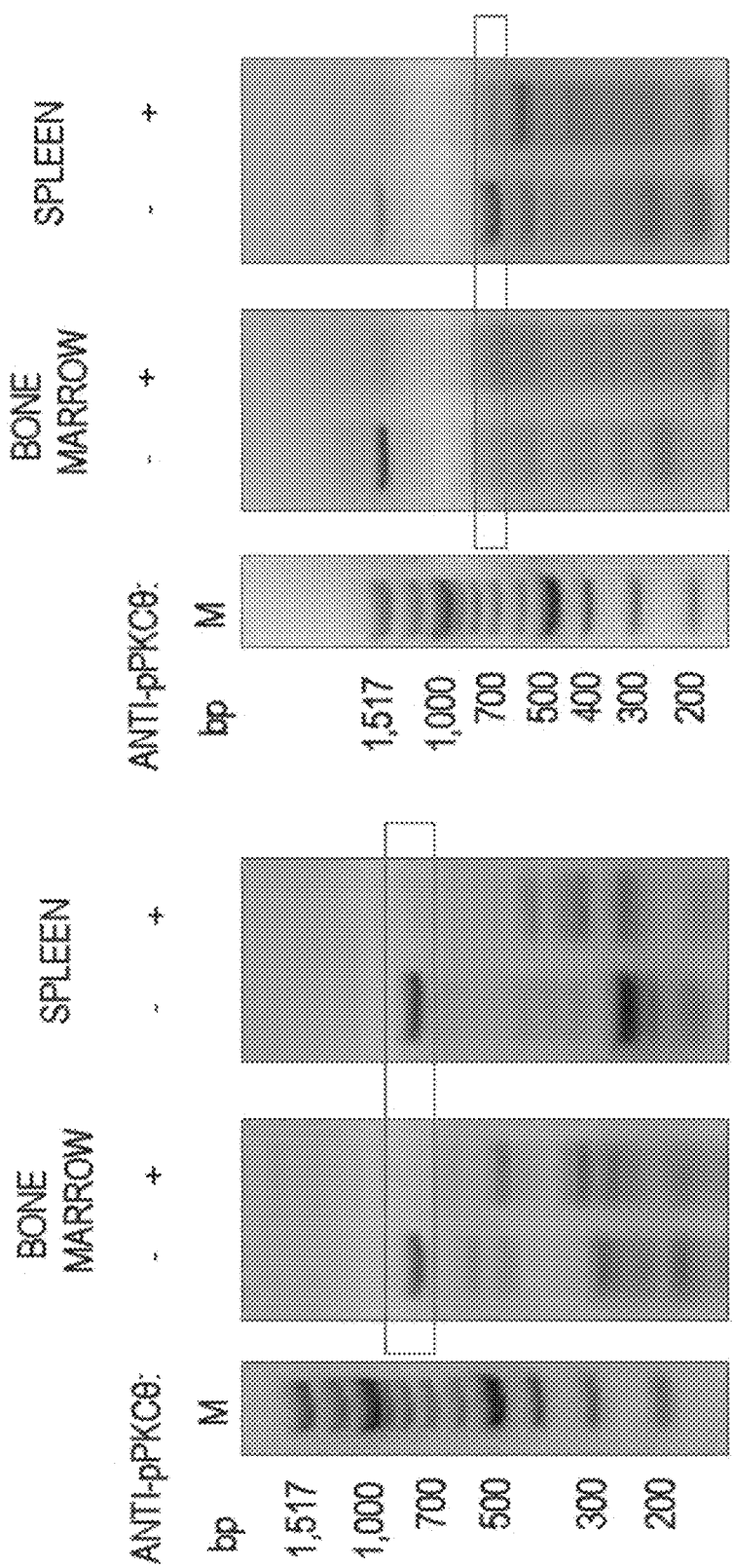

Having observed that differences in RNA splice variants occur in anti-pPKC iTregs, in vitro and in vivo (FIGS. 57 and 58, respectively), we next asked whether anti-pPKCθ delivery affected RNA processing of PCMT1 in iTregs, as well. Conventional PCMT1 mRNA has 7 exons with a 3'UTR that contains approximately 700 bp. When we treated iTregs with anti-pPKCθ, PCMT1 transcripts showed exon skipping which produced shorter mrRNA variants together with longer than expected 3'UTRs (FIG. 59D). Tconvs treated with anti-pPKCθ had 3'UTRs similar in length to untreated Tconvs but were missing the 7-exon PCMT1 mRNA (FIG. 64C). These suggest that PCMT1 mRNA variants generated in anti-pPKCθ iTregs are likely to be unstable and not efficiently translated in vitro. We were also interested in whether anti-pPKCθ treatment instilled durable differences in iTregs recovered from the bone marrow or spleen of humanized mice experiencing GvHD. PCMT1 expression was significantly downregulated in anti-pPKCθ iTregs found in the spleen, whereas we did not detect significantly diminished PCMT1 in anti-pPKCθ-iTregs from the bone marrow (FIG. 59E). Strikingly, we detected different splice variants of PCMT1, as well as shorter 3'UTR lengths, in anti-pPKCθ iTregs isolated from the bone marrow, while iTregs in the spleen possessed similar patterns of PCMT1 processing, regardless of prior treatment (FIG. 59F). In similar fashion, naïve T cells showed significantly reduced PCMT1 transcripts in the spleen and comparable levels in the bone marrow of mice which received anti-pPKCθ-treated iTregs, compared to mice receiving untreated iTregs (FIG. 64D). Interestingly, the PCMT1 splicing pattern exhibited by naïve T cells was reversed, compared to in vivo-recovered iTregs (FIG. 64E). Altogether, these data demonstrate that in iTregs, PKCθ plays an important role in regulating the protein methyltransferase, PCMT1, both post-translationally and post-transcriptionally.

Effects of Anti-PCMT1 Delivery in iTregs

Figure 60A:
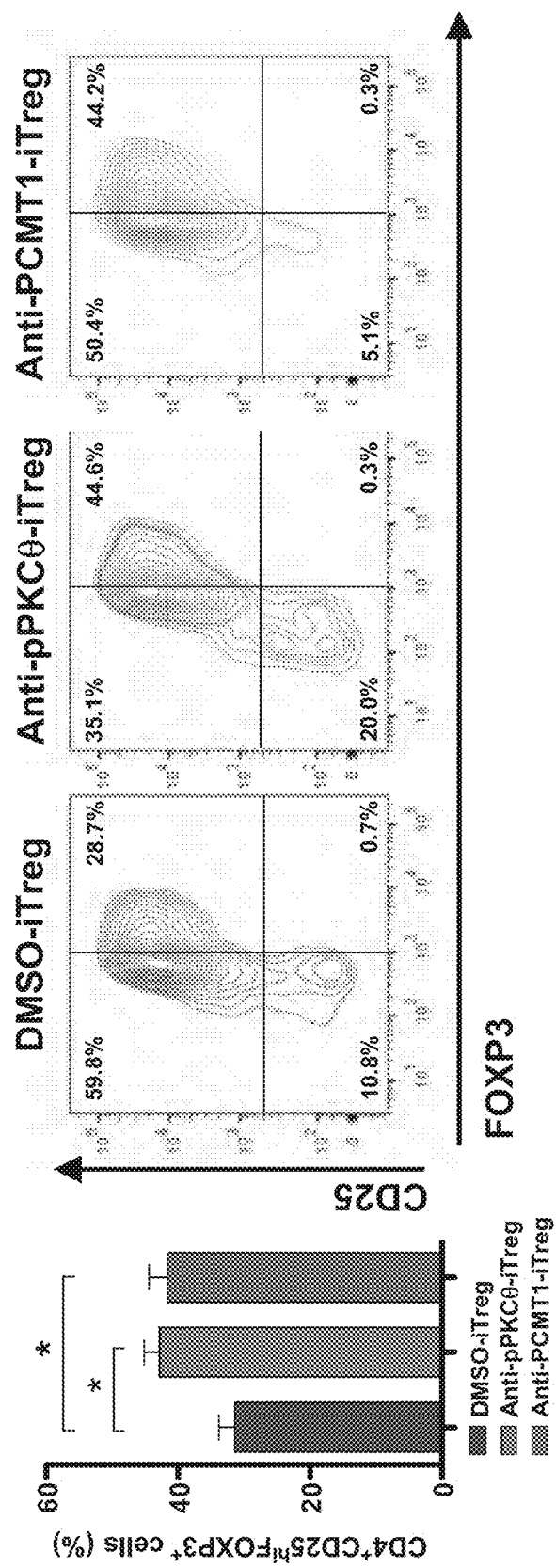
Figure 60B:
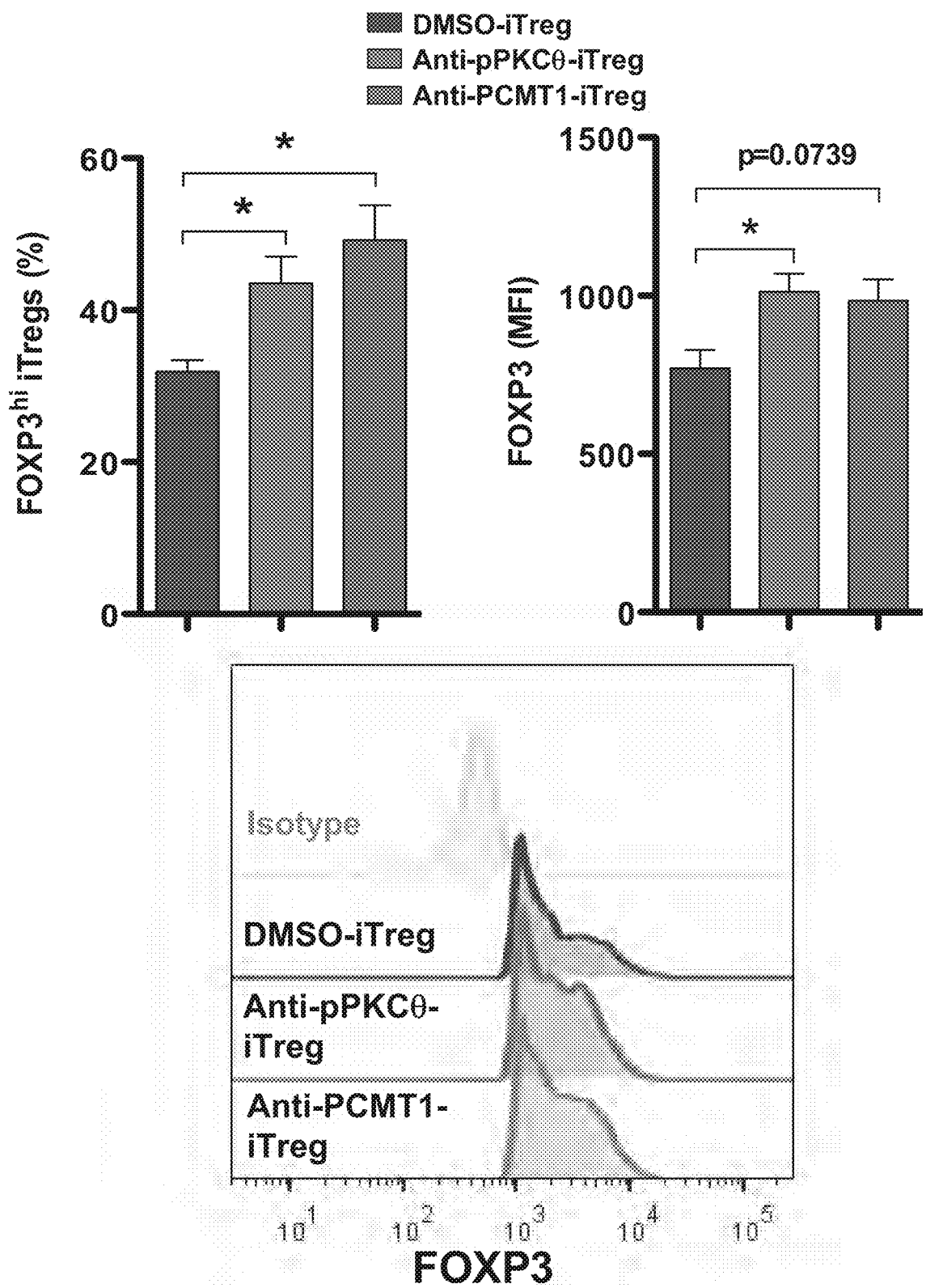

On the strength of the data we generated to this point, we sought to further investigate how modulating PCMT1 affected mRNA-RBP interactions in iTregs. To do this, we delivered anti-PCMT1, complexed to $P_{13}D_5$, into human CD4 T cells, then differentiated the cells in culture towards an iTreg phenotype. We then compared the phenotype of anti-PCMT1 iTregs to anti-PKCθ iTregs. Interestingly, we observed a significant increase in the percentage of CD4$^+$ CD25+FOXP3+ iTregs generated following anti-PCMT1 delivery, compared to untreated iTregs. However, the percentage of CD4+CD25+FOXP3+ iTregs was comparable between iTregs treated with anti-pPKCθ or with anti-PCMT1 (FIG. 60A). In addition, FOXP3 expression was higher in anti-pPKCθ- and in anti-PCMT1-treated iTregs, as both treatments produced a greater percentage of iTregs that were FOXP3hi, compared to untreated iTregs (FIG. 60B). We previously found that anti-PKCθ-treated iTregs expressed significantly more IFNγ and this could be associated with their superior suppressive function. Therefore, we also assessed IFNγ expression in anti-PCMT1 iTregs. Delivering either anti-pPKCθ or anti-PCMT1 into CD4 T cells increased the percentage of IFNγ$^{hi}$-expressing iTregs and suggests that PKCθ and PCMT1 operate within the same pathway to regulate iTreg suppressive functions (FIG. 60C).

Figure 60D:
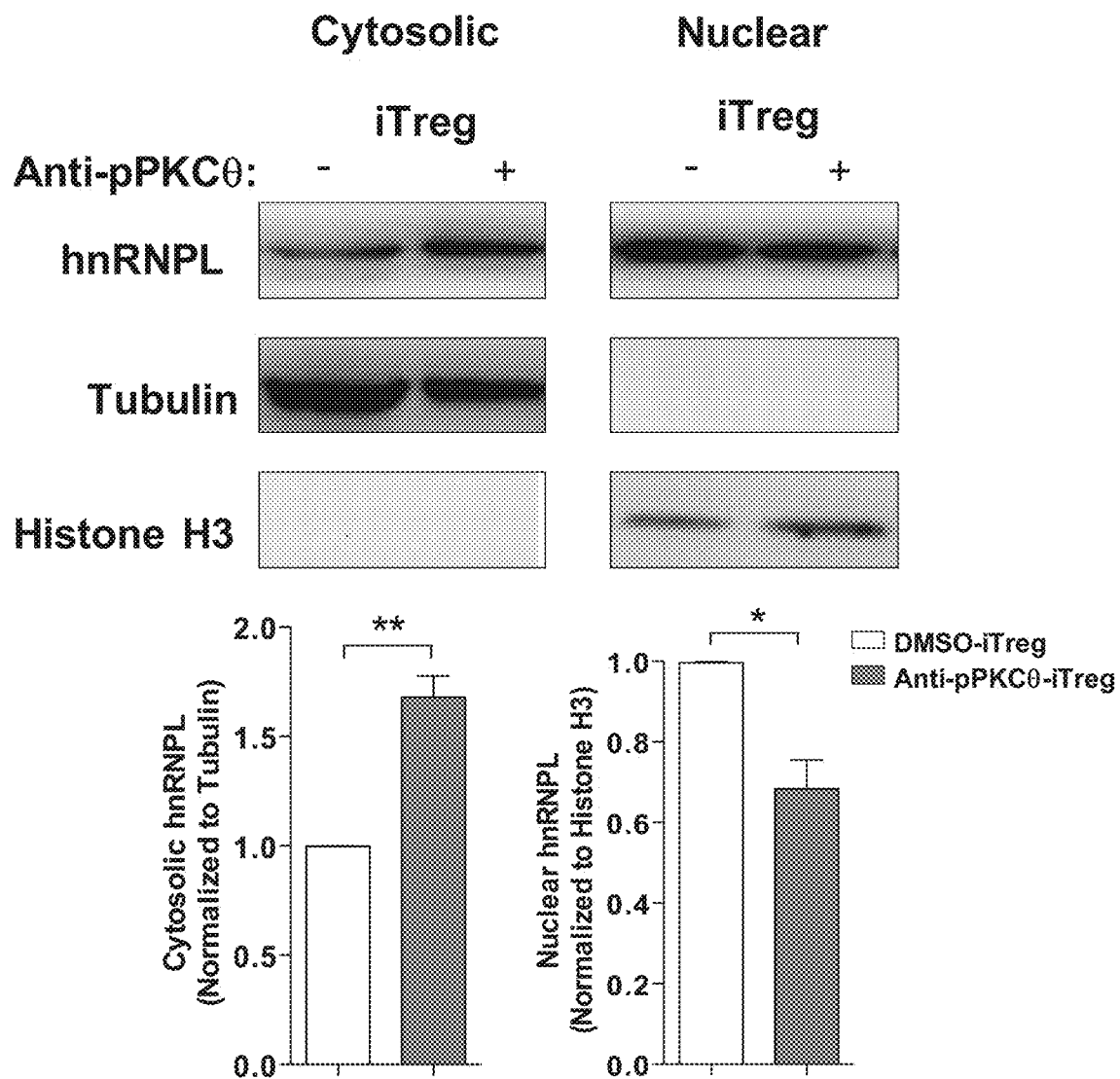

PCMT1 has been implicated in multiple RNA processing functions, including regulating its nuclear export to facilitate protein translation. We speculated that this likely is further mediated by its regulation of or interaction with RBPs. Among these, hnRNPL has been shown to be a key regulator of iTreg post-transcriptional regulation. To explore the possible link between PCMT1 and hnRNPL, we first asked whether anti-pPKCθ treatment affected hnRNPL expression. We found that, following anti-pPKCθ delivery, hnRNPL cytosolic expression decreased, while nuclear hnRNPL levels were enhanced (FIG. 60D). These results suggested to us that hnRNPL cellular localization may play a role in iTreg differentiation, and that its cytosolic vs nuclear accumulation may be regulated in a PKCθ-dependent fashion.

Figure 60E:
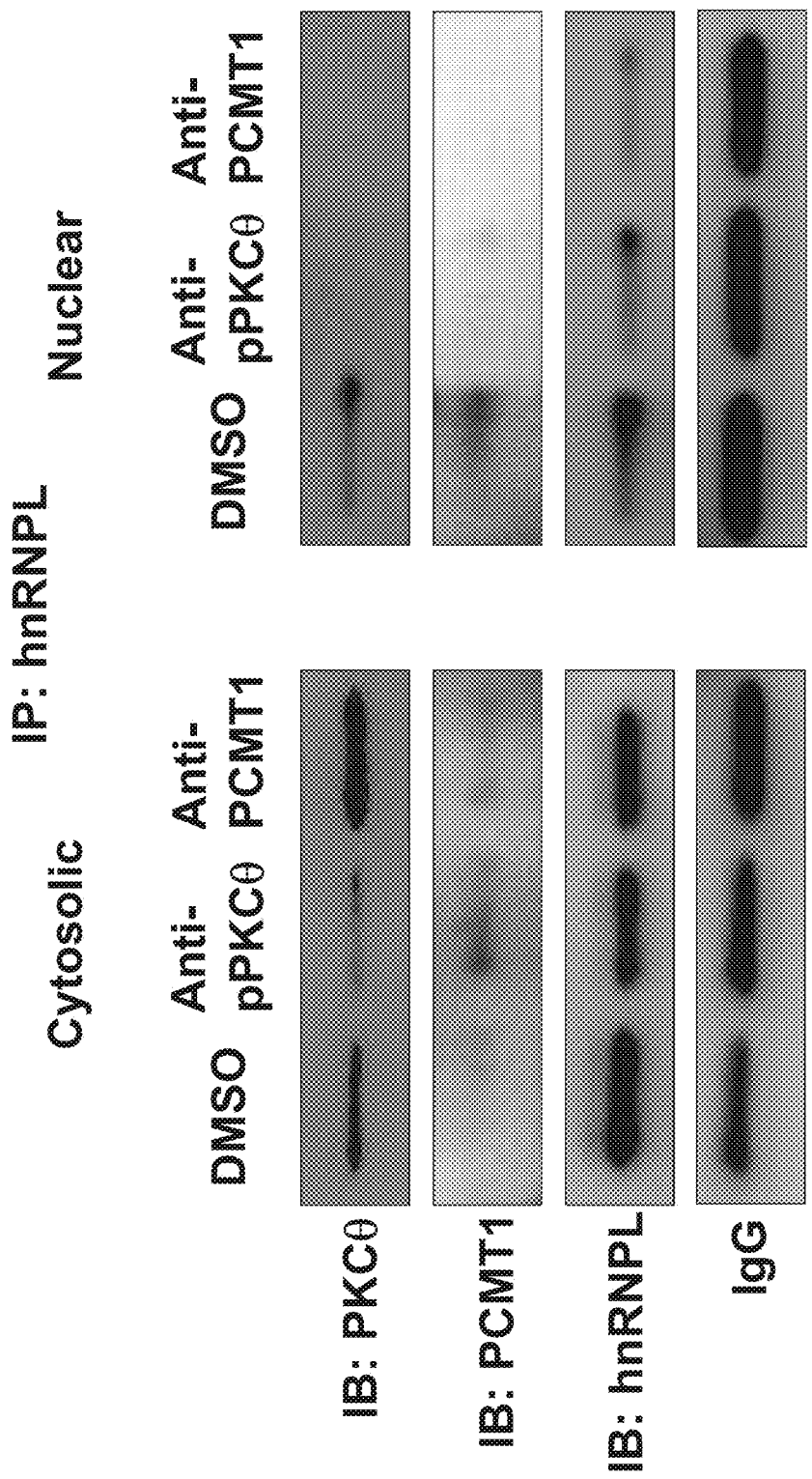

Our in vitro data suggested the PKCθ and PCMT1 may act within the same signaling pathway to regulate FOXP3 and IFNγ expression. Therefore, we asked if either of these pathways converge at the level of hnRNPL interaction. To determine whether these proteins physically interact with hnRNPL, we immunoprecipitated cytosolic and nuclear hnRNPL and examined the degree of PKCθ- and PCMT1-hnRNPL interaction in iTregs treated either with anti-pPKCθ or with anti-PCMT1. We observed that, in untreated iTregs, hnRNPL and PKCθ interact both in the cytosol and the nucleus, while hnRNPL-PCMT1 interactions are primarily nuclear. The nuclear interaction of both proteins with hnRNPL was significantly diminished in iTregs following either anti-pPKCθ- or anti-PCMT1-treatment. Surprisingly, hnRNPL-PKCθ association was significantly lower in the cytosol of anti-pPKCθ-treated iTregs while anti-PCMT1 iTregs exhibited a marked increase in hnRNPL-PKCθ interactions (FIG. 60E). These results confirmed PKCq and PCMT1, both, interact with hnRNPL and that the cellular distribution of these interactions are impacted in anti-pPKCθ and anti-PCMT1 iTregs.

Figure 60F:
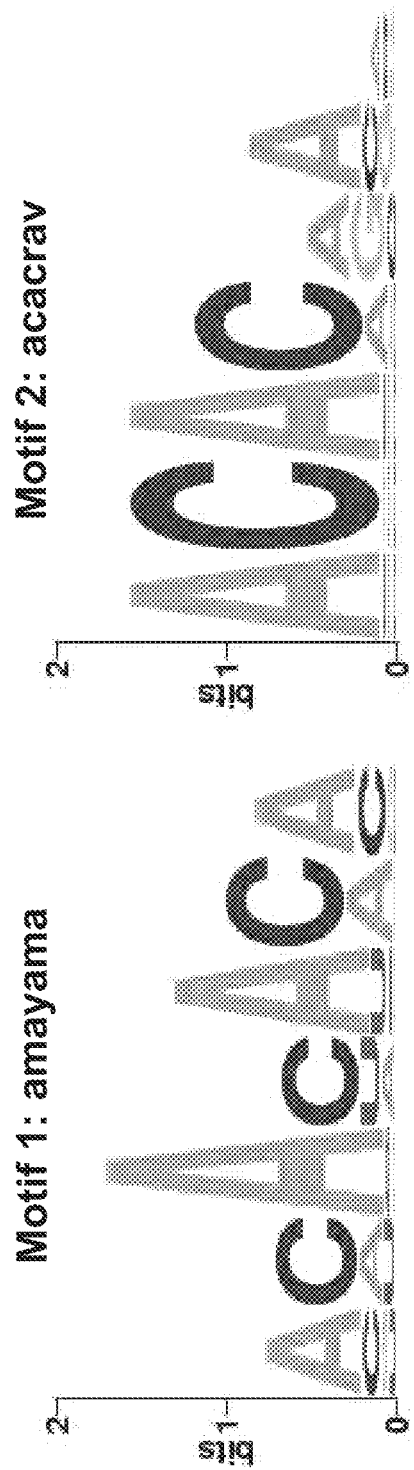
Figure 60G:
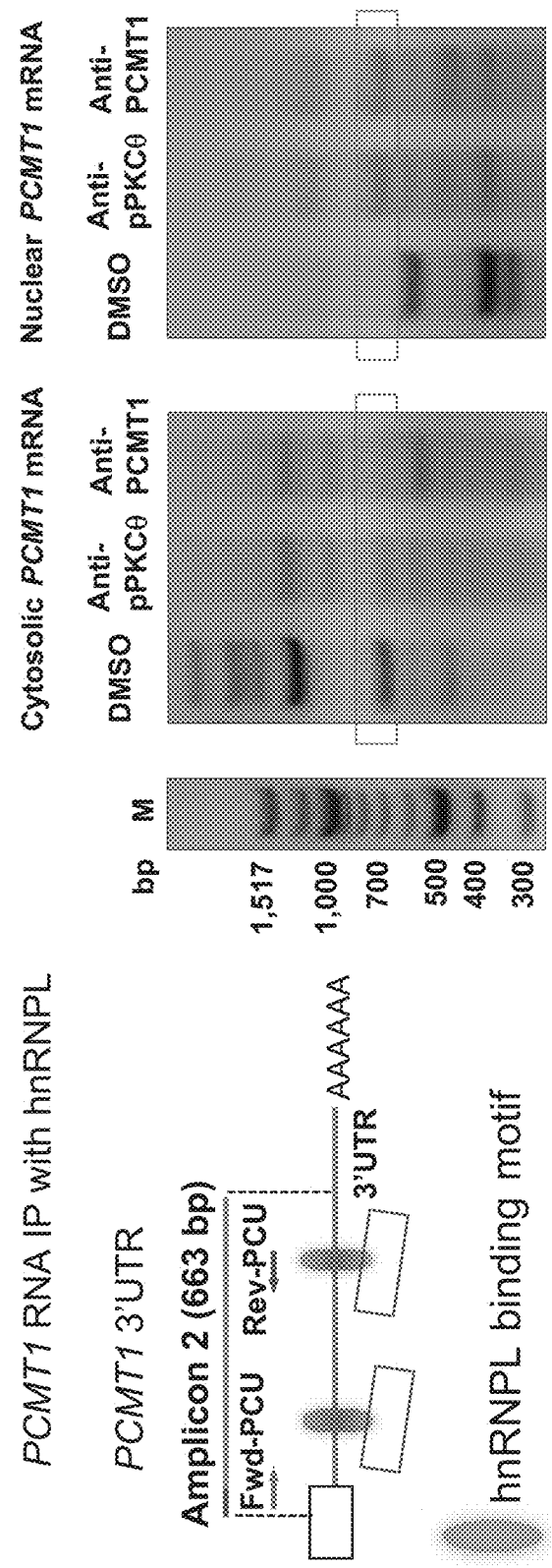
Figure 66A:
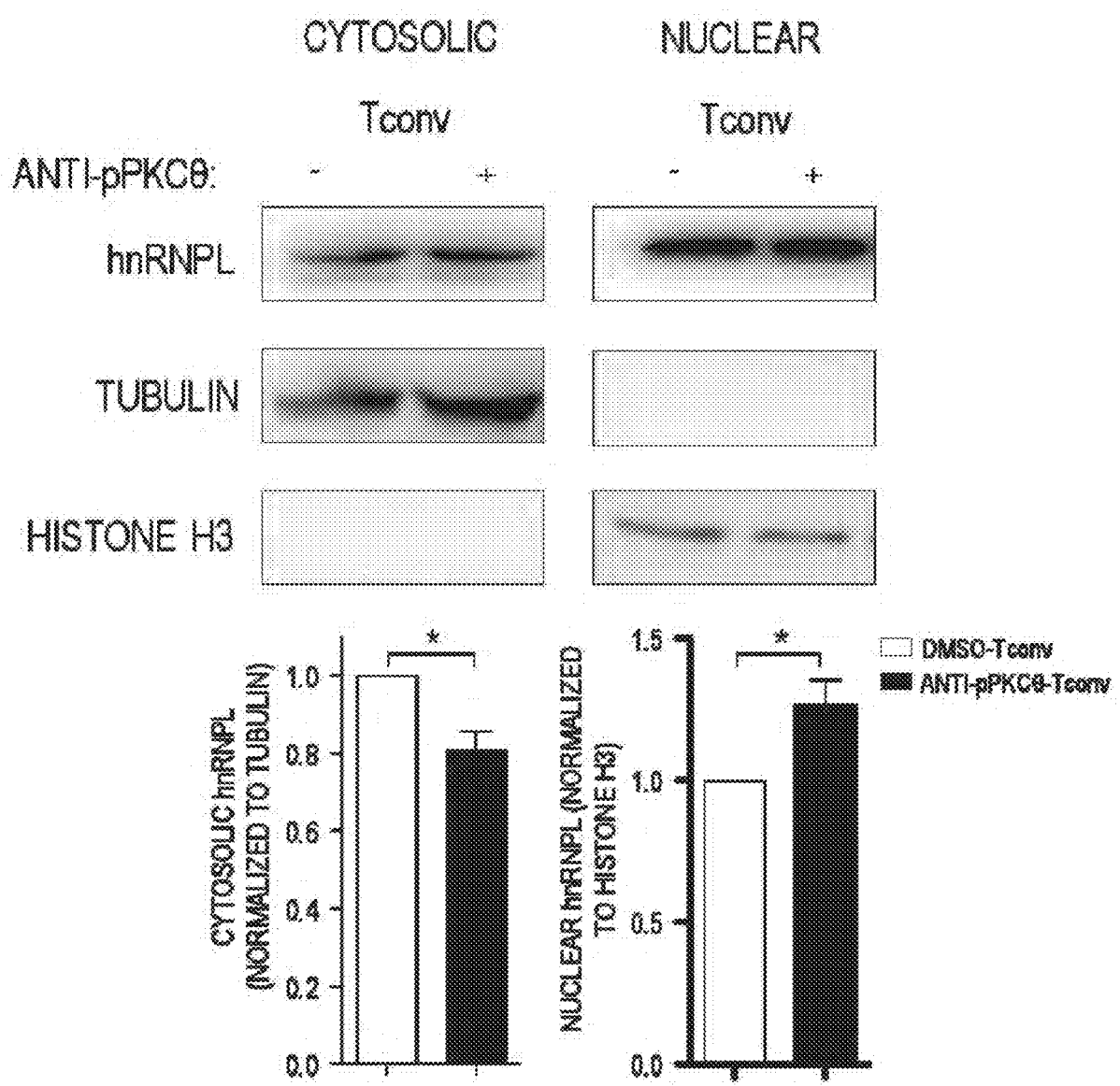
Figure 66C:
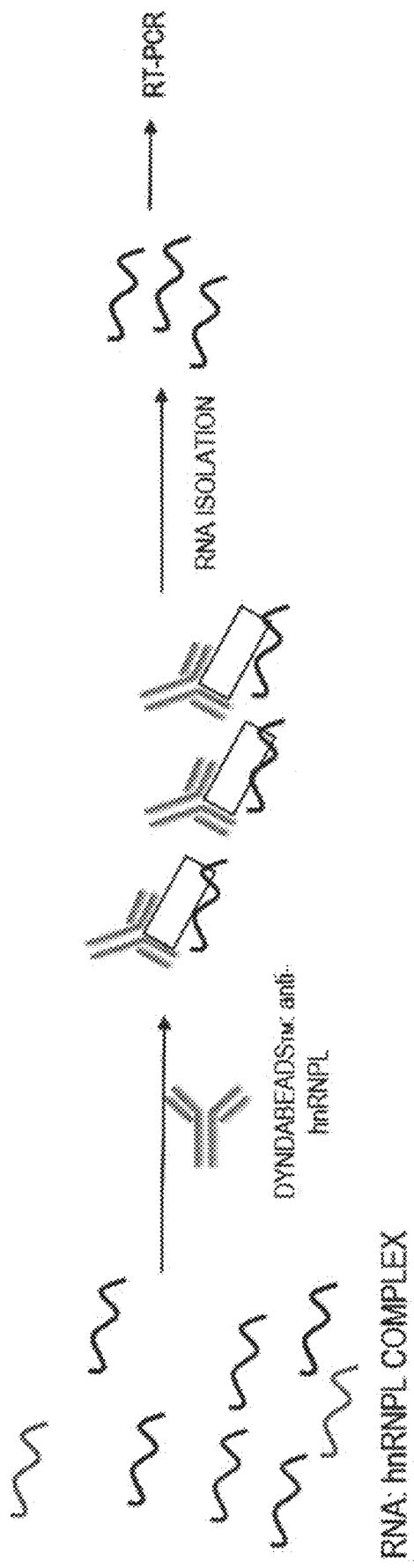
Figure 66D:
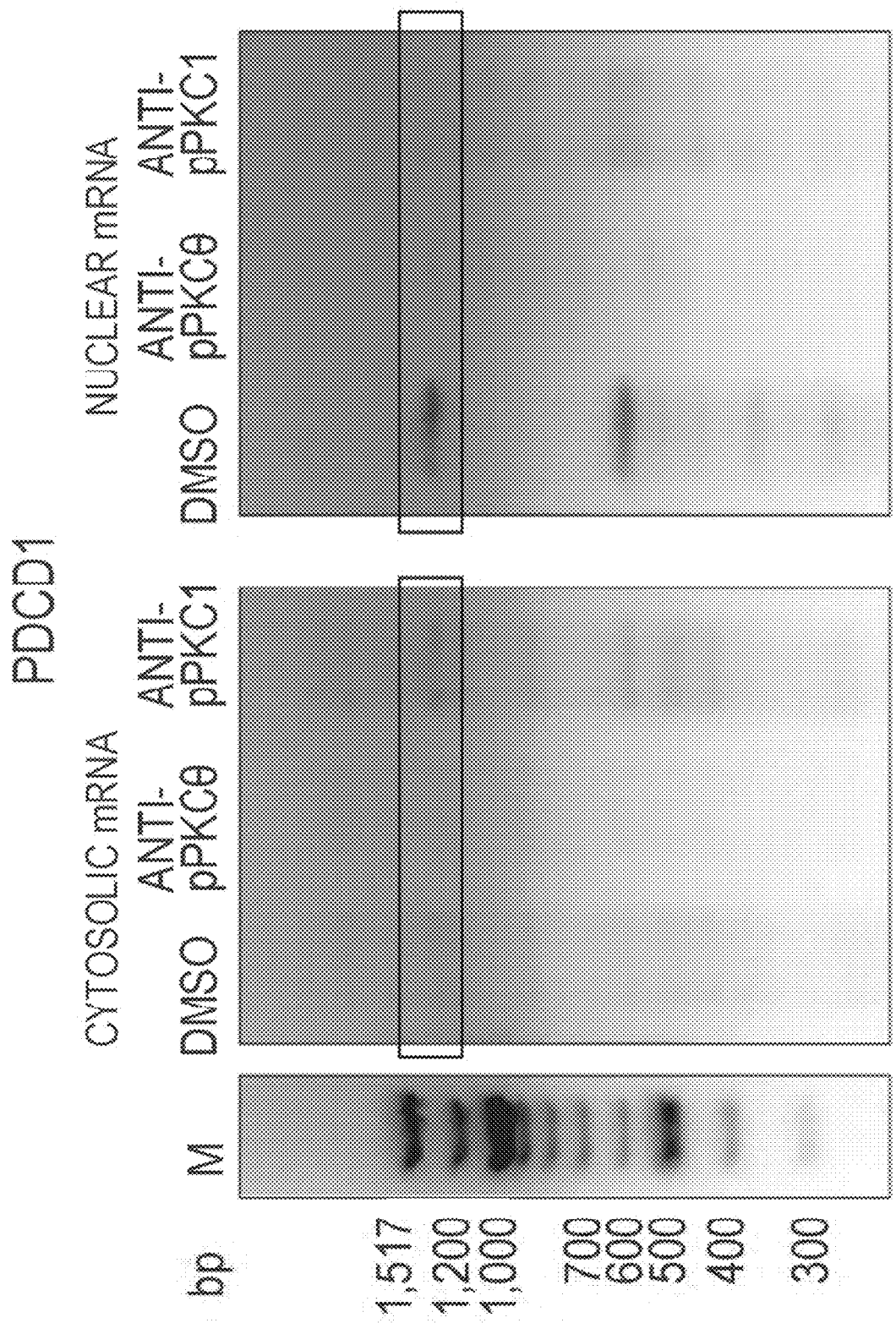
Figure 66E:
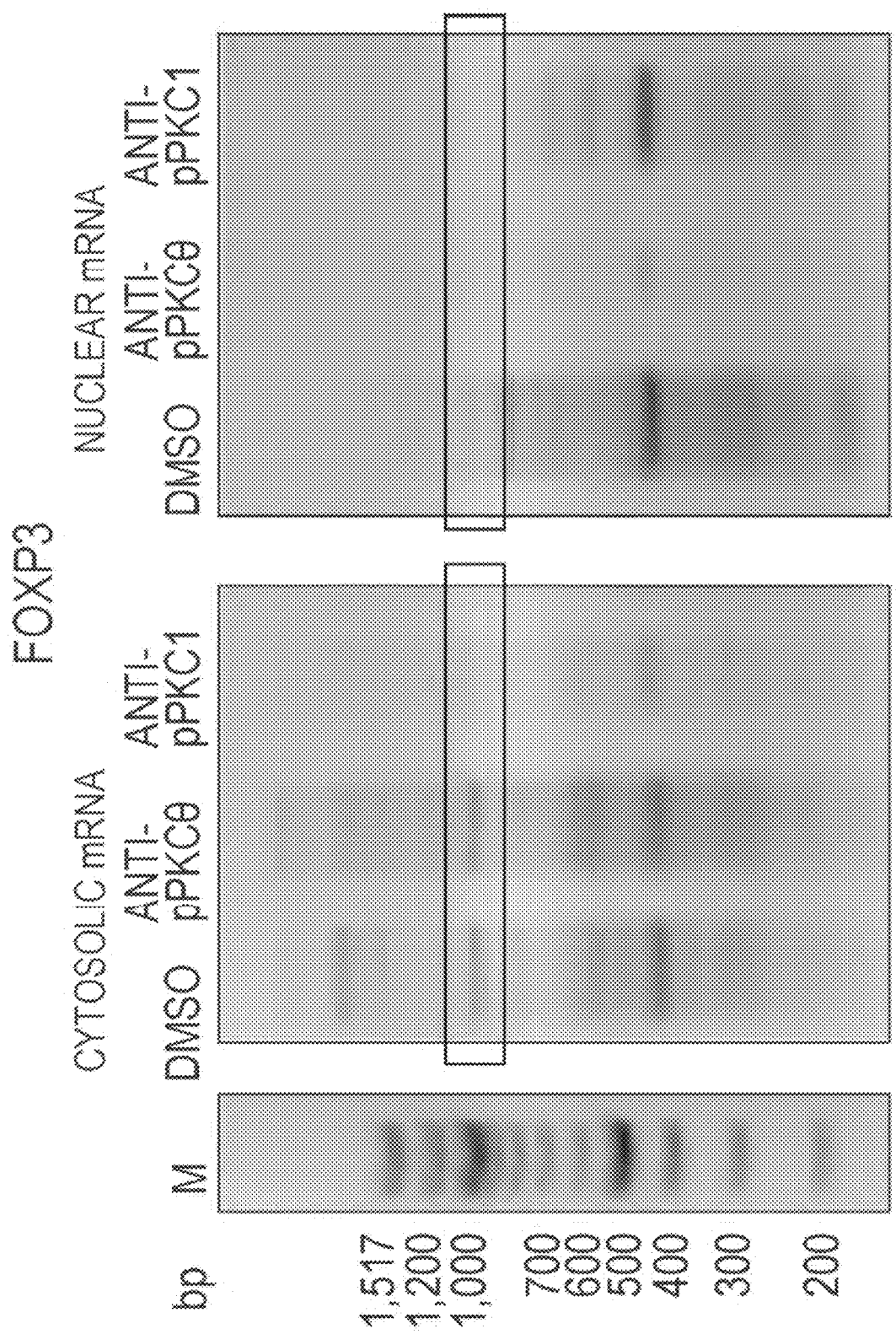
Figure 66H:
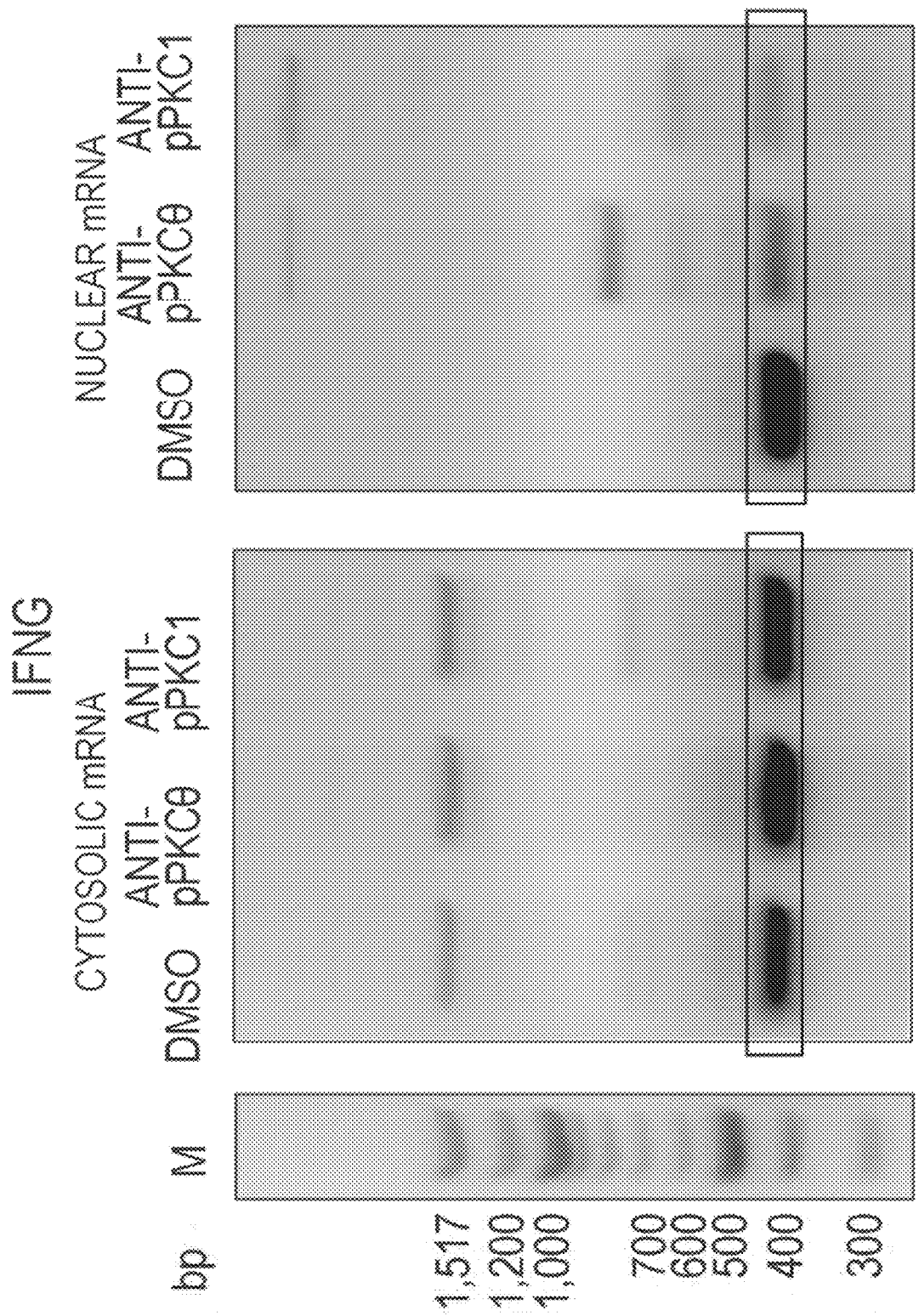
Figure 66G:
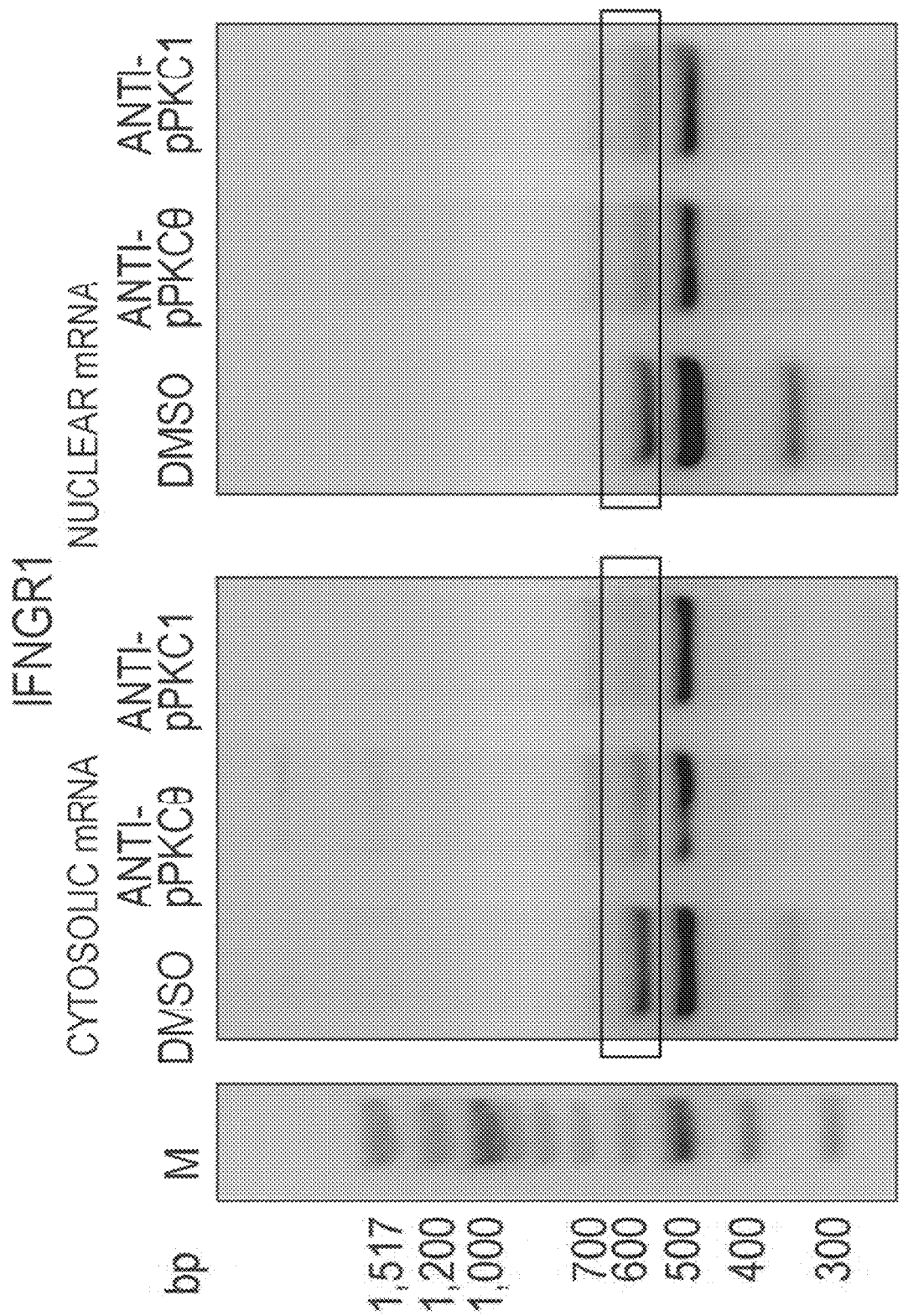

A major function of RBPs, such as hnRNPL, is to aid in mRNA export prior to translation. Given the reduced nuclear interactions of hnRNPL with PKCθ and PCMT1 following antibody delivery, we asked whether this also negatively affected the ability of hnRNPL to bind PCMT1 mRNA. We used several bioinformatics tools to identify hnRNPL RNA binding motifs within the 3'UTR of PCMT1 (FIG. 60G). The CISBP-RNA database showed two CA-rich RNA binding motifs for hnRNPL (FIG. 60F). CA-rich elements within 3' UTR sequences serve as a central hub for further RNA processing events such as RNA stability and nuclear export (Iadevaia et al., 2015). In general, incorrectly spliced mRNAs, such as those with retained introns or aberrant exon skipping, can undergo either nuclear RNA decay or nonsense-mediated RNA decay in the cytoplasm. Only correctly spliced, stable mRNAs are properly exported and translated (Bergeron et al., 2015). To investigate whether hnRNPL-PCMT1 or hnRNPL-PKCθ association is important for correctly spliced, stable mRNA export in iTregs, we isolated cytoplasmic and nuclear RNA from iTregs followed by RNA immunoprecipitation. We designed 3'UTR-specific primers to amplify putative hnRNPL binding sites, including two putative hnRNPL binding sites within the 3'UTR of PCMT1. We subsequently identified hnRNPL binding sites located within the 3'UTR of all the key iTreg genes studied here, namely FOXP3, IFNG, IFNGR1, and PDCD1 (FIG. 65A). Strikingly, we found robust hnRNPL-PCMT1 mRNA association in the nucleus and the cytosol of untreated iTregs, and these interactions were markedly reduced in iTregs treated either with anti-pPKCθ or with anti-PCMT1 (FIG. 60G). We detected strong interaction of hnRNPL-PDCD1 mRNA mainly in the nucleus, however, anti-PCMT1-treated iTregs enhanced their stable PDCD1 mRNA export (FIG. 60G). We did not detect cytosolic association of stable PDCD1 mRNA and hnRNPL in anti-pPKCθ-treated iTregs (FIG. 66D). Cytosolic hnRNPL-FOXP3 interactions remained intact in anti-pPKCq-treated iTregs but were lost in anti-PCMT1-treated iTregs (FIG. 66E). In contrast to PKCθ- and PCMT1-mediated tight regulation of stable PCMT1, FOXP3, and PDCD1 mRNA export by hnRNPL, we found that nuclear export of stable IFNG and IFNGR1 mRNA was not affected by anti-pPKCθ and anti-PCMT1 delivery (FIG. 66F, G). These results revealed that stable mRNA export of PCMT1 is tightly regulated by hnRNPL association with PCMT1 and PKCθ. More importantly, both PKCθ and PCMT1 can regulate selective mRNA export of key iTreg genes in gene-specific manner.

PCMT1 as an iTreg Instability Marker

Figure 61B:
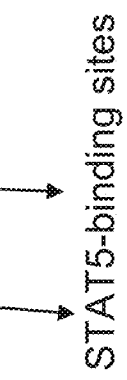
Figure 61C:
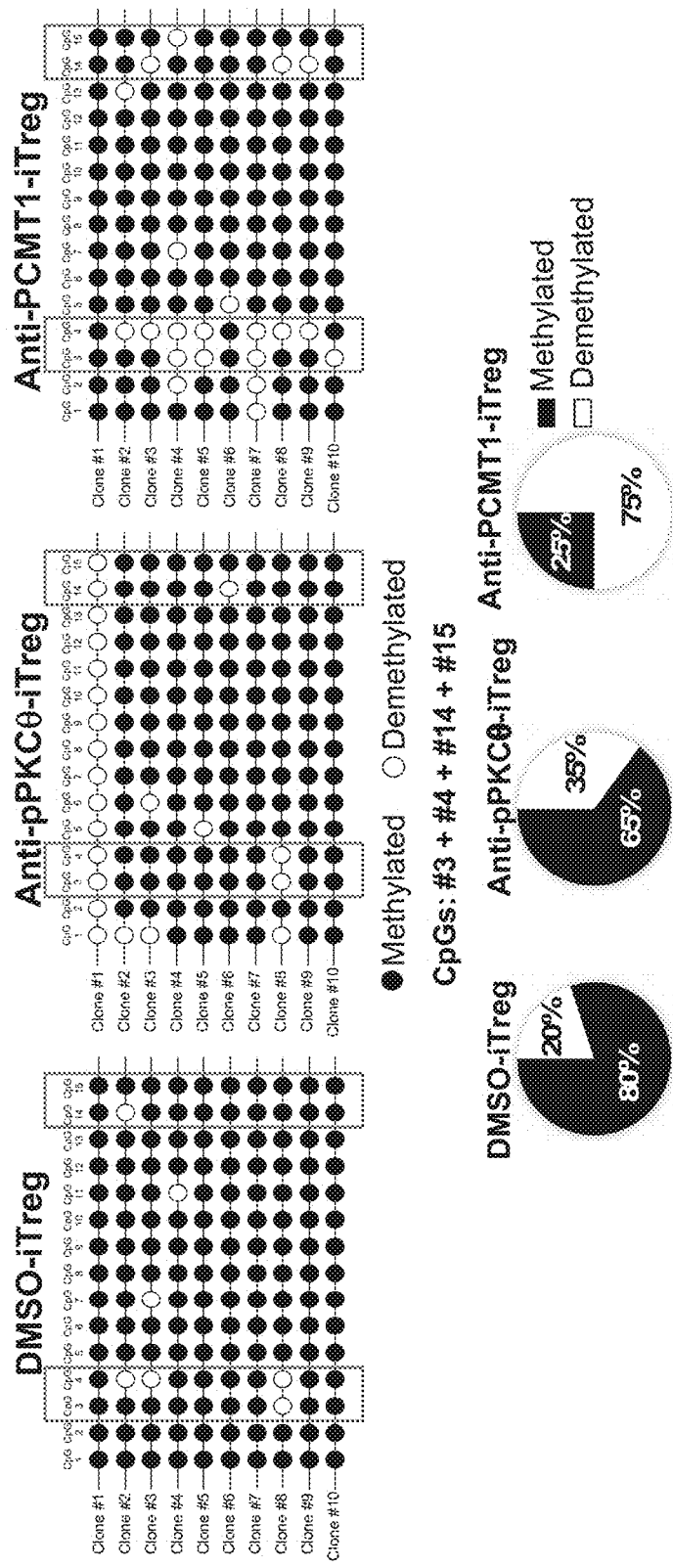
Figure 61D:
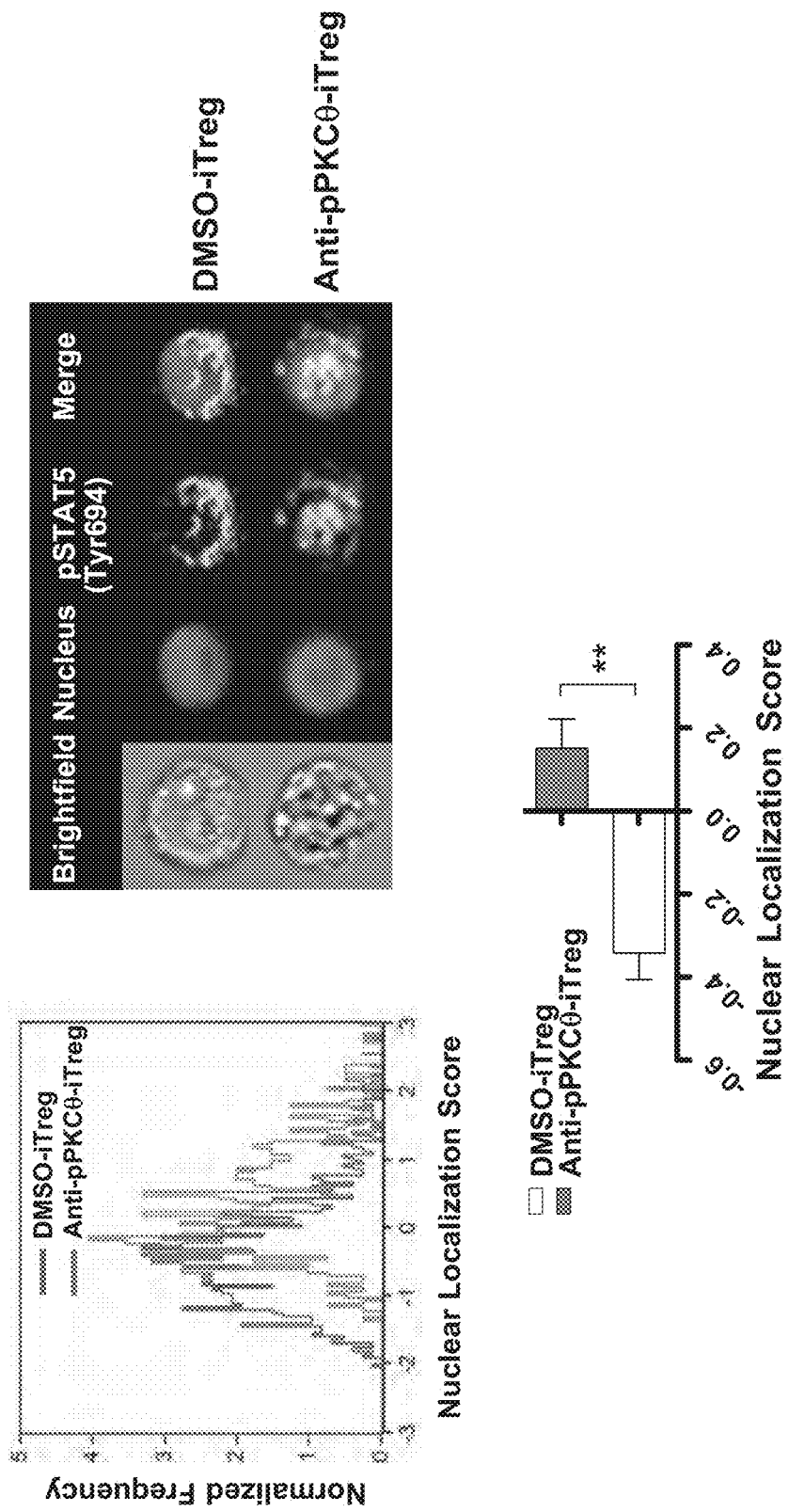

In many aspects, delivering anti-PCMT1 into iTregs phenocopied the results we obtained when we generated anti-pPKCθ-iTregs. This included producing equivalent populations of FOXP3hi and IFNγ$^{hi}$ iTregs. Therefore, we asked whether PCMT1 directly regulates FOXP3 gene expression. Using chromatin immunoprecipitation, followed by qPCR, we determined that PCMT1 binds directly to FOXP3 in iTregs. Moreover, anti-pPKCθ- and anti-PSMT1 treatment dramatically reduced PCMT1 interactions with FOXP3 in iTregs (FIG. 61A). These data suggest that PKCθ and PCMT1 are critical for binding to FOXP3. Expression of FOXP3 is tightly regulated by several transcription factors that bind to the Treg-specific demethylation region (TSDR), following its demethylation and, to date, a highly demethylated TSDR is the most reliable marker for stable FOXP3 expression. In most iTregs, the TSDR is methylated, resulting in unstable FOXP3 expression (Toker et al., in press; Li et al., 2014). This instability is thought to result from decreased STAT5 binding within the TSDR (Huehn et al., 2009; Ogawa et al., 2014). We identified 15 CpG islands within the human FOXP3 TSDR sequence, including two that flanked the proximal STAT5 binding site, and two that overlapped with the distal STAT5 binding site (FIG. 61B). As a logical extension to our discovery that PCMT1, as a methyltransferase that directly binds to FOXP3, we evaluated the level of TSDR methylation in untreated iTregs, compared with that in anti-pPKCθ- and anti-PCMT1-treated iTregs, using bisulfite sequencing of 10 individual clones isolated from each of the three iTreg treatment conditions as indicated (FIG. 61C). Of the three conditions, untreated iTregs showed the lowest percentage (20%) of demethylated CpGs in the clones analyzed. Interestingly, in anti-pPKCθ-treated iTregs, in approximately 35% CpG sites in the TSDR sites were demethylated. Following anti-PCMT1 treatment, however, we found that of the clones tested, 75% CpG sites that either flanked or overlapped with STAT5 binding sites were demethylated (FIG. 61C), strongly suggesting that inhibiting PCMT1 may increase the stability of FOXP3 expression by demethylating the TSDR. We further speculated that increased demethylation of CpG islands surrounding the STAT5 binding sites would increase nuclear retention of pSTAT5. To examine this possibility, we used imaging flow cytometry to evaluate levels of nuclear pSTAT5 in DMSO- and anti-pPKCq-treated iTregs, in vitro. Consistent with our prediction, anti-pPKCq-treated iTregs exhibited significantly greater amounts of nuclear pSTAT5, compared to iTregs differentiated in the presence of DMSO (FIG. 61D).

Overall, we provide strong evidence that PKCθ negatively regulates iTreg induction through its modulation of two key components of RNA processing, PCMT1 and hnRNPL, through multiple cellular mechanisms. Furthermore, our data suggest this inhibitory pathway can be interrupted in iTregs through the intracellular delivery either of anti-pPKCθ or anti-PCMT1, to modulate these mechanisms in favor of enhancing iTreg suppressive functions. Finally, we identified, for the first time, that the protein repair methyltransferase, PCMT1, acts as a key iTreg instability factor through its control of FOXP3 TSDR methylation.

Discussion

A great deal has been learned about transcriptional regulation of immune cell responses. A growing area of interest focuses on alternative splicing and RNA processing in regulating T cell differentiation and function following antigenic stimulation, as distinct protein isoforms for many T cell genes have been identified (Lynch et al., 2000; Lynch et al., 2004; Martinez et al., 2012; Matter et al., 2002; Arch et al., 1992). These processes operate together with RNA binding proteins, transcription factors, and epigenetic modifiers (Ip et al., 2007' Martinez et al., 2012). Although numerous immune-related genes undergo alternative splicing and RNA processing, differential isoform expression and RNA processing in regulatory T cell differentiation remains largely unexplored.

Our studies provide a novel, comprehensive analysis of altered RNA processing in the context of iTreg differentiation and function. We applied several methods to investigate PKCθ modulation of splicing regulators, RNA splicing, stability, and nuclear export. We specifically targeted pPKCθ using a cell-penetrating antibody, to probe post-transcriptional RNA processing in iTregs. We discovered that PKC☐ influenced RNA processing of several iTreg genes including CD45, FOXP3, PDCD1, IFNG, and IFNGR1 in a cell-, and tissue-specific fashion. Furthermore, splicing regulator analysis revealed two RNA regulatory proteins, hnRNPL and PCMT1, were controlled by PKCθ at multiple levels. We found that PKCθ regulated subcellular localization of hnRNPL and its binding to mRNA. Additionally, we showed PKCθ regulated PCMT1 alternative splicing, stabilized PCMT1 mRNA through hnRNPL binding, and enabled its nuclear export followed by its translation into stable protein. However, anti-pPKCθ delivery into iTregs altered the PCMT1 splicing pattern, and destabilized and prevented the nuclear export of PCMT1 mRNA, due to loss of hnRNPL binding. Utilizing our cell-penetrating peptide-intracellular antibody delivery strategy to target PCMT1, we revealed a novel mechanism to promote iTreg differentiation and function. We determined that PCMT1 directly binds to the FOXP3 gene and, more interestingly, inhibiting PCMT1 increased FOXP3 TSDR demethylation, thereby enhancing FOXP3 stability and iTreg maintenance. In conjunction with our recent discovery of generating a unique, suppressive population of FOXP3$^{hi}$PD1$^{hi}$IFNγ$^{hi}$ iTregs when we manipulated PKCθ using intracellular anti-pPKCθ delivery, this study supports the notion that PKCθ directly regulates iTreg differentiation and stability through modulating pivotal RNA processing regulators.

Unexpectedly, we found that pSTAT1 (Y701) levels were increased in anti-pPKCθ-treated iTregs, whereas pAKT (S473) levels were diminished, compared to untreated iTregs. Reduced pAKT coupled with upregulated pSTAT1 has previously been associated with enhanced IFNγ production by CD4$^+$CD25$^+$FOXP3$^+$ Tregs in mice. Moreover, both AKT and STAT1 were found to function within the same pathway, both induced by IFNγ, and served to control skin graft rejection in vivo. IFNγ produced by these Tregs also induced indoleamine 2,3-dioxygenase (IDO) production by antigen-presenting cells, to further suppress immune cell activity (Wei et al., 2010). Anti-pPKCθ-treated iTregs showed higher IFNγ expression and greater suppressive capacity, both in vitro and in vivo, suggesting this pathway may critically contribute to iTregs' suppressive function through autonomous IFNγ signaling. Anti-pPKCθ-treated iTregs also express high levels of PD1, which may also be related to this pathway. A downstream phosphatase of PD1 signaling, SHP-2, was shown to interact with cytosolic STAT1, reducing its recruitment to the IFNγR, and dampening Th1 function (Wu et al., 2012). Further studies investigating how PD1 and IFNγ signaling pathways might intersect downstream of PKCθ modulation in iTregs are needed to fully elucidate cellular mechanisms that regulate suppressive ability and Th1-Treg plasticity.

Members of the PKC family can influence mRNA splicing in various cell types (Lynch et al., 2000; Revil et al., 2007; Zara et al., 2011). PKCα, PKCδ, and PKCθ have been shown to activate SC35 which functions in co-transcriptional regulation of alternative splicing (McCuaig et al., 2015; Zara et al., 2011; Cataldi et al., 2009). As previously indicated, we found PKCθ regulated cytoplasmic versus nuclear distribution of splicing regulators. Among these, we focused on hnRNPL as it was uniquely altered in iTregs following PKCθ inhibition. Unlike other splicing regulators we investigated, only hnRNPL was sequestered in the cytosol after anti-pPKCθ delivery. This correlated with increased exon skipping of CD45, resulting in greater expression of CD45RO, which is consistent with reduced levels of nuclear hnRNPL in anti-pPKCθ-treated iTregs, compared to untreated iTregs. On the other hand, we saw no differences in the splicing patterns of FOXP3, PDCD1, IFNG, and IFNGR1 in iTregs, regardless of treatment, suggesting hnRNPL may not contribute to the alternative splicing of these genes. We did observe shorter 3'UTR lengths in PDCD1, but not in FOXP3, IFNG, and IFNGR1, mRNAs. These results suggested to us that anti-pPKCθ-treated iTregs implement gene-specific 3'UTR processing which may result in stable PD1 expression in vitro. Similar mechanisms may account for the in vivo RNA dynamics we observed, in the context of an immune response and Treg differentiation. Anti-pPKCθ-treated iTregs, which exhibited elevated PD1 expression and superior suppressive function, were long-lasting and accumulated in high numbers in the BM and spleen of mice following adoptive Treg transfer in humanized mouse model of GvHD. Studies have reported that Tregs can lose FOXP3 expression and take on a proinflammatory phenotype in several disease environments (Overacre et al., 2016). However, we determined that only anti-pPKCθ-treated iTregs maintained their FOXP3 expression in the BM, since we were unable to amplify stable mRNA in untreated iTregs. Of note, we detected tissue-specific changes in the alternative splicing patterns of FOXP3, PDCD1, IFNG, and IFNGR1, in anti-pPKCθ-treated iTregs. Moreover, only in anti-pPKCθ-treated iTregs recovered from the BM could we detect stable mRNA production, since splenic iTregs did not exhibit differences in 3'UTR processing of any of these iTreg genes. A host of immune cells are available to act differentially on iTregs ιν ωιωο, through direct and indirect mechanisms. Thus, one potential explanation for the differences in alternative splicing patterns we observed in anti-pPKCθ-treated iTregs in vitro and in vivo, may be attributed to the interactions of iTregs with other cell types, and additional studieds will be needed to identify these in vivo modulators.

Most strikingly, our data reveal an unknown contribution of a protein methyltransferase, PCMT1, and found to be regulated by PKCθ signaling. We showed that PCMT1 expression was downregulated when PKCθ was inhibited. Additionally, in anti-pPKCθ-treated iTregs, we observed phosphorylated PCMT1 in the nucleus, suggesting that post-translational control of PCMT1 is modulated by PKCθ signaling. The current literature suggests that PCMT1 regulates the PI3K/AKT/mTOR signaling pathway. Increased activation of AKT/GSK3β signaling is seen in the hippocampus of Pcmt1 knockout mice (Dung et al., 2016; Farrar et al., 2002). Additionally, phosphorylation of GSK3p at serine 9, which inhibits GSK3β function was low in Pcmt1$^{+/+}$ mice indicating an abundance of activated GSK3p and suggesting Pcmt1 and GSK3β may function in a positive feedback loop (Farrar et al., 2005). Considering that PKCθ and GSK3β work in opposition, it is interesting to speculate that GSK3β may phosphorylate PCMT1 to regulates its function when PKCθ is inhibited in iTregs. The AKTIGSK3β pathway is critical signaling axis in iTreg differentiation, since inhibiting mTOR promotes regulatory T cell induction (Singh et al., 2015; Sambri et al., 2011). Collectively, these suggest that inhibiting PCMT1 would promote regulatory T cell induction and agree with the data we put forth in this report.

Our data also indicate that PKCθ can regulate PCMT1 post-transcriptionally. Anti-pPKCθ-treated iTregs exhibited distinct PCMT1 splicing patterns and less unstable mRNA, in vitro. Furthermore, and consistent with our in vitro data, tissue- and cell-specific we observed a "switch" in PCMT1 RNA processing, in vivo as well. Based on these robust post-translational and post-transcriptional modification to PCMT1 downstream of PKCθ signaling, we delivered anti-PCMT1 to iTregs to further investigate PCMT1 functions in iTreg differentiation. As we predicted, anti-PCMT1 delivery also generated a higher percentage of iTregs which showed high FOXP3 and IFNγ expression, in vitro. Moreover, we found PCMT1 also interacted with hnRNPL, Anti-pPKCθ and anti-PCMT1 delivery, both, inhibited the interaction of these respective proteins with hnRNPL in the nucleus. This resulted in an inverse correlation of these interacting proteins in the cytosol. Cytosolic hnRNPL-PKCθ association was diminished, while hnRNPL-PCMT1 interactions increased following anti-pPKCθ delivery. Conversely, in anti-PCMT1-treated iTregs, cytosolic hnRNPL-PKCθ binding increased, while hnRNPL-PCMT1 interactions were attenuated. Previous reports suggested that PCMT1 is a parc of RNA nuclear export complex and can associate with multiple RBPs (Dufu et al., 2010). Considering PCMT1-hnRNPL interaction in the context of RNA export, we found that PKCθ regulates hnRNPL-RNA interactions in iTregs. Interestingly, inhibiting PKCθ or PCMT1 abrogated stable PCMT1 mRNA export to the cytoplasm, likely due to loss of hnRNPL-PCMT1 binding, and suggests that PCMT1 also regulates its own RNA export. It was also observed that PKCθ and PCMT1 selectively regulated RNA export and hnRNPL interactions with FOXP3, PDCD1, IFNG, and IFNGR1 mRNA. It remains to be determined whether anti-pPKCθ and anti-PCMT1 delivery differentially influence translational control of these mRNAs in the cytosol of iTregs.

Parallel findings obtained following anti-pPKCθ and anti-PCMT1 delivery also revealed the possibility that generating more stable iTregs resulted from epigenetic regulation of FOXP3 together with unique expression of IFNγ. To date, the most reliable marker for determining Treg stability is the methylation status of the FOXP3 TSDR (Schmidt et al., 2016). Other reports indicate that IFNγ-expressing Tregs exhibited a more stable Treg phenotype, in part due to a more highly-demethylated TSDR (Daniel et al., 2014). Intriguingly, we observed direct binding of PCMT1 to FOXP3 and IFNG genes in iTregs, and this binding could be prevented by intracellular delivery either of anti-pPKCθ or anti-PCMT1. Our data show that anti-pPKCθ delivery primarily affected PCMT1 binding to IFNG, while anti-PCMT1 delivery targeted PCMT1-FOXP3 interactions. As PCMT1 contains a domain with global methyltransferase activity, we further analyzed the methylation status of the FOXP3 TSDR in anti-PCMT1-treated iTregs. Strikingly, we observed significantly lower TSDR methylation in anti-PCMT1-treated iTregs and, more importantly, demethylated CpGs overlapped with the STAT5 binding site, consistent with a requirement for STAT5 binding for the maintenance of FOXP3 gene expression. A deeper analysis of the TSDR methylation pattern in anti-PCMT1-treated iTregs revealed that the fourth CpG island showed consistently high demethylation. We followed up this observation by running the PROMO algorithm to identify putative transcription factor binding sites surrounding this CpG. We were intrigued to find that the GATA-1 transcription factor binding site spans this demethylated CpG, and it is in close proximity to XBP1, TFIID, and RXR-α binding sites, as well (Messeguer et al., 2002; Farre et al., 2003). GATA-1 is considered a "Treg phenotype-locking" transcription factor and was found to enhance transcriptional activity of FOXP3 (Fu et al., 2012; Akimova et al., 2017). Hence, our results reinforce the idea that targeting PCMT is a beneficial strategy for strengthening iTreg stability and suppressive function.

In addition to epigenetic regulation of FOXP3 by PCMT1, further studies will elaborate the contribution of PCMT1 to FOXP3 stability at the post-translational level. PCMT1 regulates a histone deacetylase called SIRT1, which was shown to be important in Tregs. SIRT1 binds to and deacetylates FOXP3 in the cytoplasm and leads to protein instability. This interaction can sterically be inhibited by a kinase called MST1 upon its phosphorylation activity. PCMT1 inhibits MST1 activity by interacting from its kinase domain and this interaction may cause MST1 methylation that could inhibit MST1 activity and enhance FOXP3 deacetylation by SIRT1 (Li et al., 2015; Yan et al., 2013; Liang et al., 2017; Shi et al., 2017). Therefore, inhibiting PCMT1 at the protein level would also stabilize FOXP3 protein thereby promote Treg function. Our findings justify the further evaluation of RNA regulatory proteins and PKCθ signaling in the context of Treg suppressive function. Modulation of PKCθ and PCMT1 culminates in regulated alternative splicing and RNA processing decisions in iTregs so as to generate highly stable and suppressive phenotype. Thus, it is important to further clarify the conditions of human iTreg differentiation and alterations in RNA regulatory machinery in light of Treg-based immunotherapy approaches.

Altogether our data reveal that the T cell-specific kinase, PKCθ, and the protein methyltransferansferase, PCMT1, are intimately involved in controlling iTreg differentiation, stability, and function in vitro and in vivo. Furthermore, using novel cell-penetrating peptide mimics we could deliver functional antibodies across the cell membrane of human CD4 T cells, which allowed us to define and manipulate, in vitro, the cellular mechanisms that regulate iTreg differentiation. This approach shows great promise as a tool for probing intracellular signaling pathways, as well as for manipulating human immune cells, ex vivo, in the context of advancing cell-based therapies.

```
Sequences
FOXP3 3'UTR (945 bp)
                                                              (SEQ ID NO: 28)
GCTGGAGTTCCGCAAGAAACGGAGCCAGAGGCCCAGCAGGTGTTCCAACCCTACACCTGGCCCCTGA

CCTCAAGATCAAGGAAAGGAGGATGGACGAACAGGGGCCAAACTGGTGGGAGGCAGAGGTGGT

GGGGGCAGGGATGATAGGCCCTGGATGTGCCCACAGGGACCAAGAAGTGAGGTTTCCACTGTCTTG

CCTGCCAGGGCCCCTGTTCCCCCGCTGGCAGCCACCCCCTCCCCCATCATATCCTTTGCCCCAAGG

CTGCTCAGAGGGGCCCCGGTCCTGGCCCCAGCCCCCACCTCCGCCCCAGACACACCCCCCAGTCG

AGCCCTGCAGCCAAACAGAGCCTTCACAACCAGCCACACAGAGCCTGCCTCAGCTGCTCGCACAGA

TTACTTCAGGGCTGGAAAAGTCACACAGACACACAAAATGTCACAATCCTGTCCCTCACTCAACACAA

ACCCCAAAACACAGAGAGCCTGCCTCAGTACACTCAAACAACCTCAAAGCTGCATCATCACACAATC

ACACACAAGCACAGCCCTGACAACCCACACACCCCAAGGCACGCACCCACAGCCAGCCTCAGGGCC

CACAGGGGCACTGTCAACACAGGGGTGTGCCCAGAGGCCTACACAGAAGCAGCGTCAGTACCCTCA

GGATCTGAGGTCCCAACACGTGCTCGCTCACACACACGGCCTGTTAGAATTCACCTGTGTATCTCAC

GCATATGCACACGCACAGCCCCCCAGTGGGTCTCTTGAGTCCCGTGCAGACACACACAGCCACACA

CACTGCCTTGCCAAAAATACCCCGTGTCTCCCCTGCCACTCACCTCACTCCCATTCCCTGAGCCCTG

ATCCATGCCTCAGCTTAGACTGCAGAGGAACTACTCATTTATTTGGGATCCAAGGCCCCCAACCCAC

AGTACCGTCCCCAATAAA

IFNG 3'UTR (557 bp)
GGAGTCAGATGCTGTTTCGAGGTCGAAGAGCATCCCAGTAATGGTTGTCCTGCCTGCAATATTTGAA

TTTTAAATCTAAATCTATTTATTAATATTTAACATTATTTATATGGGGAATATATTTTTAGACTCATCAAT

CAAATAAGTATTTATAATAGCAACTTTTGTGTAATGAAAATGAATATCTATTAATATATGTATTATTTATA

ATTCCTATATCCTGTGACTGTCTCACTTAATCCTTTGTTTTCTGACTAATTAGGCAAGGCTATGTGATT

ACAAGGCTTTATCTCAGGGGCCAACTAGGCAGCCAACCTAAGCAAGATCCCATGGGTTGTGTGTTTA

TTTCACTTGATGATACAATGAACACTTATAAGTGAAGTGATACTATCCAGTTACTGCCGGTTTGAAAAT

ATGCCTGCAATCTGAGCCAGTGCTTTAATGGCATGTCAGACAGAACTTGAATGTGTCAGGTGACCCT

GATGAAAACATAGCATCTCAGGAGATTTCATGCCTGGTGCTTCCAAATATTGTTACAACTGTGACTG

TACCCAAA

IFNGR1 3'UTR (437 bp)
                                                              (SEQ ID NO: 29)
ATCTACTTGTGGATGATAGCGGTAAAGAGTCCTTGATTGGTTATAGACCAACAGAAGATTCCAAAGA

ATTTTCATGAGATCAGCTAAGTTGCACCAACTTTGAAGTCTGATTTTCCTGGACAGTTTTCTGCTTTAA

TTTCATGAAAAGATTATGATCTCAGAAATTGTATCTTAGTTGGTATCAACCAAATGGAGTGACTTAGTG

TACATGAAAGCGTAAAGAGGATGTGTGGCATTTTCACTTTTGGCTTGTAAAGTACAGACTTTTTTTTT

TTTTAAACAAAAAAAGCATTGTAACTTATGAACCTTTACATCCAGATAGGTTACCAGTAACGGAACAGT

ATCCAGTACTCCTGGTTCCTAGGTGAGCAGGTGATGCCCCAGGGACCTTTGTAGCCACTTCACTTTT

TTTCTTTTCTCTGCCTTGGTATAGCAT
```

PCMT1 3'UTR (663 bp)

(SEQ ID NO: 30)

AAGCAGTGGTCCAGGTGGAAGTGATTTTATCTTCTGCTCTTTCTTCTTCCACACATGCAAGGGATGAA

*TTGTAAAAGCAACATCAGCTTGACCAGTATAAAATTACAGTGGATTGCTCATCTCAGTCCTCAAAGCT*

*TTTTGAAAACCAACACCATCACAGCTTGTTTTGGACTTTGTTACACTGTTATTTTCAGCATGAAAATGT*

*GTGTTTTTTAGGGTTTCTGATTCTTCAAAGAGGCACAGAGCCAAATTGGTAGAGGAAGGATGCAAAG*

*TATAAATTTGTGTAATATTACTTTAACATGCCCATATTTTACTTGGAAATATTAAAAGAAAGGGTTCTGT*

*AAAATGGAAAACTTAGTTTGTGAATTGATTTTGAGGAGTGGTTTTTCTTTTCTTGGACACTTAATTCTGT*

*TCTGATATTAATTTATCAGATTGCTTTTGTGCATTGGATAACACCACCATTCACAAGTTAAGATTCTTG*

*GTATTTGGATATCTGTTAGATGCTACTAAGAAAATAGAGATGAGCTTTCTTTTTAAAGCTTTTGATGTG*

*GTGTCATAGAATAGCATGTTGTAGATACAATCAGCTGCTTTGTTACCTTAAAACTAGGCATTTGTAAAT*

*ATTAAACCATAAGATGGCAGGTGAT*GTCCTGTAAACACTCAGC

PDCD1 3'UTR (1298 bp)

(SEQ ID NO: 31)

TTTCCAGTGGCGAGAGAAGACCCCGGAGCCCCCCGTGCCCTGTGTCCCTGAGCAGACGGAGTATG

CCACCATTGTCTTTCCTAGCGGAATGGGCACCTCATCCCCGCCCGCACGGGCTCAGCTGACGGCC

CTCGGAGTGCCCAGCCACTGAGGCCTGAGGATCGACACTGCTCTTGGCCCCTCTCA

*CCGGCTTCCTTGGCCACCAGTGTTCTGCAGACCCTCCACCATGAGCCCGGGTCAGCGCATTTCCTCA*

*GGAGAAGCAGGCAGGGTGCAGGCCATTGCAGGCCGTCCAGGGGCTGAGCTGCCTGGGGGCGACCGGG*

*GCTCCAGCCTGCACCTGCACCAGGCACAGCCCCACCACAGGACTCATGTCTCAATGCCCACAGTGAGC*

*CCAGGCAGCAGGTGTCACCGTCCCCTACAGGGAGGGCCAGATGCAGTCACTGCTTCAGGTCCTGCCA*

*GCACAGAGCTGCCTGCGTCCAGCTCCCTGAATCTCTGCTGCTGCTGCTGCTGCTGCTGCTGCTGCCT*

*GCGGCCCGGGGCTGAAGGCGCCGTGGCCCTGCCTGACGCCCCGGAGCCTCCTGCCTGAACTTGGGG*

*GCTGGTTGGAGATGGCCTTGGAGCAGCCAAGGTGCCCCTGGCAGTGGCATCCCGAAACGCCCTGG*

*ACGCAGGGCCCAAGACTGGGCACAGGAGTGGGAGGTACATGGGGCTGGGGACTCCCCAGGAGTTA*

*TCTGCTCCCTGCAGGCCTAGAGAAGTTTCAGGGAAGGTCAGAAGAGCTCCTGGCTGTGGTGGGCAG*

*GGCAGGAAACCCCTCCACCTTTACACATGCCCAGGCAGCACCTCAGGCCCTTTGTGGGGCAGGGAA*

*GCTGAGGCAGTAAGCGGGCAGGCAGAGCTGGAGGCCTTTCAGGCCCAGCCAGCACTCTGGCCTCC*

*TGCCGCCGCATTCCACCCCAGCCCCTCACACCACTCGGGAGAGGGACATCCTACGGTCCCAAGGTC*

*AGGAGGGCAGGGCTGGGGTTGACTCAGGCCCCTCCCAGCTGTGGCCACCTGGGTGTTGGGAGGGC*

*AGAAGTGCAGGCACCTAGGGCCCCCCATGTGCCCACCCTGGGAGCTCTCCTTGGAACCCATTCCTG*

*AAATTATTTAAAGGGGTTGGCCGGGCTCCCACCAGGGCCTGGGTGGGAAGGTACAGGCGTTCCCCC*

*GGGGCCTAGTACCCCCGCCGTGGCCTATCCACTCCTCACATCCACACACTGCACCCCCACTCCTGG*

*GGCAGGGCCACCAGCATCCAGGCGGCCAGCAGG*CACCTGAGTGGCTGGGACAA

TABLE 2

List of splicing primers.

| Gene | Forward Primer (5'-3') | Reverse Primer (5'-3') |
|---|---|---|
| ACTB (Control) | GTTGTCGACGACGAGCG (SEQ ID NO: 32) | GCACAGAGCCTCGCCTT3 (SEQ ID NO: 33) |
| CD45 | ATGCAGTTTCTTAGGGA CACG (SEQ ID NO: 35) | CCAGAAGGGCTCAGAGTG GT (SEQ ID NO: 36) |
| FOXP3 | GCCCAACCCCAGGCCTG GCAAGC (SEQ ID NO: 37) | ATTTGGGAAGGTGCAGAG CAGT (SEQ ID NO: 38) |
| IFNG | CTCTTGGCTGTTACTGC CAGG (SEQ ID NO: 39) | TTCAAATATTGCAGGCAG GACAACC (SEQ ID NO: 40) |
| IFNGR1 | CCTTGTCATGCAGGGTG TGA (SEQ ID NO: 41) | CCGCTATCATCCACAAGT AGAT (SEQ ID NO: 42) |
| PCMT1 | CTGTACCTGCTCCGAGT GTG (SEQ ID NO: 44) | CCACCTGGACCACTGCTT (SEQ ID NO: 45) |
| PDCD1 | CCTGAGCAGTGGAGAAG G (SEQ ID NO: 46) | TCTTCTCTCGCCACTGGA AA (SEQ ID NO: 47) |

TABLE 3

List of 3'UTR primers.

| Gene | Forward Primer | Reverse Primer |
|---|---|---|
| ACTB (Control) | GTTGTCGACGACGAGCG (SEQ ID NO: 48) | GCACAGAGCCTCGCCTT (SEQ ID NO: 49) |
| FOXP3 | GCTGGAGTTCCGCAAGA AAC (SEQ ID NO: 50) | TTTATTGGGGACGGTACT GTGGG (SEQ ID NO: 51) |
| IFNG | GGAGTCAGATGCTGTTT CGAGGTC (SEQ ID NO: 52) | TTTGGGTACAGTCACAGT TGT (SEQ ID NO: 53) |
| IFNGR1 | ATCTACTTGTGGATGAT AGCGG (SEQ ID NO: 54) | ATGCTATACCAAGGCAGA GAA (SEQ ID NO: 55) |
| PCMT1 | AAGCAGTGGTCCAGGTGG (SEQ ID NO: 56) | GCTGAGTGTTTACAGGAC (SEQ ID NO: 57) |
| PDCD1 | TTTCCAGTGGCGAGAGAA GA (SEQ ID NO: 58) | TTGTCCCAGCCACTCAGG TG (SEQ ID NO: 59) |

REFERENCES

Abou-El-Enein et al., *Clin. Pharmacol. Ther.*, 101:35 (2017).
Akimova et al., *JCI Insight.*, 2:1-20 (2017).
Allemand et al., *Proc. Natl. Acad. Sci. USA*, 102:3605 (2005).
Altman and Kong, *Drug Discov. Today*, 19:1217 (2014).
Anderson et al., *Autoimmunity*, 39:469 (2006).
Arch et al., *Science*, 257:682 (1992).
Baier et al., *Curr Opinion Cell Biol.*, 21:262 (2009).
Barbee et al., *Ann. Pharmacother.*, 49:907 (2015).
Barouch-Bentov et al., *J. Immunol.*, 175:5126 (2005).
Barrat et al., *J. Exp. Med.*, 195:603 (2002).
Beck et al., *Nat. Rev. Immunol.*, 10:345 (2010).
Benekli et al., *Bone Marrow Transplant.*, 38:365 (2006).
Benson et al., *J. Exp. Med.*, 204:1765 (2007).
Beres et al., *Front. Immunol.*, 4:1 (2013).
Bergeron et al., *Mol. Cell. Biol.*, 35:2503 (2015).
Bi et al., *Nat. Immunol.*, 2:556 (2001).
Black, *Annu. Rev. Biochem.*, 72:291 (2003).
Blaustein et al., *Nat. Struct. Mol. Biol.*, 12:1037 (2005).
Blazar et al., *Nat. Rev. Immunol.*, 12:443 (2012).
Bluestone, *Nat. Rev. Immunol.*, 5:343 (2005).
Boieri et al., *Front. Immunol.*, 7: (2016).
Booth et al., *J. Immunol.*, 184:4317 (2010).
Boronenkov et al., *Mol. Biol. Cell.*, 9:3547 (1998).
Boschelli, *Curr. Top. Med. Chem.*, 9:640 (2009).
Bowyer et al., *Br. J. Cancer*, 114:1084 (2016).
Brekke et al., *Nat. Rev. Drug Discov.*, 2:52 (2003).
Bremm et al., *J. Immunol. Methods*, 373:36 (2011).
Brennan et al., *N. Enql. J. Med.*, 355:1967 (2006).
Brezar et al., *Front. Immunol.*, 6:1 (2015).
Bronk et al., *Front Immunol.*, 3:259 (2012).
Brunkow et al., *Nat. Genet.*, 27:8 (2001).
Cartwright et al., *Mol Biol Cell*, 22:3491 (2011).
Caspi et al., *J. Immunol.*, 152:890 (1994).
Cataldi et al., *Anat. Rec.*, 292:1135 (2009).
Cazalla et al., *Mol. Cell. Biol.*, 22:6871 (2002).
Chae et al., *Cancer Immunol. Immunother.*, 66:25 (2017).
Chalfant et al., *J. Biol. Chem.*, 273:910 (1998).
Chan et al., *Nat. Rev. Immunol.*, 10:301 (2010).
Chand et al., *Curr. Pharm. Des.*, 18:4725 (2012).
Chandler et al., *Proc. Natl. Acad. Sci. U.S.A*, 94:3596 (1997).
Chen et al., *J. Exp. Med.*, 198:1875 (2003).
Chowdary et al., *J. Autoimmun.*, 39:377 (2012).
Chu et al., *J. Exp. Med.*, 192:123 (2000).
Chuang, et al., *Nat. Immunol.*, 12:1113 (2011).
Colwill et al., *EMBO J.*, 15:265 (1996).
Cooke et al., *Blood*, 88:3230 (1996).
Cooper et al., *Cell*, 136:777 (2009).
Crabtree, *Annu. Rev. Biochem.*, 63:1045 (1994).
Curotto de Lafaille et al., *Immunity*, 30:626 (2009).
Cywin et al., *Bioorganic Med. Chem. Lett.*, 17:225 (2007).
Daniel et al., *BMC Immunol.*, 16:45 (2015).
Daniel et al., *Hum. Immunol.*, 77:146 (2016).
Daniel et al., *Int. Rev. Immunol.*, 33:195 (2014).
Daugherty et al., *Adv. Drug Deliv. Rev.*, 58:686 (2006).
de Weerd et al., *Clin. Exp. Immunol.*, 175:296 (2014).
Delgoffe et al., *Nature*, 501:252 (2013).
deRonde and Tew, *Biopolymers*, 104:265 (2015).
Do et al., *Mucosal. Immunol.*, 9:137 (2016).
Dufu et al., *Genes Dev.*, 24:2043 (2010).
Dung et al., *BMB Rep.*, 49:437 (2016).
Edmond et al., *EMBO J.*, 30:510 (2011).
Enünlü et al., *Biophys. Res. Commun.*, 309:44 (2003).
Evenou et al., *J. Pharmacol. Exp. Ther.*, 330:792 (2009).
Fang et al., *J. Cell Sci. Ther.*, 4: (2013).
Farrar et al., *Aging Cell*, 4:1 (2005).
Farrar et al., *J. Biol. Chem.*, 277:27856 (2002).
Farre et al., *Nucleic Acids Res.*, 31:3651 (2003).
Fehérvári et al., *Int. Immunol.*, 16:1769 (2004).
Ferber et al., *J. Immunol.*, 156:5 (1996).
Fischbach et al., *Sci. Transl. Med.*, 5: (2013).
Fontenot et al., *Immunity*, 22:329 (2005).
Fu et al., *J. Immunol.*, 194:388 (2015).
Fu et al., *Nat. Immunol.*, 13:972 (2012).
Fu, *RNA*, 1:663 (1995).
Ganguly et al., *Blood*, 124:2131 (2014).
Ganguly et al., *Front. Immunol.*, 7:1 (2016).

Gaudreau et al., *J. Immunol.*, 188:5377 (2012).
Gaudreau et al., *Sci. Rep.*, 6:27379 (2016).
Gavin et al., *Proc. Natl. Acad. Sci. U.S.A.*, 103:6659 (2006).
Gongalves-Lopes et al., *Microbes Infect.*, 18:639 (2016).
Grabowski, *Cell*, 92:709 (1998).
Graveley et al., *Mol. Cell.*, 1:765 (1998).
Gruber et al., *Immunol. Lett.*, 132:6 (2010).
Gruber et al., *Mol. Immunol.*, 46:2071 (2009).
Gruber et al., *Rev. RNA*, 5:183 (2014).
Gruber et al., *Sci. Siqnal.*, 2: (2009).
Guang et al., *Mol. Cell. Biol.*, 25:6303 (2005).
Guillard et al., *Trends Biotech.*, 33:163 (2015).
Gupta et al., *Mol. Immunol.*, 46:213 (2008).
Hage-Sleiman et al., *J. Immunol. Res.*: (2015).
Hahn et al., *Front. Immunol.*, 6: (2015).
Hammarskjold et al., *J. Cell Biol.*, 216:1875 (2017).
Han et al., *Biochem. J.*, 430:379 (2010).
Hawse et al., *J. Immunol.*, 199:589 (2017).
He et al., *J. Invest. Dermatol.*, 134:975 (2014).
Heinrichs et al., *Oncoimmunoloqy*, 5: e1146842 (2016).
Hermiston et al., *J. Clin. Invest.*, 109:9 (2002).
Herrmann et al., *J. Biol. Chem.*, 279:48774 (2004).
Heyd et al., *Mol. Cell.*, 40:126 (2010).
Ho et al., *Biochem.*, 40:10334 (2001).
Hoffmann et al., *J. Exp. Med.*, 196:389 (2002).
Hong et al., *Proc. Natl. Acad. Sci. U.S.A*, 102:6449 (2005).
Hori et al., *Science*, 299:1057 (2003).
Horwitz et al., *Nat. Med.*, 3:1037 (1997).
House et al., *Nat. Struct. Mol. Biol.*, 13:937 (2006).
Hsieh et al., *BMJ Case Rep.*: (2017).
Huehn et al., *Nat. Rev. Immunol.*, 9:83 (2009).
Hui et al., *RNA*, 9:931 (2003).
Hung et al., *RNA*, 14:284 (2008).
Iadevaia et al., *Biomolecules*, 5:2207 (2015).
Imai and Takaoka, *Nat Rev Cancer*, 6:714 (2006).
Inoue, et al., *J. Biol. Chem.*, 252:7610 (1977).
Ip et al., *RNA*, 13:563 (2007).
Isakov and Altman, *Front Immunol.*, 3:273, (2012).
Isakov et al., *Annu. Rev. Immunol.*, 20:761 (2002).
Isakov, *J Clin Cell Immunol*, 12: (2012).
Isakov, *J. Clin. Cell Immunol.*, (2012).
Joffre et al., *Blood*, 103:4216 (2004).
Jones et al., *J. Immunol.*, 158:5997 (1997).
Kafasla et al., *Nat. Immunol.*, 15:492 (2014).
Kandus et al., *Transplantation*, 89:1022 (2010).
Kavanagh et al., *Nucleic Acids Res.*, 33:1309 (2005).
Keene, *Nat. Rev. Genet.*, 8:533 (2007).
Khattri et al., *Nat. Immunol.*, 4:337 (2003).
Koenecke et al., *J. Immunol.*, 189:2890 (2012).
Komanduri et al., *Blood*, 117:751 (2011).
Kong et al., *Nat. Immunol.*, 12:1105 (2011).
Konig et al., *PLoS One*, 7:1 (2012).
Kornblihtt et al., *Nat. Rev. Mol. Cell Biol.*, 14:153 (2013).
Krakowski et al., *Eur. J. Immunol.*, 26:1641 (1996).
Kukreja et al., *J. Clin. Invest.*, 109:131 (2002).
Kwon et al., Endo. *Metabol. Immune Disord. Drug Tarqets*, 10:367 (2010).
Kwon et al., *J. Immunol.*, 188:5887 (2012).
Lal et al., *Blood*, 114:3727 (2009).
Lamba and Ghosh, *Curr. Pharmaceut. Design*, 18:2936 (2012).
Lee et al., *PLoS Biol.*, 5:0281 (2007).
Lee et al., *PLoS One*, 10: (2015).
Lemaire et al., *Eur. J. Immunol.*, 29:823 (1999).
Lewkowicz et al., *J. Immunol.*, 177:7155 (2006).
Li et al., *Cell*, 158:734 (2014).
Li et al., *J. Biol. Chem.*, 290:30762 (2015).
Li et al., *J. Cell Sci.*, 129:2448 (2016).
Liang et al., *Sci. Rep.*, 7:9201 (2017).
Lin et al., *Blood*, 124:3699 (2014).
Lin et al., *Nat. Struct. Mol. Biol.*, 15:819 (2008).
Lindley et al., *Diabetes*, 54:92 (2005).
Liu et al., *J. Exp. Med.*, 203:1701 (2006).
Lopez-Huertas et al., *J. Biol. Chem.*, 286:27363 (2011).
Lu et al., *Biol. Blood Marrow Transplant.*, 15:1347 (2009).
Lu et al., *Clin. Transplant.*, 26:158 (2012).
Lu et al., *Proc. Natl. Acad. Sci.*, 111:E3432 (2014).
Lynch, *Mol. Cell. Biol.*, 20:70 (2000).
Lynch, *Nat. Rev. Immunol.*, 4:931 (2004).
MacKay et al., *PLoS One*, 7: (2012).
Mahmud et al., *Jak-Stat.*, 2:e23154 (2013).
Manicassamy et al., *Cell. Mol. Immunol.*, 3:263 (2006).
Manicassamy et al., *J. Immunol.*, 178:312 (2007).
Manicassamy et al., *Journal of immunoloqy*, 181:513 (2008).
Manley et al., *Genes Dev.*, 10:1569 (1996).
Marsland et al., *J. Exp. Med.*, 200:181 (2004).
Martinez et al., *Immunol. Rev.*, 253:216 (2013).
Martinez et al., *RNA*, 18:1029 (2012).
Martin-Liberal et al., *Expert Opin. Drug Saf.*, 14:957 (2015).
Matheu et al., *Nat. Commun.*, 6: (2015).
Matlin et al., *Nat. Rev. Mol. Cell Biol.*, 6:386 (2005).
Matsumoto et al, *Immunity*, 23:575 (2005).
Matter et al., *Nature*, 420:691 (2002).
McCuaig et al., *Front Immunol.*, 6:562 (2015).
McCuaig et al., *Front. Immunol.*, 6: (2015).
Meininger et al., *Nat. Commun.*, 7:11292 (2016).
Melton et al., *Mol. Cell. Biol.*, 27:6972 (2007).
Messeguer et al., *Bioinformatics*, 18:333 (2002).
Misra et al., *J. Biol. Chem.*, 277:20011 (2002).
Misra et al., *J. Immunol.*, 172:4676 (2004).
Mizui et al., *Immunity*, 28:302 (2008).
Mochly-Rosen et al., *Nat. Rev. Drug Discov.*, 11:937 (2012).
Nguyen et al., *Blood*, 109:2649 (2007).
Nielsen et al., *Cell. Immunol.*, 235:109 (2005).
Nishibori et al., *J. Exp. Med.*, 199:25 (2004).
Nurden et al., *Thromb. Haemost.*, 92:820 (2004).
Oberdoerffer et al., *Science*, 321:686 (2008).
Ogawa et al., *J. Immunol.*, 192:475 (2014).
Ohkura et al., *Immunity*, 38:414 (2013).
Okazaki et al., *J. Exp. Med.*, 208:395 (2011).
Olsson, *Immunol. Rev.*, 144:245 (1995).
Ontaneda et al., *Expert Rev. Clin. Immunol.*, 9:189 (2013).
Overacre et al., *Curr. Opin. Immunol.*, 39:39 (2016).
Ozay et al., *Mol. Ther.*, 24:2118 (2016).
Pallandre et al., *J. Immunol.*, 179:7593 (2007).
Pankratz et al., *FASEB J.*, 28:3435 (2014).
Park et al., *Cell. Immunol.*, 278:76 (2012).
Parmar et al., *Blood*, 127:962 (2016).
Patel et al., *J. Biol. Chem.*, 276:22648 (2001).
Patel et al., *J. Biol. Chem.*, 280:14302 (2005).
Paz et al., *Nucleic Acids Res.*, 42:361 (2014).
Pfeifhofer et al., *J. Exp. Med.*, 197:1525 (2003).
Pfeifhofer-Obermair et al., *Front Immunol.*, 3:220 (2012).
Pilat et al., *Am. J. Transplant.*, 10:751 (2010).
Pillai et al., *Clin. Immunol.*, 123:18 (2007).
Polansky et al., *Eur. J. Immunol.*, 38:1654 (2008).
Prasad et al., *Mol. Cell. Biol.*, 23:4139 (2003).
Preußner et al., *Nucleic Acids Res.*, 40:5666 (2012).
Qian et al., *Nucleic Acids Res.*, 39:6161 (2011).
Radziewicz et al., *J. Clin. Invest.*, 119:450 (2009).
Raimondi et al., *J. Immunol.*, 176:2808 (2006).
Ray et al., *Nature*, 499:172 (2013).
Reichert, *mAbs*, 4:413 (2012).

Revil et al., *Mol. Cell. Biol.*, 27:8431 (2007).
Riley et al., *Immunity*, 30:656 (2009).
Riley et al., *Immunity*, 30:656 (2009).s
Roderick et al., *J. Exp. Med.*, 210:1311 (2013).
Roncarolo et al., *Nat. Rev. Immunol.*, 7:585 (2007).
Rosa Bacchetta et al., *J. Exp. Med.*, 179:493 (1994).
Rosenberg et al., *Science*, 348:62 (2015).
Rossbach et al., *Mol. Cell. Biol.*, 29:1442 (2009).
Rosse, et al., *Nat. Rev. Mol. Cell Biol.*, 11:103 (2010).
Rothrock et al., *EMBO J.*, 24:2792 (2005).
Rothrock et al., *Mol. Cell.*, 12:1317 (2003).
Roybal et al., *Sci. Signal.*, 3: (2010).
Rudensky, *Immunol. Rev.*, 241:260 (2012).
Ryder et al., *J. Rheumatol.*, 39:279 (2010).
Sakaguchi et al., *Nat. Rev. Immunol.*, 10:490 (2010).
Sambri et al., *J. Biol. Chem.*, 286:43690 (2011).
Sarris et al., *Immunity*, 28:402 (2008).
Sawitzki et al., *J. Exp. Med.*, 201:1925 (2005).
Schmidt et al., *PLoS One*, 11:1 (2016).
Screaton et al., *Proc. Natl. Acad. Sci. U.S.A.*, 94:4615-4619 (1997).
Screaton1 et al., *EMBO J.*, 14:4336 (1995).
Seco et al., *Protein*, 80:269 (2012).
Sedwick et al., *Mol. Immunol.*, 41:675 (2004).
Sela et al., *J. Exp. Med.*, 208:2489 (2011).
Sgolastra et al., *Biomacromolecules*, 15:812 (2014).
Shav-Tal et al., *FEBS Lett.*, 531:109 (2002).
Sheppard et al., *FEBS Lett.*, 574:37 (2004).
Shevach, *Immunity*, 30:636 (2009).
Shi et al., *Blood*, 120:1624 (2012).
Shi et al., *Transl. Stroke Res.*, 8:474 (2017).
Shin et al., *Front Immunol.* 5:249 (2014).
Simonetta et al., *Eur. J. Immunol.*, 40:2528 (2010).
Singer et al., *Front. Immunol.*, 5:1 (2014).
Singh et al., *Curr. Treat. Options Oncol.*, 17: (2016).
Singh et al., *J. Immunol.*, 195:5667 (2015).
Smith et al., *Immunology*, 119:203 (2006).
Smith et al., *J. Biol. Chem.*, 272:15675 (1997).
Solomou et al., *Blood*, 107:3983 (2006).
Spence et al., *Curr. Opin. Immunol.*, 37:11 (2015).
Stangl et al., *Nat. Struct. Biol.*, 10:33 (2003).
Stroopinsky et al., *Cancer Immunol. Immunother.*, 61:1233 (2012).
Sumoza-Toledo et al., *J.Immunol.*, 176:5779 (2006).
Sun et al., *Nature*, 404:402 (2000).
Sun, *Front. Immunol.*, 3:1 (2012).
Sutcliffe et al., *Front Immunol.*, 3:260 (2012).
Sutcliffe et al., *Mol. Cell.*, 41:704 (2011).
Sutcliffe et al., *Transcription*, 2:189 (2011).
Taams et al., *Hum. Immunol.*, 66:222 (2005).
Tabellini et al., *Exp. Cell Res.*, 287:143 (2003).
Tang et al., *Perspect. Med.*, 3: (2013).
Taylor et al., *Blood*, 104:3804 (2004).
Taylor et al., *Blood*, 99:3493 (2002).
Tezgel et al., *Mol. Ther.*, 21:201 (2013).
Thaventhiran, *J. Clin. Cell. Immunol.*, 1: (2013).
Theocharides et al., *Haematologica*, 101:5 (2016).
Toker et al., *Sci. Signal.*: (2018).
Torchilin, *Drug Discov. Today Technol.*, 5 (2008).
Torchilin, *Drug Discov. Today Technol.*, 5: (2009).
Tran et al., *J. Immunol.*, 164:2759 (2000).
Trojan et al., *PLoS One*, 12:1 (2017).
Trojan et al., *Transpl. Immunol.*, 39:1 (2016).
Trowbridge et al., *Annu. Rev. Immunol.*, 12:85 (1994).
Trowbridge et al., *BBA-Mol. Cell Res.*, 1095:46 (1991).
Trzonkowski et al., *Clin. Immunol.*, 133:22 (2009).
Trzonkowski et al., *Sci. Transl. Med.*, 7: (2015).
Uehata et al., *Cell*, 153:1036 (2013).
Urtreger et al., *IUBMB Life*, 64:18 (2012).
Valenzuela et al., *J. Clin. Invest.*, 119:3774 (2009).
Van Oordt et al., *J. Cell Biol.*, 149:307 (2000).
Venet et al., *J. Immunol.*, 177:6540 (2006).
Vignali et al., *Nat. Rev. Immunol.*, 8:523 (2008).
Vu et al., *J. Biol. Chem.*, 288:8575 (2013).
Walsh et al., *J. Clin. Invest.*, 114:1398 (2004).
Walter et al., *Arthritis Rheumatol.*, 68:103 (2016).
Wang et al., *Cell Rep.*, 5:849 (2013).
Wang et al., *Curr. Opin. Genet. Dev.*, 7:205 (1997).
Wang et al., *Front Immunol.*, 3:197 (2012).
Wang et al., *J. Clin. Invest.*, 116:2434 (2006).
Wang et al., *Proc. Natl. Acad. Sci. U.S.A.*, 94:4360 (1997).
Wang et al., *Scand. J. Immunol.*, 54:453 (2001).
Wartewig et al., *Nature*: (2017).
Waterston et al., *Nature*, 420:520 (2002).
Wei et al., *Am. J. Transplant.*, 10:69 (2010).
Weiss et al., *Cell*, 76:263 (1994a).
Willenborg et al., *J. Immunol.*, 157:3223 (1996).
Woo et al., *Eur. J. Immunol.*, 40:1768 (2010).
Wood et al., *Nat. Rev. Immunol.*, 3:199 (2003).
Wood et al., *Trends Immunol.*, 27:183 (2006).
Wu et al., *J. Immunol.*, 189:3497 (2012).
Xie et al., *Science*, 280:443 (1998).
Yan et al., *Int. J. Cardiol.*, 168:3291 (2013).
Yang et al., *J. Proteome Res.*, 12:4566 (2013).
Yokosuka et al., *Immunity*, 29:589 (2008).
Yokosuka et al., *J. Exp. Med.*, 209:1201 (2012).
Zanin-Zhorov et al., *Science*, 328:372 (2010).
Zanin-Zhorov et al., *Trends Immunol.*, 32:358 (2011).
Zara et al., *Histol. Histopathol.*, 26:59 (2011).
Zhang et al., *Adv. Pharmacol.*, 66:267 (2013).
Zhang et al., *Blood*, 117:299 (2011).
Zhang et al., *Immunity*, 44:1034 (2016).
Zhong et al., *Mol. Cell.*, 35:1 (2009).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. An ex vivo method to prepare regulatory T cells, comprising:
providing complexes comprising a modulator of T cells that induces regulatory T cells (Tregs) and a polymer comprising a compound of formula (I):

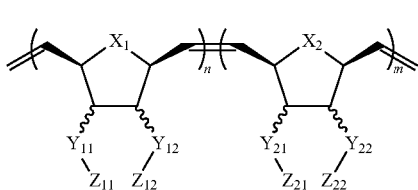

wherein each of $X_1$ and $X_2$ independently is O or —$CH_2$—; each of $Y_{11}$ and $Y_{12}$ is independently a linking group comprising a carbonyl group; each of $Z_{11}$ and $Z_{12}$ comprises

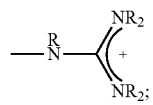

each of $Y_{21}$ and $Y_{22}$ is independently a linking group comprising a carbonyl group; each of $Z_{21}$ and $Z_{22}$ is $OR_z$, wherein each $R_z$ is independently alkyl, substituted alkyl, aryl, or substituted aryl; each of R and $R_2$ is hydrogen; and each of m and n independently is selected from an integer from 2 to 50; and
contacting a population of mammalian cells comprising T cells with the complexes in an amount and under conditions effective to induce an increased number of Tregs relative to a corresponding population that is contacted with the polymer but not the modulator or contacted with the modulator but not the polymer, or not contacted with the complexes, wherein the modulator is a modulator of protein kinase C-theta, wherein the modulator comprises an antibody or a fragment thereof that is specific for the phosphorylated form of protein kinase C-theta, and wherein the antibody or the fragment thereof binds to protein kinase C-theta that is phosphorylated at residue 538.

2. The method of claim 1 wherein the antibody or the fragment thereof comprises a humanized antibody.

3. The method of claim 1 wherein the mammalian cells are human cells.

4. The method of claim 1 wherein the population comprises peripheral blood mononuclear cells (PBMCs).

5. The method of claim 1 wherein the population comprises $CD4^+$ T cells.

6. The method of claim 1 wherein the population that is contacted with the complexes is further contacted with an agent that activates the cells in the population.

7. The method of claim 1 wherein the population that is contacted with the complexes is further contacted with anti-CD3 and/or anti-CD28 antibodies or CD3 or CD28 binding fragments thereof.

8. The method of claim 1 wherein the Tregs in the population contacted with the complexes have enhanced suppressor function relative to Tregs in the corresponding population.

9. The method of claim 1 wherein the Tregs in the population contacted with the complexes have increased amounts or concentrations of phospho-STAT5 and/or CTLA-4 relative to Tregs in the corresponding population.

10. The method of claim 1 wherein the increased number of Tregs comprise cytosolic protein kinase C-theta.

11. The method of claim 1 wherein the Tregs in the population contacted with the complexes have increased amounts or concentrations of CD25 or FOXP3 relative to Tregs in the corresponding population.

12. The method of claim 1 wherein the polymer comprises a monomer of the formula:

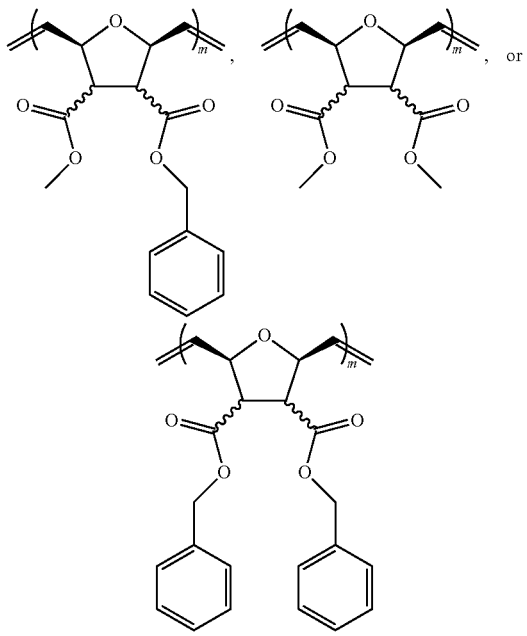

or the block copolymers:

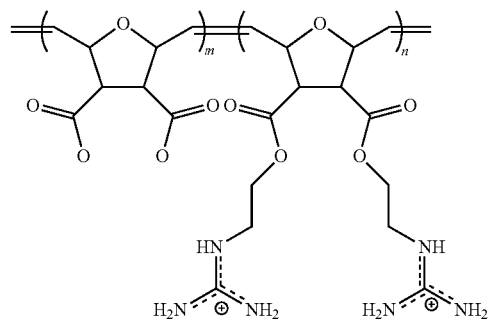

wherein m is 5 to 25 and n is 3 to 15.

13. The method of claim 1 further comprising isolating the Tregs in the population contacted with the complexes.

* * * * *

SEQUENCE LISTING

<160> NUMBER OF SEQ ID NOS: 65

<210> SEQ ID NO 1
<211> LENGTH: 17
<212> TYPE: DNA
<213> ORGANISM: Artificial Sequence
<220> FEATURE:

<223> OTHER INFORMATION: A synthetic primer

<400> SEQUENCE: 1
gttgtcgacg acgagcg                                                     17

<210> SEQ ID NO 2
<211> LENGTH: 17
<212> TYPE: DNA
<213> ORGANISM: Artificial Sequence
<220> FEATURE:
<223> OTHER INFORMATION: A synthetic primer

<400> SEQUENCE: 2
gcacagagcc tcgcctt                                                     17

<210> SEQ ID NO 3
<211> LENGTH: 20
<212> TYPE: DNA
<213> ORGANISM: Artificial Sequence
<220> FEATURE:
<223> OTHER INFORMATION: A synthetic primer

<400> SEQUENCE: 3
ctacctgggc ataggcaacg                                                  20

<210> SEQ ID NO 4
<211> LENGTH: 18
<212> TYPE: DNA
<213> ORGANISM: Artificial Sequence
<220> FEATURE:
<223> OTHER INFORMATION: A synthetic primer

<400> SEQUENCE: 4
gcttttcaca ttctggct                                                    18

<210> SEQ ID NO 5
<211> LENGTH: 20
<212> TYPE: DNA
<213> ORGANISM: Artificial Sequence
<220> FEATURE:
<223> OTHER INFORMATION: A synthetic primer

<400> SEQUENCE: 5
tgaccaaggc ttcatctgtg                                                  20

<210> SEQ ID NO 6
<211> LENGTH: 20
<212> TYPE: DNA
<213> ORGANISM: Artificial Sequence
<220> FEATURE:
<223> OTHER INFORMATION: A synthetic primer

<400> SEQUENCE: 6
gaggaactct gggaatgtgc                                                  20

<210> SEQ ID NO 7
<211> LENGTH: 21
<212> TYPE: DNA
<213> ORGANISM: Artificial Sequence
<220> FEATURE:
<223> OTHER INFORMATION: A synthetic primer

<400> SEQUENCE: 7
ctcttggctg ttactgccag g                                                21

```
<210> SEQ ID NO 8
<211> LENGTH: 21
<212> TYPE: DNA
<213> ORGANISM: Artificial Sequence
<220> FEATURE:
<223> OTHER INFORMATION: A synthetic primer

<400> SEQUENCE: 8
ctccacactc ttttggatgc t                                        21

<210> SEQ ID NO 9
<211> LENGTH: 20
<212> TYPE: DNA
<213> ORGANISM: Artificial Sequence
<220> FEATURE:
<223> OTHER INFORMATION: A synthetic primer

<400> SEQUENCE: 9
ggttgccaag ccttgtctga                                          20

<210> SEQ ID NO 10
<211> LENGTH: 19
<212> TYPE: DNA
<213> ORGANISM: Artificial Sequence
<220> FEATURE:
<223> OTHER INFORMATION: A synthetic primer

<400> SEQUENCE: 10
agggagttca catgcgcct                                           19

<210> SEQ ID NO 11
<211> LENGTH: 20
<212> TYPE: DNA
<213> ORGANISM: Artificial Sequence
<220> FEATURE:
<223> OTHER INFORMATION: A synthetic primer

<400> SEQUENCE: 11
tcactgttct gggtctggag                                          20

<210> SEQ ID NO 12
<211> LENGTH: 20
<212> TYPE: DNA
<213> ORGANISM: Artificial Sequence
<220> FEATURE:
<223> OTHER INFORMATION: A synthetic primer

<400> SEQUENCE: 12
cacttggcag tgaggaaaga                                          20

<210> SEQ ID NO 13
<211> LENGTH: 24
<212> TYPE: DNA
<213> ORGANISM: Artificial Sequence
<220> FEATURE:
<223> OTHER INFORMATION: A synthetic primer

<400> SEQUENCE: 13
aaggtttctc agcaaactac agtg                                     24

<210> SEQ ID NO 14
<211> LENGTH: 22
<212> TYPE: DNA
<213> ORGANISM: Artificial Sequence
<220> FEATURE:
<223> OTHER INFORMATION: A synthetic primer
```

```
<400> SEQUENCE: 14
gggaagaagc tgtgatctgg tc                                              22

<210> SEQ ID NO 15
<211> LENGTH: 19
<212> TYPE: DNA
<213> ORGANISM: Artificial Sequence
<220> FEATURE:
<223> OTHER INFORMATION: A synthetic primer

<400> SEQUENCE: 15
ccctggtggt tggtgtcgt                                                  19

<210> SEQ ID NO 16
<211> LENGTH: 21
<212> TYPE: DNA
<213> ORGANISM: Artificial Sequence
<220> FEATURE:
<223> OTHER INFORMATION: A synthetic primer

<400> SEQUENCE: 16
gcctggctcc tattgtccct c                                               21

<210> SEQ ID NO 17
<211> LENGTH: 23
<212> TYPE: DNA
<213> ORGANISM: Artificial Sequence
<220> FEATURE:
<223> OTHER INFORMATION: A synthetic primer

<400> SEQUENCE: 17
ctatcaatag ccgagaaacc atg                                             23

<210> SEQ ID NO 18
<211> LENGTH: 20
<212> TYPE: DNA
<213> ORGANISM: Artificial Sequence
<220> FEATURE:
<223> OTHER INFORMATION: A synthetic primer

<400> SEQUENCE: 18
ctcatccaac ggagactccc                                                 20

<210> SEQ ID NO 19
<211> LENGTH: 20
<212> TYPE: DNA
<213> ORGANISM: Artificial Sequence
<220> FEATURE:
<223> OTHER INFORMATION: A synthetic primer

<400> SEQUENCE: 19
acatttgagg agctgcgact                                                 20

<210> SEQ ID NO 20
<211> LENGTH: 20
<212> TYPE: DNA
<213> ORGANISM: Artificial Sequence
<220> FEATURE:
<223> OTHER INFORMATION: A synthetic primer

<400> SEQUENCE: 20
cctccagaga cacctgcttc                                                 20

<210> SEQ ID NO 21
<211> LENGTH: 20
```

```
<212> TYPE: DNA
<213> ORGANISM: Artificial Sequence
<220> FEATURE:
<223> OTHER INFORMATION: A synthetic primer

<400> SEQUENCE: 21
gctgaagaag cccttatga                                                      20

<210> SEQ ID NO 22
<211> LENGTH: 20
<212> TYPE: DNA
<213> ORGANISM: Artificial Sequence
<220> FEATURE:
<223> OTHER INFORMATION: A synthetic primer

<400> SEQUENCE: 22
tcttcctccg ggctttaact                                                     20

<210> SEQ ID NO 23
<211> LENGTH: 20
<212> TYPE: DNA
<213> ORGANISM: Artificial Sequence
<220> FEATURE:
<223> OTHER INFORMATION: A synthetic primer

<400> SEQUENCE: 23
tgaccaaggc ttcatctgtg                                                     20

<210> SEQ ID NO 24
<211> LENGTH: 20
<212> TYPE: DNA
<213> ORGANISM: Artificial Sequence
<220> FEATURE:
<223> OTHER INFORMATION: A synthetic primer

<400> SEQUENCE: 24
gaggaactct gggaatgtgc                                                     20

<210> SEQ ID NO 25
<211> LENGTH: 21
<212> TYPE: DNA
<213> ORGANISM: Artificial Sequence
<220> FEATURE:
<223> OTHER INFORMATION: A synthetic primer

<400> SEQUENCE: 25
ctcttggctg ttactgccag g                                                   21

<210> SEQ ID NO 26
<211> LENGTH: 21
<212> TYPE: DNA
<213> ORGANISM: Artificial Sequence
<220> FEATURE:
<223> OTHER INFORMATION: A synthetic primer

<400> SEQUENCE: 26
ctccacactc ttttggatgc t                                                   21

<210> SEQ ID NO 27
<211> LENGTH: 20
<212> TYPE: DNA
<213> ORGANISM: Artificial Sequence
<220> FEATURE:
<223> OTHER INFORMATION: A synthetic primer

<400> SEQUENCE: 27
```

```
tgtttggggg tagaggattt                                                 20

<210> SEQ ID NO 28
<211> LENGTH: 945
<212> TYPE: DNA
<213> ORGANISM: Homo sapiens

<400> SEQUENCE: 28
gctggagttc cgcaagaaac ggagccagag gcccagcagg tgttccaacc ctacacctgg     60
cccctgacct caagatcaag gaaaggagga tggacgaaca ggggccaaac tggtgggagg    120
cagaggtggt gggggcaggg atgataggcc ctggatgtgc ccacagggac caagaagtga    180
ggtttccact gtcttgcctg ccagggcccc tgttccccg ctggcagcca ccccctcccc     240
catcatatcc tttgccccaa ggctgctcag aggggcccg gtcctggccc cagccccac      300 ctccgcccca gacacacccc ccagtcgagc cctgcagcca aacagagcct tcacaaccag    360
ccacacagag cctgcctcag ctgctcgcac agattacttc agggctggaa aagtcacaca    420
gacacacaaa atgtcacaat cctgtccctc actcaacaca aaccccaaaa cacagagagc    480
ctgcctcagt acactcaaac aacctcaaag ctgcatcatc acacaatcac acacaagcac    540
agccctgaca acccacacac cccaaggcac gcacccacag ccagcctcag ggcccacagg    600
ggcactgtca acacaggggt gtgcccagag gcctacacag aagcagcgtc agtaccctca    660
ggatctgagg tcccaacacg tgctcgctca cacacacggc ctgttagaat tcacctgtgt    720
atctcacgca tatgcacacg cacagccccc cagtgggtct cttgagtccc gtgcagacac    780
acacagccac acacactgcc ttgccaaaaa taccccgtgt ctcccctgcc actcacctca    840
ctcccattcc ctgagccctg atccatgcct cagcttagac tgcagaggaa ctactcattt    900
atttgggatc caaggccccc aacccacagt accgtcccca ataaa                    945

<210> SEQ ID NO 29
<211> LENGTH: 437
<212> TYPE: DNA
<213> ORGANISM: Homo sapiens

<400> SEQUENCE: 29
atctacttgt ggatgatagc ggtaaagagt ccttgattgg ttatagacca acagaagatt     60
ccaaagaatt ttcatgagat cagctaagtt gcaccaactt tgaagtctga ttttcctgga    120
cagttttctg ctttaatttc atgaaaagat tatgatctca gaaattgtat cttagttggt    180
atcaaccaaa tggagtgact tagtgtacat gaaagcgtaa agaggatgtg tggcattttc    240
acttttggct tgtaaagtac agacttttt ttttttttaa acaaaaaaag cattgtaact     300
tatgaacctt tacatccaga taggttacca gtaacggaac agtatccagt actcctggtt    360
cctaggtgag caggtgatgc cccagggacc tttgtagcca cttcactttt tttcttttct    420
ctgccttggt atagcat                                                   437

<210> SEQ ID NO 30
<211> LENGTH: 663
<212> TYPE: DNA
<213> ORGANISM: Homo sapiens

<400> SEQUENCE: 30
aagcagtggt ccaggtggaa gtgattttat cttctgctct tcttcttcc acacatgcaa      60 gggatgaatt gtaaaagcaa catcagcttg accagtataa aattacagtg gattgctcat    120
ctcagtcctc aaagcttttt gaaaaccaac accatcacag cttgttttgg actttgttac    180
```

```
actgttattt tcagcatgaa aatgtgtgtt ttttagggt ttctgattct tcaaagaggc      240
acagagccaa attggtagag gaaggatgca aagtataaat ttgtgtaata ttactttaac      300
atgcccatat tttacttgga aatattaaaa gaaagggttc tgtaaaatgg aaaacttagt      360
ttgtgaattg attttgagga gtggttttttc ttttcttgga cacttaattc tgttctgata      420
ttaatttatc agattgcttt tgtgcattgg ataacaccac cattcacaag ttaagattct      480
tggtatttgg atatctgtta gatgctacta agaaaataga gatgagcttt ctttttaaag      540
cttttgatgt ggtgtcatag aatagcatgt tgtagataca atcagctgct ttgttacctt      600
aaaactaggc atttgtaaat attaaaccat aagatggcag gtgatgtcct gtaaacactc      660
agc                                                                   663
```

<210> SEQ ID NO 31
<211> LENGTH: 1298
<212> TYPE: DNA
<213> ORGANISM: Homo sapiens

<400> SEQUENCE: 31

```
tttccagtgg cgagagaaga ccccggagcc ccccgtgccc tgtgtccctg agcagacgga       60
gtatgccacc attgtctttc ctagcggaat gggcacctca tccccgccc  gcagggctc      120 agctgacggc cctcggagtg cccagccact gaggcctgag gatggacact gctcttggcc      180
cctctgaccg gcttccttgg ccaccagtgt tctgcagacc ctccaccatg agcccgggtc      240
agcgcatttc ctcaggagaa gcaggcaggg tgcaggccat tgcaggccgt ccaggggctg      300
agctgcctgg gggcgaccgg ggctccagcc tgcacctgca ccaggcacag ccccaccaca      360
ggactcatgt ctcaatgccc acagtgagcc caggcagcag gtgtcaccgt cccctacagg      420
gagggccaga tgcagtcact gcttcaggtc ctgccagcac agagctgcct gcgtccagct      480
ccctgaatct ctgctgctgc tgctgctgct gctgctgctg cctgcggccc ggggctgaag      540
gcgccgtggc cctgcctgac gccccggagc ctcctgcctg aacttggggg ctggttggag      600
atggccttgg agcagccaag gtgccctgg  cagtggcatc ccgaaacgcc ctggacgcag      660
ggcccaagac tgggcacagg agtgggaggt acatgggggct ggggactccc caggagttat      720
ctgctccctg caggcctaga gaagtttcag ggaaggtcag aagagctcct ggctgtggtg      780
ggcagggcag gaaaccctc  caccttaca  catgcccagg cagcacctca ggcccttgt       840 ggggcaggga agctgaggca gtaagcgggc aggcagagct ggaggccttt caggcccagc      900
cagcactctg gcctcctgcc gccgcattcc accccagccc ctcacaccac tcgggagagg      960
gacatcctac ggtcccaagg tcaggagggc agggctgggg ttgactcagg cccctcccag     1020
ctgtggccac ctgggtgttg ggagggcaga agtgcaggca cctagggccc ccatgtgcc      1080 caccctggga gctctccttg gaacccattc ctgaaattat ttaaagggggt tggccgggct     1140 cccaccaggg cctgggtggg aaggtacagg cgttcccccg gggcctagta ccccgccgt      1200 ggcctatcca ctcctcacat ccacacactg caccccact  cctggggcag ggccaccagc     1260
atccaggcgg ccagcaggca cctgagtggc tgggacaa                             1298
```

<210> SEQ ID NO 32
<211> LENGTH: 17
<212> TYPE: DNA
<213> ORGANISM: Artificial Sequence
<220> FEATURE:
<223> OTHER INFORMATION: A synthetic primer

```
<400> SEQUENCE: 32
gttgtcgacg acgagcg                                                   17

<210> SEQ ID NO 33
<211> LENGTH: 17
<212> TYPE: DNA
<213> ORGANISM: Artificial Sequence
<220> FEATURE:
<223> OTHER INFORMATION: A synthetic primer

<400> SEQUENCE: 33
gcacagagcc tcgcctt                                                   17

<210> SEQ ID NO 34
<211> LENGTH: 20
<212> TYPE: DNA
<213> ORGANISM: Artificial Sequence
<220> FEATURE:
<223> OTHER INFORMATION: A synthetic primer

<400> SEQUENCE: 34
tatcacccca cctaaaccaa                                                20

<210> SEQ ID NO 35
<211> LENGTH: 21
<212> TYPE: DNA
<213> ORGANISM: Artificial Sequence
<220> FEATURE:
<223> OTHER INFORMATION: A synthetic primer

<400> SEQUENCE: 35
atgcagtttc ttagggacac g                                              21

<210> SEQ ID NO 36
<211> LENGTH: 20
<212> TYPE: DNA
<213> ORGANISM: Artificial Sequence
<220> FEATURE:
<223> OTHER INFORMATION: A synthetic primer

<400> SEQUENCE: 36
ccagaagggc tcagagtggt                                                20

<210> SEQ ID NO 37
<211> LENGTH: 23
<212> TYPE: DNA
<213> ORGANISM: Artificial Sequence
<220> FEATURE:
<223> OTHER INFORMATION: A synthetic primer

<400> SEQUENCE: 37
gcccaacccc aggcctggca agc                                            23

<210> SEQ ID NO 38
<211> LENGTH: 22
<212> TYPE: DNA
<213> ORGANISM: Artificial Sequence
<220> FEATURE:
<223> OTHER INFORMATION: A synthetic primer

<400> SEQUENCE: 38
atttgggaag gtgcagagca gt                                             22

<210> SEQ ID NO 39
<211> LENGTH: 21
```

<212> TYPE: DNA
<213> ORGANISM: Artificial Sequence
<220> FEATURE:
<223> OTHER INFORMATION: A synthetic primer

<400> SEQUENCE: 39
ctcttggctg ttactgccag g                                              21

<210> SEQ ID NO 40
<211> LENGTH: 25
<212> TYPE: DNA
<213> ORGANISM: Artificial Sequence
<220> FEATURE:
<223> OTHER INFORMATION: A synthetic primer

<400> SEQUENCE: 40
ttcaaatatt gcaggcagga caacc                                          25

<210> SEQ ID NO 41
<211> LENGTH: 20
<212> TYPE: DNA
<213> ORGANISM: Artificial Sequence
<220> FEATURE:
<223> OTHER INFORMATION: A synthetic primer

<400> SEQUENCE: 41
ccttgtcatg cagggtgtga                                                20

<210> SEQ ID NO 42
<211> LENGTH: 22
<212> TYPE: DNA
<213> ORGANISM: Artificial Sequence
<220> FEATURE:
<223> OTHER INFORMATION: A synthetic primer

<400> SEQUENCE: 42
ccgctatcat ccacaagtag at                                             22

<210> SEQ ID NO 43
<211> LENGTH: 557
<212> TYPE: DNA
<213> ORGANISM: Homo sapiens

<400> SEQUENCE: 43
ggagtcagat gctgtttcga ggtcgaagag catcccagta atggttgtcc tgcctgcaat     60
atttgaattt taaatctaaa tctatttatt aatatttaac attatttata tggggaatat    120 attttagac tcatcaatca aataagtatt tataatagca acttttgtgt aatgaaaatg    180
aatatctatt aatatatgta ttatttataa ttcctatatc ctgtgactgt ctcacttaat    240
cctttgtttt ctgactaatt aggcaaggct atgtgattac aaggctttat ctcaggggcc    300
aactaggcag ccaacctaag caagatccca tgggttgtgt gtttatttca cttgatgata    360
caatgaacac ttataagtga agtgatacta tccagttact gccggtttga aaatatgcct    420
gcaatctgag ccagtgccttt aatggcatgt cagacagaac ttgaatgtgt caggtgaccc    480
tgatgaaaac atagcatctc aggagatttc atgcctggtg cttccaaata ttgttgacaa    540
ctgtgactgt acccaaa                                                   557

<210> SEQ ID NO 44
<211> LENGTH: 20
<212> TYPE: DNA
<213> ORGANISM: Artificial Sequence
<220> FEATURE:

<223> OTHER INFORMATION: A synthetic primer

<400> SEQUENCE: 44
ctgtacctgc tccgagtgtg                                                         20

<210> SEQ ID NO 45
<211> LENGTH: 18
<212> TYPE: DNA
<213> ORGANISM: Artificial Sequence
<220> FEATURE:
<223> OTHER INFORMATION: A synthetic primer

<400> SEQUENCE: 45
ccacctggac cactgctt                                                           18

<210> SEQ ID NO 46
<211> LENGTH: 18
<212> TYPE: DNA
<213> ORGANISM: Artificial Sequence
<220> FEATURE:
<223> OTHER INFORMATION: A synthetic primer

<400> SEQUENCE: 46
cctgagcagt ggagaagg                                                           18

<210> SEQ ID NO 47
<211> LENGTH: 20
<212> TYPE: DNA
<213> ORGANISM: Artificial Sequence
<220> FEATURE:
<223> OTHER INFORMATION: A synthetic primer

<400> SEQUENCE: 47
tcttctctcg ccactggaaa                                                         20

<210> SEQ ID NO 48
<211> LENGTH: 17
<212> TYPE: DNA
<213> ORGANISM: Artificial Sequence
<220> FEATURE:
<223> OTHER INFORMATION: A synthetic primer

<400> SEQUENCE: 48
gttgtcgacg acgagcg                                                            17

<210> SEQ ID NO 49
<211> LENGTH: 17
<212> TYPE: DNA
<213> ORGANISM: Artificial Sequence
<220> FEATURE:
<223> OTHER INFORMATION: A synthetic primer

<400> SEQUENCE: 49
gcacagagcc tcgcctt                                                            17

<210> SEQ ID NO 50
<211> LENGTH: 20
<212> TYPE: DNA
<213> ORGANISM: Artificial Sequence
<220> FEATURE:
<223> OTHER INFORMATION: A synthetic primer

<400> SEQUENCE: 50
gctggagttc cgcaagaaac                                                         20

```
<210> SEQ ID NO 51
<211> LENGTH: 23
<212> TYPE: DNA
<213> ORGANISM: Artificial Sequence
<220> FEATURE:
<223> OTHER INFORMATION: A synthetic primer

<400> SEQUENCE: 51
tttattgggg acggtactgt ggg                                              23

<210> SEQ ID NO 52
<211> LENGTH: 24
<212> TYPE: DNA
<213> ORGANISM: Artificial Sequence
<220> FEATURE:
<223> OTHER INFORMATION: A synthetic primer

<400> SEQUENCE: 52
ggagtcagat gctgtttcga ggtc                                             24

<210> SEQ ID NO 53
<211> LENGTH: 21
<212> TYPE: DNA
<213> ORGANISM: Artificial Sequence
<220> FEATURE:
<223> OTHER INFORMATION: A synthetic primer

<400> SEQUENCE: 53
tttgggtaca gtcacagttg t                                                21

<210> SEQ ID NO 54
<211> LENGTH: 22
<212> TYPE: DNA
<213> ORGANISM: Artificial Sequence
<220> FEATURE:
<223> OTHER INFORMATION: A synthetic primer

<400> SEQUENCE: 54
atctacttgt ggatgatagc gg                                               22

<210> SEQ ID NO 55
<211> LENGTH: 21
<212> TYPE: DNA
<213> ORGANISM: Artificial Sequence
<220> FEATURE:
<223> OTHER INFORMATION: A synthetic primer

<400> SEQUENCE: 55
atgctatacc aaggcagaga a                                                21

<210> SEQ ID NO 56
<211> LENGTH: 18
<212> TYPE: DNA
<213> ORGANISM: Artificial Sequence
<220> FEATURE:
<223> OTHER INFORMATION: A synthetic primer

<400> SEQUENCE: 56
aagcagtggt ccaggtgg                                                    18

<210> SEQ ID NO 57
<211> LENGTH: 18
<212> TYPE: DNA
<213> ORGANISM: Artificial Sequence
<220> FEATURE:
<223> OTHER INFORMATION: A synthetic primer
```

<400> SEQUENCE: 57
gctgagtgtt tacaggac                                                    18

<210> SEQ ID NO 58
<211> LENGTH: 20
<212> TYPE: DNA
<213> ORGANISM: Artificial Sequence
<220> FEATURE:
<223> OTHER INFORMATION: A synthetic primer

<400> SEQUENCE: 58
tttccagtgg cgagagaaga                                                  20

<210> SEQ ID NO 59
<211> LENGTH: 20
<212> TYPE: DNA
<213> ORGANISM: Artificial Sequence
<220> FEATURE:
<223> OTHER INFORMATION: A synthetic primer

<400> SEQUENCE: 59
ttgtcccagc cactcaggtg                                                  20

<210> SEQ ID NO 60
<211> LENGTH: 420
<212> TYPE: DNA
<213> ORGANISM: Artificial Sequence
<220> FEATURE:
<223> OTHER INFORMATION: A synthetic oligonucleotide sequence

<400> SEQUENCE: 60
tacattctca gacagggaca tggagatgat ctgtctgggg gtagaggacc tagagggccc       60
ggctgggcag ccgcttcctg cactgtctgt tgggacgtcc cttctgact gggtttctcc       120 agaagctgaa tggggatgt ttctgggaca cagattatgt tttcatatcg gggtctgcat       180
ctgggccctg ttgtcacagc ccccgacttg cccagatttt tccgccattg acgtcatggc      240
ggccggatgc gccgggcttc atcgacacca gggaggaaga gaagagggca gatacccac       300 cccacaggtt tcgttccgag aactggctgc cctgtcctgc agcaggcttg gcccaggtgg      360
ggtgacatgg gtgctggtgg atctggtagg tgatgtccat ctggccacta tgacaagccc      420

<210> SEQ ID NO 61
<211> LENGTH: 945
<212> TYPE: DNA
<213> ORGANISM: Homo sapiens

<400> SEQUENCE: 61
gctggagttc cgcaagaaac ggagccagag gcccagcagg tgttccaacc ctacacctgg       60
cccctgacct caagatcaag gaaaggagga tggacgaaca ggggccaaac tggtgggagg      120
cagaggtggt gggggcaggg atgataggcc ctggatgtgc ccacagggac caagaagtga      180
ggtttccact gtcttgcctg ccagggcccc tgttcccccg ctggcagcca ccccctcccc      240
catcatatcc tttgccccaa ggctgctcag aggggcccccg gtcctggccc cagcccccac    300
ctccgcccca gacacacccc ccagtcgagc cctgcagcca acagagcct tcacaaccag       360 ccacacagag cctgcctcag ctgctcgcac agattacttc agggctggaa aagtcacaca     420
gacacacaaa atgtcacaat cctgtccctc actcaacaca aacccaaaaa cacagagagc    480
ctgcctcagt acactcaaac aacctcaaag ctgcatcatc acacaatcac acacaagcac    540
agccctgaca acccacacac cccaaggcac gcacccacag ccagcctcag ggcccacagg    600

```
ggcactgtca acacagtggt gtgcccagag gcctacacag aagcagcgtc agtaccctca    660
ggatctgagg tcccaacacg tgctcgctca cacacacggc ctgttagaat tcacctgtgt    720
atctcacgca tatgcacacg cacagccccc cagtgggtct cttgagtccc gtgcagacac    780
acacagccac acacactgcc ttgccaaaaa taccccgtgt ctcccctgcc actcacctca    840
ctcccattcc ctgagccctg atccatgcct cagcttagac tgcagaggaa ctactcattt    900
atttgggatc caaggccccc aacccacagt accgtcccca ataaa                   945

<210> SEQ ID NO 62
<211> LENGTH: 558
<212> TYPE: DNA
<213> ORGANISM: Homo sapiens

<400> SEQUENCE: 62
ggagtcagat gctgtttcga ggtcgaagag catcccagta atggttgtcc tgcctgcaat     60
atttgaattt taaatctaaa tctatttatt aatatttaac attatttata tggggaatat    120
attttagac tcatcaatca aataagtatt tataatagca acttttgtgt aatgaaaatg     180
aatatctatt aatatatgta ttattttataa ttcctatatc ctgtgactgt ctcacttaat    240
cctttgtttt ctgactaatt aggcaaggct atgtgattac aaggctttat ctcaggggcc    300
aactaggcag ccaacctaag caagatccca tgggttgttg tgtttatttc acttgatgat    360
acaatgaaca cttataagtg aagtgatact atccagttac tgccggtttg aaaatatgcc    420
tgcaatctga gccagtgctt taatggcatg tcagacagaa cttgaatgtg tcaggtgacc    480
ctgatgaaaa catagcatct caggagattt catgcctggt gcttccaaat attgttgaca    540
actgtgactg tacccaaa                                                  558

<210> SEQ ID NO 63
<211> LENGTH: 437
<212> TYPE: DNA
<213> ORGANISM: Homo sapiens

<400> SEQUENCE: 63
atctacttgt ggatgatagc ggtaaagagt ccttgattgg ttatagacca acagaagatt     60
ccaaagaatt ttcatgagat cagctaagtt gcaccaactt tgaagtctga ttttcctgga    120
cagttttctg ctttaatttc atgaaaagat tatgatctca gaaattgtat cttagttggt    180
atcaaccaaa tggagtgact tagtgtacat gaaagcgtaa agaggatgtg tggcattttc    240
acttttggct tgtaaagtac agactttttt ttttttttaa acaaaaaaag cattgtaact    300
tatgaacctt tacatccaga taggttacca gtaacggaac agtatccagt actcctggtt    360
cctaggtgag caggtgatgc cccagggacc tttgtagcca cttcactttt tttcttttct    420
ctgccttggt atagcat                                                   437

<210> SEQ ID NO 64
<211> LENGTH: 663
<212> TYPE: DNA
<213> ORGANISM: Homo sapiens

<400> SEQUENCE: 64
aagcagtggt ccaggtggaa gtgatttat cttctgctct ttcttcttcc acacatgcaa      60
gggatgaatt gtaaaagcaa catcagcttg accagtataa aattacagtg gattgctcat    120
ctcagtcctc aaagcttttt gaaaaccaac accatcacag cttgttttgg actttgttac    180
```

```
actgttattt tcagcatgaa aatgtgtgtt tttttagggt ttctgattct tcaaagaggc      240
acagagccaa attggtagag gaaggatgca aagtataaat ttgtgtaata ttactttaac      300
atgcccatat tttacttgga aatattaaaa gaaagggttc tgtaaaatgg aaaacttagt      360
ttgtgaattg attttgagga gtggttttc ttttcttgga cacttaattc tgttctgata       420
ttaatttatc agattgcttt tgtgcattgg ataacaccac cattcacaag ttaagattct      480
tggtatttgg atatctgtta gatgctacta agaaaataga gatgagcttt ctttttaaag      540
cttttgatgt ggtgtcatag aatagcatgt tgtagataca atcagctgct ttgttacctt      600
aaaactaggc atttgtaaat attaaaccat aagatggcag gtgatgtcct gtaaacactc      660
agc                                                                    663

<210> SEQ ID NO 65
<211> LENGTH: 1298
<212> TYPE: DNA
<213> ORGANISM: Homo sapiens

<400> SEQUENCE: 65
tttccagtgg cgagagaaga ccccggagcc ccccgtgccc tgtgtccctg agcagacgga       60
gtatgccacc attgtctttc ctagcggaat gggcacctca tccccgccc gcagggggctc     120 agctgacggc cctcggagtg cccagccact gaggcctgag gatggacact gctcttggcc     180
cctctgaccg gcttccttgg ccaccagtgt tctgcagacc ctccaccatg agcccgggtc     240
agcgcatttc ctcaggagaa gcaggcaggg tgcaggccat tgcaggccgt ccaggggctg     300
agctgcctgg gggcgaccgg ggctccagcc tgcacctgca ccaggcacag ccccaccaca     360
ggactcatgt ctcaatgccc acagtgagcc caggcagcag gtgtcaccgt cccctacagg     420
gagggccaga tgcagtcact gcttcaggtc ctgccagcac agagctgcct gcgtccagct     480
ccctgaatct ctgctgctgc tgctgctgct gctgctgctg cctgcggccc ggggctgaag     540
gcgccgtggc cctgcctgac gccccggagc ctcctgcctg aacttgggg ctggttggag      600 atggccttgg agcagccaag gtgccctgg cagtggcatc ccgaaacgcc ctggacgcag       660
ggcccaagac tgggcacagg agtgggaggt acatggggct ggggactccc caggagttat     720
ctgctccctg caggcctaga gaagtttcag ggaaggtcag aagagctcct ggctgtggtg     780
ggcagggcag gaaacccctc caccttaca catgcccagg cagcacctca ggcccttgt       840 ggggcaggga agctgaggca gtaagcgggc aggcagagct ggaggccttt caggcccagc     900
cagcactctg gcctcctgcc gccgcattcc accccagccc ctcacaccac tcgggagagg     960
gacatcctac ggtcccaagg tcaggagggc agggctgggg ttgactcagg cccctcccag    1020
ctgtggccac ctgggtgttg ggagggcaga agtgcaggca cctagggccc cccatgtgcc    1080
caccctggga gctctccttg gaacccattc ctgaaattat ttaaagggt tggccgggct     1140 cccaccaggg cctgggtggg aaggtacagg cgttccccg gggcctagta ccccgccgt      1200 ggcctatcca ctcctcacat ccacacactg caccccact cctggggcag ggccaccagc    1260
atccaggcgg ccagcaggca cctgagtggc tgggacaa                             1298
```